(12) United States Patent
Zhang et al.

(10) Patent No.: US 11,225,477 B2
(45) Date of Patent: Jan. 18, 2022

(54) INHIBITORS OF INFLUENZA VIRUS REPLICATION, APPLICATION METHODS AND USES THEREOF

(71) Applicant: SUNSHINE LAKE PHARMA CO., LTD., Guangdong (CN)

(72) Inventors: Yingjun Zhang, Dongguan (CN); Qingyun Ren, Dongguan (CN); Changhua Tang, Dongguan (CN); Xiaohong Lin, Dongguan (CN); Junjun Yin, Dongguan (CN); Kai Yi, Dongguan (CN)

(73) Assignee: Sunshine Lake Pharma Co., Ltd., Guangdong (CN)

( * ) Notice: Subject to any disclaimer, the term of this patent is extended or adjusted under 35 U.S.C. 154(b) by 0 days.

(21) Appl. No.: 16/897,256

(22) Filed: Jun. 9, 2020

(65) Prior Publication Data
US 2020/0299294 A1  Sep. 24, 2020

Related U.S. Application Data

(62) Division of application No. 15/780,231, filed as application No. PCT/CN2016/109079 on Dec. 8, 2016, now Pat. No. 10,717,732.

(30) Foreign Application Priority Data

Dec. 9, 2015  (CN) .......................... 201510908329.2

(51) Int. Cl.
| | | |
|---|---|---|
| *C07D 471/04* | (2006.01) | |
| *C07D 519/00* | (2006.01) | |
| *A61K 45/06* | (2006.01) | |
| *A61K 31/52* | (2006.01) | |
| *A61K 31/519* | (2006.01) | |
| *A61K 31/517* | (2006.01) | |
| *A61K 31/5377* | (2006.01) | |
| *A61K 31/506* | (2006.01) | |
| *A61P 31/16* | (2006.01) | |

(52) U.S. Cl.
CPC .......... *C07D 471/04* (2013.01); *A61K 31/506* (2013.01); *A61K 31/517* (2013.01); *A61K 31/519* (2013.01); *A61K 31/52* (2013.01); *A61K 31/5377* (2013.01); *A61K 45/06* (2013.01); *A61P 31/16* (2018.01); *C07D 519/00* (2013.01)

(58) Field of Classification Search
CPC .................................................. C07D 471/04
See application file for complete search history.

(56) References Cited

U.S. PATENT DOCUMENTS

| | | |
|---|---|---|
| 8,829,007 B2 | 9/2014 | Charifson et al. |
| 8,871,774 B2 | 10/2014 | Charifson et al. |
| 8,987,454 B2 | 3/2015 | Salituro et al. |
| 9,051,319 B2 | 6/2015 | Charifson et al. |
| 9,345,708 B2 | 5/2016 | Charifson et al. |
| 9,394,302 B2 | 7/2016 | Charifson et al. |
| 9,808,459 B2 | 11/2017 | Charifson et al. |
| 2012/0171245 A1 | 6/2012 | Charifson et al. |
| 2013/0345218 A1 | 12/2013 | Charifson et al. |
| 2014/0005197 A1 | 1/2014 | Charifson et al. |
| 2016/0251354 A1 | 9/2016 | Tanoury et al. |
| 2017/0226102 A1 | 8/2017 | Jonckers et al. |
| 2017/0253600 A1 | 9/2017 | Jonckers et al. |

FOREIGN PATENT DOCUMENTS

WO   2013184985 A1   12/2013

OTHER PUBLICATIONS

Schönherr "Profound Methyl Effects in Drug Discovery and a Call for New C—H Methylation Reactions" Angew. Chem. Int. Ed. 2013, 52, 12256-12267.*
Shah "The role of fluorine in medicinal chemistry" Journal of Enzyme Inhibition and Medicinal Chemistry, Oct. 2007; 22(5): 527-540.*
Bioorganic & Medicinal Chemistry Letters 25 (2015) 1990-1994.
Journal of Medicinal Chemistry (2014), 57(15), 6668-6678.
Innovations in Pharmaceutical Technology, 2003, 74, 76-78.
Journal of Medicinal Chemistry, 2015, 58(18), 7195-7216.
Antiviral Research, 2016, 133, 23-31.

* cited by examiner

*Primary Examiner* — David K O'Dell
(74) *Attorney, Agent, or Firm* — Kam Wah Law

(57) ABSTRACT

The invention provides a novel class of compounds as inhibitors of influenza virus replication, preparation methods thereof, pharmaceutical compositions containing these compounds, and uses of these compounds and pharmaceutical compositions thereof in the treatment of influenza.

17 Claims, No Drawings

INHIBITORS OF INFLUENZA VIRUS REPLICATION, APPLICATION METHODS AND USES THEREOF

CROSS-REFERENCE TO RELATED APPLICATIONS

This is a divisional application of the U.S. patent application Ser. No. 15/780,231, filed May 30, 2018, which is a U.S. national stage application of the International Patent Application No. PCT/CN2016/109079, filed Dec. 8, 2016, which claims priority to Chinese Patent Application No. 201510908329.2, filed Dec. 9, 2015, all of which are incorporated herein by reference in their entirety.

FIELD OF THE INVENTION

The invention belongs to the pharmaceutical field, specifically, it relates to novel compounds used as inhibitors of influenza virus replication, preparation methods thereof, pharmaceutical compositions containing these compounds, and uses of these compounds and pharmaceutical compositions thereof in the treatment of influenza. More specifically, the compounds of the invention can be used as inhibitors of RNA polymerase of the influenza virus.

BACKGROUND

Influenza is an acute respiratory infectious disease and harmful to human health, which is caused by the influenza virus and characterized by high prevalence, widespread, rapid propagation. Influenza virus can cause serious symptoms in the elderly and children with weaker immune systems, and immunocompromised patients, such as pneumonia or cardiopulmonary failure. Influenza virus was first discovered by Wilson Smith, a British, who called influenza virus as H1N1. The H denotes hemagglutinin; the N denotes neuraminidase, and the numbers represent different types. Influenza virus has caused the global pandemic for many times since the discovery, and the outbreak of influenza virus happens every decade or so, which causes enormous losses in worldwide. Influenza spreads around the world in a yearly outbreak, resulting in about 250,000 to 500,000 deaths, and about three to five million cases of severe illness, and a total of about 5% to 15% of people in worldwide are infected. Every time a pandemic was due to the emergence of new strains in humans. Usually, these new strains are caused by the spread of existing influenza virus from other animal species to humans Influenza viruses are RNA viruses belong to the family of orthomyxoviridae, which belong to the genus of influenza virus. According to the differences of the virion nucleoprotein (NP) and matrix protein (M) antigenic characteristics and genetic characteristics, influenza viruses are divided into three types: A, B and C. The three types of influenza viruses have similar biochemical and biological characteristics. The virus particle is 80-120 nanometers in diameter and usually roughly spherical, although filamentous forms can occur. Virus is constituted with three layers, and the inner layer is the viral nucleocapsid containing nucleoprotein (NP), P protein and RNA. NP is a soluble antigen (S antigen) with type specificity and antigenic stability. P protein (P1, P2, P3) may be polymerase required for RNA transcription and replication. Middle viral envelope consists of a lipoid layer and a layer of membrane protein (MP), MP has antigenic stability and type specificity. Outer layer is a radial tuber consisting of two different glycoprotein projections, i.e., hemagglutinin (H) and neuraminidase (N). H is a tool for viral absorbtion on sensitive cell surface which can cause agglutination of erythrocyte, N is a tool for breaking away from cell surface after the completing of virus replication, which is capable of hydrolyzing mucus protein and N-acetylneuraminic acid that locates at the end of cell surface specific glycoprotein receptor. H and N both have variation characteristics, and only have the strain specific antigen, the antibody of which has a protective effect.

Influenzavirus A has one species, influenza A virus. Wild aquatic birds are the natural hosts for a large variety of influenza A. Occasionally, viruses are transmitted to other species and may then cause devastating outbreaks in domestic poultry or give rise to human influenza pandemics. The type A virus is the most virulent human pathogen among the three influenza types and cause the severest disease, and can be transmitted to other species and may then cause human influenza pandemic. The influenza A virus can be subdivided into different serotypes based on the antibody response to these viruses. The serotypes that have been confirmed in humans, ordered by the number of known human pandemic deaths, are: H1N1, which caused Spanish Flu in 1918; H2N2, which caused Asian Flu in 1957; H3N2, which caused Hong Kong Flu in 1968; H5N1, which caused pandemic threats in the influenza season of 2007-2008; H7N7, which has unusual zoonotic potential; H1N2, endemic in humans and pigs; H9N2; H7N2; H7N3; and H10N7.

Influenzavirus B has one species, influenza B virus, which causes local epidemic influenza and can not cause the global influenza pandemic. The only animals known to be susceptible to influenza B infection are humans and the seal. This type of influenza mutates at a rate 2-3 times slower than type A and consequently is less genetically diverse, with only one influenza B serotype. As a result of this lack of antigenic diversity, a degree of immunity to influenza B is usually acquired at an early age. However, influenza B mutates enough that lasting immunity is not possible. This reduced rate of antigenic change, combined with its limited host range (inhibiting cross species antigenic shift), ensures that pandemics of influenza B do not occur.

Influenzavirus C has one species, influenza C virus, which exists in sporadic form, and usually only causes mild disease in children. Influenzavirus C usually can not cause influenza pandemic, and infect humans and pigs.

Unusually for a virus, its genome is not a single piece of nucleic acid; instead, it contains seven or eight pieces of segmented negative-sense RNA. The genome of influenza A viruses encodes 11 proteins: hemagglutinin (H), neuraminidase (N), nucleoprotein (N), M1, M2, NS1, NS2 (NEP), PA, PB1 (polymerase basic 1), PB1-F2 and PB2. Hemagglutinin (H) and neuraminidase (N) are the two large glycoproteins on the outside of the viral particles. HA is a lectin that mediates binding of the virus to target cells and entry of the viral genome into the target cell, while NA is involved in the release of progeny virus from infected cells, by cleaving sugars that bind the mature viral particles. Thus, these proteins are targets for antiviral drugs. Furthermore, they are antigens to which antibodies can be raised. Influenza A viruses are classified into subtypes based on antibody responses to H and N. These different types of HA and NA form the basis of the H and N distinctions in, for example, H5N1.

Vaccination and usage of antiviral drugs are important tools for responding to influenza pandemic. Due to the high mutation rate of the flu virus antigen, the vaccine can't be produced in large scale before influenza pandemic. The two classes of antiviral drugs used against influenza are M2 protein inhibitors (amantadine and rimantadine) and neuraminidase inhibitors (oseltamivir, zanamivir, peramivir and Laninamivir). However, the influenza viruses have developed drug resistance to all these drugs. Therefore, continuing demand for new anti-influenza treatment agent is existing.

Favipiravir, a new antiviral agent, having a new mechanism, has been launched, which plays antiviral action by inhibiting RNA polymerase of the influenza virus to target the inhibition of viral gene replication, but the therapeutic effect and the drug resistance of influenza viruses still need to be proved. Therefore, other compounds as anti-influenza agents of this mechanism still needed to be researched.

SUMMARY OF THE INVENTION

The invention discloses a novel class of compounds used as inhibitors of RNA polymerase of the influenza virus. These compounds and compositions thereof can be used in the manufacture of a medicament for preventing, managing, treating or lessening virus infection in patients.

In one aspect, provided herein is a compound having Formula (I) or a stereoisomer, a tautomer, an N-oxide, a solvate, a metabolite, a pharmaceutically acceptable salt or a prodrug thereof,

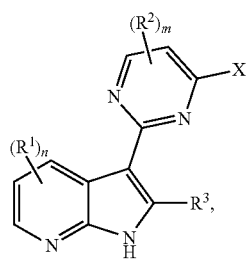

(I)

wherein $R^1$, $R^2$, $R^3$, X, m and n are as defined herein.

In certain embodiments, each $R^1$ and $R^3$ is independently H, F, Cl, Br, CN, $NO_2$, —C(=O)$R^a$, —C(=O)O$R^b$, —C(=O)N$R^cR^d$, O$R^b$, —N$R^cR^d$, $R^b$O—$C_{1-4}$ alkylene, $R^dR^cN$—$C_{1-4}$ alkylene, $C_{1-6}$ alkyl, $C_{2-6}$ alkenyl, $C_{2-6}$ alkynyl, $C_{3-8}$ cycloalkyl, $C_{3-8}$ cycloalkyl-$C_{1-4}$ alkylene, 3- to 12-membered heterocyclyl, (3- to 12-membered heterocyclyl)-$C_{1-4}$ alkylene, $C_{6-10}$ aryl, $C_{6-10}$ aryl-$C_{1-4}$ alkylene, 5- to 10-membered heteroaryl or (5- to 10-membered heteroaryl)-$C_{1-4}$ alkylene, and wherein each of the $C_{1-6}$ alkyl, $C_{2-6}$ alkenyl, $C_{2-6}$ alkynyl, $C_{3-8}$ cycloalkyl, $C_{3-8}$ cycloalkyl-$C_{1-4}$ alkylene, 3- to 12-membered heterocyclyl, (3- to 12-membered heterocyclyl)-$C_{1-4}$ alkylene, $C_{6-10}$ aryl, $C_{6-10}$ aryl-$C_{1-4}$ alkylene, 5- to 10-membered heteroaryl and (5- to 10-membered heteroaryl)-$C_{1-4}$ alkylene is independently unsubstituted or substituted with one, two, three or four substituents independently selected from F, Cl, Br, CN, O$R^b$, —N$R^cR^d$, $C_{1-6}$ alkyl, $C_{1-6}$ haloalkyl, $R^b$O—$C_{1-4}$ alkylene or $R^dR^cN$—$C_{1-4}$ alkylene;

n is 0, 1, 2 or 3;

each $R^2$ is independently F, $C_{2-6}$ alkynyl, O$R^b$, $C_{3-12}$ carbocyclyl, $C_{3-12}$ carbocyclyl-$C_{1-4}$ alkylene, 3- to 12-membered heterocyclyl, (3- to 12-membered heterocyclyl)-$C_{1-4}$ alkylene, $C_{6-10}$ aryl, $C_{6-10}$ aryl-$C_{1-4}$ alkylene, 5- to 14-membered heteroaryl, (5- to 14-membered heteroaryl)-$C_{1-4}$ alkylene; or two adjacent $R^2$, together with the atoms to which they are attached, form a $C_{3-12}$ carbocyclic ring, 3- to 12-membered heterocyclic ring, $C_{6-10}$ aromatic ring or 5- to 10-membered heteroaromatic ring, and wherein each of the $C_{2-6}$ alkynyl, $C_{3-12}$ carbocyclyl, $C_{3-12}$ carbocyclyl-$C_{1-4}$ alkylene, 3- to 12-membered heterocyclyl, (3- to 12-membered heterocyclyl)-$C_{1-4}$ alkylene, $C_{6-10}$ aryl, $C_{6-10}$ aryl-$C_{1-4}$ alkylene, 5- to 14-membered heteroaryl, (5- to 14-membered heteroaryl)-$C_{1-4}$ alkylene, $C_{3-12}$ carbocyclic ring, 3- to 12-membered heterocyclic ring, $C_{6-10}$ aromatic ring and 5- to 10-membered heteroaromatic ring is independently unsubstituted or substituted with one, two, three, four or five R', with the proviso that when m is 1, $R^2$ is not F;

each R' is independently F, Cl, Br, CN, $NO_2$, oxo (=O), O$R^b$, —N$R^cR^d$, $R^b$O—$C_{1-4}$ alkylene, $R^dR^cN$—$C_{1-4}$ alkylene, —C(=O)$R^a$, —C(=O)O$R^b$, —C(=O)N$R^cR^d$, $C_{1-10}$ alkyl, $C_{1-6}$ haloalkyl, $C_{3-6}$ cycloalkyl, $C_{3-6}$ cycloalkyl-$C_{1-4}$ alkylene, 3- to 6-membered heterocyclyl, (3- to 6-membered heterocyclyl)-$C_{1-4}$ alkylene, $C_{6-10}$ aryl, $C_{6-10}$ aryl-$C_{1-4}$ alkylene, 5- to 6-membered heteroaryl or (5- to 6-membered heteroaryl)-$C_{1-4}$ alkylene, and wherein each of the $C_{1-10}$ alkyl, $C_{1-6}$ haloalkyl, $C_{3-6}$ cycloalkyl, $C_{3-6}$ cycloalkyl-$C_{1-4}$ alkylene, 3- to 6-membered heterocyclyl, (3- to 6-membered heterocyclyl)-$C_{1-4}$ alkylene, $C_{6-10}$ aryl, $C_{6-10}$ aryl-$C_{1-4}$ alkylene, 5- to 6-membered heteroaryl and (5- to 6-membered heteroaryl)-$C_{1-4}$ alkylene is independently unsubstituted or substituted with one, two, three, or four substituents independently selected from F, Cl, Br, CN, $NO_2$, O$R^b$, —N$R^cR^d$, $C_{1-6}$ alkyl, $C_{1-6}$ haloalkyl, $R^b$O—$C_{1-4}$ alkylene or $R^dR^cN$—$C_{1-4}$ alkylene;

m is 1 or 2;

X has one of the following sub-formulae:

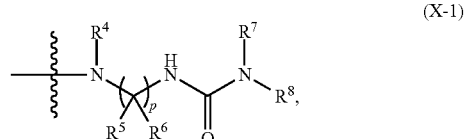

(X-1)

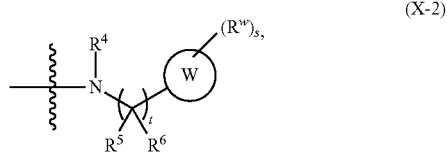

(X-2)

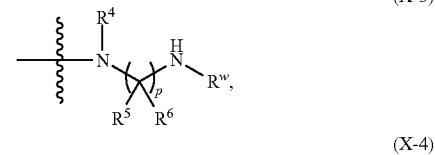

(X-3)

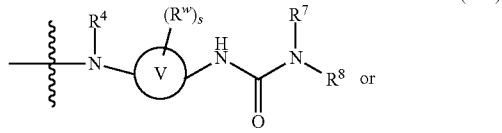

(X-4) or

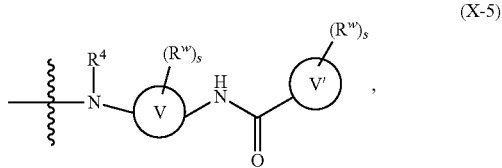

(X-5)

wherein $R^4$ is H or $C_{1-6}$ alkyl, and wherein the $C_{1-6}$ alkyl is optionally substituted with one, two, three, or four U;

each $R^5$, $R^6$, $R^7$ and $R^8$ is independently H or $C_{1-6}$ alkyl; or $R^5$ and $R^6$, together with the carbon atom to which they are attached, form a $C_{3-8}$ cycloalkyl group, 3- to 6-membered heterocyclic ring, $C_{6-10}$ aromatic ring or 5- to 10-membered heteroaromatic ring; or $R^7$ and $R^8$, together with the nitrogen atom to which they are attached, form a 3- to 6-membered heterocyclic ring or 5- to 10-membered heteroaromatic ring, and wherein each $C_{1-6}$ alkyl, $C_{3-8}$ cycloalkyl, 3- to 6-membered heterocyclic ring, $C_{6-10}$ aromatic ring or 5- to 10-membered heteroaromatic ring is independently unsubstituted or substituted with one, two, three, or four U;

W is a $C_{3-12}$ carbocyclic ring or 3- to 12-membered heterocyclic ring;

each V and V' is independently a $C_{3-12}$ cycloalkane ring, 3- to 12-membered heterocyclic ring, $C_{6-10}$ aromatic ring or 5- to 10-membered heteroaromatic ring;

each $R^w$ is independently F, Cl, Br, CN, NO$_2$, oxo (=O), —C(=O)R$^a$, —C(=O)OR$^b$, —C(=O)NR$^c$R$^d$, —S(=O)$_2$R$^e$, —S(=O)$_2$NR$^c$C(=O)R$^a$, —S(=O)$_2$NR$^c$R$^d$, (R$^b$O)$_2$P(=O)—C$_{0-2}$ alkylene, OR$^b$, —NR$^c$R$^d$, R$^b$O—C$_{1-2}$ alkylene, R$^d$R'N—C$_{1-2}$ alkylene, C$_{1-6}$ alkyl, 5- to 6-membered heteroaryl or 5- to 6-membered heterocyclyl, and wherein each of the C$_{1-6}$ alkyl, 5- to 6-membered heteroaryl or 5- to 6-membered heterocyclyl is independently unsubstituted or substituted with one, two, three, or four U;

each U is independently F, Cl, Br, NO$_2$, CN, oxo (=O), N3, OR$^b$, —NR$^c$R$^d$, C$_{1-6}$ alkyl or C$_{1-6}$ haloalkyl;

each s and t is independently 0, 1, 2 or 3;

p is 1, 2 or 3; and each R$^a$, R$^b$, R$^c$, R$^d$ and R$^e$ is independently H, C$_{1-6}$ alkyl, C$_{1-6}$ haloalkyl, C$_{2-6}$ alkenyl, C$_{2-6}$ alkynyl, C$_{3-6}$ cycloalkyl, C$_{3-6}$ cycloalkyl-C$_{1-4}$ alkylene, 3- to 6-membered heterocyclyl, (3- to 6-membered heterocyclyl)-C$_{1-4}$ alkylene, C$_{6-10}$ aryl, C$_{6-10}$ aryl-C$_{1-4}$ alkylene, 5- to 10-membered heteroaryl, (5- to 10-membered heteroaryl)-C$_{1-4}$ alkylene; or R$^c$ and R$^d$, together with the nitrogen atom to which they are attached, form a 3- to 6-membered heterocyclic ring, and wherein each of the C$_{1-6}$ alkyl, C$_{2-6}$ alkenyl, C$_{2-6}$ alkynyl, C$_{3-6}$ cycloalkyl, C$_{3-6}$ cycloalkyl-C$_{1-4}$ alkylene, 3- to 6-membered heterocyclyl, (3- to 6-membered heterocyclyl)-C$_{1-4}$ alkylene, C$_{6-10}$ aryl, C$_{6-10}$ aryl-C$_{1-4}$ alkylene, 5- to 10-membered heteroaryl, (5- to 10-membered heteroaryl)-C$_{1-4}$ alkylene and 3- to 6-membered heterocyclic ring is independently unsubstituted or substituted with one, two, three, or four substituents independently selected from F, Cl, CN, OH, NH$_2$, C$_{1-6}$ alkyl, C$_{1-6}$ haloalkyl, C$_{1-6}$ alkoxy or C$_{1-6}$ alkylamino.

In other embodiments, the invention relates to a compound having Formula (II), or a stereoisomer, a tautomer, an N-oxide, a solvate, a metabolite, a pharmaceutically acceptable salt or a prodrug thereof,

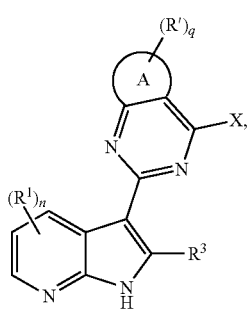

(II)

wherein A, R$^1$, R$^3$, X, R', n and q are as defined herein.

In other embodiments, A is a $C_{3-12}$ carbocyclic ring, 3- to 12-membered heterocyclic ring, $C_{6-10}$ aromatic ring or 5- to 10-membered heteroaromatic ring; and q is 0, 1, 2, 3, 4 or 5.

In other embodiments, each R$^1$ and R$^3$ is independently H, F, Cl, —C(=O)R$^a$, —C(=O)OR$^b$, —C(=O)NR$^c$R$^d$, OR$^b$, —NR$^c$R$^d$, C$_{1-3}$ alkyl, C$_{3-6}$ cycloalkyl, 5- to 6-membered heterocyclyl, phenyl or 5- to 6-membered heteroaryl, and wherein each of the C$_{1-3}$ alkyl, C$_{3-6}$ cycloalkyl, 5- to 6-membered heterocyclyl, phenyl or 5- to 6-membered heteroaryl is independently unsubstituted or substituted with one, two, three or four substituents independently selected from F, Cl, OR$^b$, —NR$^c$R$^d$, C$_{1-3}$ alkyl, C$_{1-3}$ haloalkyl or R$^b$O—C$_{1-2}$ alkylene.

In other embodiments, each R$^2$ is independently F, C$_{2-6}$ alkynyl, OR$^b$, C$_{3-6}$ carbocyclyl, C$_{3-6}$ carbocyclyl-C$_{1-2}$ alkylene, 5- to 6-membered heterocyclyl, (5- to 6-membered heterocyclyl)-C$_{1-2}$ alkylene, phenyl, naphthyl, phenyl-C$_{1-2}$ alkylene, 5- to 6-membered heteroaryl, (5- to 6-membered heteroaryl)-C$_{1-2}$ alkylene; or two adjacent R$^2$, together with the atoms to which they are attached, form a C$_{5-6}$ carbocyclic ring, 5- to 6-membered heterocyclic ring, benzene ring or 5- to 6-membered heteroaromatic ring, and wherein each of the C$_{2-6}$ alkynyl, C$_{3-6}$ carbocyclyl, C$_{3-6}$ carbocyclyl-C$_{1-2}$ alkylene, 5- to 6-membered heterocyclyl, (5- to 6-membered heterocyclyl)-C$_{1-2}$ alkylene, phenyl, naphthyl, phenyl-C$_{1-2}$ alkylene, 5- to 6-membered heteroaryl, (5- to 6-membered heteroaryl)-C$_{1-2}$ alkylene, C$_{5-6}$ carbocyclic ring, 5- to 6-membered heterocyclic ring, benzene ring and 5- to 6-membered heteroaromatic ring is independently unsubstituted or substituted with one, two, three, four or five R', with the proviso that when m is 1, R$^2$ is not F.

In other embodiments, each R' is independently F, Cl, Br, CN, NO$_2$, OR$^b$, —NR$^c$R$^d$, —C(=O)R$^a$, —C(=O)NR$^c$R$^d$, C$_{1-9}$ alkyl, C$_{1-3}$ haloalkyl, C$_{3-6}$ cycloalkyl, 5- to 6-membered heterocyclyl, phenyl, phenyl-C$_{1-2}$ alkylene or 5- to 6-membered heteroaryl, and wherein each of the C$_{1-9}$ alkyl, C$_{1-3}$ haloalkyl, C$_{3-6}$ cycloalkyl, 5- to 6-membered heterocyclyl, phenyl, phenyl-C$_{1-4}$ alkylene and 5- to 6-membered heteroaryl is independently unsubstituted or substituted with one, two, three, or four substituents independently selected from F, Cl, Br, CN, NO$_2$, OR$^b$, —NR$^c$R$^d$, methyl, ethyl, n-propyl or i-propyl.

In other embodiments, each R$^a$, R$^b$, R$^c$, R$^d$ and R$^e$ is independently H, methyl, ethyl, i-propyl, n-propyl, n-butyl, t-butyl, C$_{1-3}$ haloalkyl, C$_{3-6}$ cycloalkyl, C$_{3-6}$ cycloalkyl-C$_{1-2}$ alkylene, 3- to 6-membered heterocyclyl, phenyl, phenyl-C$_{1-2}$ alkylene; or R$^c$ and R$^d$, together with the nitrogen atom to which they are attached, form a 5- to 6-membered heterocyclic ring, and wherein each of methyl, ethyl, i-propyl, n-propyl, n-butyl, t-butyl, C$_{3-6}$ cycloalkyl, C$_{3-6}$ cycloalkyl-C$_{1-2}$ alkylene, 3- to 6-membered heterocyclyl, phenyl, phenyl-C$_{1-2}$ alkylene and 5- to 6-membered heterocyclic ring is independently unsubstituted or substituted with one, two, three, or four substituents independently selected from F, Cl, CN, OH, NH$_2$, C$_{1-3}$ alkyl, C$_{1-3}$ haloalkyl or methoxy.

In other embodiments, X has one of the following sub-formulae:

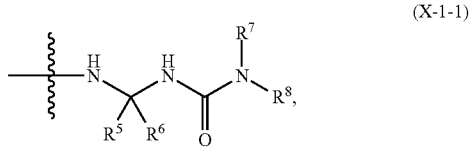

(X-1-1)

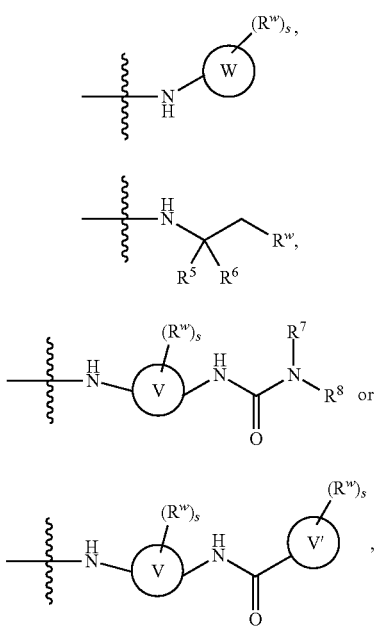

(X-2-1)

(X-3-1)

(X-4-1)

(X-5-1)

wherein W, V, V', $R^5$, $R^6$, $R^7$, $R^8$, $R^w$ and s are as defined herein.

In other embodiments, W is a $C_{6-8}$ carbocyclic ring or 6- to 8-membered heterocyclic ring.

In other embodiments, V is a $C_{3-8}$ cycloalkane ring, 3- to 8-membered heterocyclic ring, benzene ring or 5- to 6-membered heteroaromatic ring.

In other embodiments, V' is a $C_{3-8}$ cycloalkane ring, 3- to 8-membered heterocyclic ring, benzene ring or 5- to 6-membered heteroaromatic ring.

In other embodiments, each $R^w$ is independently F, Cl, Br, CN, $NO_2$, oxo (=O), —C(=O)$R^a$, —C(=O)$OR^b$, —C(=O)$NR^cR^d$, —S(=O)$_2R^e$, —S(=O)$_2NR^cC(=O)R^a$, —S(=O)$_2NR^cR^d$, $(R^bO)_2P$(=O)—$C_{0-2}$ alkylene, $OR^b$, —$NR^cR^d$, $R^bO$—$C_{1-2}$ alkylene, $R^dR^cN$—$C_{1-2}$ alkylene, methyl, ethyl, i-propyl, n-propyl, n-butyl, t-butyl, tetrazolyl, isoxazolyl, oxazolyl, 1,2,4-oxadiazolyl, 1,3,4-oxadiazolyl or pyrazolyl, and wherein each of methyl, ethyl, i-propyl, n-propyl, n-butyl, t-butyl, tetrazolyl, isoxazolyl, oxazolyl, 1,2,4-oxadiazolyl, 1,3,4-oxadiazolyl and pyrazolyl is independently unsubstituted or substituted with one, two, three, or four U.

In other embodiments, each U is independently F, Cl, Br, $CF_3$, $NO_2$, CN, oxo (=O), $N_3$, $OR^b$, —$NR^cR^d$, methyl, ethyl, i-propyl, n-propyl, n-butyl or t-butyl.

In other embodiments, A is a $C_{5-6}$ carbocyclic ring, 5- to 6-membered heterocyclic ring, benzene ring, naphthalene ring or 5- to 6-membered heteroaromatic ring.

In other embodiments, each $R^2$ is independently F, ethynyl, propynyl, $OR^b$, $C_{3-6}$ carbocyclyl, 5- to 6-membered heterocyclyl, phenyl, naphthyl, phenyl-$C_{1-2}$ alkylene, furyl, benzofuryl, pyrrolyl, pyridyl, pyrazolyl, imidazolyl, benzimidazolyl, triazolyl, tetrazolyl, oxazolyl, oxadiazolyl, 1,3,5-triazinyl, thiazolyl, thienyl, benzothienyl, pyrazinyl, pyridazinyl, pyrimidyl, indolyl, purinyl, quinolyl, isoquinolyl, phenoxthinyl,

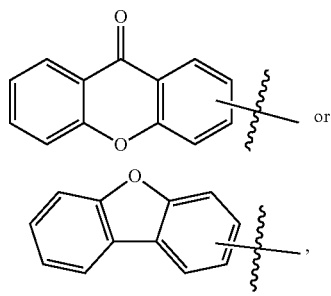 or and wherein each ethynyl, propynyl, $C_{3-6}$ carbocyclyl, 5- to 6-membered heterocyclyl, phenyl, naphthyl, phenyl-$C_{1-2}$ alkylene, furyl, benzofuryl, pyrrolyl, pyridyl, pyrazolyl, imidazolyl, benzimidazolyl, triazolyl, tetrazolyl, oxazolyl, oxadiazolyl, 1,3,5-triazinyl, thiazolyl, thienyl, benzothienyl, pyrazinyl, pyridazinyl, pyrimidyl, indolyl, purinyl, quinolyl, isoquinolyl, phenoxthinyl,

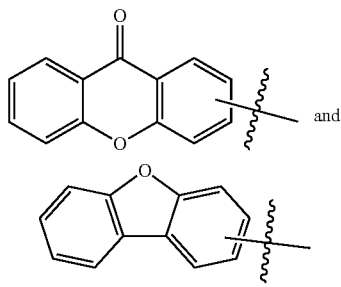 and is independently unsubstituted or substituted with one, two, three, four or five R', with the proviso that when m is 1, $R^2$ is not F.

In other embodiments, X has one of the following sub-formulae:

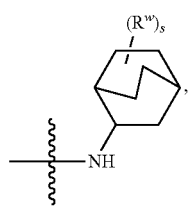

(X-2-2)

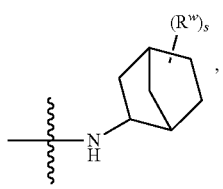

(X-2-3)

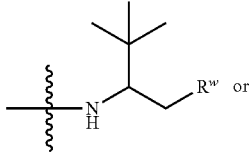 or (X-3-2)

-continued (X-3-3)

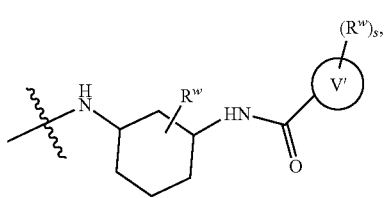

wherein $R^w$, s and V' are as defined herein.

In other embodiments, A is a $C_{5-6}$ carbocyclic ring, 5- to 6-membered heterocyclic ring, benzene, naphthalene, furan, benzofuran, pyrrole, pyridine, pyrazole, imidazole, benzoimidazole, triazole, tetrazole, oxazole, oxadiazole, 1,3,5-triazine, thiazole, thiophene, benzothiphene, pyrazine, pyridazine, pyrimidine, indole, purine, quinoline or isoquinoline.

In other embodiments, the invention relates to a compound having Formula (III) or a stereoisomer, a tautomer, an N-oxide, a solvate, a metabolite, a pharmaceutically acceptable salt or a prodrug thereof, (III)

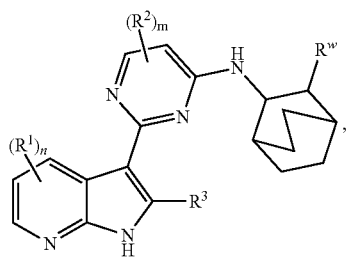

wherein $R^1$, $R^2$, $R^3$, m, n and $R^w$ are as defined herein.

In other embodiments, the invention relates to a compound having Formula (IV) or a stereoisomer, a tautomer, an N-oxide, a solvate, a metabolite, a pharmaceutically acceptable salt or a prodrug thereof, (IV)

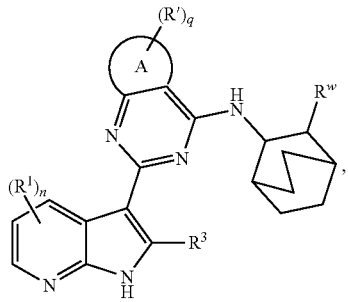

wherein A, $R^1$, $R^3$, R', n, q and $R^w$ are as defined herein.

In other embodiments, the invention relates to a compound having Formula (V) or a stereoisomer, a tautomer, an N-oxide, a solvate, a metabolite, a pharmaceutically acceptable salt or a prodrug thereof, (V)

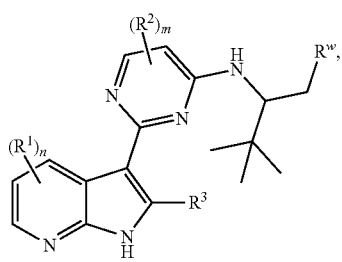

wherein $R^1$, $R^2$, $R^3$, m, n and $R^w$ are as defined herein.

In other embodiments, the invention relates to a compound having Formula (VI) or a stereoisomer, a tautomer, an N-oxide, a solvate, a metabolite, a pharmaceutically acceptable salt or a prodrug thereof, (VI)

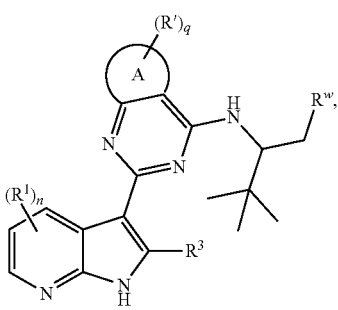

wherein A, $R^1$, $R^3$, R', n, q and $R^w$ are as defined herein.

In other embodiments, the invention relates to a compound having Formula (VII) or a stereoisomer, a tautomer, an N-oxide, a solvate, a metabolite, a pharmaceutically acceptable salt or a prodrug thereof, (VII)

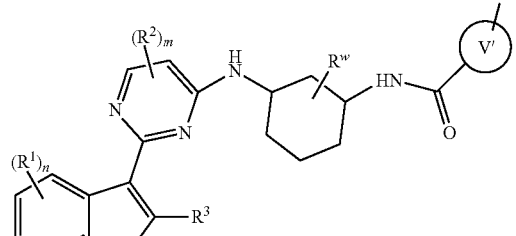

wherein $R^1$, $R^2$, $R^3$, m, n, s, V' and $R^w$ are as defined herein.

In other embodiments, the invention relates to a compound having Formula (VIII) or a stereoisomer, a tautomer, an N-oxide, a solvate, a metabolite, a pharmaceutically acceptable salt or a prodrug thereof,

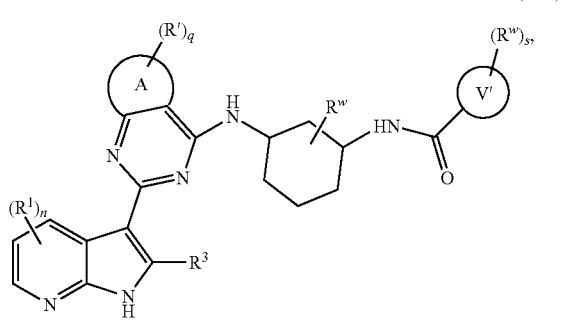

(VIII)

wherein A, $R^1$, $R^3$, R', n, q, s, V' and $R^w$ are as defined herein.

In one aspect, provided herein is a pharmaceutical composition comprising the compound disclosed herein.

In certain embodiments, the pharmaceutical composition provided herein further comprises a pharmaceutically acceptable carrier, adjuvant, vehicle or a combination thereof.

In certain embodiments, the pharmaceutical composition provided herein further comprises one or more therapeutic agents.

In other embodiments, the therapeutic agent disclosed herein is an anti-influenza virus agent or anti-influenza virus vaccine.

In other embodiments, the pharmaceutical composition is in the form of liquid, solid, semi-solid, gel or spray.

In other embodiments, the pharmaceutical composition disclosed herein, wherein the therapeutic agent is amantadine, rimantadine, oseltamivir, zanamivir, peramivir, laninamivir, laninamivir octanoate hydrate, favipiravir, arbidol, ribavirin, stachyflin, ingavirin, fludase, CAS no. 1422050-75-6, JNJ-872, AL-794, an influenza vaccine (FluMist Quadrivalent®, Fluarix® Quadrivalent, Fluzone® Quadrivalent, Flucelvax® or FluBlok®) or a combination thereof.

In another aspect, provided herein is use of the compound or the pharmaceutical composition disclosed herein in the manufacture of a medicament for preventing, managing, treating or lessening a disorder or disease caused by virus infection in a patient.

In certain embodiments, the virus infection disclosed herein is influenza virus infection.

In another aspect, provided herein is use of the compound or the pharmaceutical composition disclosed herein in the manufacture of a medicament for inhibiting RNA polymerase of the influenza virus.

In another aspect, provided herein is the compound or the pharmaceutical composition disclosed herein for use in preventing, managing, treating or lessening a disorder or disease caused by virus infection.

In certain embodiments, the virus infection disclosed herein is influenza virus infection.

In another aspect, provided herein is the compound or the pharmaceutical composition disclosed herein for use in inhibiting RNA polymerase of influenza virus.

In another aspect, provided herein is a method of preventing, managing, treating or lessening a disorder or disease caused by virus infection in a patient, comprising administering to the patient a therapeutically effective amount of the compound or the pharmaceutical composition disclosed herein.

In certain embodiments, the virus infection disclosed herein is influenza virus infection.

In another aspect, provided herein is a method of inhibiting RNA polymerase of the an influenza virus in a patient, comprising administering to the patient a therapeutically effective amount of the compound or the pharmaceutical composition disclosed herein.

Unless otherwise stated, all stereoisomers, geometric isomers, tautomers, solvates, hydrates, metabolites, salts and pharmaceutically acceptable prodrugs of the compounds disclosed herein are within the scope of the invention.

In one embodiment, the salt is a pharmaceutically acceptable salt. The phrase "pharmaceutically acceptable" refers to that the substance or composition must be chemically and/or toxicologically compatible with the other ingredients comprising a formulation, and/or the mammal being treated therewith.

In another embodiment, the salts are not necessarily pharmaceutically acceptable salts, and which may be useful as intermediates for preparing and/or purifying compounds of the invention and/or for separating enantiomers of compounds of the invention.

Furthermore, the compounds disclosed herein, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms.

In another embodiment, the compound disclosed herein may contain several asymmetric centers and therefore exist in the form of racemic mixture generally described. Furthermore, it is intended that all racemic mixture, parts of the racemic mixture, and enantiomer and diastereomers purified by separation form part of the present invention.

The compounds disclosed herein may exists in the form of possible isomers, including rotamers, atropisomers, tautomer or a mixture thereof. It is intended that mixtures of isomers, including rotamers, atropisomers, tautomers, parts of the mixtures of isomers, rotamers, atropisomers, tautomers, and the isomers, including rotamers, atropisomers, tautomer purified by separation form part of the present invention.

In another aspect, the compounds of the invention include isotopically enriched compounds as defined herein, for example those into which radioactive isotopes, such as $^3H$, $^{14}C$ and $^{18}F$, or those into which non-radioactive isotopes, such as $^2H$ and $^{13}C$ are present.

In other aspect, provided herein is a method of preparing, separating or purifying the compound of Formula (I).

The foregoing merely summarizes certain aspects disclosed herein and is not intended to be limiting in nature. These aspects and other aspects and embodiments are described more fully below.

DETAILED DESCRIPTION OF THE INVENTION

Definitions and General Terminology

Reference will now be made in detail to certain embodiments of the invention, examples of which are illustrated in the accompanying structures and formulas. The invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described herein. In the event that one or more of the incorporated literature, patents, and similar materials differs from or contradicts this application, including but not limited to defined terms, term usage, described techniques, or the like, this application controls.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

Unless otherwise defined, all technical and scientific terms used herein have the same meaning as is commonly understood by one skilled in the art to which this invention belongs. All patents and publications referred to herein are incorporated by reference in their entirety.

As used herein, the following definitions shall be applied unless otherwise indicated. For purposes disclosed herein, the chemical elements are identified in accordance with the Periodic Table of the Elements, CAS version, and the *Handbook of Chemistry and Physics*, 75 th Ed. 1994. Additionally, general principles of organic chemistry are described in Thomas Sorrell et al., "*Organic Chemistry*", University Science Books, Sausalito: 1999, and Michael B. Smith et al., "March's Advanced Organic Chemistry", John Wiley & Sons, New York: 2007, all of which are incorporated herein by reference in their entireties.

As used herein, the term "subject" refers to an animal. Typically the animal is a mammal. The subject also refers to for example, primates (e.g., humans), cows, sheep, goats, horses, dogs, cats, rabbits, rats, mice, fish, birds and the like. In certain embodiments, the subject is a primate. In other embodiments, the subject is a human.

The term "subject" can be used interchangeably with "patient" in the invention. The term "subject" and "patient" refer to animals (eg., birds such as chicken, quail or turkey, or mammals), specially mammals including non-primates (eg., cattle, pigs, horses, sheep, rabbits, guinea pigs, rats, dogs, cats and mice) and primates (eg., monkeys, chimpanzees and humans), more specially humans. In some embodiments, the subject is a non-human animal, such as livestock (eg., horses, cattle, pigs or sheep) or pet (eg., dogs, cats, guinea pigs or rabbits). In other some embodiments, the "patient" refers to a human.

Any formula given herein is also intended to represent isotopically unenriched forms as well as isotopically enriched forms of the compounds. Isotopically enriched compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, sulfur, fluorine, and chlorine, such as $^2H$, $^3H$, $^{13}C$, $^{14}C$, $^{15}N$, $^{16}O$, $^{17}O$, $^{31}P$, $^{32}P$, $^{36}S$, $^{18}F$ and $^{37}Cl$, respectively.

The compounds disclosed herein containing isotopes described above or other atom isotopes and pharmaceutical salts thereof are included within the scope of the present invention. Certain isotopically-labeled compounds of the present invention, for example those into which radioactive isotopes such as $^3H$ or $^{14}C$ are incorporated, are useful in drug and/or substrate tissue distribution assays. Because of easy preparation and detection, isotopes such as tritiated, i.e., $^3H$, and carbon-14, i.e., $^{14}C$ are preferred. Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. Therefore, the heavier isotopes may be preferred in somewhere.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "*Stereochemistry of Organic Compounds*", John Wiley & Sons, Inc., New York, 1994. The compounds disclosed herein may contain asymmetric or chiral centers, and therefore exist in different stereoisomeric forms. It is intended that all stereoisomeric forms of the compounds disclosed herein, including, but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and 1 or (+) and (−) are employed to designate the sign of rotation of plane-polarized light by the compound, with (−) or 1 meaning that the compound is levorotatory. A compound prefixed with (+) or d is dextrorotatory. A specific stereoisomer may be referred to as an enantiomer, and a mixture of such stereoisomers is called an enantiomeric mixture. A specific stereoisomer is referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process.

Depending on the choice of the starting materials and procedures, the compounds can be present in the form of one of the possible stereoisomers or as mixtures thereof, such as racemates and diastereoisomer mixtures, depending on the number of asymmetric carbon atoms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration.

The compounds disclosed herein may contain asymmetric or chiral centers, and therefore exist in different stereoisomeric forms. It is intended that all stereoisomeric forms of the compounds disclosed herein, including but not limited to, diastereomers, enantiomers, atropisomers and geometric (conformational) isomers as well as mixtures thereof such as racemic mixtures, form part of the present invention.

Unless otherwise specified, the Formula described herein also contain all the isomers thereof (such as, enantiomers, diastereomers, atropisomers and geometric (conformational) isomers; such as all (R)- and (S)-isomers, (Z) and (E) isomers around the double bond, (Z) and (E) conformational isomers. Therefore, single stereochemical isomers as well as enantiomeric, diastereomeric, or geometric mixtures of the present compounds are within the scope disclosed herein.

The term "tautomer" or "tautomeric form" refers to structural isomers of different energies which are interconvertible via a low energy barrier. Where tautomerization is possible (e.g., in solution), a chemical equilibrium of tautomers can be reached. For example, proton tautomers (also known as prototropic tautomers) include interconversions via migration of a proton, such as keto-enol and imine-enamine isomerizations. Valence tautomers include interconversions by reorganization of some of the bonding electrons. A specific example of keto-enol tautomerization is the interconversion of pentane-2,4-dione and 4-hydroxypent-3-en-2-one tautomers. Another example of tautomerization is phenol-keto tautomerization. The specific example of phenol-keto tautomerisms is pyridin-4-ol and pyridin-4(1H)-one tautomerism. Unless otherwise stated, all tautomeric forms of the compounds disclosed herein are within the scope of the invention.

An "N-oxide" refers to one or more than one nitrogen atoms oxidised to form an N-oxide, where a compound contains several amine functions. Particular examples of N-oxides are the N-oxides of a tertiary amine or a nitrogen atom of a nitrogen-containing heterocycle. N-oxides can be formed by treatment of the corresponding amine with an oxidizing agent such as hydrogen peroxide or a per-acid (e.g., a peroxycarboxylic acid) (See, *Advanced Organic Chemistry*, by Jerry March, 4th Edition, Wiley Interscience, pages). More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

The term "solvate" refers to an association or complex of one or more solvent molecules and a compound disclosed herein. Some non-limiting examples of solvents that form solvates include water, isopropanol, ethanol, methanol, dimethylsulfoxide, ethyl acetate, acetic acid and ethanolamine. The term "hydrate" refers to the complex where the solvent molecule is water.

A "metabolite" is a product produced through metabolism in the body of a specified compound or salt thereof. The metabolites of a compound may be identified using routine techniques known in the art and their activities determined using tests such as those described herein. Such products may result for example from oxidation, reduction, hydrolysis, amidation, deamidation, esterification, deesterification, enzyme cleavage, and the like, of the administered compound. Accordingly, the invention includes metabolites of compounds disclosed herein, including metabolites produced by contacting a compound disclosed herein with a mammal for a sufficient time period.

A "pharmaceutically acceptable salts" refers to organic or inorganic salts of a compound disclosed herein. Pharmaceutically acceptable salts are well known in the art. For example, S. M. Berge et al., describe pharmaceutically acceptable salts in detail in *J. Pharmaceutical Sciences*, 1977, 66: 1-19, which is incorporated herein by reference. Some non-limiting examples of pharmaceutically acceptable and nontoxic salts include salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid and malonic acid or by using other methods used in the art such as ion exchange. Other pharmaceutically acceptable salts include adipate, alginate, ascorbate, aspartate, benzenesulfonate, benzoate, bisulfate, borate, butyrate, camphanic acid salt, camphorsulfonate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, laurylsulfate, malate, malonate, methanesulfonate, 2-naphthalenesulfonate, nicotinate, nitrate, oleate, palmitate, pamoate, pectinate, persulfate, 3-phenylpropionate, picrate, pivalate, propionate, stearate, thiocyanate, p-toluenesulfonate, undecanoate, valerate salts, and the like. Salts derived from appropriate bases include alkali metal, alkaline earth metal, ammonium and $N^+(C_{1-4}\ alkyl)_4$ salts. This invention also envisions the quaternization of any basic nitrogen-containing groups of the compounds disclosed herein. Water or oil soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, $C_{1-8}$ sulfonate or aryl sulfonate.

The term "prodrug" refers to a compound that is transformed in vivo into a compound of Formula (I). Such a transformation can be affected, for example, by hydrolysis of the prodrug form in blood or enzymatic transformation to the parent form in blood or tissue. Prodrugs of the compounds disclosed herein may be, for example, esters. Some common esters which have been utilized as prodrugs are phenyl esters, aliphatic ($C_{1-24}$) esters, acyloxymethyl esters, carbonates, carbamates and amino acid esters. For example, a compound disclosed herein that contains a hydroxy group may be acylated at this position in its prodrug form. Other prodrug forms include phosphates, such as, those phosphate compounds derived from the phosphonation of a hydroxy group on the parent compound. A thorough discussion of prodrugs is provided in T. Higuchi and V. Stella, *Pro-drugs as Novel Delivery Systems*, Vol. 14 of the A.C.S. Symposium Series, Edward B. Roche, ed., *Bioreversible Carriers in Drug Design*, American Pharmaceutical Association and Pergamon Press, 1987, J. Rautio et al., Prodrugs: Design and Clinical Applications, *Nature Review Drug Discovery*, 2008, 7, 255-270, and S. J. Hecker et al., Prodrugs of Phosphates and Phosphonates, *Journal of Medicinal Chemistry*, 2008, 51, 2328-2345, all of which are incorporated herein by reference in their entireties.

Any asymmetric atom (e.g., carbon or the like) of the compound(s) disclosed herein can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. If the compound contains a double bond, the substituent may be cis-(Z) or trans-(E) configuration.

Therefore, as the invention described, the compound disclosed herein may exist in the form of any possible isomer, such as rotational isomer, atropisomer, tautomer, or a mixture thereof, i.e., substantially pure geometric (cis- or trans-) isomer, diastereoisomer, optical isomer (enantiomer), racemate or a mixture thereof.

Any resulting mixtures of stereoisomers can be separated on the basis of the physicochemical differences of the constituents, into the pure or substantially pure geometric isomers, optical isomers, diastereoisomers, racemate, for example, by chromatography and/or fractional crystallization.

Any resulting racemates of final products or intermediates can be resolved into the optical antipodes by methods known to those skilled in the art, e.g., by separation of the diastereomeric salts thereof. Racemic products can also be resolved by chiral chromatography, e.g., high performance liquid chromatography (HPLC) using a chiral adsorbent. Preferred enantiomers can also be prepared by asymmetric syntheses. See, for example, Jacques, et al., *Enantiomers, Racemates and Resolutions* (Wiley Interscience, New York, 1981); *Principles of Asymmetric Synthesis* (2nd Ed. Robert E. Gawley, Jeffrey Aubé, Elsevier, Oxford, U K, 2012); Eliel, E. L. *Stereochemistry of Carbon Compounds* (McGraw-Hill, N Y, 1962); Wilen, S. H. *Tables of Resolving Agents and Optical Resolutions* p. 268 (E. L. Eliel, Ed., Univ. of Notre Dame Press, Notre Dame, Ind. 1972).

As described herein, compounds disclosed herein may optionally be substituted with one or more substituents, such as are illustrated generally below, or as exemplified by particular classes, subclasses, and species of the invention. It will be appreciated that the phrase "optionally substituted" is used interchangeably with the phrase "substituted or unsubstituted". The term "optional" or "optionally" refers to that a subsequently described event or circumstance may but need not occur, and that the description includes instances where the event or circumstance occurs and instances in which it does not. In general, whenever the term "optionally" is or is not before the term "substituted", it refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position. Substituents described herein may be, but are not limited to, F, Cl, Br, CN, N3, OH, $NH_2$, $NO_2$, oxo (=O), —C(=O)$R^a$, —C(=O)$OR^b$, —C(=O)$NR^cR^d$, —S(=O)$_2R^e$, —S(=O)$_2NR^cC$(=O)$R^a$, —S(=O)$_2NR^cR^d$, ($R^bO)_2P$(=O)—$C_{0-2}$ alkylene, $OR^b$, —$NR^cR^d$, $R^bO$—$C_{1-4}$ alkylene, $R^dR^cN$—$C_{1-4}$ alkylene, $C_{1-6}$ alkyl, $C_{1-6}$ aliphatic radical, $C_{1-6}$ halolkyl, $C_{1-6}$ alkoxy, $C_{1-6}$ alkylamino, $C_{2-6}$ alkenyl, $C_{2-6}$ alkynyl, $C_{3-8}$ cycloalkyl, $C_{3-8}$ cycloalkyl-$C_{1-4}$ alkylene, 3- to 12-membered heterocyclyl, (3- to 12-membered heterocyclyl)-$C_{1-4}$ alkylene, $C_{6-10}$ aryl, $C_{6-10}$ aryl-$C_{1-4}$ alkylene, 5- to 14-membered heteroaryl or (5- to 14-membered heteroaryl)-$C_{1-4}$ alkylene, and wherein $R^a$, $R^b$, $R^c$, $R^d$ and $R^e$ are as defined herein.

Furthermore, what need to be explained is that the phrase "each . . . is independently" and "each (of) . . . and . . . is independently", unless otherwise stated, should be broadly understood. The specific options expressed by the same symbol are independent of each other in different groups; or the specific options expressed by the same symbol are independent of each other in same groups.

At various places in the present specification, substituents of compounds disclosed herein are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

At various places in the present specification, linking substituents are described. Where the structure clearly requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "alkyl" or "alkyl group" refers to a saturated linear or branched-chain monovalent hydrocarbon radical of 1 to 20 carbon atoms. Unless otherwise specified, the alkyl group contains 1-20 carbon atoms. In some embodiments, the alkyl group contains 1-10 carbon atoms. In other embodiments, the alkyl group contains 1-9 carbon atoms. In other embodiments, the alkyl group contains 1-8 carbon atoms. In other embodiments, the alkyl group contains 1-6 carbon atoms. In still other embodiments, the alkyl group contains 1-4 carbon atoms. In yet other embodiments, the alkyl group contains 1-3 carbon atoms.

Some non-limiting examples of the alkyl group include, methyl (Me, —$CH_3$), ethyl (Et, —$CH_2CH_3$), n-propyl (n-Pr, —$CH_2CH_2CH_3$), isopropyl (i-Pr, —$CH(CH_3)_2$), n-butyl (n-Bu, —$CH_2CH_2CH_2CH_3$), isobutyl (i-Bu, —$CH_2CH$ ($CH_3)_2$), sec-butyl (s-Bu, —$CH(CH_3)CH_2CH_3$), tert-butyl (t-Bu, —$C(CH_3)_3$), n-pentyl (—$CH_2CH_2CH_2CH_2CH_3$), 2-pentyl (—$CH(CH_3)CH_2CH_2CH_3$), 3-pentyl (—CH ($CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH$ ($CH_3)CH_2CH_3$), n-hexyl (—$CH_2CH_2CH_2CH_2CH_2CH_3$), 2-hexyl (—$CH(CH_3)CH_2CH_2CH_2CH_3$), 3-hexyl (—CH ($CH_2CH_3)(CH_2CH_2CH_3$)), 2-methyl-2-pentyl (—$C(CH_3)$ $_2CH_2CH_2CH_3$), 3-methyl-2-pentyl (—$CH(CH_3)CH(CH_3)$ $CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—C ($CH_3)_2CH(CH_3)_2$), 3,3-dimethyl-2-butyl (—$CH(CH_3)C$ ($CH_3)_3$), n-heptyl and n-octyl, etc. Wherein the alkyl group can be independently unsubstituted or substituted with one or more substituents described herein.

The term "alkyl" or the prefix "alk-" is inclusive of both straight chain and branched saturated carbon chain.

The term "alkylene" refers to a saturated divalent hydrocarbon group derived from a straight or branched chain saturated hydrocarbon by the removal of two hydrogen atoms. Unless otherwise stated, the alkylene group contains 1-10 carbon atoms. In other embodiments, the alkylene group contains 1-6 carbon atoms. In still other embodiments, the alkylene group contains 1-4 carbon atoms. In yet other embodiments, the alkylene group contains 1-2 carbon atoms. Such alkylene group is exemplified by methylene (—$CH_2$—), ethylene (—$CH_2CH_2$—), isopropylene (—CH ($CH_3)CH_2$—), and the like. Wherein the alkylene group may be independently unsubstituted or substituted with one or more substitutents described herein.

The term "alkenyl" refers to a linear or branched chain monovalent hydrocarbon radical of 2 to 12 carbon atoms, or 2 to 8 carbon atoms, or 2 to 6 carbon atoms, or 2 to 4 carbon atoms, with at least one site of unsaturation, i.e., a carbon-carbon, $sp^2$ double bond, wherein the alkenyl radical may be independently unsubstituted or substituted with one or more substituents described herein, and includes radicals having "cis" and "trans" orientations, or alternatively, "E" and "Z" orientations. Examples of the alkenyl group include, but are not limited to, vinyl (—CH=$CH_2$), allyl (—$CH_2CH$=$CH_2$), and the like.

The term "alkynyl" refers to a linear or branched chain monovalent hydrocarbon radical of 2 to 12 carbon atoms, or 2 to 8 carbon atoms, or 2 to 6 carbon atoms, or 2 to 4 carbon atoms, with at least one site of unsaturation, i.e., a carbon-carbon, sp triple bond, wherein the alkynyl radical is independently unsubstituted or substituted with one or more substituents described herein. Examples of alkynyl group include, but are not limited to, acetenyl (—C≡CH), propargyl (—$CH_2C$≡CH), 1-propynyl (—C≡C—$CH_3$), and the like.

The term "alkoxy" refers to an alkyl group, as previously defined, attached to the parent molecular moiety via an oxygen atom. Unless otherwise specified, the alkoxy group contains 1-20 carbon atoms. In some embodiments, the alkoxy group contains 1-10 carbon atoms. In other embodiments, the alkoxy group contains 1-8 carbon atoms. In still other embodiments, the alkoxy group contains 1-6 carbon atoms. In yet other embodiments, the alkoxy group contains 1-4 carbon atoms. And in still yet other embodiments, the alkoxy group contains 1-3 carbon atoms.

Some non-limiting examples of the alkoxy group include, methoxy (MeO, —OCH$_3$), ethoxy (EtO, —OCH$_2$CH$_3$), 1-propoxy (n-PrO, n-propoxy, —OCH$_2$CH$_2$CH$_3$), 2-propoxy (i-PrO, i-propoxy, —OCH(CH$_3$)$_2$), 1-butoxy (n-BuO, n-butoxy, —OCH$_2$CH$_2$CH$_2$CH$_3$), 2-methyl-1-propoxy (i-BuO, i-butoxy, —OCH$_2$CH(CH$_3$)$_2$), 2-butoxy (s-BuO, s-butoxy, —OCH(CH$_3$)CH$_2$CH$_3$), 2-methyl-2-propoxy (t-BuO, t-butoxy, —OC(CH$_3$)$_3$), 1-pentoxy (n-pentoxy, —OCH$_2$CH$_2$CH$_2$CH$_2$CH$_3$), 2-pentoxy (—OCH(CH$_3$)CH$_2$CH$_2$CH$_3$), 3-pentoxy (—OCH(CH$_2$CH$_3$)$_2$), 2-methyl-2-butoxy (—OC(CH$_3$)$_2$CH$_2$CH$_3$), 3-methyl-2-butoxy (—OCH(CH$_3$)CH(CH$_3$)$_2$), 3-methyl-1-butoxy (—OCH$_2$CH$_2$CH(CH$_3$)$_2$), 2-methyl-1-butoxy (—OCH$_2$CH(CH$_3$)CH$_2$CH$_3$), and the like. Wherein the alkoxy group is independently unsubstituted or substituted with one or more substitutents disclosed herein.

The terms "haloalkyl", "haloalkenyl" or "haloalkoxy" refer to alkyl, alkenyl, or alkoxy, as the case may be, substituted with one or more halogen atoms. Some non-limiting examples of "haloalkyl", "haloalkenyl" or "haloalkoxy" groups include trifluoromethyl, trifluoromethoxy, and the like.

The term "carbocycle", "carbocyclyl", "carbocyclic" or "carbocyclic ring" used interchangeably herein refers to a ring having 3 to 14 ring carbon atoms, which is saturated or contains one or more units of unsaturation. In some embodiments, the number of carbon atom is 3 to 12; in other embodiments, the number of carbon atom is 3 to 10; in other embodiments, the number of carbon atom is 3 to 8; in other embodiments, the number of carbon atom is 5 to 6; in other embodiments, the number of carbon atom is 6 to 8. The "carbocyclyl" includes a monocyclic, bicyclic, or polycyclic fused ring, spiro ring or bridged ring system, and a polycyclic ring system containing one carbocyclic ring fused with one or more non-aromatic carbocyclic ring or heterocyclic ring, or one or more aromatic ring, or a combination thereof, wherein the linked group or point exists on carbocyclic ring. The bicyclic carbocyclyl groups includes bridged bicyclic carbocyclyl, fused bicyclic carbocyclyl and spiro bicyclic carbocyclyl group, and fused bicyclic system contains two rings which share two adjacent ring atoms. Bridged bicyclic group contains two rings which share three or four adjacent ring atoms. Spiro bicyclic system contains two ring which share one ring atom. Some non-limiting examples of the carbocyclyl group include cycloalkyl, cycloalkenyl and cycloalkynyl. Further non-limiting examples of carbocyclyl groups include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like. Bridged bicyclic carbocyclyl group includes, but are not limited to, bicyclo[2.2.2]octyl, bicyclo[2.2.1]heptyl, bicyclo[3.3.1]nonyl, bicyclo[3.2.3]nonyl, and the like.

The term "cycloalkyl" refers to a saturated ring having 3 to 12 ring carbon atoms as a monocyclic, bicyclic, or tricyclic ring system, which has one or more attachments attaching to the rest of the molecule. In some embodiments, the cycloalkyl group contains 3 to 10 ring carbon atoms. In other embodiments, the cycloalkyl group contains 3 to 8 ring carbon atoms. In still other embodiments, the cycloalkyl group contains 3 to 6 ring carbon atoms. In yet other embodiments, the cycloalkyl group contains 5 to 6 ring carbon atoms. The cycloalkyl radical is independently unsubstituted or substituted with one or more substituents described herein.

The term "heterocycle", "heterocyclyl", or "heterocyclic ring" as used interchangeably herein refers to a saturated or partially unsaturated non-aromatic monocyclic, bicyclic or tricyclic ring containing 3-12 ring atoms of which at least one ring atom is selected from nitrogen, sulfur and oxygen, and of which may has one ore more attachments attached to the rest of the molecule. The term "heterocyclyl" includes a monocyclic, bicyclic, or polycyclic fused, spiro, bridged heterocyclic ring system, and a polycyclic ring system containing one heterocyclic ring fused with one or more non-aromatic carbocyclic ring or heterocyclic ring, or one or more aromatic ring, or a combination thereof, wherein the linked group or attachment exists on heterocyclic ring. Biheterocyclyl radical includes bridged biheterocyclyl, fused biheterocyclyl and spiro biheterocyclyl. Unless otherwise specified, the heterocyclyl group may be carbon or nitrogen linked, and a —CH$_2$— group can be optionally replaced by a —C(=O)— group. In which, the sulfur can be optionally oxygenized to S-oxide and the nitrogen can be optionally oxygenized to N-oxide. In some embodiments, the heterocyclyl group is a 3- to 8-membered mono- or bicyclic heterocyclyl group; in other embodiments, the heterocyclyl group is a 3- to 6-membered mono- or bicyclic heterocyclyl group; in other embodiments, the heterocyclyl group is a 6- to 8-membered mono- or bicyclic heterocyclyl group; in other embodiments, the heterocyclyl group is a 5- to 6-membered heterocyclyl group; in other embodiments, the heterocyclyl group is a 4-membered heterocyclyl group; in other embodiments, the heterocyclyl group is a 5-membered heterocyclyl group; in other embodiments, the heterocyclyl group is a 6-membered heterocyclyl group; in other embodiments, the heterocyclyl group is a 7-membered heterocyclyl group; in other embodiments, the heterocyclyl group is a 8-membered heterocyclyl group.

Some non-limiting examples of the heterocyclyl group include oxiranyl, azetidinyl, oxetanyl, thietanyl, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxolanyl, dithiolanyl, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, dithianyl, thioxanyl, homopiperazinyl, homopiperidinyl, oxepanyl, thiepanyl, oxazepinyl, diazepinyl, thiazepinyl, indolinyl, 1,2,3,4-tetrahydroisoquinolyl, 1,3-benzodioxolyl, 2-oxa-5-azabicyclo[2.2.1]hept-5-yl. Some non-limiting examples of heterocyclyl wherein —CH$_2$— group is replaced by —C(=O)— moiety include 2-oxopyrrolidinyl, oxo-1,3-thiazolidinyl, 2-piperidinonyl, 3,5-dioxopiperidinyl, pyrimidinedione-yl. Some non-limiting examples of heterocyclyl wherein the ring sulfur atom is oxidized is sulfolanyl and 1,1-dioxo-thiomorpholinyl. Some non-limiting examples of the bridged heterocyclyl group include, 2-oxabicyclo[2.2.2]octyl, 1-azabicyclo[2.2.2]octyl, 3-azabicyclo[3.2.1]octyl, and the like. The heterocyclyl group may be optionally substituted with one or more substituents disclosed herein.

The term "bridged" refers to a bond, an atom or an unbranched atoms chain connecting two different parts of a molecule. The two atoms (usually but not always two tertiary carbon atoms) linked by the bridge denotes "bridgeheads".

The term "spiro" refers to a ring system containing one atom that is the only one shared atom (usually a quaternary carbon) between two rings.

The term "n-membered", where n is an integer typically described as the number of ring-forming atoms in a moiety where the number of ring-forming atoms is n. For example, piperidyl is an example of 6-membered heterocyclyl and 1,2,3,4-tetrahydro-naphthyl group is an example of a 10-membered carbocyclyl group.

The term "heteroatom" refers to oxygen (O), sulfur (S), nitrogen (N), phosphorus (P) and silicon (Si), including any oxidized form of nitrogen, sulfur, or phosphorus; the quaternized form of any basic nitrogen; or a substitutable nitrogen of a heterocyclic ring, for example, N (as in 3,4-dihydro-2H-pyrrolyl), NH (as in pyrrolidinyl) or NR (as in N-substituted pyrrolidinyl).

The term "halogen" refers to fluoro (F), chloro (Cl), bromo (Br), or iodo (I).

The term "azido" or "N$_3$" refers to an azide moiety. This radical may be attached, for example, to a methyl group to form azidomethane (methyl azide, MeN$_3$); or attached to a phenyl group to form phenyl azide (PhN$_3$).

The term "aryl" used alone or as a great part of "arylalkyl", "arylalkoxy", refers to monocyclic, bicyclic and tricyclic carbocyclic ring systems having a total of six to fourteen ring members, or six to twelve ring members, or six to ten ring members, wherein at least one ring in the system is aromatic, wherein each ring in the system contains 3 to 7 ring members and that has a single point or multipoint of attachment to the rest of the molecule. The term "aryl" may be used interchangeably with the term "aryl ring" or "aromatic ring". Some non-limiting examples of the aryl group include phenyl, naphthyl and anthryl. The aryl group may be optionally unsubstituted or substituted with one or more substituents disclosed herein.

The term "heteroaryl" used alone or as a great part of "heteroarylalkyl" or "heteroarylalkoxy", refers to monocyclic, bicyclic and tricyclic ring systems having a total of five to fourteen ring members, or five to twelve ring members, or five to ten ring members, or five to six ring members, wherein at least one ring in the system is aromatic, and in which at least one ring member is selected from heteroatom, and wherein each ring in the system contains 5 to 7 ring members and that has a single point or multipoint of attachment to the rest of the molecule. Unless otherwise specified, the heteroaryl group may be carbon or nitrogen linked, and a —CH$_2$— group can be optionally replaced by a —C(=O)— group. In which, the sulfur can be optionally oxygenized to S-oxide and the nitrogen can be optionally oxygenized to N-oxide. The term "heteroaryl" and "heteroaromatic ring" or "heteroaromatic compound" can be used interchangeably herein. In one embodiment, the heteroaryl group is a 5- to 12-membered heteroaryl comprising 1, 2, 3 or 4 heteroatoms independently selected from O, S and N. In another embodiment, the heteroaryl group is a 5- to 10-membered heteroaryl comprising 1, 2, 3 or 4 heteroatoms independently selected from O, S and N. In another embodiment, the heteroaryl group is a 5- to 6-membered heteroaryl comprising 1, 2, 3 or 4 heteroatoms independently selected from O, S and N. In another embodiment, the heteroaryl group is a 5 membered heteroaryl comprising 1, 2, 3 or 4 heteroatoms independently selected from O, S and N. In another embodiment, the heteroaryl group is a 6 membered heteroaryl comprising 1, 2, 3 or 4 heteroatoms independently selected from 0, S and N.

Some non-limiting examples of the heteroaryl group include the following monocyclic ring, 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5H-tetrazolyl, 2H-tetrazolyl), triazolyl (e.g., 2-triazolyl, 5-triazolyl, 4H-1,2,4-triazolyl, 1H-1,2,4-triazolyl and 1,2,3-triazolyl), 2-thienyl, 3-thienyl, pyrazolyl (e.g., 2-pyrazolyl and 3-pyrazolyl), isothiazolyl, 1,2,3-oxadiazolyl, 1,2,5-oxadiazolyl, 1,2,4-oxadiazolyl, 1,3,4-oxadiazolyl, 1,2,3-thiadiazolyl, 1,3,4-thiadiazolyl, 1,2,5-thiadiazolyl, pyrazinyl, 1,3,5-triazinyl, and the following bicycles, but are not limited to: benzimidazolyl, benzofuryl, benzothiophenyl, indolyl (e.g., 2-indolyl), purinyl, quinolinyl (e.g., 2-quinolinyl, 3-quinolinyl, 4-quinolinyl), isoquinolinyl (e.g., 1-isoquinolinyl, 3-isoquinolinyl or 4-isoquinolinyl), oxathianyl,

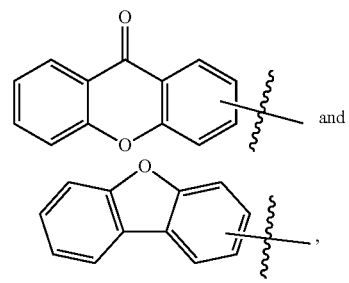

The heteroaryl group is optionally substituted with one or more substituents disclosed herein.

The terms "carboxy" or "carboxyl", whether used alone or with other terms, such as "carboxyalkyl", refer to —CO$_2$H. The term "carbonyl", whether used alone or with other terms, such as "aminocarbonyl", "acyloxy", denotes —(C=O)—.

The term "alkylamino" refers to "N-alkylamino" and "N,N-dialkylamino" wherein the amino groups are independently substituted with one alkyl radical or two alkyl radicals, respectively. In some embodiments, the alkylamino group is a lower alkylamino group having one or two $C_{1-6}$ alkyl groups attached to nitrogen atom. In other embodiments, the alkylamino group is a $C_{1-3}$ lower alkylamino group. Suitable alkylamino radical may be monoalkylamino or dialkylamino. Examples of the alkylamino radical include, but are not limited to, N-methylamino, N-ethylamino, N,N-dimethylamino, N,N-diethylamino, and the like.

The term "arylamino" refers to an amino group substituted with one or two aryl groups. Some non-limiting examples of such group included N-phenylamino. In some embodiments, the aryl group of the arylamino may be further substituted.

The term "aminoalkyl" refers to a $C_{1-10}$ linear or branched-chain alkyl group substituted with one or more amino groups. In some embodiments, the aminoalkyl is a $C_{1-6}$ lower aminoalkyl substituted with one or more amino groups. Some non-limiting examples of the aminoalkyl group include aminomethyl, aminoethyl, aminopropyl, aminobutyl and aminohexyl.

As described herein, a bond drawn from a substituent to the center of one ring within a ring system represents substitution of substituents at any substitutable position on the rings, and wherein the ring system includes mono-, bi- or polycyclic ring system. For example, formula a represents substitution of substituents at any substitutable position on the bicyclic ring system of ring A and ring B, i.e., formula b-1 to formula b-8:

formula a formula b-1
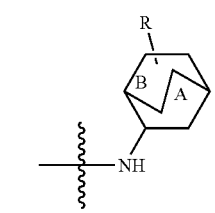

formula b-2
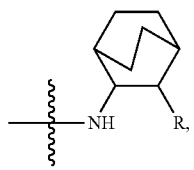

formula b-3
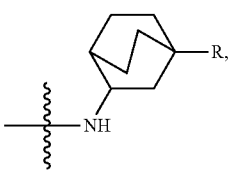

formula b-4
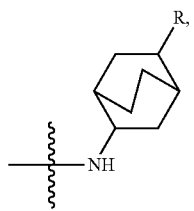

formula b-5
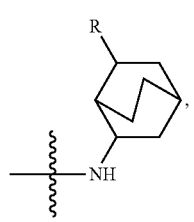

formula b-6
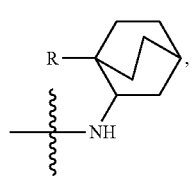

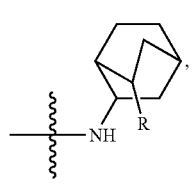

formula b-7
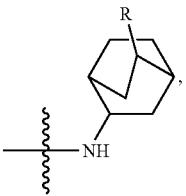

formula b-8
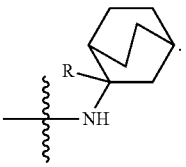

As described herein, a bond drawn from a substituent to the center of one ring within a ring system represents the bond can attach to the rest of the molecule at any attachable position on the rings. For example, formula c represents substitution of substituents at any substitutable position on the rings, i.e., formula d-1 and formula d-2.

formula c
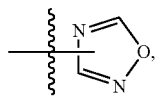

formula d-1
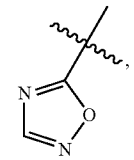

formula d-2

The term "unsaturated" refers to a moiety having one or more units of unsaturation.

The term "comprising" or "comprise" is meant to be open ended, including the indicated component but not excluding other elements.

As described herein, the term "pharmaceutically acceptable carrier" includes any solvents, dispersion media, coating agents, surfactants, antioxidants, preservatives (e.g., antibacterial agents, antifungal agents), isotonic agents, salt, drug stabilizers, binders, excipients, dispersants, lubricants, sweetening agents, flavoring agents, coloring agents, or a combination thereof, all of which are well known to the skilled in the art. (e.g., *Remington's Pharmaceutical Sciences,* 18th Ed. Mack Printing Company, 1990, pp. 1289-1329, all of which are incorporated herein by reference). Except any conventional carrier is incompatible with the active ingredient, the pharmaceutically acceptable carriers are effectively used in the treatment or pharmaceutical compositions.

As used herein, the term "inhibition of the replication of influenza viruses" includes both the reduction in the amount of virus replication (e.g., the reduction by at least 10%) and the complete arrest of virus replication (i.e., 100% reduction in the amount of virus replication). In some embodiments, the replication of influenza viruses are inhibited by at least 50%, at least 65%, at least 75%, at least 85%, at least 90%, or at least 95%.

As used herein, an "effective amount" refers to an amount sufficient to elicit the desired biological response. In the present invention, the desired biological response is to inhibit the replication of influenza virus, to reduce the amount of influenza viruses or to reduce or ameliorate the severity, duration, progression, or onset of a influenza virus infection, prevent the advancement of an influenza virus infection, prevent the recurrence, development, onset or progression of a symptom associated with an influenza virus infection, or enhance or improve the prophylactic or therapeutic effect(s) of another therapy used against influenza infections. The precise amount of compound administered to a subject will depend on the mode of administration, the type and severity of the infection and on the characteristics of the subject, such as general health, age, sex, body weight and tolerance to drugs. The skilled artisan will be able to determine appropriate dosages depending on these and other factors. When co-administered with other anti viral agents, e.g., when co-administered with an anti-influenza medication, an "effective amount" of the second agent will depend on the type of drug used. Suitable dosages are known for approved agents and can be adjusted by the skilled artisan according to the condition of the subject, the type of condition(s) being treated and the amount of a compound described herein being used. In cases where no amount is expressly noted, an effective amount should be assumed. For example, compounds described herein can be administered to a subject in a dosage range from between approximately 0.01 to 100 mg/kg body weight/day for therapeutic or prophylactic treatment.

As used herein, the terms "treat", "treatment" and "treating" refer to both therapeutic and prophylactic treatments. For example, therapeutic treatments includes the reduction or amelioration of the progression, severity and/or duration of influenza viruses mediated conditions, or the amelioration of one or more symptoms (specifically, one or more discernible symptoms) of influenza viruses mediated conditions, resulting from the administration of one or more therapies (e.g., one or more therapeutic agents such as a compound or composition of the invention). In specific embodiments, the therapeutic treatment includes the amelioration of at least one measurable physical parameter of an influenza virus mediated condition. In other embodiments the therapeutic treatment includes the inhibition of the progression of an influenza virus mediated condition, either physically by, e.g., stabilization of a discernible symptom, physiologically by, e.g., stabilization of a physical parameter, or both. In other embodiments the therapeutic treatment includes the reduction or stabilization of influenza viruses mediated infections. Antiviral drugs can be used in the community setting to treat people who already have influenza to reduce the severity of symptoms and reduce the number of days that they are sick.

The term "protecting group" or "PG" refers to a substituent that is commonly employed to block or protect a particular functionality while reacting with other functional groups on the compound. For example, an "amino-protecting group" is a substituent attached to an amino group that blocks or protects the amino functionality in the compound. Suitable amino-protecting groups include acetyl, trifluoroacetyl, t-butoxy-carbonyl (BOC, Boc), benzyloxycarbonyl (CBZ, Cbz) and 9-fluorenylmethylenoxy-carbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include —CH$_2$CH$_2$SO$_2$Ph, cyanoethyl, 2-(trimethylsilyl)ethyl, 2-(trimethylsilyl)ethoxy-methyl, 2-(p-toluenesulfonyl)ethyl, 2-(p-nitrophenylsulfonyl)-ethyl, 2-(diphenylphosphino)-ethyl, nitroethyl and the like. For a general description of protecting groups and their use, see T. W. Greene, *Protective Groups in Organic Synthesis*, John Wiley & Sons, New York, 1991; and P. J. Kocienski, *Protecting Groups*, Thieme, Stuttgart, 2005.

Description of Compounds of the Invention

The invention discloses novel compounds used as inhibitors of influenza virus replication and influenza virus RNA polymerase. These compounds and compositions thereof can be used as therapeutic agents for preventing, managing, treating or lessening virus infection in patients.

In one aspect, provided herein is a compound having Formula (I) or a stereoisomer, a tautomer, an N-oxide, a solvate, a metabolite, a pharmaceutically acceptable salt or a prodrug thereof,

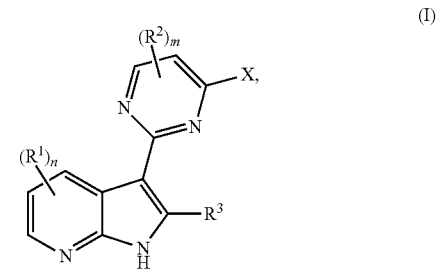

(I)

wherein R$^1$, R$^2$, R$^3$, X, m and n are as defined herein.

In certain embodiments, each R$^1$ and R$^3$ is independently H, F, Cl, Br, CN, NO$_2$, —C(=O)R$^a$, —C(=O)OR$^b$, —C(=O)NR$^c$R$^d$, OR$^b$, —NR$^c$R$^d$, R$^b$O—C$_{1-4}$ alkylene, R$^d$R'N—C$_{1-4}$ alkylene, C$_{1-6}$ alkyl, C$_{2-6}$ alkenyl, C$_{2-6}$ alkynyl, C$_{3-8}$ cycloalkyl, C$_{3-8}$ cycloalkyl-C$_{1-4}$ alkylene, 3- to 12-membered heterocyclyl, (3- to 12-membered heterocyclyl)-C$_{1-4}$ alkylene, C$_{6-10}$ aryl, C$_{6-10}$ aryl-C$_{1-4}$ alkylene, 5- to 10-membered heteroaryl or (5- to 10-membered heteroaryl)-C$_{1-4}$ alkylene, and wherein each of the C$_{1-6}$ alkyl, C$_{2-6}$ alkenyl, C$_{2-6}$ alkynyl, C$_{3-8}$ cycloalkyl, C$_{3-8}$ cycloalkyl-C$_{1-4}$ alkylene, 3- to 12-membered heterocyclyl, (3- to 12-membered heterocyclyl)-C$_{1-4}$ alkylene, C$_{6-10}$ aryl, C$_{6-10}$ aryl-C$_{1-4}$ alkylene, 5- to 10-membered heteroaryl and (5- to 10-membered heteroaryl)-C$_{1-4}$ alkylene is independently unsubstituted or substituted with one, two, three or four substituents independently selected from F, Cl, Br, CN, OR$^b$, —NR$^c$R$^d$, C$_{1-6}$ alkyl, C$_{1-6}$ haloalkyl, R$^b$O—C$_{1-4}$ alkylene or R$^d$R'N—C$_{1-4}$ alkylene;

n is 0, 1, 2 or 3;

each R$^2$ is independently F, C$_{2-6}$ alkynyl, OR$^b$, C$_{3-12}$ carbocyclyl, C$_{3-12}$ carbocyclyl-C$_{1-4}$ alkylene, 3- to 12-membered heterocyclyl, (3- to 12-membered heterocyclyl)-C$_{1-4}$ alkylene, C$_{6-10}$ aryl, C$_{6-10}$ aryl-C$_{1-4}$ alkylene, 5- to 14-membered heteroaryl, (5- to 14-membered heteroaryl)-C$_{1-4}$ alkylene; or two adjacent R$^2$, together with the atoms to which they are attached, form a C$_{3-12}$ carbocyclic ring, 3- to 12-membered heterocyclic ring, C$_{6-10}$ aromatic ring or 5- to 10-membered heteroaromatic ring, and wherein each of the $C_{2-6}$ alkynyl, $C_{3-12}$ carbocyclyl, $C_{3-12}$ carbocyclyl-$C_{1-4}$ alkylene, 3- to 12-membered heterocyclyl, (3- to 12-membered heterocyclyl)-$C_{1-4}$ alkylene, $C_{6-10}$ aryl, $C_{6-10}$ aryl-$C_{1-4}$ alkylene, 5- to 14-membered heteroaryl, (5- to 14-membered heteroaryl)-$C_{1-4}$ alkylene, $C_{3-12}$ carbocyclic ring, 3- to 12-membered heterocyclic ring, $C_{6-10}$ aromatic ring and 5- to 10-membered heteroaromatic ring is independently unsubstituted or substituted with one, two, three, four or five R', with the proviso that when m is 1, $R^2$ is not F;

each R' is independently F, Cl, Br, CN, $NO_2$, oxo (=O), $OR^b$, $-NR^cR^d$, $R^bO-C_{1-4}$ alkylene, $R^dR^cN-C_{1-4}$ alkylene, $-C(=O)R^a$, $-C(=O)OR^b$, $-C(=O)NR^cR^d$, $C_{1-10}$ alkyl, $C_{1-6}$ haloalkyl, $C_{3-6}$ cycloalkyl, $C_{3-6}$ cycloalkyl-$C_{1-4}$ alkylene, 3- to 6-membered heterocyclyl, (3- to 6-membered heterocyclyl)-$C_{1-4}$ alkylene, $C_{6-10}$ aryl, $C_{6-10}$ aryl-$C_{1-4}$ alkylene, 5- to 6-membered heteroaryl or (5- to 6-membered heteroaryl)-$C_{1-4}$ alkylene, and wherein each of the $C_{1-10}$ alkyl, $C_{1-6}$ haloalkyl, $C_{3-6}$ cycloalkyl, $C_{3-6}$ cycloalkyl-$C_{1-4}$ alkylene, 3- to 6-membered heterocyclyl, (3- to 6-membered heterocyclyl)-$C_{1-4}$ alkylene, $C_{6-10}$ aryl, $C_{6-10}$ aryl-$C_{1-4}$ alkylene, 5- to 6-membered heteroaryl and (5- to 6-membered heteroaryl)-$C_{1-4}$ alkylene is independently unsubstituted or substituted with one, two, three, or four substituents independently selected from F, Cl, Br, CN, $NO_2$, $OR^b$, $-NR^cR^d$, $C_{1-6}$ alkyl, $C_{1-6}$ haloalkyl, $R^bO-C_{1-4}$ alkylene or $R^dR^cN-C_{1-4}$ alkylene;

m is 1 or 2;

X has one of the following sub-formulae:

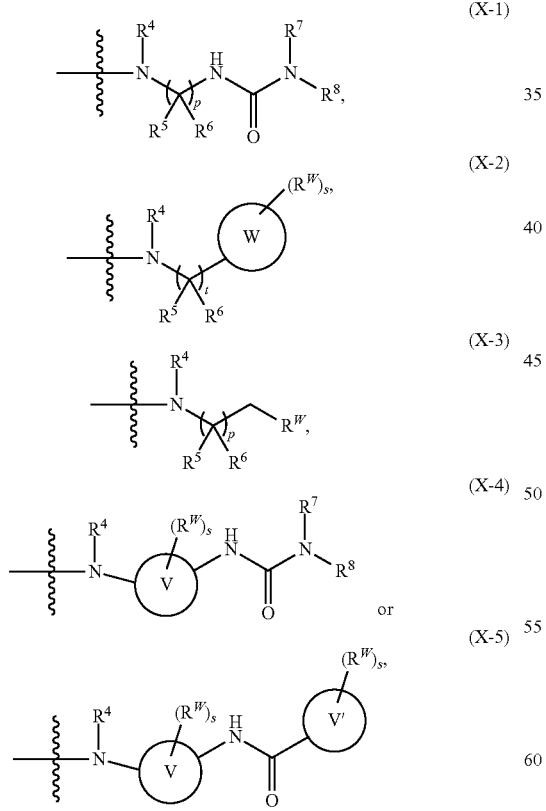

wherein $R^4$ is H or $C_{1-6}$ alkyl, and wherein the $C_{1-6}$ alkyl is optionally substituted with one, two, three, or four U;

each $R^5$, $R^6$, $R^7$ and $R^8$ is independently H or $C_{1-6}$ alkyl; or $R^5$ and $R^6$, together with the carbon atom to which they are attached, form a $C_{3-8}$ cycloalkyl group, 3- to 6-membered heterocyclic ring, $C_{6-10}$ aromatic ring or 5- to 10-membered heteroaromatic ring; or $R^7$ and $R^8$, together with the nitrogen atom to which they are attached, form a 3- to 6-membered heterocyclic ring or 5- to 10-membered heteroaromatic ring, and wherein each $C_{1-6}$ alkyl, $C_{3-8}$ cycloalkyl, 3- to 6-membered heterocyclic ring, $C_{6-10}$ aromatic ring or 5- to 10-membered heteroaromatic ring is independently unsubstituted or substituted with one, two, three, or four U;

W is a $C_{3-12}$ carbocyclic ring or 3- to 12-membered heterocyclic ring;

each V and V' is independently a $C_{3-12}$ cycloalkane ring, 3- to 12-membered heterocyclic ring, $C_{6-10}$ aromatic ring or 5- to 10-membered heteroaromatic ring;

each $R^w$ is independently F, Cl, Br, CN, $NO_2$, oxo (=O), $-C(=O)R^a$, $-C(=O)OR^b$, $-C(=O)NR^cR^d$, $-S(=O)_2R^e$, $-S(=O)_2NR^cC(=O)R^a$, $-S(=O)_2NR^cR^d$, $(R^bO)_2P(=O)-C_{0-2}$ alkylene, $OR^b$, $-NR^cR^d$, $R^bO-C_{1-2}$ alkylene, $R^dR^cN-C_{1-2}$ alkylene, $C_{1-6}$ alkyl, 5- to 6-membered heteroaryl or 5- to 6-membered heterocyclyl, and wherein each of the $C_{1-6}$ alkyl, 5- to 6-membered heteroaryl or 5- to 6-membered heterocyclyl is independently unsubstituted or substituted with one, two, three, or four U;

each U is independently F, Cl, Br, $NO_2$, CN, oxo (=O), N3, $OR^b$, $-NR^cR^d$, $C_{1-6}$ alkyl or $C_{1-6}$ haloalkyl;

each s and t is independently 0, 1, 2 or 3;

p is 1, 2 or 3; and each $R^a$, $R^b$, $R^c$, $R^d$ and $R^e$ is independently H, $C_{1-6}$ alkyl, $C_{1-6}$ haloalkyl, $C_{2-6}$ alkenyl, $C_{2-6}$ alkynyl, $C_{3-6}$ cycloalkyl, $C_{3-6}$ cycloalkyl-$C_{1-4}$ alkylene, 3- to 6-membered heterocyclyl, (3- to 6-membered heterocyclyl)-$C_{1-4}$ alkylene, $C_{6-10}$ aryl, $C_{6-10}$ aryl-$C_{1-4}$ alkylene, 5- to 10-membered heteroaryl, (5- to 10-membered heteroaryl)-$C_{1-4}$ alkylene; or $R^c$ and $R^d$, together with the nitrogen atom to which they are attached, form a 3- to 6-membered heterocyclic ring, and wherein each of the $C_{1-6}$ alkyl, $C_{2-6}$ alkenyl, $C_{2-6}$ alkynyl, $C_{3-6}$ cycloalkyl, $C_{3-6}$ cycloalkyl-$C_{1-4}$ alkylene, 3- to 6-membered heterocyclyl, (3- to 6-membered heterocyclyl)-$C_{1-4}$ alkylene, $C_{6-10}$ aryl, $C_{6-10}$ aryl-$C_{1-4}$ alkylene, 5- to 10-membered heteroaryl, (5- to 10-membered heteroaryl)-$C_{1-4}$ alkylene and 3- to 6-membered heterocyclic ring is independently unsubstituted or substituted with one, two, three, or four substituents independently selected from F, Cl, CN, OH, $NH_2$, $C_{1-6}$ alkyl, $C_{1-6}$ haloalkyl, $C_{1-6}$ alkoxy or $C_{1-6}$ alkylamino.

In other embodiments, the invention relates to a compound having Formula (II), or a stereoisomer, a tautomer, an N-oxide, a solvate, a metabolite, a pharmaceutically acceptable salt or a prodrug thereof,

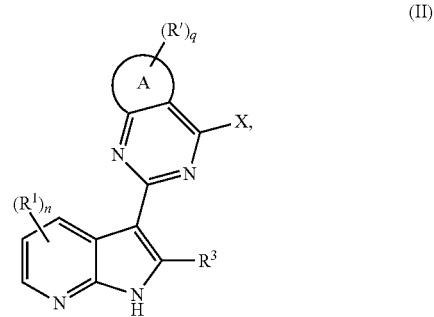

wherein A, $R^1$, $R^3$, X, R', n and q are as defined herein.

In other embodiments, A is a $C_{3-12}$ carbocyclic ring, 3- to 12-membered heterocyclic ring, $C_{6-10}$ aromatic ring or 5- to 10-membered heteroaromatic ring; and q is 0, 1, 2, 3, 4 or 5.

In other embodiments, each $R^1$ and $R^3$ is independently H, F, Cl, —C(=O)$R^a$, —C(=O)O$R^b$, —C(=O)N$R^c R^d$, O$R^b$, —N$R^c R^d$, $C_{1-3}$ alkyl, $C_{3-6}$ cycloalkyl, 5- to 6-membered heterocyclyl, phenyl or 5- to 6-membered heteroaryl, and wherein each of the $C_{1-3}$ alkyl, $C_{3-6}$ cycloalkyl, 5- to 6-membered heterocyclyl, phenyl or 5- to 6-membered heteroaryl is independently unsubstituted or substituted with one, two, three or four substituents independently selected from F, Cl, O$R^b$, —N$R^c R^d$, $C_{1-3}$ alkyl, $C_{1-3}$ haloalkyl or $R^b$O—$C_{1-2}$ alkylene.

In other embodiments, each $R^2$ is independently F, $C_{2-6}$ alkynyl, O$R^b$, $C_{3-6}$ carbocyclyl, $C_{3-6}$ carbocyclyl-$C_{1-2}$ alkylene, 5- to 6-membered heterocyclyl, (5- to 6-membered heterocyclyl)-$C_{1-2}$ alkylene, phenyl, naphthyl, phenyl-$C_{1-2}$ alkylene, 5- to 6-membered heteroaryl, (5- to 6-membered heteroaryl)-$C_{1-2}$ alkylene; or two adjacent $R^2$, together with the atoms to which they are attached, form a $C_{5-6}$ carbocyclic ring, 5- to 6-membered heterocyclic ring, benzene ring or 5- to 6-membered heteroaromatic ring, and wherein each of the $C_{2-6}$ alkynyl, $C_{3-6}$ carbocyclyl, $C_{3-6}$ carbocyclyl-$C_{1-2}$ alkylene, 5- to 6-membered heterocyclyl, (5- to 6-membered heterocyclyl)-$C_{1-2}$ alkylene, phenyl, naphthyl, phenyl-$C_{1-2}$ alkylene, 5- to 6-membered heteroaryl, (5- to 6-membered heteroaryl)-$C_{1-2}$ alkylene, $C_{5-6}$ carbocyclic ring, 5- to 6-membered heterocyclic ring, benzene ring and 5- to 6-membered heteroaromatic ring is independently unsubstituted or substituted with one, two, three, four or five R', with the proviso that when m is 1, $R^2$ is not F.

In other embodiments, each R' is independently F, Cl, Br, CN, NO$_2$, O$R^b$, —N$R^c R^d$, —C(=O)$R^a$, —C(=O)N$R^c R^d$, $C_{1-9}$ alkyl, $C_{1-3}$ haloalkyl, $C_{3-6}$ cycloalkyl, 5- to 6-membered heterocyclyl, phenyl, phenyl-$C_{1-2}$ alkylene or 5- to 6-membered heteroaryl, and wherein each of the $C_{1-9}$ alkyl, $C_{1-3}$ haloalkyl, $C_{3-6}$ cycloalkyl, 5- to 6-membered heterocyclyl, phenyl, phenyl-$C_{1-4}$ alkylene and 5- to 6-membered heteroaryl is independently unsubstituted or substituted with one, two, three, or four substituents independently selected from F, Cl, Br, CN, NO$_2$, O$R^b$, —N$R^c R^d$, methyl, ethyl, n-propyl or i-propyl.

In other embodiments, each $R^a$, $R^b$, $R^c$, $R^d$ and $R^e$ is independently H, methyl, ethyl, i-propyl, n-propyl, n-butyl, t-butyl, $C_{1-3}$ haloalkyl, $C_{3-6}$ cycloalkyl, $C_{3-6}$ cycloalkyl-$C_{1-2}$ alkylene, 3- to 6-membered heterocyclyl, phenyl, phenyl-$C_{1-2}$ alkylene; or $R^c$ and $R^d$, together with the nitrogen atom to which they are attached, form a 5- to 6-membered heterocyclic ring, and wherein each of methyl, ethyl, i-propyl, n-propyl, n-butyl, t-butyl, $C_{3-6}$ cycloalkyl, $C_{3-6}$ cycloalkyl-$C_{1-2}$ alkylene, 3- to 6-membered heterocyclyl, phenyl, phenyl-$C_{1-2}$ alkylene and 5- to 6-membered heterocyclic ring is independently unsubstituted or substituted with one, two, three, or four substituents independently selected from F, Cl, CN, OH, NH$_2$, $C_{1-3}$ alkyl, $C_{1-3}$ haloalkyl or methoxy.

In other embodiments, X has one of the following sub-formulae:

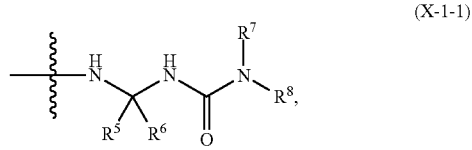

(X-1-1)

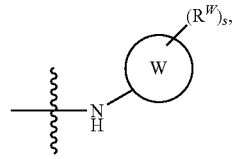

(X-2-1)

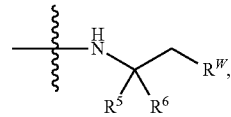

(X-3-1)

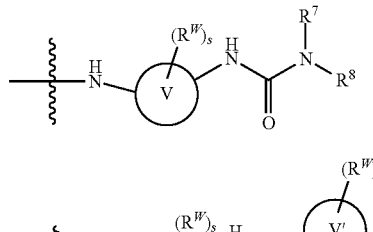

(X-4-1)

or

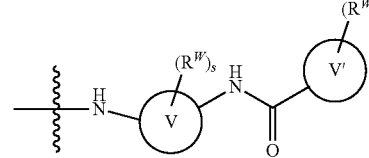

(X-5-1)

wherein W, V, V', $R^5$, $R^6$, $R^7$, $R^8$, $R^w$ and s are as defined herein.

In other embodiments, W is a $C_{6-8}$ carbocyclic ring or 6- to 8-membered heterocyclic ring.

In other embodiments, V is a $C_{3-8}$ cycloalkane ring, 3- to 8-membered heterocyclic ring, benzene ring or 5- to 6-membered heteroaromatic ring.

In other embodiments, V' is a $C_{3-8}$ cycloalkane ring, 3- to 8-membered heterocyclic ring, benzene ring or 5- to 6-membered heteroaromatic ring.

In other embodiments, each $R^w$ is independently F, Cl, Br, CN, NO$_2$, oxo (=O), —C(=O)$R^a$, —C(=O)O$R^b$, —C(=O)N$R^c R^d$, —S(=O)$_2 R^e$, —S(=O)$_2$N$R^c$C(=O)$R^a$, —S(=O)$_2$N$R^c R^d$, ($R^b$O)$_2$P(=O)—$C_{0-2}$ alkylene, O$R^b$, —N$R^c R^d$, $R^b$O—$C_{1-2}$ alkylene, $R^d R^c$N—$C_{1-2}$ alkylene, methyl, ethyl, i-propyl, n-propyl, n-butyl, t-butyl, tetrazolyl, isoxazolyl, oxazolyl, 1,2,4-oxadiazolyl, 1,3,4-oxadiazolyl or pyrazolyl, and wherein each of methyl, ethyl, i-propyl, n-propyl, n-butyl, t-butyl, tetrazolyl, isoxazolyl, oxazolyl, 1,2,4-oxadiazolyl, 1,3,4-oxadiazolyl and pyrazolyl is independently unsubstituted or substituted with one, two, three, or four U.

In other embodiments, each U is independently F, Cl, Br, CF$_3$, NO$_2$, CN, oxo (=O), N$_3$, O$R^b$, —N$R^c R^d$, methyl, ethyl, i-propyl, n-propyl, n-butyl or t-butyl.

In other embodiments, A is a $C_{5-6}$ carbocyclic ring, 5- to 6-membered heterocyclic ring, benzene ring, naphthalene ring or 5- to 6-membered heteroaromatic ring.

In other embodiments, each $R^2$ is independently F, ethynyl, propynyl, O$R^b$, $C_{3-6}$ carbocyclyl, 5- to 6-membered heterocyclyl, phenyl, naphthyl, phenyl-$C_{1-2}$ alkylene, furyl, benzofuryl, pyrrolyl, pyridyl, pyrazolyl, imidazolyl, benzimidazolyl, triazolyl, tetrazolyl, oxazolyl, oxadiazolyl, 1,3,5-triazinyl, thiazolyl, thienyl, benzothienyl, pyrazinyl, pyridazinyl, pyrimidyl, indolyl, purinyl, quinolyl, isoquinolyl, phenoxthinyl,

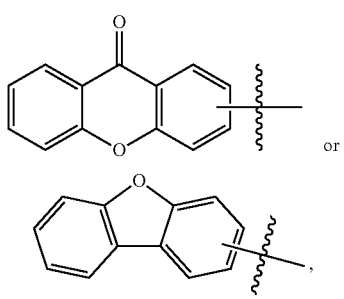

or

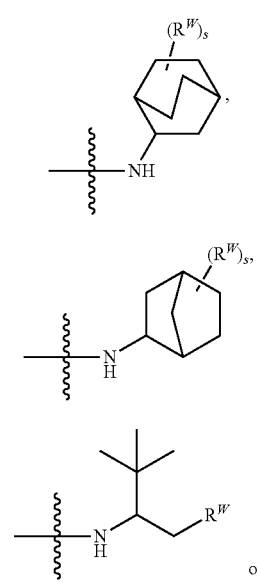

and wherein each ethynyl, propynyl, C$_{3-6}$ carbocyclyl, 5- to 6-membered heterocyclyl, phenyl, naphthyl, phenyl-C$_{1-2}$ alkylene, furyl, benzofuryl, pyrrolyl, pyridyl, pyrazolyl, imidazolyl, benzimidazolyl, triazolyl, tetrazolyl, oxazolyl, oxadiazolyl, 1,3,5-triazinyl, thiazolyl, thienyl, benzothienyl, pyrazinyl, pyridazinyl, pyrimidyl, indolyl, purinyl, quinolyl, isoquinolyl, phenoxthinyl,

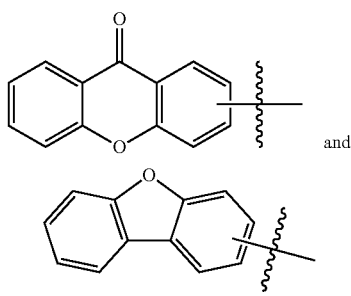

and is independently unsubstituted or substituted with one, two, three, four or five R', with the proviso that when m is 1, R$^2$ is not F.

In other embodiments, X has one of the following sub-formulae:

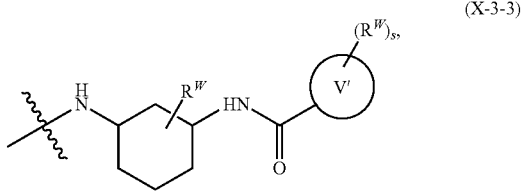

(X-3-3)

wherein R$^w$, s and V' are as defined herein

In other embodiments, A is a C$_{5-6}$ carbocyclic ring, 5- to 6-membered heterocyclic ring, benzene, naphthalene, furan, benzofuran, pyrrole, pyridine, pyrazole, imidazole, benzoimidazole, triazole, tetrazole, oxazole, oxadiazole, 1,3,5-triazine, thiazole, thiophene, benzothiphene, pyrazine, pyridazine, pyrimidine, indole, purine, quinoline or isoquinoline.

In other embodiments, the invention relates to a compound having Formula (III) or a stereoisomer, a tautomer, an N-oxide, a solvate, a metabolite, a pharmaceutically acceptable salt or a prodrug thereof,

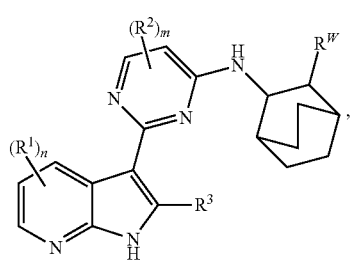

(III)

wherein R$^1$, R$^2$, R$^3$, m, n and R$^w$ are as defined herein.

In other embodiments, the invention relates to a compound having Formula (IV) or a stereoisomer, a tautomer, an N-oxide, a solvate, a metabolite, a pharmaceutically acceptable salt or a prodrug thereof,

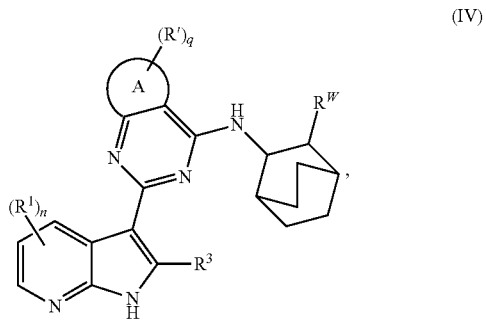

(IV)

wherein A, R$^1$, R$^3$, R', n, q and R$^w$ are as defined herein.

In other embodiments, the invention relates to a compound having Formula (V) or a stereoisomer, a tautomer, an N-oxide, a solvate, a metabolite, a pharmaceutically acceptable salt or a prodrug thereof,

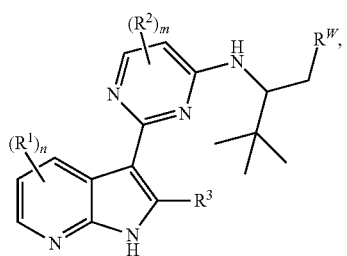

(V)

wherein $R^1$, $R^2$, $R^3$, m, n and $R^w$ are as defined herein.

In other embodiments, the invention relates to a compound having Formula (VI) or a stereoisomer, a tautomer, an N-oxide, a solvate, a metabolite, a pharmaceutically acceptable salt or a prodrug thereof,

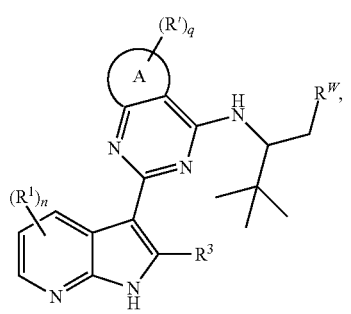

(VI)

wherein A, $R^1$, $R^3$, R', n, q and $R^w$ are as defined herein.

In other embodiments, the invention relates to a compound having Formula (VII) or a stereoisomer, a tautomer, an N-oxide, a solvate, a metabolite, a pharmaceutically acceptable salt or a prodrug thereof,

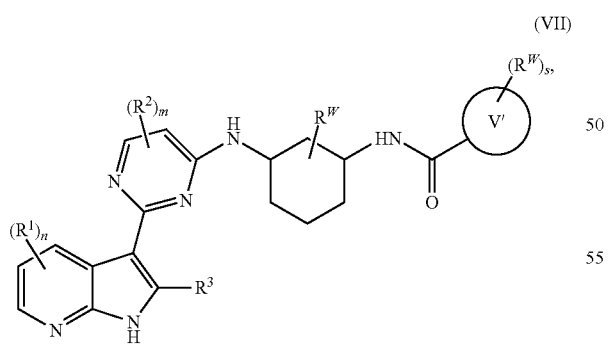

(VII)

wherein $R^1$, $R^2$, $R^3$, m, n, s, V' and $R^w$ are as defined herein.

In other embodiments, the invention relates to a compound having Formula (VIII) or a stereoisomer, a tautomer, an N-oxide, a solvate, a metabolite, a pharmaceutically acceptable salt or a prodrug thereof,

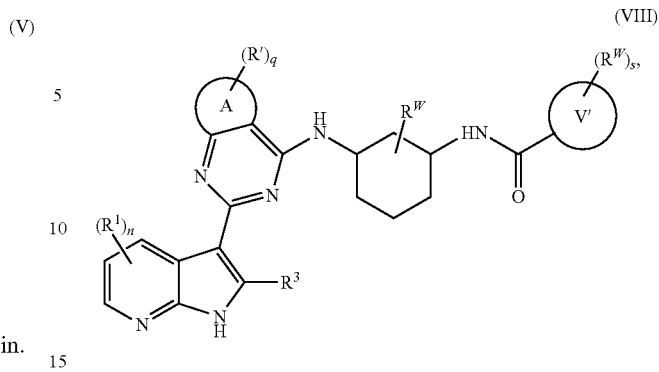

(VIII)

wherein A, $R^1$, $R^3$, R', n, q, s, V' and $R^w$ are as defined herein.

In other embodiments, the invention relates to a compound having one of the following structures, or a stereoisomer, a tautomer, an N-oxide, a solvate, a metabolite, a pharmaceutically acceptable salt or a prodrug thereof, but the compound is not limited to these structures:

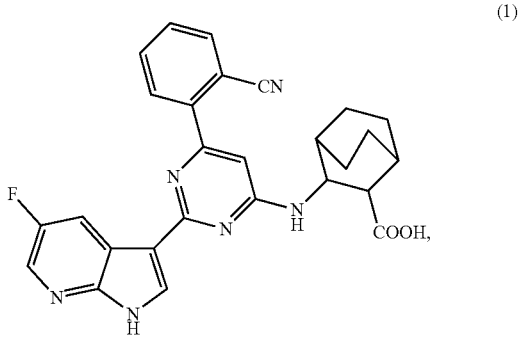

(1)

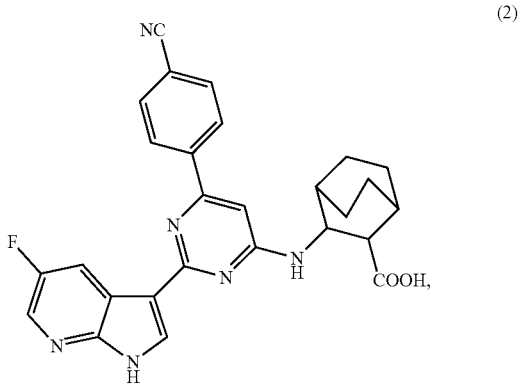

(2)

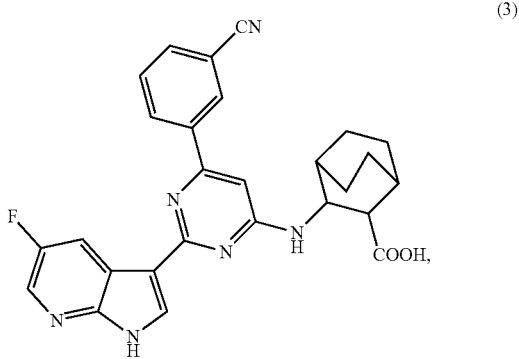

(3)

(4)
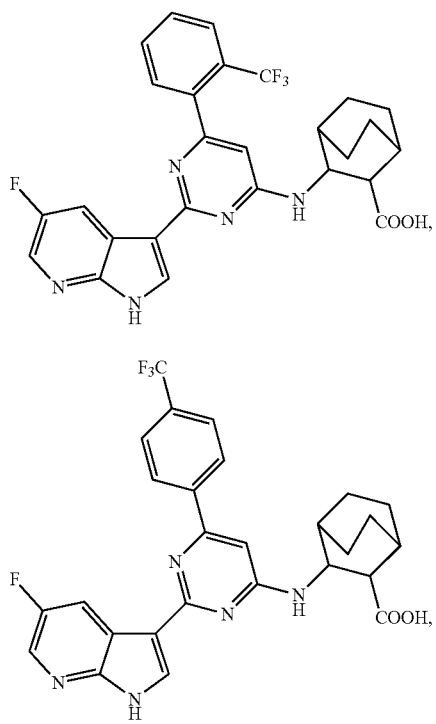
(5)
(6)
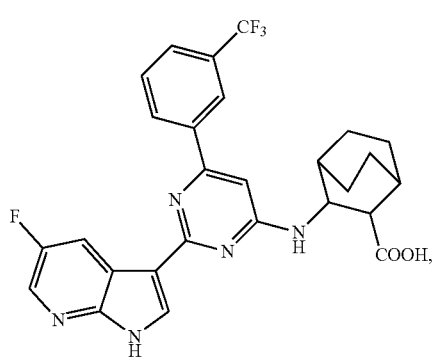
(7)
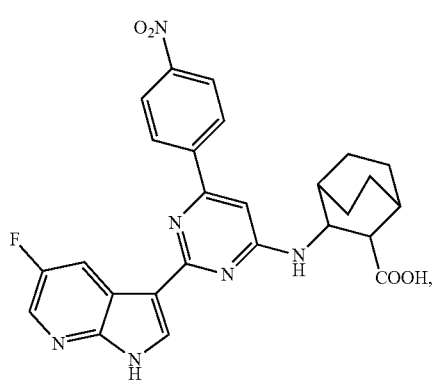
(8)
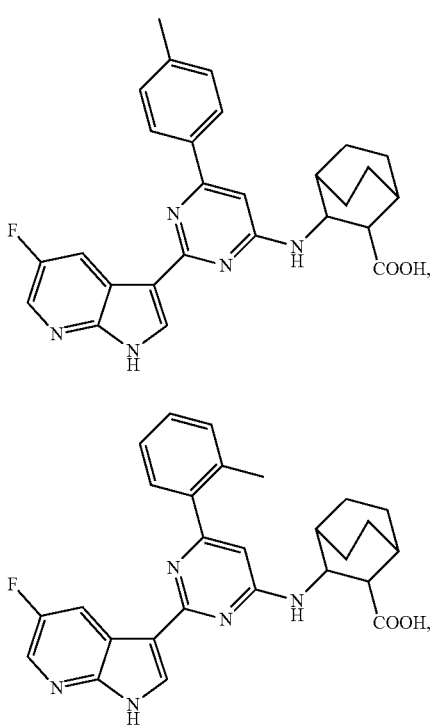
(9)
(10)
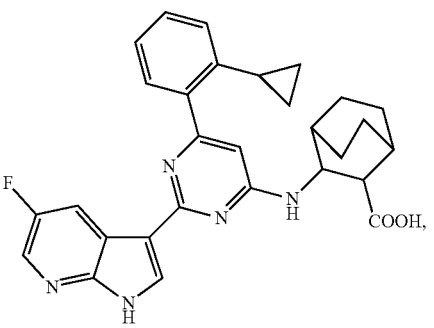
(11)
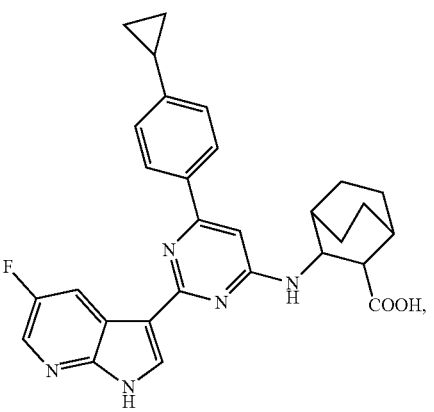

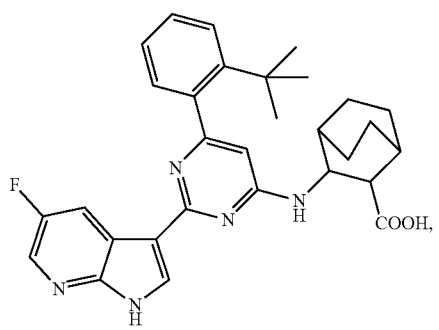
(12)
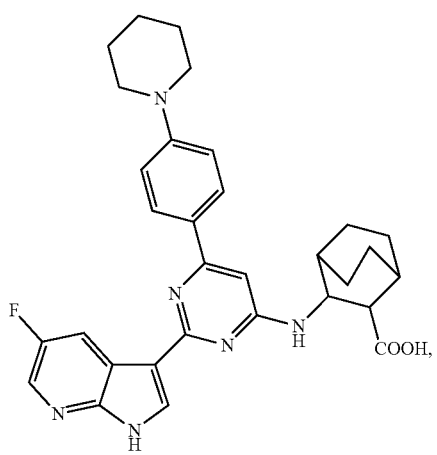
(13)
(14)
(15)
(16)
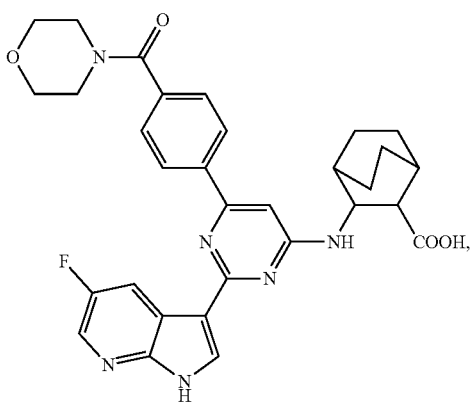
(17)
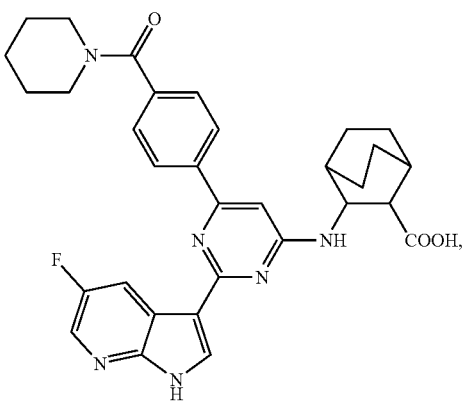
(18)

-continued
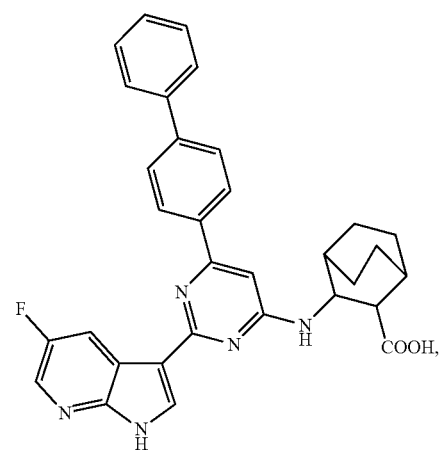
(19)
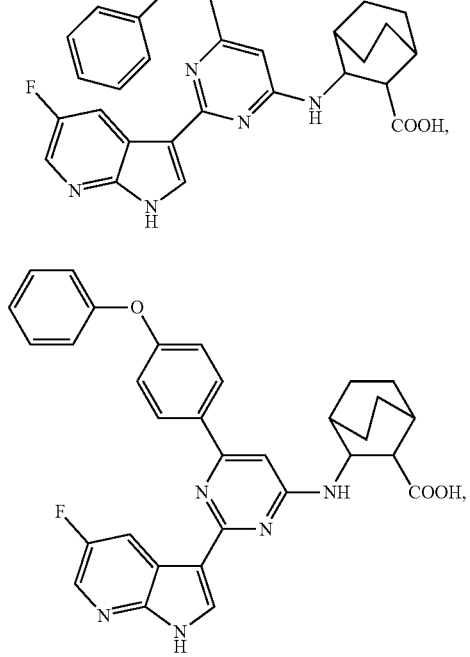
(20)
(21)
(22)
-continued
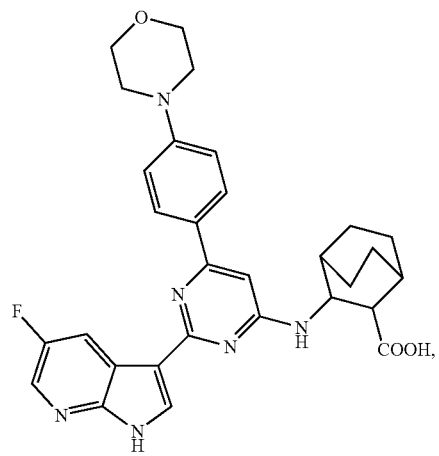
(23)
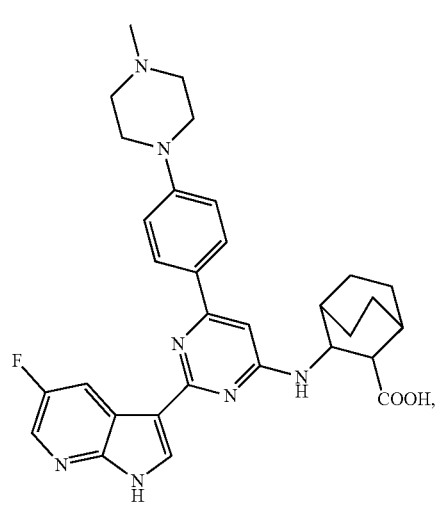
(24)
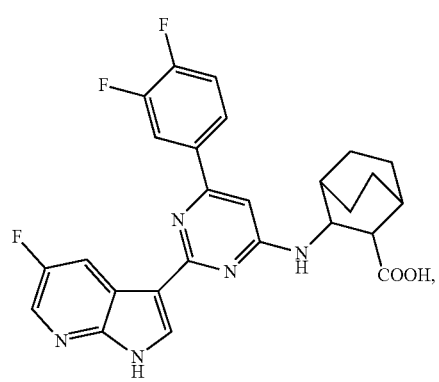
(25)

(26)
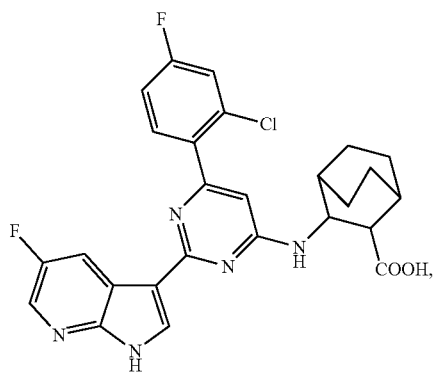
(27)
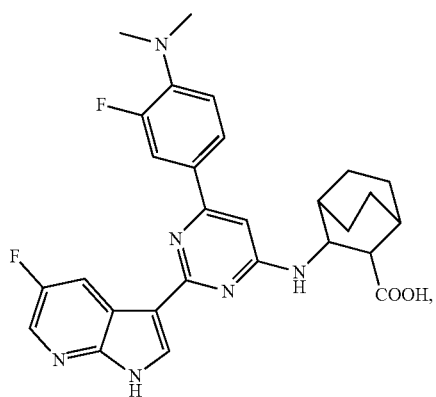
(28)
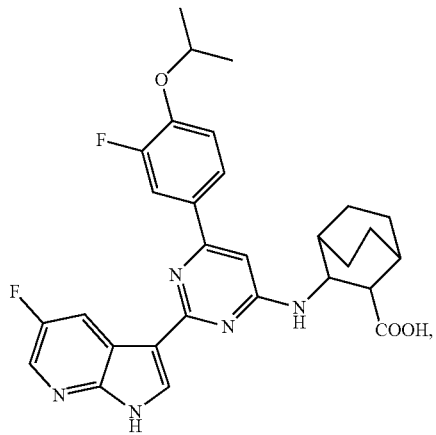
(29)
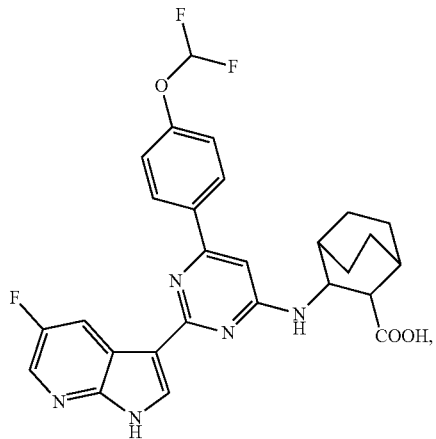
(30)
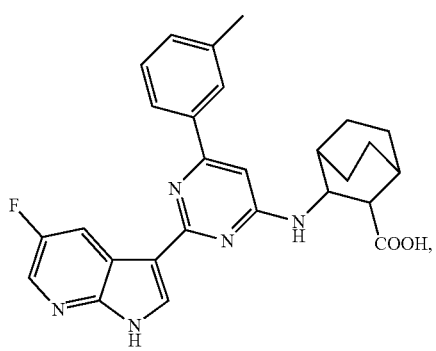
(31)
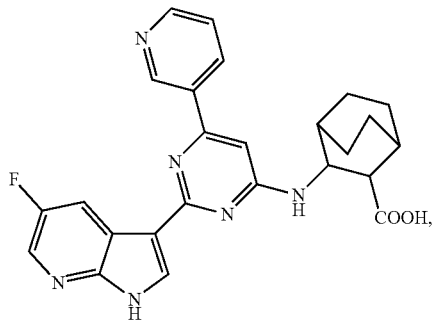
(32)
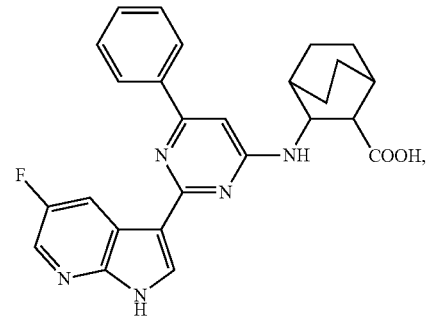
(33)
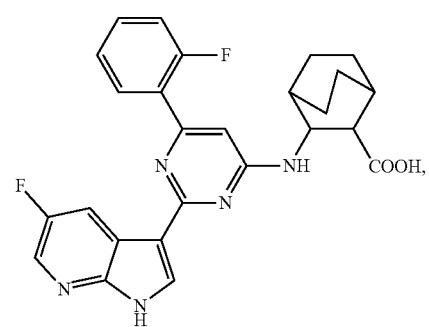

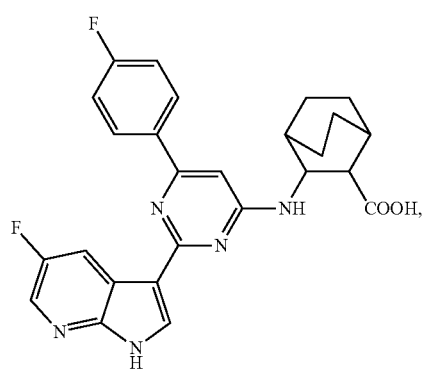 (34)
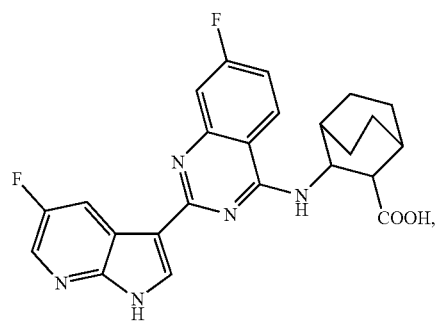 (39)
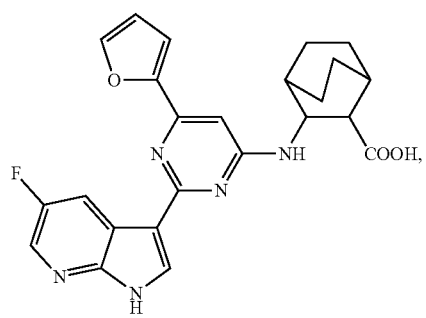 (35)
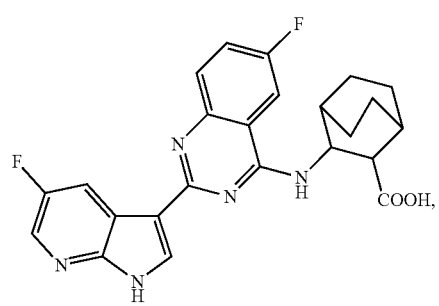 (40)
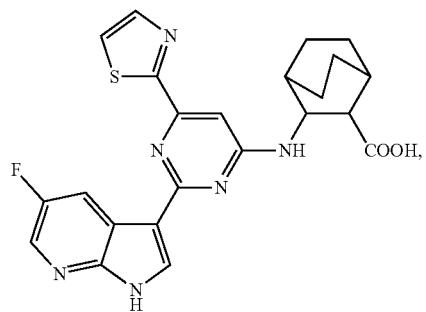 (36)
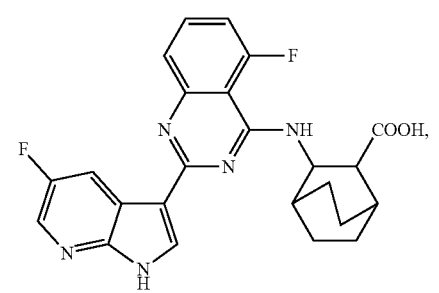 (41)
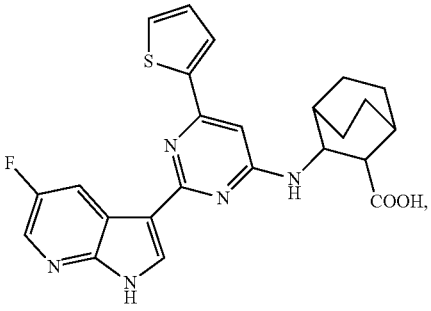 (37)
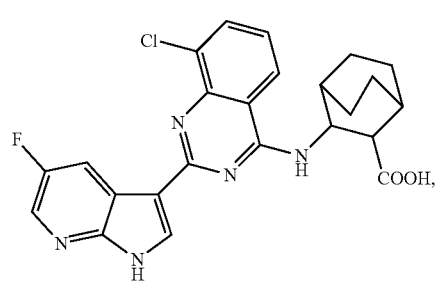 (42)
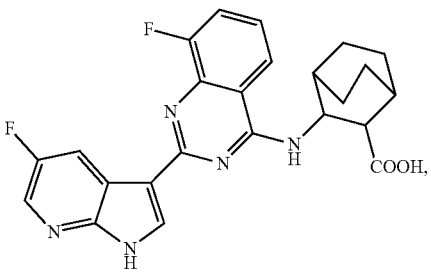 (38)
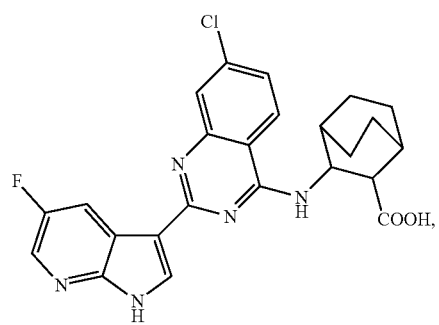 (43)

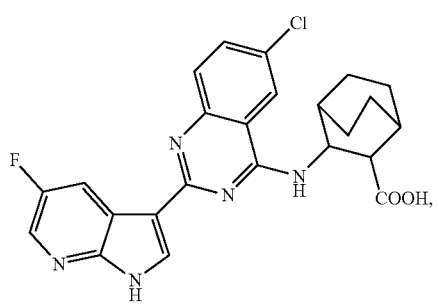
(44)
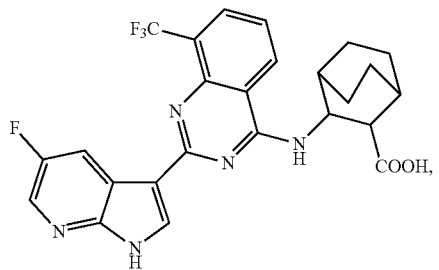
(45)
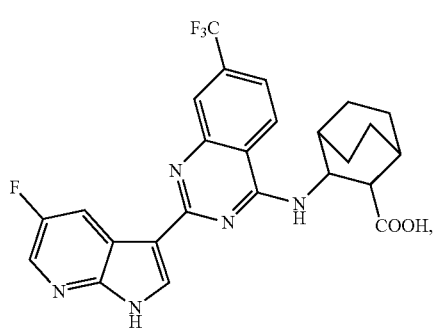
(46)
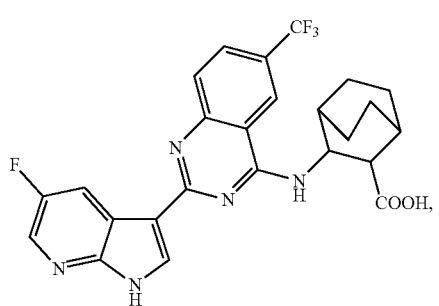
(47)
(48)
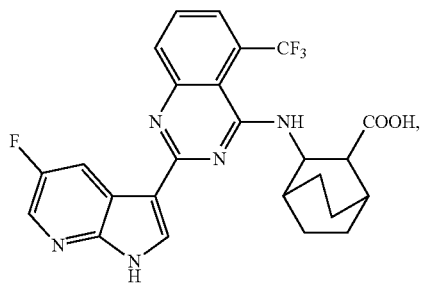
(49)
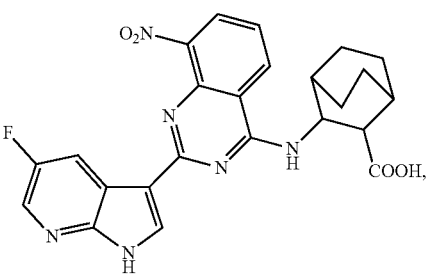
(50)
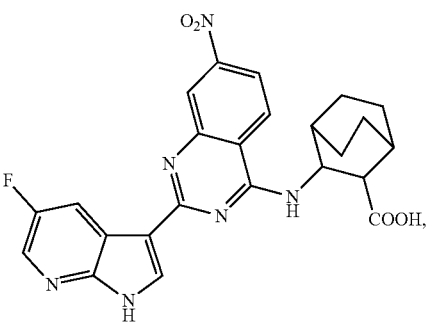
(51)
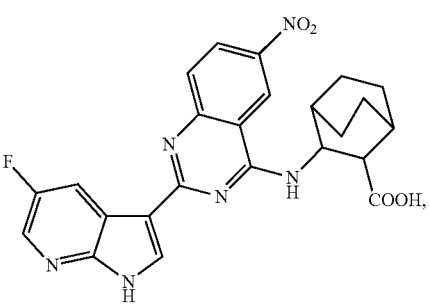
(52)
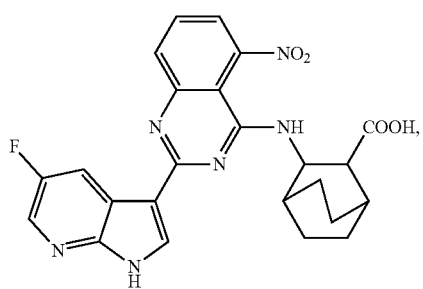
(53)

47
-continued
(54)
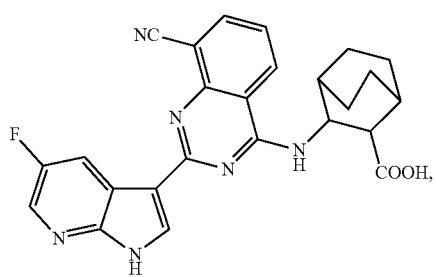
(55)
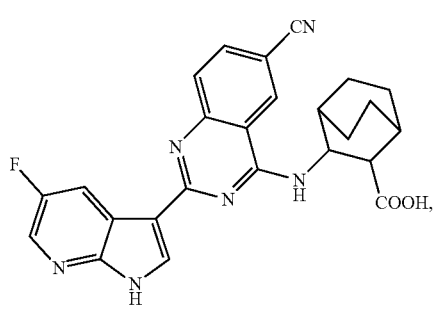
(56)
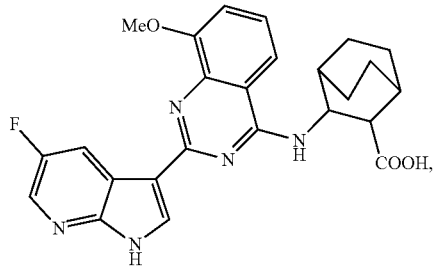
(57)
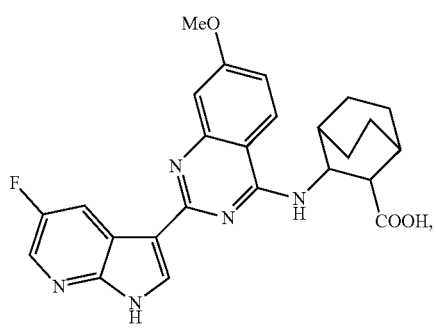
(58)
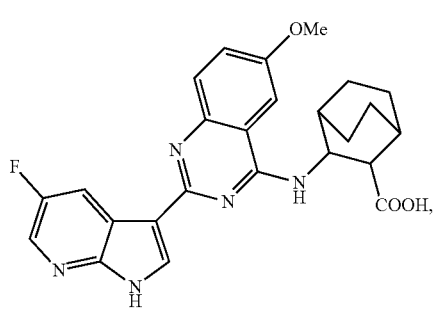
48
-continued
(59)
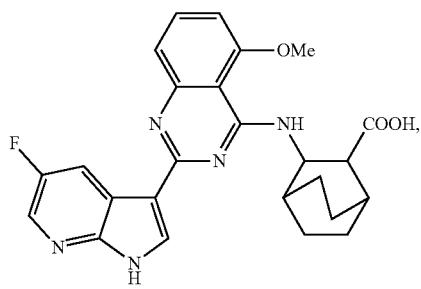
(60)
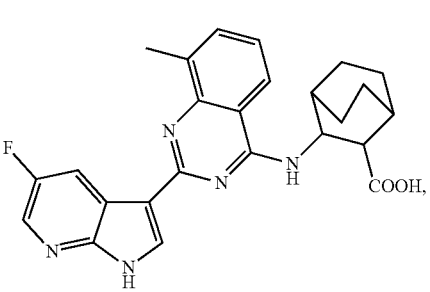
(61)
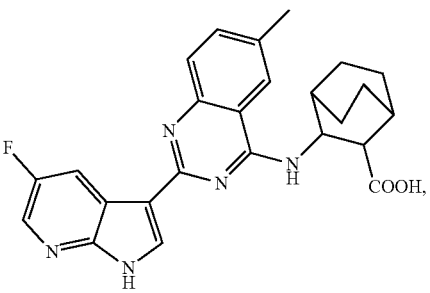
(62)
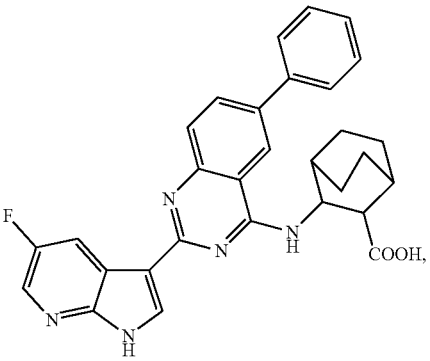
(63)
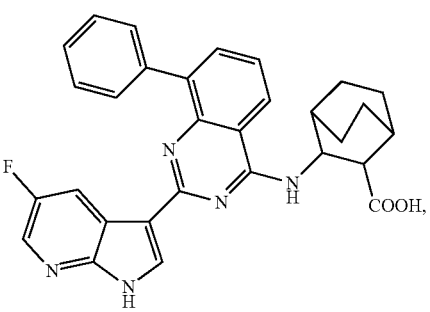

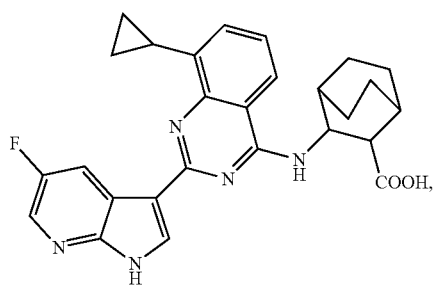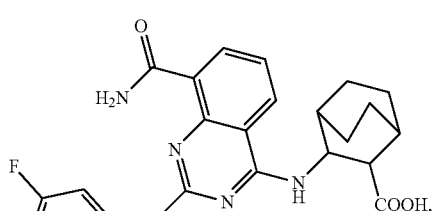

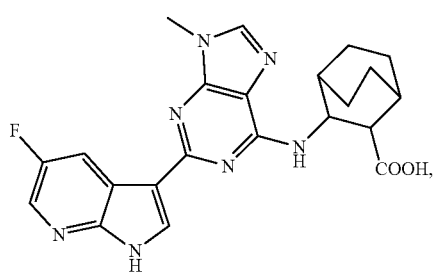
(74)
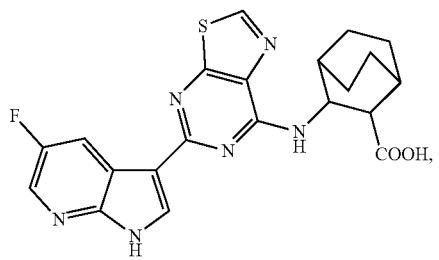
(75)
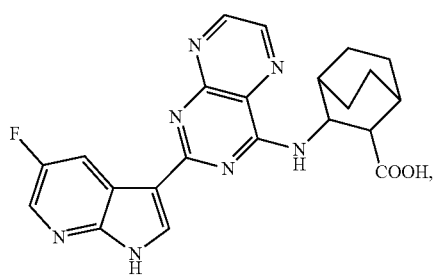
(76)
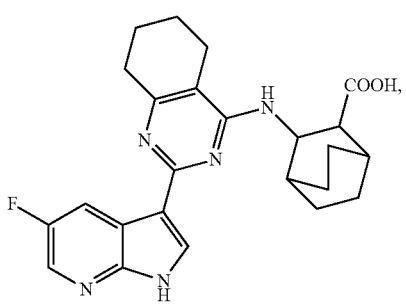
(77)
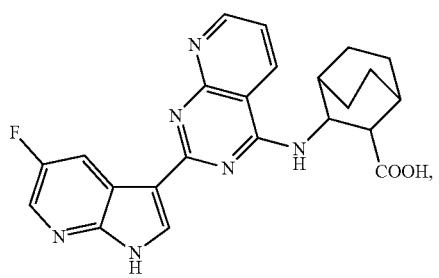
(78)
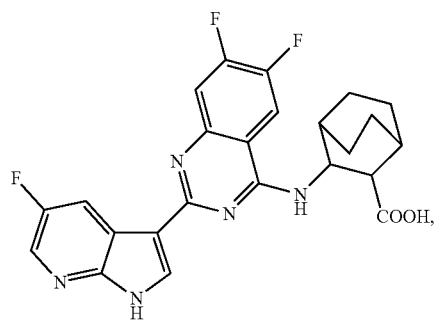
(79)
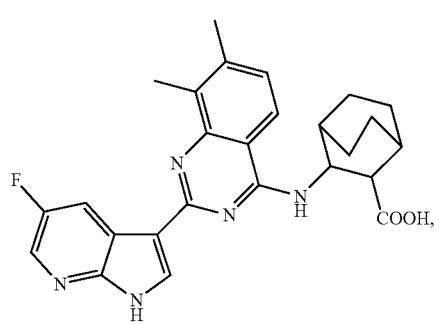
(80)
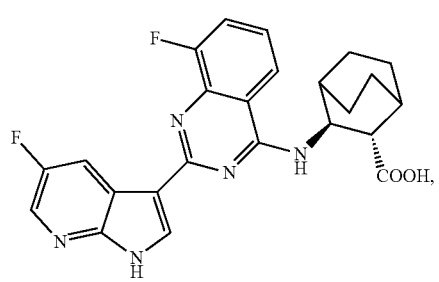
(81)
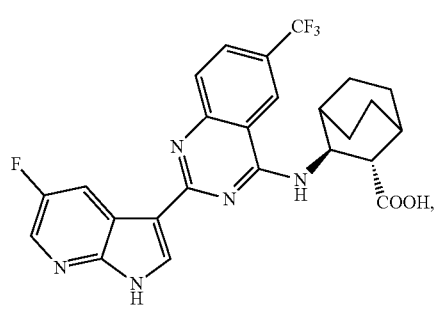
(82)
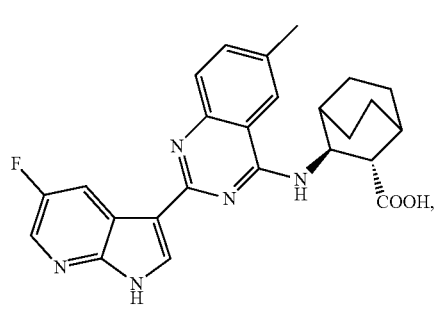
(83)

53
-continued
(84)
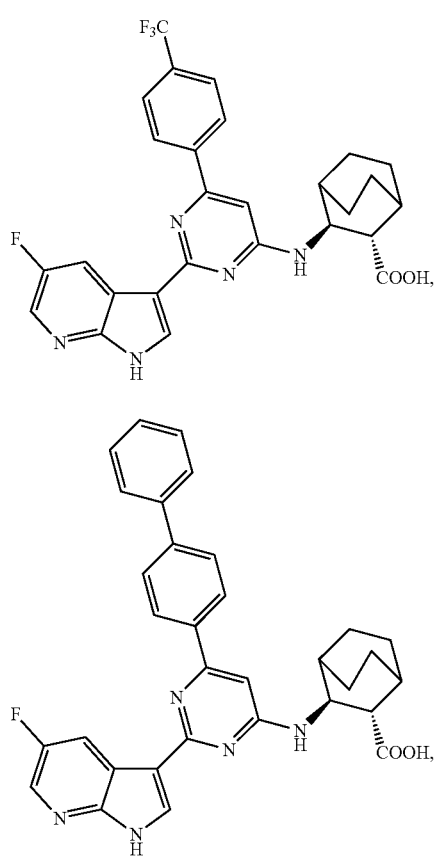
(85)
(86)
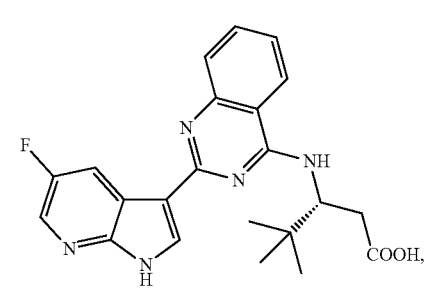
(87)
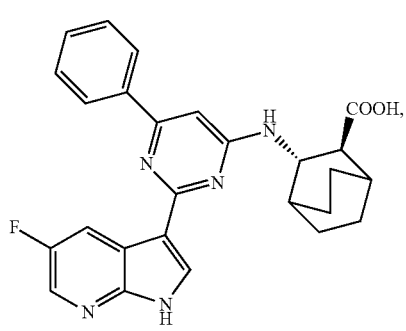
54
-continued
(88)
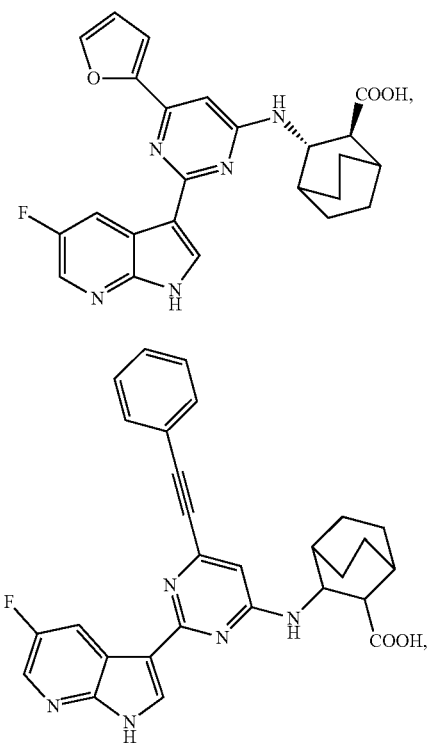
(89)
(90)
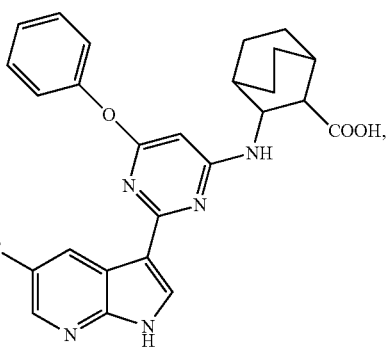
(91)
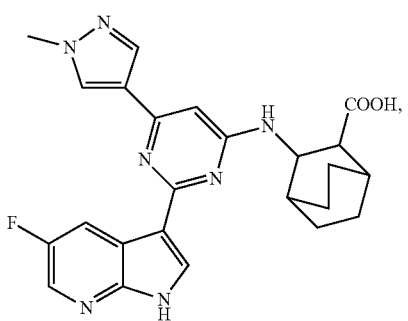

(92) 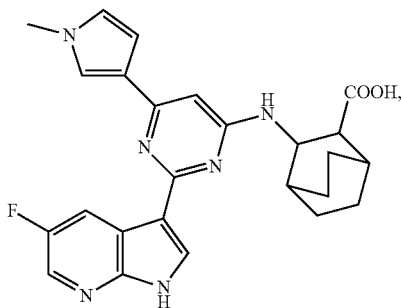
(93) 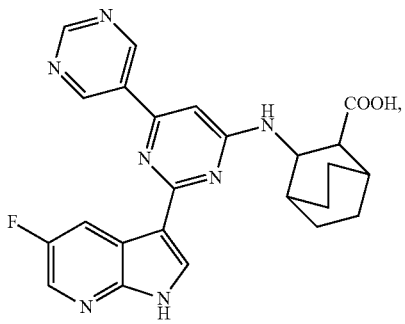
(94) 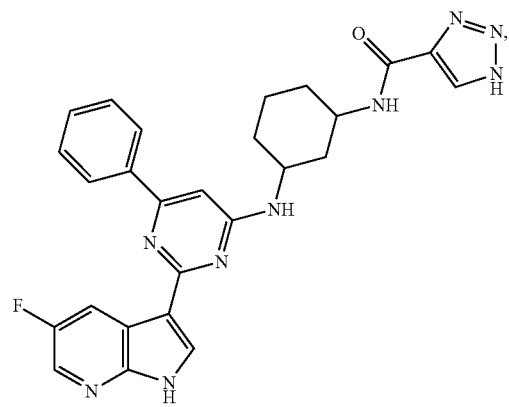
(95) 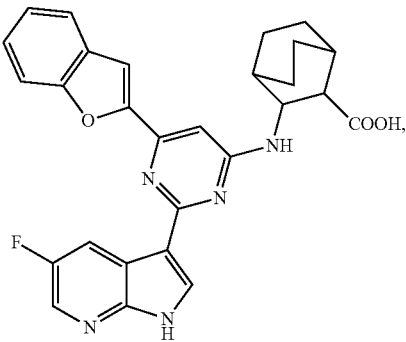
(96) 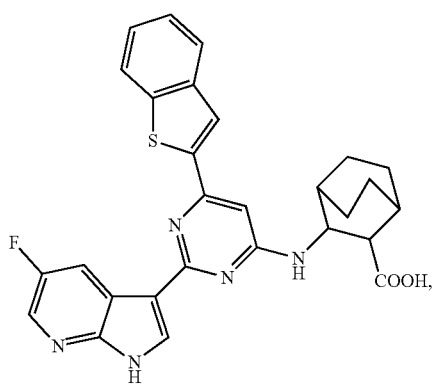
(97) 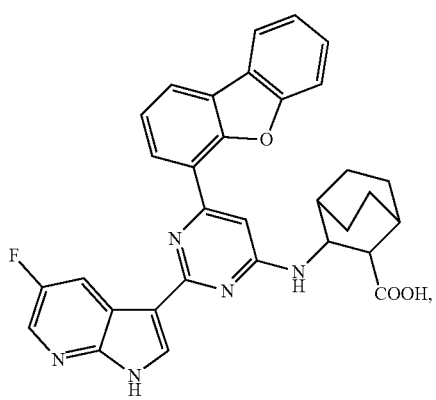
(98) 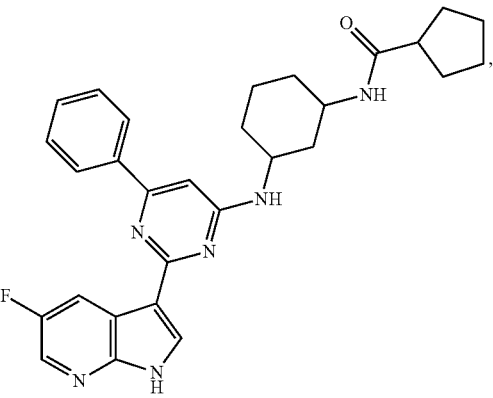
(99) 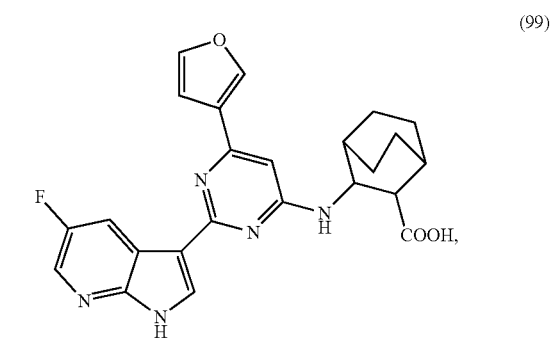

-continued
(100) 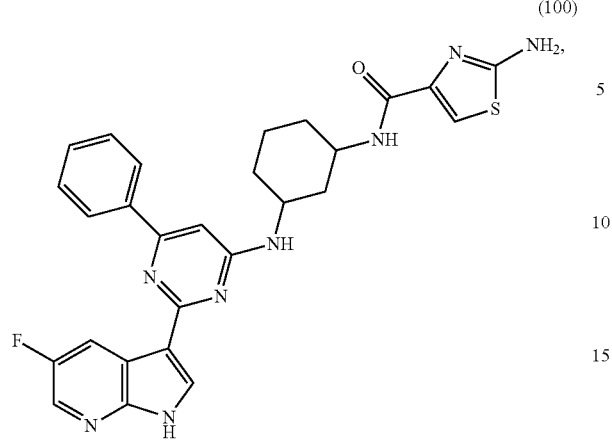
(101) 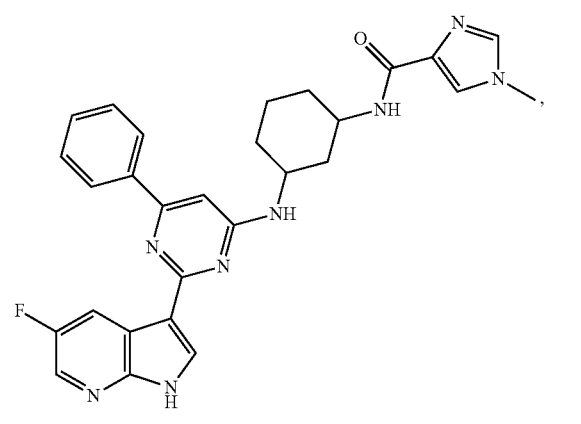
(102) 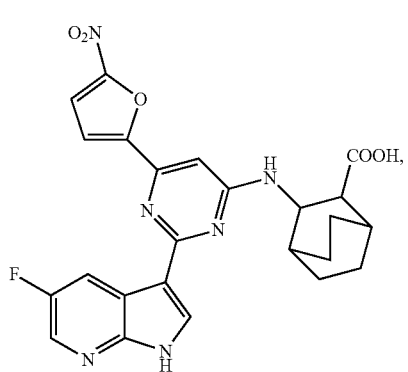
(103) 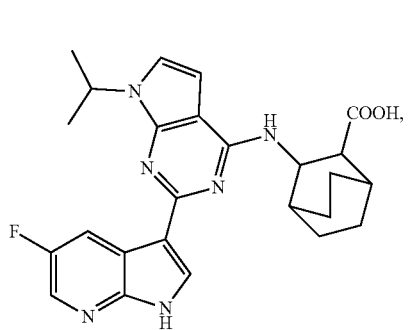
-continued
(104) 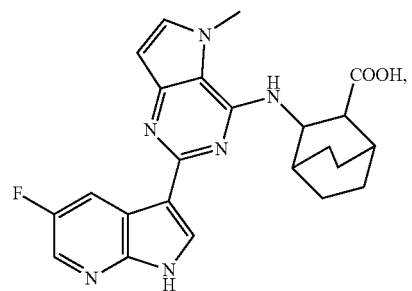
(105) 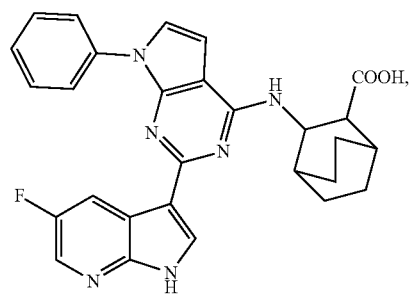
(106) 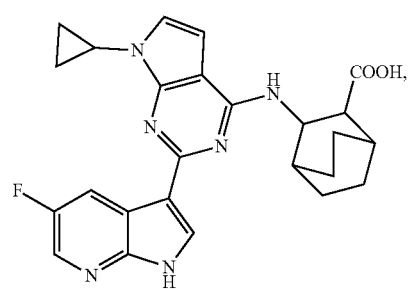
(107) 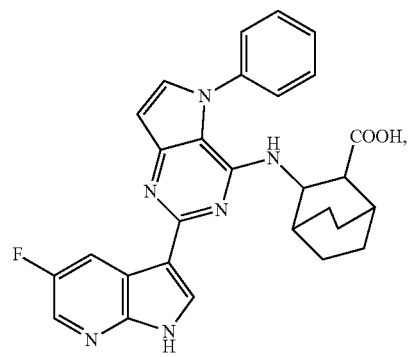
(108) 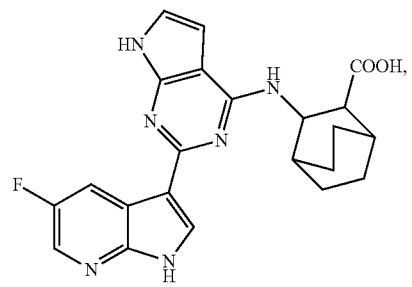

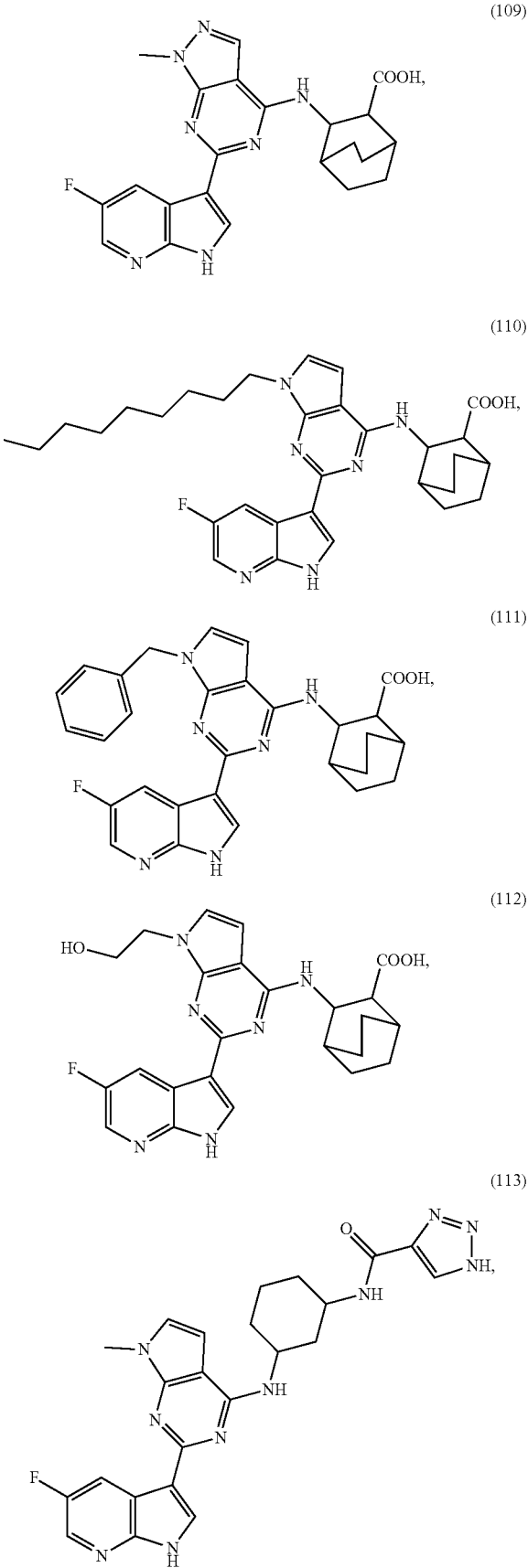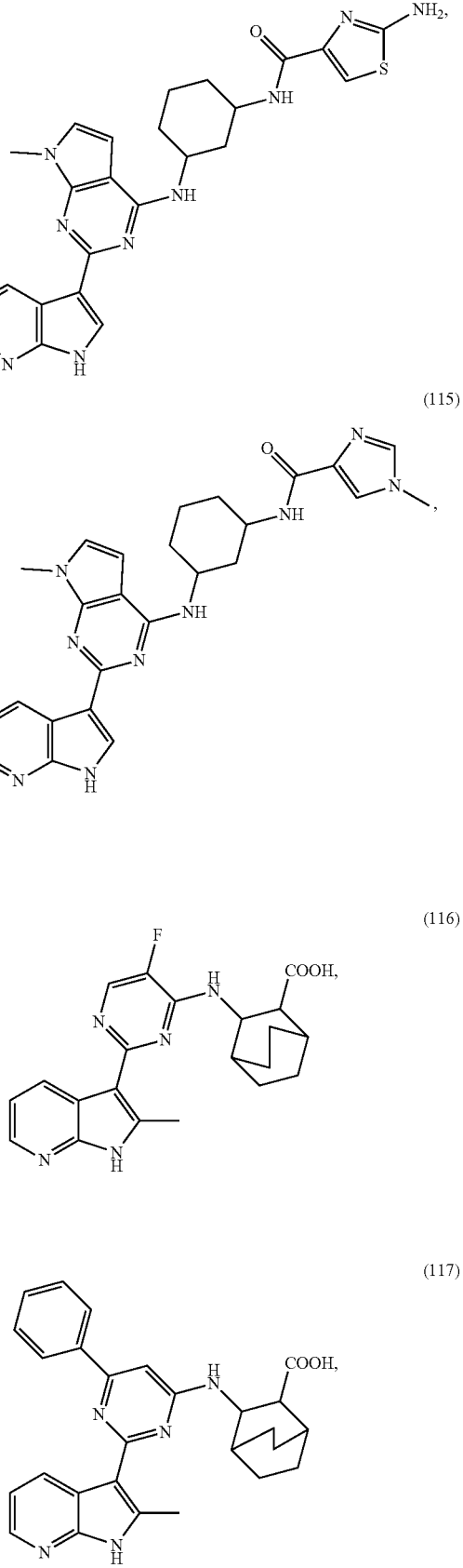

(118) 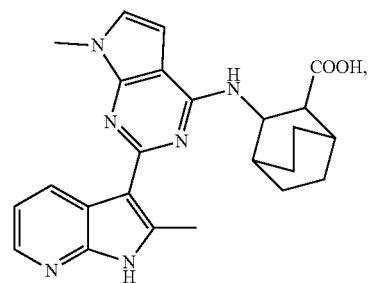
(119) 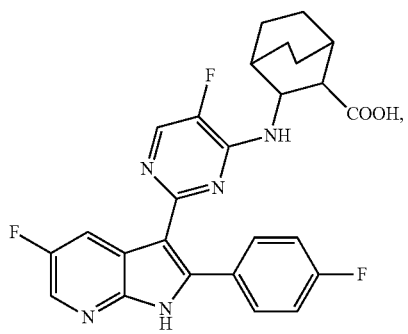
(120) 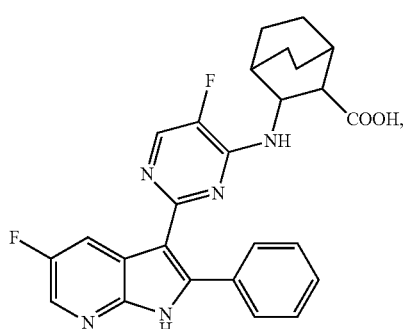
(121) 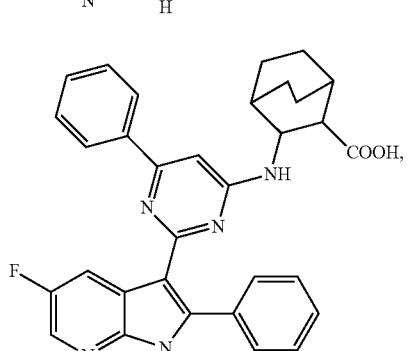
(122) 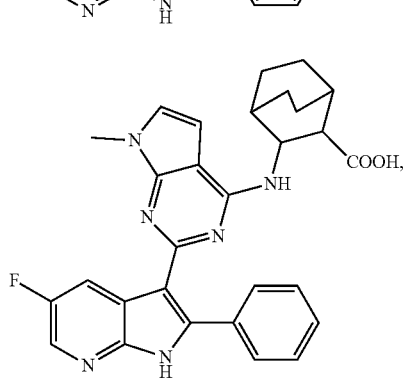
(123) 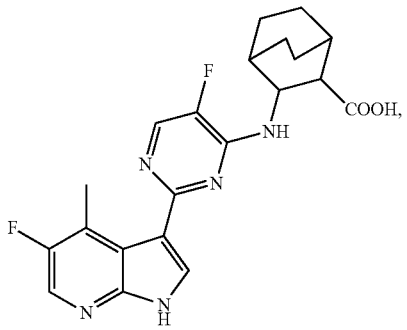
(124) 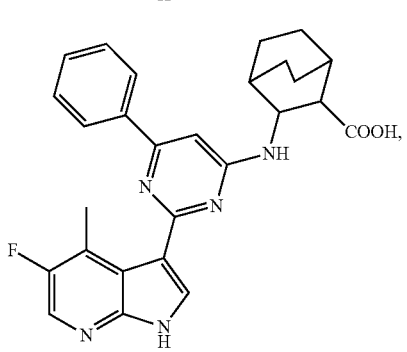
(125) 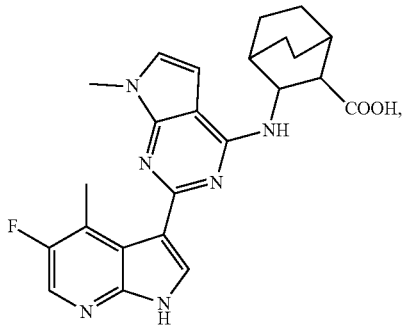
(126) 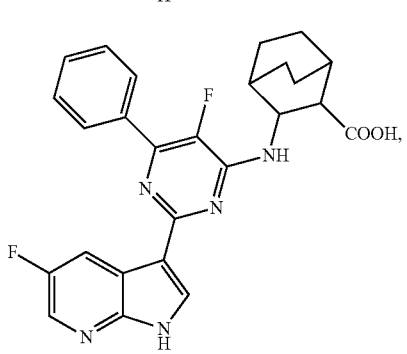
(127)

(128)
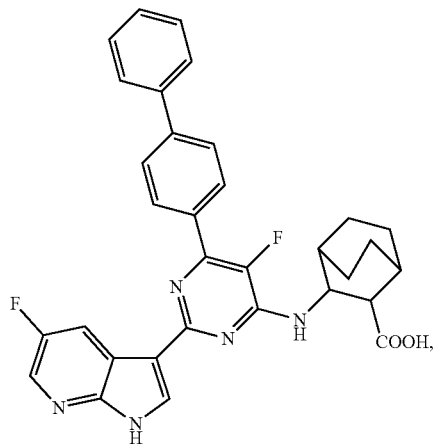
(129)
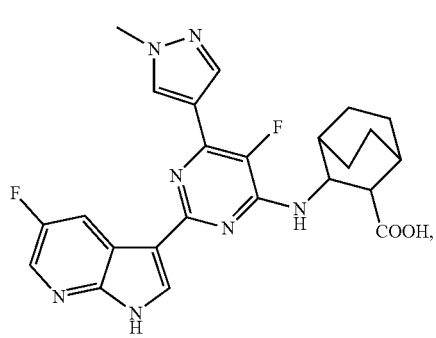
(130)
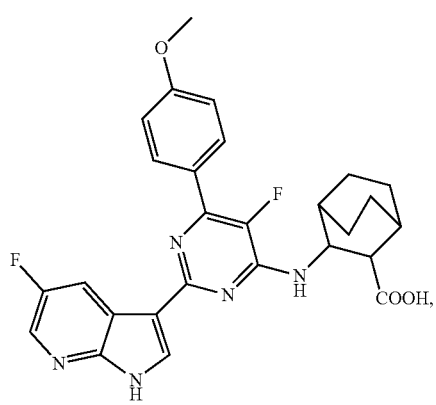
(131)
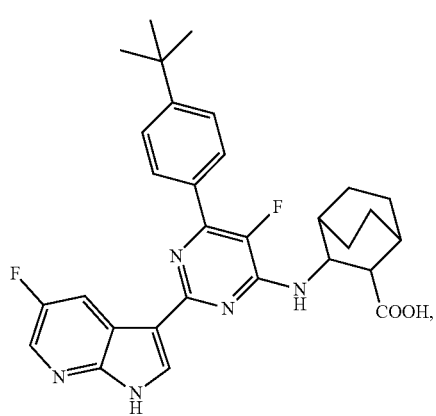
(132)
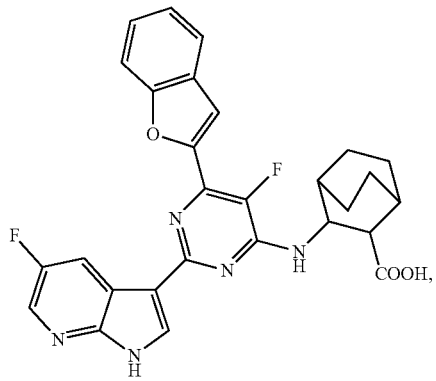
(133)
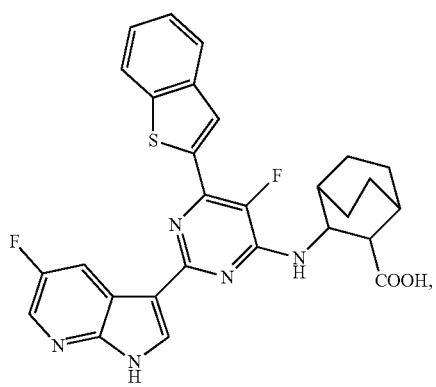
(134)
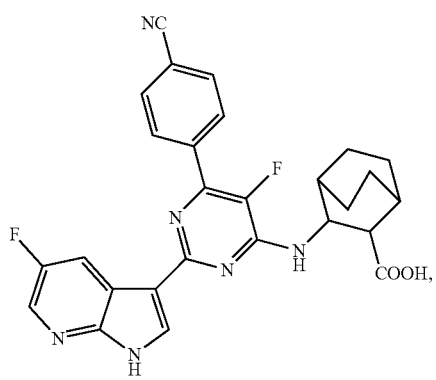
(135)
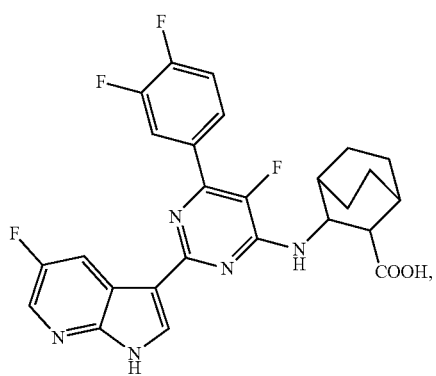

(136)
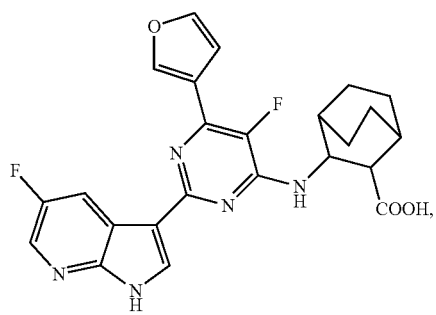
(137)
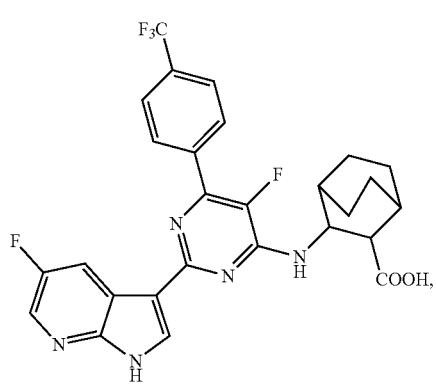
(138)
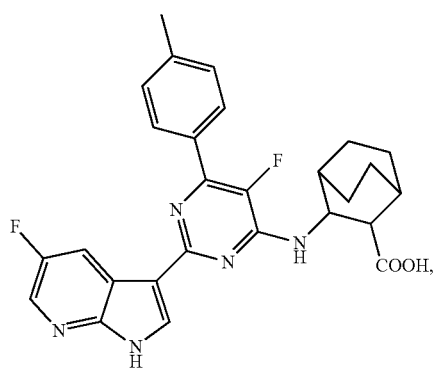
(139)
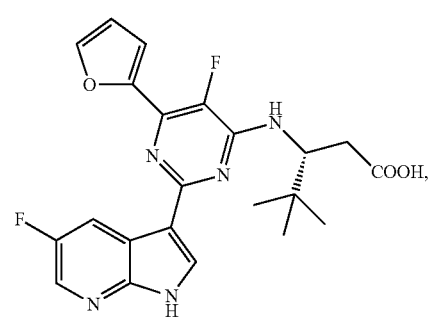
(140)
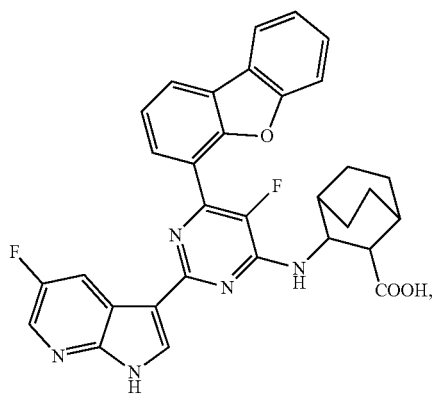
(141)
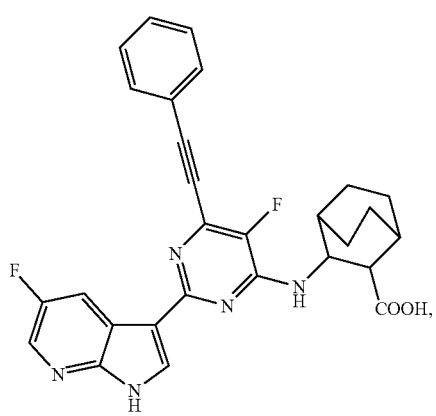
(142)
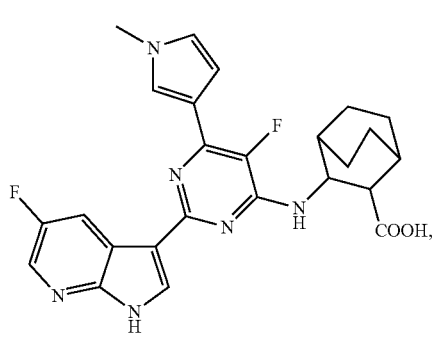
(143)
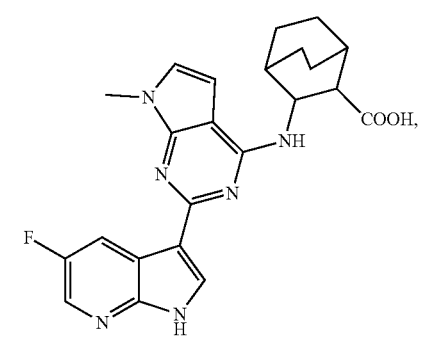

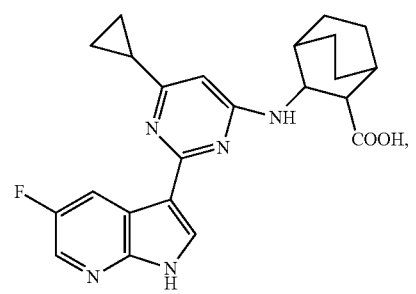
(144)
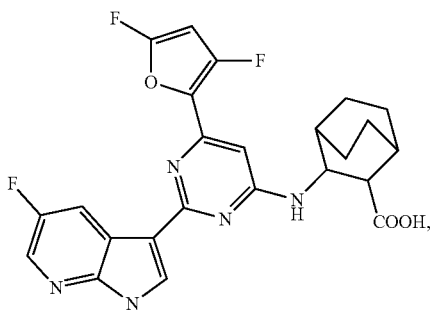
(149)
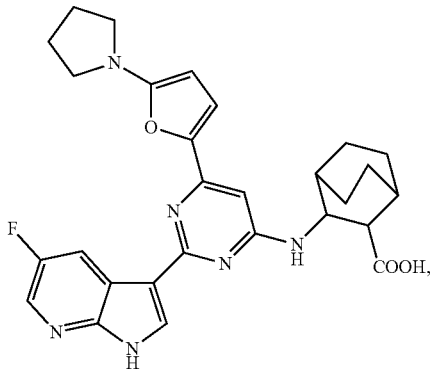
(150)
(145)
(146)
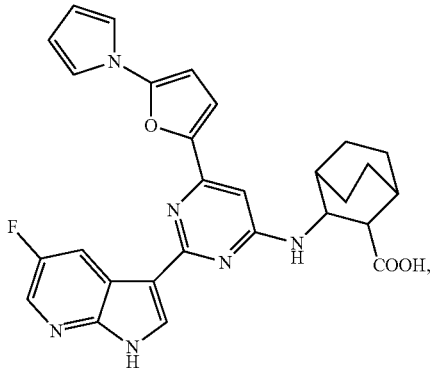
(151)
(147)
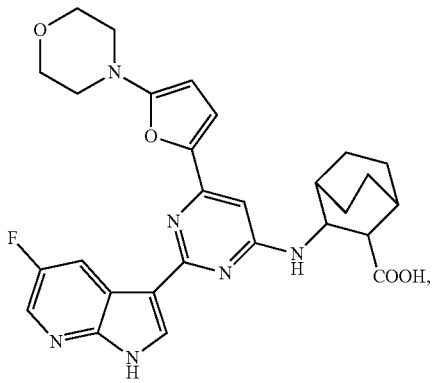
(152)
(148)

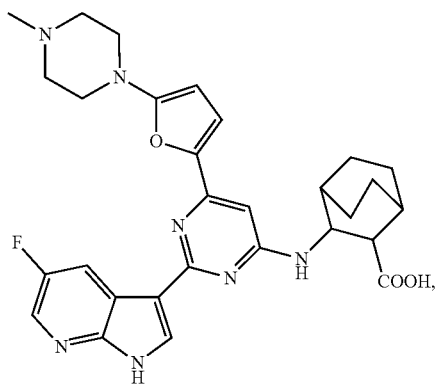
(153)
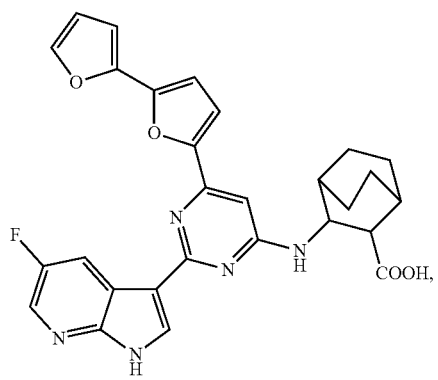
(154)
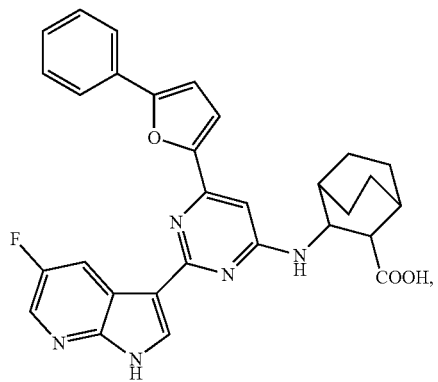
(155)
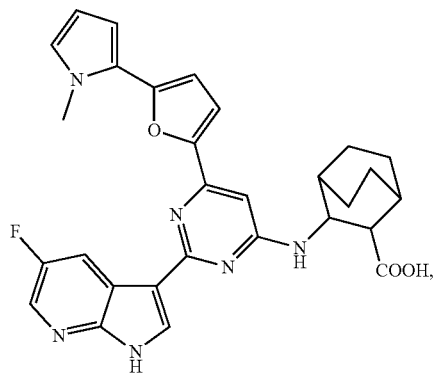
(156)
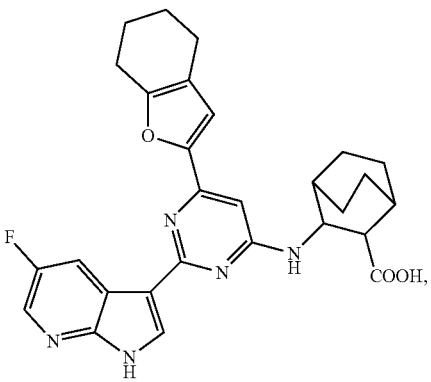
(157)
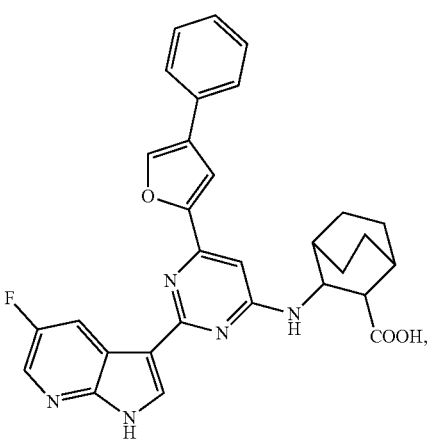
(158)
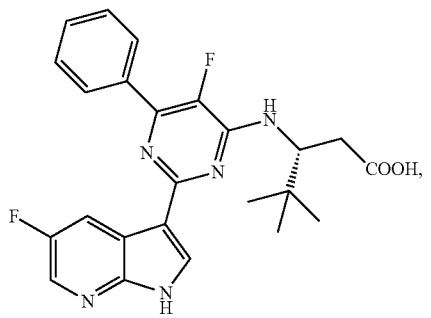
(159)
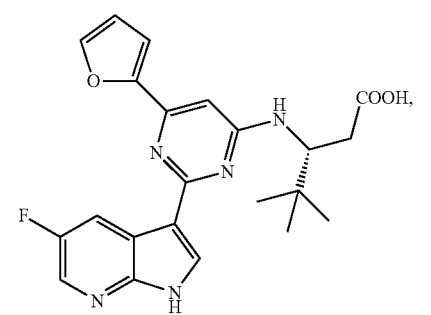
(160)

(161) 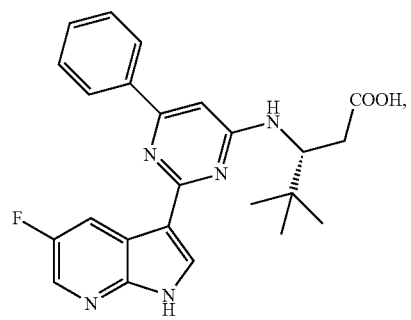
(162) 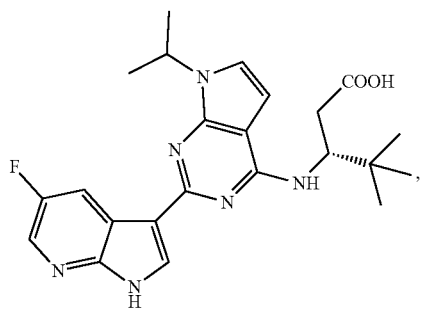
(163) 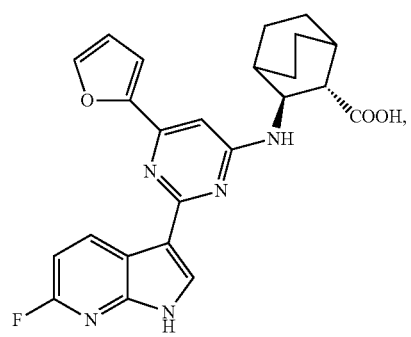
(164) 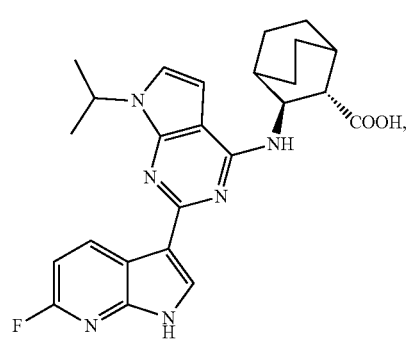
(165) 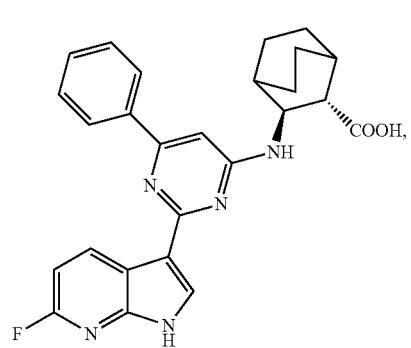
(166) 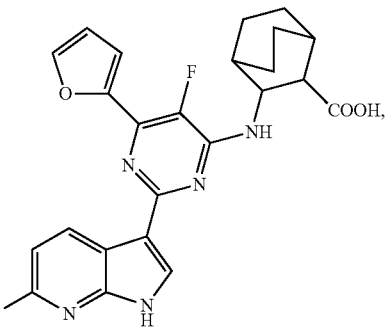
(167) 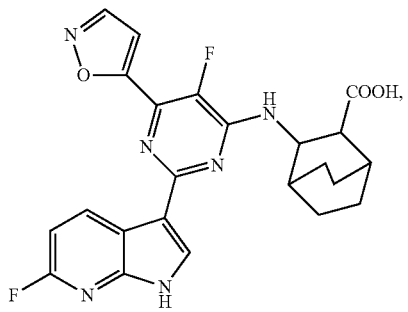
(168) 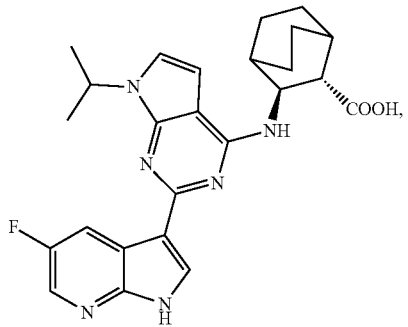
(169) 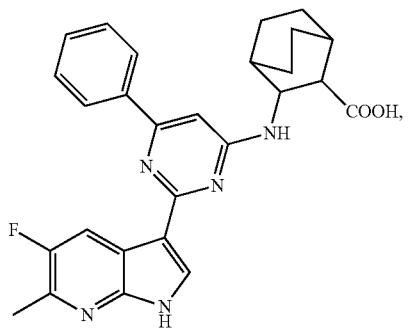

-continued

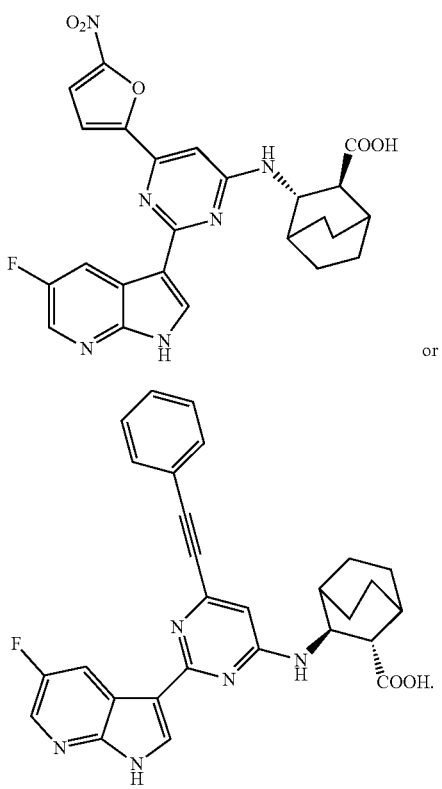

(170)

or (171)

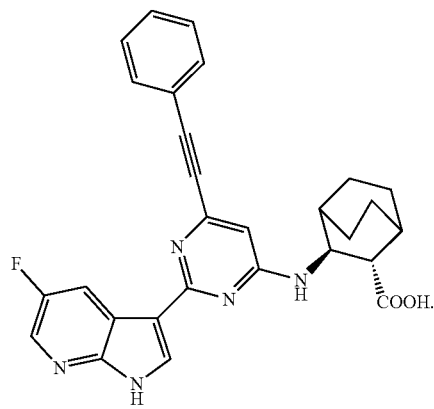

In one aspect, provided herein is a pharmaceutical composition comprising the compound disclosed herein.

In certain embodiments, the pharmaceutical composition provided herein further comprises a pharmaceutically acceptable carrier, adjuvant, vehicle or a combination thereof.

In certain embodiments, the pharmaceutical composition provided herein further comprises one or more therapeutic agents.

In other embodiments, the therapeutic agent disclosed herein is an anti-influenza virus agent or anti-influenza virus vaccine.

In other embodiments, the pharmaceutical composition is in the form of liquid, solid, semi-solid, gel or spray.

In other embodiments, the pharmaceutical composition, wherein the therapeutic agent is amantadine, rimantadine, oseltamivir, zanamivir, peramivir, laninamivir, laninamivir octanoate hydrate, favipiravir, arbidol, ribavirin, stachyflin, ingavirin, fludase, CAS no. 1422050-75-6, JNJ-872, AL-794, an influenza vaccine (FluMist Quadrivalent®, Fluarix® Quadrivalent, Fluzone® Quadrivalent, Flucelvax® or FluBlok®) or a combination thereof.

In another aspect, provided herein is use of the compound or the pharmaceutical composition disclosed herein in the manufacture of a medicament for preventing, managing, treating or lessening a disorder or disease caused by virus infection in a patient.

In certain embodiments, the virus infection disclosed herein is influenza virus infection.

In another aspect, provided herein is use of the compound or the pharmaceutical composition disclosed herein in the manufacture of a medicament for inhibiting RNA polymerase of the influenza virus.

In one embodiment, the salt is a pharmaceutically acceptable salt. The phrase "pharmaceutically acceptable" refers to that the substance or composition must be chemically and/or toxicologically compatible with the other ingredients comprising a formulation, and/or the mammal being treated therewith.

In another embodiment, the salts are not necessarily pharmaceutically acceptable salts, and which may be useful as intermediates for preparing and/or purifying compounds of the invention and/or for separating enantiomers of compounds of the invention.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, subsalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "*Remington's Pharmaceutical Sciences*", 20th ed., Mack Publishing Company, Easton, Pa., (1985); and in "*Handbook of Pharmaceutical Salts: Properties, Selection, and Use*" by Stahl and Wermuth (Wiley-VCH, Weinheim, Germany, 2002).

Furthermore, the compounds disclosed herein, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms.

Any formula given herein is also intended to represent isotopically unenriched forms as well as isotopically enriched forms of the compounds. Isotopically enriched compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, sulfur, fluorine, and chlorine, such as $^2$H (deuterium, D), $^3$H, $^{11}$C, $^{13}$C, $^{14}$C, $^{18}$F, $^{31}$P, $^{32}$P, $^{36}$S, $^{37}$Cl, $^{125}$I, respectively.

In another aspect, the compounds of the invention include isotopically enriched compounds as defined herein, for example those into which radioactive isotopes, such as $^3$H, $^{14}$C and $^{18}$F, or those into which non-radioactive isotopes, such as $^2$H and $^{13}$C are present. Such isotopically enriched compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F-enriched compound may be particularly desirable for PET or SPECT studies. Isotopically-enriched compounds of Formula (I) can generally be prepared by conventional techniques known to those skilled in the art or by processes analogous to those described in the accompanying Examples and Preparations using an appropriate isotopically-labeled reagent in place of the non-labeled reagent previously employed.

Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index, for example increased in vivo half-life or reduced dosage requirements or an improvement in therapeutic index. It is understood that deuterium in this context is regarded as a substituent of a compound of Formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). Pharmaceutically acceptable solvates in accordance with the invention include those wherein the solvent of crystallization may be isotopically substituted, e.g., $D_2O$, $d_6$-acetone, DMSO-$d_6$.

Pharmaceutical Composition of the Compound of the Invention, Preparations and Administration The invention provides a pharmaceutical composition containing a therapeutic effective amount of the compound of the invention or a stereoisomer thereof. In one embodiment, the pharmaceutical composition further comprises at least one pharmaceutically acceptable carriers, diluents, adjuvants or excipients, and optionally other treating and/or preventing ingredients. In one embodiment, the pharmaceutical composition comprises an effective amount of at least one pharmaceutically acceptable carriers, diluents, adjuvants or excipients.

A pharmaceutically acceptable carrier may contain inert ingredients which do not unduly inhibit the biological activity of the compound(s) described herein. The pharmaceutically acceptable carriers should be biocompatible, i.e., non-toxic, non-inflammatory, non-immunogenic and devoid of other undesired reactions upon the administration to a subject. Standard pharmaceutical formulation techniques can be employed.

As described above, the pharmaceutically acceptable compositions disclosed herein further comprise a pharmaceutically acceptable carrier, an adjuvant, or a vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. *Remington: The Science and Practice of Pharmacy,* 21st edition, 2005, ed. D. B. Troy, Lippincott Williams & Wilkins, Philadelphia, and *Encyclopedia of Pharmaceutical Technology*, eds. J. Swarbrick and J. C. Boylan, 1988-1999, Marcel Dekker, New York, the contents of each of which is incorporated by reference herein, are disclosed various carriers used in formulating pharmaceutically acceptable compositions and known techniques for the preparation thereof. Except insofar as any conventional carrier medium incompatible with the compounds disclosed herein, such as by producing any undesirable biological effect or otherwise interacting in a deleterious manner with any other components of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, methyl cellulose, hydroxypropyl methyl cellulose, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutically acceptable compositions can be administered to humans and other animals orally, rectally, parenterally, intracisternally, intravaginally, intraperitoneally, topically (as by powders, ointments, drops or patch), bucally, as an oral or nasal spray, or the like, depending on the severity of the infection being treated.

Liquid formulations for oral administration include, but not limited to, pharmaceutically acceptable emulsions, micro-emulsion, solution, suspension, syrup and elixir. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Addition to inert diluents, the oral compositions can also contain adjuvants such as wetting agents, emulsifiers or suspending agent, sweeteners, flavorings and fragrances.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound or a composition described herein, it is often desirable to slow the absorption of the compound from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolic acid. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are specifically suppositories which can be prepared by mixing the compounds described herein with suitable non-irritating excipients or carriers such as cocoa butter, polyethylene glycol or a suppository wax which are solid at ambient temperature but liquid at body temperature and therefore melt in the rectum or vaginal cavity and release the active compound.

The solid dosage forms for oral administration include capsules, tablets, pills, powders and granules. In such solid dosage forms, the active compounds are mixed with at least one pharmaceutically acceptable inert excipients or carrier, such as sodium citrate or calcium phosphate and/or (a) fillers or swelling agents such as starch, lactose, sucrose, glucose, mannitol and silicic acid; (b) adhesives such as carboxymethylcellulose, alginates, gelatin, polyethylene pyrrole ketone, sucrose and gum arabic; (c) moisturizing agents such as glycerol; (d) disintegrating agents such as agar, calcium carbonate, potato starch or tapioca starch, alginic acid, certain silicates and sodium carbonate; (e) blocker solution, such as paraffin; (f) absorption promoter such as quaternary ammonium compounds; (g) wetting agents such as cetyl alcohol and glycerol monostearate; (h) absorbents such as kaolin and bentonite, (i) lubricants such as talc, calcium stearate, magnesium stearate, solid polyethylene glycol, laurylsodium sulfate, and mixtures thereof. In the case of capsules, tablets and pills, the pharmaceutical compositions may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings and other coatings well known in the pharmaceutical formulating art. In such solid dosage forms, the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound described herein include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compositions described herein may be administered orally, parenterally, by inhalation spray, topically, rectally, nasally, buccally, vaginally or via an implanted reservoir. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. Specifically, the compositions are administered orally, intraperitoneally or intravenously. Specifically, the compositions are administered orally, intraperitoneally or intravenously.

Sterile injectable forms of the compositions described herein may be aqueous or oleaginous suspension. These suspensions may be formulated according to techniques known in the art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil can be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions described herein may be orally administered in any orally acceptable dosage form including, but not limited to, capsules, tablets, aqueous suspensions or solutions. In the case of tablets for oral use, carriers commonly used include, but are not limited to, lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions described herein may be administered in the form of suppositories for rectal administration. These can be prepared by mixing the agent with a suitable non-irritating excipient which is solid at room temperature but liquid at rectal temperature and therefore will melt in the rectum to release the drug. Such materials include, but are not limited to, cocoa butter, beeswax and polyethylene glycols.

The pharmaceutical compositions described herein may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, specifically, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The compounds for use in the methods of the invention can be formulated in unit dosage form. The term "unit dosage form" refers to physically discrete units suitable as unitary dosage for subjects undergoing treatment, with each unit containing a predetermined quantity of active material calculated to produce the desired therapeutic effect, optionally in association with a suitable pharmaceutical carrier. The unit dosage form can be for a single daily dose or one of multiple daily doses (e.g., about 1 to 4 or more times per day). When multiple daily doses are used, the unit dosage form can be the same or different for each dose.

Uses of the Compounds and Pharmaceutical Compositions

The compounds and pharmaceutical compositions provided herein can be used in the manufacture of medicaments for preventing, treating or lessening a disorder or disease caused by virus infection in a patient. In some embodiment, the virus infection is influenza virus infection.

Also provided herein are the uses of the compounds and pharmaceutical compositions described above in the manufacture of medicaments which are inhibitors of influenza virus RNA polymerase.

Provided herein is a method of treating, preventing or delaying the infections caused by viruses, and wherein the method comprises administering to the patent a therapeutically effective amount of the compound or the pharmaceutical composition described herein to a patient in need of treatment. Wherein the virus is an influenza virus. And, the compounds or pharmaceutical compositions thereof can be co-administered with other therapies or therapeutic agents. The co-administration can be performed simultaneously, sequentially, or in a certain time interval.

Doses of the compound or pharmaceutical composition needed for implementing functions such as treating, preventing or delaying usually depend on the particular compound to be administered, patient, specific disease or disorder and severity thereof, route and frequency of administration and so on, and need to be determined by the attending doctor in accordance with specific conditions. For example, when the compound or pharmaceutical composition of the present invention is administrated intravenously, the administration may be once a week or even longer intervals.

As described above, the present invention provides a novel class of compounds, and wherein the compounds can be used as inhibitors of the influenza virus RNA polymerase. The compounds of the invention are suitable for preparing medicaments as various dosage forms, which can be used for treating seasonal flu, avian flu, swine flu as well as tamiflu-resistant influenza virus mutants.

Besides being useful for human treatment, these compounds are also useful for veterinary treatment of animals such as companion animals, exotic animals and farm animals. In other embodiments, the animals disclosed herein include horses, dogs, and cats. As used herein, the compounds disclosed herein include the pharmaceutically acceptable derivatives thereof.

General Synthetic Procedures

For the purpose of describing the invention, the following examples are listed. It should be understood that, the invention is not limited to these examples, and the present invention only provide the method to practice the invention.

Generally, the compounds disclosed herein may be prepared by methods described herein, wherein the substituents are as defined for Formula (I), except where further noted. The following non-limiting schemes and examples are presented to further exemplify the invention.

Persons skilled in the art will recognize that the chemical reactions described may be readily adapted to prepare a number of other compounds disclosed herein, and alternative methods for preparing the compounds disclosed herein are deemed to be within the scope disclosed herein. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds disclosed herein.

In the examples described below, unless otherwise indicated all temperatures are set forth in degrees Celsius. Reagents were purchased from commercial suppliers such as Aldrich Chemical Company, Arco Chemical Company, Alfa Chemical Company and J&K Scientific Ltd. and were used without further purification unless otherwise indicated. Common solvents were purchased from commercial suppliers such as Shantou XiLong Chemical Factory, Guangdong Guanghua Reagent Chemical Factory Co. Ltd., Guangzhou Reagent Chemical Factory, Tianjin YuYu Fine Chemical Ltd., Tianjing Fuchen Chemical Reagent Factory, Wuhan XinHuayuan technology development co., LTD., Qingdao Tenglong Reagent Chemical Ltd., Qingdao Ocean Chemical Factory, Beijin Ouhe Technology Co., Ltd., Shanghai Topbiochem Technology Co., Ltd, and Accela ChemBio Co., Ltd.

Anhydrous THF, 1,4-dioxane, toluene, and ether were obtained by refluxing the solvent with sodium. Anhydrous $CH_2Cl_2$ and $CHCl_3$ were obtained by refluxing the solvent with calcium hydride. EtOAc, PE, n-hexane, N,N-dimethylacetamide and N,N-dimethylformamide were treated with anhydrous $Na_2SO_4$ prior use.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was conducted using a silica gel column. Silica gel (300-400 mesh) was purchased from Qingdao Ocean Chemical Factory.

$^1$H NMR spectra were recorded at rt with a Bruker 400 MHz or 600 MHz spectrometer using $CDCl_3$, $d_6$-DMSO, $CD_3OD$ or $d_6$-acetone as solvent (reported in ppm), and using TMS (0 ppm) or chloroform (7.26 ppm) as the reference standard. When peak multiplicities were reported, the following abbreviations were used: s (singlet), d (doublet), t (triplet), m (multiplet), br (broadened), dd (doublet of doublets), and dt (doublet of triplets). Coupling constants, when given, are reported in Hertz (Hz).

Low-resolution mass spectral (MS) data were determined on an Agilent 6120 Quadrupole HPLC-MS spectrometer equipped with an Agilent Zorbax SB-C18 column (2.1×30 mm, 3.5 μm). The flow rate was 0.6 mL/min; the mobile phases consisted of a combination of A (0.1% formic acid in $CH_3CN$) and B (0.1% formic acid in $H_2O$) in gradient mode (5% to 95%), and an ESI source was used, the peak of HPLC was recorded with UV-Vis detection at 210/254 nm.

Purification of compound by preparative chromatography was implemented on Agilent 1260 Series high performance liquid chromatography (Pre-HPLC) or Calesep Pump 250 Series high performance liquid chromatography (Pre-HPLC) with UV detection at 210/254 nm (column: NOVASEP, 50/80 mm. DAC).

The following abbreviations are used throughout the specification:
AcOH, HAc, HOAc, $CH_3COOH$ acetic acid
AcOK, KOAc, $CH_3COOK$ potassium acetate
BnOH phenylcarbinol
$Bu_4NF$ tetrabutylammonium fluoride
BOC, Boc tert-butoxycarbonyl
$(Boc)_2O$ di-tert-butyl dicarbonate
n-BuOH n-butyl alcohol
$CHCl_3$ chloroform CDCl$_3$ chloroform-d
CD$_3$OD methyl alcohol-d$_4$
DCM, CH$_2$Cl$_2$ dichloromethane
CH$_3$CN, MeCN acetonitrile
CH$_3$Cl chloromethane
CH$_3$I iodomethane
CH$_3$SO$_2$Cl, MsCl methylsufonyl chloride
Cbz benzyloxycarbonyl
CL clearance
DIEA, DIPEA, iPr$_2$Net N,N-diisopropylethylamine
DMF N,N-dimethylformamide, dimethylformamide
DMF-DMA N,N-dimethylformamide dimethyl acetal
DME dimethyl ether
DMAP 4-dimethylaminopyridine
DMSO dimethylsulfoxide
DMSO-d$_6$ dimethyl sulfoxide-d$_6$, deuterated DMSO
DPPA diphenylphosphoryl azide
EA, EtOAc ethyl acetate
Et$_3$N, TEA triethylamine
Et$_2$O diethyl ether
EtOH ethyl alcohol
EC$_{50}$ 50% effective concentration
g gram
wt weight fraction
h hour, hours
H$_2$ hydrogen
H$_2$O water
HCl hydrogen chloride
H$_2$O$_2$ hydrogen peroxide
H$_3$PO$_4$ phosphoric acid
H$_2$SO$_4$ sulfuric acid
HNO$_3$ nitric acid
HCOOK potassium formate
HCOONH$_4$ ammonium formate
HPLC high performance liquid chromatography
HPTLC high performance thin layer chromatography
HRMS high resolution mass spectrum
I$_2$ iodine
Fe iron
MgSO$_4$ magnesium sulfate
CH$_3$OH, MeOH methanol
MeI, CH$_3$I iodomethane
mL, ml milliliter
min minute, minutes
N$_2$ nitrogen
NH$_3$ ammonia
NMP N-methylprrolidone
NaHCO$_3$ sodium bicarbonate
NaBH$_4$ sodium borohydride
NaBH$_3$CN sodium cyanoborohydride
NaOMe, NaOCH$_3$, CH$_3$ONa sodium methoxide
NaOH sodium hydroxide
NaCl sodium chloride
NaH$_2$PO$_4$ sodium dihydrogen phosphate
NaH sodium hydride
NaI sodium iodide
Na$_2$SO$_4$ sodium sulfate
Na$_2$S$_2$O$_3$ sodium thio sulfate
NBS N-bromosuccinimide
NIS N-iodosuccinimide
NCS N-chlorosuccinimide
NH$_4$Cl ammonium chloride
NH$_2$OHHCl hydroxylamine hydrochloride
psi pound per square inch
Pd/C palladium on activated carbon
Pd(OAc)$_2$ palladium diacetate
Pd(OH)$_2$ palladium hydroxide
Pd(PPh$_3$)$_4$ tetrakis(triphenylphosphine)palladium
Pd(PPh$_3$)$_2$Cl$_2$ bis(triphenylphosphine)palladium(II) chloride
Pd(dppf)Cl$_2$, PdCl$_2$(dppf) [1,1'-bis(diphenylphosphino)ferrocene]dichloropalladium(II)
Pd(dppf)Cl$_2$CH$_2$Cl$_2$ 1,1'-bis(diphenylphosphino)ferrocene-palladium(II)dichloride dichloromethane complex
Pd(dtbpf)Cl$_2$ [1,1'-bis(di-tert-butylphosphino)ferrocene]dichloropalladium(II)
Pd$_2$(dba)$_3$ tris(dibenzylideneacetone)dipalladium
P(t-Bu)$_3$ tri-tert-butylphosphine
PE petroleum ether (60-90° C.)
POCl$_3$ phosphorus oxychloride
K$_2$CO$_3$ potassium carbonate
K$_3$PO$_4$ potassium phosphate
KOH potassium hydroxide
RT, rt, r.t. room temperature
Rt retention time
SOCl$_2$ thionyl chloride
SI therapeutic index
t-BuOK potassium tert-butoxide
THF tetrahydrofuran
TFA trifluoroacetic acid
TBAI tetrabutylammonium iodide
TBS tris(hydroxymethyl)aminomethane saline buffer
TsCl tosyl chloride
Ts Tosyl
Vss apparent volume of distribution
X-Phos 2-(dicyclohexylphosphino)-2',4',6'-tri-i-propyl-1,1'-biphenyl
Zn zinc
μL microliter The following schemes list the synthetic steps of the compounds of the invention, and wherein R$^1$, R$^2$, R$^3$, R$^w$, R', n, q, s, V' and A are as defined herein, R$^h$ is H or F, and R$^g$ is OH or Cl.

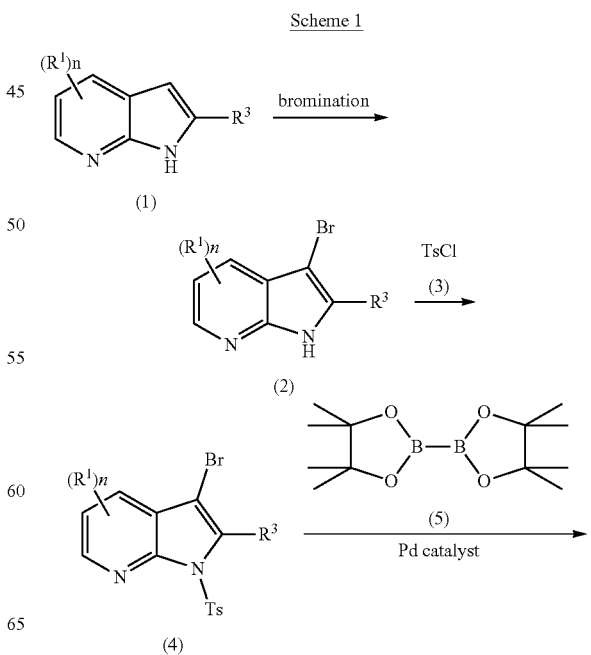

Scheme 1

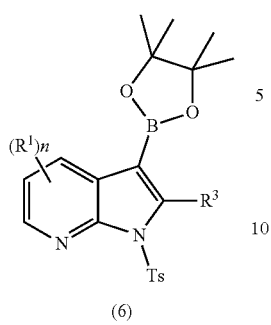

The intermediate having Formula (6) can be prepared by the process illustrated in scheme 1. Firstly, compound (1) can react with a bromination reagent (eg., bromine, NBS, etc.) at rt in a polar solvent (eg., N,N-dimethylformamide) or medium polar solvent (eg., dichloromethane) to give compound (2). Compound (2) can react with p-tosyl chloride (3) to give compound (4). Compound (4) can react with compound (5) in the presence of a palladium catalyst (eg., Pd(dppf)Cl$_2$, Pd(PPh$_3$)$_4$, etc.,) to give intermediate (6).

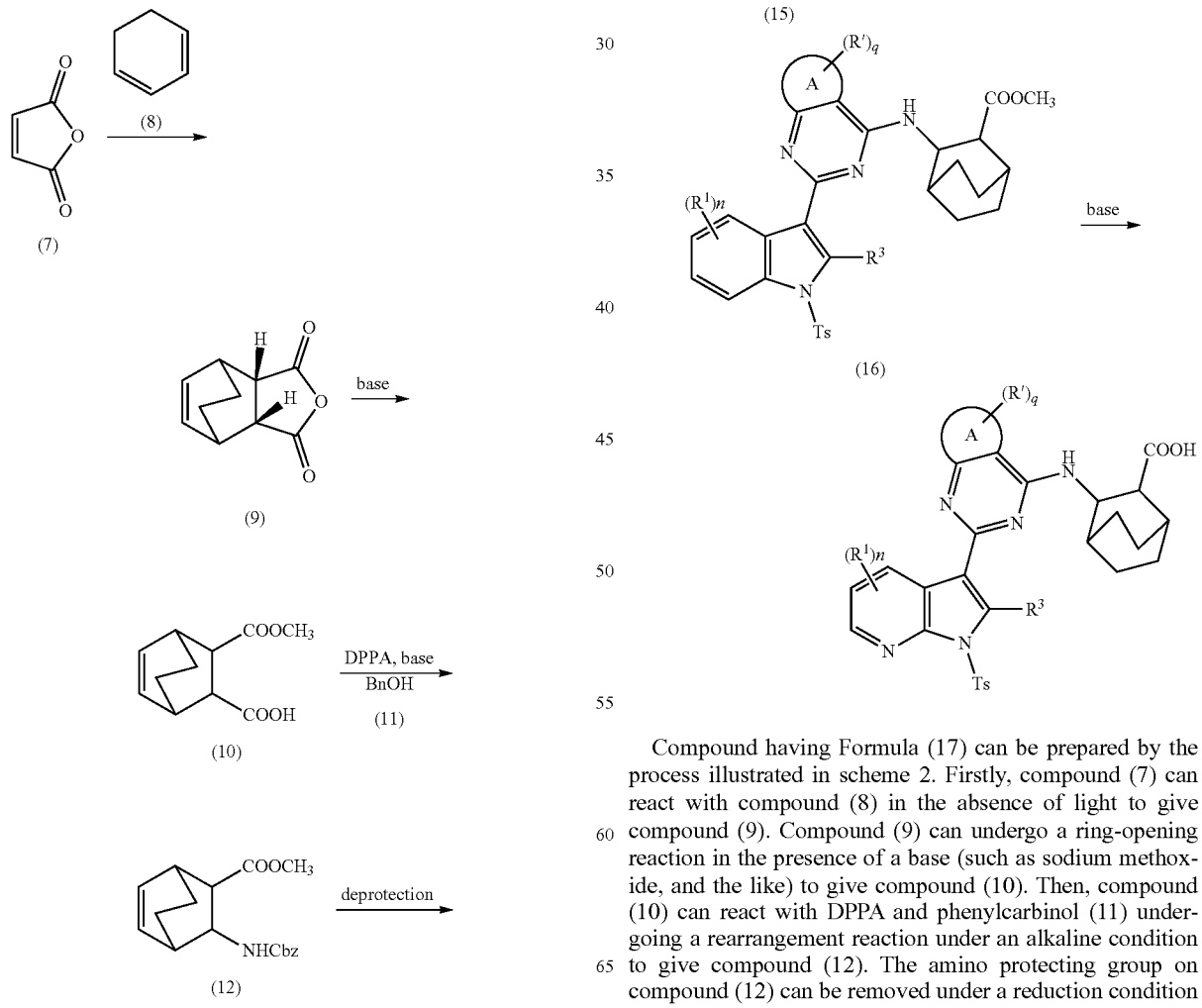

Compound having Formula (17) can be prepared by the process illustrated in scheme 2. Firstly, compound (7) can react with compound (8) in the absence of light to give compound (9). Compound (9) can undergo a ring-opening reaction in the presence of a base (such as sodium methoxide, and the like) to give compound (10). Then, compound (10) can react with DPPA and phenylcarbinol (11) undergoing a rearrangement reaction under an alkaline condition to give compound (12). The amino protecting group on compound (12) can be removed under a reduction condition to give compound (13). Coupling reaction between compound (13) and compound (14) can happen under an alkaline condition to give compound (15). Suzuki cross-coupling reaction can occur between compound (15) and compound (6) in the presence of a palladium catalyst to give compound (16). At last, protecting groups on compound (16) can be removed in the presence of a base to give compound (17).

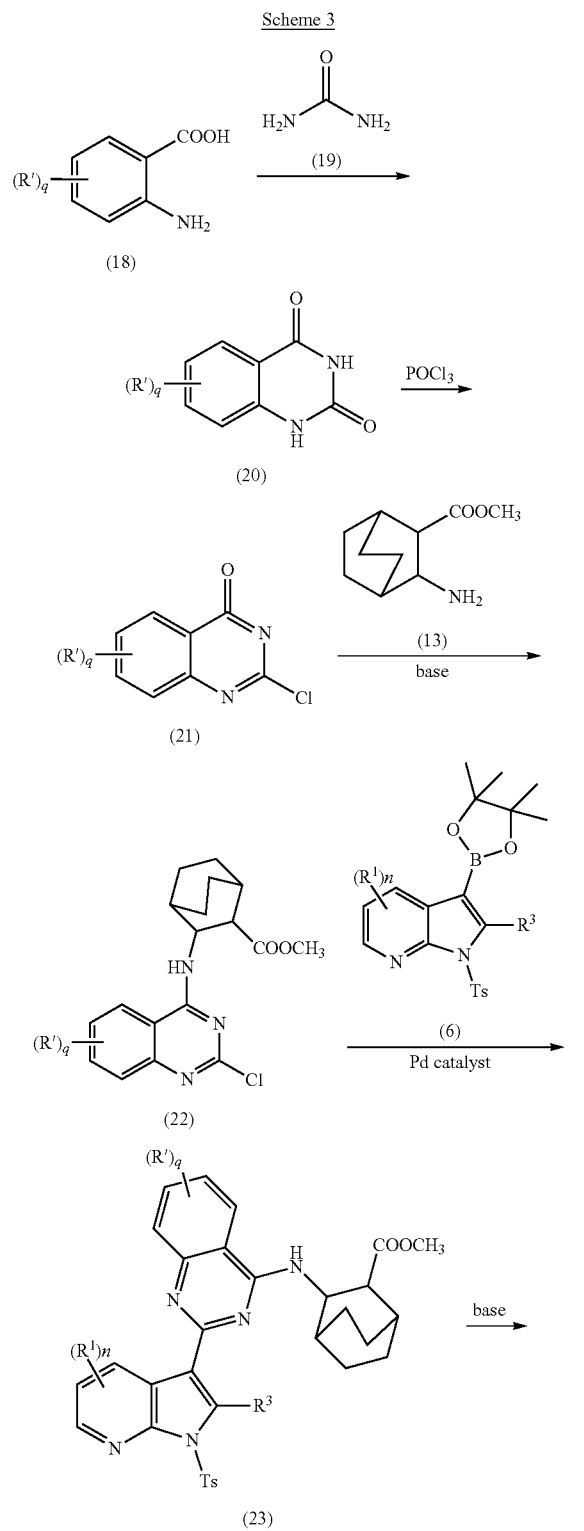

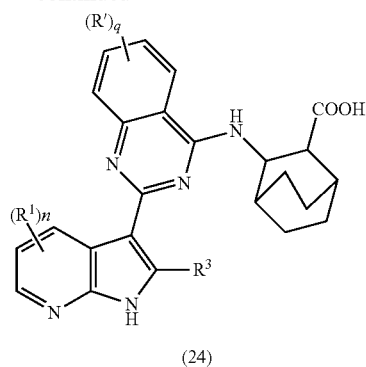

Compound having Formula (24) can be prepared by the process illustrated in scheme 3. Firstly, compound (18) can react with urea (19) under a heating condition to give compound (20). Compound (20) can undergo a chlorination reaction in the presence of phosphorus oxychloride to give compound (21). Then compound (21) can react with compound (13) under an alkaline condition to give compound (22). Suzuki cross-coupling reaction can occur between compound (22) and compound (6) in the presence of a palladium catalyst to give compound (23). At last, protecting groups on compound (23) can be removed in the presence of a base to give compound (24).

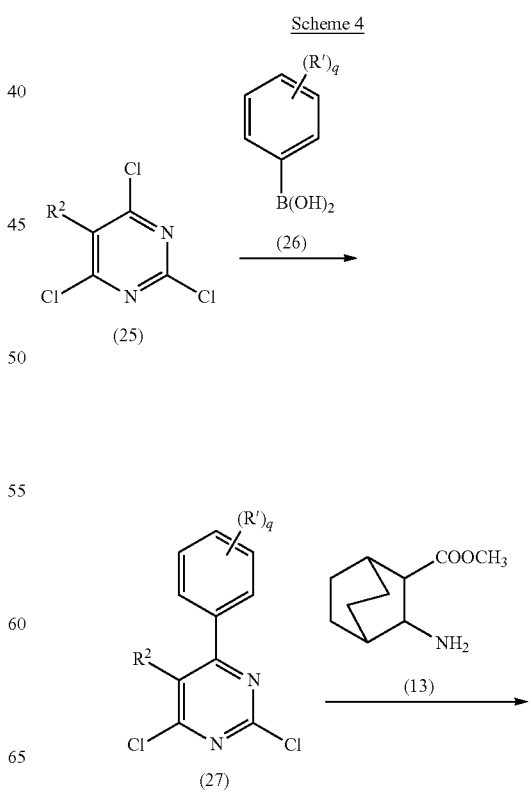

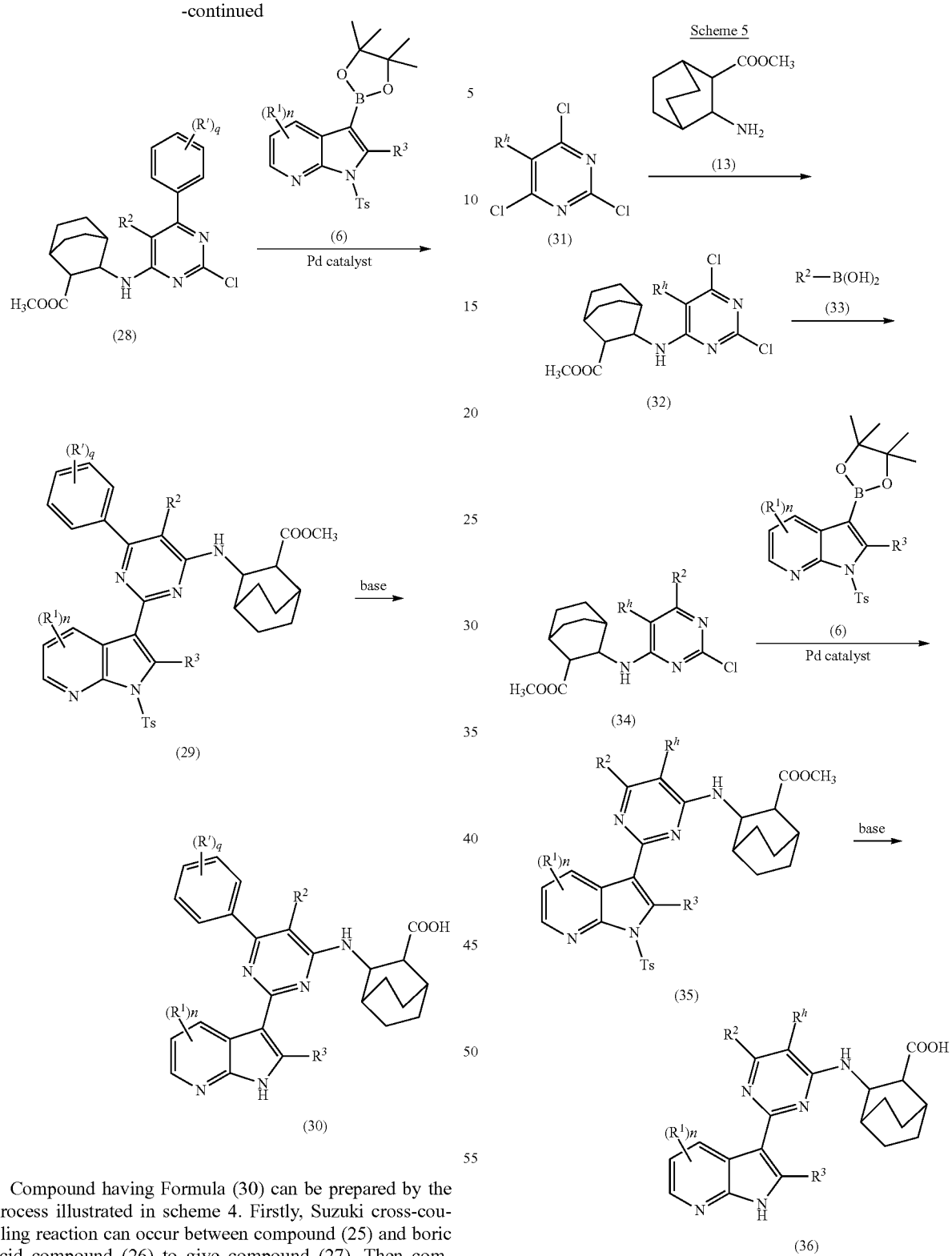

Compound having Formula (30) can be prepared by the process illustrated in scheme 4. Firstly, Suzuki cross-coupling reaction can occur between compound (25) and boric acid compound (26) to give compound (27). Then compound (27) can react with compound (13) under an alkaline condition to give compound (28). And Suzuki cross-coupling reaction can occur between compound (28) and compound (6) in the presence of a palladium catalyst to give compound (29). At last, protecting groups on compound (29) can be removed in the presence of a base to give compound (30).

Compound having Formula (36) can be prepared by the process illustrated in scheme 5. Firstly, compound (31) can react with compound (13) under an alkaline condition to give compound (32). Then compound (32) and boric acid compound (33) can undergo Suzuki cross-coupling reaction to give compound (34). And Suzuki cross-coupling reaction can occur between compound (34) and compound (6) in the presence of a palladium catalyst to give compound (35). At last, protecting groups on compound (35) can be removed in the presence of a base to give compound (36).

Scheme 6

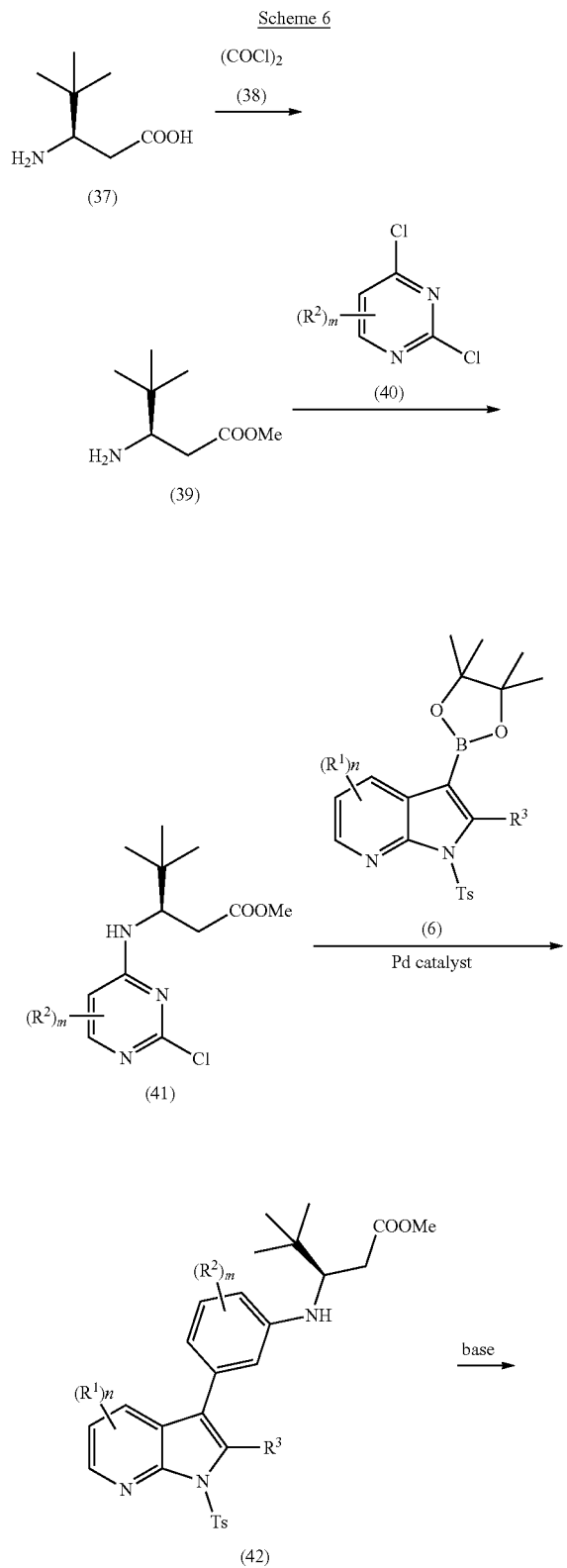

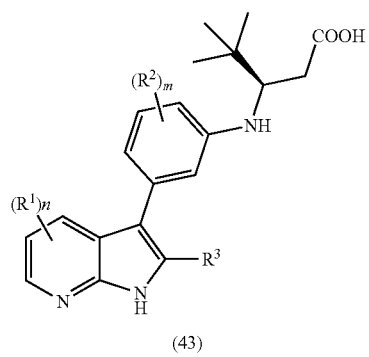

Compound having Formula (43) can be prepared by the process illustrated in scheme 6. Firstly, compound (37) can react with compound (38) to give compound (39). Then compound (39) and compound (40) can undergo a condensation reaction to give compound (41). And Suzuki cross-coupling reaction can occur between compound (41) and compound (6) in the presence of a palladium catalyst to give compound (42). At last, protecting groups on compound (42) can be removed in the presence of a base to give compound (43).

Scheme 7

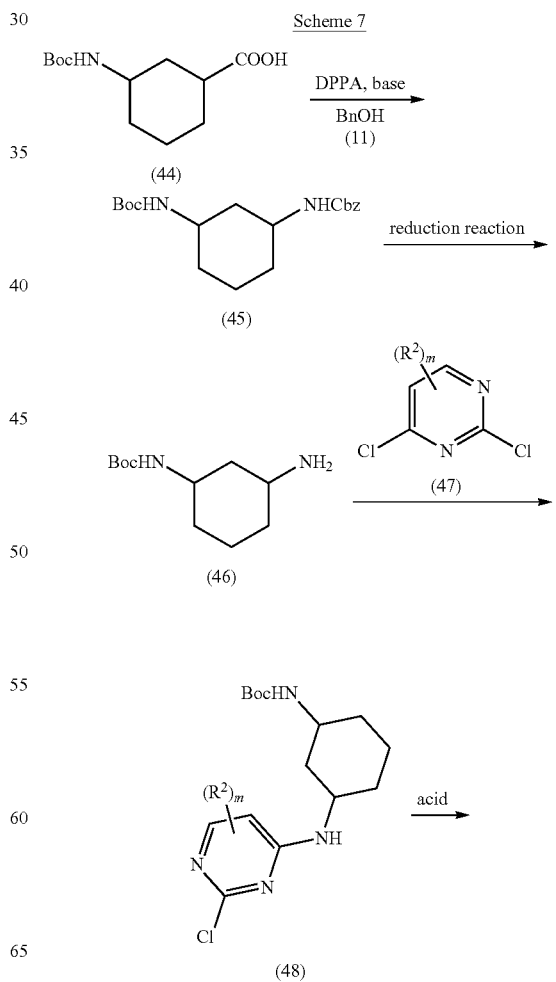

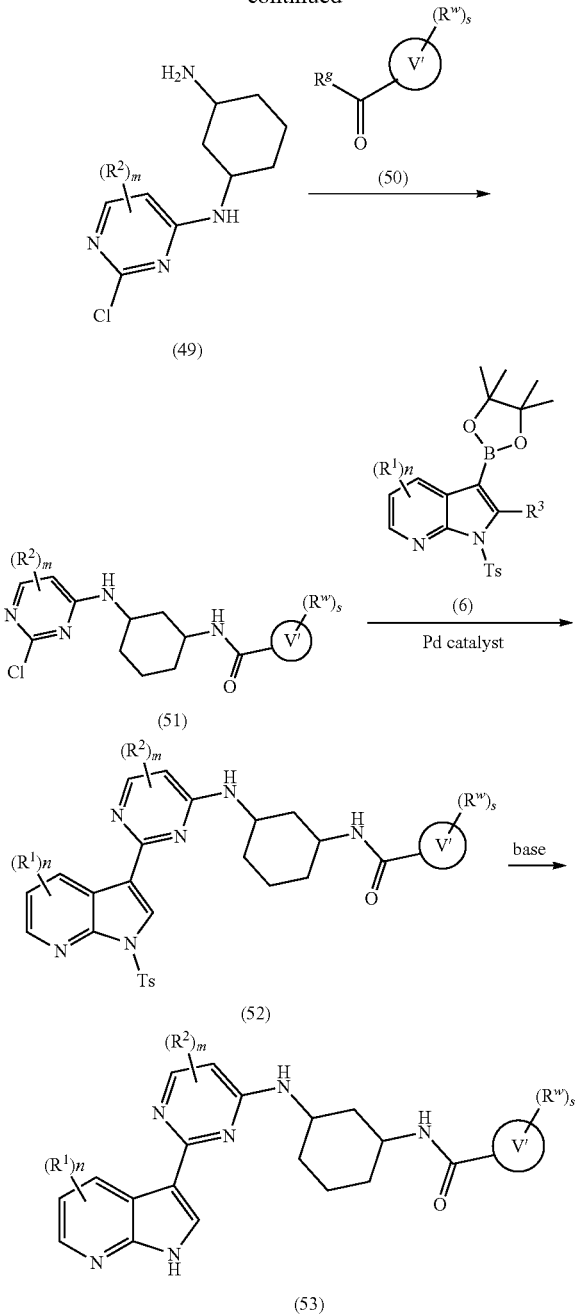

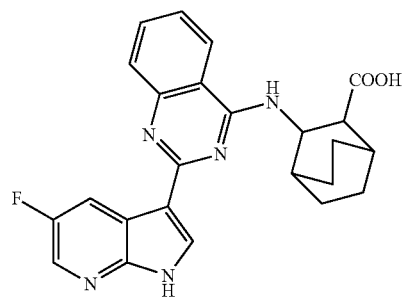 [SMILES: O=C(O)C1C2CCC(CC2)C1Nc1nc(-c2c[nH]c3ncc(F)cc23)nc2ccccc12]

Compound having Formula (53) can be prepared by the process illustrated in scheme 7. Firstly, compound (44) can react with DPPA and compound (11) under an alkaline condition to give compound (45). Then compound (45) can undergo a reduction reaction under a certain condition (such as in the presence of Pd/C catalyst and in a hydrogen atmosphere) to give compound (46). Compound (46) can react with compound (47) under an alkaline condition to give compound (48). Then an amino protection group on compound (48) can be removed under an acid condition to give compound (49). Compound (49) and compound (50) can undergo a condensation reaction to give compound (51). And Suzuki cross-coupling reaction can occur between compound (51) and compound (6) in the presence of a palladium catalyst to give compound (52). At last, a protecting group on compound (52) can be removed under an alkaline condition to give compound (53).

Description of the Preferred Embodiments

The following examples are used for illustrating the invention, but can not be construed to limit the scope of the invention.

EXAMPLES OF PREPARATION

Using parts of the compounds of the invention as examples, the preparations of the compounds of the present invention have been described in detail in the following examples.

Example 1: (+/−)-trans-3-((2-(5-fluoro-1H-pyrrolo[2,3-b]pyridin-3-yl)quinazolin-4-yl) amino)bicyclo[2.2.2]octane-2-carboxylic Acid Step 1: meso-endo-tetrahydro-4,7-ethanoisobenzofuran-1,3-dione To a 2000 mL dried flask were added maleic anhydride (100 g, 1.02 mol) and chloroform (1000.0 mL) in turn, then the mixture was cooled to 0° C., and 1,3-cyclohexadiene (112.5 mL, 1.12 mol) was added dropwise. After the addition, the mixture was warmed to rt, and stirred overnight in the absence of light. After the reaction was completed, the mixture was concentrated in vacuo to remove the solvent. To the residue was added methanol (700.0 mL), and the resulting mixture was heated to 50° C. and stirred for 10 min, then cooled to 0° C. and stirred for 30 min. The mixture was filtered, and the filter cake was dried in vacuo at 45° C. to give the title compound as a white solid (147 g, 81%).

MS (ESI, pos. ion) m/z: 179.1 [M+H]$^+$;

$^1$H NMR (400 MHz, DMSO-d$_6$) δ (ppm): 6.28 (dd, J=4.2, 3.4 Hz, 2H), 3.29 (s, 2H), 3.04 (s, 2H), 1.61 (d, J=7.9 Hz, 2H), 1.22 (d, J=7.6 Hz, 2H).

Step 2: (+/−)-trans-3-(methoxycarbonyl)bicyclo[2.2.2]oct-5-ene-2-carboxylic Acid To a dried flask was added meso-endo-tetrahydro-4,7-ethanoisobenzofuran-1,3-dione (33.50 g, 188.01 mmol), then a solution of sodium methoxide in methanol (5 M, 300.8 mL) was added dropwise at 0° C. After the addition, the mixture was warmed to rt and stirred for 4 days, then concentrated in vacuo to remove part of the methanol (about 120 mL). The residue was added slowly into 0° C. aqueous hydrochloric acid solution (277 mL, 18% wt), and there was a white solid precipitated out. The mixture was concentrated in vacuo to remove methanol, and the residue was stirred at 0° C. for 30 min, then filtered by suction. The filter cake was washed with water three times and dried in vacuo to give the title compound as a white solid (37.19 g, 94%).

MS (ESI, neg. ion) m/z: 209.0 [M−H]⁻;

¹H NMR (600 MHz, DMSO-d₆) δ (ppm): 12.28 (s, 1H), 6.34 (s, 1H), 6.17 (s, 1H), 3.65 (s, 3H), 2.94 (s, 1H), 2.91 (d, J=4.4 Hz, 1H), 2.86 (d, J=2.4 Hz, 1H), 2.72 (s, 1H), 1.48-1.58 (m, 1H), 1.34-1.44 (m, 1H), 1.26-1.16 (m, 1H), 1.09-0.99 (m, 1H).

Step 3: methyl (+/−)-trans-3-(((benzyloxy)carbonyl) amino)bicyclo[2.2.2]oct-5-ene-2-carboxylate A solution of (+/−)-trans-3-(methoxycarbonyl)bicyclo [2.2.2]oct-5-ene-2-carboxylic acid (6.0 g, 29 mmol) in toluene (50 mL) was degassed and filled with nitrogen for three times, then diphenyl azidophosphate (7.0 mL, 32 mmol) and triethylamine (4.0 mL, 29 mmol) were added in turn by syringe. The mixture was heated to 90° C. and stirred for 2 hours, then phenylcarbinol (3.0 mL, 29 mmol) was added dropwise by syringe. The mixture was stirred for further 3 days maintaining at this temperature. The reaction mixture was cooled to rt, and ethyl acetate (60 mL) was added to dilute the mixture. The resulting mixture was washed with saturated aqueous sodium bicarbonate (60 mL×2) and saturated brine (50 mL) in turn, and the organic layer was dried over anhydrous sodium sulfate, filtered, then the filtrate concentrated in vacuo. The residue was purified by silica gel column chromatography (PE/EtOAc (v/v)=8/1) to give the title compound as a yellow oil (8.25 g, 92%).

MS (ESI, pos. ion) m/z: 316.1 [M+H]⁺.

Step 4: methyl (+/−)-trans-methyl 3-aminobicyclo [2.2.2]octane-2-carboxylate

To an autoclave were added (+/−)-trans-methyl 3-(((benzyloxy)carbonyl)amino) bicyclo[2.2.2]oct-5-ene-2-carboxylate (8.21 g, 26.0 mmol), tetrahydrofuran (20 mL) and methanol (20 mL) in turn. To the solution was added Pd/C (10% wt of Pd, 1.40 g), and the mixture was stirred at rt overnight under a hydrogen pressure of 2.76 bar. The reaction mixture was filtered through a celite pad to remove the catalyst, then the filter cake was washed with methanol (20 mL) and ethyl acetate (20 mL) in turn. The combined filtrates were concentrated in vacuo to give colourless oil, which was purified by silica-gel column chromatography (DCM/MeOH (v/v)=20/1-10/1) to give the title compound as colourless oil (3.95 g, 83%).

MS (ESI, pos. ion) m/z: 184.2 [M+H]⁺;

¹H NMR (400 MHz, CDCl₃) δ (ppm): 3.68 (s, 3H), 3.31 (d, J=6.7 Hz, 1H), 2.11 (d, J=6.7 Hz, 1H), 1.98-1.91 (m, 1H), 1.83-1.71 (m, 1H), 1.60-1.33 (m, 10H).

Step 5: (+/−)-trans-methyl 3-((2-chloroquinazolin-4-yl)amino)bicyclo[2.2.2]octane-2-carboxylate To THF (20 mL) were added (+/−)-trans-methyl 3-aminobicyclo[2.2.2]octane-2-carboxylate (1.83 g, 9.99 mmol), 2,4-dichloroquinazoline (2.5 g, 15 mmol) and DIPEA (8.7 mL, 50 mmol). The mixture was stirred at rt overnight. The reaction mixture was quenched with water (100 mL). The resulting mixture was extracted with ethyl acetate (50 mL×2). The combined organic layers were washed with saturated brine (80 mL), dried over anhydrous sodium sulfate and filtered. The filtrate was concentrated in vacuo, and the residue was purified by silica gel column chromatography (PE/EtOAc (v/v)=4/1) to give the title compound as a white solid (3.13 g, 95%).

MS (ESI, pos. ion) m/z: 356.8 [M+H]⁺.

Step 6: 3-bromo-5-fluoro-1H-pyrrolo[2,3-b]pyridine

To the solution of 5-fluoro-1H-pyrrolo[2,3-b]pyridine (1 g, 7.34 mmol) in DMF (10 mL) was added bromine (0.75 mL, 14.5 mmol). The mixture was stirred at rt for 4 hours. The reaction mixture was quenched with saturated aqueous sodium thiosulfate (100 mL). The resulting mixture was extracted with ethyl acetate (100 mL×2). The combined organic layers were washed with saturated brine (100 mL×3), dried over anhydrous sodium sulfate and filtered. The filtrate was concentrated in vacuo, and the residue was purified by silica gel column chromatography (PE/EtOAc (v/v)=4/1) to give the title compound as yellow powder (0.6 g, 40%).

MS (ESI, pos. ion) m/z: 216.9 [M+H]⁺;

¹H NMR (400 MHz, DMSO-d₆) δ (ppm): 12.23 (s, 1H), 8.35-8.21 (m, 1H), 7.81 (d, J=2.7 Hz, 1H), 7.71 (dd, J=8.9, 2.6 Hz, 1H).

Step 7: 3-bromo-5-fluoro-1-tosyl-1H-pyrrolo[2,3-b] pyridine

To a solution of 3-bromo-5-fluoro-1H-pyrrolo[2,3-b]pyridine (0.74 g, 2.0 mmol) in THF (5 mL) was added NaH (127 mg, 3.0 mmol) at 0° C., and the mixture was stirred for 30 min maintaining at this temperature, then TsCl (458 mg, 2.4 mmol) was added. The resulting mixture was warmed to rt and stirred overnight. The reaction mixture was quenched with water (50 mL), and the resulting mixture was partitioned. The aqueous layer was extracted with ethyl acetate (50 mL×2). The combined organic layers were washed with saturated brine (80 mL), dried over anhydrous sodium sulfate, and filtered. The filtrate was concentrated in vacuo, and the residue was purified by silica gel column chromatography (PE/EtOAc (v/v)=4/1) to give the title compound as a yellow solid (740 mg, 90%).

MS (ESI, pos. ion) m/z: 370.8 [M+H]⁺;

¹H NMR (400 MHz, CDCl₃) δ (ppm): 8.32 (s, 1H), 8.06 (d, J=8.3 Hz, 2H), 7.84 (s, 1H), 7.47 (dd, J=7.8, 2.6 Hz, 1H), 7.29 (d, J=8.3 Hz, 2H), 2.38 (s, 3H).

Step 8: 5-fluoro-3-(4,4,5,5-tetramethyl-1,3,2-dioxaborolan-2-yl)-1-tosyl-1H-pyrrolo[2,3-b]pyridine To DME (5 mL) were added 3-bromo-5-fluoro-1-tosyl-1H-pyrrolo[2,3-b]pyridine (175 mg, 0.22 mmol), Pd(dppf)Cl₂ (70 mg, 0.09 mmol) and KOAc (144 mg, 0.47 mmol). The air in the mixture was removed by bubbling with nitrogen for 10 min, then to the mixture was added bis (pinacolato)diboron (190 mg, 0.71 mmol). The mixture in a tube was sealed and stirred at 105° C. for 2 h under microwave condition. After the reaction was completed, the reaction mixture was diluted with ethyl acetate (20 mL). Then the mixture was filtered through a celite pad, and the filter cake was washed with ethyl acetate (20 mL×2). The combined filtrates were concentrated in vacuo, and the residue was purified by silica-gel column chromatography (PE/EtOAc (v/v)=4/1) to give the title compound as a yellow solid (130 mg, 65.9%).

MS (ESI, pos. ion) m/z: 417.9 [M+H]$^+$;

$^1$H NMR (400 MHz, CDCl$_3$) δ (ppm): 8.27 (d, J=1.2 Hz, 1H), 8.19 (s, 1H), 8.08 (d, J=8.3 Hz, 2H), 7.89 (dd, J=8.5, 2.7 Hz, 1H), 7.30 (s, 1H), 7.28 (s, 1H), 2.39 (s, 3H), 1.37 (s, 12H).

Step 9: (+/−)-trans-methyl 3-((2-(5-fluoro-1-tosyl-1H-pyrrolo[2,3-b]pyridin-3-yl)quinazolin-4-yl)amino)bicyclo[2.2.2]octane-2-carboxylate To a mixed solvent of 2-methyltetrahydrofuran (8 mL) and water (1 mL) were added 5-fluoro-3-(4,4,5,5-tetramethyl-1,3,2-dioxaborolan-2-yl)-1-tosyl-1H-pyrrolo[2,3-b]pyridine (305 mg, 0.73 mmol), K$_3$PO$_4$ (276 mg, 1.31 mmol), Pd$_2$(dba)$_3$ (46 mg, 0.1 mmol), methyl 3-((2-chloroquinazolin-4-yl)amino)bicyclo[2.2.2]octane-2-carboxylate (150 mg, 0.43 mmol) and X-phos (23 mg, 0.1 mmol). The air in the mixture was removed by bubbling with nitrogen for 10 min. The mixture in a sealed tube was stirred at 110° C. for 3 hours. The mixture was diluted with ethyl acetate (20 mL) and then filtered through a celite pad. The filtrate was partitioned and the organic layer was concentrated in vacuo, then the residue was purified by silica gel column chromatography (PE/EtOAc (v/v)=4/1) to give the title compound as a white solid (255 mg, 97%).

MS (ESI, pos. ion) m/z: 600.2 [M+H]$^+$;

$^1$H NMR (400 MHz, CDCl$_3$) δ (ppm): 8.86 (dd, J=9.0, 2.8 Hz, 1H), 8.78 (s, 1H), 8.33 (d, J=1.9 Hz, 1H), 8.16 (d, J=8.4 Hz, 2H), 7.89 (d, J=8.2 Hz, 1H), 7.73 (dd, J=15.8, 7.6 Hz, 2H), 7.44 (t, J=7.2 Hz, 1H), 7.29 (d, J=8.9 Hz, 3H), 5.87 (d, J=6.3 Hz, 1H), 4.98 (s, 1H), 3.76 (s, 3H), 2.39 (s, 3H), 2.16-2.08 (m, 2H), 1.81-1.69 (m, 6H), 1.29-1.24 (m, 2H).

Step 10: (+/−)-trans-3-((2-(5-fluoro-1H-pyrrolo[2,3-b]pyridin-3-yl)quinazolin-4-yl)amino) bicyclo[2.2.2]octane-2-carboxylic Acid To a solution of (+/−)-trans-methyl 3-((2-(5-fluoro-1-tosyl-1H-pyrrolo[2,3-b]pyridin-3-yl)quinazolin-4-yl)amino)bicyclo[2.2.2]octane-2-carboxylate (150 mg, 0.25 mmol) in THF/MeOH (v/v=1/1, 8 mL) was added aqueous sodium hydroxide solution (4 M, 0.2 mL, 0.8 mmol). The mixture was stirred at 30° C. overnight, then diluted with water (10 mL). The resulting mixture was acidified with hydrochloric acid (1 M) to pH about 6.0, then extracted with ethyl acetate (15 mL×3). The combined organic layers were washed with saturated brine, dried over anhydrous sodium sulfate, filtered, and the filtrate was concentrated in vacuo to remove the solvent. The residue was purified by silica gel column chromatography (DCM/MeOH (v/v)=10/1) to give the title compound as a white solid (80 mg, 74%).

MS (ESI, pos. ion) m/z: 432.2 [M+H]$^+$;

HRMS (ESI, pos. ion) m/z: 432.1831 [M+H]$^+$, (C$_{24}$H$_{23}$FN$_5$O$_2$) [M+H]$^+$ theoretical value: 432.1836;

$^1$H NMR (400 MHz, DMSO-d$_6$) δ (ppm): 13.18 (s, 1H), 9.49 (s, 1H), 8.92 (s, 1H), 8.63 (d, J=7.9 Hz, 1H), 8.57 (d, J=8.4 Hz, 1H), 8.43 (s, 1H), 8.00 (s, 1H), 7.88 (s, 1H), 7.69 (s, 1H), 5.19 (s, 1H), 3.16 (s, 1H), 2.14 (s, 1H), 2.06 (s, 1H), 1.85 (s, 3H), 1.57 (m, 6H).

Example 2: (+/−)-trans-3-((2-(5-fluoro-1H-pyrrolo[2,3-b]pyridin-3-yl)-5,6,7,8-tetrahydro quinazolin-4-yl)amino)bicyclo[2.2.2]octane-2-carboxylic Acid

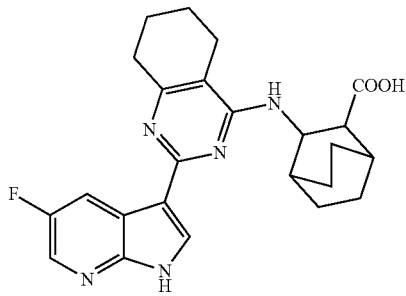 [SMILES: O=C(O)C1C2CCC(CC2)C1Nc1nc(-c2c[nH]c3ncc(F)cc23)nc2c1CCCC2]

Step 1: (+/−)-trans-methyl 3-((2-chloro-5,6,7,8-tetrahydroquinazolin-4-yl)amino)bicyclo[2.2.2]octane-2-carboxylate To THF (15 mL) were added (+/−)-trans-methyl 3-aminobicyclo[2.2.2]octane-2-carboxylate (0.68 g, 3.69 mmol), 2,4-dichloro-5,6,7,8-tetrahydroquinazoline (1.13 g, 2.46 mmol) and DIPEA (4.5 mL, 24.6 mmol). The mixture was stirred at 65° C. overnight. The reaction mixture was quenched with water (100 mL). The resulting mixture was extracted with ethyl acetate (50 mL×2). The combined organic layers were washed with saturated brine (80 mL), dried over anhydrous sodium sulfate and filtered. The filtrate was concentrated in vacuo, and the residue was purified by silica gel column chromatography (PE/EtOAc (v/v)=4/1) to give the title compound as a white solid (862 mg, 17%).

MS (ESI, pos. ion) m/z: 350.2 [M+H]$^+$;

$^1$H NMR (400 MHz, CDCl$_3$) δ (ppm): 4.75 (d, J=5.1 Hz, 1H), 4.43 (t, J=5.3 Hz, 1H), 3.77 (s, 3H), 2.68 (t, J=5.9 Hz, 2H), 2.35 (d, J=5.7 Hz, 1H), 2.29-2.23 (m, 2H), 2.05 (s, 1H), 1.96 (d, J=2.5 Hz, 1H), 1.89-1.76 (m, 6H), 1.67-1.54 (m, 5H), 1.26 (d, J=7.1 Hz, 1H).

Step 2: (+/−)-trans-methyl 3-((2-(5-fluoro-1-tosyl-1H-pyrrolo[2,3-b]pyridin-3-yl)-5,6,7,8-tetrahydroquinazolin-4-yl)amino)bicyclo[2.2.2]octane-2-carboxylate To a mixed solvent of 2-methyltetrahydrofuran (8 mL) and water (1 mL) were added 5-fluoro-3-(4,4,5,5-tetramethyl-1,3,2-dioxaborolan-2-yl)-1-tosyl-1H-pyrrolo[2,3-b]pyridine (251 mg, 0.59 mmol), K$_3$PO$_4$ (253 mg, 1.18 mmol), Pd$_2$(dba)$_3$ (83 mg, 0.1 mmol), (+/−)-trans-methyl 3-((2-chloro-5,6,7,8-tetrahydroquinazolin-4-yl)amino)bicyclo [2.2.2]octane-2-carboxylate (150 mg, 0.43 mmol) and X-phos (43 mg, 0.1 mmol). The air in the mixture was removed by bubbling with nitrogen for 10 min. The mixture in a sealed tube was stirred at 110° C. for 3 hours. The mixture was diluted with ethyl acetate (20 mL), and the resulting mixture was filtered through a celite pad. The filtrate was concentrated in vacuo, and the residue was purified by silica gel column chromatography (PE/EtOAc (v/v)=4/1) to give the title compound as a white solid (245 mg, 98%).

MS (ESI, pos. ion) m/z: 605.3 [M+H]$^+$;

$^1$H NMR (400 MHz, CDCl$_3$) δ (ppm): 8.66 (dd, J=9.0, 2.8 Hz, 1H), 8.61 (s, 1H), 8.12 (d, J=8.4 Hz, 2H), 7.28 (s, 3H), 3.71 (s, 3H), 2.78 (t, J=5.6 Hz, 2H), 2.39 (d, J=3.2 Hz, 4H), 2.06 (s, 1H), 2.01 (s, 1H), 1.89 (d, J=5.6 Hz, 5H), 1.76-1.67 (m, 5H), 1.37 (s, 3H), 1.27 (d, J=6.0 Hz, 3H).

Step 3: (+/−)-trans-methyl 3-((2-(5-fluoro-1H-pyrrolo[2,3-b]pyridin-3-yl)-5,6,7,8-tetrahydro quinazolin-4-yl) amino)bicyclo[2.2.2]octane-2-carboxylate To a solution of (+/−)-trans-methyl 3-((2-(5-fluoro-1-tosyl-1H-pyrrolo[2,3-b]pyridin-3-yl)-5,6,7,8-tetrahydroquinazolin-4-yl)amino)bicyclo[2.2.2]octane-2-carboxylate (295 mg, 0.49 mmol) in acetonitrile (3 mL) was added a solution of hydrogen chloride in 1,4-dioxane (4 M, 0.3 mL, 1.2 mmol). The mixture was stirred at 65° C. for 6.5 hours, and then diluted with water (10 mL). The resulting mixture was extracted with ethyl acetate (20 mL×3). The combined organic layers were washed with saturated brine (30 mL×2), dried over anhydrous sodium sulfate, filtered and concentrated in vacuo. The residue was purified by silica gel column chromatography (PE/EtOAc (v/v)=2/1) to give the title compound as a white solid (143 mg, 65%).

MS (ESI, pos. ion) m/z: 450.3 [M+H]⁺;

¹H NMR (400 MHz, CDCl₃) δ (ppm): 10.58 (s, 1H), 8.70 (dd, J=9.4, 2.6 Hz, 1H), 8.36 (s, 1H), 8.23 (s, 1H), 4.81 (t, J=5.7 Hz, 1H), 4.66 (d, J=6.6 Hz, 1H), 3.64 (s, 3H), 2.81 (d, J=5.6 Hz, 2H), 2.41 (d, J=5.7 Hz, 1H), 2.35 (d, J=6.0 Hz, 2H), 2.05 (s, 2H), 1.88 (d, J=5.2 Hz, 5H), 1.73-1.49 (m, 7H).

Step 4: (+/−)-trans-3-((2-(5-fluoro-1H-pyrrolo[2,3-b]pyridin-3-yl)-5,6,7,8-tetrahydroquinazolin-4-yl) amino)bicyclo[2.2.2]octane-2-carboxylic Acid To a solution of (+/−)-trans-methyl 3-((2-(5-fluoro-1H-pyrrolo[2,3-b]pyridin-3-yl)-5,6,7,8-tetrahydroquinazolin-4-yl)amino)bicyclo[2.2.2]octane-2-carboxylate (105 mg, 0.27 mmol) in THF/MeOH (v/v=1/1, 8 mL) was added aqueous sodium hydroxide solution (4 M, 0.6 mL, 2.4 mmol). The mixture was stirred at 30° C. overnight, then diluted with water (10 mL). The resulting mixture was acidified with hydrochloric acid (1 M) to pH about 6.0, then extracted with ethyl acetate (20 mL×3). The combined organic layers were washed with saturated brine, dried over anhydrous sodium sulfate, filtered, and the filtrate was concentrated in vacuo to remove the solvent. The residue was purified by silica gel column chromatography (DCM/MeOH (v/v)=10/1) to give the title compound as a white solid (105 mg, 88%).

MS (ESI, pos. ion) m/z: 436.3 [M+H]⁺;

HRMS (ESI, pos. ion) m/z: 436.2143 [M+H]⁺, (C₂₄H₂₆FN₅O₂) [M+H]⁺ theoretical value: 436.2149;

¹H NMR (400 MHz, DMSO-d₆) δ (ppm): 12.35 (s, 1H), 8.57 (dd, J=9.7, 2.6 Hz, 1H), 8.41 (s, 1H), 8.26 (s, 1H), 6.68 (s, 1H), 4.78 (s, 1H), 2.97 (d, J=6.4 Hz, 1H), 2.68 (s, 2H), 2.51 (s, 3H), 2.41 (s, 1H), 2.00 (s, 1H), 1.92 (s, 1H), 1.77 (s, 6H), 1.33 (d, J=7.2 Hz, 2H), 1.21 (s, 2H).

Example 3: (+/−)-trans-3-((2-(5-fluoro-1H-pyrrolo[2,3-b]pyridin-3-yl)-6-(4-methoxyphenyl) pyrimidin-4-yl)amino)bicyclo[2.2.2]octane-2-carboxylic Acid

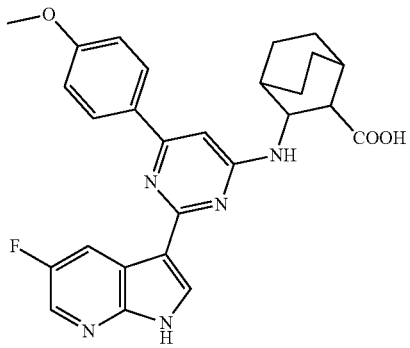 [SMILES: COc1ccc(-c2cc(NC3C4CCC(CC4)C3C(=O)O)nc(-c3c[nH]c4ncc(F)cc34)n2)cc1]

Step 1: 2,4-dichloro-6-(4-methoxyphenyl)pyrimidine

To a solution of 2,4,6-trichloropyrimidine (5.5 mL, 48 mmol) in THF (70 mL) were added palladium acetate (0.147 g, 0.64 mmol), triphenylphosphine (0.353 g, 1.28 mmol), 4-methoxybenzeneboronic acid (5 g, 31.9 mmol) and aqueous sodium carbonate solution (1 M, 64 mL, 64 mmol). The mixture was stirred at 60° C. for 6 h. After the reaction was completed, the mixture was cooled to rt, and concentrated in vacuo to remove the solvent. To the residue was added H₂O (100 mL), and the mixture was extracted with ethyl acetate (100 mL×3). The combined organic layers were washed with saturated brine (100 mL), dried over anhydrous sodium sulfate, filtered, and the filtrate was concentrated in vacuo. The residue was purified by silica gel column chromatography (PE) to give the title compound as a white solid (5.58 g, 68%).

MS (ESI, pos.ion) m/z: 255.0 [M+H]⁺;
¹H NMR (400 MHz, CDCl₃) δ (ppm): 8.07 (dd, J=9.4, 2.4 Hz, 2H), 7.60 (s, 1H), 7.08-6.99 (m, 2H), 3.91 (s, 3H).

Step 2: (+/−)-trans-methyl 3-((2-chloro-6-(4-methoxyphenyl)pyrimidin-4-yl)amino) bicyclo[2.2.2]octane-2-carboxylate To a solution of 2,4-dichloro-6-(4-methoxyphenyl)pyrimidine (1 g, 3.92 mmol) and (+/−)-trans-methyl 3-aminobicyclo[2.2.2]octane-2-carboxylate (1 g, 5.88 mmol) in N,N-dimethylformamide (20 mL) was added potassium carbonate (0.813 g, 5.88 mmol). The mixture was stirred at 50° C. overnight. After the reaction was completed, the mixture was diluted with H₂O (70 mL), and the resulting mixture was extracted with ethyl acetate (100 mL×3). The combined organic layers were washed with saturated brine (100 mL), dried over anhydrous sodium sulfate, filtered, and the filtrate was concentrated in vacuo to remove the solvent. The residue was purified by silica gel column chromatography (n-hexane/EtOAc (v/v)=20/1-5/1) to give the title compound as a white solid (1.01 g, 64%).

MS (ESI, pos.ion) m/z: 402.2 [M+H]⁺;
¹H NMR (400 MHz, CDCl₃) δ (ppm): 7.98 (d, J=8.7 Hz, 2H), 6.98 (d, J=8.9 Hz, 2H), 6.72 (s, 1H), 5.46 (d, J=6.3 Hz, 1H), 4.32 (s, 1H), 3.88 (s, 4H), 3.74 (s, 3H), 2.39 (d, J=5.1

Hz, 1H), 2.08 (s, 1H), 1.90-1.84 (m, 1H), 1.78-1.71 (m, 2H), 1.70-1.63 (m, 4H), 1.58 (d, J=10.2 Hz, 2H).

Step 3: (+/−)-trans-methyl 3-((2-(5-fluoro-1-tosyl-1H-pyrrolo[2,3-b]pyridin-3-yl)-6-(4-methoxyphenyl)pyrimidin-4-yl)amino)bicyclo[2.2.2]octane-2-carboxylate To a microwave tube were added (+/−)-trans-methyl 3-((2-chloro-6-(4-methoxyphenyl) pyrimidin-4-yl)amino) bicyclo[2.2.2]octane-2-carboxylate (550 mg, 1.368 mmol), 5-fluoro-3-(4,4,5,5-tetramethyl-1,3,2-dioxaborolan-2-yl)-1-tosyl-1H-pyrrolo[2,3-b]pyridine (630 mg, 1.513 mmol), potassium carbonate (380 mg, 2.75 mmol), Pd(dppf)Cl$_2$ (120 mg, 0.147 mmol), 1,4-dioxane (15 mL) and H$_2$O (0.5 mL). The air in the mixture was removed by bubbling with nitrogen for 10 min. The mixture in microwave tube was stirred at 110° C. undergoing a microwave reaction for 2 h. The mixture was filtered through a celite pad, and the filter cake was washed with ethyl acetate. The combined filtrates was concentrated in vacuo, and the residue was purified by silica gel column chromatography (n-hexane/EtOAc (v/v)=15/1) to give the title compound as a yellow solid (816 mg, 91%).

MS (ESI, pos. ion) m/z: 656.2 [M+H]$^+$;
$^1$H NMR (600 MHz, CDCl$_3$) δ (ppm): 8.70 (s, 1H), 8.32 (d, J=1.8 Hz, 1H), 8.13 (s, 1H), 8.11 (s, 1H), 8.08 (s, 1H), 8.06 (s, 1H), 7.29 (s, 1H), 7.28 (s, 1H), 7.06 (s, 1H), 7.04 (s, 1H), 6.68 (s, 1H), 5.25 (s, 1H), 3.91 (s, 3H), 3.73 (s, 3H), 2.45 (d, J=5.3 Hz, 1H), 2.38 (s, 3H), 1.98 (s, 1H), 1.84 (d, J=11.8 Hz, 2H), 1.75-1.65 (m, 6H), 1.62-1.53 (m, 2H).

Step 4: (+/−)-trans-methyl 3-((2-(5-fluoro-1H-pyrrolo[2,3-b]pyridin-3-yl)-6-(4-methoxyphenyl)pyrimidin-4-yl)amino)bicyclo[2.2.2]octane-2-carboxylate To a solution of (+/−)-trans-methyl 3-((2-(5-fluoro-1-tosyl-1H-pyrrolo[2,3-b]pyridin-3-yl)-6-(4-methoxyphenyl)pyrimidin-4-yl)amino)bicyclo[2.2.2]octane-2-carboxylate (816 mg, 1.244 mmol) in 1,4-dioxane (10 mL) was added a solution of hydrogen chloride in dioxane (4 M, 10 mL, 40 mmol). The mixture was stirred at 65° C. overnight. After the reaction was completed, the mixture was diluted with ethyl acetate (20 mL), and the resulting mixture was washed with saturated aqueous sodium bicarbonate (20 mL). The organic layer was dried over anhydrous sodium sulfate, filtered, and the filtrate was concentrated in vacuo. The residue was purified by silica gel column chromatography (n-hexane/EtOAc (v/v)=5/1) to give the title compound as a brown solid (350 mg, 56%).

MS (ESI, pos. ion) m/z: 502.2 [M+H]$^+$.

Step 5: (+/−)-trans-3-((2-(5-fluoro-1H-pyrrolo[2,3-b]pyridin-3-yl)-6-(4-methoxyphenyl) pyrimidin-4-yl)amino)bicyclo[2.2.2]octane-2-carboxylic Acid To a solution of (+/−)-trans-methyl 3-((2-(5-fluoro-1H-pyrrolo[2,3-b]pyridin-3-yl)-6-(4-methoxyphenyl)pyrimidin-4-yl)amino)bicyclo[2.2.2]octane-2-carboxylate (350 mg, 0.69 mmol) in a mixed solvent of MeOH (5 mL), THF (5 mL) and H$_2$O (5 mL) was added sodium hydroxide (280 mg, 7.00 mmol). The mixture was stirred at rt overnight. After the reaction was completed, the mixture was diluted with 2-methyl tetrahydrofuran (20 mL), and the mixture was adjusted with diluted hydrochloric acid (1 M) to pH 6.0. The resulting mixture was extracted with 2-methyl tetrahydrofuran (20 mL×3). The combined organic layers were dried over anhydrous sodium sulfate, filtered, and the filtrate was concentrated in vacuo. The residue was purified by silica gel column chromatography (n-hexane/EtOAc (v/v)=1/1) to give the title compound as a light yellow solid (270 mg, 79%).

MS (ESI, pos. ion) m/z: 476.4 [M+H]$^+$;
$^1$H NMR (400 MHz, CD$_3$OD) δ (ppm): 8.78 (dd, J=9.5, 2.5 Hz, 1H), 8.40 (s, 1H), 8.17 (s, 1H), 8.04 (s, 1H), 8.02 (s, 1H), 7.09 (s, 1H), 7.07 (s, 1H), 6.68 (s, 1H), 3.89 (s, 3H), 2.56 (d, J=5.9 Hz, 1H), 2.09 (s, 1H), 2.03 (s, 1H), 1.91 (d, J=11.4 Hz, 2H), 1.80-1.70 (m, 4H), 1.57 (s, 1H), 1.54 (s, 1H);
$^{13}$C NMR (151 MHz, DMSO-d$_6$) δ (ppm): 176.05, 163.07, 162.34, 161.21, 156.85, 155.26, 146.46, 131.73, 131.53, 130.62, 128.21, 119.09, 119.03, 115.16, 114.56, 114.33, 60.24, 55.72, 28.80, 28.57, 26.02, 24.17, 21.38, 19.42, 14.53.

Example 4: (+/−)-trans-3-((2-(5-fluoro-1H-pyrrolo[2,3-b]pyridin-3-yl)-6-phenylpyrimidin-4-yl)amino)bicyclo[2.2.2]octane-2-carboxylic Acid

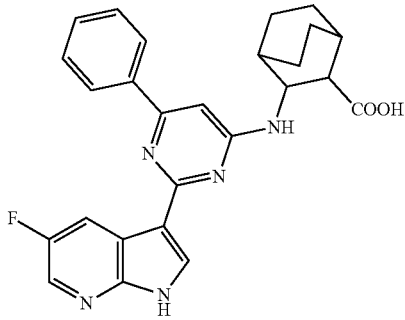 [SMILES: O=C(O)C1C2CCC(CC2)C1Nc1cc(-c2ccccc2)nc(-c2c[nH]c3ncc(F)cc23)n1]

Step 1: 2,4-dichloro-6-phenylpyrimidine

To a solution of 2,4,6-trichloropyrimidine (0.29 mL, 2.5 mmol) in THF (5 mL) were added palladium acetate (8 mg, 0.035 mmol), triphenylphosphine (18 mg, 0.065 mmol), phenylboronic acid (0.20 g, 1.6 mmol) and aqueous sodium carbonate solution (1 M, 3.3 mL, 3.3 mmol). The mixture was stirred at 60° C. for 6 h under nitrogen protection. After the reaction was completed, the mixture was cooled to rt, and concentrated in vacuo to remove the organic solvent. To the residue was added H$_2$O (10 mL), and the resulting mixture was extracted with ethyl acetate (10 mL×3). The combined organic layers were washed with saturated brine (10 mL), dried over anhydrous sodium sulfate, filtered, and the filtrate was concentrated in vacuo. The residue was purified by silica gel column chromatography (PE) to give the title compound as a white solid (0.225 g, 61%).

MS (ESI, pos. ion) m/z: 225.0 [M+H]$^+$;
$^1$H NMR (400 MHz, CDCl$_3$) δ (ppm): 8.15-8.04 (m, 2H), 7.70 (s, 1H), 7.63-7.50 (m, 3H).

Step 2: (+/−)-trans-methyl 3-((2-chloro-6-phenylpyrimidin-4-yl)amino)bicyclo[2.2.2]octane-2-carboxylate To a solution of 2,4-dichloro-6-phenylpyrimidine (1.52 g, 6.7 mmol) and (±)-trans-methyl 3-aminobicyclo[2.2.2]octane-2-carboxylate (1.84 g, 10.0 mmol) in N,N-dimethylformamide (10 mL) was added potassium carbonate (0.92 g, 6.7 mmol). The mixture was stirred at rt overnight. After the reaction was completed, the mixture was diluted with H$_2$O (50 mL), and the resulting mixture was extracted with ethyl acetate (40 mL×3). The combined organic layers were washed with saturated brine (50 mL), dried over anhydrous sodium sulfate and filtered, and the filtrate was concentrated in vacuo. The residue was purified by silica gel column chromatography (n-hexane/EtOAc (v/v)=20/1-10/1) to give the title compound as a white solid (1.65 g, 66%).

MS (ESI, pos.ion) m/z: 372.2 [M+H]$^+$;

$^1$H NMR (400 MHz, CDCl$_3$) δ (ppm): 8.04-7.91 (m, 2H), 7.51-7.41 (m, 3H), 6.78 (s, 1H), 5.41 (s, 1H), 4.32 (s, 1H), 3.73 (s, 3H), 2.38 (d, J=5.1 Hz, 1H), 2.07 (s, 1H), 1.86 (m, 1H), 1.73 (m, 1H), 1.70-1.60 (m, 4H), 1.57 (m, 2H), 1.51-1.41 (m, 1H).

Step 3: (+/−)-trans-methyl 3-((2-(5-fluoro-1-tosyl-1H-pyrrolo[2,3-b]pyridin-3-yl)-6-phenylpyrimidin-4-yl)amino)bicyclo[2.2.2]octane-2-carboxylate To a microwave tube were added 5-fluoro-3-(4,4,5,5-tetramethyl-1,3,2-dioxaborolan-2-yl)-1-tosyl-1H-pyrrolo[2,3-b]pyridine (240 mg, 0.57 mmol), (+/−)-trans-methyl 3-((2-chloro-6-phenylpyrimidin-4-yl)amino)bicyclo[2.2.2]octane-2-carboxylate (220 mg, 0.59 mmol), potassium carbonate (160 mg, 1.16 mmol), Pd(dppf)Cl$_2$ (43 mg, 0.06 mmol), 1,4-dioxane (4 mL) and H$_2$O (0.5 mL). The air in the mixture was removed by bubbling with nitrogen for 10 min. The mixture in microwave tube was stirred at 110° C. undergoing a microwave reaction for 1 h. The mixture was filtered through a celite pad, and the filter cake was washed with ethyl acetate (30 mL). The combined filtrates were concentrated in vacuo, and the residue was purified by silica gel column chromatography (n-hexane/EtOAc (v/v)=10/1) to give the title compound as a white solid (218 mg, 60%).

MS (ESI, pos. ion) m/z: 626.3 [M+H]$^+$;

$^1$H NMR (400 MHz, CDCl$_3$) δ (ppm): 8.78-8.65 (m, 2H), 8.33 (d, J=1.8 Hz, 1H), 8.14 (d, J=8.4 Hz, 2H), 8.11 (d, J=8.2 Hz, 2H), 7.60-7.47 (m, 3H), 7.31 (s, 2H), 6.75 (s, 1H), 5.19 (s, 1H), 4.56 (s, 1H), 3.75 (s, 3H), 2.46 (d, J=5.4 Hz, 1H), 2.39 (s, 3H), 2.11 (d, J=2.3 Hz, 1H), 1.99 (s, 1H), 1.92-1.78 (m, 2H), 1.77-1.60 (m, 5H).

Step 4: (+/−)-trans-methyl 3-((2-(5-fluoro-1H-pyrrolo[2,3-b]pyridin-3-yl)-6-phenylpyrimidin-4-yl)amino)bicyclo[2.2.2]octane-2-carboxylate To a solution of (+/−)-trans-methyl 3-((2-(5-fluoro-1-tosyl-1H-pyrrolo[2,3-b]pyridin-3-yl)-6-phenylpyrimidin-4-yl)amino)bicyclo[2.2.2]octane-2-carboxylate (215 mg, 0.3 mmol) in 1,4-dioxane (5 mL) was added a solution of hydrogen chloride in 1,4-dixoane (4 M, 0.6 mL, 2.4 mmol). The mixture was stirred at 70° C. overnight. After the reaction was completed, the mixture was diluted with ethyl acetate (10 mL), and the mixture was washed with saturated aqueous sodium bicarbonate (20 mL). The organic layer was dried over anhydrous sodium sulfate and concentrated in vacuo. The residue was purified by silica gel column chromatography (n-hexane/EtOAc (v/v)=15/1) to give the title compound as a light yellow solid (125 mg, 77%).

MS (ESI, pos.ion) m/z: 472.2 [M+H]$^+$;

$^1$H NMR (400 MHz, CD$_3$OD) δ (ppm): 8.78 (s, 1H), 8.64 (d, J=9.3 Hz, 1H), 8.34 (s, 1H), 7.84 (d, J=4.8 Hz, 2H), 7.64 (s, 3H), 6.74 (s, 1H), 5.12 (s, 1H), 3.66 (s, 3H), 2.74 (d, J=5.7 Hz, 1H), 2.12 (s, 1H), 1.77 (m, 9H), 1.30 (s, 2H).

Step 5: (+/−)-trans-3-((2-(5-fluoro-1H-pyrrolo[2,3-b]pyridin-3-yl)-6-phenylpyrimidin-4-yl)amino)bicyclo[2.2.2]octane-2-carboxylic Acid To a solution of (+/−)-trans-methyl 3-((2-(5-fluoro-1H-pyrrolo[2,3-b]pyridin-3-yl)-6-phenylpyrimidin-4-yl)amino)bicyclo[2.2.2]octane-2-carboxylate (285 mg, 0.60 mmol) in a mixed solvent of methanol (2 mL), THF (2 mL) and water (2 mL) was added sodium hydroxide (250 mg, 6.25 mmol). The mixture was stirred at rt overnight. After the reaction was completed, the mixture was concentrated in vacuo to remove the organic solvent. The residue was diluted with 2-methyl tetrahydrofuran (10 mL), and the mixture was adjusted with diluted hydrochloric acid (1 M) to pH 5.5-6.0. The resulting mixture was extracted with 2-methyl tetrahydrofuran (15 mL×3). The combined organic layers were dried over anhydrous sodium sulfate, filtered, and the filtrate was concentrated in vacuo. The residue was purified by silica gel column chromatography (DCM/MeOH (v/v)=50/1) to give the title compound as a light yellow solid (120 mg, 43%).

MS (ESI, pos.ion) m/z: 458.3 [M+H]$^+$;

$^1$H NMR (400 MHz, DMSO-d$_6$) δ (ppm): 12.27 (s, 1H), 8.64 (s, 1H), 8.39 (d, J=2.2 Hz, 1H), 8.29 (s, 1H), 8.11 (s, 2H), 7.64-7.41 (m, 4H), 6.76 (s, 1H), 4.65 (s, 1H), 2.01 (m, 2H), 1.81 (m, 2H), 1.46 (m, 8H);

$^{13}$C NMR (151 MHz, DMSO-d$_6$) δ (ppm): 175.94, 162.91, 162.39, 156.77, 155.25, 154.46, 146.46, 138.34, 131.76, 131.36, 130.31, 129.23, 126.76, 119.05, 115.41, 114.21, 98.26, 31.75, 29.54, 28.51, 24.18, 22.56, 21.38, 19.43.

Example 4a: (2S,3S)-3-((2-(5-fluoro-1H-pyrrolo[2,3-b]pyridin-3-yl)-6-phenylpyrimidin-4-yl) amino) bicyclo[2.2.2]octane-2-carboxylic Acid

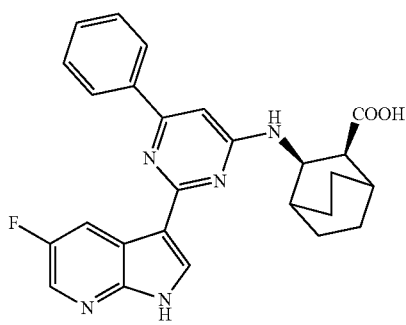 [SMILES: O=C(O)[C@H]1C2CCC(CC2)[C@H]1Nc1cc(-c2ccccc2)nc(-c2c[nH]c3ncc(F)cc23)n1]

Step 1: (2S,3S)-ethyl 3-aminobicyclo[2.2.2]octane-2-carboxylate hydrochloride

The title compound can be prepared by the synthetic method disclosed in patent application WO 2015073491.

Step 2: (2S,3S)-ethyl 3-((2-chloro-6-phenylpyrimidin-4-yl)amino)bicyclo[2.2.2]octane-2-carboxylate The title compound can be prepared by the synthetic method described in step 2 of example 4, using (2S,3S)-ethyl 3-aminobicyclo[2.2.2]octane-2-carboxylate hydrochloride (316 mg, 1.35 mmol), 2,4-dichloro-6-phenylpyrimidine (334 mg, 1.49 mmol), potassium carbonate (560 mg, 4.05 mmol) as reagents and DMF (6 mL) as solvent. The title compound was a light yellow solid (291 mg, 56%).

Step 3: (2S,3S)-ethyl 3-((2-(5-fluoro-1-tosyl-1H-pyrrolo[2,3-b]pyridin-3-yl)-6-phenylpyrimidin-4-yl)amino)bicyclo[2.2.2]octane-2-carboxylate The title compound can be prepared by the synthetic method described in step 3 of example 4, using (2S,3S)-ethyl 3-((2-chloro-6-phenylpyrimidin-4-yl)amino)bicyclo[2.2.2]octane-2-carboxylate (291 mg, 0.75 mmol), 5-fluoro-3-(4,4,5,5-tetramethyl-1,3,2-dioxaborolan-2-yl)-1-tosyl-1H-pyrrolo[2,3-b]pyridine (437 mg, 1.05 mmol), potassium carbonate (207 mg, 1.50 mmol), Pd(dppf)Cl$_2$ (58 mg, 0.08 mmol), 1,4-dioxane (5 mL) and water (0.5 mL), the title compound is a light yellow solid (249 mg, 52%).

Step 4: (2S,3S)-3-((2-(5-fluoro-1H-pyrrolo[2,3-b]pyridin-3-yl)-6-phenylpyrimidin-4-yl)amino) bicyclo[2.2.2]octane-2-carboxylic Acid To a solution of (2S,3S)-ethyl 3-((2-(5-fluoro-1-tosyl-1H-pyrrolo[2,3-b]pyridin-3-yl)-6-phenylpyrimidin-4-yl)amino)bicyclo[2.2.2]octane-2-carboxylate (249 mg, 0.39 mmol) in THF/MeOH (v/v=1/1, 6 mL) was added aqueous sodium hydroxide solution (4 M, 0.98 mL, 3.90 mmol). The mixture was stirred at 30° C. overnight. To the reaction mixture was added water (10 mL), and the resulting mixture was acidified with hydrochloric acid (1 M) to pH about 5.5. The mixture was extracted with ethyl acetate (20 mL×3), and the combined organic layers were dried over anhydrous sodium sulfate, then filtered. The filtrate was concentrated in vacuo and the residue was purified by silica gel column chromatography (DCM/MeOH (v/v)=10/1) to give the title compound as a yellow solid (109 mg, 61%).
MS (ESI, pos.ion) m/z: 458.2 [M+H]$^+$;
HRMS (ESI, pos. ion) m/z: 458.1983[M+H]$^+$, (C$_{26}$H$_{25}$FN$_5$O$_2$) [M+H]$^+$ theoretical value: 458.1992;
$^1$H NMR (600 MHz, DMSO-d$_6$) δ (ppm): 12.27 (s, 1H), 8.63 (s, 1H), 8.39 (s, 1H), 8.29 (s, 1H), 8.10 (s, 2H), 7.53 (m, 4H), 6.77 (s, 1H), 4.65 (s, 1H), 1.99 (s, 2H), 1.81 (s, 2H), 1.74-1.54 (m, 4H), 1.47-1.39 (m, 2H).

Example 5: (+/−)-trans-3-((2-(5-fluoro-1H-pyrrolo[2,3-b]pyridin-3-yl)-6-(2-fluorophenyl) pyrimidin-4-yl) amino)bicyclo[2.2.2]octane-2-carboxylic Acid

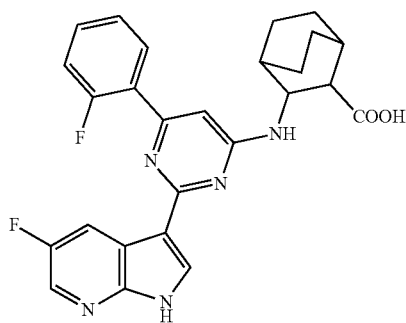 [SMILES: O=C(O)C1C2CCC(CC2)C1Nc1cc(-c2ccccc2F)nc(-c2c[nH]c3ncc(F)cc23)n1]

Step 1: 2,4-dichloro-6-(2-fluorophenyl)pyrimidine

To a solution of 2,4,6-trichloropyrimidine (3.0 mL, 25.57 mmol) in THF (20 mL) were added palladium acetate (0.1 g, 0.4 mmol), triphenylphosphine (0.24 g, 0.87 mmol), 2-fluorophenylboronic acid (3 g, 21 mmol) and aqueous sodium carbonate solution (1 M, 43 mL, 43 mmol). The mixture was stirred at 60° C. for 4 h under nitrogen protection. After the reaction was completed, the mixture was cooled to rt, and concentrated in vacuo. To the residue was added H$_2$O (100 mL), and the resulting mixture was extracted with ethyl acetate (100 mL×3). The combined organic layers were washed with saturated brine (100 mL), dried over anhydrous sodium sulfate, filtered, and the filtrate was concentrated in vacuo. The residue was purified by silica gel column chromatography (PE) to give the title compound as a white solid (3.5 g, 67%).
MS (ESI, pos. ion) m/z: 243.1 [M+H]$^+$.

Step 2: (+/−)-trans-methyl 3-((2-chloro-6-(2-fluorophenyl)pyrimidin-4-yl)amino)bicyclo[2.2.2]octane-2-carboxylate To a solution of 2,4-dichloro-6-(2-fluorophenyl)pyrimidine (2.01 g, 8.2 mmol) and (+/−)-trans-methyl 3-aminobicyclo[2.2.2]octane-2-carboxylate (1.50 g, 8.2 mmol) in N,N-dimethylformamide (10 mL) was added potassium carbonate (1.10 g, 8 mmol). The mixture was stirred at rt overnight. After the reaction was completed, to the mixture was added H$_2$O (40 mL), and the resulting mixture was extracted with ethyl acetate (40 mL×3). The combined organic layers were washed with saturated brine (50 mL), dried over anhydrous sodium sulfate, filtered, and the filtrate was concentrated in vacuo. The residue was purified by silica gel column chromatography (n-hexane) to give the title compound as a white solid (2.26 g, 71%).
MS (ESI, pos.ion) m/z: 390.2 [M+H]$^+$;
$^1$H NMR (400 MHz, CDCl$_3$) δ (ppm): 8.11 (td, J=7.8, 1.6 Hz, 1H), 7.44 (td, J=7.3, 1.7 Hz, 1H), 7.26 (d, J=7.5 Hz, 1H), 7.16 (dd, J=11.6, 8.3 Hz, 1H), 6.89 (s, 1H), 5.37 (d, J=4.5 Hz, 1H), 4.38-4.28 (m, 1H), 3.76 (s, 3H), 2.39 (d, J=5.3 Hz, 1H), 2.06 (s, 1H), 1.88 (d, J=2.6 Hz, 1H), 1.82-1.61 (m, 8H).

Step 3: (+/−)-trans-methyl 3-((2-(5-fluoro-1-tosyl-1H-pyrrolo[2,3-b]pyridin-3-yl)-6-(2-fluorophenyl)pyrimidin-4-yl)amino)bicyclo[2.2.2]octane-2-carboxylate To a mixed solvent of 1,4-dioxane (15 mL) and H$_2$O (0.5 mL) were added (+/−)-trans-methyl 3-((2-chloro-6-(2-fluorophenyl)pyrimidin-4-yl)amino)bicyclo[2.2.2]octane-2-carboxylate (590 mg, 1.51 mmol), 5-fluoro-3-(4,4,5,5-tetramethyl-1,3,2-dioxaborolan-2-yl)-1-tosyl-1H-pyrrolo[2,3-b]pyridine (630 mg, 1.51 mmol), potassium carbonate (419 mg, 3.03 mmol) and Pd(dppf)Cl$_2$ (124 mg, 0.15 mmol). The air in the mixture was removed by bubbling with nitrogen for 10 min, and then stirred at 110° C. undergoing a microwave reaction for 1 h. The mixture was filtered through a celite pad, and the filter cake was washed with ethyl acetate (20 mL). The combined filtrates was concentrated in vacuo, and the residue was purified by silica gel column chromatography (n-hexane/EtOAc (v/v)=15/1) to give the title compound as a yellow solid (500 mg, 51%).
MS (ESI, pos.ion) m/z: 644.2 [M+H]$^+$;
$^1$H NMR (600 MHz, CDCl$_3$) δ (ppm): 8.71 (s, 1H), 8.66 (dd, J=8.8, 2.6 Hz, 1H), 8.33 (d, J=1.9 Hz, 1H), 8.22-8.18 (m, 1H), 8.13 (d, J=8.1 Hz, 2H), 7.46 (dd, J=12.2, 6.5 Hz, 1H), 7.39 (s, 1H), 7.36 (s, 2H), 7.35 (s, 1H), 7.30 (s, 1H), 6.83 (s, 1H), 4.95 (s, 1H), 4.73 (s, 1H), 3.81 (s, 3H), 3.75 (s, 3H), 3.62 (s, 1H), 2.46 (d, J=4.9 Hz, 1H), 2.42 (d, J=5.0 Hz, 1H), 2.10 (d, J=2.1 Hz, 1H), 2.00 (s, 1H), 1.60 (d, J=14.8 Hz, 1H), 1.53-1.47 (m, 1H), 1.41-1.38 (m, 1H), 1.37 (d, J=1.3 Hz, 1H), 1.19 (s, 1H).

Step 4: (+/−)-trans-methyl 3-((2-(5-fluoro-1H-pyrrolo[2,3-b]pyridin-3-yl)-6-(2-fluorophenyl) pyrimidin-4-yl)amino)bicyclo[2.2.2]octane-2-carboxylate To a solution of hydrogen chloride in 1,4-dixoane (4 M, 10 mL, 40 mmol) was added (+/−)-trans-methyl 3-((2-(5-fluoro-1-tosyl-1H-pyrrolo[2,3-b]pyridin-3-yl)-6-(2-fluorophenyl) pyrimidin-4-yl)amino)bicyclo[2.2.2]octane-2-carboxylate (380 mg, 0.59 mmol). The mixture was stirred at 65° C. for 4 h. After the reaction was completed, the mixture was concentrated, and the residue was diluted with ethyl acetate (10 mL). The mixture was washed with saturated aqueous sodium bicarbonate (20 mL) and saturated brine (20 mL). The organic layer was dried over anhydrous sodium sulfate and filtered, then the filtrate was concentrated in vacuo. The residue was purified by silica gel column chromatography (n-hexane/EtOAc (v/v)=5/1) to give the title compound as a brown solid (352 mg, 75%).

MS (ESI, pos.ion) m/z: 490.3 [M+H]$^+$.

Step 5: (+/−)-trans-3-((2-(5-fluoro-1H-pyrrolo[2,3-b]pyridin-3-yl)-6-(2-fluorophenyl)pyrimidin-4-yl)amino)bicyclo[2.2.2]octane-2-carboxylic Acid To a solution of (+/−)-trans-methyl 3-((2-(5-fluoro-1H-pyrrolo[2,3-b]pyridin-3-yl)-6-(2-fluorophenyl)pyrimidin-4-yl)amino)bicyclo[2.2.2]octane-2-carboxylate (130 mg, 0.26 mmol) in a mixed solvent of methanol (3 mL), THF (3 mL) and water (3 mL) was added sodium hydroxide (107 mg, 2.67 mmol). The mixture was stirred at rt overnight. After the reaction was completed, the mixture was concentrated in vacuo to remove the organic solvent, and the residue was diluted with 2-methyl tetrahydrofuran (10 mL). The mixture was adjusted with diluted hydrochloric acid (1 mol/L) to pH 5.5. The resulting mixture was extracted with 2-methyl tetrahydrofuran (15 mL×3). The combined organic layers were dried over anhydrous sodium sulfate, filtered, and the filtrate was concentrated in vacuo. The residue was purified by silica gel column chromatography (n-hexane/EtOAc (v/v)=1/1) to give the title compound as a light yellow solid (93 mg, 74%).

MS (ESI, pos. ion) m/z: 476.2 [M+H]$^+$;

$^1$H NMR (400 MHz, CDCl$_3$) δ (ppm): 11.13 (s, 1H), 8.70 (dd, J=9.2, 2.4 Hz, 1H), 8.59 (s, 1H), 8.25 (t, J=7.1 Hz, 1H), 8.04 (s, 1H), 7.45 (dd, J=12.9, 5.8 Hz, 1H), 7.35 (t, J=7.6 Hz, 1H), 7.18 (dd, J=11.5, 8.3 Hz, 1H), 6.78 (s, 1H), 5.30 (s, 1H), 4.90 (s, 1H), 2.56 (s, 1H), 2.20 (s, 1H), 1.95-1.65 (m, 10H).

Example 6: (+/−)-trans-3-((2-(5-fluoro-1H-pyrrolo[2,3-b]pyridin-3-yl)-6-(4-fluorophenyl) pyrimidin-4-yl)amino)bicyclo[2.2.2]octane-2-carboxylic Acid

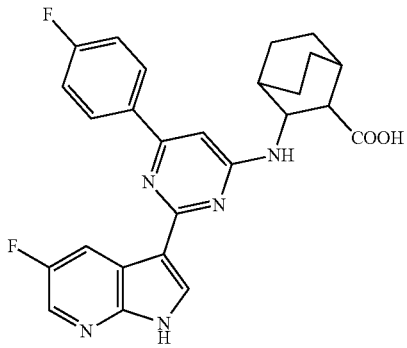 [SMILES: O=C(O)C1C2CCC(CC2)C1Nc1cc(-c2ccc(F)cc2)nc(-c2c[nH]c3ncc(F)cc23)n1]

Step 1: 2,4-dichloro-6-(4-fluorophenyl)pyrimidine

To a solution of 2,4,6-trichloropyrimidine (6.3 mL, 54 mmol) in THF (35 mL) were added palladium acetate (0.16 g, 0.70 mmol), triphenylphosphine (0.39 g, 1.4 mmol), p-fluorophenylboronic acid (5 g, 36 mmol) and aqueous sodium carbonate solution (1 mol/L, 71 mL, 71 mmol). The mixture was stirred at 60° C. under nitrogen protection for 6 h. After the reaction was completed, the mixture was cooled to rt, and concentrated in vacuo. To the residue was added H$_2$O (100 mL), and the resulting mixture was extracted with ethyl acetate (100 mL×3). The combined organic layers were washed with saturated brine (300 mL), dried over anhydrous sodium sulfate, filtered, and the filtrate was concentrated in vacuo. The residue was purified by silica gel column chromatography (PE) to give the title compound as a white solid (8.01 g, 92%).

MS (ESI, pos.ion) m/z: 242.9 [M+H]$^+$.

Step 2: (+/−)-trans-methyl 3-((2-chloro-6-(4-fluorophenyl)pyrimidin-4-yl)amino)bicyclo[2.2.2]octane-2-carboxylate To a solution of 2,4-dichloro-6-(4-fluorophenyl)pyrimidine (2.01 g, 8.2 mmol) and (+/−)-trans-methyl 3-aminobicyclo[2.2.2]octane-2-carboxylate (1.50 g, 8.2 mmol) in N,N-dimethylformamide (10 mL) was added potassium carbonate (1.10 g, 8 mmol). The mixture was stirred at rt overnight. To the reaction mixture was added water (40 mL), and the resulting the mixture was extracted with ethyl acetate (40 mL×3). The combined organic layers were washed with saturated brine (50 mL), dried over anhydrous sodium sulfate, filtered, and the filtrate was concentrated in vacuo. The residue was purified by silica gel column chromatography (n-hexane) to give the title compound as a white solid (1.75 g, 55%).

MS (ESI, pos. ion) m/z: 390.1 [M+H]$^+$.

Step 3: (+/−)-trans-methyl 3-((2-(5-fluoro-1-tosyl-1H-pyrrolo[2,3-b]pyridin-3-yl)-6-(4-fluorophenyl) pyrimidin-4-yl)amino)bicyclo[2.2.2]octane-2-carboxylate To a mixed solvent of 1,4-dioxane (15 mL) and H$_2$O (0.5 mL) were added (+/−)-trans-methyl 3-((2-chloro-6-(4-fluorophenyl)pyrimidin-4-yl)amino)bicyclo[2.2.2]octane-2-carboxylate (600 mg, 1.54 mmol), 5-fluoro-3-(4,4,5,5-tetramethyl-1,3,2-dioxaborolan-2-yl)-1-tosyl-1H-pyrrolo[2,3-b]pyridine (640 mg, 1.53 mmol), potassium carbonate (426 mg, 3.08 mmol), Pd(dppf)Cl$_2$ (126 mg, 0.15 mmol). The mixture in microwave tube was stirred at 110° C. undergoing a microwave reaction for 1 h under nitrogen protection. The mixture was filtered through a celite pad, and the filter cake was washed with ethyl acetate (20 mL). The combined filtrates were concentrated in vacuo, and the residue was purified by silica gel column chromatography (n-hexane/EtOAc (v/v)=15/1) to give the title compound as a yellow solid (500 mg, 51%).

MS (ESI, pos. ion) m/z: 644.2 [M+H]$^+$;

$^1$H NMR (400 MHz, CDCl$_3$) δ (ppm): 8.72 (s, 1H), 8.66 (dd, J=8.8, 2.7 Hz, 1H), 8.34 (s, 1H), 8.17-8.06 (m, 4H), 7.31 (s, 2H), 7.23 (t, J=8.6 Hz, 2H), 6.70 (s, 1H), 3.74 (s, 3H), 3.51 (s, 1H), 2.45 (d, J=5.1 Hz, 1H), 2.43 (d, J=3.8 Hz, 1H), 2.39 (s, 3H), 2.13 (s, 2H), 1.99 (s, 2H), 1.93 (s, 2H), 1.85 (d, J=11.3 Hz, 2H).

Step 4: (+/−)-trans-methyl 3-((2-(5-fluoro-1H-pyrrolo[2,3-b]pyridin-3-yl)-6-(4-fluorophenyl) pyrimidin-4-yl)amino)bicyclo[2.2.2]octane-2-carboxylate To a solution of hydrogen chloride in 1,4-dixoane (4 M, 10 mL, 40 mmol) was added (+/−)-trans-methyl 3-((2-(5-fluoro-1-tosyl-1H-pyrrolo[2,3-b]pyridin-3-yl)-6-(4-fluorophenyl)pyrimidin-4-yl)amino)bicyclo[2.2.2]octane-2-carboxylate (620 mg, 0.96 mmol). The mixture was stirred at 65° C. for 4 h. After the reaction was completed, the mixture was concentrated in vacuo, and the residue was diluted with ethyl acetate (20 mL). The resulting mixture was washed with saturated aqueous sodium bicarbonate (20 mL) and saturated brine (20 mL). The organic layer was dried over anhydrous sodium sulfate and filtered, then the filtrate was concentrated in vacuo. The residue was purified by silica gel column chromatography (n-hexane/EtOAc (v/v)=5/1) to give the title compound as a light yellow solid (352 mg, 75%).

MS (ESI, pos.ion) m/z: 490.3 [M+H]$^+$.

Step 5: (+/−)-trans-3-((2-(5-fluoro-1H-pyrrolo[2,3-b]pyridin-3-yl)-6-(4-fluorophenyl)pyrimidin-4-yl)amino)bicyclo[2.2.2]octane-2-carboxylic Acid To a solution of (+/−)-trans-methyl 3-((2-(5-fluoro-1H-pyrrolo[2,3-b]pyridin-3-yl)-6-(4-fluorophenyl)pyrimidin-4-yl)amino)bicyclo[2.2.2]octane-2-carboxylate (352 mg, 0.72 mmol) in a mixed solvent of methanol (5 mL), THF (5 mL) and water (2 mL) was added sodium hydroxide (290 mg, 7.25 mmol). The mixture was stirred at rt overnight. After the reaction was completed, the mixture was concentrated in vacuo, and the residue was diluted with 2-methyl tetrahydrofuran (10 mL). The mixture was adjusted with diluted hydrochloric acid (1 M) to pH 5.5. The resulting mixture was extracted with 2-methyl tetrahydrofuran (15 mL×3). The combined organic layers were dried over anhydrous sodium sulfate, filtered, and the filtrate was concentrated in vacuo. The residue was purified by silica gel column chromatography (n-hexane/EtOAc (v/v)=1/1) to give the title compound as a light yellow solid (241 mg, 70%).

MS (ESI, pos. ion) m/z: 476.4 [M+H]$^+$;

$^1$H NMR (400 MHz, CD$_3$OD) δ (ppm): 8.77 (dd, J=9.6, 2.5 Hz, 1H), 8.41 (s, 1H), 8.18 (s, 1H), 8.12 (dd, J=8.7, 5.5 Hz, 2H), 7.26 (t, J=8.7 Hz, 2H), 6.74 (s, 1H), 2.59 (d, J=4.5 Hz, 1H), 2.09 (s, 1H), 2.04 (d, J=6.0 Hz, 2H), 1.93-1.54 (m, 8H);

$^{13}$C NMR (151 MHz, DMSO-d$_6$) δ (ppm): 175.72, 165.03, 163.23, 162.76, 158.21, 157.11, 155.48, 151.94, 146.36, 139.67, 130.12, 128.51, 125.38, 118.92, 116.40, 116.26, 73.99, 60.43, 50.98, 49.45, 34.85, 30.89, 25.42, 21.50.

Example 7: (+/−)-trans-3-((2-(5-fluoro-1H-pyrrolo[2,3-b]pyridin-3-yl)pyrido[2,3-d]pyrimidin-4-yl)amino)bicyclo[2.2.2]octane-2-carboxylic Acid

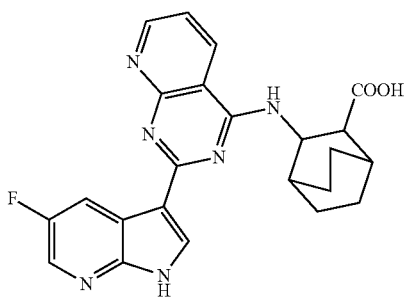 [SMILES: O=C(O)C1C2CCC(CC2)C1Nc1nc(-c2c[nH]c3ncc(F)cc23)nc2ncccc12]

Step 1: (+/−)-trans-methyl 3-((2-chloropyrido[2,3-d]pyrimidin-4-yl)amino)bicyclo[2.2.2]octane-2-carboxylate To acetonitrile (15 mL) were added (+/−)-trans-methyl 3-aminobicyclo[2.2.2]octane-2-carboxylate (405 mg, 2.21 mmol), 2,4-dichloropyrido[2,3-d]pyrimidine (401 mg, 2.00 mmol) and potassium phosphate (1.28 g, 6.03 mmol). The mixture was stirred at 80° C. overnight under nitrogen protection. The mixture was filtered through a celite pad, and the filter cake was washed with ethyl acetate (30 mL). The combined filtrates were concentrated in vacuo, and the residue was purified by silica gel chromatography (PE/MeOH (v/v)=2/1-1/2) to give the title compound as a light yellow solid (676 mg, 97%).

MS (ESI, pos. ion) m/z: 347.2 [M+H]$^+$;

$^1$H NMR (400 MHz, CDCl$_3$) δ (ppm): 8.97-8.89 (m, 1H), 8.48 (d, J=7.2 Hz, 1H), 7.32 (dd, J=8.2, 4.4 Hz, 1H), 7.11 (s, 1H), 4.71 (s, 1H), 3.76 (s, 3H), 2.65 (d, J=4.3 Hz, 1H), 2.05 (d, J=2.3 Hz, 1H), 1.99 (s, 1H), 1.85 (d, J=11.0 Hz, 2H), 1.73-1.54 (m, 5H), 1.45 (m, 1H).

Step 2: (+/−)-trans-methyl 3-((2-(5-fluoro-1-tosyl-1H-pyrrolo[2,3-b]pyridin-3-yl)pyrido[2,3-d]pyrimidin-4-yl)amino)bicyclo[2.2.2]octane-2-carboxylate To a mixed solvent of 2-methyltetrahydrofuran (5 mL) and water (1 mL) were added 5-fluoro-3-(4,4,5,5-tetramethyl-1,3,2-dioxaborolan-2-yl)-1-tosyl-1H-pyrrolo[2,3-b]pyridine (223 mg, 0.53 mmol), K$_3$PO$_4$ (190 mg, 0.90 mmol), Pd$_2$(dba)$_3$ (42 mg, 0.05 mmol), (+/−)-trans-methyl 3-((2-chloropyrido[2,3-d]pyrimidin-4-yl)amino)bicyclo[2.2.2]octane-2-carboxylate (155 mg, 0.45 mmol) and X-phos (22 mg, 0.05 mmol). The mixture was stirred at 78° C. overnight under nitrogen protection. The mixture was diluted with ethyl acetate (40 mL), and the resulting mixture was filtered through a celite pad. The filtrate was partitioned, and the organic layer was concentrated in vacuo, and then the residue was purified by silica gel column chromatography (DCM/MeOH (v/v)=50/1-20/1) to give the title compound as light yellow foam (96 mg, 36%).

MS (ESI, pos. ion) m/z: 601.3 [M+H]⁺;

¹H NMR (600 MHz, CDCl₃) δ (ppm): 9.07 (dd, J=4.3, 1.6 Hz, 1H), 8.93 (dd, J=8.7, 2.8 Hz, 1H), 8.90 (s, 1H), 8.33 (d, J=2.1 Hz, 1H), 8.17 (d, J=8.4 Hz, 2H), 8.14 (dd, J=8.1, 1.5 Hz, 1H), 7.38 (dd, J=8.1, 4.4 Hz, 1H), 7.31 (d, J=8.2 Hz, 2H), 5.99 (d, J=6.4 Hz, 1H), 5.01 (s, 1H), 3.75 (s, 3H), 2.54 (d, J=5.5 Hz, 1H), 2.40 (s, 3H), 2.17-2.11 (m, 2H), 2.02-1.97 (m, 1H), 1.77-1.72 (m, 3H), 1.65 (m, 4H).

Step 3: (+/−)-trans-3-((2-(5-fluoro-1H-pyrrolo[2,3-b]pyridin-3-yl)pyrido[2,3-d]pyrimidin-4-yl) amino) bicyclo[2.2.2]octane-2-carboxylic Acid To a solution of (+/−)-trans-methyl 3-((2-(5-fluoro-1-tosyl-1H-pyrrolo[2,3-b]pyridin-3-yl)pyrido[2,3-d]pyrimidin-4-yl)amino)bicyclo[2.2.2]octane-2-carboxylate (92 mg, 0.15 mmol) in THF/MeOH/H₂O (v/v/v=1/1/1, 3 mL) was added sodium hydroxide (62 mg, 1.55 mmol). The mixture was stirred at rt overnight, then the mixture was diluted with water (15 mL), and the resulting mixture was acidified with hydrochloric acid (1 M) to pH about 6.0. The mixture was stirred at rt for 30 min, and filtered to give the title compound as a brown solid (45 mg, 68%).

MS (ESI, pos. ion) m/z: 433.2 [M+H]⁺;

¹H NMR (400 MHz, DMSO-d₆) δ (ppm): 12.48 (s, 1H), 8.93 (d, J=5.7 Hz, 2H), 8.71 (d, J=7.7 Hz, 1H), 8.49 (s, 1H), 8.41 (s, 1H), 8.32 (s, 1H), 7.46 (d, J=5.1 Hz, 1H), 4.94 (s, 1H), 3.01 (d, J=5.9 Hz, 1H), 2.07 (s, 2H), 1.92-1.80 (m, 3H), 1.72-1.40 (m, 5H).

Example 8: (R)-3-((2-(5-fluoro-1H-pyrrolo[2,3-b]pyridin-3-yl)quinazolin-4-yl)amino)-4,4-dimethylpentanoic Acid

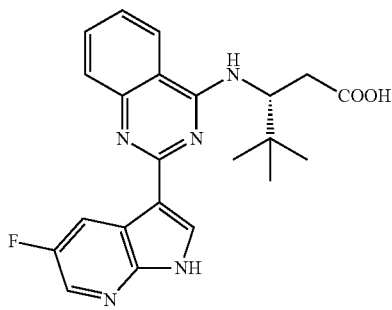 [SMILES: CC(C)(C)[C@@H](CC(=O)O)Nc1nc(-c2c[nH]c3ncc(F)cc23)nc2ccccc12]

Step 1: (R)-methyl 3-amino-4,4-dimethylpentanoate

To a solution of (R)-3-amino-4,4-dimethylpentanoic acid (1.01 g, 6.96 mmol) in methanol (60 mL) was added dropwise slowly oxalyl chloride (0.9 mL, 10 mmol) at 0° C., and the mixture was stirred for 1 h maintaining at this temperature. The mixture was heated to 65° C. and stirred for 2 h. The mixture was concentrated in vacuo to dry, then the residue was washed with toluene (30 mL×3) and filtered to give the title compound as a white solid (1.11 g, 99%).

MS (ESI, pos. ion) m/z: 160.3 [M+H]⁺.

Step 2: (R)-methyl 3-((2-chloroquinazolin-4-yl) amino)-4,4-dimethylpentanoate

To a solution of (R)-methyl 3-amino-4,4-dimethylpentanoate (700 mg, 4.39 mmol) in tetrahydrofuran (20 mL) were added DIPEA (3.63 mL, 22.0 mmol) and 2,4-dichloroquinazoline (875 mg, 4.39 mmol). The mixture was stirred at rt overnight. The mixture was concentrated in vacuo and the residue was purified by silica gel chromatography (PE/EtOAc (v/v)=5/1) to give the title compound as a white solid (907 mg, 64%).

MS (ESI, pos. ion) m/z: 322.1 [M+H]⁺;

¹H NMR (400 MHz, CDCl₃) δ (ppm): 7.77-7.74 (m, 2H), 7.48 (dd, J=11.3, 5.0 Hz, 1H), 6.93 (d, J=9.5 Hz, 1H), 4.85 (ddd, J=9.7, 6.8, 4.9 Hz, 1H), 3.68 (s, 3H), 2.74 (dd, J=15.1, 4.8 Hz, 1H), 2.64 (dd, J=15.1, 6.9 Hz, 1H), 1.05 (s, 9H).

Step 3: (R)-methyl 3-((2-(5-fluoro-1-tosyl-1H-pyrrolo[2,3-b]pyridin-3-yl)quinazolin-4-yl) amino)-4,4-dimethylpentanoate To a mixed solvent of 1,4-dioxane (8 mL) and water (1 mL) were added 5-fluoro-3-(4,4,5,5-tetramethyl-1,3,2-dioxaborolan-2-yl)-1-tosyl-1H-pyrrolo[2,3-b]pyridine (400 mg, 0.62 mmol), potassium carbonate (155 mg, 1.12 mmol), Pd(dppf)Cl₂ (45 mg, 0.05 mmol) and (R)-methyl 3-((2-chloroquinazolin-4-yl)amino)-4,4-dimethylpentanoate (180 mg, 0.56 mmol). The mixture was degassed for 10 minutes by nitrogen bubbling. The mixture in a sealed tube was stirred at 110° C. for 2 hours. The mixture was diluted with ethyl acetate (20 mL), and the resulting mixture was filtered through a celite pad. The filtrate was partitioned and the organic layer was concentrated in vacuo. The residue was purified by silica gel column chromatography (PE/EtOAc (v/v)=6/1) to give the title compound as a yellow solid (200 mg, 62%).

MS (ESI, pos.ion) m/z: 644.2 [M+H]⁺;

¹H NMR (400 MHz, CDCl₃) δ (ppm): 8.85 (dd, J=9.0, 2.8 Hz, 1H), 8.34 (d, J=1.9 Hz, 1H), 8.14 (d, J=8.3 Hz, 2H), 7.89 (d, J=8.0 Hz, 1H), 7.76 (t, J=7.6 Hz, 2H), 7.46 (t, J=7.5 Hz, 1H), 7.30 (d, J=8.3 Hz, 2H), 6.37 (d, J=9.4 Hz, 1H), 5.06 (ddd, J=9.2, 7.5, 5.1 Hz, 1H), 3.59 (s, 3H), 2.82 (dd, J=14.8, 4.9 Hz, 1H), 2.68 (dd, J=14.8, 7.5 Hz, 1H), 2.39 (s, 3H), 1.12 (s, 9H).

Step 4: (R)-3-((2-(5-fluoro-1H-pyrrolo[2,3-b]pyridin-3-yl)quinazolin-4-yl)amino)-4,4-dimethyl pentanoic Acid To a solution of (R)-methyl 3-((2-(5-fluoro-1-tosyl-1H-pyrrolo[2,3-b]pyridin-3-yl) quinazolin-4-yl)amino)-4,4-dimethylpentanoate (190 mg, 0.33 mmol) in THF/MeOH (v/v=1/1, 4 mL) was added aqueous sodium hydroxide solution (4 M, 0.83 mL, 3.33 mmol). The mixture was stirred at 30° C. overnight, then diluted with water (10 mL). The resulting mixture was acidified with hydrochloric acid (1 M) to pH about 6.0, then extracted with ethyl acetate (15 mL×3). The combined organic layers were washed with saturated brine (40 mL), dried over anhydrous sodium sulfate, filtered and concentrated in vacuo. The residue was purified by silica gel column chromatography (DCM/MeOH (v/v)=10/1) to give the title compound as a white solid (55 mg, 41%).

MS (ESI, pos.ion) m/z: 408.3 [M+H]$^+$;

$^1$H NMR (600 MHz, DMSO-d$_6$) δ (ppm): 12.33 (s, 1H), 8.82 (d, J=9.6 Hz, 1H), 8.42 (d, J=7.5 Hz, 2H), 8.31 (s, 1H), 7.75 (s, 2H), 7.43 (s, 1H), 5.16 (m, 1H), 2.75 (d, J=14.6 Hz, 1H), 2.70-2.63 (m, 1H), 1.03 (s, 9H);

$^{13}$C NMR (151 MHz, DMSO-d$_6$) δ (ppm): 173.83, 160.54, 158.60, 156.92, 155.33, 146.52, 133.17, 131.90, 131.71, 124.61, 123.58, 119.17, 119.12, 116.21, 116.07, 113.52, 55.86, 36.15, 35.86, 27.14.

Example 9: (+/−)-trans-3-((2-(5-fluoro-1H-pyrrolo[2,3-b]pyridin-3-yl)-6-(furan-2-yl) pyrimidin-4-yl)amino)bicyclo[2.2.2]octane-2-carboxylic Acid

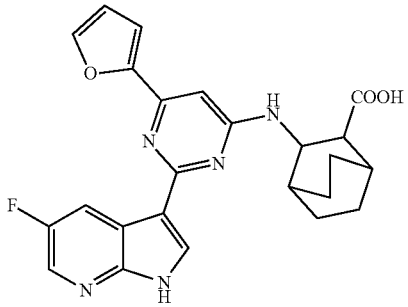 [SMILES: O=C(O)C1C2CCC(CC2)C1Nc1cc(-c2ccco2)nc(-c2c[nH]c3ncc(F)cc23)n1]

Step 1: 2,4-dichloro-6-(furan-2-yl)pyrimidine

To a solution of 2,4,6-trichloropyrimidine (100 mg, 0.55 mmol) in THF (4 mL) were added tetrakis(triphenylphosphine)palladium (43 mg, 0.05 mmol), 2-furylboronic acid (61 mg, 0.55 mol) and aqueous sodium bicarbonate solution (1 M, 1.64 mL, 1.64 mmol). The mixture was stirred at 80° C. overnight under nitrogen protection. To the reaction mixture was added water (50 mL), and the resulting mixture was extracted with ethyl acetate (50 mL×3). The combined organic layers were washed with saturated brine (50 mL), dried over anhydrous sodium sulfate and filtered. The filtrate was concentrated in vacuo and the residue was purified by silica gel column chromatography (PE) to give the title compound as a green solid (42 mg, 36%).

MS (ESI, pos.ion) m/z: 215.0 [M+H]$^+$;

$^1$H NMR (400 MHz, CDCl$_3$) δ (ppm): 7.67 (d, J=0.7 Hz, 1H), 7.58 (s, 1H), 7.43 (d, J=3.4 Hz, 1H), 6.65 (dd, J=3.4, 1.6 Hz, 1H).

Step 2: (+/−)-trans-methyl 3-((2-chloro-6-(furan-2-yl)pyrimidin-4-yl)amino)bicyclo[2.2.2]octane-2-carboxylate To a solution of (+/−)-trans-methyl 3-aminobicyclo[2.2.2]octane-2-carboxylate (429 mg, 2.34 mmol) and 2,4-dichloro-6-(furan-2-yl)pyrimidine (420 mg, 1.95 mmol) in DMF (5 mL) were added potassium carbonate (809 mg, 5.86 mmol). Then the mixture was stirred at room temperature overnight. Water (40 mL) was added to the mixture and the resulting mixture was extracted with EtOAc (40 mL×3). The combined organic layers were washed with saturated brine (100 mL), dried over anhydrous Na$_2$SO$_4$ and filtered, then the filtrate was concentrated in vacuo. The residue obtained was purified by silica gel column chromatography (PE/EtOAc (v/v)=5/1) to give the title compound as a white solid (383 mg, 54%).

MS (ESI, pos. ion) m/z: 362.1 [M+H]$^+$;

$^1$H NMR (400 MHz, CDCl$_3$) δ (ppm): 7.56 (s, 1H), 7.22 (s, 1H), 6.93 (s, 1H), 6.55 (d, J=1.6 Hz, 1H), 5.47 (d, J=5.5 Hz, 1H), 4.44 (s, 1H), 3.70 (s, 3H), 2.44-2.33 (m, 1H), 1.96 (d, J=2.5 Hz, 1H), 1.88 (s, 1H), 1.84-1.58 (m, 8H).

Step 3: (+/−)-trans-methyl 3-((2-(5-fluoro-1-tosyl-1H-pyrrolo[2,3-b]pyridin-3-yl)-6-(furan-2-yl) pyrimidin-4-yl)amino)bicyclo[2.2.2]octane-2-carboxylate A microwave tube was charged with 5-fluoro-3-(4,4,5,5-tetramethyl-1,3,2-dioxaborolan-2-yl)-1-tosyl-1H-pyrrolo[2,3-b]pyridine (276 mg, 0.33 mmol, 50%), (+/−)-trans-methyl 3-((2-chloro-6-(furan-2-yl)pyrimidin-4-yl)amino)bicyclo[2.2.2]octane-2-carboxylate (100 mg, 0.28 mmol), potassium carbonate (114 mg, 0.83 mmol), Pd(dppf)Cl$_2$ (45 mg, 0.06 mmol), 1,4-dioxane (3 mL) and H$_2$O (0.2 mL). The resulting solution was bubbled with nitrogen for 10 minutes to remove the air and then the mixture in the tube was subjected to a microwave reaction at 110° C. for 2 h. The reaction mixture was passed through a celite and the filter cake was washed with EtOAc (50 mL). The filtrate was washed with saturated brine (50 mL), dried over anhydrous Na$_2$SO$_4$, filtered, and the filtrate was concentrated in vacuo. The residue was purified by silica gel column chromatography (n-hexane/EtOAc (v/v)=5/1) to give the title compound as a yellow solid (72 mg, 42%).

MS (ESI, pos.ion) m/z: 616.2[M+H]$^+$;

$^1$H NMR (400 MHz, CDCl$_3$) δ (ppm): 8.70-8.64 (m, 2H), 8.33 (d, J=2.0 Hz, 1H), 8.12 (d, J=8.3 Hz, 2H), 7.59 (s, 1H), 7.30 (s, 1H), 7.26 (d, J=3.2 Hz, 1H), 6.67 (s, 1H), 6.60 (dd, J=3.3, 1.7 Hz, 1H), 4.76 (s, 1H), 3.75 (s, 3H), 2.45 (s, 1H), 2.39 (s, 3H), 2.10 (s, 1H), 1.98 (s, 1H), 1.42 (m, 8H).

Step 4: (+/−)-trans-3-((2-(5-fluoro-1H-pyrrolo[2,3-b]pyridin-3-yl)-6-(furan-2-yl)pyrimidin-4-yl) amino)bicyclo[2.2.2]octane-2-carboxylic Acid To a solution of (+/−)-trans-methyl 3-((2-(5-fluoro-1-tosyl-1H-pyrrolo[2,3-b]pyridin-3-yl)-6-(furan-2-yl)pyrimidin-4-yl)amino)bicyclo[2.2.2]octane-2-carboxylate (75 mg, 0.12 mmol) in THF/MeOH (v/v=1/1, 4 mL) was added NaOH aqueous solution (4 M, 0.30 mL, 1.20 mmol) and the resulting mixture was stirred overnight at 30° C. Water (10 mL) was added to the mixture and the resulting mixture was adjusted with HCl (1 M) to pH about 5.5. Then the mixture was extracted with EtOAc (20 mL×3). The organic layers were combined, washed with saturated brine (50 mL), dried over anhydrous Na$_2$SO$_4$, filtered, and the filtrate was concentrated in vacuo. The residue obtained was purified by silica gel column chromatography (DCM/MeOH (v/v)=10/1) to give the title compound as a yellow solid (35 mg, 64%).

MS (ESI, pos.ion) m/z: 472.1 [M+H]$^+$;

HRMS (ESI, pos. ion) m/z: 448.1776 [M+H]$^+$, (C$_{24}$H$_{23}$FN$_5$O$_3$) [M+H]$^+$ theoretical value: 448.1785;

$^1$H NMR (400 MHz, DMSO-d$_6$) δ (ppm): 12.27 (s, 1H), 8.60 (s, 1H), 8.32 (s, 1H), 8.28 (s, 1H), 7.88 (s, 1H), 7.55 (s, 1H), 7.24 (s, 1H), 6.69 (s, 1H), 6.63 (s, 1H), 4.62 (s, 1H), 1.99 (s, 2H), 1.83-1.33 (m, 10H).

Example 9a: (2S,3S)-3-((2-(5-fluoro-1H-pyrrolo[2,3-b]pyridin-3-yl)-6-(furan-2-yl)pyrimidin-4-yl)amino)bicyclo[2.2.2]octane-2-carboxylic Acid

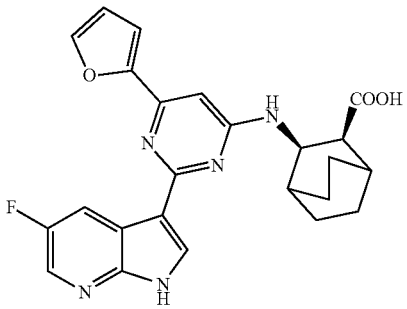 [SMILES: O=C(O)[C@H]1C2CCC(CC2)[C@H]1Nc1cc(-c2ccco2)nc(-c2c[nH]c3ncc(F)cc23)n1]

Step 1: (2S,3S)-ethyl 3-aminobicyclo[2.2.2]octane-2-carboxylate hydrochloride

The title compound can be prepared according to the synthetic method disclosed in patent application WO 2015073491.

Step 2: (2S,3S)-ethyl 3-((2-chloro-6-(furan-2-yl)pyrimidin-4-yl)amino)bicyclo[2.2.2]octane-2-carboxylate The title compound can be prepared by the synthetic method described in step 2 of example 9, using (2S,3S)-methyl 3-aminobicyclo[2.2.2]octane-2-carboxylate hydrochloride (331 mg, 1.42 mmol), 2,4-dichloro-6-(furan-2-yl)pyrimidine (278 mg, 1.29 mmol), potassium carbonate (590 mg, 4.26 mmol) as reagents and DMF (6 mL) as solvent. The title compound was a light yellow solid (247 mg, 51%).

Step 3: (2S,3S)-ethyl 3-((2-(5-fluoro-1-tosyl-1H-pyrrolo[2,3-b]pyridin-3-yl)-6-(furan-2-yl) pyrimidin-4-yl)amino)bicyclo[2.2.2]octane-2-carboxylate The title compound can be prepared by the synthetic method described in step 3 of example 9, using (2S,3S)-ethyl 3-((2-chloro-6-(furan-2-yl)pyrimidin-4-yl)amino)bicyclo[2.2.2]octane-2-carboxylate (78 mg, 0.21 mmol), 5-fluoro-3-(4,4,5,5-tetramethyl-1,3,2-dioxaborolan-2-yl)-1-tosyl-1H-pyrrolo[2,3-b]pyridine (203 mg, 0.29 mmol, 60%), potassium carbonate (87 mg, 0.63 mmol), Pd(dppf)Cl$_2$ (15 mg, 0.02 mmol), 1,4-dioxane (3 mL) and water (0.2 mL). The title compound was a light yellow solid (81 mg, 61%).

Step 4: (2S,3S)-3-((2-(5-fluoro-1H-pyrrolo[2,3-b]pyridin-3-yl)-6-(furan-2-yl)pyrimidin-4-yl) amino)bicyclo[2.2.2]octane-2-carboxylic Acid To a solution of (2S,3S)-ethyl 3-((2-(5-fluoro-1-tosyl-1H-pyrrolo[2,3-b]pyridin-3-yl)-6-(furan-2-yl)pyrimidin-4-yl)amino)bicyclo[2.2.2]octane-2-carboxylate (81 mg, 0.13 mmol) in THF/EtOH (v/v=1/1, 4 mL) was added aqueous sodium hydroxide solution (4 M, 0.33 mL, 1.30 mmol). The mixture was stirred at 30° C. overnight. To the reaction mixture was added water (10 mL), and the resulting mixture was acidified with hydrochloric acid (1 M) to pH about 5.5. The mixture was extracted with ethyl acetate (20 mL×3), and the combined organic layers were dried over anhydrous sodium sulfate, then filtered. The filtrate was concentrated in vacuo and the residue was purified by silica gel column chromatography (DCM/MeOH (v/v)=10/1) to give the title compound as a yellow solid (35 mg, 64%).

MS (ESI, pos.ion) m/z: 448.5 [M+H]$^+$;
HRMS (ESI, pos. ion) m/z: 448.1763 [M+H]$^+$, (C$_{24}$H$_{23}$FN$_5$O$_3$) [M+H]$^+$ theoretical value: 448.1785;
$^1$H NMR (400 MHz, DMSO-d$_6$) δ (ppm): 12.29 (s, 1H), 8.62 (s, 1H), 8.33 (s, 1H), 8.28 (s, 1H), 7.88 (s, 1H), 7.58 (s, 1H), 7.24 (s, 1H), 6.69 (s, 1H), 6.65 (s, 1H), 4.63 (s, 1H), 1.99 (s, 2H), 1.80-1.38 (m, 8H).

Example 10: (+/−)-trans-3-((2-(5-fluoro-1H-pyrrolo[2,3-b]pyridin-3-yl)-6-(2-phenylethynyl) pyrimidin-4-yl)amino)bicyclo[2.2.2]octane-2-carboxylic Acid

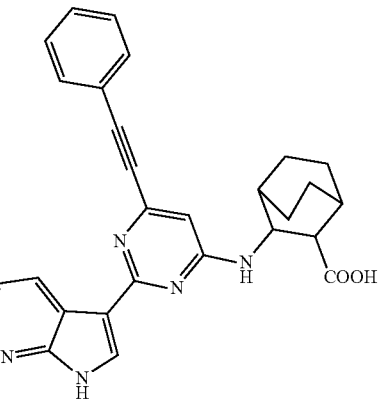

Step 1: 2,4-dichloro-6-(2-phenylethynyl)pyrimidine

To a solution of 2,4,6-trichloropyrimidine (101 mg, 0.55 mmol) in toluene (3 mL) was added tributyl(2-phenylethynyl)stannane (259 mg, 0.66 mmol), triphenylarsine (67 mg, 0.22 mmol), Pd(PPh$_3$)Cl$_2$ (40 mg, 0.06 mmol). The reaction mixture was heated to 80° C. and stirred for 6 h under nitrogen protection. The mixture was concentrated in vacuo and the obtained residue was purified by silica gel column chromatography (PE) to give the title compound as a white solid (129 mg, 94%).

MS (ESI, pos.ion) m/z: 249.3 [M+H]$^+$;
$^1$H NMR (400 MHz, CDCl$_3$) δ (ppm): 8.40 (t, J=7.9 Hz, 2H), 8.29 (d, J=8.7 Hz, 1H), 7.88-7.74 (m, 2H).

Step 2: (+/−)-trans-methyl 3-((2-chloro-6-(phenylethynyl)pyrimidin-4-yl)amino)bicyclo[2.2.2]octane-2-carboxylate To a solution of (+/−)-trans-methyl 3-aminobicyclo[2.2.2]octane-2-carboxylate (405 mg, 2.21 mmol) and 2,4-dichloro-6-(phenylethynyl)pyrimidine (500 mg, 2.01 mmol) in DMF (5 mL) was added potassium carbonate (306 mg, 2.21 mmol). Then the mixture was stirred at room temperature overnight. Water (40 mL) was added to the mixture and the resulting mixture was extracted with EtOAc (40 mL×3). The combined organic layers were washed with saturated brine (50 mL), dried over anhydrous Na$_2$SO$_4$ and concentrated in vacuo. The obtained residue was purified by silica gel column chromatography (PE/EtOAc (v/v)=5/1) to give the title compound as a white solid (470 mg, 59%).

MS (ESI, pos.ion) m/z: 396.1 [M+H]$^+$;

$^1$H NMR (400 MHz, CDCl$_3$) δ (ppm): 7.59 (d, J=6.8 Hz, 2H), 7.41-7.37 (m, 3H), 6.55 (s, 1H), 5.50 (s, 1H), 3.76 (s, 3H), 2.36 (d, J=5.3 Hz, 1H), 1.84 (s, 1H), 1.70-1.42 (m, 10H).

Step 3: (+/−)-trans-methyl 3-((2-(5-fluoro-1-tosyl-1H-pyrrolo[2,3-b]pyridin-3-yl)-6-(phenylethynyl) pyrimidin-4-yl)amino)bicyclo[2.2.2]octane-2-carboxylate A microwave tube was charged with 5-fluoro-3-(4,4,5,5-tetramethyl-1,3,2-dioxaborolan-2-yl)-1-tosyl-1H-pyrrolo[2,3-b]pyridine (253 mg, 0.30 mmol, 50%), (+/−)-trans-methyl 3-((2-chloro-6-(phenylethynyl)pyrimidin-4-yl)amino)bicyclo[2.2.2]octane-2-carboxylate (100 mg, 0.25 mmol), potassium carbonate (105 mg, 0.76 mmol), Pd(dppf)Cl$_2$ (42 mg, 0.05 mmol), 1,4-dioxane (3 mL) and H$_2$O (0.2 mL). The resulting mixture was bubbled with nitrogen for 3 minutes to remove the air and then the mixture in the tube was subjected to a microwave reaction at 110° C. for 2 h. The reaction mixture was passed through a celite and the filter cake was washed with EtOAc (50 mL). The combined organic layers were washed with saturated brine (50 mL), dried over anhydrous Na$_2$SO$_4$ and filtered, and the filtrate was concentrated in vacuo. The residue was purified by silica gel column chromatography (n-hexane/EtOAc (v/v) =5/1) to give the title compound as a yellow solid (37 mg, 23%).

$^1$H NMR (400 MHz, CDCl$_3$) δ (ppm): 8.70 (s, 1H), 8.65 (dd, J=8.8, 2.7 Hz, 1H), 8.32 (s, 1H), 8.12 (d, J=8.3 Hz, 2H), 7.73 (dd, J=5.6, 3.4 Hz, 2H), 7.69-7.63 (m, 2H), 7.55 (dd, J=5.6, 3.3 Hz, 2H), 7.43 (s, 1H), 7.31 (s, 1H), 6.52 (s, 1H), 3.81 (s, 1H), 3.75 (s, 3H), 2.42 (s, 1H), 2.39 (s, 3H), 2.11 (s, 1H), 1.97 (s, 1H), 1.80-1.64 (m, 8H).

Step 4: (+/−)-trans-3-((2-(5-fluoro-1H-pyrrolo[2,3-b]pyridin-3-yl)-6-(2-phenylethynyl)pyrimidin-4-yl) amino)bicyclo[2.2.2]octane-2-carboxylic Acid To a solution of (+/−)-trans-methyl 3-((2-(5-fluoro-1-tosyl-1H-pyrrolo[2,3-b]pyridine-3-yl)-6-(phenylethynyl) pyrimidin-4-yl)amino)bicyclo[2.2.2]octane-2-carboxylate (37 mg, 0.06 mmol) in THF/MeOH (v/v=1/1, 2 mL) was added NaOH aqueous solution (4 M, 0.15 mL, 0.60 mmol) and the mixture was stirred overnight at 30° C. Water (10 mL) was added to the mixture and the resulting mixture was adjusted with HCl (1 M) to pH about 5.5, then extracted with EtOAc (20 mL×3). The combined organic layers were washed with saturated brine, dried over anhydrous Na$_2$SO$_4$ and filtered, then the filtrate was concentrated in vacuo. The residue was purified by silica gel column chromatography (DCM/MeOH (v/v)=10/1) to give the title compound as a yellow solid (19 mg, 69%).

MS (ESI, pos.ion) m/z: 482.5 [M+H]$^+$;

$^1$H NMR (400 MHz, DMSO-d$_6$) δ (ppm): 12.33 (s, 1H), 8.60 (s, 1H), 8.43 (s, 1H), 8.38 (t, J=9.5 Hz, 4H), 8.30 (s, 1H), 7.66 (s, 1H), 6.88 (s, 1H), 4.71 (s, 1H), 2.67 (s, 1H), 2.33 (s, 1H), 1.44 (s, 8H).

Example 10a: (2S,3S)-3-((2-(5-fluoro-1H-pyrrolo[2,3-b]pyridin-3-yl)-6-(2-phenylethynyl) pyrimidin-4-yl)amino)bicyclo[2.2.2]octane-2-carboxylic Acid

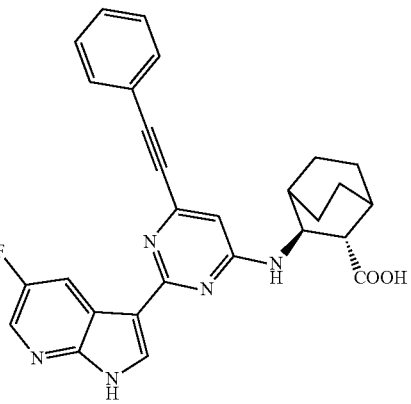

Step 1: (2S,3S)-ethyl 3-aminobicyclo[2.2.2]octane-2-carboxylate hydrochloride

The title compound can be prepared according to the synthetic method disclosed in patent application WO 2015073491.

Step 2: (2S,3S)-ethyl 3-((2-chloro-6-(phenylethynyl)pyrimidin-4-yl)amino)bicyclo[2.2.2]octane-2-carboxylate The title compound can be prepared by the synthetic method described in step 2 of example 10, using (2S,3S)-methyl 3-aminobicyclo[2.2.2]octane-2-carboxylate hydrochloride (386 mg, 1.65 mmol), 2,4-dichloro-6-(phenylethynyl)pyrimidine (410 mg, 1.65 mmol), potassium carbonate (684 mg, 4.95 mmol) as reagents and DMF (5 mL) as solvent. The title compound was a yellow solid (458 mg, 68%).

MS (ESI, pos.ion) m/z: 410.3 [M+H]$^+$;

$^1$H NMR (400 MHz, CDCl$_3$) δ (ppm): 7.63-7.57 (m, 2H), 7.43-7.36 (m, 3H), 6.57 (s, 1H), 5.50 (s, 1H), 4.22 (q, J=7.1 Hz, 2H), 2.34 (d, J=5.1 Hz, 1H), 2.09 (s, 1H), 1.85 (d, J=2.4 Hz, 1H), 1.78-1.63 (m, 6H), 1.57 (d, J=9.8 Hz, 2H), 1.29 (t, J=7.1 Hz, 3H).

Step 3: (2S,3S)-ethyl 3-((2-(5-fluoro-1-tosyl-1H-pyrrolo[2,3-b]pyridin-3-yl)-6-(phenylethynyl) pyrimidin-4-yl)amino)bicyclo[2.2.2]octane-2-carboxylate The title compound can be prepared by the synthetic method described in step 3 of example 10, using 5-fluoro-3-(4,4,5,5-tetramethyl-1,3,2-dioxaborolan-2-yl)-1-tosyl-1H-pyrrolo[2,3-b]pyridine (541 mg, 0.59 mmol, 45%), (2S,3S)-ethyl 3-((2-chloro-6-(phenylethynyl pyrimidin-4-yl) amino)bicyclo[2.2.2]octane-2-carboxylate (200 mg, 0.49 mmol), potassium carbonate (202 mg, 1.46 mmol) and Pd(dppf)Cl$_2$ (79 mg, 0.10 mmol) as reagents, and a mixture of 1,4-dioxane (3 mL) and water (0.2 mL) as mixed solvent. The title compound was a yellow solid (46 mg, 14%).

MS (ESI, pos.ion) m/z: 664.2[M+H]$^+$.

Step 4: (2S,3S)-3-((2-(5-fluoro-1H-pyrrolo[2,3-b]pyridin-3-yl)-6-(2-phenylethynyl)pyrimidin-4-yl)amino)bicyclo[2.2.2]octane-2-carboxylic Acid The title compound can be prepared by the synthetic method described in step 4 of example 10, using (2S,3S)-ethyl 3-((2-(5-fluoro-1-tosyl-1H-pyrrolo[2,3-b]pyridin-3-yl)-6-(phenylethynyl)pyrimidin-4-yl)amino)bicyclo[2.2.2]octane-2-carboxylate (46 mg, 0.07 mmol), a aqueous NaOH solution (4 M, 0.18 mL, 0.70 mmol), and mixed solvent THF/MeOH(v/v=1/1, 2 mL). The title compound was a yellow solid (10 mg, 30%).

MS (ESI, pos. ion) m/z: 482.1 [M+H]+;

$^1$H NMR (400 MHz, DMSO-d$_6$) δ (ppm): 12.35 (s, 1H), 8.56 (d, J=8.6 Hz, 1H), 8.28 (s, 2H), 7.93 (s, 1H), 7.64 (s, 2H), 7.49 (s, 3H), 6.58 (s, 1H), 4.64 (s, 1H), 2.56 (s, 1H), 1.87-1.49 (m, 10H).

Example 11: (+/−)-trans-3-((2-(5-fluoro-1H-pyrrolo[2,3-b]pyridin-3-yl)-6-phenoxypyrimidin-4-yl)amino)bicyclo[2.2.2]octane-2-carboxylic Acid

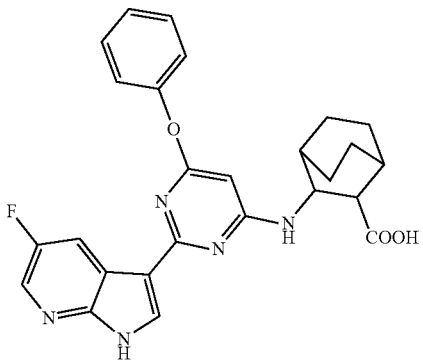 [SMILES: O=C(O)C1C2CCC(CC2)C1Nc1cc(Oc2ccccc2)nc(-c2c[nH]c3ncc(F)cc23)n1]

Step 1: 2,4-dichloro-6-phenoxypyrimidine

To a solution of 2,4,6-trichloropyrimidine (500 mg, 2.73 mmol) in acetone (6 mL) were added dropwise slowly a mixture of phenol (257 mg, 2.73 mmol) and NaOH (112 mg, 2.78 mmol) at 0° C. The mixture was stirred for 3 h at room temperature. Then 30 mL of H$_2$O was added to the mixture. The resulting mixture was extracted with EtOAc (30 mL×3). The combined organic layers were washed with saturated brine (50 mL), dried over anhydrous Na$_2$SO$_4$ and filtered. The filtrate was concentrated in vacuo. The residue was purified by silica gel column chromatography (PE/EtOAc (v/v)=20/1) to give the title compound as colourless oil (569 mg, 87%).

MS (ESI, pos.ion) m/z: 249.3 [M+H]+;

$^1$H NMR (400 MHz, CDCl$_3$) δ (ppm): 7.48 (t, J=8.0 Hz, 2H), 7.34 (t, J=7.5 Hz, 1H), 7.18-7.14 (m, 2H), 6.80 (s, 1H).

Step 2: (+/−)-trans-methyl 3-((2-chloro-6-phenoxypyrimidin-4-yl)amino)bicycle[2.2.2]octane-2-carboxylate To a solution of (+/−)-trans-methyl 3-aminobicyclo[2.2.2]octane-2-carboxylate (460 mg, 2.51 mmol) and 2,4-dichloro-6-phenoxy-pyrimidine (550 mg, 2.28 mmol) in DMF (5 mL) was added potassium carbonate (346 mg, 2.51 mmol). Then the mixture was stirred at room temperature overnight. Water (40 mL) was added to the mixture and the resulting mixture was extracted with EtOAc (40 mL×3). The combined organic layers were washed with saturated brine (50 mL), dried over anhydrous Na$_2$SO$_4$ and concentrated in vacuo. The residue was purified by silica gel column chromatography (n-hexane/EtOAc (v/v)=1/1) to give the title compound as a white solid (386 mg, 44%).

MS (ESI, pos.ion) m/z: 388.1 [M+H]+;

$^1$H NMR (400 MHz, CDCl$_3$) δ (ppm): 7.59 (d, J=6.8 Hz, 2H), 7.41-7.37 (m, 3H), 6.55 (s, 1H), 5.50 (s, 1H), 3.76 (s, 3H), 2.36 (d, J=5.3 Hz, 1H), 1.84 (s, 1H), 1.70-1.42 (m, 10H).

Step 3: (+/−)-trans-methyl 3-((2-(5-fluoro-1-tosyl-1H-pyrrolo[2,3-b]pyridin-3-yl)-6-phenoxypyrimidin-4-yl)amino)bicyclo[2.2.2]octane-2-carboxylate A sealed tube was charged with 5-fluoro-3-(4,4,5,5-tetramethyl-1,3,2-dioxaborolan-2-yl)-1-tosyl-1H-pyrrolo[2,3-b]pyridine (258 mg, 0.31 mmol, 50%), (+/−)-trans-methyl 3-((2-chloro-6-phenoxypyrimidin-4-yl)amino)bicyclo[2.2.2]octane-2-carboxylate (100 mg, 0.26 mmol), potassium carbonate (106 mg, 0.77 mmol), Pd(dppf)Cl$_2$ (42 mg, 0.05 mmol), 1,4-dioxane (3 mL) and H$_2$O (0.2 mL). The resulting mixture in the sealed tube was stirred at 110° C. for 3 h under nitrogen protection. The reaction mixture was passed through a celite and the filter cake was washed with EtOAc (50 mL). The filtrate was washed with saturated brine (50 mL), dried over Na$_2$SO$_4$ and filtered, and the filtrate was concentrated in vacuo to dry. The residue was purified by silica gel column chromatography (n-hexane/EtOAc (v/v)=5/1) to give the title compound as a yellow solid (80 mg, 48%).

MS (ESI, pos.ion) m/z: 642.6[M+H]+;

$^1$H NMR (400 MHz, CDCl$_3$) δ (ppm): 8.45 (s, 1H), 8.34 (s, 1H), 8.28 (s, 1H), 8.10 (d, J=8.3 Hz, 2H), 7.46 (t, J=7.8 Hz, 2H), 7.31 (d, J=8.3 Hz, 3H), 7.20 (d, J=7.8 Hz, 2H), 6.39 (s, 1H), 5.16 (s, 1H), 4.64 (s, 1H), 3.64 (s, 3H), 2.40 (s, 3H), 2.32 (d, J=6.3 Hz, 1H), 2.01 (s, 1H), 1.71 (d, J=11.5 Hz, 2H), 1.55-1.30 (m, 6H).

Step 4: (+/−)-trans-3-((2-(5-fluoro-1H-pyrrolo[2,3-b]pyridin-3-yl)-6-phenoxypyrimidin-4-yl)amino)bicyclo[2.2.2]octane-2-carboxylic Acid To a solution of (+/−)-trans-methyl 3-((2-(5-fluoro-1-tosyl-1H-pyrrolo[2,3-b]pyridine-3-yl)-6-phenoxypyrimidin-4-yl)amino)bicyclo[2.2.2]octane-2-carboxylate (173 mg, 0.27 mmol) in a mixed solvent THF/MeOH (v/v=1/1, 3 mL) was added NaOH aqueous solution (4 M, 0.67 mL, 2.70 mmol), and the mixture was stirred overnight at 30° C. Water (10 mL) was added to the mixture and the resulting mixture was adjusted with HCl (1 M) to pH about 5.5. Then the mixture was extracted with EtOAc (20 mL×3). The combined organic layers were washed with saturated brine, dried over anhydrous Na$_2$SO$_4$ and filtered, then the filtrate was concentrated in vacuo. The residue was purified by silica gel column chromatography (DCM/MeOH (v/v)=10/1) to give the title compound as a yellow solid (70 mg, 55%).

MS (ESI, pos. ion) m/z: 474.1 [M+H]+;

$^1$H NMR (600 MHz, DMSO-d$_6$) δ (ppm): 12.37 (s, 1H), 12.20 (s, 1H), 8.50 (s, 1H), 8.29 (s, 1H), 7.43 (s, 2H), 7.29-7.17 (m, 3H), 7.10 (d, J=5.0 Hz, 1H), 6.73 (s, 1H), 4.55 (s, 1H), 3.60 (s, 1H), 3.36 (s, 3H), 2.68 (s, 1H), 1.77 (m, 8H).

Example 12: (+/−)-trans-3-((2-(5-fluoro-1H-pyrrolo[2,3-b]pyridin-3-yl)-6-(1-methyl-1H-pyrazol-4-yl)pyrimidin-4-yl)amino)bicyclo[2.2.2]octane-2-carboxylic Acid

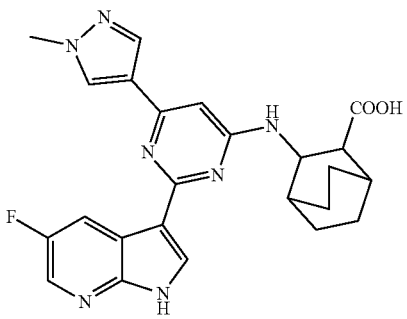 [SMILES: Cn1cc(-c2cc(NC3C4CCC(CC4)C3C(=O)O)nc(-c3c[nH]c4ncc(F)cc34)n2)cn1]

Step 1: 2,4-dichloro-6-(1-methyl-1H-pyrazol-4-yl)pyrimidine

To a solution of 2,4,6-trichloropyrimidine (100 mg, 0.55 mmol) in THF (4 mL) were added Pd(PPh$_3$)$_2$Cl$_2$ (38 mg, 0.05 mmol), (1-methylpyrazol-4-yl)boronic acid (68 mg, 0.55 mol) and Na$_2$CO$_3$ aqueous solution (1 M, 1.10 mL, 1.10 mmol). The reaction mixture was heated to 70° C. under nitrogen protection and stirred for 4 h. Then 50 mL of water was added to the mixture. The mixture was extracted with EtOAc (50 mL×3). The combined organic layers were washed with saturated brine (50 mL), dried over anhydrous Na$_2$SO$_4$ and filtered, then the filtrate was concentrated in vacuo to dry. The residue was purified by silica gel column chromatography (n-hexane/EtOAc (v/v)=5/1) to give the title compound as a white solid (94 mg, 75%).

MS (ESI, pos. ion) m/z: 229.0 [M+H]$^+$;
$^1$H NMR (400 MHz, CDCl$_3$) δ (ppm): 8.12 (s, 1H), 8.03 (s, 1H), 7.34 (s, 1H), 4.00 (s, 3H).

Step 2: (+/−)-trans-methyl 3-((2-chloro-6-(1-methyl-1H-pyrazol-4-yl)pyrimidin-4-yl)amino) bicyclo[2.2.2]octane-2-carboxylate To a solution of (+/−)-trans-methyl 3-aminobicyclo[2.2.2]octane-2-carboxylate (88 mg, 0.48 mmol), 2,4-dichloro-6-(1-methyl-1H-pyrazol-4-yl)pyrimidine (92 mg, 0.40 mmol) in DMF (2 mL) was added potassium carbonate (167 mg, 1.20 mmol). Then the mixture was stirred at room temperature overnight. Water (40 mL) was added to the mixture and the resulting mixture was extracted with EtOAc (40 mL×3). The combined organic layers were washed with saturated brine (100 mL), dried over anhydrous Na$_2$SO$_4$ and filtered, and the filtrate was concentrated in vacuo. The residue was purified by silica gel column chromatography (PE/EtOAc (v/v)=1/1) to give the title compound as a white solid (87 mg, 58%).

MS (ESI, pos.ion) m/z: 376.1 [M+H]$^+$;
$^1$H NMR (400 MHz, CDCl$_3$) δ (ppm): 8.02 (s, 1H), 7.94 (s, 1H), 6.52 (s, 1H), 5.37 (s, 1H), 3.96 (s, 3H), 3.75 (s, 3H), 2.38 (d, J=5.0 Hz, 1H), 2.07 (d, J=5.7 Hz, 1H), 1.86 (d, J=2.6 Hz, 1H), 1.49 (m, 8H).

Step 3: (+/−)-trans-methyl 3-((2-(5-fluoro-1-tosyl-1H-pyrrolo[2,3-b]pyridin-3-yl)-6-(1-methyl-1H-pyrazol-4-yl)pyrimidin-4-yl)amino)bicyclo[2.2.2]octane-2-carboxylate A microwave tube was charged with 5-fluoro-3-(4,4,5,5-tetramethyl-1,3,2-dioxaborolan-2-yl)-1-tosyl-1H-pyrrolo[2,3-b]pyridine (231 mg, 0.28 mmol, 50%), (+/−)-trans-methyl 3-((2-chloro-6-(1-methylpyrazol-4-yl)pyrimidin-4-yl)amino)bicyclo[2.2.2]octane-2-carboxylate (87 mg, 0.23 mmol), potassium acetate (95 mg, 0.69 mmol), Pd(dppf)Cl$_2$ (37 mg, 0.05 mmol), 1,4-dioxane (3 mL) and H$_2$O (0.2 mL). The resulting mixture was bubbled with nitrogen for 10 minutes and then the mixture was stirred at 110° C. with microwave heating for 2 h. The reaction mixture was filtered through a celite pad and the filter cake was washed with EtOAc (50 mL). The filtrate was washed with saturated brine (50 mL), dried over Na$_2$SO$_4$ and filtered, and the filtrate was concentrated in vacuo. The residue was purified by silica gel column chromatography (n-hexane/EtOAc (v/v)=5/1) to give the title compound as a brown solid (54 mg, 37%).

MS (ESI, pos.ion) m/z: 630.2[M+H]$^+$;
$^1$H NMR (400 MHz, CDCl$_3$) δ (ppm): 8.66 (s, 1H), 8.63 (dd, J=8.9, 2.6 Hz, 1H), 8.33 (s, 1H), 8.12 (d, J=8.2 Hz, 2H), 8.06 (s, 1H), 8.01 (s, 1H), 7.30 (s, 1H), 6.47 (s, 1H), 5.15 (s, 1H), 4.49 (s, 1H), 4.03 (s, 3H), 3.74 (s, 3H), 2.43 (d, J=5.1 Hz, 1H), 2.39 (s, 3H), 2.10 (s, 1H), 1.97 (s, 1H), 1.52-1.39 (m, 8H).

Step 4: (+/−)-trans-3-((2-(5-fluoro-1H-pyrrolo[2,3-b]pyridin-3-yl)-6-(1-methyl-1H-pyrazol-4-yl)pyrimidin-4-yl)amino)bicyclo[2.2.2]octane-2-carboxylic Acid To a solution of (+/−)-trans-methyl 3-((2-(5-fluoro-1-tosyl-1H-pyrrolo[2,3-b]pyridine-3-yl)-6-(1-methyl-1H-pyrazol-4-yl)pyrimidin-4-yl)amino)bicyclo[2.2.2]octane-2-carboxylat e (54 mg, 0.09 mmol) in THF/MeOH (v/v=1/1, 3 mL) was added NaOH aqueous solution (4 M, 0.23 mL, 0.90 mmol), and the mixture was stirred overnight at 30° C. Water (10 mL) was added to the mixture and the resulting mixture was adjusted with HCl (1M) to pH about 5.5. Then the mixture was extracted with EtOAc (20 mL×3). The combined organic layers were dried over anhydrous Na$_2$SO$_4$ and filtered. The filtrate was concentrated in vacuo. The residue obtained was purified by silica gel column chromatography (DCM/MeOH (v/v)=10/1) to give the title compound as a yellow solid (17 mg, 43%).

MS (ESI, pos.ion) m/z: 462.1 [M+H]$^+$;
HRMS (ESI, pos. ion) m/z: 462.2062 [M+H]$^+$, (C$_{24}$H$_{25}$FN$_7$O$_2$) [M+H]$^+$ theoretical value: 462.2054;
$^1$H NMR (600 MHz, DMSO-d$_6$) δ (ppm): 12.23 (s, 1H), 8.63 (s, 1H), 8.32 (s, 1H), 8.27 (s, 1H), 7.99 (s, 1H), 7.31 (s, 1H), 6.43 (s, 1H), 4.61 (s, 1H), 3.92 (s, 3H), 1.98 (s, 1H), 1.79 (s, 1H), 1.74-1.26 (m, 8H).

Example 13: (+/−)-trans-3-((2-(5-fluoro-1H-pyrrolo[2,3-b]pyridin-3-yl)-6-(1-methyl-1H-pyrrol-3-yl)pyrimidin-4-yl)amino)bicyclo[2.2.2]octane-2-carboxylic Acid

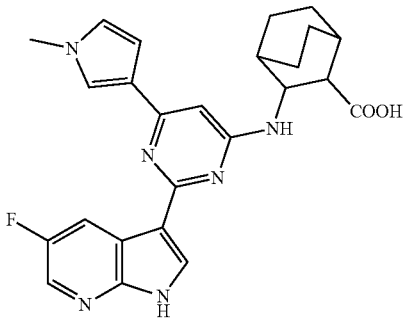 [SMILES: Cn1ccc(-c2cc(NC3C4CCC(CC4)C3C(=O)O)nc(-c3c[nH]c4ncc(F)cc34)n2)c1]

Step 1: 2,4-dichloro-6-(1-methyl-1H-pyrrol-3-yl)pyrimidine

To a solution of 2,4,6-trichloropyrimidine (500 mg, 2.73 mmol) in THF (20 mL) was added Pd(PPh$_3$)$_2$Cl$_2$ (191 mg, 0.27 mmol), (1-methylpyrrol-3-yl)boronic acid (627 mg, 2.73 mol) and Na$_2$CO$_3$ aqueous solution (1 M, 5.45 mL, 5.45 mmol). The reaction mixture was heated to 70° C. and stirred for 4 h under nitrogen protection. Then 50 mL of water was added to the mixture. The resulting mixture was extracted with EtOAc (50 mL×3). The combined organic layers were washed with saturated brine (100 mL), dried over anhydrous Na$_2$SO$_4$ and filtered, then the filtrate was concentrated in vacuo. The residue was purified by silica gel column chromatography (n-hexane/EtOAc (v/v)=5/1) to give the title compound as a white solid (484 mg, 78%).

MS (ESI, pos.ion) m/z: 228.2 [M+H]$^+$;
$^1$H NMR (400 MHz, CDCl$_3$) δ (ppm): 7.48 (s, 1H), 7.25 (s, 1H), 6.70-6.58 (m, 2H), 3.73 (s, 3H).

Step 2: (+/−)-trans-methyl 3-((2-chloro-6-(1-methyl-1H-pyrrol-3-yl)pyrimidin-4-yl)amino) bicycle[2.2.2]octane-2-carboxylate To a solution of (+/−)-trans-methyl 3-aminobicyclo[2.2.2]octane-2-carboxylate (466 mg, 2.54 mmol), 2,4-dichloro-6-(1-methylpyrrol-3-yl)pyrimidine (484 mg, 2.12 mmol) in DMF (6 mL) was added potassium carbonate (879 mg, 6.36 mmol). Then the mixture was stirred at room temperature overnight. Water (40 mL) was added to the mixture and the resulting mixture was extracted with EtOAc (40 mL×3). The combined organic layers were washed with saturated brine (100 mL), dried over anhydrous Na$_2$SO$_4$ and concentrated in vacuo. The residue was purified by silica gel column chromatography (n-hexane/EtOAc (v/v)=5/1) to give the title compound as a white solid (234 mg, 29%).

MS (ESI, pos. ion) m/z: 375.1 [M+H]$^+$;
$^1$H NMR (400 MHz, CDCl$_3$) δ (ppm): 7.39 (s, 1H), 6.62 (s, 1H), 6.57 (s, 1H), 6.44 (s, 1H), 5.32 (s, 2H), 4.24 (d, J=5.8 Hz, 1H), 3.74 (s, 3H), 3.69 (s, 3H), 2.37 (d, J=4.8 Hz, 1H), 1.86 (d, J=2.5 Hz, 1H), 1.71-1.40 (m, 8H).

Step 3: (+/−)-trans-methyl 3-((2-(5-fluoro-1-tosyl-1H-pyrrolo[2,3-b]pyridin-3-yl)-6-(1-methyl-1H-pyrrol-3-yl)pyrimidin-4-yl)amino)bicyclo[2.2.2]octane-2-carboxylate A microwave tube was charged with 5-fluoro-3-(4,4,5,5-tetramethyl-1,3,2-dioxaborolan-2-yl)-1-tosyl-1H-pyrrolo[2, 3-b]pyridine (647 mg, 0.78 mmol), (+/−)-trans-methyl 3-((2-chloro-6-(1-methylpyrrol-3-yl)pyrimidin-4-yl)amino)bicyclo[2.2.2]octane-2-carboxylate (243 mg, 0.65 mmol), potassium acetate (268 mg, 1.95 mmol), Pd(dppf)Cl$_2$(105 mg, 0.13 mmol), 1,4-dioxane (3 mL) and H$_2$O (0.2 mL). The resulting mixture was bubbled with nitrogen for 10 minutes and stirred at 110° C. with microwave heating for 2 h. The reaction mixture was filtered through a celite pad and the filter cake was washed with EtOAc (50 mL). The obtained filtrate was washed with saturated brine (50 mL), dried over anhydrous Na$_2$SO$_4$ and filtered, and the filtrate was concentrated in vacuo. The residue was purified by silica gel column chromatography (n-hexane/EtOAc (v/v)=5/1) to give the title compound as a brown solid (330 mg, 81%).

MS (ESI, pos. ion) m/z: 629.2[M+H]$^+$;
$^1$H NMR (400 MHz, CDCl$_3$) δ (ppm): 8.70-8.61 (m, 2H), 8.31 (s, 1H), 8.10 (d, J=8.2 Hz, 2H), 7.42 (s, 1H), 7.27 (s, 1H), 6.67 (s, 2H), 6.43 (s, 1H), 5.32 (s, 1H), 3.80 (s, 3H), 3.76 (s, 3H), 2.43 (d, J=5.0 Hz, 1H), 2.38 (s, 3H), 1.96 (s, 1H), 1.73 (s, 10H).

Step 4: (+/−)-trans-3-((2-(5-fluoro-1H-pyrrolo[2,3-b]pyridin-3-yl)-6-(1-methyl-1H-pyrrol-3-yl)pyrimidin-4-yl)amino)bicyclo[2.2.2]octane-2-carboxylate To a solution of (+/−)-trans-methyl 3-((2-(5-fluoro-1-tosyl-1H-pyrrolo[2,3-b]pyridin-3-yl)-6-(1-methyl-1H-pyrrol-3-yl)pyrimidin-4-yl)amino)bicyclo[2.2.2]octane-2-carboxylate (330 mg, 0.52 mmol) in THF/MeOH (v/v=1/1, 3 mL) was added NaOH aqueous solution (4 M, 1.30 mL, 5.20 mmol) and the resulting mixture was stirred overnight at 30° C. Water (10 mL) was added to the mixture and the resulting mixture was adjusted with HCl (1 M) to pH about 5.5. Then the mixture was extracted with EtOAc (20 mL×3). The combined organic layers were washed with saturated brine (50 mL), dried over anhydrous Na$_2$SO$_4$ and filtered.

The filtrate was concentrated in vacuo. The residue was purified by silica gel column chromatography (DCM/MeOH (v/v)=10/1) to give the title compound as a yellow solid (42 mg, 17%).

MS (ESI, pos.ion) m/z: 461.1 [M+H]$^+$;
HRMS (ESI, pos. ion) m/z: 461.2114 [M+H]$^+$, (C$_{24}$H$_{23}$FN$_5$O$_3$) [M+H]$^+$ theoretical value: 461.2101;
$^1$H NMR (600 MHz, DMSO-d$_6$) δ (ppm): 12.27 (s, 1H), 8.63 (s, 1H), 8.27 (s, 2H), 7.51 (s, 1H), 7.28 (s, 1H), 6.81 (s, 1H), 6.55 (s, 1H), 6.41 (s, 1H), 4.60 (s, 1H), 3.62 (s, 3H), 2.03-1.30 (m, 10H).

Example 14: (+/−)-trans-3-((2-(5-fluoro-1H-pyrrolo[2,3-b]pyridin-3-yl)-[4,5'-bipyrimidin]-6-yl)amino)bicyclo[2.2.2]octane-2-carboxylic Acid

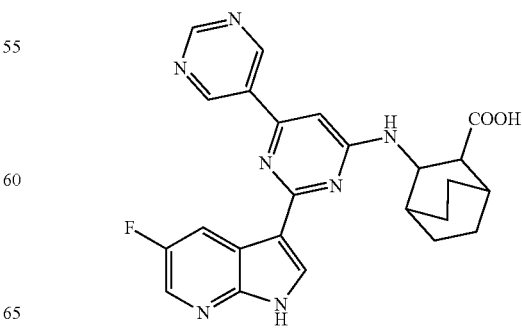

Step 1: 2,6-dichloro-4,5'-bipyrimidine

To a solution of 2,4,6-trichloropyrimidine (100 mg, 0.55 mmol) in acetonitrile (4 mL) was added Pd(dppf)Cl$_2$ (89 mg, 0.11 mmol), pyrimidin-5-ylboronic acid (67 mg, 0.55 mol), CsCO$_3$ (266 mg, 0.82 mmol) and H$_2$O (0.5 mL). The reaction mixture was heated to 95° C. under nitrogen protection and stirred for 5 h. Then 50 mL of water was added to the mixture. The mixture was extracted with EtOAc (50 mL×3). The combined organic layers were washed with saturated brine (50 mL), dried over anhydrous Na$_2$SO$_4$ and concentrated in vacuo. The residue was purified by silica gel column chromatography (PE/EtOAc (v/v)=5/1) to give the title compound as a red solid (44 mg, 36%).

MS (ESI, pos.ion) m/z: 228.0 [M+H]$^+$;
$^1$H NMR (400 MHz, CDCl$_3$) δ (ppm): 9.41 (s, 3H), 7.76 (s, 1H).

Step 2: (+/−)-trans-methyl 3-((2-chloro-[4,5'-bipyrimidin]-6-yl)amino)bicycle[2.2.2]octane-2-carboxylate To a solution of (+/−)-trans-methyl 3-aminobicyclo[2.2.2]octane-2-carboxylate (73 mg, 0.40 mmol), 2,6-dichloro-4,5'-bipyrimidine (76 mg, 0.33 mmol) in DMF (2 mL) was added potassium carbonate (138 mg, 1.00 mmol). Then the mixture was stirred at room temperature overnight. Water (40 mL) was added to the mixture and the resulting mixture was extracted with EtOAc (40 mL×3). The combined organic layers were washed with saturated brine (50 mL), dried over anhydrous Na$_2$SO$_4$ and filtered. The filtrate was concentrated in vacuo to dry. The residue was purified by silica gel column chromatography (PE/EtOAc (v/v)=1/1) to give the title compound as a white solid (65 mg, 52%).

MS (ESI, pos. ion) m/z: 374.4[M+H]$^+$;
$^1$H NMR (400 MHz, CDCl$_3$) δ (ppm): 9.32 (s, 3H), 6.95 (s, 1H), 5.77 (s, 1H), 4.36 (s, 1H), 3.77 (s, 3H), 2.41 (d, J=3.4 Hz, 1H), 1.88 (s, 1H), 1.83-1.65 (m, 8H).

Step 3: (+/−)-trans-methyl 3-((2-(5-fluoro-1-tosyl-1H-pyrrolo[2,3-b]pyridin-3-yl)-[4,5'-bipyrimidin]-6-yl)amino)bicyclo[2.2.2]octane-2-carboxylate A microwave tube was charged with 5-fluoro-3-(4,4,5,5-tetramethyl-1,3,2-dioxaborolan-2-yl)-1-tosyl-1H-pyrrolo[2,3-b]pyridine (173 mg, 0.21 mmol, 50%), (+/−)-trans-methyl 3-((2-chloro-[4,5'-bipyrimidin]-6-yl)amino)bicycle[2.2.2]octane-2-carboxylate (65 mg, 0.17 mmol), potassium acetate (72 mg, 0.52 mmol), Pd(dppf)Cl$_2$ (28 mg, 0.03 mmol), 1,4-dioxane (3 mL) and water (0.2 mL). The resulting solution was bubbled with nitrogen for 10 minutes to remove the air and then stirred at 110° C. for 2 h with microwave heating. The reaction mixture was filtered through a celite pad and the filter cake was washed with EtOAc (50 mL). The filtrate was washed with saturated brine (50 mL), dried over Na$_2$SO$_4$, filtered, and the filtrate was concentrated in vacuo. The residue was purified by silica gel column chromatography (n-hexane/EtOAc (v/v)=5/1) to give the title compound as a brown solid (50 mg, 46%).

MS (ESI, pos. ion) m/z: 628.7 [M+H]$^+$;
$^1$H NMR (400 MHz, CDCl$_3$) δ (ppm): 9.41 (s, 2H), 9.35 (s, 1H), 8.73 (s, 1H), 8.35 (s, 1H), 8.15 (d, J=8.3 Hz, 2H), 5.37 (s, 1H), 3.76 (s, 3H), 2.46 (s, 1H), 2.40 (s, 3H), 2.14 (s, 1H), 2.05-1.99 (m, 2H), 1.49-1.41 (m, 8H).

Step 4: (+/−)-trans-3-((2-(5-fluoro-1H-pyrrolo[2,3-b]pyridin-3-yl)-[4,5'-bipyrimidin]-6-yl) bicyclo[2.2.2]octane-2-carboxylate To a solution of (+/−)-trans-methyl 3-((2-(5-fluoro-1-tosyl-1H-pyrrolo[2,3-b]pyridine-3-yl)-[4,5'-bipyrimidin]-6-yl)amino)bicyclo[2.2.2]octane-2-carboxylate (50 mg, 0.08 mmol) in THF/MeOH (v/v=1/1, 2 mL) was added NaOH aqueous solution (4 M, 0.2 mL, 0.80 mmol) and the mixture was stirred overnight at 30° C. Water (10 mL) was added to the mixture and the mixture was adjusted with HCl (1 M) to pH about 5.5. Then the mixture was extracted with EtOAc (20 mL×3). The combined organic layers were washed with saturated brine (50 mL), dried over anhydrous Na$_2$SO$_4$ and filtered. The filtrate was concentrated in vacuo to remove the solvent. The obtained residue was purified by silica gel column chromatography (DCM/MeOH (v/v)=10/1) to give the title compound as a yellow solid (20 mg, 55%).

MS (ESI, pos.ion) m/z: 460.5 [M+H]$^+$;
HRMS (ESI, pos. ion) m/z: 460.1905 [M+H]$^+$, (C$_{24}$H$_{23}$FN$_7$O$_2$) [M+H]$^+$ theoretical value: 460.1897;
$^1$H NMR (600 MHz, DMSO-d$_6$) δ (ppm): 12.36 (s, 1H), 9.60 (s, 1H), 9.44 (s, 1H), 9.31 (s, 1H), 8.60 (s, 1H), 8.48 (s, 1H), 8.29 (s, 1H), 7.78 (s, 1H), 6.88 (s, 1H), 4.69 (s, 1H), 2.01 (s, 2H), 1.88-1.32 (m, 8H).

Example 15: (+/−)-cis-N-(3-((2-(5-fluoro-1H-pyrrolo[2,3-b]pyridin-3-yl)-6-phenyl pyrimidin-4-yl)amino)cyclohexyl)-1H-1,2,3-triazole-4-carboxamide

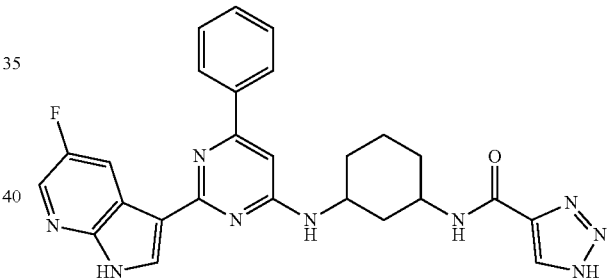

Step 1: (+/−)-cis-3-tert-butoxycarbonylamino-1-benzyloxycarbonylaminocyclohexane To a solution of (+/−)-cis-3-((tert-butoxycarbonyl)amino) cyclohexanecarboxylic acid (5 g, 20.6 mmol) in toluene (60 mL) were added triethylamine (4.6 mL, 33.0 mmol) and diphenylphosphoryl azide (5.32 mL, 24.7 mmol), and the mixture was stirred for 3 h at rt. Then benzyl alcohol (4.27 mL, 41.1 mmol) was added, and the resulting mixture was stirred at 100° C. overnight under nitrogen protection. The reaction mixture was diluted with ethyl acetate (60 mL), and the resulting mixture was washed with saturated brine (60 mL). The organic layer was dried over anhydrous sodium sulfate and concentrated in vacuo. The residue was purified by silica gel column chromatography (PE/EtOAc (v/v)=5/1) to give the title compound as dark yellow oil (7.16 g, 100%).

Step 2: (+/−)-cis-N-tert-butoxycarbonyl-1,3-cyclohexanediamine

A solution of (+/−)-cis-3-tert-butoxycarbonylamino-1-benzyloxycarbonylamino cyclohexane (7.2 g, 21 mmol) in methanol (100 mL) was placed in an autoclave, and to the solution was added Pd/C (10% Pd, 2 g). The resulting mixture was stirred at rt overnight in hydrogen atmosphere under a pressure of 2 MPa. The reaction mixture was filtered through a celite pad to remove the catalyst, then the filter cake was washed with a mixture of methanol (200 mL) and ethyl acetate (200 mL). The filtrate was concentrated in vacuo to dry and the residue was purified by silica-gel column chromatography (DCM/MeOH (v/v)=20/1-10/1) to give the title compound as colourless oil (1.65 g, 37%).

MS (ESI, pos.ion) m/z: 215.1 [M+H]$^+$.

Step 3: 2,4-dichloro-6-phenylpyrimidine

To a solution of 2,4,6-trichloropyrimidine (0.29 mL, 2.5 mmol) in tetrahydrofuran (5 mL) were added palladium acetate (8 mg, 0.035 mmol), triphenylphosphine (18 mg, 0.065 mmol), phenylboronic acid (0.20 g, 1.6 mmol) and aqueous sodium carbonate solution (1 M, 3.3 mL, 3.3 mmol). The mixture was stirred at 60° C. for 6 h, then cooled to rt and concentrated to remove the organic solvent. To the residue was added H$_2$O (10 mL), and the mixture was extracted with EtOAc (10 mL×3). The combined organic layers were washed with saturated brine (30 mL), dried over anhydrous sodium sulfate and filtered. The filtrate was concentrated in vacuo to dry and the residue was purified by silica gel column chromatography (PE) to give the title compound as a white solid (0.225 g, 61%).

MS (ESI, pos.ion) m/z: 224.95 [M+H]$^+$;
$^1$H NMR (400 MHz, CDCl$_3$) δ (ppm): 8.15-8.04 (m, 2H), 7.70 (s, 1H), 7.63-7.50 (m, 3H).

Step 4: (+/−)-cis-tert-butyl (3-((2-chloro-6-phenylpyrimidin-4-yl)amino)cyclohexyl) carbamate To a solution of 2,4-dichloro-6-phenylpyrimidine (727 mg, 3.23 mmol) and (+/−)-cis-N-tert-butoxycarbonyl-1,3-cyclohexanediamine (630 mg, 2.94 mmol) in N,N-dimethylformamide (5 mL) was added potassium carbonate (1.22 g, 8.82 mmol). The mixture was stirred at rt overnight. To the reaction mixture was added water (50 mL) and the resulting mixture was extracted with EtOAc (40 mL×3). The combined organic layers were washed with saturated brine (100 mL), dried over anhydrous Na$_2$SO$_4$, and filtered. The filtrate was concentrated in vacuo and the residue was purified by silica gel column chromatography (n-hexane/EtOAc (v/v)=5/1) to give the title compound as a white solid (516 mg, 43%).

MS-ESI: (ESI, pos.ion) m/z: 403.1 [M+H]$^+$;
$^1$H NMR (400 MHz, CDCl$_3$) δ (ppm): 8.02-7.93 (m, 2H), 7.53-7.44 (m, 3H), 6.59 (s, 1H), 4.45 (s, 1H), 3.60 (s, 1H), 2.43 (d, J=11.8 Hz, 1H), 2.10 (d, J=14.5 Hz, 2H), 1.89 (d, J=14.0 Hz, 1H), 1.63 (s, 4H), 1.57-1.43 (m, 11H).

Step 5: N$^1$-(2-chloro-6-phenylpyrimidin-4-yl)cyclohexane-1,3-diamine

To a solution of hydrochloric acid in 1,4-dioxane (1.1 mL, 5.5 mmol, 5 mol/L) was added (+/−)-cis-tert-butyl (3-((2-chloro-6-phenylpyrimidin-4-yl)amino)cyclohexyl)carbamate (220 mg, 0.55 mmol), and the mixture was stirred at rt overnight. The reaction mixture was concentrated in vacuo to remove the solvent and to the residue was added an appropriate amount of water. The resulting mixture was adjusted with saturated aqueous sodium carbonate to pH 9. The mixture was extracted with ethyl acetate (20 mL×3), and the combined organic layers were washed with saturated brine (50 mL), dried over anhydrous sodium sulfate, then filtered. The filtrate was concentrated in vacuo to dryness to give the title compound as a white solid (144 mg, 87%).

MS (ESI, pos.ion) m/z: 303.1 [M+H]$^+$;
$^1$H NMR (400 MHz, CDCl$_3$) δ (ppm): 7.99-7.89 (m, 2H), 7.58-7.41 (m, 3H), 6.57 (s, 1H), 5.74 (s, 1H), 2.25-2.14 (m, 1H), 2.00 (d, J=13.2 Hz, 1H), 1.88 (d, J=9.8 Hz, 2H), 1.58-1.37 (m, 2H), 1.30-1.12 (m, 4H).

Step 6: (+/−)-cis-N-(3-((2-chloro-6-phenylpyrimidin-4-yl)amino)cyclohexyl)-1H-1,2,3-triazole-4-carboxamide To a solution of N$^1$-(2-chloro-6-phenylpyrimidin-4-yl)cyclohexane-1,3-diamine (65 mg, 0.21 mmol) in a mixed solvent of tetrahydrofuran (4 mL) and dimethyl sulfoxide (1 mL) were added N,N-diisopropylethylamine (0.11 mL, 0.7 mmol) and 1H-1,2,3-triazole-4-carboxylic acid (48 mg, 0.42 mmol). The mixture was stirred at rt for 10 min, then HATU (163 mg, 0.43 mmol) was added, and the resulting mixture was stirred at rt for 3 hours. To the reaction mixture was added water (10 mL), and the resulting mixture was extracted with ethyl acetate (10 mL×3). The combined organic layers were washed with saturated brine (30 mL), dried over anhydrous sodium sulfate and filtered. The filtrate was concentrated in vacuo to give the title compound as a colorless solid (85 mg, 100%).

MS (ESI, pos.ion) m/z: 398.5 [M+H]$^+$.

Step 7: (+/−)-cis-N-(3-((2-(5-fluoro-1-tosyl-1H-pyrrolo[2,3-b]pyridin-3-yl)-6-phenylpyrimidin-4-yl)amino)cyclohexyl)-1H-1,2,3-triazole-4-carboxamide To a microwave tube were added 5-fluoro-3-(4,4,5,5-tetramethyl-1,3,2-dioxaborolan-2-yl)-1-tosyl-1H-pyrrolo[2,3-b]pyridine (652 mg, 0.55 mmol, 50%), (+/−)-cis-N-(3-((2-chloro-6-phenylpyrimidin-4-yl)amino)cyclohexyl)-1H-1,2,3-triazole-4-carboxamide (85 mg, 0.21 mmol), potassium carbonate (88 mg, 0.64 mmol), Pd(dppf)Cl$_2$ (34 mg, 0.04 mmol), 1,4-dioxane (3 mL) and water (0.2 mL). The air in the mixture was removed by bubbling with nitrogen for 10 min, then the mixture in the microwave tube was stirred at 120° C. with microwave heating for 4 hours. The mixture was filtered through a celite pad, and the filter cake was washed with ethyl acetate (50 mL). The filtrate was washed with saturated brine (50 mL), dried over anhydrous sodium sulfate and filtered. The filtrate was concentrated in vacuo and the residue was purified by silica gel column chromatography (n-hexane/EtOAc (v/v)=5/1) to give the title compound as a yellow solid (139 mg, 100%).

MS (ESI, pos.ion) m/z: 652.2[M+H]$^+$.

Step 8: (+/−)-cis-N-(3-((2-(5-fluoro-1H-pyrrolo[2,3-b]pyridin-3-yl)-6-phenylpyrimidin-4-yl) amino)cyclohexyl)-1H-1,2,3-triazole-4-carboxamide To a solution of (+/−)-cis-N-(3-((2-(5-fluoro-1-tosyl-1H-pyrrolo[2,3-b]pyridin-3-yl)-6-phenylpyrimidin-4-yl)amino)cyclohexyl)-1H-1,2,3-triazole-4-carboxamide (192 mg, 0.29 mmol) in methanol (1 mL) was added a solution of sodium methoxide in methanol (5 M, 0.6 mL, 2.9 mmol). The mixture was stirred at 30° C. overnight. The reaction mixture was concentrated in vacuo to dry and to the residue was added water (10 mL). The resulting mixture was extracted with ethyl acetate (20 mL×3), and the combined organic layers were washed with saturated brine (50 mL), dried over anhydrous sodium sulfate and filtered. The filtrate was concentrated in vacuo and the residue was purified by silica gel column chromatography (DCM/MeOH (v/v)=10/1) to give the title compound as a white solid (25 mg, 60%).

MS (ESI, pos.ion) m/z: 498.2 [M+H]⁺;

HRMS (ESI, pos. ion) m/z: 498.2169 [M+H]⁺, ($C_{26}H_{25}FN_9O$) [M+H]⁺ theoretical value: 498.2166;

¹H NMR (400 MHz, DMSO-$d_6$) δ (ppm): 12.29 (s, 1H), 8.58 (s, 1H), 8.41 (s, 2H), 8.29 (s, 1H), 8.11 (s, 2H), 7.58-7.48 (m, 3H), 7.42 (s, 1H), 6.76 (s, 1H), 4.15 (s, 1H), 4.04 (s, 1H), 2.30-1.79 (m, 6H).

Example 16: (+/−)-trans-3-((6-(benzofuran-2-yl)-2-(5-fluoro-1H-pyrrolo[2,3-b]pyridin-3-yl) pyrimidin-4-yl)amino)bicyclo[2.2.2]octane-2-carboxylic Acid

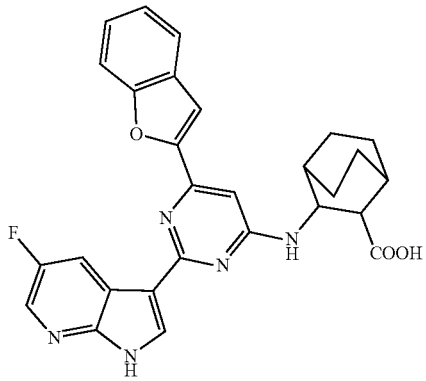 [SMILES: O=C(O)C1C2CCC(CC2)C1Nc1cc(-c2cc3ccccc3o2)nc(-c2c[nH]c3ncc(F)cc23)n1]

Step 1: 4-(benzofuran-2-yl)-2,6-dichloropyrimidine

To a solution of 2,4,6-trichloropyrimidine (50 mg, 0.27 mmol) in a mixed solvent of toluene (3 mL) and ethanol (1 mL) were added tetrakis(triphenylphosphine)palladium (31 mg, 0.03 mmol), benzofuran-2-ylboronic acid (44 mg, 0.28 mmol) and aqueous sodium carbonate solution (1 M, 0.82 mL, 0.82 mmol). The mixture was stirred at 85° C. for 4 h under nitrogen protection. To the reaction mixture was added water (10 mL), and the resulting mixture was extracted with ethyl acetate (10 mL×3). The combined organic layers were washed with saturated brine (30 mL), dried over anhydrous sodium sulfate and filtered. The filtrate was concentrated in vacuo and the residue was purified by silica gel column chromatography (PE) to give the title compound as a white solid (26 mg, 36%).

MS (ESI, pos.ion) m/z: 265.0 [M+H]⁺;

¹H NMR (400 MHz, CDCl₃) δ (ppm): 7.80 (d, J=4.1 Hz, 2H), 7.73 (d, J=7.8 Hz, 1H), 7.60 (d, J=8.4 Hz, 1H), 7.48 (t, J=7.8 Hz, 1H), 7.35 (t, J=7.5 Hz, 1H).

Step 2: (+/−)-trans-methyl 3-((6-(benzofuran-2-yl)-2-chloropyrimidin-4-yl)amino)bicyclo[2.2.2]octane-2-carboxylate (+/−)-trans-Methyl 3-aminobicyclo[2.2.2]octane-2-carboxylate (628 mg, 3.43 mmol) and 4-(benzofuran-2-yl)-2,6-dichloropyrimidine (758 mg, 2.86 mmol) were dissolved in DMF (5 mL), then potassium carbonate (1.19 g, 8.58 mmol) was added. The mixture was stirred at rt overnight. To the reaction mixture was added water (40 mL), and the resulting mixture was extracted with ethyl acetate (40 mL×3). The combined organic layers were washed with saturated brine (100 mL), dried over anhydrous sodium sulfate and filtered. The filtrate was concentrated in vacuo and the residue was purified by silica gel column chromatography (PE/EtOAc (v/v)=20/1) to give the title compound as a white solid (553 mg, 47%).

MS (ESI, pos. ion) m/z: 412.2 [M+H]⁺;

¹H NMR (400 MHz, CDCl₃) δ (ppm): 7.68 (d, J=7.5 Hz, 1H), 7.62-7.54 (m, 2H), 7.40 (dd, J=9.4, 5.9 Hz, 2H), 6.91 (s, 1H), 5.57 (s, 1H), 4.36 (s, 1H), 3.78 (s, 3H), 2.40 (d, J=5.2 Hz, 1H), 2.34 (d, J=3.7 Hz, 1H), 1.90 (d, J=2.6 Hz, 1H), 1.85-1.69 (m, 8H).

Step 3: (+/−)-trans-methyl 3-((6-(benzofuran-2-yl)-2-(5-fluoro-1-tosyl-1H-pyrrolo[2,3-b]pyridine-3-yl) pyrimidin-4-yl)amino)bicyclo[2.2.2]octane-2-carboxylate To a microwave tube were added 5-fluoro-3-(4,4,5,5-tetramethyl-1,3,2-dioxaborolan-2-yl)-1-tosyl-1H-pyrrolo[2,3-b]pyridine (455 mg, 0.44 mmol, 50%), (+/−)-trans-methyl 3-((6-(benzofuran-2-yl)-2-chloropyrimidin-4-yl)amino)bicyclo[2.2.2]octane-2-carboxylate (166 mg, 0.40 mmol), potassium carbonate (165 mg, 1.20 mmol), Pd(dppf)Cl₂ (65 mg, 0.08 mmol), 1,4-dioxane (3 mL) and water (0.2 mL). The air in the mixture was removed by bubbling with nitrogen for 10 min, then the mixture in the microwave tube was stirred at 110° C. with microwave heating for 2 hours. The mixture was filtered through a celite pad, and the filter cake was washed with ethyl acetate (50 mL). The filtrate was washed with saturated brine (50 mL), dried over anhydrous sodium sulfate and filtered. The filtrate was concentrated in vacuo and the residue was purified by silica gel column chromatography (n-hexane/EtOAc (v/v)=5/1) to give the title compound as a yellow solid (57 mg, 35%).

MS (ESI, pos.ion) m/z: 666.3[M+H]⁺;

¹H NMR (400 MHz, CDCl₃) δ (ppm): 8.77-8.67 (m, 2H), 8.35 (d, J=1.7 Hz, 1H), 8.15 (d, J=8.3 Hz, 2H), 7.74 (d, J=7.7 Hz, 1H), 7.65 (s, 1H), 7.59 (d, J=8.2 Hz, 1H), 7.40 (d, J=8.4 Hz, 1H), 7.32 (t, J=8.2 Hz, 3H), 6.89 (s, 1H), 5.24 (s, 1H), 4.60 (s, 1H), 3.77 (s, 3H), 2.47 (d, J=5.5 Hz, 1H), 2.40 (s, 3H), 2.12 (s, 1H), 2.01 (s, 1H), 1.97-1.62 (m, 8H).

Step 4: (+/−)-trans-3-((6-(benzofuran-2-yl)-2-(5-fluoro-1H-pyrrolo[2,3-b]pyridin-3-yl) pyrimidin-4-yl)amino)bicyclo[2.2.2]octane-2-carboxylic Acid To a solution of (+/−)-trans-methyl 3-((6-(benzofuran-2-yl)-2-(5-fluoro-1-tosyl-1H-pyrrolo[2,3-b]pyridin-3-yl)pyrimidin-4-yl)amino)bicyclo[2.2.2]octane-2-carboxylate (57 mg, 0.09 mmol) in THF/MeOH (v/v=1/1, 2 mL) was added aqueous sodium hydroxide solution (4 M, 0.23 mL, 0.90 mmol). The mixture was stirred at 30° C. overnight. To the reaction mixture was added water (10 mL), and the resulting mixture was acidified with hydrochloric acid (1 M) to pH about 5.5. The mixture was extracted with ethyl acetate (20 mL×3), and the combined organic layers were dried over anhydrous sodium sulfate, then filtered. The filtrate was concentrated in vacuo to remove the solvent and the residue was purified by silica gel column chromatography (DCM/MeOH (v/v)=10/1) to give the title compound as a yellow solid (22 mg, 52%).

MS (ESI, pos.ion) m/z: 498.3 [M+H]⁺;

HRMS (ESI, pos. ion) m/z: 498.1931 [M+H]⁺, ($C_{28}H_{25}FN_5O_3$) [M+H]⁺ theoretical value: 498.1941;

¹H NMR (400 MHz, DMSO-$d_6$) δ (ppm): 12.33 (s, 1H), 8.60 (s, 1H), 8.43 (s, 1H), 8.38 (t, J=9.5 Hz, 4H), 8.30 (s, 1H), 7.66 (s, 1H), 6.88 (s, 1H), 4.71 (s, 1H), 2.67 (s, 1H), 2.33 (s, 1H), 1.79-1.41 (m, 8H);

$^{13}$C NMR (151 MHz, DMSO-d$_6$) δ (ppm): 185.05, 162.79, 162.67, 155.32, 155.14, 154.87, 152.39, 146.48, 131.92, 131.87, 131.66, 128.61, 126.28, 123.98, 122.63, 119.01, 111.88, 106.59, 67.49, 50.06, 29.49, 28.75, 28.45, 25.60, 24.20, 21.38, 19.43.

Example 17: (+/−)-trans-3-((6-(benzo[b]thiophen-2-yl)-2-(5-fluoro-1H-pyrrolo[2,3-b]pyridin-3-yl)pyrimidin-4-yl)amino)bicyclo[2.2.2]octane-2-carboxylic Acid

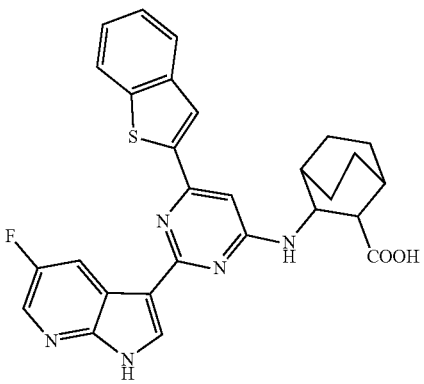

Step 1: 4-(benzo[b]thiophen-2-yl)-2,6-dichloropyrimidine

To a solution of 2,4,6-trichloropyrimidine (50 mg, 0.27 mmol) in a mixed solvent of toluene (3 mL) and ethanol (1 mL) were added tetrakis(triphenylphosphine)palladium (31 mg, 0.03 mmol), benzo[b]thiophen-2-ylboronic acid (49 mg, 0.28 mmol) and aqueous sodium carbonate solution (1 M, 0.82 mL, 0.82 mmol). The mixture was stirred at 85° C. for 4 h under nitrogen protection. To the reaction mixture was added water (10 mL), and the resulting mixture was extracted with ethyl acetate (10 mL×3). The combined organic layers were washed with saturated brine (30 mL), dried over anhydrous sodium sulfate and filtered. The filtrate was concentrated in vacuo and the residue was purified by silica gel column chromatography (PE) to give the title compound as a white solid (24 mg, 31%).

MS (ESI, pos.ion) m/z: 280.9 [M+H]$^+$;
$^1$H NMR (400 MHz, CDCl$_3$) δ (ppm): 8.17 (s, 1H), 7.91 (t, J=6.4 Hz, 2H), 7.64 (s, 1H), 7.51-7.43 (m, 2H).

Step 2: (+/−)-trans-methyl 3-((6-(benzo[b]thiophen-2-yl)-2-chloropyrimidin-4-yl)amino)bicycle [2.2.2]octane-2-carboxylate (+/−)-trans-Methyl 3-aminobicyclo[2.2.2]octane-2-carboxylate (409 mg, 2.23 mmol) and 4-(benzo[b]thiophen-2-yl)-2,6-dichloropyrimidine (523 mg, 1.86 mmol) were dissolved in DMF (5 mL), then potassium carbonate (771 mg, 5.58 mmol) was added. The mixture was stirred at rt overnight. To the reaction mixture was added water (40 mL), and the resulting mixture was extracted with ethyl acetate (40 mL×3). The combined organic layers were washed with saturated brine (50 mL), dried over anhydrous sodium sulfate and filtered. The filtrate was concentrated in vacuo and the residue was purified by silica gel column chromatography (PE/EtOAc (v/v)=20/1) to give the title compound as a white solid (357 mg, 45%).

MS (ESI, pos.ion) m/z: 428.6 [M+H]$^+$;
$^1$H NMR (400 MHz, CDCl$_3$) δ (ppm): 8.05 (s, 1H), 7.91-7.81 (m, 2H), 7.43-7.36 (m, 2H), 6.80 (s, 1H), 5.50 (s, 1H), 4.35 (s, 1H), 3.78 (s, 3H), 2.41 (d, J=4.9 Hz, 1H), 2.10 (s, 1H), 1.90 (d, J=2.6 Hz, 1H), 1.84-1.63 (m, 6H), 1.58-1.43 (m, 2H).

Step 3: (+/−)-trans-methyl 3-((6-(benzo [b]thiophen-2-yl)-2-(5-fluoro-1-tosyl-1H-pyrrolo[2,3-b]pyridine-3-yl)pyrimidin-4-yl)amino)bicyclo[2.2.2]octane-2-carboxylate To a microwave tube were added 5-fluoro-3-(4,4,5,5-tetramethyl-1,3,2-dioxaborolan-2-yl)-1-tosyl-1H-pyrrolo[2,3-b]pyridine (233 mg, 0.28 mmol), (+/−)-trans-methyl 3-((6-(benzo [b]thiophen-2-yl)-2-chloropyrimidin-4-yl)amino)bicyclo[2.2.2]octane-2-carboxylate (100 mg, 0.23 mmol), potassium carbonate (96 mg, 0.70 mmol), Pd(dppf)Cl$_2$ (38 mg, 0.05 mmol), 1,4-dioxane (3 mL) and water (0.2 mL). The air in the mixture was removed by bubbling with nitrogen for 10 min, then the mixture in the microwave tube was stirred at 110° C. with microwave heating for 2 hours. The mixture was filtered through a celite pad, and the filter cake was washed with ethyl acetate (50 mL). The filtrated was washed with saturated brine (50 mL), dried over anhydrous sodium sulfate and filtered. The filtrate was concentrated in vacuo and the residue was purified by silica gel column chromatography (n-hexane/EtOAc (v/v)=5/1) to give the title compound as a yellow solid (147 mg, 92%).

MS (ESI, pos.ion) m/z: 682.2[M+H]$^+$;
$^1$H NMR (400 MHz, CDCl$_3$) δ (ppm): 8.79 (dd, J=9.0, 2.8 Hz, 1H), 8.71 (s, 1H), 8.35 (d, J=1.8 Hz, 1H), 8.14 (d, J=8.3 Hz, 2H), 7.99 (s, 1H), 7.96-7.92 (m, 1H), 7.90-7.85 (m, 1H), 7.44-7.39 (m, 2H), 7.30 (d, J=8.3 Hz, 2H), 6.80 (s, 1H), 5.28 (s, 1H), 4.55 (s, 1H), 3.77 (s, 3H), 2.47 (d, J=5.2 Hz, 1H), 2.40 (s, 3H), 2.12 (s, 1H), 1.99 (s, 1H), 1.92-1.63 (m, 8H).

Step 4: (+/−)-trans-3-((6-(benzo [b]thiophen-2-yl)-2-(5-fluoro-1H-pyrrolo[2,3-b]pyridin-3-yl) pyrimidin-4-yl)amino)bicyclo[2.2.2]octane-2-carboxylic Acid To a solution of (+/−)-trans-methyl 3-((6-(benzo [b]thiophen-2-yl)-2-(5-fluoro-1-tosyl-1H-pyrrolo[2,3-b]pyridin-3-yl)pyrimidin-4-yl)amino)bicyclo[2.2.2]octane-2-carboxylate (147 mg, 0.22 mmol) in THF/MeOH (v/v=1/1, 2 mL) was added aqueous sodium hydroxide solution (4 M, 0.55 mL, 2.20 mmol). The mixture was stirred at 30° C. overnight. To the reaction mixture was added water (10 mL), and the resulting mixture was acidified with hydrochloric acid (1 M) to pH about 5.5. The mixture was extracted with ethyl acetate (20 mL×3), and the combined organic layers were washed with saturated brine (50 mL) and dried over anhydrous sodium sulfate, then filtered. The filtrate was concentrated in vacuo to remove the solvent and the residue was purified by silica gel column chromatography (DCM/MeOH (v/v)=10/1) to give the title compound as a yellow solid (54 mg, 49%).

MS (ESI, pos.ion) m/z: 514.2 [M+1]±;
HRMS (ESI, pos. ion) m/z: 514.1710 [M+H]$^+$, (C$_{24}$H$_{25}$FN$_7$O$_2$) [M+H]$^+$ theoretical value: 514.1713;
$^1$H NMR (400 MHz, DMSO-d$_6$) δ (ppm): 12.32 (s, 1H), 8.69 (s, 1H), 8.34 (s, 1H), 8.32 (s, 1H), 8.11 (s, 1H), 8.09-8.05 (m, 1H), 7.97 (s, 1H), 7.60 (s, 1H), 7.43 (dd, J=5.8, 3.1 Hz, 2H), 6.85 (s, 1H), 4.62 (s, 1H), 1.99 (s, 2H), 1.84-1.40 (m, 8H);

$^{13}$C NMR (151 MHz, DMSO-d$_6$) δ (ppm): 175.97, 162.74, 162.41, 157.35, 154.96, 146.50, 144.31, 140.47, 140.21, 131.98, 131.69, 125.96, 125.21, 124.98, 123.21, 119.04, 118.97, 114.52, 50.72, 28.75, 28.56, 26.01, 25.59, 24.22, 21.37, 19.45.

Example 18: (+/−)-trans-3-((6-(dibenzo[b,d]furan-4-yl)-2-(5-fluoro-1H-pyrrolo[2,3-b]pyridin-3-yl)pyrimidin-4-yl)amino)bicyclo[2.2.2]octane-2-carboxylic Acid

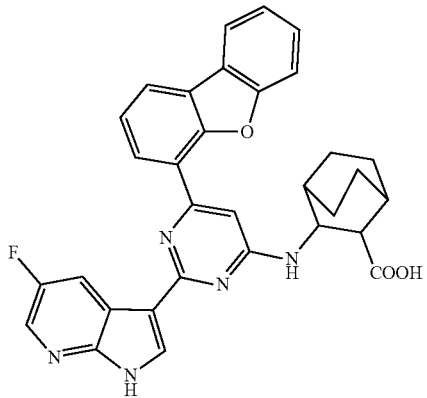 [SMILES: O=C(O)C1C2CCC(CC2)C1Nc1cc(-c2cccc3c2oc2ccccc23)nc(-c2c[nH]c3ncc(F)cc23)n1]

Step 1: 2,4-dichloro-6-(dibenzo[b,d]furan-4-yl)pyrimidine

To a solution of 2,4,6-trichloropyrimidine (500 mg, 2.73 mmol) in 1,2-dimethoxyethane (32 mL) were added tetrakis(triphenylphosphine)palladium (316 mg, 0.27 mmol), dibenzo[b,d]furan-4-ylboronic acid (583 mg, 2.75 mmol) and aqueous sodium carbonate solution (1 M, 8.18 mL, 8.18 mmol). The mixture was stirred at 80° C. for 2 h. To the reaction mixture was added water (30 mL), and the resulting mixture was extracted with ethyl acetate (30 mL×3). The combined organic layers were washed with saturated brine (30 mL), dried over anhydrous sodium sulfate and filtered. The filtrate was concentrated in vacuo and the residue was purified by silica gel column chromatography (PE) to give the title compound as a white solid (550 mg, 31%).

MS (ESI, pos.ion) m/z: 315.0 [M+H]$^+$;
$^1$H NMR (400 MHz, CDCl$_3$) δ (ppm): 8.58 (s, 1H), 8.56-8.51 (m, 1H), 8.19-8.15 (m, 1H), 8.04 (d, J=7.7 Hz, 1H), 7.74 (d, J=8.3 Hz, 1H), 7.57 (dt, J=15.4, 4.4 Hz, 2H), 7.46 (t, J=7.5 Hz, 1H).

Step 2: (+/−)-trans-methyl 3-((2-chloro-6-(dibenzo[b,d]furan-4-yl)pyrimidin-4-yl)amino)bicycle [2.2.2]octane-2-carboxylate (+/−)-trans-Methyl 3-aminobicyclo[2.2.2]octane-2-carboxylate (418 mg, 2.28 mmol) and 2,4-dichloro-6-(dibenzo[b,d]furan-4-yl)pyrimidine (600 mg, 1.90 mmol) were dissolved in DMF (6 mL), then potassium carbonate (789 mg, 5.71 mmol) was added. The mixture was stirred at rt overnight. To the reaction mixture was added water (40 mL), and the resulting mixture was extracted with ethyl acetate (40 mL×3). The combined organic layers were washed with saturated brine (50 mL), dried over anhydrous sodium sulfate and filtered. The filtrate was concentrated in vacuo and the residue was purified by silica gel column chromatography (PE/EtOAc (v/v)=20/1) to give the title compound as a white solid (586 mg, 67%).

MS (ESI, pos.ion) m/z: 462.3 [M+H]$^+$;
$^1$H NMR (400 MHz, CDCl$_3$) δ (ppm): 8.45 (d, J=7.6 Hz, 1H), 8.07 (d, J=7.4 Hz, 1H), 8.01 (d, J=7.6 Hz, 1H), 7.55-7.38 (m, 5H), 5.54 (s, 1H), 4.46 (s, 1H), 3.72 (s, 3H), 2.46 (d, J=5.3 Hz, 1H), 2.10 (s, 1H), 2.03 (s, 1H), 1.94-1.67 (m, 8H).

Step 3: (+/−)-trans-methyl 3-((6-(dibenzo [b,d]furan-4-yl)-2-(5-fluoro-1-tosyl-1H-pyrrolo[2,3-b]pyridine-3-yl)pyrimidin-4-yl)amino)bicyclo[2.2.2]octane-2-carboxylate To a microwave tube were added 5-fluoro-3-(4,4,5,5-tetramethyl-1,3,2-dioxaborolan-2-yl)-1-tosyl-1H-pyrrolo[2,3-b]pyridine (237 mg, 0.29 mmol, 50%), (+/−)-trans-methyl 3-((2-chloro-6-(dibenzo [b,d]furan-4-yl)pyrimidin-4-yl)amino)bicyclo[2.2.2]octane-2-carboxylate (110 mg, 0.24 mmol), potassium carbonate (98 mg, 0.71 mmol), Pd(dppf)Cl$_2$ (38 mg, 0.05 mmol), 1,4-dioxane (3 mL) and water (0.2 mL). The air in the mixture was removed by bubbling with nitrogen for 10 min, then the mixture in the microwave tube was stirred at 110° C. with microwave heating for 2 hours. The mixture was filtered through a celite pad, and the filter cake was washed with ethyl acetate (50 mL). The filtrated was washed with saturated brine (50 mL), dried over anhydrous sodium sulfate and filtered. The filtrate was concentrated in vacuo to dry and the residue was purified by silica gel column chromatography (n-hexane/EtOAc (v/v)=5/1) to give the title compound as a yellow solid (91 mg, 53%).

MS (ESI, pos.ion) m/z: 716.3[M+H]$^+$;
$^1$H NMR (400 MHz, CDCl$_3$) δ (ppm): 8.81 (dd, J=8.9, 2.7 Hz, 1H), 8.77 (s, 1H), 8.53 (d, J=7.8 Hz, 1H), 8.35 (s, 1H), 8.15 (d, J=8.1 Hz, 2H), 8.11 (d, J=7.7 Hz, 1H), 8.04 (d, J=7.4 Hz, 1H), 7.77 (d, J=8.5 Hz, 1H), 7.55 (dd, J=14.7, 9.1 Hz, 2H), 7.44 (d, J=7.5 Hz, 1H), 7.39 (d, J=4.3 Hz, 2H), 7.31 (s, 1H), 5.28 (s, 1H), 4.73 (d, J=4.7 Hz, 1H), 3.73 (s, 3H), 2.52 (d, J=5.7 Hz, 1H), 2.40 (s, 3H), 2.13 (s, 2H), 1.74 (m, 8H).

Step 4: (+/−)-trans-3-((6-(dibenzo[b,d]furan-4-yl)-2-(5-fluoro-1H-pyrrolo[2,3-b]pyridin-3-yl) pyrimidin-4-yl)amino)bicyclo[2.2.2]octane-2-carboxylic Acid To a solution of (+/−)-trans-methyl 3-((6-(dibenzo [b,d]furan-4-yl)-2-(5-fluoro-1-tosyl 1H-pyrrolo[2,3-b]pyridin-3-yl)pyrimidin-4-yl)amino)bicyclo[2.2.2]octane-2-carboxylate (91 mg, 0.13 mmol) in THF/MeOH (v/v=1/1, 2 mL) was added aqueous sodium hydroxide solution (4 M, 0.33 mL, 1.30 mmol). The mixture was stirred at 30° C. overnight. To the reaction mixture was added water (10 mL), and the resulting mixture was acidified with hydrochloric acid (1 M) to pH about 5.5. The mixture was extracted with ethyl acetate (20 mL×3), and the combined organic layers were washed with saturated brine (50 mL) and dried over anhydrous sodium sulfate, then filtered. The filtrate was concentrated in vacuo and the residue was purified by silica gel column chromatography (DCM/MeOH (v/v)=10/1) to give the title compound as a yellow solid (45 mg, 65%).

MS (ESI, pos.ion) m/z: 548.3 [M+H]$^+$;
HRMS (ESI, pos. ion) m/z: 548.2118 [M+H]$^+$, (C$_{32}$H$_{26}$FN$_5$O$_3$) [M+H]$^+$ theoretical value: 548.2098;

$^1$H NMR (400 MHz, DMSO-d$_6$) δ (ppm): 12.30 (s, 1H), 8.71 (d, J=7.6 Hz, 1H), 8.52 (d, J=7.0 Hz, 1H), 8.44 (s, 1H), 8.30 (d, J=7.2 Hz, 2H), 8.25 (d, J=7.6 Hz, 1H), 7.81 (d, J=7.2 Hz, 1H), 7.73 (s, 1H), 7.62 (t, J=7.6 Hz, 2H), 7.48 (t, J=7.5 Hz, 1H), 7.43 (s, 1H), 4.71 (s, 1H), 2.58 (s, 1H), 1.93-1.37 (m, 10H);

$^{13}$C NMR (151 MHz, DMSO-d$_6$) δ (ppm): 176.04, 172.49, 163.00, 162.42, 156.90, 156.75, 155.86, 155.30, 153.79, 146.50, 131.80, 131.72, 131.61, 128.44, 127.44, 125.15, 123.96, 123.92, 123.72, 123.22, 122.94, 121.79, 119.12, 119.06, 115.75, 115.11, 112.07, 102.42, 67.48, 50.65, 49.82, 29.49, 28.83, 28.53, 26.07, 25.59, 24.25, 21.52, 21.45, 19.52.

Example 19: (+/−)-cis-N-(3-((2-(5-fluoro-1H-pyrrolo[2,3-b]pyridin-3-yl)-6-phenyl pyrimidin-4-yl)amino)cyclohexyl)pyrrolidine-1-carboxamide

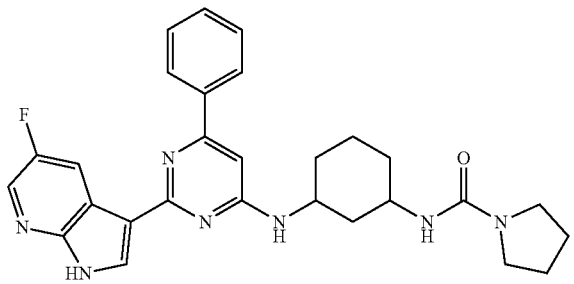 [SMILES: O=C(NC1CCCC(Nc2cc(-c3ccccc3)nc(-c3c[nH]c4ncc(F)cc34)n2)C1)N1CCCC1]

Step 1: N-(3-((2-chloro-6-phenylpyrimidin-4-yl)amino)cyclohexyl)pyrrolidine-1-carboxamide To a solution of N$^1$-(2-chloro-6-phenylpyrimidin-4-yl)cyclohexane-1,3-diamine (75 mg, 0.25 mmol) in tetrahydrofuran (4 mL) was added N,N-diisopropylethylamine (0.12 mL, 0.74 mmol) and pyrrolidine-1-carbonyl chloride (49 mg, 0.37 mmol). The mixture was stirred at rt overnight. To the reaction mixture was added water (10 mL), and the resulting mixture was extracted with ethyl acetate (10 mL×3). The combined organic layers were washed with saturated brine (30 mL), dried over anhydrous sodium sulfate and filtered. The filtrate was concentrated in vacuo to dryness to give the title compound as a colorless solid (99 mg, 100%).

MS (ESI, pos.ion) m/z: 400.3[M+H]$^+$;
$^1$H NMR (400 MHz, CD$_3$OD) δ (ppm): 7.91 (s, 2H), 7.49 (d, J=2.1 Hz, 3H), 6.75 (s, 1H), 1.96-1.85 (m, 5H), 1.42 (s, 1H), 1.25 (m, 8H).

Step 2: (+/−)-cis-N-(3-((2-(5-fluoro-1-tosyl-1H-pyrrolo[2,3-b]pyridin-3-yl)-6-phenylpyrimidin-4-yl)amino)cyclohexyl)pyrrolidine-1-carboxamide To a microwave tube were added 5-fluoro-3-(4,4,5,5-tetramethyl-1,3,2-dioxaborolan-2-yl)-1-tosyl-1H-pyrrolo[2,3-b]pyridine (249 mg, 0.30 mmol, 50%), N-(3-((2-chloro-6-phenylpyrimidin-4-yl)amino)cyclohexyl)pyrrolidine-1-carboxamide (100 mg, 0.25 mmol), potassium carbonate (103 mg, 0.75 mmol), Pd(dppf)Cl$_2$ (40 mg, 0.05 mmol), 1,4-dioxane (3 mL) and water (0.2 mL). The mixture in the microwave tube was stirred at 120° C. with microwave heating for 4 hours. The mixture was filtered through a celite pad, and the filter cake was washed with ethyl acetate (50 mL). The filtrate was washed with saturated brine (50 mL), dried over anhydrous sodium sulfate and filtered. The filtrate was concentrated in vacuo and the residue was purified by silica gel column chromatography (n-hexane/EtOAc (v/v) =5/1) to give the title compound as a yellow solid (83 mg, 51%).

MS (ESI, pos.ion) m/z: 654.3 [M+H]$^+$;
$^1$H NMR (400 MHz, CD$_3$OD) δ (ppm): 8.66 (s, 1H), 8.29 (s, 1H), 8.09 (t, J=7.5 Hz, 4H), 7.52 (d, J=7.5 Hz, 4H), 7.40 (d, J=8.2 Hz, 2H), 6.77 (s, 1H), 5.88 (d, J=7.9 Hz, 1H), 4.59 (s, 2H), 3.80 (s, 1H), 2.39 (s, 3H), 1.85-1.92 (m, 6H), 1.34 (m, 8H).

Step 3: (+/−)-cis-N-(3-((2-(5-fluoro-1H-pyrrolo[2,3-b]pyridin-3-yl)-6-phenylpyrimidin-4-yl) amino)cyclohexyl)pyrrolidine-1-carboxamide To a solution of (+/−)-cis-N-(3-((2-(5-fluoro-1-tosyl-1H-pyrrolo[2,3-b]pyridine-3-yl)-6-phenylpyrimidin-4-yl)amino)cyclohexyl)pyrrolidine-1-carboxamide (83 mg, 0.13 mmol) in methanol (1 mL) was added a solution of sodium methoxide in methanol (5 M, 0.26 mL, 1.3 mmol). The mixture was stirred at 30° C. overnight. The reaction mixture was concentrated in vacuo to dry and to the residue was added water (10 mL). The resulting mixture was extracted with ethyl acetate (20 mL×3), and the combined organic layers were washed with saturated brine (50 mL), dried over anhydrous sodium sulfate, then filtered. The filtrate was concentrated in vacuo and the residue was purified by silica gel column chromatography (DCM/MeOH (v/v)=10/1) to give the title compound as a white solid (32 mg, 50%).

MS (ESI, pos.ion) m/z: 500.3 [M+H]$^+$;
HRMS (ESI, pos. ion) m/z: 500.2568 [M+H]$^+$, (C$_{28}$H$_{31}$FN$_7$O) [M+H]$^+$ theoretical value: 500.2574;
$^1$H NMR (400 MHz, DMSO-d$_6$) δ (ppm): 12.28 (s, 1H), 8.58 (s, 1H), 8.39 (s, 1H), 8.29 (s, 1H), 8.11 (s, 2H), 7.55-7.50 (m, 3H), 7.36 (s, 1H), 6.76 (s, 1H), 5.84 (d, J=7.9 Hz, 1H), 4.11 (s, 1H), 3.66 (d, J=7.8 Hz, 1H), 3.19 (d, J=6.4 Hz, 4H), 2.16 (s, 2H), 1.80 (s, 6H), 1.53-1.24 (m, 4H);
$^{13}$C NMR (151 MHz, DMSO-d$_6$) δ (ppm): 162.78, 162.43, 156.85, 156.37, 155.26, 146.48, 138.46, 131.76, 131.56, 130.28, 129.19, 126.77, 119.08, 119.03, 115.08, 56.50, 49.14, 48.61, 45.76, 33.01, 32.36, 29.43, 25.47, 25.42, 23.50, 22.54, 19.01.

Example 20: (+/−)-trans-3-((2-(5-fluoro-1H-pyrrolo[2,3-b]pyridin-3-yl)-6-(furan-3-yl) pyrimidin-4-yl)amino)bicyclo[2.2.2]octane-2-carboxylic Acid

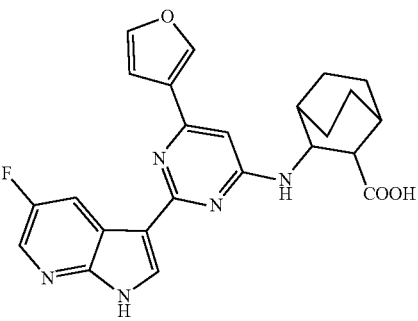 [SMILES: O=C(O)C1C2CCC(CC2)C1Nc1cc(-c2ccoc2)nc(-c2c[nH]c3ncc(F)cc23)n1]

Step 1: 2,4-dichloro-6-(furan-3-yl)pyrimidine

To a solution of 2,4,6-trichloropyrimidine (500 mg, 2.73 mmol) in 1,2-dimethoxyethane (32 mL) were added tetrakis (triphenylphosphine)palladium (317 mg, 0.27 mmol), 3-furylboronic acid (308 mg, 2.75 mmol) and aqueous sodium carbonate solution (1 M, 8.18 mL, 8.18 mmol). The mixture was stirred at 80° C. for 1 h. To the reaction mixture was added water (30 mL), and the resulting mixture was extracted with ethyl acetate (30 mL×3). The combined organic layers were washed with saturated brine (60 mL), dried over anhydrous sodium sulfate and filtered. The filtrate was concentrated in vacuo to dry and the residue was purified by silica gel column chromatography (PE) to give the title compound as a white solid (317 mg, 31%).

$^1$H NMR (400 MHz, CDCl$_3$) δ (ppm): 8.26 (s, 1H), 7.57 (s, 1H), 7.36 (s, 1H), 6.89 (s, 1H).

Step 2: (+/−)-trans-methyl 3-((2-chloro-6-(furan-3-yl)pyrimidin-4-yl)amino)bicycle[2.2.2]octane-2-carboxylate (+/−)-trans-Methyl 3-aminobicyclo[2.2.2]octane-2-carboxylate (324 mg, 1.77 mmol) and 2,4-dichloro-6-(furan-3-yl)pyrimidine (317 mg, 1.47 mmol) were dissolved in DMF (6 mL), then potassium carbonate (611 mg, 4.42 mmol) was added. The mixture was stirred at rt overnight. To the reaction mixture was added water (40 mL), and the resulting mixture was extracted with ethyl acetate (40 mL×3). The combined organic layers were washed with saturated brine (50 mL), dried over anhydrous sodium sulfate and filtered. The filtrate was concentrated in vacuo and the residue was purified by silica gel column chromatography (PE/EtOAc (v/v)=20/1) to give the title compound as a white solid (353 mg, 66%).

MS (ESI, pos.ion) m/z: 362.1 [M+H]$^+$.

Step 3: (+/−)-trans-methyl 3-((2-(5-fluoro-1-tosyl-1H-pyrrolo[2,3-b]pyridin-3-yl)-6-(furan-3-yl)pyrimidin-4-yl)amino)bicyclo[2.2.2]octane-2-carboxylate To a microwave tube were added 5-fluoro-3-(4,4,5,5-tetramethyl-1,3,2-dioxaborolan-2-yl)-1-tosyl-1H-pyrrolo[2,3-b]pyridine (290 mg, 0.35 mmol, 50%), (+/−)-trans-methyl 3-((2-chloro-6-(furan-3-yl)pyrimidin-4-yl)amino)bicyclo[2.2.2]octane-2-carboxylate (105 mg, 0.29 mmol), potassium carbonate (120 mg, 0.85 mmol), Pd(dppf)Cl$_2$ (47 mg, 0.06 mmol), 1,4-dioxane (3 mL) and water (0.2 mL). The air in the mixture was removed by bubbling with nitrogen for 10 min, then the mixture in the microwave tube was stirred at 110° C. with microwave heating for 2 hours. The mixture was filtered through a celite pad, and the filter cake was washed with ethyl acetate (50 mL). The filtrate was washed with saturated brine (50 mL), dried over anhydrous sodium sulfate and filtered. The filtrate was concentrated in vacuo to dry and the residue was purified by silica gel column chromatography (n-hexane/EtOAc (v/v)=5/1) to give the title compound as a yellow solid (179 mg, 100%).

MS (ESI, pos. ion) m/z: 616.2[M+H]$^+$;
$^1$H NMR (400 MHz, CDCl$_3$) δ (ppm): 8.66 (s, 1H), 8.63 (dd, J=8.9, 2.7 Hz, 1H), 8.32 (s, 1H), 8.19 (s, 1H), 8.12 (d, J=8.2 Hz, 2H), 7.55 (s, 1H), 7.39 (d, J=4.6 Hz, 2H), 7.30 (s, 1H), 6.91 (s, 1H), 5.21 (s, 1H), 4.72 (s, 1H), 3.74 (s, 3H), 2.45-2.42 (m, 1H), 2.39 (s, 3H), 2.10 (s, 1H), 1.96 (s, 1H), 1.81 (m, 8H).

Step 4: (+/−)-trans-3-((2-(5-fluoro-1H-pyrrolo[2,3-b]pyridin-3-yl)-6-(furan-3-yl)pyrimidin-4-yl)amino)bicyclo[2.2.2]octane-2-carboxylic Acid To a solution of (+/−)-trans-methyl 3-((2-(5-fluoro-1-tosyl-1H-pyrrolo[2,3-b]pyridin-3-yl)-6-(furan-3-yl)pyrimidin-4-yl)amino)bicyclo[2.2.2]octane-2-carboxylate (180 mg, 0.29 mmol) in THF/MeOH (v/v=1/1, 4 mL) was added aqueous sodium hydroxide solution (4 M, 0.73 mL, 2.90 mmol). The mixture was stirred at 30° C. overnight. To the reaction mixture was added water (10 mL), and the resulting mixture was acidified with hydrochloric acid (1 M) to pH about 5.5. The mixture was extracted with ethyl acetate (20 mL×3), and the combined organic layers were washed with saturated brine, dried over anhydrous sodium sulfate, then filtered. The filtrate was concentrated in vacuo and the residue was purified by silica gel column chromatography (DCM/MeOH (v/v)=10/1) to give the title compound as a yellow solid (62 mg, 47%).

MS (ESI, pos.ion) m/z: 448.3 [M+H]$^+$;
HRMS (ESI, pos. ion) m/z: 448.1785 [M+H]$^+$, (C$_{24}$H$_{23}$FN$_7$O$_3$) [M+H]$^+$ theoretical value: 448.1784;
$^1$H NMR (400 MHz, DMSO-d$_6$) δ (ppm): 12.25 (s, 1H), 8.62 (s, 1H), 8.41 (s, 1H), 8.35 (s, 1H), 8.27 (s, 1H), 7.81 (s, 1H), 7.43 (s, 1H), 6.98 (s, 1H), 6.48 (s, 1H), 4.63 (s, 1H), 3.17 (s, 1H), 1.99 (s, 2H), 1.88-1.44 (m, 8H);
$^{13}$C NMR (101 MHz, DMSO-d$_6$) δ (ppm): 175.99, 172.43, 162.82, 162.39, 157.27, 154.88, 146.46, 144.88, 143.19, 131.75, 131.60, 131.46, 126.56, 119.05, 118.97, 116.07, 114.90, 108.96, 56.50, 50.48, 49.74, 49.05, 28.78, 28.60, 25.99, 24.13, 21.50, 21.40, 19.41.

Example 21: (+/−)-cis-2-amino-N-(3-((2-(5-fluoro-1H-pyrrolo[2,3-b]pyridin-3-yl)-6-phenylpyrimidin-4-yl)amino)cyclohexyl)thiazole-4-carboxamide

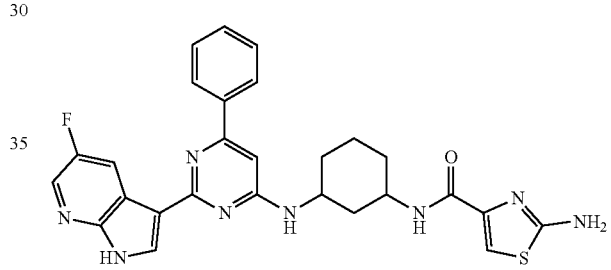

Step 1: 2-amino-N-(3-((2-chloro-6-phenylpyrimidin-4-yl)amino)cyclohexyl)thiazole-4-carboxamide To a solution of N$^1$-(2-chloro-6-phenylpyrimidin-4-yl)cyclohexane-1,3-diamine (63 mg, 0.21 mmol) in a mixed solvent of tetrahydrofuran (4 mL) and dimethyl sulfoxide (1 mL) was added N,N-diisopropylethylamine (0.08 mL, 0.62 mmol) and 2-aminothiazole-4-carboxylic acid (59 mg, 0.42 mmol). The mixture was stirred at rt overnight. To the reaction mixture was added water (10 mL), and the resulting mixture was extracted with ethyl acetate (10 mL×3). The combined organic layers were washed with saturated brine (10 mL), dried over anhydrous sodium sulfate and filtered. The filtrate was concentrated in vacuo to give the title compound as a white solid (89 mg, 100%).

MS (ESI, pos. ion) m/z: 429.2[M+H]$^+$;
$^1$H NMR (400 MHz, CD$_3$OD) δ (ppm): 7.92 (s, 2H), 7.49 (s, 3H), 7.26 (s, 1H), 6.77 (s, 1H), 4.59 (s, 1H), 2.68 (s, 1H), 2.32 (d, J=11.1 Hz, 1H), 2.11-1.90 (m, 4H), 1.59 (d, J=13.1 Hz, 1H).

Step 2: (+/−)-cis-2-amino-N-(3-((2-(5-fluoro-1-tosyl-1H-pyrrolo[2,3-b]pyridin-3-yl)-6-phenylpyrimidin-4-yl)amino)cyclohexyl)thiazole-4-carboxamide To a microwave tube were added 5-fluoro-3-(4,4,5,5-tetramethyl-1,3,2-dioxaborolan-2-yl)-1-tosyl-1H-pyrrolo[2, 3-b]pyridine (209 mg, 0.25 mmol, 50%), (+/−)-cis-2-amino-N-(3-((2-chloro-6-phenylpyrimidin-4-yl)amino)cyclohexyl)thiazole-4-carboxamide (90 mg, 0.21 mmol), potassium phosphate (133 mg, 0.63 mmol), Pd$_2$(dba)$_3$ (20 mg, 0.02 mmol), 1,4-dioxane (3 mL) and water (0.2 mL). The air in the mixture was removed by bubbling with nitrogen for 10 min, then the mixture in the microwave tube was stirred at 120° C. under microwave heating for 4 hours. The mixture was filtered through a celite pad, and the filter cake was washed with ethyl acetate (50 mL). The filtrate was washed with saturated brine (50 mL), dried over anhydrous sodium sulfate and filtered. The filtrate was concentrated in vacuo and the residue was purified by silica gel column chromatography (n-hexane/EtOAc (v/v)=5/1) to give the title compound as a yellow solid (43 mg, 30%).

Step 3: (+/−)-cis-2-amino-N-(3-((2-(5-fluoro-1H-pyrrolo[2,3-b]pyridin-3-yl)-6-phenylpyrimidin-4-yl)amino)cyclohexyl)thiazole-4-carboxamide To a solution of (+/−)-cis-2-amino-N-(3-((2-(5-fluoro-1-tosyl-1H-pyrrolo[2,3-b]pyridin-3-yl)-6-phenylpyrimidin-4-yl)amino)cyclohexyl)thiazole-4-carboxamide (43 mg, 0.06 mmol) in methanol (1 mL) was added a solution of sodium methoxide in methanol (5 M, 0.12 mL, 0.6 mmol). The mixture was stirred at 30° C. overnight. The reaction mixture was concentrated in vacuo and to the residue was added water (10 mL). The resulting mixture was extracted with ethyl acetate (20 mL×3), and the combined organic layers were washed with saturated brine (50 mL), dried over anhydrous sodium sulfate, then filtered. The filtrate was concentrated in vacuo to remove the solvent and the residue was purified by silica gel column chromatography (DCM/MeOH (v/v)=10/1) to give the title compound as a white solid (32 mg, 50%).

MS (ESI, pos.ion) m/z: 529.2 [M+H]$^+$;
HRMS (ESI, pos. ion) m/z: 529.1940 [M+H]$^+$, (C$_{27}$H$_{26}$FN$_8$OS) [M+H]$^+$ theoretical value: 529.1934;
$^1$H NMR (400 MHz, DMSO-d$_6$) δ (ppm): 12.28 (s, 1H), 8.60 (s, 1H), 8.40 (s, 1H), 8.29 (s, 1H), 8.11 (s, 2H), 7.58-7.48 (m, 4H), 7.38 (s, 1H), 7.18 (s, 1H), 7.08 (s, 2H), 6.77 (s, 1H), 4.12 (s, 1H), 3.94 (s, 1H), 1.86 (s, 2H), 1.44 (m, 6H);
$^{13}$C NMR (151 MHz, DMSO-d$_6$) δ (ppm): 168.62, 162.43, 160.44, 156.86, 155.27, 146.48, 146.21, 138.44, 131.77, 131.58, 130.31, 130.12, 129.20, 126.80, 119.07, 119.02, 115.10, 111.69, 48.86, 32.08, 31.75, 30.86, 29.47, 29.15, 22.55, 14.42.

Example 22: (+/−)-cis-N-(3-((2-(5-fluoro-1H-pyrrolo[2,3-b]pyridin-3-yl)-6-phenyl pyrimidin-4-yl)amino)cyclohexyl)-1-methyl-1H-imidazole-4-carboxamide

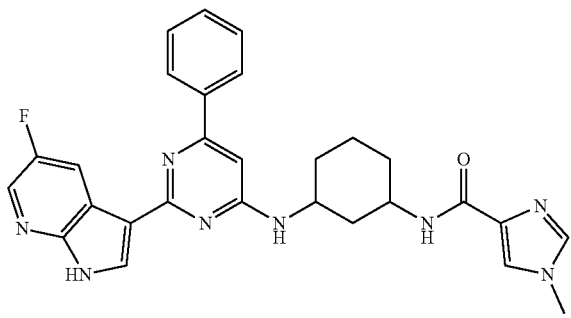 [SMILES: Cn1cnc(C(=O)NC2CCCC(Nc3cc(-c4ccccc4)nc(-c4c[nH]c5ncc(F)cc45)n3)C2)c1]

Step 1: (+/−)-cis-N-(3-((2-chloro-6-phenylpyrimidin-4-yl)amino)cyclohexyl)-1-methyl-1H-imidazole-4-carboxamide To a solution of N$^1$-(2-chloro-6-phenylpyrimidin-4-yl)cyclohexane-1,3-diamine (221 mg, 0.73 mmol) in a mixed solvent of tetrahydrofuran (4 mL) and dimethyl sulfoxide (1 mL) were added N,N-diisopropylethylamine (0.11 mL, 0.7 mmol) and 1-methyl-1H-imidazole-4-carboxylic acid (184 mg, 1.46 mmol). The mixture was stirred at rt for 10 min, then HATU (555 mg, 1.46 mmol) was added. The resulting mixture was stirred at rt for 3 h. To the reaction mixture was added water (10 mL), and the resulting mixture was extracted with ethyl acetate (10 mL×3). The combined organic layers were washed with saturated brine (30 mL), dried over anhydrous sodium sulfate and filtered. The filtrate was concentrated in vacuo to give the title compound as a colorless solid (180 mg, 60%).

MS (ESI, pos.ion) m/z: 411.2 [M+H]$^+$.

Step 2: (+/−)-cis-N-(3-((2-(5-fluoro-1-tosyl-1H-pyrrolo[2,3-b]pyridin-3-yl)-6-phenylpyrimidin-4-yl)amino)cyclohexyl)-1-methyl-1H-imidazole-4-carboxamide To a microwave tube were added 5-fluoro-3-(4,4,5,5-tetramethyl-1,3,2-dioxaborolan-2-yl)-1-tosyl-1H-pyrrolo[2,3-b]pyridine (162 mg, 0.23 mmol, 60%), (+/−)-cis-N-(3-((2-chloro-6-phenylpyrimidin-4-yl)amino)cyclohexyl)-1-methyl-1H-imidazole-4-carboxamide (80 mg, 0.19 mmol), potassium carbonate (80 mg, 0.58 mmol), Pd(dppf)Cl$_2$ (31 mg, 0.04 mmol), 1,4-dioxane (3 mL) and water (0.2 mL). The air in the mixture was removed by bubbling with nitrogen for 10 min, then the mixture in the microwave tube was stirred at 120° C. with microwave heating for 4 hours. The mixture was filtered through a celite pad, and the filter cake was washed with ethyl acetate (50 mL). The filtrate was washed with saturated brine (50 mL), dried over anhydrous sodium sulfate and filtered. The filtrate was concentrated in vacuo to dry and the residue was purified by silica gel column chromatography (n-hexane/EtOAc (v/v)=5/1) to give the title compound as a yellow solid (20 mg, 15%).

MS (ESI, pos.ion) m/z: 665.2[M+H]$^+$;
$^1$H NMR (400 MHz, CD$_3$OD) δ (ppm): 8.73 (d, J=3.2 Hz, 1H), 8.68 (s, 1H), 8.40 (d, J=8.7 Hz, 1H), 8.29 (s, 1H), 8.10 (d, J=8.2 Hz, 4H), 7.63 (s, 2H), 7.53 (d, J=7.5 Hz, 2H), 7.39 (d, J=7.9 Hz, 2H), 6.79 (s, 1H), 4.10 (s, 1H), 3.77 (s, 3H), 2.45 (s, 1H), 2.39 (s, 3H), 2.27-2.17 (m, 2H), 2.10-1.97 (m, 4H), 1.62 (s, 2H).

Step 3: (+/−)-cis-N-(3-((2-(5-fluoro-1H-pyrrolo[2,3-b]pyridin-3-yl)-6-phenylpyrimidin-4-yl) amino)cyclohexyl)-1-methyl-1H-imidazole-4-carboxamide To a solution of (+/−)-cis-N-(3-((2-(5-fluoro-1-tosyl-1H-pyrrolo[2,3-b]pyridin-3-yl)-6-phenylpyrimidin-4-yl)amino)cyclohexyl)-1-methyl-1H-imidazole-4-carboxamide (20 mg, 0.03 mmol) in methanol (1 mL) was added a solution of sodium methoxide in methanol (5 M, 0.06 mL, 0.3 mmol). The mixture was stirred at 30° C. overnight. The reaction mixture was concentrated in vacuo and to the residue was added water (10 mL). The resulting mixture was extracted with ethyl acetate (20 mL×3), and the combined organic layers were washed with saturated brine (50 mL), then filtered. The filtrate was concentrated in vacuo to remove the solvent and the residue was purified by silica gel column chromatography (DCM/MeOH (v/v)=10/1) to give the title compound as a white solid (10 mg, 65%).

HRMS (ESI, pos. ion) m/z: 511.2385 [M+H]$^+$, ($C_{28}H_{28}FN_8O$) [M+H]$^+$ theoretical value: 511.2370;

$^1$H NMR (400 MHz, DMSO-$d_6$) δ (ppm): 12.27 (s, 1H), 8.59 (s, 1H), 8.40 (s, 1H), 8.29 (s, 1H), 8.11 (s, 1H), 7.72 (d, J=8.4 Hz, 1H), 7.64 (s, 1H), 7.61 (s, 1H), 7.57-7.50 (m, 2H), 7.37 (s, 1H), 6.75 (s, 1H), 4.14 (s, 1H), 3.68 (s, 3H), 2.20 (s, 2H), 1.84 (s, 2H), 1.55-1.33 (m, 4H).

Example 23: (+/−)-trans-3-((2-(5-fluoro-1H-pyrrolo[2,3-b]pyridin-3-yl)-6-(thiophen-2-yl) pyrimidin-4-yl)amino)bicyclo[2.2.2]octane-2-carboxylic Acid

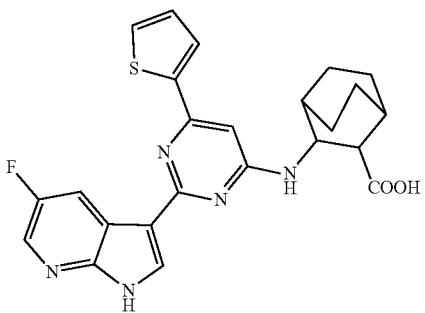 [SMILES: O=C(O)C1C2CCC(CC2)C1Nc1cc(-c2cccs2)nc(-c2c[nH]c3ncc(F)cc23)n1]

Step 1: 2,4-dichloro-6-(thiophen-2-yl)pyrimidine

To a solution of thiophene (500 mg, 5.94 mmol) in anhydrous tetrahydrofuran (20 mL) was added n-butyl-lithium (2.4 mL, 6.0 mmol, 2.5 mol/L) at −15° C., and the mixture was stirred for 1 h at −15° C. Then to the mixture was added ZnCl-TMEDA (495 mg, 1.96 mmol), and the resulting mixture was stirred for 1 h. Then palladium dichloride (105 mg, 0.59 mmol), triphenylphosphine (658 mg, 1.19 mmol) and 2,4,6-trichloropyrimidine (1.09 g, 5.94 mmol) were added to the mixture in turn. The resulting mixture was heated to 55° C. under nitrogen protection, and then stirred at this temperature overnight. To the reaction mixture was added water (50 mL), and the resulting mixture was extracted with ethyl acetate (50 mL×3). The combined organic layers were washed with saturated brine (100 mL), dried over anhydrous sodium sulfate and filtered. The filtrate was concentrated in vacuo and the residue was purified by silica gel column chromatography (PE) to give the title compound as a white solid (616 mg, 45%).

MS (ESI, pos.ion) m/z: 230.2 [M+H]$^+$;

$^1$H NMR (400 MHz, CDCl$_3$) δ (ppm): 7.86 (d, J=3.7 Hz, 1H), 7.66 (d, J=4.9 Hz, 1H), 7.51 (s, 1H), 7.24-7.17 (m, 1H).

Step 2: (+/−)-trans-methyl 3-((2-chloro-6-(thiophen-2-yl)pyrimidin-4-yl)amino)bicycle[2.2.2]octane-2-carboxylate (+/−)-trans-Methyl 3-aminobicyclo[2.2.2]octane-2-carboxylate (586 mg, 3.20 mmol) and 2,4-dichloro-6-(thiophen-2-yl)pyrimidine (616 mg, 2.67 mmol) were dissolved in DMF (6 mL), then potassium carbonate (1.11 g, 8.00 mmol) was added. The mixture was stirred at rt overnight. To the reaction mixture was added water (40 mL), and the resulting mixture was extracted with ethyl acetate (40 mL×3). The combined organic layers were washed with saturated brine (100 mL), dried over anhydrous sodium sulfate and filtered. The filtrate was concentrated in vacuo and the residue was purified by silica gel column chromatography (PE/EtOAc (v/v)=5/1) to give the title compound as a white solid (180 mg, 18%).

MS (ESI, pos.ion) m/z: 378.1 [M+H]$^+$;

$^1$H NMR (400 MHz, CDCl$_3$) δ (ppm): 7.74 (d, J=3.1 Hz, 1H), 7.50 (d, J=4.9 Hz, 1H), 7.17-7.10 (m, 1H), 6.68 (s, 1H), 5.47 (s, 1H), 4.30 (s, 1H), 3.76 (s, 3H), 2.39 (d, J=4.6 Hz, 1H), 2.08 (s, 1H), 1.87 (d, J=2.5 Hz, 1H), 1.82-1.65 (m, 8H).

Step 3: (+/−)-trans-methyl 3-((2-(5-fluoro-1-tosyl-1H-pyrrolo[2,3-b]pyridin-3-yl)-6-(thiophen-2-yl) pyrimidin-4-yl)amino)bicyclo[2.2.2]octane-2-carboxylate To a microwave tube were added 5-fluoro-3-(4,4,5,5-tetramethyl-1,3,2-dioxaborolan-2-yl)-1-tosyl-1H-pyrrolo[2,3-b]pyridine (176 mg, 0.25 mmol, 60%), methyl 3-((2-chloro-6-(thiophen-2-yl)pyrimidin-4-yl)amino) bicyclo[2.2.2]octane-2-carboxylate (80 mg, 0.21 mmol), potassium carbonate (87 mg, 0.64 mmol), Pd(dppf)Cl$_2$ (34 mg, 0.04 mmol), 1,4-dioxane (3 mL) and water (0.2 mL). The air in the mixture was removed by bubbling with nitrogen for 10 min, then the mixture in the microwave tube was stirred at 110° C. with microwave heating for 2 hours. The mixture was filtered through a celite pad, and the filter cake was washed with ethyl acetate (50 mL). The filtrate was washed with saturated brine (50 mL), dried over anhydrous sodium sulfate and filtered. The filtrate was concentrated in vacuo and the residue was purified by silica gel column chromatography (n-hexane/EtOAc(v/v)=5/1) to give the title compound as a yellow solid (40 mg, 30%).

MS (ESI, pos.ion) m/z: 632.3[M+H]$^+$.

Step 4: (+/−)-trans-3-((2-(5-fluoro-1H-pyrrolo[2,3-b]pyridin-3-yl)-6-(thiophen-2-yl)pyrimidin-4-yl) amino) bicyclo[2.2.2]octane-2-carboxylic Acid To a solution of (+/−)-trans-methyl 3-((2-(5-fluoro-1-tosyl-1H-pyrrolo[2,3-b]pyridine-3-yl)-6-(thiophen-2-yl)pyrimidin-4-yl)amino)bicyclo[2.2.2]octane-2-carboxylate (40 mg, 0.06 mmol) in THF/MeOH (v/v=1/1, 2 mL) was added aqueous sodium hydroxide solution (4 M, 0.15 mL, 0.60 mmol). The mixture was stirred at 30° C. overnight. To the reaction mixture was added water (10 mL), and the resulting mixture was acidified with hydrochloric acid (1 M) to pH about 5.5. The mixture was extracted with ethyl acetate (20 mL×3), and the combined organic layers were washed with saturated brine (50 mL), dried over anhydrous sodium sulfate, then filtered. The filtrate was concentrated in vacuo to remove the solvent and the residue was purified by silica gel column chromatography (DCM/MeOH (v/v)=10/1) to give the title compound as a yellow solid (20 mg, 68%).

MS (ESI, pos.ion) m/z: 464.3 [M+H]$^+$;

HRMS (ESI, pos. ion) m/z: 464.1526 [M+H]$^+$, ($C_{24}H_{23}FN_5O_2S$) [M+H]$^+$ theoretical value: 464.1556;

$^1$H NMR (600 MHz, DMSO-$d_6$) δ (ppm): 12.27 (s, 1H), 8.67 (s, 1H), 8.29 (s, 2H), 7.73 (d, J=4.8 Hz, 2H), 7.48 (s, 1H), 7.26-7.17 (m, 1H), 6.68 (s, 1H), 4.58 (s, 1H), 1.98-1.91 (m, 2H), 1.84-1.38 (m, 8H).

Example 24: (+/−)-trans-3-((2-(5-fluoro-1H-pyrrolo[2,3-b]pyridin-3-yl)-6-(5-nitrofuran-2-yl) pyrimidin-4-yl)amino)bicyclo[2.2.2]octane-2-carboxylic Acid

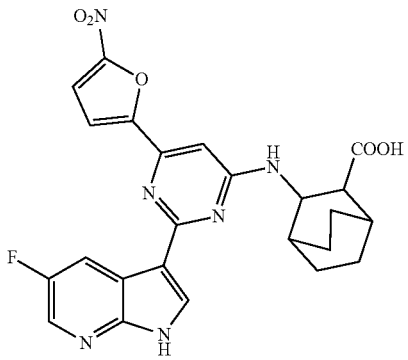 [SMILES: O=C(O)C1C2CCC(CC2)C1Nc1cc(-c2ccc([N+](=O)[O-])o2)nc(-c2c[nH]c3ncc(F)cc23)n1]

Step 1: 2,4-dichloro-6-(5-nitrofuran-2-yl)pyrimidine

To concentrated sulfuric acid (10 mL) was added 2,4-dichloro-6-(furan-2-yl) pyrimidine (2.15 g, 10.00 mmol). The mixture was placed in an ice-bath and stirred, then concentrated nitric acid (0.85 mL, 12 mmol) was added dropwise slowly to the mixture. Then the resulting mixture was warmed to room temperature and continued stirred. The reaction was stopped, and the reaction mixture was added dropwise slowly to ice-water (50 mL) to quench the reaction. The resulting mixture was extracted with ethyl acetate (50 mL×3). The combined organic layers were washed with saturated brine (80 mL), dried over anhydrous sodium sulfate and filtered. The filtrate was concentrated in vacuo and the residue was purified by silica gel column chromatography (PE/EtOAc (v/v)=10/1) to give the title compound as yellow power (1.02 g, 39%).

MS (ESI, pos. ion) m/z: 260.10 [M+H]$^+$;

$^1$H NMR (400 MHz, CDCl$_3$) δ(ppm) 7.81 (s, 1H), 7.57 (d, J=3.8 Hz, 1H), 7.48 (d, J=3.8 Hz, 1H).

Step 2: (+/−)-trans-methyl 3-((2-chloro-6-(5-nitrofuran-2-yl)pyrimidin-4-yl)amino)bicyclo[2.2.2]octane-2-carboxylate A suspension of 2,4-dichloro-6-(5-nitrofuran-2-yl)pyrimidine (300 mg, 1.15 mmol), (+/−)-trans-methyl 3-aminobicyclo[2.2.2]octane-2-carboxylate (280 mg, 1.38 mmol) and K$_2$CO$_3$ (320 mg, 2.31 mmol) in DMF (10 mL) was stirred at rt overnight. The reaction was quenched with water (100 mL), and the resulting mixture was extracted with ethyl acetate (50 mL×3). The combined organic layers were washed with saturated brine (80 mL), dried over anhydrous sodium sulfate and filtered. The filtrate was concentrated in vacuo and the residue was purified by silica gel column chromatography (PE/EtOAc (v/v)=5/1) to give the title compound as a white solid (344 mg, 73%).

MS (ESI, pos. ion) m/z: 407.20 [M+H]$^+$;

$^1$H NMR (400 MHz, CDCl$_3$) δ (ppm): 7.42 (d, J=3.7 Hz, 1H), 7.36 (d, J=3.2 Hz, 1H), 6.89 (s, 1H), 4.33 (s, 1H), 3.80 (s, 3H), 2.40 (d, J=4.4 Hz, 1H), 2.06 (s, 1H), 1.87 (s, 1H), 1.81-1.56 (m, 9H).

Step 3: (+/−)-trans-methyl 3-((2-(5-fluoro-1-tosyl-1H-pyrrolo[2,3-b]pyridin-3-yl)-6-(5-nitrofuran-2-yl) pyrimidin-4-yl)amino)bicyclo[2.2.2]octane-2-carboxylate To 1,4-dioxane (8 mL) were added 5-fluoro-3-(4,4,5,5-tetramethyl-1,3,2-dioxaborolan-2-yl)-1-tosyl-1H-pyrrolo[2,3-b]pyridine (170 mg, 0.41 mmol), K$_2$CO$_3$ (154 mg, 1.11 mmol), PdCl$_2$(dppf) (30 mg, 0.04 mmol) and (+/−)-trans-methyl 3-((2-chloro-6-(5-nitrofuran-2-yl) pyrimidin-4-yl)amino)bicyclo[2.2.2]octane-2-carboxylate (150 mg, 0.37 mmol). Then H$_2$O (1 mL) was added to the mixture, and the air in the mixture was removed by bubbling with nitrogen for 10 min. The mixture was sealed in a tube, and stirred for 3 h at 115° C. The mixture was filtered to remove solid impurities, and the filtrate was concentrated to remove the solvent. The residue was purified by silica gel column chromatography (PE/EtOAc (v/v)=10/1-5/1) to give the title compound as a white solid (126 mg, 52%).

MS (ESI, pos. ion) m/z: 661.0 [M+H]$^+$;

$^1$H NMR (400 MHz, CDCl$_3$) δ (ppm) 8.70 (s, 1H), 8.59 (dd, J=8.8, 2.7 Hz, 1H), 8.34 (d, J=1.7 Hz, 1H), 8.15 (d, J=8.2 Hz, 2H), 7.49 (d, J=3.8 Hz, 1H), 7.41 (d, J=3.7 Hz, 1H), 7.31 (d, J=8.2 Hz, 2H), 6.85 (s, 1H), 5.37 (s, 1H), 3.78 (s, 3H), 2.44 (s, 1H), 2.40 (s, 3H), 2.13 (s, 1H), 2.07 (s, 1H), 2.00 (s, 1H), 1.75-1.61 (m, 8H).

Step 4: (+/−)-trans-methyl 3-((2-(5-fluoro-1H-pyrrolo[2,3-b]pyridin-3-yl)-6-(5-nitro furan-2-yl)pyrimidin-4-yl)amino)bicyclo[2.2.2]octane-2-carboxylate To a solution of hydrogen chloride in 1,4-dioxane (4 mol/L, 0.20 mL) was added (+/−)-trans-methyl 3-((2-(5-fluoro-1-tosyl-1H-pyrrolo[2,3-b]pyridin-3-yl)-6-(5-nitrofuran-2-yl) pyrimidin-4-yl)amino)bicyclo[2.2.2]octane-2-carboxylate (43 mg, 0.07 mmol), and the mixture was stirred at 55° C. The reaction was stopped, and the reaction mixture was concentrated in vacuo to remove the solvent and HCl to give a light yellow solid (32 mg, 97%), which was used for the next step without further purification.

MS (ESI, pos. ion) m/z: 507.30 [M+H]$^+$.

Step 5: (+/−)-trans-3-((2-(5-fluoro-1H-pyrrolo[2,3-b]pyridin-3-yl)-6-(5-nitrofuran-2-yl) pyrimidin-4-yl)amino)bicyclo[2.2.2]octane-2-carboxylic Acid To a solution of (+/−)-trans-methyl 3-((2-(5-fluoro-1H-pyrrolo[2,3-b]pyridin-3-yl)-6-(5-nitrofuran-2-yl)pyrimidin-4-yl)amino)bicyclo[2.2.2]octane-2-carboxylate (20 mg, 0.04 mmol) in THF (5 mL) was added a solution of LiOH (5 mg, 0.16 mmol) in water (0.5 mL). The mixture was stirred at 50° C. overnight, then acidified with hydrochloric acid (1 M) to pH about 6. The resulting mixture was extracted with 2-methyl tetrahydrofuran (15 mL×3). The combined organic layers were washed with saturated brine (20 mL), dried over anhydrous sodium sulfate and filtered. The filtrate was concentrated in vacuo to remove the solvent and the residue was purified by silica gel column chromatography (DCM/MeOH (v/v)=10/1-5/1) to give the title compound as a white solid (6 mg, 31%).

MS (ESI, pos. ion) m/z: 493.20 [M+H]$^+$;

$^1$H NMR (600 MHz, DMSO-d$_6$) δ (ppm) 12.36 (s, 1H), 8.60 (d, J=9.0 Hz, 1H), 8.41 (s, 1H), 8.30 (s, 1H), 7.88 (s, 1H), 7.81 (d, J=6.5 Hz, 1H), 7.59 (s, 1H), 6.86 (s, 1H), 5.33 (s, 1H), 4.64 (s, 1H), 2.03-1.96 (m, 2H), 1.61 (m, 9H).

Example 24a: (2S,3S)-3-((2-(5-fluoro-1H-pyrrolo[2,3-b]pyridin-3-yl)-6-(5-nitrofuran-2-yl) pyrimidin-4-yl)amino)bicyclo[2.2.2]octane-2-carboxylic Acid

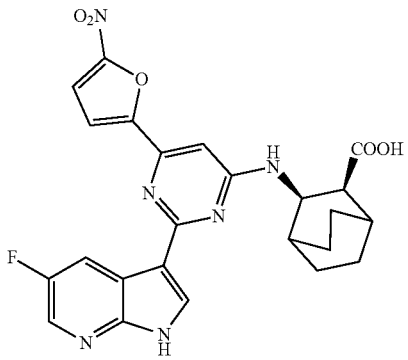 [SMILES: O=C(O)[C@H]1C2CCC(CC2)[C@H]1Nc1cc(-c2ccc([N+](=O)[O-])o2)nc(-c2c[nH]c3ncc(F)cc23)n1]

Step 1: (2S,3S)-ethyl 3-aminobicyclo[2.2.2]octane-2-carboxylate hydrochloride

The title compound can be prepared according to the synthetic method disclosed in patent application WO 2015073491.

Step 2: (2S,3S)-ethyl 3-((2-chloro-6-(5-nitrofuran-2-yl)pyrimidin-4-yl)amino)bicyclo[2.2.2]octane-2-carboxylate The title compound can be prepared by the synthetic method described in step 2 of example 24, using 2,4-dichloro-6-(5-nitrofuran-2-yl)pyrimidine (300 mg, 1.15 mmol), (2S,3S)-ethyl 3-aminobicyclo[2.2.2]octane-2-carboxylate hydrochloride (328 mg, 1.40 mmol), potassium carbonate (477 mg, 3.45 mmol) as reagents and DMF (10 mL) as solvent. The title compound was a white solid (271 mg, 56%).

MS (ESI, pos. ion) m/z: 421.1 [M+H]$^+$.

Step 3: (2S,3S)-ethyl 3-((2-(5-fluoro-1-tosyl-1H-pyrrolo[2,3-b]pyridin-3-yl)-6-(5-nitrofuran-2-yl)pyrimidin-4-yl)amino)bicyclo[2.2.2]octane-2-carboxylate The title compound can be prepared by the synthetic method described in step 3 of example 24, using 5-fluoro-3-(4,4,5,5-tetramethyl-1,3,2-dioxaborolan-2-yl)-1-tosyl-1H-pyrrolo[2,3-b]pyridine (298 mg, 0.43 mmol, 60%), K$_2$CO$_3$ (155 mg, 1.11 mmol), Pd(dppf)Cl$_2$ (29 mg, 0.04 mmol) and (2S,3S)-ethyl 3-((2-chloro-6-(5-nitrofuran-2-yl)pyrimidin-4-yl)amino) bicyclo[2.2.2]octane-2-carboxylate (148 mg, 0.35 mmol) as reagents and a mixture of 1,4-dioxane (8 mL) and H$_2$O (1 mL) as mixed solvent. The title compound was a white solid (125 mg, 53%).

Step 4: (2S,3S)-ethyl 3-((2-(5-fluoro-1H-pyrrolo[2,3-b]pyridin-3-yl)-6-(5-nitrofuran-2-yl) pyrimidin-4-yl)amino)bicyclo[2.2.2]octane-2-carboxylate The title compound can be prepared by the synthetic method described in step 4 of example 24, using (2S,3S)-ethyl 3-((2-(5-fluoro-1-tosyl-1H-pyrrolo[2,3-b]pyridin-3-yl)-6-(5-nitrofuran-2-yl)pyrimidin-4-yl)amino)bicyclo[2.2.2]octane-2-carboxylate (125 mg, 0.19 mmol) and a solution of HCl in 1,4-dioxane (4 mol/L, 0.50 mL). The title compound was a light yellow solid (95 mg, 99%), which was used in the next step without further purification.

MS (ESI, pos. ion) m/z: 521.1 [M+H]$^+$.

Step 5: (2S,3S)-3-((2-(5-fluoro-1H-pyrrolo[2,3-b]pyridin-3-yl)-6-(5-nitrofuran-2-yl)pyrimidin-4-yl)amino)bicyclo[2.2.2]octane-2-carboxylic Acid The title compound can be prepared by the synthetic method described in step 5 of example 24, using (2S,3S)-ethyl 3-((2-(5-fluoro-1H-pyrrolo[2,3-b]pyridin-3-yl)-6-(5-nitrofuran-2-yl)pyrimidin-4-yl)amino)bicyclo[2.2.2]octane-2-carboxylate (95 mg, 0.18 mmol), a solution of LiOH (17 mg, 0.72 mmol) in water (0.5 mL), and solvent THF (5 mL). The title compound was a white solid (27 mg, 30%).

HRMS (ESI, pos. ion) m/z: 493.1638 [M+H]$^+$, (C$_{24}$H$_{22}$FN$_6$O$_5$) [M+H]$^+$ theoretical value: 493.1636;

$^1$H NMR (400 MHz, DMSO-d$_6$) δ (ppm): 12.35 (s, 1H), 8.59 (d, J=8.7 Hz, 1H), 8.40 (s, 1H), 8.30 (s, 1H), 7.86 (d, J=3.7 Hz, 1H), 7.80 (d, J=6.7 Hz, 1H), 7.57 (d, J=3.2 Hz, 1H), 6.85 (s, 1H), 4.64 (s, 1H), 2.44 (s, 1H), 1.99 (s, 1H), 1.96 (s, 1H), 1.77-1.39 (m, 8H);

$^{13}$C NMR (101 MHz, DMSO-d$_6$) δ (ppm): 175.82, 162.93, 162.64, 154.77, 152.13, 150.63, 146.48, 132.19, 131.96, 131.71, 118.94, 115.82, 115.10, 113.30, 110.03, 98.24, 50.58, 50.03, 28.69, 28.41, 25.98, 24.15, 21.28, 19.36.

Example 25: (+/−)-trans-3-((2-(5-fluoro-1H-pyrrolo[2,3-b]pyridin-3-yl)-7-isopropyl-7H-pyrrolo[2,3-d]pyrimidin-4-yl)amino)bicyclo[2.2.2]octane-2-carboxylic Acid

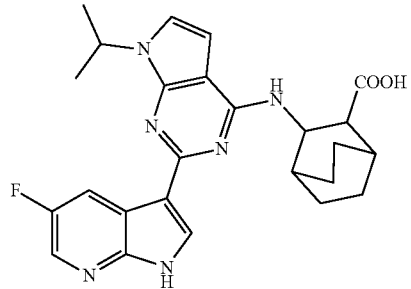 [SMILES: CC(C)n1ccc2c(NC3C4CCC(CC4)C3C(=O)O)nc(-c3c[nH]c4ncc(F)cc34)nc21]

Step 1: 2,4-dichloro-7-isopropyl-7H-pyrrolo[2,3-d]pyrimidine

To a solution of 2,4-dichloro-7H-pyrrolo[2,3-d]pyrimidine (500 mg, 2.66 mmol) in DMF (5 mL) was added NaH (130 mg, 3.19 mmol, 60%) at 0° C., and the mixture was stirred at this temperature for 30 min. Then 2-iodopropane (904 mg, 5.32 mmol) was added to the mixture, and the resulting mixture was stirred at rt overnight. The reaction was quenched with water (50 mL), and the resulting mixture was partitioned. The aqueous layer was extracted with ethyl acetate (50 mL×2). The combined organic layers were washed with saturated brine (80 mL), dried over anhydrous sodium sulfate and filtered. The filtrate was concentrated in vacuo and the residue was purified by silica gel column chromatography (PE/EtOAc (v/v)=10/1) to give the title compound as a yellow solid (356 mg, 58%).

MS (ESI, pos. ion) m/z: 231.05 [M+H]$^+$.

Step 2: (+/−)-trans-methyl 3-((2-chloro-7-isopropyl-7H-pyrrolo[2,3-d]pyrimidin-4-yl)amino) bicyclo[2.2.2]octane-2-carboxylate (+/−)-trans-Methyl 3-aminobicyclo[2.2.2]octane-2-carboxylate (390 mg, 1.96 mmol) and 2,4-dichloro-7-isopropyl-7H-pyrrolo[2,3-d]pyrimidine (410 mg, 1.78 mmol) were dissolved in tetrahydrofuran (5 mL), then potassium carbonate (493 mg, 3.56 mmol) was added. The mixture was stirred at rt overnight. The reaction was stopped, and to the reaction mixture was added water (50 mL) to quench the reaction. The resulting mixture was partitioned and the aqueous layer was extracted with ethyl acetate (50 mL×2). The combined organic layers were washed with saturated brine (80 mL), dried over anhydrous sodium sulfate and filtered. The filtrate was concentrated in vacuo and the residue was purified by silica gel column chromatography (PE/EtOAc (v/v)=10/1 to give the title compound as a yellow solid (333 mg, 50%).

MS (ESI, pos.ion) m/z: 425.15 [M+H]$^+$;

$^1$H NMR (400 MHz, CDCl$_3$) δ (ppm): 7.39 (d, J=4.2 Hz, 1H), 7.02 (d, J=3.6 Hz, 1H), 6.43 (s, 1H), 5.25 (s, 1H), 5.04 (dt, J=13.5, 6.8 Hz, 1H), 4.62 (s, 1H), 3.76 (s, 3H), 2.42 (d, J=5.4 Hz, 1H), 2.02 (s, 1H), 1.95 (d, J=2.3 Hz, 1H), 1.88-1.74 (m, 2H), 1.69-1.62 (m, 5H), 1.45-1.49 (m, 6H).

Step 3: (+/−)-trans-methyl 3-((2-(5-fluoro-1-tosyl-1H-pyrrolo[2,3-b]pyridin-3-yl)-7-isopropyl-7H-pyrrolo[2,3-d]pyrimidin-4-yl)amino)bicyclo[2.2.2]octane-2-carboxylate To a mixture of 5-fluoro-3-(4,4,5,5-tetramethyl-1,3,2-dioxaborolan-2-yl)-1-tosyl-1H-pyrrolo[2,3-b]pyridine (200 mg, 0.48 mmol), K$_2$CO$_3$ (166 mg, 1.19 mmol), Pd(dppf)Cl$_2$ (32 mg, 0.04 mmol) and (+/−)-trans-methyl 3-((2-chloro-7-isopropyl-7H-pyrrolo[2,3-d]pyrimidin-4-yl)amino)bicyclo[2.2.2]octane-2-carboxylate (150 mg, 0.40 mmol) in 1,4-dioxane (8.0 mL) was added H$_2$O (1 mL). The air in the mixture was removed by bubbling with nitrogen for 10 min. The mixture in a tube was sealed and stirred at 110° C. for 1.5 h. After the reaction was completed, the mixture was filtered to remove solid impurities. Then the filtrate was concentrated in vacuo. The residue was purified by silica gel chromatograph (PE/EtOAc (v/v)=10/1-5/1) to give a white solid (124 mg, 49%).

Step 4: (+/−)-trans-3-((2-(5-fluoro-1H-pyrrolo[2,3-b]pyridin-3-yl)-7-isopropyl-7H-pyrrolo [2,3-d]pyrimidin-4-yl)amino)bicyclo[2.2.2]octane-2-carboxylic Acid A solution of sodium hydroxide (78 mg, 1.97 mmol) in water (1 mL) was added to a solution of (+/−)-trans-methyl 3-((2-(5-fluoro-1-tosyl-1H-pyrrolo[2,3-b]pyridin-3-yl)-7-isopropyl-7H-pyrrolo[2,3-d]pyrimidin-4-yl)amino)bicyclo[2.2.2]octane-2-carboxylate (124 mg, 0.20 mmol) in THF/MeOH (v/v=5 mL/5 mL). The reaction mixture was stirred at r.t overnight. Water (10 mL) was added. The reaction mixture was adjusted to pH about 6 with hydrochloric acid (1 M). The resulting mixture was extracted with EtOAc (15 mL×3). The combined organic layers were washed with saturated brine, dried over anhydrous Na$_2$SO$_4$ and filtered, and the filtrate was concentrated in vacuo. The residue was purified by silica gel chromatograph (DCM/MeOH (v/v)=10/1-5/1) to give the title compound as a white solid (38 mg, 42%).

MS (ESI, pos. ion) m/z: 463.55 [M+H]$^+$;

HRMS (ESI, pos. ion) m/z: 463.2262[M+H]$^+$, (C$_{25}$H$_{28}$FN$_7$O$_2$) [M+H]$^+$ theoretical value: 463.2258;

$^1$H NMR (600 MHz, DMSO-d$_6$) δ (ppm): 12.08 (s, 1H), 8.68 (d, J=8.8 Hz, 1H), 8.31-8.18 (m, 2H), 7.21 (d, J=2.5 Hz, 2H), 6.64 (s, 1H), 5.08-4.96 (m, 1H), 4.79 (s, 1H), 2.72 (d, J=6.3 Hz, 1H), 2.03 (d, J=12.3 Hz, 2H), 1.88-1.69 (m, 3H), 1.68-1.53 (m, 3H), 1.49 (dd, J=6.3, 3.3 Hz, 6H), 1.38 (d, J=10.9 Hz, 2H), 1.19 (m, 1H).

Example 26: (+/−)-trans-3-((2-(5-fluoro-1H-pyrrolo[2,3-b]pyridin-3-yl)-5-methyl-5H-pyrrolo[3,2-d]pyrimidin-4-yl)amino)bicyclo[2.2.2]octane-2-carboxylic Acid

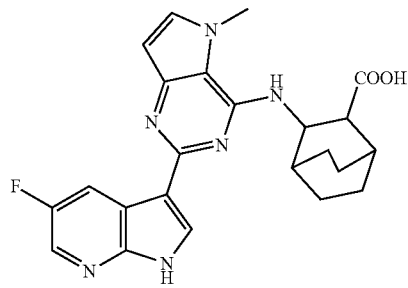 [SMILES: Cn1ccc2nc(-c3c[nH]c4ncc(F)cc34)nc(NC3C4CCC(CC4)C3C(=O)O)c21]

Step 1: 2,4-dichloro-5-methyl-5H-pyrrolo[3,2-d]pyrimidine

To a solution of 2,4-dichloro-5H-pyrrolo[3,2-d]pyrimidine (500 mg, 2.66 mmol) in DMF (8 mL) was added NaH (127 mg, 3.19 mmol, 60%) at 0° C. The reaction mixture was stirred for 30 min at 0° C., then iodomethane (3.78 g, 26.60 mmol) was added. The reaction mixture was stirred at rt overnight. Water (50 mL) was added to quench the reaction, and the mixture was partitioned. The aqueous layer was extracted with EtOAc (50 mL×2). The combined organic layers were washed with saturated brine (80 mL), dried over anhydrous Na$_2$SO$_4$ and filtered. The filtrate was concentrated in vacuo and the residue was purified by silica gel chromatograph (PE/EtOAc (v/v)=10/1) to give the title compound as a yellow solid (275 mg, 51%).

MS (ESI, pos. ion) m/z: 202.00 [M+H]$^+$;

$^1$H NMR (400 MHz, CDCl$_3$) δ (ppm): 7.47 (d, J=3.1 Hz, 1H), 6.64 (d, J=3.0 Hz, 1H), 4.16 (s, 3H).

Step 2: (+/−)-trans-methyl 3-((2-chloro-5-methyl-5H-pyrrolo[3,2-d]pyrimidin-4-yl)amino) bicyclo[2.2.2]octane-2-carboxylate To a solution of (+/−)-trans-methyl 3-aminobicyclo[2.2.2]octane-2-carboxylate (236 mg, 1.17 mmol) and 2,4-dichloro-5-methyl-5H-pyrrolo[3,2-d]pyrimidine (301 mg, 2.13 mmol) in THF (5 mL) was added K$_2$CO$_3$ (301 mg, 2.16 mmol). Then the mixture was stirred at room temperature overnight. After the reaction was completed, the reaction mixture was quenched with water (50 mL) and the resulting mixture was partitioned. The aqueous layer was extracted with ethyl acetate (50 mL×2), and the combined organic layers were washed with saturated brine (80 mL), dried over anhydrous Na$_2$SO$_4$ and filtered. The filtrate was concentrated in vacuo. The residue obtained was purified by silica gel column chromatography (PE/EtOAc (v/v)=10/1) to give the title compound as a yellow solid (122 mg, 33%).

MS (ESI, pos. ion) m/z: 350.15 [M+H]$^+$.

Step 3: (+/−)-trans-methyl 3-((2-(5-fluoro-1-tosyl-1H-pyrrolo[2,3-b]pyridin-3-yl)-5-methyl-5H-pyrrolo[3,2-d]pyrimidin-4-yl)amino)bicyclo[2.2.2]octane-2-carboxylate To a mixture of 5-fluoro-3-(4,4,5,5-tetramethyl-1,3,2-dioxaborolan-2-yl)-1-tosyl-1H-pyrrolo[2,3-b]pyridine (153 mg, 0.43 mmol), K$_2$CO$_3$ (156 mg, 1.13 mmol), Pd(dppf)Cl$_2$ (28 mg, 0.04 mmol) and (+/−)-trans-methyl 3-((2-chloro-5-methyl-5H-pyrrolo[3,2-d]pyrimidin-4-yl)amino)bicyclo[2.2.2]octane-2-carboxylate (136 mg, 0.39 mmol) in 1,4-dioxane (8.0 mL) was added H$_2$O (1 mL). The air in the mixture was removed by bubbling with nitrogen for 10 min, and then the mixture was stirred at 110° C. for 1.5 h with microwave heating. The reaction mixture filtered through a celite pad to remove solid impurities, and the filtrate was concentrated in vacuo to remove the solvent. The residue was purified by silica gel chromatograph (PE/EtOAc (v/v)=10/1-5/1) to give the title compound as a white solid (75 mg, 32%).

MS (ESI, pos. ion) m/z: 604.40 [M+H]$^+$.

Step 4: (+/−)-trans-3-((2-(5-fluoro-1H-pyrrolo[2,3-b]pyridin-3-yl)-5-methyl-5H-pyrrolo[3,2-d]pyrimidin-4-yl)amino)bicyclo[2.2.2]octane-2-carboxylic Acid A solution of sodium hydroxide (51 mg, 1.24 mmol) in water (1 mL) was added to a solution of (+/−)-trans-methyl 3-((2-(5-fluoro-1-tosyl-1H-pyrrolo[2,3-b]pyridin-3-yl)-5-methyl-5H-pyrrolo[3,2-d]pyrimidin-4-yl)amino)bicyclo[2.2.2]octane-2-carboxylate (75 mg, 0.12 mmol) in THF/MeOH (v/v=5 mL/5 mL). The reaction mixture was stirred at rt overnight. Water (10 mL) was added. The mixture was adjusted to pH about 6 with aqueous hydrochloric acid (1 M) solution. The resulting mixture was extracted with EtOAc (15 mL×3). The combine organic layers were washed with saturated brine (40 mL), dried over Na$_2$SO$_4$ and filtered. The filtrate was concentrated in vacuo and the residue was purified by silica gel chromatograph (DCM/MeOH (v/v)=10/1-5/1) to give the title compound as a white solid (21 mg, 39%).

MS (ESI, pos. ion) m/z: 435.20 [M+H]$^+$;

HRMS (ESI, pos. ion) m/z: 435.1944 [M+H]$^+$, (C$_{23}$H$_{24}$FN$_6$O$_2$) [M+H]$^+$ theoretical value: 435.1945;

$^1$H NMR (600 MHz, DMSO-d$_6$) δ (ppm): 12.72 (s, 1H), 8.65-8.56 (m, 2H), 8.38 (s, 1H), 7.64 (s, 1H), 7.11 (s, 1H), 6.47 (d, J=2.6 Hz, 1H), 5.14 (s, 1H), 4.15 (s, 3H), 2.08 (s, 1H), 2.03 (s, 1H), 1.83 (d, J=8.2 Hz, 3H), 1.58-1.48 (m, 5H).

Example 27: (+/−)-trans-3-((2-(5-fluoro-1H-pyrrolo[2,3-b]pyridin-3-yl)-7-phenyl-7H-pyrrolo[2,3-d]pyrimidin-4-yl)amino)bicyclo[2.2.2]octane-2-carboxylic Acid

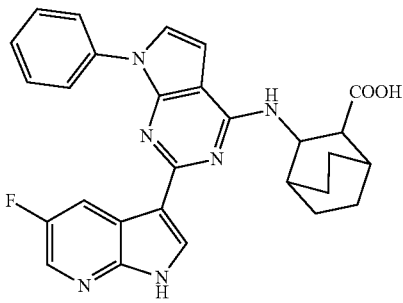 [SMILES: O=C(O)C1C2CCC(CC2)C1Nc1nc(-c2c[nH]c3ncc(F)cc23)nc2c1ccn2-c1ccccc1]

Step 1: 2,4-dichloro-7-phenyl-7H-pyrrolo[2,3-d]pyrimidine

To a solution of 2,4-dichloro-7H-pyrrolo[2,3-d]pyrimidine (300 mg, 1.60 mmol) in DCM (5 mL) was added phenylboronic acid (215 mg, 1.76 mmol), Cu(OAc)$_2$ (580 mg, 3.19 mmol) and Et$_3$N (1.61 g, 15.95 mmol). The mixture was stirred at rt in oxygen atmosphere overnight. Water (50 mL) was added to quench the reaction, and the mixture was partitioned. The aqueous layer was extracted with EtOAc (50 mL×2). The combined organic layers were washed with saturated brine (80 mL), dried over anhydrous Na$_2$SO$_4$ and filtered. The filtrate was concentrated in vacuo and the residue was purified by silica gel chromatograph (PE/EtOAc (v/v)=10/1) to give the title compound as a yellow solid (296 mg, 70%).

MS (ESI, pos. ion) m/z: 265.35 [M+H]$^+$.

Step 2: (+/−)-trans-methyl 3-((2-chloro-7-phenyl-7H-pyrrolo[2,3-d]pyrimidin-4-yl)amino) bicyclo[2.2.2]octane-2-carboxylate (+/−)-trans-Methyl 3-aminobicyclo[2.2.2]octane-2-carboxylate (245 mg, 1.23 mmol) and 2,4-dichloro-7-phenyl-7H-pyrrolo[2,3-d]pyrimidine (296 mg, 1.12 mmol) were dissolved in DMF (10 mL), then potassium carbonate (310 mg, 2.24 mmol) was added. The mixture was stirred at rt overnight. To the reaction mixture was added water (50 mL) to quench the reaction, and the resulting mixture was partitioned. The aqueous layer was extracted with ethyl acetate (50 mL×2). The combined organic layers were washed with saturated brine (80 mL), dried over anhydrous sodium sulfate and filtered. The filtrate was concentrated in vacuo and the residue was purified by silica gel column chromatography (PE/EtOAc (v/v)=10/1) to give the title compound as a yellow solid (156 mg, 34%).

MS (ESI, pos. ion) m/z: 412.15 [M+H]$^+$.

Step 3: (+/−)-trans-methyl 3-((2-(5-fluoro-1-tosyl-1H-pyrrolo[2,3-b]pyridin-3-yl)-7-phenyl-7H-pyrrolo[2,3-d]pyrimidin-4-yl)amino)bicyclo[2.2.2]octane-2-carboxylate To 1,4-dioxane (8 mL) were added 5-fluoro-3-(4,4,5,5-tetramethyl-1,3,2-dioxaborolan-2-yl)-1-tosyl-1H-pyrrolo[2,3-b]pyridine (185 mg, 0.42 mmol), K$_2$CO$_3$ (160 mg, 1.14 mmol), PdCl₂(dppf) (30 mg, 0.04 mmol) and (+/−)-trans-methyl 3-((2-chloro-7-phenyl-7H-pyrrolo[2,3-d]pyrimidin-4-yl)amino)bicycle [2.2.2]octane-2-carboxylate (156 mg, 0.38 mmol). Then H₂O (1 mL) was added to the mixture, and the air in the mixture was removed by bubbling with nitrogen for 10 min. The mixture was sealed in a tube, and stirred for 1.5 h at 110° C. The mixture was filtered to remove solid impurities. The filtrate was concentrated in vacuo, and the residue was purified by silica gel column chromatography (PE/EtOAc (v/v)=10/1-5/1) to give the title compound as a white solid (135 mg, 53%).

Step 4: (+/−)-trans-3-((2-(5-fluoro-1H-pyrrolo[2,3-b]pyridin-3-yl)-7-phenyl-7H-pyrrolo[2,3-d]pyrimidin-4-yl)amino)bicyclo[2.2.2]octane-2-carboxylic Acid To a solution of (+/−)-trans-methyl 3-((2-(5-fluoro-1-tosyl-1H-pyrrolo[2,3-b]pyridine-3-yl)-7-phenyl-7H-pyrrolo[2,3-d]pyrimidin-4-yl)amino)bicyclo[2.2.2]octane-2-carboxylate (120 mg, 0.18 mmol) in THF/MeOH (v/v=5 mL/5 mL) was added a solution of sodium hydroxide (78 mg, 1.81 mmol) in water (1 mL). The mixture was stirred at rt overnight. To the reaction mixture was added water (10 mL), and the resulting mixture was acidified with hydrochloric acid (1 M) to pH about 6. The mixture was extracted with ethyl acetate (15 mL×3), and the combined organic layers were washed with saturated brine (40 mL), dried over anhydrous sodium sulfate, then filtered. The filtrate was concentrated in vacuo and the residue was purified by silica gel column chromatography (DCM/MeOH (v/v)=10/1-5/1) to give the title compound as a white solid (61 mg, 68%).

MS (ESI, pos. ion) m/z: 497.15 [M+H]⁺;
HRMS (ESI, pos. ion) m/z: 497.2106[M+H]⁺, (C₂₈H₂₆FN₆O₂) [M+H]⁺ theoretical value: 497.2101;
¹H NMR (600 MHz, DMSO-d₆) δ (ppm): 12.12 (s, 1H), 8.62 (d, J=8.1 Hz, 1H), 8.26 (s, 1H), 8.22 (d, J=2.4 Hz, 1H), 7.95 (d, J=7.8 Hz, 2H), 7.60 (t, J=7.8 Hz, 2H), 7.52 (d, J=3.4 Hz, 1H), 7.45-7.38 (m, 2H), 6.90 (s, 1H), 4.81 (s, 1H), 2.74 (d, J=6.3 Hz, 1H), 2.04 (d, J=15.2 Hz, 2H), 1.87-1.73 (m, 3H), 1.67-1.55 (m, 3H), 1.49-1.39 (m, 3H);
¹³C NMR (151 MHz, DMSO-d₆) δ (ppm): 176.15, 156.76, 156.24, 155.12, 150.20, 146.42, 138.64, 131.65, 131.44, 130.44, 129.64, 126.48, 123.68, 123.25, 118.99, 118.86, 115.71, 101.44, 50.64, 49.04, 28.93, 28.81, 26.05, 24.25, 21.55, 19.53.

Example 28: (+/−)-trans-3-((7-cyclopropyl-2-(5-fluoro-1H-pyrrolo[2,3-b]pyridin-3-yl)-7H-pyrrolo[2,3-d]pyrimidin-4-yl)amino)bicyclo[2.2.2]octane-2-carboxylic Acid

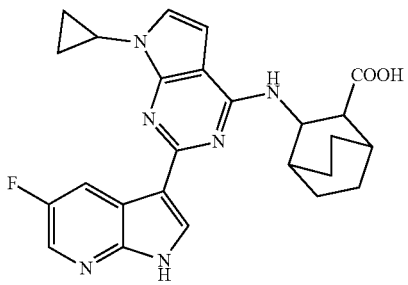 [SMILES: O=C(O)C1C2CCC(CC2)C1Nc1nc(-c2c[nH]c3ncc(F)cc23)nc2c1ccn2C1CC1]

Step 1: 2,4-dichloro-7-cyclopropyl-7H-pyrrolo[2,3-d]pyrimidine

To a solution of 2,4-dichloro-7H-pyrrolo[2,3-d]pyrimidine (500 mg, 2.66 mmol) in DMF (5 mL) was added NaH (130 mg, 3.25 mmol, 60%) at 0° C., and the mixture was stirred at this temperature for 30 min. Then cyclopropyl bromide (643 mg, 5.32 mmol) and cuprous iodide (3.19 g, 16.7 mmol) was added to the mixture, and the resulting mixture was stirred at 120° C. overnight. To the reaction mixture was added water (50 mL), and the resulting mixture was extracted with ethyl acetate (50 mL×2). The combined organic layers were washed with saturated brine (80 mL), dried over anhydrous sodium sulfate and filtered. The filtrate was concentrated in vacuo and the residue was purified by silica gel column chromatography (PE/EtOAc (v/v)=10/1) to give the title compound as a yellow solid (453 mg, 75%).

MS (ESI, pos. ion) m/z: 229.10 [M+H]⁺;
¹H NMR (400 MHz, CDCl₃) δ (ppm): 7.25 (d, J=3.6 Hz, 1H), 6.64 (d, J=3.6 Hz, 1H), 6.00 (ddd, J=16.2, 10.9, 5.8 Hz, 1H), 5.31 (d, J=10.2 Hz, 1H), 5.19 (d, J=17.1 Hz, 1H), 4.87 (d, J=5.7 Hz, 2H).

Step 2: (+/−)-trans-methyl 3-((2-chloro-7-cyclopropyl-7H-pyrrolo[2,3-d]pyrimidin-4-yl) amino)bicyclo [2.2.2]octane-2-carboxylate (+/−)-trans-Methyl 3-aminobicyclo[2.2.2]octane-2-carboxylate (360 mg, 1.80 mmol) and 2,4-dichloro-7-cyclopropyl-7H-pyrrolo[2,3-d]pyrimidine (374 mg, 1.64 mmol) were dissolved in DMF (5 mL), then potassium carbonate (453 mg, 3.28 mmol) was added. The mixture was stirred at rt overnight. To the reaction mixture was added water (50 mL) to quench the reaction, and the resulting mixture was partitioned. The aqueous layer was extracted with ethyl acetate (50 mL×2). The combined organic layers were washed with saturated brine (80 mL), dried over anhydrous sodium sulfate and filtered. The filtrate was concentrated in vacuo and the residue was purified by silica gel column chromatography (PE/EtOAc (v/v)=10/1) to give the title compound as a yellow solid (370 mg, 60%).

MS (ESI, pos.ion) m/z: 376.15 [M+H]⁺.

Step 3: (+/−)-trans-methyl 3-((7-cyclopropyl-2-(5-fluoro-1-tosyl-1H-pyrrolo[2,3-b]pyridin-3-yl)-7H-pyrrolo[2,3-d]pyrimidin-4-yl)amino)bicyclo[2.2.2]octane-2-carboxylate To 1,4-dioxane (8 mL) were added 5-fluoro-3-(4,4,5,5-tetramethyl-1,3,2-dioxaborolan-2-yl)-1-tosyl-1H-pyrrolo[2,3-b]pyridine (172 mg, 0.41 mmol), K₂CO₃ (156 mg, 1.39 mmol), Pd(dppf)Cl₂ (28 mg, 0.05 mmol) and (+/−)-trans-methyl 3-((2-chloro-7-cyclopropyl-7H-pyrrolo[2,3-d]pyrimidin-4-yl)amino)bicycle[2.2.2]octane-2-carboxylate (174 mg, 0.46 mmol). Then H₂O (1 mL) was added to the mixture, and the air in the mixture was removed by bubbling with nitrogen for 10 min. The mixture was stirred for 1.5 h at 110° C. with microwave heating. The mixture was filtered through a celite pad to remove solid impurities. The filtrate was concentrated in vacuo to remove the solvent, and the residue was purified by silica gel column chromatography (PE/EtOAc (v/v)=10/1-5/1) to give the title compound as a white solid (120 mg, 41%).

Step 4: (+/−)-trans-3-((7-cyclopropyl-2-(5-fluoro-1H-pyrrolo[2,3-b]pyridin-3-yl)-7H-pyrrolo[2,3-d]pyrimidin-4-yl)amino)bicyclo[2.2.2]octane-2-carboxylic Acid To a solution of (+/−)-trans-methyl 3-((7-cyclopropyl-2-(5-fluoro-1-tosyl-1H-pyrrolo[2,3-b]pyridin-3-yl)-7H-pyrrolo[2,3-d]pyrimidin-4-yl)amino)bicyclo[2.2.2]octane-2-carboxylate (120 mg, 0.19 mmol) in THF/MeOH (v/v=5 mL/5 mL) was added a solution of NaOH (78 mg, 1.91 mmol) in water (1 mL). The mixture was stirred at rt overnight, then acidified with diluted hydrochloric acid (1 M) to pH about 6. The resulting mixture was extracted with ethyl acetate (15 mL×3). The combined organic layers were washed with saturated brine (40 mL), dried over anhydrous sodium sulfate and filtered. The filtrate was concentrated in vacuo to remove the solvent and the residue was purified by silica gel column chromatography (DCM/MeOH (v/v)=10/1-5/1) to give the title compound as a white solid (43 mg, 49%).

MS (ESI, pos. ion) m/z: 461.15 [M+H]$^+$;

HRMS (ESI, pos. ion) m/z: 461.2113[M+H]$^+$, ($C_{25}H_{26}FN_6O_2$) [M+H]$^+$ theoretical value: 461.2101;

$^1$H NMR (600 MHz, DMSO-d$_6$) δ (ppm): 12.17 (s, 1H), 8.65 (d, J=7.6 Hz, 1H), 8.28 (s, 2H), 7.45 (s, 1H), 7.09 (s, 1H), 6.71 (s, 1H), 6.07 (s, 1H), 5.19 (d, J=9.3 Hz, 1H), 5.08 (d, J=16.9 Hz, 1H), 4.87 (s, 2H), 2.72 (s, 2H), 2.02 (s, 2H), 1.87-1.73 (m, 3H), 1.48-1.40 (m, 5H).

Example 29: (+/−)-trans-3-((2-(5-fluoro-1H-pyrrolo[2,3-b]pyridin-3-yl)-5-phenyl-5H-pyrrolo[3,2-d]pyrimidin-4-yl)amino)bicyclo[2.2.2]octane-2-carboxylic Acid

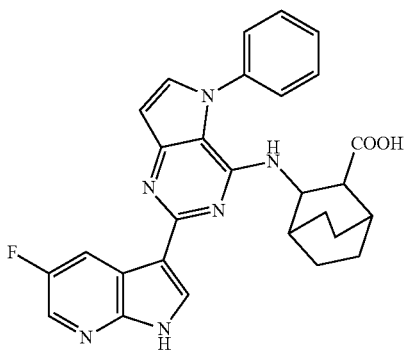 [SMILES: O=C(O)C1C2CCC(CC2)C1Nc1nc(-c2c[nH]c3ncc(F)cc23)nc2ccn(-c3ccccc3)c12]

Step 1: 2,4-dichloro-5-phenyl-5H-pyrrolo[3,2-d]pyrimidine

To a solution of 2,4-dichloro-5H-pyrrolo[3,2-d]pyrimidine (1.00 g, 5.26 mmol) in DCM (5 mL) was added phenylboronic acid (710 mg, 5.79 mmol), cupric acetate (1.82 g, 10.52 mmol), Et$_3$N (5.32 g, 53.62 mmol). Then the reaction mixture was stirred in oxygen atmosphere at rt overnight. Water (50 mL) was added to quench the reaction, and the mixture was partitioned. The aqueous layer was extracted with EtOAc (50 mL×2). The combined organic layers were washed with saturated brine (80 mL), dried over anhydrous Na$_2$SO$_4$ and filtered. The filtrate was concentrated in vacuo and the residue was purified by silica gel chromatograph (PE/EtOAc (v/v)=10/1) to give the title compound as a yellow solid (1.03 g, 74%).

MS (ESI, pos. ion) m/z: 265.20 [M]$^+$.

Step 2: (+/−)-trans-methyl 3-((2-chloro-5-phenyl-5H-pyrrolo[3,2-d]pyrimidin-4-yl)amino) bicyclo[2.2.2]octane-2-carboxylate To a solution of (+/−)-trans-methyl 3-aminobicyclo[2.2.2]octane-2-carboxylate (267 mg, 1.3 mmol), 2,4-dichloro-5-phenyl-5H-pyrrolo[3,2-d]pyrimidine (322 mg, 1.22 mmol) in THF (5 mL) was added K$_2$CO$_3$ (337 mg, 2.44 mmol). Then the mixture was stirred at room temperature overnight. The reaction mixture quenched with water (50 mL), and the resulting mixture was partitioned. The aqueous layer was extracted with EtOAc (50 mL×2), and the combined organic layers were washed with saturated brine (80 mL), dried over anhydrous Na$_2$SO$_4$ and filtered. The filtrate was concentrated in vacuo. The residue was purified by silica gel column chromatography (PE/EtOAc (v/v)=10/1) to give the title compound as a yellow solid (150 mg, 30%).

MS (ESI, pos.ion) m/z: 411.10 [M+H]$^+$.

Step 3: (+/−)-trans-methyl 3-((2-(5-fluoro-1-tosyl-1H-pyrrolo[2,3-b]pyridin-3-yl)-5-phenyl-5H-pyrrolo[3,2-d]pyrimidin-4-yl)amino)bicyclo[2.2.2]octane-2-carboxylate To a mixture of 5-fluoro-3-(4,4,5,5-tetramethyl-1,3,2-dioxaborolan-2-yl)-1-tosyl-1H-pyrrolo[2,3-b]pyridine (150 mg, 0.36 mmol), K$_2$CO$_3$ (140 mg, 0.99 mmol), Pd(dppf)Cl$_2$ (25 mg, 0.02 mmol) and (+/−)-trans-methyl 3-((2-chloro-5-phenyl-5H-pyrrolo[3,2-d]pyrimidin-4-yl)amino)bicyclo[2.2.2]octane-2-carboxylate (136 mg, 0.33 mmol) in 1,4-dioxane (8.0 mL) was added water (1 mL). The air in the mixture was removed by bubbling with nitrogen for 10 min and then the mixture was stirred at 110° C. for 1.5 h with microwave heating. The reaction mixture was filtered through a celite pad to remove solid impurities, and the filtrate was concentrated in vacuo. The residue was purified by silica gel chromatograph (PE/EtOAc (v/v)=10/1-5/1) to give the title compound as a white solid (185 mg, 84%).

Step 4: (+/−)-trans-3-((2-(5-fluoro-1H-pyrrolo[2,3-b]pyridin-3-yl)-5-phenyl-5H-pyrrolo[3,2-d]pyrimidin-4-yl)amino)bicyclo[2.2.2]octane-2-carboxylic Acid A solution of NaOH (123 mg, 2.78 mmol) in water (1 mL) was added to a solution of (+/−)-trans-methyl 3-((2-(5-fluoro-1-tosyl-1H-pyrrolo[2,3-b]pyridin-3-yl)-5-phenyl-5H-pyrrolo[3,2-d]pyrimidin-4-yl)amino)bicyclo[2.2.2]octane-2-carboxylate (185 mg, 0.28 mmol) in THF/MeOH (v/v=5 mL/5 mL). The reaction mixture was stirred at rt overnight. Water (10 mL) was added, and the resulting mixture was adjusted to pH about 6 with aqueous hydrochloric acid solution (1 M). The mixture was extracted with EtOAc (15 mL×3). The combined organic layers were washed with saturated brine, dried over anhydrous Na$_2$SO$_4$ and filtered. The filtrate was concentrated in vacuo and the residue was purified by silica gel column chromatography (DCM/MeOH (v/v)=10/1-5/1) to give the title compound as a white solid (63 mg, 46%).

MS (ESI, pos. ion) m/z: 497.10 [M+H]$^+$;

HRMS (ESI, pos. ion) m/z: 497.2094[M+H]$^+$, ($C_{28}H_{26}FN_7O_2$) [M+H]$^+$ theoretical value: 497.2101;

$^1$H NMR (600 MHz, DMSO-d$_6$) δ (ppm): 12.13 (s, 1H), 8.69 (dd, J=9.8, 2.7 Hz, 1H), 8.30 (d, J=2.4 Hz, 1H), 8.26 (d, J=1.3 Hz, 1H), 7.68 (d, J=3.0 Hz, 1H), 7.66-7.61 (m, 3H), 7.59 (d, J=7.6 Hz, 3H), 6.66 (d, J=3.1 Hz, 1H), 4.74 (s, 1H), 2.03 (s, 1H), 1.88 (d, J=2.4 Hz, 1H), 1.83 (s, 1H), 1.68 (d, J=9.2 Hz, 1H), 1.53 (m, 4H), 1.34 (m, 4H).

Example 30: (+/−)-trans-3-((2-(5-fluoro-1H-pyrrolo[2,3-b]pyridin-3-yl)-7H-pyrrolo[2,3-d]pyrimidin-4-yl)amino)bicyclo[2.2.2]octane-2-carboxylic Acid

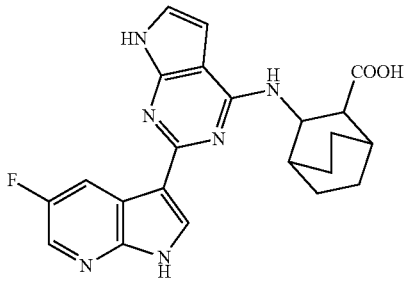 [SMILES: O=C(O)C1C2CCC(CC2)C1Nc1nc(-c2c[nH]c3ncc(F)cc23)nc2[nH]ccc12]

Step 1) 2,4-dichloro-7-tosyl-7H-pyrrolo[2,3-d]pyrimidine

To a solution of 2,4-dichloro-7H-pyrrolo[2,3-d]pyrimidine (500 mg, 2.66 mmol) in DMF (5 mL) was added NaH (120 mg, 2.93 mmol, 60%) at 0° C., and the mixture was stirred at this temperature for 30 min. Then paratoluensulfonyl chloride (608 mg, 3.19 mmol) was added to the mixture, and the resulting mixture was stirred at rt overnight. To the reaction mixture was added water (50 mL) to quench the reaction, and the resulting mixture was partitioned. The aqueous layer was extracted with ethyl acetate (50 mL×2). The combined organic layers were washed with saturated brine (80 mL), dried over anhydrous sodium sulfate and filtered. The filtrate was concentrated in vacuo and the residue was purified by silica gel column chromatography (PE/EtOAc (v/v)=10/1) to give the title compound as a yellow solid (780 mg, 86%).

MS (ESI, pos. ion) m/z: 343.90 [M+H]$^+$;

$^1$H NMR (400 MHz, CDCl$_3$) δ (ppm): 8.13 (d, J=8.3 Hz, 2H), 7.77 (d, J=4.0 Hz, 1H), 7.38 (d, J=8.2 Hz, 2H), 6.70 (d, J=4.0 Hz, 1H), 2.45 (s, 3H).

Step 2: (+/−)-trans-methyl 3-((2-chloro-7-tosyl-7H-pyrrolo[2,3-d]pyrimidin-4-yl)amino) bicyclo[2.2.2]octane-2-carboxylate (+/−)-trans-Methyl 3-aminobicyclo[2.2.2]octane-2-carboxylate (500 mg, 2.51 mmol) and 2,4-dichloro-7-tosyl-7H-pyrrolo[2,3-d]pyrimidine (780 mg, 2.28 mmol) were dissolved in DMF (10 mL), then potassium carbonate (630 mg, 4.56 mmol) was added. The mixture was stirred at rt overnight. To the reaction mixture was added water (50 mL) to quench the reaction, and the resulting mixture was extracted with ethyl acetate (50 mL×2). The combined organic layers were washed with saturated brine (80 mL), dried over anhydrous sodium sulfate and filtered. The filtrate was concentrated in vacuo and the residue was purified by silica gel column chromatography (PE/EtOAc (v/v)=10/1) to give the title compound as a yellow solid (803 mg, 72%).

MS (ESI, pos.ion) m/z: 490.50 [M+H]$^+$;

$^1$H NMR (400 MHz, CDCl$_3$) δ (ppm): 8.09 (d, J=8.2 Hz, 2H), 7.44 (d, J=3.9 Hz, 1H), 7.32 (d, J=8.1 Hz, 2H), 6.48 (s, 1H), 4.52 (t, J=5.8 Hz, 1H), 3.73 (s, 3H), 2.42 (s, 3H), 1.99 (s, 1H), 1.86 (s, 1H), 1.73 (s, 2H), 1.70-1.37 (m, 9H).

Step 3: (+/−)-trans-methyl 3-((2-(5-fluoro-1-tosyl-1H-pyrrolo[2,3-b]pyridin-3-yl)-7-tosyl-7H-pyrrolo[2,3-d]pyrimidin-4-yl)amino)bicyclo[2.2.2]octane-2-carboxylate To a mixture of 5-fluoro-3-(4,4,5,5-tetramethyl-1,3,2-dioxaborolan-2-yl)-1-tosyl-1H-pyrrolo[2,3-b]pyridine (187 mg, 0.45 mmol), K$_2$CO$_3$ (170 mg, 1.23 mmol), Pd(dppf)Cl$_2$ (30 mg, 0.04 mmol) and (+/−)-trans-methyl 3-((2-chloro-7-tosyl-7H-pyrrolo[2,3-d]pyrimidin-4-yl) amino)bicyclo[2.2.2]octane-2-carboxylate (200 mg, 0.41 mmol) in 1,4-dioxane (8.0 mL) was added water (1 mL). The air in the mixture was removed by bubbling with nitrogen for 10 min, and the mixture was stirred at 110° C. for 1.5 h. The reaction mixture was filtered through a celite pad to remove the solid impurity, and the filtrate was concentrated in vacuo. The residue was purified by silica gel chromatograph (PE/EtOAc (v/v)=10/1-5/1) to give the title compound as a white solid (292 mg, 96%).

Step 4: (+/−)-trans-3-((2-(5-fluoro-1H-pyrrolo[2,3-b]pyridin-3-yl)-7H-pyrrolo[2,3-d]pyrimidin-4-yl)amino)bicyclo[2.2.2]octane-2-carboxylic Acid A solution of NaOH (120 mg, 2.84 mmol) in water (1 mL) was added to a solution of (+/−)-trans-methyl 3-((2-(5-fluoro-1-tosyl-1H-pyrrolo[2,3-b]pyridin-3-yl)-7-tosyl-7H-pyrrolo[2,3-d]pyrimidin-4-yl)amino)bicyclo[2.2.2]octane-2-carboxylate (212 mg, 0.28 mmol) in THF/MeOH (v/v=5 mL/5 mL). The reaction mixture was stirred at rt overnight. Water (10 mL) was added, and the reaction mixture was adjusted to pH about 6 with aqueous hydrochloric acid (1 M) solution. The mixture was extracted with EtOAc (15 mL×3). The combined organic layers were washed with saturated brine (40 mL), dried over anhydrous Na$_2$SO$_4$ and filtered. The filtrate was concentrated in vacuo, and the residue was purified by silica gel column chromatograph (DCM/MeOH (v/v)=10/1-5/1) to give the title compound as a white solid (51 mg, 43%).

MS (ESI, pos. ion) m/z: 421.10 [M+H]$^+$;

HRMS (ESI, pos. ion) m/z: 421.1800[M+H]$^+$, (C$_{22}$H$_{23}$FN$_6$O$_2$) [M+H]$^+$ theoretical value: 421.1788;

$^1$H NMR (600 MHz, DMSO-d$_6$) δ (ppm): 12.04 (s, 1H), 11.32 (s, 1H), 8.73 (d, J=10.2 Hz, 1H), 8.25 (s, 1H), 8.15 (s, 1H), 7.19 (d, J=6.5 Hz, 1H), 7.03 (s, 1H), 6.61 (s, 1H), 4.80 (s, 1H), 2.73 (d, J=6.1 Hz, 1H), 2.02 (s, 1H), 1.93-1.33 (m, 7H), 1.23 (s, 2H);

$^{13}$C NMR (151 MHz, DMSO-d$_6$) δ (ppm): 176.16, 156.73, 155.99, 155.07, 146.29, 131.48, 131.23, 130.08, 129.91, 129.48, 120.66, 119.06, 115.95, 100.99, 99.44, 50.45, 48.94, 29.01, 28.87, 26.00, 24.14, 21.53, 19.43.

Example 31: (+/−)-trans-3-((6-(5-fluoro-1H-pyrrolo[2,3-b]pyridin-3-yl)-1-methyl-1H-pyrazolo[3,4-d]pyrimidin-4-yl)amino)bicyclo[2.2.2]octane-2-carboxylic Acid

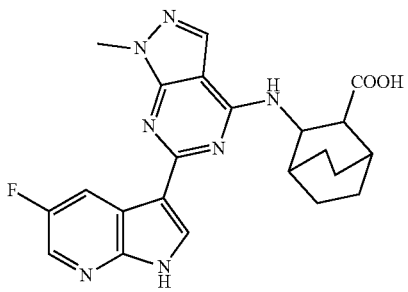 [SMILES: Cn1ncc2c(NC3C4CCC(CC4)C3C(=O)O)nc(-c3c[nH]c4ncc(F)cc34)nc21]

Step 1: 4,6-dichloro-1-methyl-1H-pyrazolo[3,4-d]pyrimidine

To a solution of 4,6-dichloro-1H-pyrazolo[3,4-d]pyrimidine (110 mg, 0.58 mmol) in DMF (8 mL) was added $K_2CO_3$ (160 mg 1.16 mmol). The reaction mixture was stirred for 30 min at rt, and iodomethane (3.78 g, 26.60 mmol) was added. The reaction mixture was stirred at rt overnight. Water (50 mL) was added to quench the reaction, and the mixture was partitioned. The aqueous layer was extracted with EtOAc (50 mL×2). The combined organic layers were washed with saturated brine (80 mL), dried over anhydrous $Na_2SO_4$ and filtered. The filtrate was concentrated in vacuo and the residue was purified by silica gel chromatograph (PE/EtOAc (v/v)=10/1) to give the title compound as a yellow solid (48 mg, 41%).

$^1$H NMR (400 MHz, $CDCl_3$) δ (ppm): 8.16 (s, 1H), 4.13 (s, 3H).

Step 2: (+/−)-trans-methyl 3-((6-chloro-1-methyl-1H-pyrazolo[3,4-d]pyrimidin-4-yl)amino) bicyclo[2.2.2]octane-2-carboxylate To a solution of (+/−)-trans-methyl 3-aminobicyclo[2.2.2]octane-2-carboxylate (132 mg, 0.67 mmol) and 4,6-dichloro-1-methyl-1H-pyrazolo[3,4-d]pyrimidine (123 mg, 0.61 mmol) in THF (5 mL) was added $K_2CO_3$ (167 mg, 1.21 mmol). Then the mixture was stirred at room temperature overnight. The reaction mixture was quenched with water (50 mL), and the resulting mixture was partitioned. The aqueous layer was extracted with EtOAc (50 mL×2). The combined organic layers were washed with saturated brine (80 mL), dried over anhydrous $Na_2SO_4$ and filtered. The filtrate was concentrated in vacuo and the residue was purified by silica gel column chromatography (PE/EtOAc (v/v)=10/1) to give the title compound as a yellow solid (201 mg, 95%).

MS (ESI, pos.ion) m/z: 351.10 [M+H]$^+$;

$^1$H NMR (400 MHz, $CDCl_3$) δ (ppm): 8.00 (s, 1H), 4.62 (t, J=6.3 Hz, 1H), 3.99 (s, 3H), 3.74 (s, 3H), 2.44 (s, 1H), 1.94 (s, 1H), 1.88-1.37 (m, 10H).

Step 3: (+/−)-trans-methyl 3-((6-(5-fluoro-1-tosyl-1H-pyrrolo[2,3-b]pyridin-3-yl)-1-methyl-1H-pyrazolo[3,4-d]pyrimidin-4-yl)amino)bicyclo[2.2.2]octane-2-carboxylate To a mixture of 5-fluoro-3-(4,4,5,5-tetramethyl-1,3,2-dioxaborolan-2-yl)-1-tosyl-1H-pyrrolo[2,3-b]pyridine (86 mg, 0.21 mmol), $K_2CO_3$ (78 mg, 0.57 mmol), Pd(dppf)Cl$_2$ (15 mg, 0.02 mmol) and (+/−)-trans-methyl 3-((6-chloro-1-methyl-1H-pyrazolo [3,4-d]pyrimidin-4-yl)amino)bicyclo [2.2.2]octane-2-carboxylate (66 mg, 0.19 mmol) in 1,4-dioxane (8.0 mL) was added water (1 mL). The air in the mixture was removed by bubbling with nitrogen for 10 min and then the mixture was stirred at 110° C. for 1.5 h. The reaction mixture was filtered through a celite pad to remove the solid impurity. Then the filtrate was concentrated in vacuo. The residue was purified by silica gel chromatograph (PE/EtOAc (v/v)=10/1-5/1) to give the title compound as a white solid (53 mg, 47%).

MS (ESI, pos.ion) m/z: 605.10 [M+H]$^+$.

Step 4: (+/−)-trans-3-((6-(5-fluoro-1H-pyrrolo[2,3-b]pyridin-3-yl)-1-methyl-1H-pyrazolo[3,4-d]pyrimidin-4-yl)amino)bicyclo[2.2.2]octane-2-carboxylic Acid A solution of NaOH (41 mg, 0.94 mmol) in water (1 mL) was added to a solution of (+/−)-trans-methyl 3-((6-(5-fluoro-1-tosyl-1H-pyrrolo[2,3-b]pyridin-3-yl)-1-methyl-1H-pyrazolo[3,4-d]pyrimidin-4-yl)amino)bicyclo[2.2.2]octane-2-carboxylate (57 mg, 0.09 mmol) in THF/MeOH (v/v=5 mL/5 mL). The reaction mixture was stirred at rt overnight. Water (10 mL) was added to the reaction mixture, and the resulting mixture was adjusted pH to about 6 with aqueous hydrochloric acid solution (1 M). The mixture was extracted with EtOAc (15 mL×3). The combined organic layers were washed with saturated brine (40 mL), dried over anhydrous $Na_2SO_4$, filtered, and the filtrate was concentrated in vacuo. The residue was purified by silica gel column chromatograph (DCM/MeOH (v/v)=10/1-5/1) to give the title compound as a white solid (33 mg, 80%).

MS (ESI, pos. ion) m/z: 436.10 [M+H]$^+$;

HRMS (ESI, pos. ion) m/z: 436.1910[M+H]$^+$, ($C_{22}H_{23}FN_7O_2$) [M+H]$^+$ theoretical value: 436.1897;

$^1$H NMR (600 MHz, DMSO-d$_6$) δ (ppm): $^1$H NMR (600 MHz, DMSO-d$_6$) δ (ppm): 12.27 (s, 1H), 8.68 (d, J=9.3 Hz, 1H), 8.34 (s, 1H), 8.28 (s, 1H), 8.10 (s, 1H), 7.99 (d, J=6.4 Hz, 1H), 4.83 (s, 1H), 3.96 (s, 3H), 2.67 (s, 1H), 2.03 (s, 2H), 1.84-1.41 (m, 9H).

Example 32: (+/−)-trans-3-((2-(5-fluoro-1H-pyrrolo[2,3-b]pyridin-3-yl)-7-nonyl-7H-pyrrolo[2,3-d]pyrimidin-4-yl)amino)bicyclo[2.2.2]octane-2-carboxylic Acid

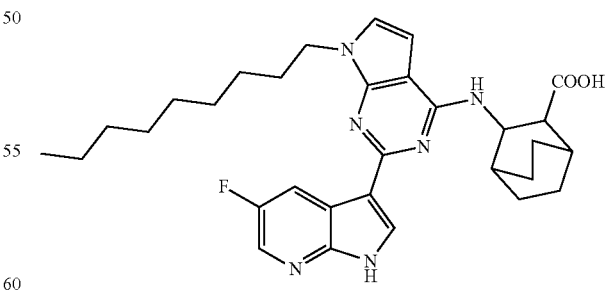

Step 1: 2,4-dichloro-7-nonyl-7H-pyrrolo[2,3-d]pyrimidine

To a solution of 2,4-dichloro-7H-pyrrolo[2,3-d]pyrimidine (500 mg, 2.66 mmol) in DMF (5 mL) was added NaH (130 mg, 3.19 mmol) at 0° C., and the mixture was stirred at this temperature for 30 min. Then bromononane (1.03 mg, 5.32 mmol) was added to the mixture, and the resulting mixture was stirred at rt overnight. To the reaction mixture was added water (50 mL), and the resulting mixture was partitioned. The aqueous layer was extracted with ethyl acetate (50 mL×2). The combined organic layers were washed with saturated brine (80 mL), dried over anhydrous sodium sulfate and filtered. The filtrate was concentrated in vacuo and the residue was purified by silica gel column chromatography (PE/EtOAc (v/v)=10/1) to give the title compound as a yellow solid (821 mg, 98%).

MS (ESI, pos. ion) m/z: 315.10 [M+H]$^+$;

$^1$H NMR (400 MHz, CDCl$_3$) δ (ppm): 7.24 (d, J=3.6 Hz, 1H), 6.59 (d, J=3.5 Hz, 1H), 4.23 (t, J=7.3 Hz, 2H), 1.84 (dt, J=14.1, 7.2 Hz, 2H), 1.31-1.23 (m, 12H), 0.87 (t, J=7.0 Hz, 3H).

Step 2: (+/−)-trans-methyl 3-((2-chloro-7-nonyl-7H-pyrrolo[2,3-d]pyrimidin-4-yl)amino) bicyclo[2.2.2]octane-2-carboxylate To a solution of (+/−)-trans-methyl 3-aminobicyclo[2.2.2]octane-2-carboxylate (572 mg, 2.87 mmol) and 2,4-dichloro-7-nonyl-7H-pyrrolo[2,3-d]pyrimidine (821 mg, 2.61 mmol) in THF (5 mL) was added DIPEA (4.6 mL, 26.13 mmol). Then the mixture was stirred at room temperature overnight. The reaction was quenched with water (50 mL), and the resulting mixture was partitioned. The aqueous layer was extracted with ethyl acetate (50 mL×2). The combined organic layers were washed with saturated brine (80 mL), dried over anhydrous sodium sulfate and filtered. The filtrate was concentrated in vacuo and the residue was purified by silica gel column chromatography (PE/EtOAc (v/v)=10/1) to give the title compound as a yellow solid (174 mg, 14%).

MS (ESI, pos.ion) m/z: 462.15 [M+H]$^+$.

Step 3: (+/−)-trans-methyl 3-((2-(5-fluoro-1-tosyl-1H-pyrrolo[2,3-b]pyridin-3-yl)-7-nonyl-7H-pyrrolo[2,3-d]pyrimidin-4-yl)amino)bicyclo[2.2.2]octane-2-carboxylate To a mixture of 5-fluoro-3-(4,4,5,5-tetramethyl-1,3,2-dioxaborolan-2-yl)-1-tosyl-1H-pyrrolo[2,3-b]pyridine (172 mg, 0.42 mmol), K$_2$CO$_3$ (156 mg, 1.13 mmol), Pd(dppf)Cl$_2$ (28 mg, 0.04 mmol) and (+/−)-trans-methyl 3-((2-chloro-7-nonyl-7H-pyrrolo[2,3-d]pyrimidin-4-yl)amino)bicyclo[2.2.2]octane-2-carboxylate (174 mg, 0.38 mmol) in 1,4-dioxane (8.0 mL) was added H$_2$O (1 mL) under a nitrogen atmosphere. The gas in the mixture was removed by bubbling with nitrogen for 10 min and then the mixture was stirred at 110° C. for 1.5 h with microwave heating. The reaction mixture was filtered through a celite pad to remove solid impurities. Then the filtrate was concentrated in vacuo to remove the solvent. The residue was purified by silica gel chromatograph (PE/EtOAc (v/v)=10/1-5/1) to give the title compound as a white solid (216 mg, 80%).

Step 4: (+/−)-trans-3-((2-(5-fluoro-1H-pyrrolo[2,3-b]pyridin-3-yl)-7-nonyl-7H-pyrrolo[2,3-d]pyrimidin-4-yl)amino)bicyclo[2.2.2]octane-2-carboxylic Acid A solution of NaOH (79 mg, 1.58 mmol) in water (1 mL) was added to a solution of (+/−)-trans-methyl 3-((2-(5-fluoro-1-tosyl-1H-pyrrolo[2,3-b]pyridin-3-yl)-7-nonyl-7H-pyrrolo [2,3-d]pyrimidin-4-yl)amino)bicyclo[2.2.2]octane-2-carboxylate (113 mg, 0.16 mmol) in THF/MeOH (v/v=5 mL/5 mL). The reaction mixture was stirred at rt overnight. Water (10 mL) was added to the reaction mixture, and the resulting mixture was adjusted pH to about 6 with aqueous hydrochloric acid solution (1 M). The mixture was extracted with EtOAc (15 mL×3). The combined organic layers were washed with saturated brine (40 mL), dried over anhydrous Na$_2$SO$_4$, filtered, and the filtrate was concentrated in vacuo. The residue was purified by silica gel chromatograph (DCM/MeOH (v/v)=10/1-5/1) to give the title compound as a white solid (31 mg, 36%).

MS (ESI, pos. ion) m/z: 547.70 [M+H]$^+$;

HRMS (ESI, pos. ion) m/z: 421.1800[M+H]$^+$, (C$_{31}$H$_{40}$FN$_6$O$_2$) [M+H]$^+$ theoretical value: 421.1788;

$^1$H NMR (400 MHz, DMSO-d$_6$) δ (ppm): 12.06 (s, 1H), 8.70 (dd, J=9.8, 2.3 Hz, 1H), 8.25 (s, 1H), 8.21 (d, J=2.5 Hz, 1H), 7.70-7.63 (m, 1H), 7.21 (d, J=6.4 Hz, 1H), 7.06 (d, J=3.2 Hz, 1H), 6.62 (s, 1H), 4.78 (s, 1H), 4.16 (t, J=6.6 Hz, 2H), 4.13-4.09 (m, 1H), 2.71 (d, J=6.7 Hz, 1H), 2.02 (d, J=11.4 Hz, 2H), 1.89-1.71 (m, 5H), 1.58 (m, 4H), 1.37-1.17 (m, 12H), 0.74 (t, J=6.6 Hz, 3H).

Example 33: (+/−)-trans-3-((7-benzyl-2-(5-fluoro-1H-pyrrolo[2,3-b]pyridin-3-yl)-7H-pyrrolo[2,3-d]pyrimidin-4-yl)amino)bicyclo[2.2.2]octane-2-carboxylic Acid

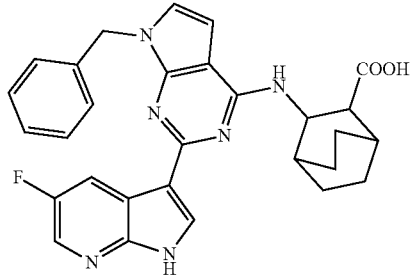 [SMILES: O=C(O)C1C2CCC(CC2)C1Nc1nc(-c2c[nH]c3ncc(F)cc23)nc2c1ccn2Cc1ccccc1]

Step 1: 7-benzyl-2,4-dichloro-7H-pyrrolo[2,3-d]pyrimidine

To a solution of 2,4-dichloro-7H-pyrrolo[2,3-d]pyrimidine (500 mg, 2.66 mmol) in DMF (5 mL) was added NaH (130 mg, 3.19 mmol, 60%) at 0° C., and the mixture was stirred at this temperature for 30 min. Then benzyl bromide (904 mg, 5.32 mmol) was added to the mixture, and the resulting mixture was stirred at rt overnight. To the reaction mixture was added water (50 mL), and the resulting mixture was extracted with ethyl acetate (50 mL×2). The combined organic layers were washed with saturated brine (80 mL), dried over anhydrous sodium sulfate and filtered. The filtrate was concentrated in vacuo to remove the solvent and the residue was purified by silica gel column chromatography (PE/EtOAc (v/v)=10/1) to give the title compound as a yellow solid (683 mg, 92%).

MS (ESI, pos. ion) m/z: 279.30 [M+H]$^+$;

$^1$H NMR (400 MHz, CDCl$_3$) δ (ppm): 7.39-7.32 (m, 3H), 7.24 (d, J=7.6 Hz, 2H), 7.19 (d, J=3.6 Hz, 1H), 6.62 (d, J=3.6 Hz, 1H), 5.43 (s, 2H).

Step 2: (+/−)-trans-methyl 3-((7-benzyl-2-chloro-7H-pyrrolo[2,3-d]pyrimidin-4-yl)amino) bicyclo[2.2.2]octane-2-carboxylate To a solution of (+/−)-trans-methyl 3-aminobicyclo[2.2.2]octane-2-carboxylate (236 mg, 1.19 mmol) and 2,4-dichloro-7-nonyl-7H-pyrrolo[2,3-d]pyrimidine (300 mg, 1.08 mmol) in THF (5 mL) was added K₂CO₃ (301 mg, 2.16 mmol). Then the mixture was stirred at room temperature overnight. The reaction mixture was quenched with water (50 mL), and the resulting mixture was partitioned. The aqueous layer was extracted with EtOAc (50 mL×2). The combined organic layers were washed with saturated brine (80 mL), dried over anhydrous Na₂SO₄ and filtered. The filtrate was concentrated in vacuo and the residue was purified by silica gel column chromatography (PE/EtOAc (v/v)=10/1) to give the title compound as a white solid (250 mg, 55%).

MS (ESI, pos.ion) m/z: 425.15 [M+H]⁺;

¹H NMR (400 MHz, CDCl₃) δ (ppm): 7.39-7.36 (m, 1H), 7.31 (dd, J=11.7, 4.5 Hz, 3H), 7.20 (d, J=7.3 Hz, 2H), 6.90-6.79 (m, 1H), 6.42 (s, 1H), 5.33 (d, J=8.4 Hz, 2H), 4.60 (d, J=6.0 Hz, 1H), 3.76 (s, 3H), 2.43 (d, J=5.2 Hz, 1H), 2.06 (s, 1H), 2.02 (s, 1H), 1.94 (d, J=2.3 Hz, 1H), 1.71 (m, 8H).

Step 3: (+/−)-trans-methyl 3-((7-benzyl-2-(5-fluoro-1-tosyl-1H-pyrrolo[2,3-b]pyridin-3-yl)-7H-pyrrolo[2,3-d]pyrimidin-4-yl)amino)bicyclo[2.2.2]octane-2-carboxylate To 1,4-dioxane (8 mL) were added 5-fluoro-3-(4,4,5,5-tetramethyl-1,3,2-dioxaborolan-2-yl)-1-tosyl-1H-pyrrolo[2,3-b]pyridine (172 mg, 0.41 mmol), K₂CO₃ (156 mg, 1.13 mmol), PdCl₂(dppf) (28 mg, 0.04 mmol) and (+/−)-trans-methyl 3-((7-benzyl-2-chloro-7H-pyrrolo[2,3-d]pyrimidin-4-yl)amino)bicyclo[2.2.2]octane-2-carboxylate (174 mg, 0.38 mmol). Then H₂O (1 mL) was added to the mixture, and the air in the mixture was removed by bubbling with nitrogen for 10 min. The mixture was stirred for 1.5 h at 110° C. with microwave heating. The mixture was filtered through a celite pad to remove the solid impurities The filtrate was concentrated in vacuo, and the residue was purified by silica gel column chromatography (PE/EtOAc (v/v)=10/1-5/1) to give the title compound as a white solid (89 mg, 32%).

Step 4: (+/−)-trans-3-((7-benzyl-2-(5-fluoro-1H-pyrrolo[2,3-b]pyridin-3-yl)-7H-pyrrolo[2,3-d]pyrimidin-4-yl)amino)bicyclo[2.2.2]octane-2-carboxylic Acid A solution of NaOH (56 mg, 1.31 mmol) in water (1 mL) was added to a solution of (+/−)-trans-methyl 3-((7-benzyl-2-(5-fluoro-1-tosyl-1H-pyrrolo[2,3-b]pyridin-3-yl)-7H-pyrrolo [2,3-d]pyrimidin-4-yl)amino)bicyclo[2.2.2]octane-2-carboxylate (89 mg, 0.13 mmol) in THF/MeOH (v/v=5 mL/5 mL). The reaction mixture was stirred at r.t. overnight. Water (10 mL) was added to the reaction mixture, and the resulting mixture was adjusted pH to about 6 with aqueous HCl solution (1 M). The mixture was extracted with EtOAc (15 mL×3). The combined organic layers were washed with saturated brine (40 mL), dried over anhydrous Na₂SO₄, filtered, and the filtrate was concentrated in vacuo. The residue was purified by silica gel column chromatograph (DCM/MeOH (v/v)=10/1-5/1) to give the title compound as a white solid (20 mg, 30%).

MS (ESI, pos. ion) m/z: 511.60 [M+H]⁺;
HRMS (ESI, pos. ion) m/z: 511.2257[M+H]⁺, (C₂₉H₂₈FN₆O₂) [M+H]⁺ theoretical value: 511.2258;

¹H NMR (600 MHz, DMSO-d₆) δ (ppm): 12.09 (s, 1H), 8.65 (d, J=8.2 Hz, 1H), 8.28-8.21 (m, 2H), 7.72-7.66 (m, 4H), 7.31 (s, 2H), 7.17 (d, J=3.1 Hz, 1H), 6.67 (s, 1H), 5.43 (s, 2H), 4.79 (s, 1H), 2.72 (d, J=6.6 Hz, 1H), 2.02 (s, 2H), 1.84-1.47 (m, 9H).

Example 34: (+/−)-trans-3-((2-(5-fluoro-1H-pyrrolo[2,3-b]pyridin-3-yl)-7-(2-hydroxyethyl)-7H-pyrrolo[2,3-d]pyrimidin-4-yl)amino)bicyclo[2.2.2]octane-2-carboxylic Acid

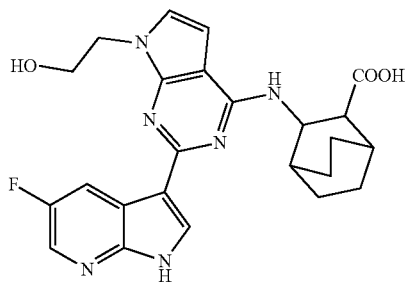 [SMILES: O=C(O)C1C2CCC(CC2)C1Nc1nc(-c2c[nH]c3ncc(F)cc23)nc2c1ccn2CCO]

Step 1: 7-(2-((tert-butyldimethylsilyl)oxy)ethyl)-2,4-dichloro-7H-pyrrolo[2,3-d]pyrimidine The solution of 2,4-dichloro-7H-pyrrolo[2,3-d]pyrimidine (500 mg, 2.66 mmol) in DMF (5 mL) was stirred at 0° C. for 5 min, then to the solution was added sodium hydride (130 mg, 3.19 mmol, 60%). The resulting mixture was stirred for 15 min at 0° C., then (2-bromoethoxy)(tert-butyl)dimethylsilane (904 mg, 5.32 mmol) was added. The mixture was warmed to rt and stirred overnight. To the reaction mixture was added water (100 mL) to quench the reaction, and the resulting mixture was extracted with ethyl acetate (50 mL×3). The combined organic layers were washed with saturated brine (80 mL), dried over anhydrous sodium sulfate and filtered. The filtrate was concentrated in vacuo and the residue was purified by silica gel column chromatography (PE/EtOAc (v/v)=10/1) to give the title compound as a white solid (516 mg, 56%).

MS (ESI, pos. ion) m/z: 346.95 [M+H]⁺;

¹H NMR (400 MHz, CDCl₃) δ (ppm): 7.35 (d, J=3.6 Hz, 1H), 6.57 (d, J=3.3 Hz, 1H), 4.36 (t, J=4.9 Hz, 2H), 3.92 (t, J=4.9 Hz, 2H), 0.83 (s, 9H), 0.08 (s, 6H).

Step 2: (+/−)-trans-methyl 3-((7-(2-((tert-butyldimethylsilyl)oxy)ethyl)-2-chloro-7H-pyrrolo [2,3-d]pyrimidin-4-yl)amino)bicyclo[2.2.2]octane-2-carboxylate A suspension of 7-(2-((tert-butyldimethylsilyl)oxy)ethyl)-2,4-dichloro-7H-pyrrolo[2,3-d]pyrimidine (516 mg, 1.49 mmol), (+/−)-trans-methyl 3-aminobicyclo[2.2.2]octane-2-carboxylate (330 mg, 1.64 mmol) and K₂CO₃ (411 mg, 2.98 mmol) in DMF (10 mL) was stirred at rt overnight, then the reaction was quenched with H₂O (100 mL). The mixture was extracted with ethyl acetate (50 mL×3), and the combined organic layers were washed with saturated brine (80 mL×3), dried over anhydrous sodium sulfate and filtered. The filtrate was concentrated in vacuo and the residue was purified by silica gel column chromatography (PE/EtOAc (v/v)=3/1) to give the title compound as a white solid (138 mg, 19%).

MS (ESI, pos. ion) m/z: 494.10 [M+H]⁺.

Step 3: (+/−)-trans-methyl 3-((7-(2-((tert-butyldim-ethylsilyl)oxy)ethyl)-2-(5-fluoro-1-tosyl-1H-pyrrolo[2,3-b]pyridin-3-yl)-7H-pyrrolo[2,3-d]pyrimidin-4-yl)amino)bicyclo[2.2.2]octane-2-carboxylate To 1,4-dioxane (8 mL) were added 5-fluoro-3-(4,4,5,5-tetramethyl-1,3,2-dioxaborolan-2-yl)-1-tosyl-1H-pyrrolo[2,3-b]pyridine (129 mg, 0.31 mmol), $K_2CO_3$ (120 mg, 0.84 mmol), $PdCl_2$(dppf) (22 mg, 0.03 mmol) and (+/−)-trans-methyl 3-((7-(2-((tert-butyldimethylsilyl) oxy)ethyl)-2-chloro-7H-pyrrolo[2,3-d]pyrimidin-4-yl)amino)bicyclo[2.2.2]octane-2-carboxylate (128 mg, 0.38 mmol). Then $H_2O$ (1 mL) was added to the mixture, and the air in the mixture was removed by bubbling with nitrogen for 10 min. The mixture was stirred for 1.5 h at 110° C. with microwave heating. The mixture was filtered through a celite pad to remove solid impurities. The filtrate was concentrated in vacuo, and the residue was purified by silica gel column chromatography (PE/EtOAc (v/v)=10/1-5/1) to give the title compound as a white solid (188 mg, 90%).

MS (ESI, pos. ion) m/z: 748.15 [M+H]$^+$;
$^1$H NMR (400 MHz, CDCl$_3$) δ (ppm): 8.75-8.69 (m, 1H), 8.67 (s, 1H), 8.32 (d, J=1.7 Hz, 1H), 8.14 (d, J=8.3 Hz, 2H), 7.30 (s, 2H), 7.08 (d, J=3.4 Hz, 1H), 6.36 (d, J=3.3 Hz, 1H), 5.10 (d, J=6.9 Hz, 1H), 4.90 (s, 1H), 4.38 (t, J=5.4 Hz, 2H), 3.99 (t, J=5.4 Hz, 2H), 3.73 (s, 3H), 2.48 (d, J=5.5 Hz, 1H), 2.39 (s, 3H), 2.08 (s, 2H), 1.98-1.70 (m, 6H), 1.64 (s, 6H), 1.53 (d, J=14.8 Hz, 2H), 0.88 (s, 9H).

Step 4: (+/−)-trans-methyl 3-((2-(5-fluoro-1H-pyrrolo[2,3-b]pyridin-3-yl)-7-(2-hydroxy ethyl)-7H-pyrrolo[2,3-d]pyrimidin-4-yl)amino)bicyclo[2.2.2]octane-2-carboxylate To a solution of hydrochloric acid in 1,4-dioxane (0.26 mL, 5 mol/L) was added (+/−)-trans-methyl 3-((7-(2-((tert-butyldimethylsilyl)oxy)ethyl)-2-(5-fluoro-1-tosyl-1H-pyrrolo [2,3-b]pyridin-3-yl)-7H-pyrrolo[2,3-d]pyrimidin-4-yl)amino)bicyclo[2.2.2]octane-2-carboxylate (188 mg, 0.25 mmol), and the mixture was stirred at rt overnight. The reaction mixture was concentrated in vacuo and the residue was purified by silica gel column chromatography (DCM/MeOH (v/v)=10/1-5/1) to give the title compound as a light yellow solid (142 mg, 89%).

MS (ESI, pos. ion) m/z: 633.20 [M+H]$^+$.

Step 5: (+/−)-trans-3-((2-(5-fluoro-1H-pyrrolo[2,3-b]pyridin-3-yl)-7-(2-hydroxyethyl)-7H-pyrrolo[2,3-d]pyrimidin-4-yl)amino)bicyclo[2.2.2]octane-2-carboxylic Acid To a solution of (+/−)-trans-methyl 3-((2-(5-fluoro-1H-pyrrolo[2,3-b]pyridin-3-yl)-7-(2-hydroxyethyl)-7H-pyrrolo[2,3-d]pyrimidin-4-yl)amino)bicyclo[2.2.2]octane-2-carboxylate (188 mg, 0.25 mmol) in THF/MeOH (v/v=5 mL/5 mL) was added a solution of sodium hydroxide (93 mg, 2.24 mmol) in water (1 mL). The mixture was stirred at rt overnight. To the reaction mixture was added water (10 mL), and the resulting mixture was acidified with hydrochloric acid (1 M) to pH about 6. The mixture was extracted with ethyl acetate (15 mL×3), and the combined organic layers were washed with saturated brine (40 mL), dried over anhydrous sodium sulfate, then filtered. The filtrate was concentrated in vacuo to remove the solvent and the residue was purified by silica gel column chromatography (DCM/MeOH (v/v)=10/1-5/1) to give the title compound as a white solid (66 mg, 63%).

MS (ESI, pos. ion) m/z: 465.10 [M+H]$^+$;
HRMS (ESI, pos. ion) m/z: 465.2042[M+H]$^+$, ($C_{24}H_{26}FN_6O_3$) [M+H]$^+$ theoretical value: 465.2050;
$^1$H NMR (600 MHz, DMSO-d$_6$) δ (ppm): 12.08 (s, 1H), 8.69 (dd, J=9.7, 2.3 Hz, 1H), 8.26 (d, J=1.0 Hz, 1H), 8.21 (d, J=2.6 Hz, 1H), 7.23 (d, J=6.7 Hz, 1H), 7.12 (d, J=3.3 Hz, 1H), 6.61 (d, J=2.4 Hz, 1H), 5.00 (s, 1H), 4.79 (s, 1H), 4.26 (dd, J=10.3, 5.6 Hz, 2H), 3.79 (t, J=5.7 Hz, 2H), 2.72 (d, J=6.7 Hz, 1H), 2.02 (s, 2H), 1.87-1.71 (m, 3H), 1.51 (m, 5H), 1.25-1.17 (m, 1H);
$^{13}$C NMR (101 MHz, DMSO-d$_6$) δ (ppm): 176.11, 157.13, 156.02, 155.79, 154.76, 150.37, 146.42, 131.53, 131.25, 130.00, 124.59, 119.03, 118.96, 116.00, 115.79, 98.73, 60.74, 50.60, 49.08, 47.01, 28.95, 26.07, 24.24, 21.57, 19.51.

Example 35: (+/−)-cis-N-(3-((2-(5-fluoro-1H-pyrrolo[2,3-b]pyridin-3-yl)-7-methyl-7H-pyrrolo[2,3-d]pyrimidin-4-yl)amino)cyclohexyl)-1H-1,2,3-triazole-4-carboxamide

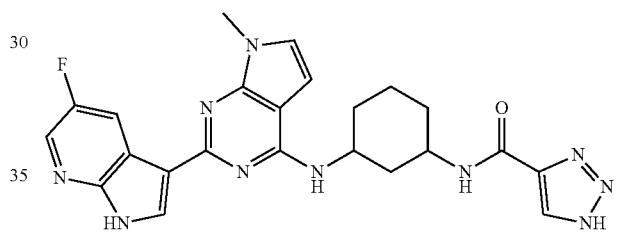

Step 1: (+/−)-cis-tert-butyl (3-((2-chloro-7-methyl-7H-pyrrolo[2,3-d]pyrimidin-4-yl)amino) cyclohexyl)carbamate To a solution of 2,4-dichloro-7-methyl-7H-pyrrolo[2,3-d]pyrimidine (362 mg, 1.80 mmol) and (+/−)-cis-N-tert-butoxycarbonyl-1,3-cyclohexanediamine (350 mg, 1.63 mmol) in N,N-dimethylformamide (3 mL) was added potassium carbonate (677 mg, 4.90 mmol). The mixture was stirred at rt overnight. The reaction mixture was diluted with $H_2O$ (50 mL) and the resulting mixture was extracted with EtOAc (40 mL×3). The combined organic layers were washed with saturated brine (100 mL), dried over anhydrous $Na_2SO_4$, and filtered. The filtrate was concentrated in vacuo and the residue was purified by silica gel column chromatography (n-hexane/EtOAc (v/v)=5/1) to give the title compound as a white solid (436 mg, 70%).

MS (ESI, pos.ion) m/z: 378.1 [M+H]$^+$.

Step 2: (+/−)-cis-M-(2-chloro-7-methyl-7H-pyrrolo[2,3-d]pyrimidin-4-yl)cyclohexane-1,3-diamine To a solution of hydrochloric acid in 1,4-dioxane (0.78 mL, 3.9 mmol, 5 mol/L) was added (+/−)-cis-tert-butyl (3-((2-chloro-7-methyl-7H-pyrrolo[2,3-d]pyrimidin-4-yl) amino) cyclohexyl)carbamate (150 mg, 0.39 mmol), and the mixture was stirred at rt overnight. The reaction mixture was concentrated in vacuo to remove the solvent and to the residue was added an appropriate amount of water. The resulting mixture was adjusted with saturated aqueous sodium carbonate to pH 9. The mixture was extracted with ethyl acetate (20 mL×3), and the combined organic layers were washed with saturated brine (50 mL), dried over anhydrous sodium sulfate and concentrated in vacuo to dry and give the title compound as a colorless solid (110 mg, 100%).

MS (ESI, pos.ion) m/z: 280.1 [M+H]$^+$.

Step 3: (+/−)-cis-N-(3-((2-chloro-7-methyl-7H-pyrrolo[2,3-d]pyrimidin-4-yl)amino)cyclohexyl)-1H-1,2,3-triazole-4-carboxamide To a solution of (+/−)-cis-N$^1$-(2-chloro-7-methyl-7H-pyrrolo[2,3-d]pyrimidin-4-yl) cyclohexane-1,3-diamine (60 mg, 0.21 mmol) in a mixed solvent of tetrahydrofuran (4 mL) and dimethyl sulfoxide (1 mL) was added N,N-diisopropylethylamine (0.11 mL, 0.64 mmol) and 1H-1,2,3-triazole-4-carboxylic acid (48 mg, 0.43 mmol). The mixture was stirred at rt for 10 minutes, and then HATU (163 mg, 0.43 mmol) was added. The resulting mixture was stirred at rt for 3 h. To the reaction mixture was added water (10 mL), and the resulting mixture was extracted with ethyl acetate (10 mL×3). The combined organic layers were washed with saturated brine (30 mL), dried over anhydrous sodium sulfate and filtered. The filtrate was concentrated in vacuo to dry and give the title compound as a colorless solid (83 mg, 100%).

MS (ESI, pos.ion) m/z: 375.2 [M+H]$^+$.

Step 4: (+/−)-cis-N-(3-((2-(5-fluoro-1-tosyl-1H-pyrrolo[2,3-b]pyridin-3-yl)-7-methyl-7H-pyrrolo[2,3-d]pyrimidin-4-yl)amino)cyclohexyl)-1H-1,2,3-triazole-4-carboxamide To a microwave tube were added 5-fluoro-3-(4,4,5,5-tetramethyl-1,3,2-dioxaborolan-2-yl)-1-tosyl-1H-pyrrolo[2,3-b]pyridine (213 mg, 0.26 mmol, 50%), (+/−)-cis-N-(3-((2-chloro-7-methyl-7H-pyrrolo[2,3-d]pyrimidin-4-yl)amino)cyclohexyl)-1H-1,2,3-triazole-4-carboxamide (80 mg, 0.21 mmol), potassium carbonate (88 mg, 0.64 mmol), Pd(dppf)Cl$_2$ (34 mg, 0.04 mmol), 1,4-dioxane (3 mL) and water (0.2 mL). The air in the mixture was removed by bubbling with nitrogen for 10 min, then the mixture in the microwave tube was stirred at 120° C. with microwave heating for 4 hours. The mixture was filtered through a celite pad, and the filter cake was washed with ethyl acetate (50 mL). The filtrate was washed with saturated brine (50 mL), dried over anhydrous sodium sulfate and filtered. The filtrate was concentrated in vacuo and the residue was purified by silica gel column chromatography (DCM/MeOH (v/v)=10/1) to give the title compound as a brown solid (37 mg, 28%).

MS (ESI, pos.ion) m/z: 629.2[M+H]$^+$.

Step 5: (+/−)-cis-N-(3-((2-(5-fluoro-1H-pyrrolo[2,3-b]pyridin-3-yl)-7-methyl-7H-pyrrolo[2,3-d]pyrimidin-4-yl)amino)cyclohexyl)-1H-1,2,3-triazole-4-carboxamide To a solution of (+/−)-cis-N-(3-((2-(5-fluoro-1-tosyl-1H-pyrrolo[2,3-b]pyridin-3-yl)-7-methyl-7H-pyrrolo[2,3-d]pyrimidin-4-yl)amino)cyclohexyl)-1H-1,2,3-triazole-4-carboxamide (37 mg, 0.06 mmol) in methanol (1 mL) was added a solution of sodium methoxide in methanol (5 M, 0.12 mL, 0.6 mmol). The mixture was stirred at 30° C. overnight. To the reaction mixture was added water (10 mL), and the resulting mixture was extracted with ethyl acetate (20 mL×3). The combined organic layers were washed with saturated brine (50 mL), dried over anhydrous sodium sulfate, then filtered. The filtrate was concentrated in vacuo and the residue was purified by silica gel column chromatography (DCM/MeOH (v/v)=10/1) to give the title compound as a white solid (9 mg, 32%).

MS (ESI, pos.ion) m/z: 475.3 [M+H]$^+$;
HRMS (ESI, pos. ion) m/z: 475.2100[M+H]$^+$, (C$_{23}$H$_{24}$FN$_{10}$O) [M+H]$^+$ theoretical value: 475.2119;
$^1$H NMR (400 MHz, DMSO-d$_6$) δ (ppm): 12.13 (s, 1H), 8.66 (d, J=8.5 Hz, 1H), 8.43 (s, 1H), 8.27 (s, 1H), 7.34 (s, 1H), 7.06 (s, 1H), 6.61 (s, 1H), 4.31 (s, 1H), 4.05 (s, 1H), 3.69 (s, 3H), 2.25 (s, 1H), 2.10 (s, 1H), 1.87 (s, 2H), 1.61-1.33 (m, 4H).

Example 36: (+/−)-cis-2-amino-N-(3-((2-(5-fluoro-1H-pyrrolo[2,3-b]pyridin-3-yl)-7-methyl-7H-pyrrolo[2,3-d]pyrimidin-4-yl)amino)cyclohexyl)thiazole-4-carboxamide

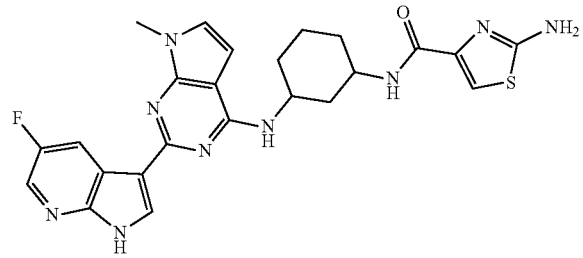 [SMILES: Cn1ccc2c(NC3CCCC(NC(=O)c4csc(N)n4)C3)nc(-c3c[nH]c4ncc(F)cc34)nc21]

Step 1: (+/−)-cis-2-amino-N-(3-((2-chloro-7-methyl-7H-pyrrolo[2,3-d]pyrimidin-4-yl)amino) cyclohexyl)thiazole-4-carboxamide To a solution of (+/−)-cis-N$^1$-(2-chloro-7-methyl-7H-pyrrolo[2,3-d]pyrimidin-4-yl)cyclohexane-1,3-diamine (62 mg, 0.22 mmol) in a mixed solvent of tetrahydrofuran (4 mL) and dimethyl sulfoxide (1 mL) was added N,N-diisopropylethylamine (0.11 mL, 0.66 mmol) and 2-aminothiazole-4-carboxylic acid (63 mg, 0.44 mmol). The mixture was stirred at rt for 10 minutes, and then HATU (168 mg, 0.44 mmol) was added. The resulting mixture was stirred at rt for 3 h. To the reaction mixture was added water (10 mL), and the resulting mixture was extracted with ethyl acetate (10 mL×3). The combined organic layers were washed with saturated brine (30 mL), dried over anhydrous sodium sulfate and filtered. The filtrate was concentrated in vacuo to dryness to give the title compound as a colorless solid (89.9 mg, 100%).

MS (ESI, pos.ion) m/z: 406.5[M+H]$^+$.

Step 2: (+/−)-cis-2-amino-N-(3-((2-(5-fluoro-1-tosyl-1H-pyrrolo[2,3-b]pyridin-3-yl)-7-methyl-7H-pyrrolo[2,3-d]pyrimidin-4-yl)amino)cyclohexyl)thiazole-4-carboxamide To a microwave tube were added 5-fluoro-3-(4,4,5,5-tetramethyl-1,3,2-dioxaborolan-2-yl)-1-tosyl-1H-pyrrolo[2,3-b]pyridine (221 mg, 0.27 mmol, 50%), (+/−)-cis-2-amino-N-(3-((2-chloro-7-methyl-7H-pyrrolo[2,3-d]pyrimidin-4-yl)amino)cyclohexyl)thiazole-4-carboxamide (90 mg, 0.22 mmol), potassium carbonate (91 mg, 0.67 mmol), Pd(dppf)

Cl$_2$ (36 mg, 0.04 mmol), 1,4-dioxane (3 mL) and water (0.2 mL). The air in the mixture was removed by bubbling with nitrogen for 10 min, then the mixture in the microwave tube was stirred at 120° C. with microwave heating for 4 hours. The mixture was filtered through a celite pad, and the filter cake was washed with ethyl acetate (50 mL). The filtrate was washed with saturated brine (50 mL), dried over anhydrous sodium sulfate and filtered. The filtrate was concentrated in vacuo to dry and the residue was purified by silica gel column chromatography (DCM/MeOH (v/v)=10/1) to give the title compound as a brown solid (56 mg, 38%).

MS (ESI, pos.ion) m/z: 629.2[M+H]$^+$;

$^1$H NMR (400 MHz, MeOD) δ (ppm): 8.80 (d, J=8.8 Hz, 1H), 8.58 (s, 1H), 8.29 (s, 1H), 8.08 (d, J=8.5 Hz, 2H), 7.38 (d, J=8.3 Hz, 2H), 7.25 (s, 1H), 7.04 (d, J=3.1 Hz, 1H), 6.58 (d, J=3.4 Hz, 1H), 3.86 (s, 3H), 2.83 (s, 3H), 2.39 (s, 2H), 1.31 (s, 8H).

Step 3: (+/−)-cis-2-amino-N-(3-((2-(5-fluoro-1H-pyrrolo[2,3-b]pyridin-3-yl)-7-methyl-7H-pyrrolo[2,3-d]pyrimidin-4-yl)amino)cyclohexyl)thiazole-4-carboxamide To a solution of (+/−)-cis-2-amino-N-(3-((2-(5-fluoro-1-tosyl-1H-pyrrolo[2,3-b]pyridine-3-yl)-7-methyl-7H-pyrrolo[2,3-d]pyrimidin-4-yl)amino)cyclohexyl)thiazole-4-carboxamide (88 mg, 0.08 mmol) in MeOH (1 mL) was added a solution of sodium methoxide in methanol (5 M, 0.16 mL, 0.8 mmol). The mixture was stirred at rt overnight, then concentrated in vacuo, and the residue was diluted with water (10 mL). The resulting mixture was extracted with ethyl acetate (20 mL×3). The combined organic layers were washed with saturated brine (50 mL), dried over anhydrous sodium sulfate, filtered, and the filtrate was concentrated in vacuo to remove the solvent. The residue was purified by silica gel column chromatography (DCM/MeOH (v/v)=10/1) to give the title compound as a white solid (26 mg, 62%).

MS (ESI, pos.ion) m/z: 506.2 [M+H]$^+$;

HRMS (ESI, pos. ion) m/z: 506.1877[M+H]$^+$, (C$_{24}$H$_{25}$FN$_9$OS) [M+H]$^+$ theoretical value: 506.1887;

$^1$H NMR (400 MHz, DMSO-d$_6$) δ (ppm): 12.13 (s, 1H), 8.66 (d, J=8.5 Hz, 1H), 8.43 (s, 1H), 8.27 (s, 1H), 7.34 (s, 1H), 7.06 (s, 1H), 6.61 (s, 1H), 4.31 (s, 1H), 4.05 (s, 1H), 3.69 (s, 3H), 2.25 (s, 1H), 2.10 (s, 1H), 1.87 (s, 2H), 1.61-1.33 (m, 4H);

$^{13}$C NMR (151 MHz, DMSO-d$_6$) δ (ppm): 168.62, 160.44, 156.72, 156.03, 155.54, 155.13, 146.44, 146.19, 131.47, 131.27, 130.19, 124.68, 118.97, 116.03, 115.88, 111.66, 99.02, 47.64, 32.27, 32.15, 31.09, 29.44, 23.52, 14.42.

Example 37: (+/−)-cis-N-(3-((2-(5-fluoro-1H-pyrrolo[2,3-b]pyridin-3-yl)-7-methyl-7H-pyrrolo[2,3-d]pyrimidin-4-yl)amino)cyclohexyl)-1-methyl-1H-imidazole-4-carboxamide

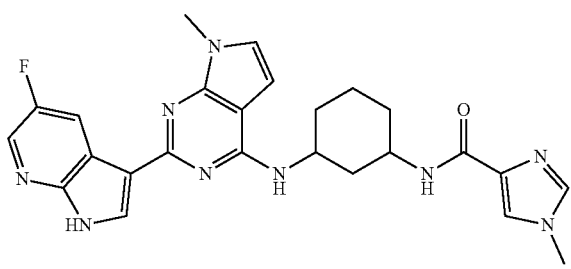 [SMILES: Cn1cnc(C(=O)NC2CCCC(Nc3nc(-c4c[nH]c5ncc(F)cc45)nc4c3ccn4C)C2)c1]

Step 1: (+/−)-cis-N-(3-((2-chloro-7-methyl-7H-pyrrolo[2,3-d]pyrimidin-4-yl)amino)cyclohexyl)-1-methyl-1H-imidazole-4-carboxamide To a solution of (+/−)-cis-M-(2-chloro-7-methyl-7H-pyrrolo[2,3-d]pyrimidin-4-yl)cyclohexane-1,3-diamine (110.5 mg, 9 mmol) in a mixed solvent of tetrahydrofuran (4 mL) and dimethyl sulfoxide (1 mL) was added N,N-diisopropylethylamine (0.16 mL, 1.19 mmol) and 1-methyl-1H-imidazole-4-carboxylic acid (99 mg, 0.78 mmol). The mixture was stirred at rt for 10 minutes, and then HATU (300 mg, 0.79 mmol) was added. The resulting mixture was stirred at rt for 3 h. To the reaction mixture was added water (10 mL), and the resulting mixture was extracted with ethyl acetate (10 mL×3). The combined organic layers were washed with saturated brine (30 mL), dried over anhydrous sodium sulfate and concentrated in vacuo to give the title compound as a colorless solid (86 mg, 56%).

MS (ESI, pos.ion) m/z: 388.2 [M+H]$^+$;

$^1$H NMR (400 MHz, MeOD) (ppm) δ: 7.65 (d, J=6.1 Hz, 2H), 6.99 (d, J=3.3 Hz, 1H), 6.56 (d, J=3.4 Hz, 1H), 3.78 (s, 3H), 3.72 (s, 3H), 2.68 (s, 2H), 2.34 (d, J=11.6 Hz, 1H), 2.06 (s, 2H), 1.93 (d, J=13.6 Hz, 1H), 1.61 (d, J=13.5 Hz, 1H), 1.44 (d, J=11.7 Hz, 1H), 1.39 (d, J=3.6 Hz, 2H).

Step 2: (+/−)-cis-N-(3-((2-(5-fluoro-1-tosyl-1H-pyrrolo[2,3-b]pyridin-3-yl)-7-methyl-7H-pyrrolo[2,3-d]pyrimidin-4-yl)amino)cyclohexyl)-1-methyl-1H-imidazole-4-carboxamide To a microwave tube were added 5-fluoro-3-(4,4,5,5-tetramethyl-1,3,2-dioxaborolan-2-yl)-1-tosyl-1H-pyrrolo[2,3-b]pyridine (249 mg, 0.30 mmol, 50%), (+/−)-cis-N-(3-((2-chloro-7-methyl-7H-pyrrolo[2,3-d]pyrimidin-4-yl)amino)cyclohexyl)-1-methyl-1H-imidazole-4-carboxamide (97 mg, 0.25 mmol), potassium carbonate (103 mg, 0.75 mmol), Pd(dppf)Cl$_2$ (40 mg, 0.05 mmol), 1,4-dioxane (3 mL) and water (0.2 mL). The air in the mixture was removed by bubbling with nitrogen for 10 min, then the mixture in the microwave tube was stirred at 120° C. with microwave heating for 4 hours. The reaction mixture was filtered through a celite pad and the filter cake was washed with ethyl acetate (50 mL). The filtrate was washed with saturated brine (50 mL), dried over anhydrous sodium sulfate and filtered. The filtrate was concentrated in vacuo and the residue was purified by silica gel column chromatography (DCM/MeOH (v/v)=10/1) to give the title compound as a brown solid (130 mg, 81%).

MS (ESI, pos.ion) m/z: 642.3[M+H]$^+$.

Step 3: (+/−)-cis-N-(3-((2-(5-fluoro-1H-pyrrolo[2,3-b]pyridin-3-yl)-7-methyl-7H-pyrrolo[2,3-d]pyrimidin-4-yl)amino)cyclohexyl)-1-methyl-1H-imidazole-4-carboxamide To a solution of (+/−)-cis-N-(3-((2-(5-fluoro-1-tosyl-1H-pyrrolo[2,3-b]pyridine-3-yl)-7-methyl-7H-pyrrolo[2,3-d]pyrimidin-4-yl)amino)cyclohexyl)-1-methyl-1H-imidazole-4-carboxamide (130 mg, 0.20 mmol) in methanol (2 mL) was added a solution of sodium methoxide in methanol (5 M, 0.40 mL, 2.00 mmol). The mixture was stirred at 30° C. overnight, then concentrated in vacuo to dry. To the reaction mixture was added water (10 mL), and the resulting mixture was extracted with ethyl acetate (20 mL×3), and the combined organic layers were washed with saturated brine (50 mL), dried over anhydrous sodium sulfate, then filtered. The filtrate was concentrated in vacuo and the residue was purified by silica gel column chromatography (DCM/MeOH (v/v)=10/1) to give the title compound as a yellow solid (70 mg, 71%).

MS (ESI, pos.ion) m/z: 488.3 [M+H]$^+$;

HRMS (ESI, pos. ion) m/z: 488.2345[M+H]$^+$, (C$_{25}$H$_{27}$FN$_9$O) [M+H]$^+$ theoretical value: 488.2323;

$^1$H NMR (400 MHz, DMSO-d$_6$) δ (ppm): 12.10 (s, 1H), 8.68 (d, J=7.9 Hz, 1H), 8.34-8.20 (m, 2H), 7.73 (d, J=8.4 Hz, 1H), 7.63 (d, J=11.7 Hz, 2H), 7.28 (d, J=7.4 Hz, 1H), 7.05 (d, J=3.1 Hz, 1H), 6.59 (d, J=3.2 Hz, 1H), 4.31 (s, 1H), 3.98 (d, J=8.3 Hz, 1H), 3.78 (s, 3H), 3.67 (s, 3H), 2.26 (d, J=10.6 Hz, 1H), 2.12 (d, J=10.7 Hz, 1H), 1.87 (d, J=10.3 Hz, 2H), 1.54-1.21 (m, 4H).

Example 38: (+/−)-trans-3-((5-fluoro-2-(2-methyl-1H-pyrrolo[2,3-b]pyridin-3-yl)pyrimidin-4-yl)amino)bicyclo[2.2.2]octane-2-carboxylic Acid

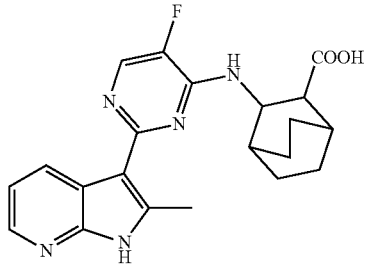 [SMILES: Cc1[nH]c2ncccc2c1-c1ncc(F)c(NC2C3CCC(CC3)C2C(=O)O)n1]

Step 1: 3-bromo-2-methyl-1H-pyrrolo[2,3-b]pyridine

To a solution of 2-methyl-1H-pyrrolo[2,3-b]pyridine (500 mg, 3.78 mmol) in DMF (8 mL) was added bromine (0.22 mL, 4.16 mmol). The reaction mixture was stirred at r.t. for 4 h. A saturated aqueous Na$_2$S$_2$O$_3$ solution (100 mL) was added, and the resulting mixture was extracted with EtOAc (100 mL×2). The combined organic phases were washed with saturated brine (100 mL×3), dried over Na$_2$SO$_4$, filtered, and the filtrate was concentrated in vacuo. The residue was purified by silica gel chromatograph (PE/EtOAc (v/v)=4/1) to give the title compound as a yellow solid (679 mg, 85%).

$^1$H NMR (400 MHz, DMSO-d$_6$) δ (ppm): 12.19 (s, 1H), 8.27 (d, J=4.8 Hz, 1H), 7.82 (d, J=7.8 Hz, 1H), 7.15 (dd, J=7.8, 4.9 Hz, 1H), 2.56 (s, 3H).

Step 2: 3-bromo-2-methyl-1-tosyl-1H-pyrrolo[2,3-b]pyridine

To a solution of 3-bromo-2-methyl-1H-pyrrolo[2,3-b]pyridine (100 mg, 0.47 mmol) in THF (5 mL) was added NaH (22 mg, 0.57 mmol, 60%) at 0° C. Then the reaction mixture was stirred for 30 min at 0° C. TsCl (100 mg, 0.52 mmol) was added and the reaction mixture was stirred at rt overnight. Water (50 mL) was added to quench the reaction, and the resulting mixture was partitioned. The aqueous layer was extracted with EtOAc (50 mL×2). The combined organic phases were washed with saturated brine (80 mL), dried over anhydrous Na$_2$SO$_4$, filtered, and the filtrate was concentrated in vacuo. The residue was purified by silica gel chromatograph (PE/EtOAc (v/v)=4/1) to give the title compound as a yellow solid (100 mg, 58%).

MS (ESI, pos. ion) m/z: 365.95 [M+H]$^+$;

$^1$H NMR (400 MHz, CDCl$_3$) δ (ppm): 8.44 (d, J=4.7 Hz, 1H), 8.04 (d, J=8.3 Hz, 2H), 7.72 (d, J=7.8 Hz, 1H), 7.29 (s, 1H), 7.27 (s, 1H), 7.24 (dd, J=7.8, 4.9 Hz, 1H), 2.79 (s, 3H), 2.39 (s, 3H).

Step 3: 2-methyl-3-(4,4,5,5-tetramethyl-1,3,2-dioxaborolan-2-yl)-1-tosyl-1H-pyrrolo[2,3-b]pyridine The air in the suspension of 3-bromo-2-methyl-1-tosyl-1H-pyrrolo[2,3-b]pyridine (100 mg, 0.27 mmol), Pd(dppf)Cl$_2$(20 mg, 0.03 mmol) and KOAc (80 mg, 0.82 mmol) in DME (5 mL) was exchanged with nitrogen and then to the mixture was added bis(pinacolato)diboron (104 mg, 0.41 mmol). The mixture was purged with nitrogen by bubbling for 10 min to remove the air, then the mixture was stirred at 105° C. for 2 h with microwave heating. To the reaction mixture was added ethyl acetate (20 mL), and the mixture was filtered through a celite pad. The filter cake was washed with ethyl acetate (20 mL×2). The combined filtrates was concentrated in vacuo, and the residue was purified by silica gel column chromatography (PE/EtOAc (v/v)=4/1) to give the title compound as a yellow solid (60 mg, 53%).

MS (ESI, pos. ion) m/z: 413.45 [M+H]$^+$.

Step 4: (+/−)-trans-methyl 3-((5-fluoro-2-(2-methyl-1-tosyl-1H-pyrrolo[2,3-b]pyridin-3-yl) pyrimidin-4-yl)amino)bicyclo[2.2.2]octane-2-carboxylate To 1,4-dioxane (10 mL) were added 2-methyl-3-(4,4,5,5-tetramethyl-1,3,2-dioxaborolan-2-yl)-1-tosyl-1H-pyrrolo[2,3-b]pyridine (50 mg, 0.12 mmol), K$_2$CO$_3$ (50 mg, 0.36 mmol), PdCl$_2$(dppf) (10 mg, 0.01 mmol) and methyl 3-((2-chloro-5-fluoropyrimidin-4-yl)amino) bicyclo[2.2.2]octane-2-carboxylate (41 mg, 0.13 mmol). Then H$_2$O (1 mL) was added to the mixture, and the air in the mixture was removed by bubbling with nitrogen for 10 min. The mixture was stirred for 1.5 h at 110° C. with microwave heating for 10 min. The mixture was filtered through a celite pad to remove solid impurities. The filtrate was concentrated in vacuo, and the residue was purified by silica gel column chromatography (PE/EtOAc (v/v)=10/1-5/1) to give the title compound as a white solid (18 mg, 26%).

Step 5: (+/−)-trans-3-((5-fluoro-2-(2-methyl-1H-pyrrolo[2,3-b]pyridin-3-yl)pyrimidin-4-yl) amino)bicyclo[2.2.2]octane-2-carboxylic Acid To a solution of (+/−)-trans-methyl 3-((5-fluoro-2-(2-methyl-1-tosyl-1H-pyrrolo[2,3-b]pyridin-3-yl)pyrimidin-4-yl)amino)bicyclo[2.2.2]octane-2-carboxylate (130 mg, 0.23 mmol) in THF/MeOH (v/v=5 mL/5 mL) was added a solution of NaOH (95 mg, 2.31 mmol) in water (1 mL). The mixture was stirred at rt overnight, then diluted with water (10 mL). The resulting mixture was acidified with hydrochloric acid (1 M) to pH about 6. The resulting mixture was extracted with ethyl acetate (15 mL×3). The combined organic layers were washed with saturated brine (40 mL), dried over anhydrous sodium sulfate and filtered. The filtrate was concentrated in vacuo to remove the solvent and the residue was purified by silica gel column chromatography (DCM/MeOH (v/v)=10/1-5/1) to give the title compound as a white solid (32 mg, 35%).

MS (ESI, pos. ion) m/z: 396.15 [M+H]$^+$;

HRMS (ESI, pos. ion) m/z: 396.1836[M+H]$^+$, ($C_{21}H_{23}FN_5O_2$) [M+H]$^+$ theoretical value: 396.1836;

$^1$H NMR (600 MHz, DMSO-$d_6$) δ (ppm): 12.49 (s, 1H), 8.61 (d, J=7.7 Hz, 1H), 8.43 (d, J=4.9 Hz, 1H), 8.34 (d, J=4.5 Hz, 1H), 8.28 (s, 1H), 7.24 (dd, J=7.5, 4.8 Hz, 1H), 4.76 (t, J=6.6 Hz, 1H), 2.90 (d, J=6.8 Hz, 1H), 2.81 (s, 3H), 2.02 (s, 1H), 1.89 (s, 1H), 1.76 (d, J=8.2 Hz, 2H), 1.66 (d, J=10.6 Hz, 1H), 1.59 (d, J=6.2 Hz, 1H), 1.54-1.31 (m, 5H);

$^{13}$C NMR (151 MHz, DMSO-$d_6$) δ (ppm): 175.75, 156.88, 152.63, 146.57, 143.67, 142.67, 142.10, 141.59, 130.17, 120.33, 117.15, 107.09, 51.22, 47.55, 29.18, 28.65, 25.58, 24.18, 21.48, 19.49, 14.49.

Example 39: (+/−)-trans-3-((2-(2-methyl-1H-pyrrolo[2,3-b]pyridin-3-yl)-6-phenylpyrimidin-4-yl)amino)bicyclo[2.2.2]octane-2-carboxylic Acid

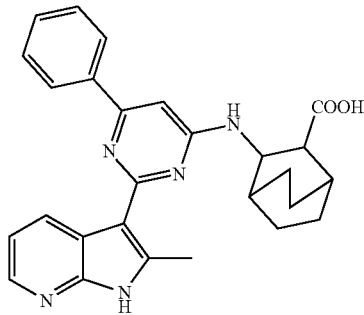 [SMILES: Cc1[nH]c2ncccc2c1-c1nc(NC2C3CCC(CC3)C2C(=O)O)cc(-c2ccccc2)n1]

Step 1: (+/−)-trans-methyl 3-((2-(2-methyl-1-tosyl-1H-pyrrolo[2,3-b]pyridin-3-yl)-6-phenyl pyrimidin-4-yl)amino)bicyclo[2.2.2]octane-2-carboxylate To 1,4-dioxane (10 mL) were added 2-methyl-3-(4,4,5,5-tetramethyl-1,3,2-dioxaborolan-2-yl)-1-tosyl-1H-pyrrolo[2,3-b]pyridine (100 mg, 0.24 mmol), $K_2CO_3$ (100 mg, 0.73 mmol), Pd(dppf)$Cl_2$ (18 mg, 0.03 mmol) and (+/−)-trans-methyl 3-((2-chloro-6-phenylpyrimidin-4-yl)amino)bicyclo[2.2.2]octane-2-carboxylate (99 mg, 0.27 mmol). Then $H_2O$ (1 mL) was added to the mixture, and the air in the mixture was removed by bubbling with nitrogen for 10 min. The mixture was stirred for 3 h at 110° C. with microwave heating. The mixture was filtered through a celite pad to remove solid impurities. The filtrate was concentrated in vacuo, and the residue was purified by silica gel column chromatography (PE/EtOAc (v/v)=10/1-5/1) to give the title compound as a white solid (130 mg, 86%).

MS (ESI, pos. ion) m/z: 623.15 [M+H]$^+$.

Step 2: (+/−)-trans-3-((2-(2-methyl-1H-pyrrolo[2,3-b]pyridin-3-yl)-6-phenylpyrimidin-4-yl) amino)bicyclo[2.2.2]octane-2-carboxylic Acid To a solution of (+/−)-trans-methyl 3-((2-(2-methyl-1-tosyl-1H-pyrrolo[2,3-b]pyridin-3-yl)-6-phenylpyrimidin-4-yl)amino)bicyclo[2.2.2]octane-2-carboxylate (130 mg, 0.21 mmol) in THF/MeOH (v/v=5 mL/5 mL) was added a solution of sodium hydroxide (85 mg, 2.09 mmol) in water (1 mL). The mixture was stirred at rt overnight. To the reaction mixture was added water (10 mL), and the resulting mixture was acidified with hydrochloric acid (1 M) to pH about 6. The mixture was extracted with ethyl acetate (15 mL×3), and the combined organic layers were washed with saturated brine (40 mL), dried over anhydrous sodium sulfate, then filtered. The filtrate was concentrated in vacuo to remove the solvent and the residue was purified by silica gel column chromatography (DCM/MeOH (v/v)=10/1-5/1) to give the title compound as a white solid (38 mg, 40%).

MS (ESI, pos. ion) m/z: 454.20 [M+H]$^+$;

HRMS (ESI, pos. ion) m/z: 454.2261 [M+H]$^+$, ($C_{27}H_{28}N_5O_2$) [M+H]$^+$ theoretical value: 454.2243;

$^1$H NMR (600 MHz, DMSO-$d_6$) δ (ppm): 11.91 (s, 1H), 8.90 (d, J=7.1 Hz, 1H), 8.21-8.15 (m, 1H), 8.09 (d, J=6.6 Hz, 2H), 7.58-7.48 (m, 3H), 7.40 (d, J=5.5 Hz, 1H), 7.14 (dd, J=7.8, 4.7 Hz, 1H), 6.71 (s, 1H), 3.94 (s, 1H), 2.96 (s, 3H), 1.85-1.51 (m, 8H), 1.23 (d, J=3.1 Hz, 4H).

Example 40: (+/−)-trans-3-((7-methyl-2-(2-methyl-1H-pyrrolo[2,3-b]pyridin-3-yl)-7H-pyrrolo[2,3-d]pyrimidin-4-yl)amino)bicyclo[2.2.2]octane-2-carboxylic Acid

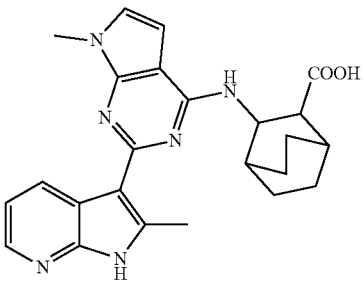 [SMILES: Cc1[nH]c2ncccc2c1-c1nc(NC2C3CCC(CC3)C2C(=O)O)c2ccn(C)c2n1]

Step 1: (+/−)-trans-methyl 3-((7-methyl-2-(2-methyl-1-tosyl-1H-pyrrolo[2,3-b]pyridin-3-yl)-7H-pyrrolo[2,3-b]pyrimidin-4-yl)amino)bicyclo[2.2.2]octane-2-carboxylate To 1,4-dioxane (8 mL) were added 2-methyl-3-(4,4,5,5-tetramethyl-1,3,2-dioxaborolan-2-yl)-1-tosyl-1H-pyrrolo[2,3-b]pyridine (100 mg, 0.24 mmol), $K_2CO_3$ (100 mg, 0.73 mmol), Pd(dppf)$Cl_2$ (24 mg, 0.02 mmol) and (+/−)-trans-methyl 3-((2-chloro-7-methyl-7H-pyrrolo[2,3-b]pyrimidin-4-yl)amino)bicyclo[2.2.2]octane-2-carboxylate (99 mg, 0.27 mmol). Then $H_2O$ (1 mL) was added to the mixture, and the air in the mixture was removed by bubbling with nitrogen for 10 min. The mixture was stirred for 1.5 h at 110° C. with microwave heating. The mixture was filtered through a celite pad to remove solid impurities. The filtrate was concentrated in vacuo, and the residue was purified by silica gel column chromatography (PE/EtOAc (v/v)=10/1-5/1) to give the title compound as a white solid (112 mg, 77%).

MS (ESI, pos. ion) m/z: 599.20 [M+H]$^+$.

Step 2: (+/−)-trans-3-((7-methyl-2-(2-methyl-1H-pyrrolo[2,3-b]pyridin-3-yl)-7H-pyrrolo[2,3-d]pyrimidin-4-yl)amino)bicyclo[2.2.2]octane-2-carboxylic Acid To a solution of (+/−)-trans-methyl 3-((7-methyl-2-(2-methyl-1-tosyl-1H-pyrrolo[2,3-b]pyridin-3-yl)-7H-pyrrolo

[2,3-b]pyrimidin-4-yl)amino)bicyclo[2.2.2]octane-2-carboxylate (113 mg, 0.19 mmol) in THF/MeOH (v/v=5 mL/5 mL) was added a solution of sodium hydroxide (79 mg, 1.89 mmol) in water (1 mL). The mixture was stirred at rt overnight. To the reaction mixture was added water (10 mL), and the resulting mixture was acidified with hydrochloric acid to pH about 6. The mixture was extracted with ethyl acetate (15 mL×3), and the combined organic layers were washed with saturated brine (40 mL), dried over anhydrous sodium sulfate, then filtered. The filtrate was concentrated in vacuo and the residue was purified by silica gel column chromatography (DCM/MeOH (v/v)=10/1-5/1) to give the title compound as a white solid (31 mg, 38%).

MS (ESI, pos. ion) m/z: 431.15 [M+H]$^+$;

HRMS (ESI, pos. ion) m/z: 431.2201 [M+H]$^+$, ($C_{24}H_{27}N_6O_2$) [M+H]$^+$ theoretical value: 431.2195;

$^1$H NMR (600 MHz, DMSO-$d_6$) δ (ppm) 11.73 (s, 1H), 8.95 (d, J=7.7 Hz, 1H), 8.15 (d, J=4.4 Hz, 1H), 7.16 (d, J=7.1 Hz, 1H), 7.10 (dd, J=7.8, 4.7 Hz, 1H), 7.06 (d, J=3.2 Hz, 1H), 6.60 (s, 1H), 4.83 (s, 1H), 3.77 (s, 3H), 2.94 (s, 3H), 2.74 (d, J=6.7 Hz, 1H), 2.00 (d, J=15.2 Hz, 2H), 1.76 (d, J=10.5 Hz, 2H), 1.62-1.34 (m, 5H), 1.24 (s, 2H).

Example 41: (+/−)-trans-3-((5-fluoro-2-(5-fluoro-2-(4-fluorophenyl)-1H-pyrrolo[2,3-b]pyridin-3-yl)pyrimidin-4-yl)amino)bicyclo[2.2.2]octane-2-carboxylic Acid

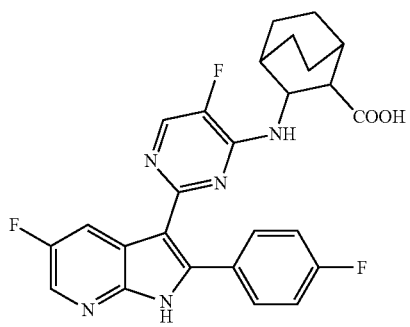 [SMILES: O=C(O)C1C2CCC(CC2)C1Nc1nc(-c2c(-c3ccc(F)cc3)[nH]c3ncc(F)cc23)ncc1F]

Step 1: 3-bromo-5-fluoropyridin-2-amine

To a solution of 5-fluoropyridin-2-amine (6 g, 53.52 mmol) in acetonitrile (120 mL) was added slowly NBS (12.64 g, 69.60 mmol), and the mixture was stirred at rt for 2 h, then concentrated in vacuo to dry. The residue was purified by silica gel column chromatography (PE/EA (v/v)=20/1) to give the title compound as a yellow solid (5.4 g, 53%).

MS (ESI, pos.ion) m/z: 193.0[M+H]$^+$;

$^1$H NMR (400 MHz, CDCl$_3$) δ (ppm): 7.95 (d, J=2.5 Hz, 1H), 7.52 (dd, J=7.3, 2.6 Hz, 1H), 4.84 (s, 2H).

Step 2: 5-fluoro-3-((4-fluorophenyl)ethynyl)pyridin-2-amine

To a solution of 3-bromo-5-fluoropyridin-2-amine (1.33 g, 6.96 mmol) in acetonitrile (14 mL) was added triethylamine (14 mL), 1-ethynyl-4-fluorobenzene (850 mg, 7.08 mmol) and Pd(PPh$_3$)$_2$Cl$_2$ (496 mg, 0.70 mmol) in turn, and the mixture was stirred at 75° C. for 6 h under nitrogen protection, then concentrated in vacuo to dry. The residue was purified by silica gel column chromatography (PE/EA (v/v)=10/1) to give the title compound as a yellow solid (770 mg, 48.0%).

MS (ESI, pos.ion) m/z: 231.3 [M+H]$^+$;

$^1$H NMR (400 MHz, CDCl$_3$) δ (ppm): 7.95 (d, J=2.9 Hz, 1H), 7.56-7.48 (m, 2H), 7.38 (dd, J=8.3, 2.9 Hz, 1H), 7.09 (dd, J=11.0, 4.3 Hz, 2H), 4.96 (s, 2H).

Step 3: 5-fluoro-2-(4-fluorophenyl)-1H-pyrrolo[2,3-b]pyridine

To a solution of 5-fluoro-3-((4-fluorophenyl)ethynyl)pyridin-2-amine (50 mg, 0.22 mmol) in DMF (1 mL) was added potassium tert-butoxide (73 mg, 0.65 mmol), and the mixture was stirred at 80° C. for 3 h under nitrogen protection, then cooled to rt. To the reaction mixture was added water (25 mL), and the resulting mixture was extracted with ethyl acetate (25 mL×3). The combined organic layers were washed with saturated brine, dried over anhydrous sodium sulfate and filtered. The filtrate was concentrated in vacuo and the residue was purified by silica gel column chromatography (PE/EA (v/v)=2/1) to give the title compound as a white solid (30 mg, 60%).

MS (ESI, pos.ion) m/z: 231.1 [M+H]$^+$;

$^1$H NMR (400 MHz, CDCl$_3$) δ (ppm): 12.29 (s, 1H), 8.19 (s, 1H), 8.00 (dd, J=8.6, 5.4 Hz, 2H), 7.83 (dd, J=9.5, 2.6 Hz, 1H), 7.34 (t, J=8.8 Hz, 2H), 6.92 (s, 1H).

Step 4: 3-bromo-5-fluoro-2-(4-fluorophenyl)-1H-pyrrolo[2,3-b]pyridine

To a solution of 5-fluoro-2-(4-fluorophenyl)-1H-pyrrolo[2,3-b]pyridine (30 mg, 0.13 mmol) in DMF (1 mL) was added bromine (0.02 mL, 0.26 mmol). The reaction mixture was stirred at rt for 2 h. A saturated aqueous Na$_2$S$_2$O$_3$ solution (20 mL) was added, and the resulting mixture was extracted with EtOAc (20 mL×2). The combined organic phases were washed with saturated brine (20 mL×3), dried over anhydrous Na$_2$SO$_4$, filtered, and the filtrate was concentrated in vacuo. The residue was purified by silica gel chromatograph (n-hexane/EtOAc (v/v)=2/1) to give the title compound as a white solid (15 mg, 37%).

MS (ESI, pos. ion) m/z: 311.0 [M+H]$^+$;

$^1$H NMR (400 MHz, DMSO-$d_6$) δ (ppm): 12.65 (s, 1H), 8.32 (s, 1H), 7.94 (dd, J=8.6, 5.5 Hz, 2H), 7.76 (dd, J=8.8, 2.5 Hz, 1H), 7.43 (t, J=8.8 Hz, 2H).

Step 5: 3-bromo-5-fluoro-2-(4-fluorophenyl)-1-tosyl-1H-pyrrolo[2,3-b]pyridine

To dried tetrahydrofuran (10 mL) was added 3-bromo-5-fluoro-2-(4-fluorophenyl)-1H-pyrrolo[2,3-b]pyridine (0.74 g, 2.0 mmol). Sodium hydride (232 mg, 5.80 mmol, 60%) was added to the solution at 0° C., and the resulting mixture was stirred at 0° C. for 30 min. Then p-toluenesulfonyl chloride (667 mg, 3.50 mmol) was added to the mixture, and the mixture was warmed to rt and stirred for 3 h. Water (100 mL) was added to quench the reaction, and the resulting mixture was extracted with EtOAc (100 mL×2). The combined organic phases were dried over anhydrous Na$_2$SO$_4$, filtered, and the filtrate was concentrated in vacuo. The residue was purified by silica gel chromatograph (PE/EtOAc (v/v)=10/1) to give the title compound as a yellow solid (360 mg, 27%).

MS (ESI, pos. ion) m/z: 463.1 [M+H]$^+$;
$^1$H NMR (400 MHz, CDCl$_3$) δ (ppm): 8.42 (d, J=1.2 Hz, 1H), 7.76 (d, J=8.2 Hz, 2H), 7.53-7.47 (m, 3H), 7.28-7.19 (m, 4H).

Step 6: 5-fluoro-2-(4-fluorophenyl)-1-tosyl-3-(4,4,5,5-tetramethyl-1,3,2-dioxaborolan-2-yl) pyrrolo[2,3-b]pyridine A microwave tube was charged with 3-bromo-5-fluoro-2-(4-fluorophenyl)-1-(p-tolylsulfonyl)pyrrolo[2,3-b]pyridine (300 mg, 0.65 mmol), bis(pinacolato)diboron (247 mg, 0.97 mmol), potassium acetate (128 mg, 1.30 mmol), Pd(dppf)Cl$_2$ (53 mg, 0.06 mmol) and dimethoxyethane (4 mL). The air in the mixture was removed by bubbling with nitrogen for 10 min and stirred at 130° C. for 2 h with microwave heating. The mixture was cooled to rt and filtered through a celite pad. The filter cake was ethyl acetate (10 mL), and the combined filtrates were dried in vacuo to dry. The residue was purified by silica gel chromatograph (n-hexane/EtOAc (v/v)=10/1) to give the title compound as yellow oil (220 mg, 67%).

MS (ESI, pos.ion) m/z: 511.4 [M+H]$^+$.

Step 7: (+/−)-trans-methyl 3-((5-fluoro-2-(5-fluoro-2-(4-fluorophenyl)-1-tosyl-1H-pyrrolo[2,3-b]pyridin-3-yl)pyrimidin-4-yl)amino)bicyclo[2.2.2]octane-2-carboxylate To a sealed tub were added 5-fluoro-2-(4-fluorophenyl)-1-tosyl-3-(4,4,5,5-tetramethyl-1,3,2-dioxaborolan-2-yl)pyrrolo[2,3-b]pyridine (200 mg, 0.38 mmol), (+/−)-trans-methyl 3-((2-chloro-5-fluoropyrimidin-4-yl)amino)bicyclo[2.2.2]octane-2-carboxylate (100 mg, 0.32 mmol), potassium carbonate (132 mg, 0.96 mmol), Pd(dppf)Cl$_2$ (52 mg, 0.06 mmol), 1,4-dioxane (3 mL) and water (0.2 mL). The mixture was stirred at 110° C. for 3 h. The mixture was filtered through a celite pad, and the filter cake was washed with ethyl acetate (50 mL). The filtrate was washed with saturated brine (50 mL), dried over anhydrous sodium sulfate and filtered. The filtrate was concentrated in vacuo and the residue was purified by silica gel column chromatography (n-hexane/EtOAc (v/v)=5/1) to give the title compound as a yellow solid (204 mg, 97%).

MS (ESI, pos.ion) m/z: 662.1[M+H]$^+$;
$^1$H NMR (400 MHz, CDCl$_3$) δ (ppm): 8.40 (d, J=2.0 Hz, 1H), 8.19 (dd, J=8.8, 2.8 Hz, 1H), 7.96 (d, J=3.1 Hz, 1H), 7.79 (s, 1H), 7.77 (s, 1H), 7.43 (s, 2H), 7.13 (t, J=8.5 Hz, 2H), 3.81 (s, 1H), 3.60 (s, 3H), 2.37 (s, 3H), 2.25 (d, J=7.1 Hz, 1H), 1.58 (m, 8H).

Step 8: (+/−)-trans-3-((5-fluoro-2-(5-fluoro-2-(4-fluorophenyl)-1H-pyrrolo[2,3-b]pyridin-3-yl)pyrimidin-4-yl)amino)bicyclo[2.2.2]octane-2-carboxylic Acid To a solution of (+/−)-trans-methyl 3-((5-fluoro-2-(5-fluoro-2-(4-fluorophenyl)-1-tosyl-1H-pyrrolo[2,3-b]pyridin-3-yl)pyrimidin-4-yl)amino)bicyclo[2.2.2]octane-2-carboxy late (200 mg, 0.30 mmol) in THF/MeOH (v/v=1/1, 3 mL) was added aqueous sodium hydroxide solution (4 M, 0.75 mL, 3.00 mmol). The mixture was stirred at 30° C. overnight, then diluted with water (10 mL). The resulting mixture was acidified with hydrochloric acid (1 M) to pH about 5.5, then extracted with ethyl acetate (20 mL×3). The combined organic layers were washed with saturated brine (50 mL), dried over anhydrous sodium sulfate, filtered and concentrated in vacuo. The residue was purified by silica gel column chromatography (DCM/MeOH (v/v)=10/1) to give the title compound as a yellow solid (74 mg, 50%).

HRMS (ESI, pos. ion) m/z: 494.1824 [M+H]$^+$, (C$_{26}$H$_{23}$F$_3$N$_5$O$_2$) [M+H]$^+$ theoretical value: 494.1804;
$^1$H NMR (400 MHz, DMSO-d$_6$) δ (ppm): 12.35 (s, 1H), 8.41 (dd, J=9.9, 2.6 Hz, 1H), 8.26 (s, 1H), 8.11 (d, J=3.6 Hz, 1H), 7.95 (s, 1H), 7.67 (dd, J=8.3, 5.6 Hz, 2H), 7.48 (d, J=7.0 Hz, 1H), 7.26 (t, J=8.8 Hz, 2H), 4.24 (t, J=7.1 Hz, 1H), 2.76 (d, J=7.3 Hz, 1H), 1.94 (s, 1H), 1.66 (d, J=8.5 Hz, 2H), 1.50 (s, 1H), 1.37-1.20 (m, 6H).

Example 42: (+/−)-trans-3-((5-fluoro-2-(5-fluoro-2-phenyl-1H-pyrrolo[2,3-b]pyridin-3-yl) pyrimidin-4-yl)amino)bicyclo[2.2.2]octane-2-carboxylic Acid

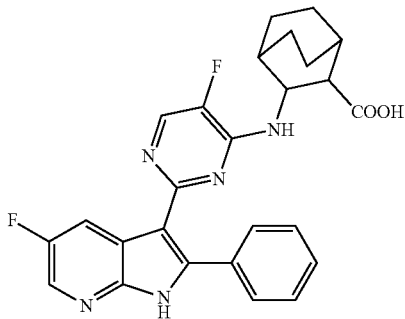 [SMILES: O=C(O)C1C2CCC(CC2)C1Nc1nc(-c2c(-c3ccccc3)[nH]c3ncc(F)cc23)ncc1F]

Step 1: 5-fluoro-3-(2-phenylethynyl)pyridin-2-amine

To a solution of 3-bromo-5-fluoropyridin-2-amine (3.8 g, 20 mmol) in acetonitrile (40 mL) was added triethylamine (40 mL), phenylacetylene (2.2 g, 22 mmol) and Pd(PPh$_3$)$_2$Cl$_2$ (1.5 g, 2.1 mmol) in turn, and the mixture was stirred at 75° C. for 5 h under nitrogen protection, then concentrated in vacuo to dry. The residue was purified by silica gel column chromatography (PE/EA (v/v)=10/1) to give the title compound as a yellow solid (2.9 g, 69%).

MS (ESI, pos.ion) m/z: 213.3 [M+H]$^+$;
$^1$H NMR (400 MHz, CDCl$_3$) δ (ppm): 7.95 (d, J=2.9 Hz, 1H), 7.56-7.48 (m, 2H), 7.38 (dd, J=8.3, 2.9 Hz, 1H), 7.09 (dd, J=11.0, 4.3 Hz, 2H), 4.96 (s, 2H).

Step 2: 5-fluoro-2-phenyl-1H-pyrrolo[2,3-b]pyridine

To a solution of 5-fluoro-3-(2-phenylethynyl)pyridin-2-amine (2.8 g, 13 mmol) in DMF (30 mL) was added potassium tert-butoxide (4.4 g, 39 mmol), and the mixture was stirred at 80° C. for 3 h under nitrogen protection, then cooled to rt. To the reaction mixture was added water (25 mL), and the resulting mixture was extracted with ethyl acetate (25 mL×3). The combined organic layers were washed with saturated brine (50 mL), dried over anhydrous sodium sulfate and filtered. The filtrate was concentrated in vacuo and the residue was purified by silica gel column chromatography (PE/EA (v/v)=2/1) to give the title compound as a white solid (2.5 g, 89%).

MS (ESI, pos.ion) m/z: 213.1 [M+H]$^+$.

Step 3: 3-bromo-5-fluoro-2-phenyl-1H-pyrrolo[2,3-b]pyridine

To a solution of 5-fluoro-2-phenyl-1H-pyrrolo[2,3-b] pyridine (2.5 g, 30 mmol) in DMF (30 mL) was added bromine (1.2 mL, 23 mmol). The reaction mixture was stirred at rt for 2 h. A saturated aqueous $Na_2S_2O_3$ solution (50 mL) was added to quench the reaction, and the resulting mixture was extracted with EtOAc (50 mL×2). The combined organic phases were washed with saturated brine (20 mL×3), dried over anhydrous $Na_2SO_4$, filtered, and the filtrate was concentrated in vacuo. The residue was purified by silica gel chromatograph (n-hexane/EtOAc (v/v)=2/1) to give the title compound as a white solid (3.20 g, 93%).

MS (ESI, pos. ion) m/z: 291.0 [M+H]$^+$;

$^1$H NMR (400 MHz, DMSO-d$_6$) δ (ppm): 10.92 (s, 1H), 8.14 (s, 1H), 7.94 (d, J=7.3 Hz, 2H), 7.65 (dd, J=8.4, 2.4 Hz, 1H), 7.60 (t, J=7.5 Hz, 2H), 7.53 (d, J=7.4 Hz, 1H).

Step 4: 3-bromo-5-fluoro-2-phenyl-1-tosyl-1H-pyrrolo[2,3-b]pyridine

To a solution of 3-bromo-5-fluoro-2-phenyl-1H-pyrrolo[2,3-b]pyridine (3.84 g, 13.2 mmol) in dried tetrahydrofuran (40 mL) was added sodium hydride (1.07 g, 26.8 mmol, 60%). The reaction mixture was stirred at 0° C. for 30 min, then p-toluenesulfonyl chloride (3.03 g, 15.9 mmol) was added. The resulting mixture was stirred at rt for 3 h, then quenched with water (100 mL), and the mixture was partitioned. The aqueous layer was extracted with EtOAc (100 mL×2). The combined organic phases were dried over anhydrous $Na_2SO_4$, filtered, and the filtrate was concentrated in vacuo to dry. The residue was purified by silica gel chromatograph (n-hexane/EtOAc (v/v)=10/1) to give the title compound as a yellow solid (1.42 g, 24%).

MS (ESI, pos. ion) m/z: 444.9 [M+H]$^+$;

$^1$H NMR (400 MHz, CDCl$_3$) δ (ppm): 8.41 (d, J=1.3 Hz, 1H), 7.79 (s, 1H), 7.77 (s, 1H), 7.56-7.49 (m, 6H), 7.23 (d, J=8.1 Hz, 2H), 2.39 (s, 3H).

Step 5: 5-fluoro-2-phenyl-3-(4,4,5,5-tetramethyl-1,3,2-dioxaborolan-2-yl)-1-tosyl-1H-pyrrolo [2,3-b] pyridine A microwave tube was charged with 3-bromo-5-fluoro-2-phenyl-1-tosyl-1H-pyrrolo[2,3-b]pyridine (1.35 g, 3.03 mmol), bis(pinacolato)diboron (1.15 g, 4.53 mmol), potassium acetate (596 mg, 6.07 mmol), Pd(dppf)Cl$_2$ (249 mg, 0.30 mmol) and dimethoxyethane (10 mL). The mixture was stirred at 130° C. for 2 h with microwave heating. The mixture was cooled to rt and filtered through a celite pad. The filter cake was washed with ethyl acetate (10 mL), and the combined filtrates were dried in vacuo to dry. The residue was purified by silica gel chromatograph (n-hexane/EtOAc (v/v)=10/1) to give the title compound as a white solid (1.14 g, 76%).

MS (ESI, pos.ion) m/z: 493.1 [M+H]$^+$.

Step 6: (+/−)-trans-methyl 3-((5-fluoro-2-(5-fluoro-2-phenyl-1-tosyl-1H-pyrrolo[2,3-b]pyridine-3-yl)pyrimidin-4-yl)amino)bicyclo[2.2.2]octane-2-carboxylate To a sealed tube were added 5-fluoro-2-phenyl-3-(4,4,5,5-tetramethyl-1,3,2-dioxaborolan-2-yl)-1-tosyl-1H-pyrrolo [2,3-b]pyridine (158 mg, 0.31 mmol), (+/−)-trans-methyl 3-((2-chloro-5-fluoropyrimidin-4-yl)amino)bicyclo[2.2.2] octane-2-carboxylate (80 mg, 0.25 mmol), potassium carbonate (106 mg, 0.77 mmol), Pd(dppf)Cl$_2$ (42 mg, 0.05 mmol), 1,4-dioxane (3 mL) and water (0.2 mL). The air in the mixture was removed by bubbling with nitrogen for 10 min and the mixture was stirred at 110° C. for 2 h. The mixture was filtered through a celite pad, and the filter cake was washed with ethyl acetate (50 mL). The filtrate was washed with saturated brine (50 mL), dried over anhydrous sodium sulfate and filtered. The filtrate was concentrated in vacuo and the residue was purified by silica gel column chromatography (n-hexane/EtOAc (v/v)=5/1) to give the title compound as a yellow solid (29 mg, 18%).

$^1$H NMR (400 MHz, CDCl$_3$) δ (ppm): 8.40 (d, J=1.8 Hz, 1H), 8.19 (dd, J=8.7, 2.8 Hz, 1H), 7.95 (d, J=3.0 Hz, 1H), 7.80 (d, J=8.3 Hz, 2H), 7.44 (d, J=6.0 Hz, 5H), 7.21 (d, J=8.0 Hz, 2H), 4.85 (d, J=7.4 Hz, 1H), 4.08 (t, J=6.8 Hz, 1H), 3.59 (s, 3H), 2.37 (s, 3H), 2.22 (d, J=6.6 Hz, 1H), 2.04 (s, 2H), 1.57-1.28 (m, 8H).

Step 7: (+/−)-trans-3-((5-fluoro-2-(5-fluoro-2-phenyl-1H-pyrrolo[2,3-b]pyridin-3-yl)pyrimidin-4-yl)amino)bicyclo[2.2.2]octane-2-carboxylic Acid To a solution of (+/−)-trans-methyl 3-((5-fluoro-2-(5-fluoro-2-phenyl-1-tosyl-1H-pyrrolo[2,3-b]pyridin-3-yl)pyrimidin-4-yl)amino)bicyclo[2.2.2]octane-2-carboxylate (29 mg, 0.05 mmol) in THF/MeOH (v/v=1/1, 3 mL) was added aqueous sodium hydroxide solution (4 M, 0.13 mL, 0.50 mmol). The reaction mixture was stirred at 30° C. overnight. To the reaction mixture was added water (10 mL), and the resulting mixture was acidified with hydrochloric acid (1 M) to pH about 5.5. The mixture was extracted with ethyl acetate (20 mL×3), and the combined organic layers were washed with saturated brine (50 mL), dried over anhydrous sodium sulfate, then filtered. The filtrate was concentrated in vacuo to remove the solvent and the residue was purified by silica gel column chromatography (DCM/MeOH (v/v)=10/1) to give the title compound as a yellow solid (19 mg, 89%).

MS (ESI, pos.ion) m/z: 476.1 [M+H]$^+$;

HRMS (ESI, pos. ion) m/z: 476.1900 [M+H]$^+$, $(C_{26}H_{24}F_2N_5O_2)$ [M+H]$^+$ theoretical value: 476.1898;

$^1$H NMR (400 MHz, DMSO-d$_6$) δ (ppm): 12.31 (s, 1H), 8.38 (dd, J=9.9, 2.7 Hz, 1H), 8.26 (s, 1H), 8.08 (d, J=3.7 Hz, 1H), 7.61 (d, J=6.9 Hz, 2H), 7.51-7.37 (m, 4H), 4.28 (s, 1H), 2.76 (d, J=6.8 Hz, 1H), 1.93 (s, 1H), 1.66 (d, J=8.5 Hz, 2H), 1.57-1.28 (m, 8H).

Example 43: (+/−)-trans-3-((2-(5-fluoro-2-phenyl-1H-pyrrolo[2,3-b]pyridin-3-yl)-6-phenyl pyrimidin-4-yl)amino)bicyclo[2.2.2]octane-2-carboxylic Acid

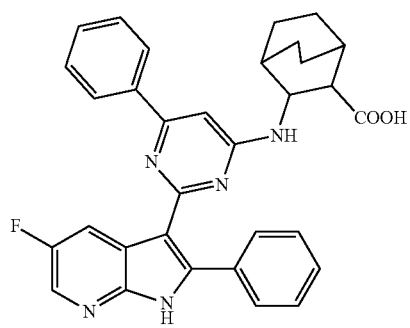 [SMILES: O=C(O)C1C2CCC(CC2)C1Nc1cc(-c2ccccc2)nc(-c2c(-c3ccccc3)[nH]c3ncc(F)cc23)n1]

Step 1: (+/−)-trans-methyl 3-((2-(5-fluoro-2-phenyl-1-tosyl-1H-pyrrolo[2,3-b]pyridin-3-yl)-6-phenylpyrimidin-4-yl)amino)bicyclo[2.2.2]octane-2-carboxylate To a sealed tube were added 5-fluoro-2-phenyl-3-(4,4,5,5-tetramethyl-1,3,2-dioxaborolan-2-yl)-1-tosyl-1H-pyrrolo[2,3-b]pyridine (133 mg, 0.26 mmol), (+/−)-trans-methyl 3-((2-chloro-6-phenylpyrimidin-4-yl)amino)bicyclo[2.2.2]octane-2-carboxylate (80 mg, 0.22 mmol), potassium carbonate (90 mg, 0.65 mmol), Pd(dppf)Cl$_2$ (36 mg, 0.04 mmol), 1,4-dioxane (3 mL) and water (0.2 mL). The air in the mixture was removed by bubbling with nitrogen for 10 min, then the mixture in the sealed tube was stirred at 110° C. for 3 hours. The mixture was filtered through a celite pad, and the filter cake was washed with ethyl acetate (50 mL). The filtrate was washed with saturated brine (50 mL), dried over anhydrous sodium sulfate and filtered. The filtrate was concentrated in vacuo and the residue was purified by silica gel column chromatography (n-hexane/EtOAc(v/v)=5/1) to give the title compound as a yellow solid (57 mg, 38%).

MS (ESI, pos.ion) m/z: 702.2[M+H]$^+$;

$^1$H NMR (400 MHz, CDCl$_3$) δ (ppm): 8.48 (d, J=9.0 Hz, 1H), 8.43 (s, 1H), 7.85 (d, J=8.2 Hz, 2H), 7.55-7.47 (m, 6H), 7.39 (d, J=6.8 Hz, 1H), 7.36-7.31 (m, 2H), 7.22 (d, J=8.1 Hz, 2H), 6.63 (s, 1H), 4.92 (s, 1H), 4.35 (s, 1H), 3.67 (s, 3H), 2.41-2.31 (m, 4H), 1.88 (s, 1H), 1.83-1.59 (m, 8H).

Step 2: (+/−)-trans-3-((2-(5-fluoro-2-phenyl-1H-pyrrolo[2,3-b]pyridin-3-yl)-6-phenylpyrimidin-4-yl)amino)bicyclo[2.2.2]octane-2-carboxylic Acid To a solution of (+/−)-trans-methyl 3-((2-(5-fluoro-2-phenyl-1-tosyl-1H-pyrrolo[2,3-b]pyridin-3-yl)-6-phenylpyrimidin-4-yl)amino)bicyclo[2.2.2]octane-2-carboxylate (51 mg, 0.07 mmol) in THF/MeOH (v/v=1/1, 1.0 mL) was added aqueous sodium hydroxide solution (4 M, 0.15 mL, 0.70 mmol). The mixture was stirred at 30° C. overnight. To the reaction mixture was added water (10 mL), and the resulting mixture was acidified with hydrochloric acid (1 M) to pH about 5.5. The mixture was extracted with ethyl acetate (20 mL×3), and the combined organic layers were washed with saturated brine (50 mL), dried over anhydrous sodium sulfate, then filtered. The filtrate was concentrated in vacuo to remove the solvent and the residue was purified by silica gel column chromatography (DCM/MeOH (v/v)=10/1) to give the title compound as a yellow solid (35 mg, 90%).

MS (ESI, pos.ion) m/z: 534.2 [M+H]$^+$;

HRMS (ESI, pos. ion) m/z: 534.2317 [M+H]$^+$, (C$_{32}$H$_{29}$FN$_5$O$_2$) [M+H]$^+$ theoretical value: 534.2305;

$^1$H NMR (400 MHz, DMSO-d$_6$) δ (ppm): 12.38 (s, 1H), 8.63 (s, 1H), 8.28 (s, 1H), 7.72-7.63 (m, 2H), 7.60 (d, J=7.4 Hz, 2H), 7.50-7.31 (m, 7H), 6.71 (s, 1H), 4.50 (s, 1H), 2.89 (s, 1H), 2.73 (s, 1H), 1.99 (s, 1H), 1.79 (s, 1H), 1.76-1.40 (m, 8H).

Example 44: (+/−)-trans-3-((2-(5-fluoro-2-phenyl-1H-pyrrolo[2,3-b]pyridin-3-yl)-7-methyl-7H-pyrrolo[2,3-d]pyrimidin-4-yl)amino)bicyclo[2.2.2]octane-2-carboxylic Acid

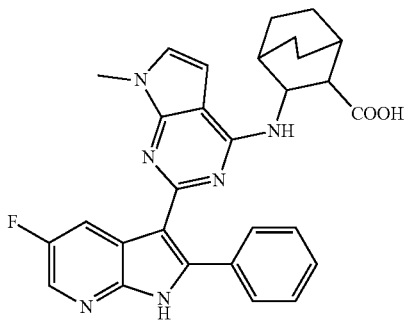 [SMILES: Cn1ccc2c(NC3C4CCC(CC4)C3C(=O)O)nc(-c3c(-c4ccccc4)[nH]c4ncc(F)cc34)nc21]

Step 1: (+/−)-trans-methyl 3-((2-(5-fluoro-2-phenyl-1-tosyl-1H-pyrrolo[2,3-b]pyridin-3-yl)-7-methyl-7H-pyrrolo[2,3-d]pyrimidin-4-yl)amino)bicyclo[2.2.2]octane-2-carboxylate To a sealed tube were added 5-fluoro-2-phenyl-3-(4,4,5,5-tetramethyl-1,3,2-dioxaborolan-2-yl)-1-tosyl-1H-pyrrolo[2,3-b]pyridine (174 mg, 0.34 mmol), (+/−)-trans-methyl 3-((2-chloro-7-methyl-7H-pyrrolo[2,3-d]pyrimidin-4-yl)amino)bicycle[2.2.2]octane-2-carboxylate (100 mg, 0.29 mmol), potassium carbonate (118 mg, 0.86 mmol), Pd(dppf)Cl$_2$ (47 mg, 0.06 mmol), 1,4-dioxane (3 mL) and water (0.2 mL). The air in the mixture was removed by bubbling with nitrogen for 10 min and the mixture was stirred at 110° C. for 3 h. The mixture was filtered through a celite pad, and the filter cake was washed with ethyl acetate (50 mL). The filtrate was washed with saturated brine (50 mL), dried over anhydrous sodium sulfate and filtered. The filtrate was concentrated in vacuo and the residue was purified by silica gel column chromatography (n-hexane/EtOAc(v/v)=5/1) to give the title compound as a yellow solid (58 mg, 30%).

$^1$H NMR (400 MHz, CDCl$_3$) δ (ppm): 8.52 (dd, J=9.0, 2.8 Hz, 1H), 8.41 (d, J=2.0 Hz, 1H), 7.87 (s, 1H), 7.85 (s, 1H), 7.52 (d, J=6.6 Hz, 2H), 7.47-7.39 (m, 3H), 7.23 (s, 1H), 7.21 (s, 1H), 6.84 (d, J=3.4 Hz, 1H), 6.32 (d, J=3.2 Hz, 1H), 4.80 (d, J=7.6 Hz, 1H), 4.62 (t, J=7.1 Hz, 1H), 3.59 (s, 3H), 3.41 (s, 3H), 2.38 (s, 3H), 2.33 (d, J=6.6 Hz, 1H), 1.92 (s, 2H), 1.71-1.63 (m, 6H), 1.49 (d, J=10.6 Hz, 2H).

Step 2: (+/−)-trans-3-((2-(5-fluoro-2-phenyl-1H-pyrrolo[2,3-b]pyridin-3-yl)-7-methyl-7H-pyrrolo[2,3-d]pyrimidin-4-yl)amino)bicyclo[2.2.2]octane-2-carboxylic Acid To a solution of (+/−)-trans-methyl 3-((2-(5-fluoro-2-phenyl-1-tosyl-1H-pyrrolo [2,3-b]pyridin-3-yl)-7-methyl-7H-pyrrolo[2,3-d]pyrimidin-4-yl)amino)bicyclo[2.2.2]octane-2-carboxylate (58 mg, 0.09 mmol) in THF/MeOH (v/v=1/1, 1.0 mL) was added a solution of sodium hydroxide in water (4 M, 0.23 mL, 0.90 mmol). The mixture was stirred at 30° C. overnight. To the reaction mixture was added water (10 mL), and the resulting mixture was acidified with hydrochloric acid (1 M) to pH about 5.5. The mixture was extracted with ethyl acetate (20 mL×3), and the combined organic layers were washed with saturated brine (50 mL), dried over anhydrous sodium sulfate, then filtered. The filtrate was concentrated in vacuo to remove the solvent and the residue was purified by silica gel column chromatography (DCM/MeOH (v/v)=10/1) to give the title compound as a yellow solid (29 mg, 66%).

MS (ESI, pos.ion) m/z: 511.2 [M+H]+;

HRMS (ESI, pos. ion) m/z: 511.2267 [M+H]+, (C29H28FN6O2) [M+H]+ theoretical value: 511.2258;

1H NMR (400 MHz, DMSO-d6) δ (ppm): 12.21 (s, 1H), 8.61 (d, J=8.0 Hz, 1H), 8.25 (s, 1H), 7.71 (d, J=6.8 Hz, 2H), 7.48-7.37 (m, 3H), 7.18 (d, J=6.9 Hz, 1H), 7.04 (d, J=3.3 Hz, 1H), 6.58 (d, J=2.9 Hz, 1H), 4.53 (t, J=6.9 Hz, 1H), 3.49 (s, 3H), 2.66 (d, J=7.1 Hz, 1H), 1.97 (s, 1H), 1.79-1.66 (m, 4H), 1.49-1.29 (m, 6H).

Example 45: (+/−)-trans-3-((5-fluoro-2-(5-fluoro-4-methyl-1H-pyrrolo[2,3-b]pyridin-3-yl) pyrimidin-4-yl)amino)bicyclo[2.2.2]octane-2-carboxylic Acid

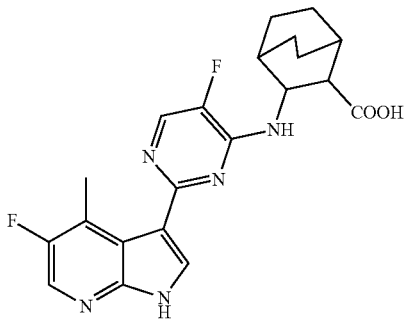 [SMILES: Cc1c(F)cnc2[nH]cc(-c3ncc(F)c(NC4C5CCC(CC5)C4C(=O)O)n3)c12]

Step 1: 5-fluoro-3-iodo-4-methylpyridin-2-amine

To a solution of 5-fluoro-4-methylpyridin-2-amine (2.00 g, 15.9 mmol) in glacial acetic acid (13 mL) were added trifluoroacetic acid (0.13 mL) and NIS (3.75 g, 16.2 mmol). The mixture was stirred at rt overnight, then poured into ice water (50 mL). The resulting mixture was adjusted with concentrated ammonia to pH9, then filtered. The filter cake was washed with water and dried in vacuo to give a yellow solid (2.87 g, 72%).

MS (ESI, pos.ion) m/z: 252.9[M+H]+;

1H NMR (400 MHz, CDCl3) δ (ppm): 7.83 (s, 1H), 4.89 (s, 3H), 2.37 (d, J=2.0 Hz, 2H).

Step 2: 5-fluoro-4-methyl-3-((trimethylsilyl)ethynyl)pyridin-2-amine

To a solution of 5-fluoro-3-iodo-4-methylpyridin-2-amine (2.88 g, 11.4 mmol) in a mixed solvent of triethylamine (58 mL) and tetrahydrofuran (11.6 mL) were added Pd(PPh3)2Cl2 (810 mg, 1.14 mmol), cuprous iodide (435 mg, 2.28 mmol) and trimethylsilylacetylene (3.23 mL, 22.9 mmol). The mixture was stirred at rt overnight under nitrogen protection and diluted with saturated aqueous ammonium chloride solution (100 mL). The resulting mixture was extracted with ethyl acetate (100 mL×3), and the combined organic layers were washed with saturated brine (200 mL), dried over anhydrous sodium sulfate, then filtered. The filtrate was concentrated in vacuo to remove the solvent and the residue was purified by silica gel column chromatography (n-hexane/EtOAc (v/v)=5/1) to give the title compound as a dark solid (1.72 g, 68%).

MS (ESI, pos.ion) m/z: 223.1 [M+H]+;

1H NMR (400 MHz, CDCl3) δ (ppm): 7.83 (s, 1H), 2.33 (d, J=1.4 Hz, 3H), 0.30 (s, 9H).

Step 3: 5-fluoro-4-methyl-1H-pyrrolo[2,3-b]pyridine

To a solution of 5-fluoro-4-methyl-3-((trimethylsilyl)ethynyl)pyridin-2-amine (1.72 g, 7.74 mmol) in DMF (16 mL) was added potassium tert-butoxide (2.60 g, 23.2 mmol), and the mixture was stirred at 80° C. for 1 h under nitrogen protection, then cooled to rt. To the reaction mixture was added water (100 mL), and the resulting mixture was extracted with ethyl acetate (100 mL×3). The combined organic layers were washed with saturated brine, dried over anhydrous sodium sulfate and filtered. The filtrate was concentrated in vacuo and the residue was purified by silica gel column chromatography (PE/EA (v/v)=5/1) to give the title compound as a white solid (550 mg, 47%).

MS (ESI, pos.ion) m/z: 151.1 [M+H]+;

1H NMR (600 MHz, CDCl3) δ (ppm): 9.62 (s, 1H), 8.16 (d, J=2.2 Hz, 1H), 7.42-7.33 (m, 1H), 6.53 (dd, J=3.1, 2.1 Hz, 1H), 2.53 (d, J=1.0 Hz, 3H).

Step 4: 3-bromo-5-fluoro-4-methyl-1H-pyrrolo[2,3-b]pyridine

To a solution of 5-fluoro-4-methyl-1H-pyrrolo[2,3-b]pyridine (540 mg, 3.60 mmol) in DMF (8 mL) was added bromine (0.37 mL, 7.19 mmol). The reaction mixture was stirred at rt for 2 h. A saturated aqueous Na2S2O3 solution (50 mL) was added to quench the reaction, and the resulting mixture was extracted with EtOAc (50 mL×3). The combined organic phases were washed with saturated brine (50 mL×3), dried over anhydrous Na2SO4, filtered, and the filtrate was concentrated in vacuo. The residue was purified by silica gel chromatograph (n-hexane/EtOAc (v/v)=5/1) to give the title compound as a white solid (760 mg, 92%).

MS (ESI, pos. ion) m/z: 231.2 [M+H]+;

1H NMR (400 MHz, DMSO-d6) δ (ppm): 12.13 (s, 1H), 8.20 (d, J=1.7 Hz, 1H), 7.72 (d, J=2.6 Hz, 1H), 2.66 (s, 3H).

Step 5: 3-bromo-5-fluoro-4-methyl-1-tosyl-1H-pyrrolo[2,3-b]pyridine

To dried tetrahydrofuran (10 mL) was added 3-bromo-5-fluoro-4-methyl-1H-pyrrolo[2,3-b]pyridine (760 mg, 3.32 mmol). Sodium hydride (265 mg, 6.63 mmol, 60%) was added to the solution at 0° C., and the resulting mixture was stirred at 0° C. for 30 min. Then p-toluenesulfonyl chloride (759 mg, 3.98 mmol) was added to the mixture, and the mixture was warmed to rt and stirred overnight. Water (100 mL) was added to quench the reaction, and the resulting mixture was extracted with EtOAc (100 mL×3). The combined organic phases were dried over anhydrous Na2SO4, filtered, and the filtrate was concentrated in vacuo. The residue was purified by silica gel chromatograph (n-hexane/EtOAc (v/v)=10/1) to give the title compound as a yellow solid (840 mg, 66%).

MS (ESI, pos. ion) m/z: 382.9 [M+H]+;

1H NMR (400 MHz, CDCl3) δ (ppm): 8.24 (s, 1H), 8.06 (d, J=8.3 Hz, 2H), 7.81 (s, 1H), 7.31 (d, J=8.2 Hz, 2H), 2.68 (d, J=1.3 Hz, 3H), 2.40 (s, 3H).

Step 6: 5-fluoro-4-methyl-3-(4,4,5,5-tetramethyl-1,3,2-dioxaborolan-2-yl)-1-tosyl-1H-pyrrolo [2,3-b]pyridine A microwave tube was charged with 3-bromo-5-fluoro-4-methyl-1-tosyl-1H-pyrrolo[2,3-b]pyridine (400 mg, 1.04 mmol), bis(pinacolato)diboron (397 mg, 1.56 mmol), potassium acetate (204 mg, 2.08 mmol), Pd(dppf)Cl$_2$ (85 mg, 0.10 mmol) and dimethoxyethane (5 mL). The air in the mixture was removed by bubbling with nitrogen for 10 min and the mixture was stirred at 130° C. for 2 h with microwave heating. The mixture was cooled to rt and filtered through a celite pad. The filter cake was washed with ethyl acetate (10 mL) and the combined filtrates were concentrated in vacuo to dry. The residue was purified by silica gel chromatograph (n-hexane/EtOAc (v/v)=10/1) to give the title compound as a white solid (352 mg, 78%).

MS (ESI, pos.ion) m/z: 431.0 [M+H]$^+$.

Step 7: (+/−)-trans-methyl 3-((5-fluoro-2-(5-fluoro-4-methyl-1-tosyl-1H-pyrrolo[2,3-b]pyridine-3-yl)pyrimidin-4-yl)amino)bicyclo[2.2.2]octane-2-carboxylate To a sealed tub were added 5-fluoro-4-methyl-3-(4,4,5,5-tetramethyl-1,3,2-dioxaborolan-2-yl)-1-tosyl-1H-pyrrolo[2,3-b]pyridine (163 mg, 0.38 mmol), (+/−)-trans-methyl 3-((2-chloro-5-fluoropyrimidin-4-yl)amino)bicyclo[2.2.2]octane-2-carboxylate (100 mg, 0.32 mmol), potassium carbonate (132 mg, 0.96 mmol), Pd(dppf)Cl$_2$ (52 mg, 0.06 mmol), 1,4-dioxane (3 mL) and water (0.2 mL). The air in the mixture was removed by bubbling with nitrogen for 10 min and the mixture was stirred at 110° C. for 3 h. The mixture was filtered through a celite pad, and the filter cake was washed with ethyl acetate (50 mL). The filtrate was washed with saturated brine (50 mL), dried over anhydrous sodium sulfate and filtered. The filtrate was concentrated in vacuo and the residue was purified by silica gel column chromatography (n-hexane/EtOAc(v/v)=5/1) to give the title compound as a yellow solid (120 mg, 65%).

MS (ESI, pos.ion) m/z: 582.1[M+H]$^+$;

$^1$H NMR (400 MHz, CDCl$_3$) δ (ppm): 8.25 (d, J=9.4 Hz, 2H), 8.10 (dd, J=11.7, 5.7 Hz, 3H), 7.30 (s, 1H), 5.19 (d, J=5.5 Hz, 1H), 4.68 (s, 1H), 3.52 (s, 3H), 2.62 (d, J=1.9 Hz, 3H), 2.45 (d, J=5.5 Hz, 1H), 2.39 (s, 3H), 2.04 (s, 1H), 1.95 (s, 2H), 1.87-1.62 (m, 8H).

Step 8: (+/−)-trans-3-((5-fluoro-2-(5-fluoro-4-methyl-1H-pyrrolo[2,3-b]pyridin-3-yl)pyrimidin-4-yl)amino)bicyclo[2.2.2]octane-2-carboxylic Acid To a solution of (+/−)-trans-methyl 3-((5-fluoro-2-(5-fluoro-4-methyl-1-tosyl-1H-pyrrolo[2,3-b]pyridin-3-yl)pyrimidin-4-yl)amino)bicyclo[2.2.2]octane-2-carboxylate (120 mg, 0.21 mmol) in THF/MeOH (v/v=1/1, 4 mL) was added aqueous sodium hydroxide solution (4 M, 0.53 mL, 2.10 mmol). The mixture was stirred at 30° C. overnight. To the reaction mixture was added water (10 mL), and the resulting mixture was acidified with hydrochloric acid (1 M) to pH about 5.5. The mixture was extracted with ethyl acetate (20 mL×3), and the combined organic layers were washed with saturated brine, dried over anhydrous sodium sulfate, then filtered. The filtrate was concentrated in vacuo to remove the solvent and the residue was purified by silica gel column chromatography (DCM/MeOH (v/v)=10/1) to give the title compound as a yellow solid (32 mg, 38%).

MS (ESI, pos.ion) m/z: 414.1 [M+H]$^+$;

HRMS (ESI, pos. ion) m/z: 414.1750 [M+H]$^+$, (C$_{21}$H$_{22}$F$_2$N$_5$O$_2$) [M+H]$^+$ theoretical value: 414.1742;

$^1$H NMR (400 MHz, DMSO-d$_6$) δ (ppm): 12.31 (s, 1H), 12.07 (s, 1H), 8.55 (s, 1H), 8.27 (d, J=2.0 Hz, 1H), 8.10 (s, 2H), 7.60-7.38 (m, 4H), 6.76 (s, 1H), 4.64 (s, 1H), 2.53 (d, J=2.5 Hz, 4H), 1.99 (s, 2H), 1.86-1.39 (m, 8H);

$^{13}$C NMR (101 MHz, DMSO-d$_6$) δ (ppm): 175.93, 167.43, 158.37, 158.31, 156.07, 153.72, 151.71, 151.60, 146.15, 138.48, 138.31, 132.21, 132.02, 131.80, 131.45, 131.14, 129.11, 126.98, 126.81, 117.69, 67.90, 50.33, 48.21, 38.59, 30.28, 29.08, 28.83, 28.74, 25.74, 24.27, 23.74, 22.84, 21.48, 19.43, 14.32, 13.61, 13.56, 11.25.

Example 46: (+/−)-trans-3-((2-(5-fluoro-4-methyl-1H-pyrrolo[2,3-b]pyridin-3-yl)-6-phenyl pyrimidin-4-yl)amino)bicyclo[2.2.2]octane-2-carboxylic Acid

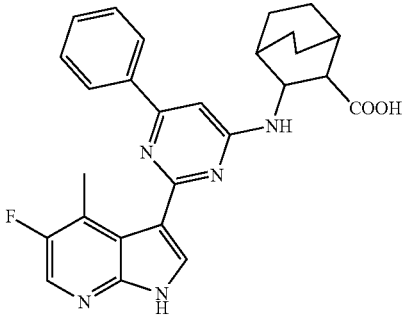 [SMILES: Cc1c(F)cnc2[nH]cc(-c3nc(NC4C5CCC(CC5)C4C(=O)O)cc(-c4ccccc4)n3)c12]

Step 1: (+/−)-trans-methyl 3-((2-(5-fluoro-4-methyl-1-tosyl-1H-pyrrolo[2,3-b]pyridin-3-yl)-6-phenylpyrimidin-4-yl)amino)bicyclo[2.2.2]octane-2-carboxylate To a sealed tube were added 5-fluoro-4-methyl-3-(4,4,5,5-tetramethyl-1,3,2-dioxaborolan-2-yl)-1-tosyl-1H-pyrrolo[2,3-b]pyridine (112 mg, 0.26 mmol), (+/−)-trans-methyl 3-((2-chloro-6-phenylpyrimidin-4-yl)amino)bicyclo[2.2.2]octane-2-carboxylate (80 mg, 0.22 mmol), potassium carbonate (89 mg, 0.65 mmol), Pd(dppf)Cl$_2$ (35 mg, 0.04 mmol), 1,4-dioxane (3 mL) and water (0.2 mL). The air in the mixture was removed by bubbling with nitrogen for 10 min and the mixture was stirred at 110° C. for 3 h. The mixture was filtered through a celite pad, and the filter cake was washed with ethyl acetate (50 mL). The filtrate was washed with saturated brine (50 mL), dried over anhydrous sodium sulfate and filtered. The filtrate was concentrated in vacuo and the residue was purified by silica gel column chromatography (n-hexane/EtOAc (v/v)=5/1) to give the title compound as a yellow solid (92 mg, 67%).

$^1$H NMR (400 MHz, CDCl$_3$) δ (ppm): 8.37 (s, 1H), 8.26 (s, 1H), 8.12 (d, J=8.3 Hz, 2H), 8.07 (d, J=5.6 Hz, 2H), 7.54-7.46 (m, 3H), 7.30 (s, 1H), 6.83 (s, 1H), 5.29 (s, 1H), 4.46 (s, 1H), 3.69 (s, 3H), 2.67 (s, 3H), 2.46 (d, J=5.1 Hz, 1H), 2.40 (s, 3H), 2.10 (s, 1H), 1.96-1.94 (m, 1H), 1.71 (m, 8H).

Step 2: (+/−)-trans-3-((2-(5-fluoro-4-methyl-1H-pyrrolo[2,3-b]pyridin-3-yl)-6-phenylpyrimidin-4-yl)amino)bicyclo[2.2.2]octane-2-carboxylic Acid To a solution of (+/−)-trans-methyl 3-((2-(5-fluoro-4-methyl-1-tosyl-1H-pyrrolo[2,3-b]pyridin-3-yl)-6-phenylpyrimidin-4-yl)amino)bicyclo[2.2.2]octane-2-carboxylate (92 mg, 0.14 mmol) in THF/MeOH (v/v=1/1, 4 mL) was added aqueous sodium hydroxide solution (4 M, 0.33 mL, 1.40 mmol). The mixture was stirred at 30° C. overnight. To the reaction mixture was added water (10 mL), and the resulting mixture was acidified with hydrochloric acid (1 M) to pH about 5.5. The mixture was extracted with ethyl acetate (20 mL×3), and the combined organic layers were washed with saturated brine (50 mL), dried over anhydrous sodium sulfate, then filtered. The filtrate was concentrated in vacuo to remove the solvent and the residue was purified by silica gel column chromatography (DCM/MeOH (v/v)=10/1) to give the title compound as a yellow solid (49 mg, 72%).

MS (ESI, pos.ion) m/z: 472.5 [M+H]$^+$;
HRMS (ESI, pos. ion) m/z: 472.2147 [M+H]$^+$, ($C_{27}H_{27}FN_5O_2$) [M+H]$^+$ theoretical value: 472.2149;
$^1$H NMR (400 MHz, DMSO-$d_6$) δ (ppm): 12.13 (s, 1H), 8.18 (s, 1H), 8.14 (s, 1H), 8.04 (s, 2H), 7.51 (d, J=7.6 Hz, 4H), 6.81 (s, 1H), 4.61 (s, 1H), 2.84 (s, 3H), 1.96 (s, 1H), 1.83-1.39 (m, 10H).

Example 47: (+/−)-trans-3-((2-(5-fluoro-4-methyl-1H-pyrrolo[2,3-b]pyridin-3-yl)-7-methyl-7H-pyrrolo[2,3-d]pyrimidin-4-yl)amino)bicyclo[2.2.2]octane-2-carboxylic Acid

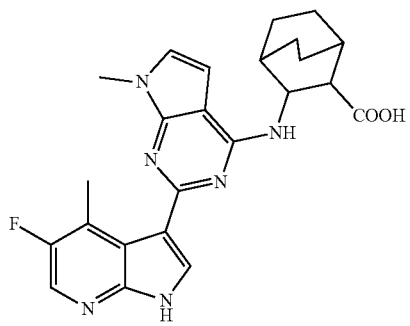 [SMILES: Cc1c(F)cnc2[nH]cc(-c3nc(NC4C5CCC(CC5)C4C(=O)O)c4ccn(C)c4n3)c12]

Step 1: (+/−)-trans-methyl 3-((2-(5-fluoro-4-methyl-1-tosyl-1H-pyrrolo[2,3-b]pyridin-3-yl)-7-methyl-7H-pyrrolo[2,3-d]pyrimidin-4-yl)amino)bicyclo[2.2.2]octane-2-carboxylate To a sealed tube were added 5-fluoro-4-methyl-3-(4,4,5,5-tetramethyl-1,3,2-dioxaborolan-2-yl)-1-tosyl-1H-pyrrolo[2,3-b]pyridine (91 mg, 0.21 mmol), (+/−)-trans-methyl 3-((2-chloro-7-methyl-7H-pyrrolo[2,3-d]pyrimidin-4-yl)amino)bicyclo[2.2.2]octane-2-carboxylate (60 mg, 0.17 mmol), potassium carbonate (71 mg, 0.51 mmol), Pd(dppf)Cl$_2$ (28 mg, 0.03 mmol), 1,4-dioxane (3 mL) and water (0.2 mL). The air in the mixture was removed by bubbling with nitrogen for 10 min and the mixture was stirred at 110° C. for 4 h. The mixture was filtered through a celite pad, and the filter cake was washed with ethyl acetate (50 mL). The filtrate was washed with saturated brine (50 mL), dried over anhydrous sodium sulfate and filtered. The filtrate was concentrated in vacuo and the residue was purified by silica gel column chromatography (n-hexane/EtOAc(v/v)=5/1) to give the title compound as a yellow solid (77 mg, 73%).
$^1$H NMR (400 MHz, CDCl$_3$) δ (ppm): 8.32 (s, 1H), 8.24 (s, 1H), 8.13 (d, J=8.2 Hz, 2H), 6.96 (d, J=3.4 Hz, 1H), 6.45 (s, 1H), 5.18 (s, 1H), 4.78 (s, 1H), 3.82 (s, 3H), 3.77 (s, 1H), 3.54 (s, 3H), 2.68 (s, 3H), 2.47 (d, J=5.1 Hz, 1H), 2.39 (s, 3H), 2.03 (s, 2H), 1.90-1.62 (m, 8H).

Step 2: (+/−)-trans-3-((2-(5-fluoro-4-methyl-1H-pyrrolo[2,3-b]pyridin-3-yl)-7-methyl-7H-pyrrolo[2,3-d]pyrimidin-4-yl)amino)bicyclo[2.2.2]octane-2-carboxylic Acid To a solution of (+/−)-trans-methyl 3-((2-(5-fluoro-4-methyl-1-tosyl-1H-pyrrolo [2,3-b]pyridin-3-yl)-7-methyl-7H-pyrrolo[2,3-d]pyrimidin-4-yl)amino)bicyclo[2.2.2]octane-2-carboxylate (75 mg, 0.12 mmol) in THF/MeOH (v/v=1/1, 4 mL) was added a solution of sodium hydroxide in water (4 M, 0.30 mL, 1.20 mmol). The mixture was stirred at 30° C. overnight. To the reaction mixture was added water (10 mL), and the resulting mixture was acidified with hydrochloric acid (1 M) to pH about 5.5. The mixture was extracted with ethyl acetate (20 mL×3), and the combined organic layers were washed with saturated brine (50 mL), dried over anhydrous sodium sulfate, then filtered. The filtrate was concentrated in vacuo to remove the solvent and the residue was purified by silica gel column chromatography (DCM/MeOH (v/v)=10/1) to give the title compound as a yellow solid (19 mg, 35%).

MS (ESI, pos.ion) m/z: 449.5 [M+H]$^+$;
HRMS (ESI, pos. ion) m/z: 449.2115 [M+H]$^+$, ($C_{24}H_{26}FN_6O_2$) [M+H]$^+$ theoretical value: 449.2101;
$^1$H NMR (400 MHz, DMSO-$d_6$) δ (ppm): 12.09 (s, 1H), 8.26-8.07 (m, 2H), 7.96 (d, J=2.1 Hz, 1H), 7.78-7.59 (m, 1H), 7.50 (d, J=6.8 Hz, 1H), 4.64 (s, 1H), 4.14 (s, 1H), 2.79 (s, 4H), 1.97 (s, 1H), 1.63 (m, 8H).

Example 48: (+/−)-trans-3-((5-fluoro-2-(5-fluoro-1H-pyrrolo[2,3-b]pyridin-3-yl)-6-phenyl pyrimidin-4-yl)amino)bicyclo[2.2.2]octane-2-carboxylic Acid

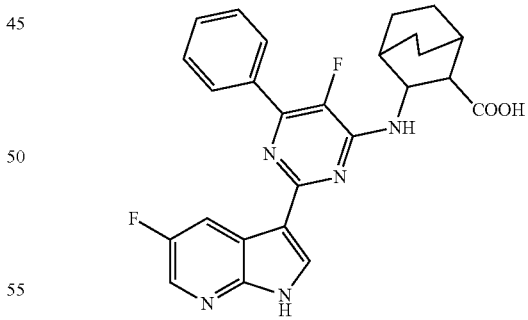

Step 1: (+/−)-trans-methyl 3-((2,6-dichloro-5-fluoropyrimidin-4-yl)amino)bicyclo[2.2.2]octane-2-carboxylate To a reaction flask were added 2,4,6-trichloro-5-fluoropyrimidine (10.00 g, 49.65 mmol), potassium carbonate (21.00 g, 148.90 mmol), (+/−)-trans-methyl 3-aminobicyclo[2.2.2]octane-2-carboxylate (10.00 g, 54.61 mmol) and DMF (50 mL). The mixture was stirred at rt for 5 h. When the reaction was completed, to the reaction mixture was added water (100 mL), and the resulting mixture was extracted with ethyl acetate (100 mL×3). The combined organic layers were washed with saturated brine (50 mL), dried over anhydrous sodium sulfate and filtered. The filtrate was concentrated in vacuo and the residue was purified by silica gel column chromatography (PE/EtOAc (v/v)=20/1) to give the title compound as a light yellow solid (12.00 g, 69%).

MS (ESI, pos. ion) m/z: 348.10[M+H]$^+$.

Step 2: (+/−)-trans-methyl 3-((2-chloro-5-fluoro-6-phenylpyrimidin-4-yl)amino)bicyclo[2.2.2]octane-2-carboxylate To acetonitrile (100 mL) were added (+/−)-trans-methyl 3-((2,6-dichloro-5-fluoropyrimidin-4-yl)amino)bicyclo[2.2.2]octane-2-carboxylate (2.00 g, 5.74 mmol), phenylboronic acid (0.70 g, 5.74 mmol), potassium acetate (1.70 g, 17.2 mmol) and Pd(dppf)Cl$_2$ (0.50 g, 0.57 mmol), then to the mixture was added water (5 mL). The resulting mixture was stirred at 80° C. for 12 h under nitrogen protection. The mixture was filtered to remove solid impurities. The filtrate was concentrated in vacuo, and the residue was purified by silica gel column chromatography (PE/EtOAc (v/v)=20/1) to give the title compound as a yellow solid (430 mg, 19%).

MS (ESI, pos. ion) m/z: 390.1[M+H]$^+$.

Step 3: (+/−)-trans-methyl 3-((5-fluoro-2-(5-fluoro-1-tosyl-1H-pyrrolo[2,3-b]pyridin-3-yl)-6-phenylpyrimidin-4-yl)amino)bicyclo[2.2.2]octane-2-carboxylate To THF (10 mL) were added 5-fluoro-3-(4,4,5,5-tetramethyl-1,3,2-dioxaborolan-2-yl)-1-tosyl-1H-pyrrolo[2,3-b]pyridine (670 mg, 0.97 mmol, 60%), potassium carbonate (570 mg, 4.10 mmol), palladium acetate (23 mg, 0.10 mmol), X-Phos (100 mg, 0.20 mmol) and (+/−)-trans-methyl 3-((2-chloro-5-fluoro-6-phenylpyrimidin-4-yl)amino)bicyclo[2.2.2]octane-2-carboxylate (400 mg, 1.02 mmol). Then H$_2$O (1 mL) was added to the mixture, and the mixture was heated to 110° C. and stirred for 12 h. The mixture was filtered to remove solid impurities. The filtrate was concentrated in vacuo, and the residue was purified by silica gel column chromatography (PE/EtOAc (v/v)=8/1) to give the title compound as a light yellow solid (200 mg, 30%).

MS (ESI, pos. ion) m/z: 644.3[M+H]$^+$.

Step 4: (+/−)-trans-3-((5-fluoro-2-(5-fluoro-1H-pyrrolo[2,3-b]pyridin-3-yl)-6-phenylpyrimidin-4-yl)amino)bicyclo[2.2.2]octane-2-carboxylic Acid To a solution of (+/−)-trans-methyl 3-((5-fluoro-2-(5-fluoro-1-tosyl-1H-pyrrolo[2,3-b]pyridin-3-yl)-6-phenylpyrimidin-4-yl)amino)bicyclo[2.2.2]octane-2-carboxylate (200 mg, 0.31 mmol) in a mixed solvent of THF (8 mL) and MeOH (4 mL) was added a solution of NaOH (124 mg, 3.10 mmol) in water (2 mL). The mixture was stirred at rt overnight, then diluted with water (10 mL). The resulting mixture was acidified with hydrochloric acid (1 M) to pH about 3 to 4. The resulting mixture was extracted with ethyl acetate (20 mL×3). The combined organic layers were washed with saturated brine (50 mL), dried over anhydrous sodium sulfate and filtered. The filtrate was concentrated in vacuo to remove the solvent and the residue was purified by silica gel column chromatography (DCM/MeOH (v/v)=10/1-5/1) to give the title compound as a white solid (100 mg, 68%).

MS (ESI, pos. ion) m/z: 476.1[M+H]$^+$;
HRMS (ESI, pos. ion) m/z: 476.1816 [M+H]$^+$, (C$_{26}$H$_{24}$F$_2$N$_5$O$_2$) [M+H]$^+$ theoretical value: 476.1898;
$^1$H NMR (400 MHz, DMSO-d$_6$) δ (ppm): 12.52 (s, 1H), 12.26 (s, 1H), 8.68 (d, J=8.0 Hz, 1H), 8.37 (d, J=7.6 Hz, 3H), 8.25 (s, 1H), 7.53 (m, 4H), 4.70 (s, 1H), 3.58 (s, 2H), 2.89 (d, J=6.2 Hz, 1H), 2.17 (s, 1H), 2.01 (s, 1H), 1.95 (s, 1H), 1.50 (m, 5H).

Example 49: (+/−)-trans-3-((5-fluoro-2-(5-fluoro-1H-pyrrolo[2,3-b]pyridin-3-yl)-6-(furan-2-yl)pyrimidin-4-yl)amino)bicyclo[2.2.2]octane-2-carboxylic Acid

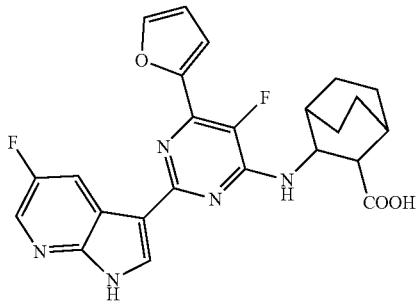 [SMILES: O=C(O)C1C2CCC(CC2)C1Nc1nc(-c2c[nH]c3ncc(F)cc23)nc(-c2ccco2)c1F]

Step 1: (+/−)-trans-methyl 3-((2-chloro-5-fluoro-6-(furan-2-yl)pyrimidin-4-yl)amino)bicyclo [2.2.2]octane-2-carboxylate To acetonitrile (100 mL) were added (+/−)-trans-methyl 3-((2,6-dichloro-5-fluoropyrimidin-4-yl)amino)bicyclo[2.2.2]octane-2-carboxylate (2.00 g, 5.74 mmol), 2-furanboronic acid (0.65 g, 5.74 mmol), potassium acetate (1.70 g, 17.2 mmol) and Pd(dppf)Cl$_2$ (0.50 g, 0.57 mmol), then to the mixture was added water (5 mL). The resulting mixture was stirred at 80° C. for 12 h under nitrogen protection. The mixture was filtered to remove solid impurities. The filtrate was concentrated in vacuo, and the residue was purified by silica gel column chromatography (PE/EtOAc (v/v)=20/1) to give the title compound as a yellow solid (700 mg, 30%).

MS (ESI, pos. ion) m/z: 380.2[M+H]$^+$.

Step 2: (+/−)-trans-methyl 3-((5-fluoro-2-(5-fluoro-1-tosyl-1H-pyrrolo[2,3-b]pyridin-3-yl)-6-(furan-2-yl)pyrimidin-4-yl)amino)bicyclo[2.2.2]octane-2-carboxylate To THF (10 mL) were added 5-fluoro-3-(4,4,5,5-tetramethyl-1,3,2-dioxaborolan-2-yl)-1-tosyl-1H-pyrrolo[2,3-b]pyridine (390 mg, 0.55 mmol, 60%), potassium carbonate (290 mg, 2.10 mmol), palladium acetate (11 mg, 0.05 mmol), X-Phos (50 mg, 0.10 mmol) and (+/−)-trans-methyl 3-((2-chloro-5-fluoro-6-phenylpyrimidin-4-yl)amino)bicyclo[2.2.2]octane-2-carboxylate (200 mg, 1.02 mmol). Then H$_2$O (1 mL) was added to the mixture, and the mixture was heated to 100° C. and stirred for 12 h. The mixture was filtered to remove solid impurities. The filtrate was concentrated in vacuo, and the residue was purified by silica gel column chromatography (PE/EtOAc (v/v)=8/1) to give the title compound as a light yellow solid (250 mg, 75%).
MS (ESI, pos. ion) m/z: 634.2 [M+H]+.

Step 3: (+/−)-trans-3-((5-fluoro-2-(5-fluoro-1H-pyrrolo[2,3-b]pyridin-3-yl)-6-(furan-2-yl) pyrimidin-4-yl)amino)bicyclo[2.2.2]octane-2-carboxylic Acid To a solution of (+/−)-trans-methyl 3-((5-fluoro-2-(5-fluoro-1-tosyl-1H-pyrrolo [2,3-b]pyridin-3-yl)-6-(furan-2-yl)pyrimidin-4-yl)amino)bicyclo[2.2.2]octane-2-carboxylate (250 mg, 0.40 mmol) in THF/MeOH (v/v=8 mL/4 mL) was added a solution of sodium hydroxide (140 mg, 4.00 mmol) in water (2 mL). The mixture was stirred at rt overnight. To the reaction mixture was added water (10 mL), and the resulting mixture was acidified with hydrochloric acid (1 M) to pH about 3 to 4. The mixture was extracted with ethyl acetate (20 mL×3), and the combined organic layers were washed with saturated brine (50 mL), dried over anhydrous sodium sulfate, then filtered. The filtrate was concentrated in vacuo and the residue was purified by silica gel column chromatography (DCM/MeOH (v/v)=10/1-5/1) to give the title compound as a white solid (120 mg, 54%).
MS (ESI, pos. ion) m/z: 466.3 [M+H]+;
HRMS (ESI, pos. ion) m/z: 466.1699 [M+H]+, $(C_{24}H_{22}F_2N_5O_3S)$ [M+H]+ theoretical value: 466.1691;
1H NMR (400 MHz, DMSO-$d_6$) δ (ppm): 12.27 (s, 1H), 8.60 (d, J=8.4 Hz, 1H), 8.27 (d, J=8.8 Hz, 2H), 8.00 (s, 1H), 7.61 (d, J=5.8 Hz, 1H), 7.24 (s, 1H), 6.75 (s, 1H), 4.71 (s, 1H), 2.88 (d, J=5.5 Hz, 1H), 2.01 (s, 1H), 1.98 (s, 1H), 1.77 (m, 3H), 1.50 (m, 5H); 13C NMR (101 MHz, DMSO-$d_6$) δ (ppm): 176.04, 157.58, 157.32, 154.93, 152.60, 148.55, 146.40, 145.65, 140.32, 137.72, 137.24, 131.91, 131.62, 131.24, 118.82, 115.48, 114.30, 112.64, 51.14, 48.29, 40.40, 40.20, 39.99, 39.78.

Example 50: (+/−)-trans-3-((6-([1,1'-biphenyl]-4-yl)-5-fluoro-2-(5-fluoro-1H-pyrrolo[2,3-b]pyridin-3-yl)pyrimidin-4-yl)amino)bicyclo[2.2.2]octane-2-carboxylic Acid

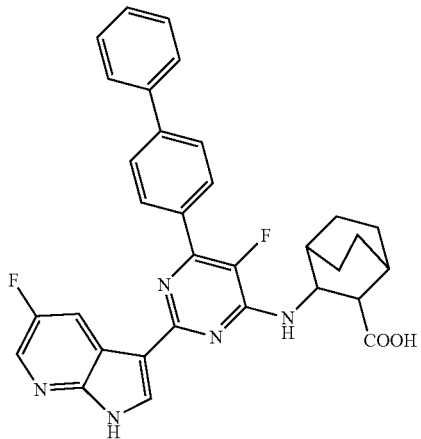 [SMILES: O=C(O)C1C2CCC(CC2)C1Nc1nc(-c2c[nH]c3ncc(F)cc23)nc(-c2ccc(-c3ccccc3)cc2)c1F]

Step 1: (+/−)-trans-methyl 3-((6-([1,1'-biphenyl]-4-yl)-2-chloro-5-fluoropyrimidin-4-yl)amino) bicyclo[2.2.2]octane-2-carboxylate To acetonitrile (50 mL) were added (+/−)-trans-methyl 3-((2,6-dichloro-5-fluoropyrimidin-4-yl)amino)bicyclo [2.2.2]octane-2-carboxylate (1.00 g, 2.87 mmol), [1,1'-biphenyl]-4-ylboronic acid (0.57 g, 2.87 mmol), potassium acetate (0.85 g, 8.62 mmol) and Pd(dppf)Cl$_2$ (0.25 g, 0.28 mmol), then to the mixture was added water (2 mL). The resulting mixture was stirred at 80° C. for 12 h under nitrogen protection. The mixture was filtered to remove solid impurities. The filtrate was concentrated in vacuo, and the residue was purified by silica gel column chromatography (PE/EtOAc (v/v)=20/1) to give the title compound as a yellow solid (600 mg, 45%).
MS (ESI, pos. ion) m/z: 466.0 [M+H]+.

Step 2: (+/−)-trans-methyl 3-((6-([1,1'-biphenyl]-4-yl)-5-fluoro-2-(5-fluoro-1-tosyl-1H-pyrrolo[2,3-b]pyridin-3-yl)pyrimidin-4-yl)amino)bicyclo[2.2.2]octane-2-carboxylate To THF (10 mL) were added 5-fluoro-3-(4,4,5,5-tetramethyl-1,3,2-dioxaborolan-2-yl)-1-tosyl-1H-pyrrolo[2,3-b]pyridine (450 mg, 0.64 mmol, 60%), potassium carbonate (355 mg, 2.57 mmol), palladium acetate (14 mg, 0.06 mmol), X-Phos (61 mg, 0.12 mmol) and (+/−)-trans-methyl 3-((6-([1,1'-biphenyl]-4-yl)-2-chloro-5-fluoropyrimidin-4-yl)amino)bicycle [2.2.2]octane-2-carboxylate (300 mg, 0.64 mmol). Then H$_2$O (0.5 mL) was added to the mixture, and the mixture was heated to 80° C. and stirred for 12 h. The mixture was filtered to remove solid impurities. The filtrate was concentrated in vacuo, and the residue was purified by silica gel column chromatography (PE/EtOAc (v/v)=8/1) to give the title compound as a light yellow solid (300 mg, 65%).
MS (ESI, pos. ion) m/z: 720.1 [M+H]+.

Step 3: (+/−)-trans-3-((6-([1,1'-biphenyl]-4-yl)-5-fluoro-2-(5-fluoro-1H-pyrrolo[2,3-b]pyridin-3-yl)pyrimidin-4-yl)amino)bicyclo[2.2.2]octane-2-carboxylic Acid To a solution of (+/−)-trans-methyl 3-((6-([1,1'-biphenyl]-4-yl)-5-fluoro-2-(5-fluoro-1-tosyl-1H-pyrrolo[2,3-b]pyridin-3-yl)pyrimidin-4-yl)amino)bicyclo[2.2.2]octane-2-carboxy late (300 mg, 0.42 mmol) in a mixed solvent of THF (8 mL) and MeOH (4 mL) was added a solution of NaOH (184 mg, 4.20 mmol) in water (2 mL). The mixture was stirred at rt overnight, then diluted with water (10 mL). The resulting mixture was acidified with hydrochloric acid (1 M) to pH about 3 to 4. The resulting mixture was extracted with ethyl acetate (20 mL×3). The combined organic layers were washed with saturated brine (50 mL), dried over anhydrous sodium sulfate and filtered. The filtrate was concentrated in vacuo to remove the solvent and the residue was purified by silica gel column chromatography (DCM/MeOH (v/v)=10/1-5/1) to give the title compound as a white solid (103 mg, 45%).
MS (ESI, pos. ion) m/z: 552.3 [M+H]+;
HRMS (ESI, pos. ion) m/z: 552.2221 [M+H]+, $(C_{32}H_{28}F_2N_5O_2)$ [M+H]+ theoretical value: 552.2211;
1H NMR (400 MHz, DMSO-$d_6$) δ (ppm): 12.31 (s, 1H), 8.58 (d, J=7.7 Hz, 1H), 8.31 (d, J=10.0 Hz, 2H), 8.18 (d, J=7.9 Hz, 2H), 7.88 (d, J=8.1 Hz, 2H), 7.78 (d, J=7.5 Hz, 2H), 7.65 (d, J=5.9 Hz, 1H), 7.51 (t, J=7.4 Hz, 2H), 7.41 (t, J=7.1 Hz, 1H), 4.76 (s, 1H), 2.93 (d, J=6.0 Hz, 1H), 2.03 (s, 2H), 1.90-1.74 (m, 3H), 1.52 (m, 5H);
13C NMR (101 MHz, DMSO-$d_6$) δ (ppm): 176.07, 157.52, 157.43, 157.30, 154.91, 152.99, 152.86, 151.95, 146.43, 144.74, 144.68, 142.89, 141.88, 140.31, 139.87, 139.62, 133.69, 133.64, 131.90, 131.61, 131.30, 130.06, 129.60, 129.54, 129.48, 128.35, 127.24, 125.35, 118.86, 118.79, 115.55, 115.33, 114.42, 114.38, 40.44, 40.23, 40.02, 39.81, 39.60, 30.89.

Example 51: (+/−)-trans-3-((5-fluoro-2-(5-fluoro-1H-pyrrolo[2,3-b]pyridin-3-yl)-6-(1-methyl-1H-pyrazol-4-yl)pyrimidin-4-yl)amino)bicyclo[2.2.2]octane-2-carboxylic Acid

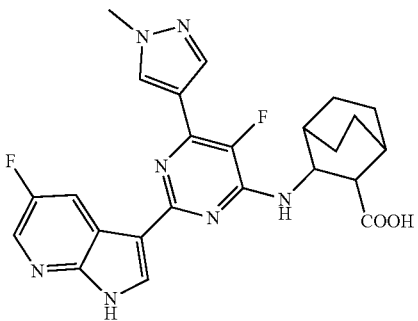 [SMILES: Cn1cc(-c2nc(-c3c[nH]c4ncc(F)cc34)nc(NC3C4CCC(CC4)C3C(=O)O)c2F)cn1]

Step 1: (+/−)-trans-methyl 3-((2-chloro-5-fluoro-6-(1-methyl-1H-pyrazol-4-yl)pyrimidin-4-yl) amino)bicyclo[2.2.2]octane-2-carboxylate To acetonitrile (25 mL) were added (+/−)-trans-methyl 3-((2,6-dichloro-5-fluoropyrimidin-4-yl)amino)bicyclo[2.2.2]octane-2-carboxylate (0.50 g, 1.44 mmol), (1-methyl-1H-pyrazol-4-yl)boronic acid (0.18 g, 1.44 mmol), potassium acetate (0.42 g, 4.31 mmol) and Pd(dppf)Cl$_2$ (0.13 g, 0.14 mmol), then to the mixture was added water (1 mL). The resulting mixture was stirred at 80° C. for 12 h under nitrogen protection. The mixture was filtered to remove the solid impurities. The filtrate was concentrated in vacuo, and the residue was purified by silica gel column chromatography (PE/EtOAc (v/v)=20/1) to give the title compound as a yellow solid (190 mg, 34%).

MS (ESI, pos. ion) m/z: 394.2 [M+H]$^+$.

Step 2: (+/−)-trans-methyl 3-((5-fluoro-2-(5-fluoro-1-tosyl-1H-pyrrolo[2,3-b]pyridin-3-yl)-6-(1-methyl-1H-pyrazol-4-yl)pyrimidin-4-yl)amino)bicyclo[2.2.2]octane-2-carboxylate To THF (10 mL) were added 5-fluoro-3-(4,4,5,5-tetramethyl-1,3,2-dioxaborolan-2-yl)-1-tosyl-1H-pyrrolo[2,3-b]pyridine (422 mg, 0.61 mmol, 60%), potassium carbonate (280 mg, 2.03 mmol), palladium acetate (22 mg, 0.10 mmol), X-Phos (100 mg, 0.20 mmol) and (+/−)-trans-methyl 3-((2-chloro-5-fluoro-6-(1-methyl-1H-pyrazol-4-yl)pyrimidin-4-yl)amino) bicyclo[2.2.2]octane-2-carboxylate (200 mg, 0.51 mmol). Then H$_2$O (0.5 mL) was added to the mixture, and the mixture was heated to 80° C. and stirred for 12 h. The mixture was filtered to remove solid impurities. The filtrate was concentrated in vacuo, and the residue was purified by silica gel column chromatography (PE/EtOAc (v/v)=8/1) to give the title compound as a light yellow solid (280 mg, 85%).

MS (ESI, pos. ion) m/z: 648.3 [M+H]$^+$.

Step 3: (+/−)-trans-3-((5-fluoro-2-(5-fluoro-1H-pyrrolo[2,3-b]pyridin-3-yl)-6-(1-methyl-1H-pyrazol-4-yl)pyrimidin-4-yl)amino)bicyclo[2.2.2]octane-2-carboxylic Acid To a solution of (+/−)-trans-methyl 3-((5-fluoro-2-(5-fluoro-1-tosyl-1H-pyrrolo [2,3-b]pyridin-3-yl)-6-(1-methyl-1H-pyrazol-4-yl)pyrimidin-4-yl)amino)bicyclo[2.2.2]octane-2-carboxylate (280 mg, 0.43 mmol) in a mixed solvent of THF (8 mL) and MeOH (4 mL) was added a solution of NaOH (172 mg, 4.30 mmol) in water (2 mL). The mixture was stirred at rt overnight, then water (10 mL) was added. The resulting mixture was acidified with hydrochloric acid (1 M) to pH about 3 to 4. The resulting mixture was extracted with ethyl acetate (20 mL×3). The combined organic layers were washed with saturated brine (50 mL), dried over anhydrous sodium sulfate and filtered. The filtrate was concentrated in vacuo to remove the solvent and the residue was purified by silica gel column chromatography (DCM/MeOH (v/v)=10/1-5/1) to give the title compound as a white solid (180 mg, 87%).

MS (ESI, pos. ion) m/z: 480.1[M+H]$^+$;
HRMS (ESI, pos. ion) m/z: 480.1964 [M+H]±, (C$_{24}$H$_{24}$F$_2$N$_7$O$_2$) [M+H]$^+$ theoretical value: 480.1960;
$^1$H NMR (400 MHz, DMSO-d$_6$) δ (ppm): 12.26 (s, 1H), 8.56 (dd, J=9.6, 2.4 Hz, 1H), 8.39 (s, 1H), 8.35-8.25 (m, 2H), 8.10 (s, 1H), 7.48 (d, J=6.5 Hz, 1H), 4.71 (s, 1H), 3.97 (s, 3H), 2.89 (d, J=6.5 Hz, 1H), 2.01 (d, J=10.8 Hz, 2H), 1.79 (m, 3H), 1.56 (m, 4H), 1.19 (s, 2H);
$^{13}$C NMR (101 MHz, DMSO-d$_6$) δ (ppm): 176.06, 157.51, 154.90, 152.16, 146.40, 140.65, 139.00, 131.99, 131.79, 131.27, 130.04, 125.35, 118.75, 116.78, 115.61, 115.40, 114.45, 51.00, 40.42, 40.21, 40.00, 39.79, 39.58, 28.84.

Example 52: (+/−)-trans-3-((5-fluoro-2-(5-fluoro-1H-pyrrolo[2,3-b]pyridin-3-yl)-6-(4-methoxyphenyl)pyrimidin-4-yl)amino)bicyclo[2.2.2]octane-2-carboxylic Acid

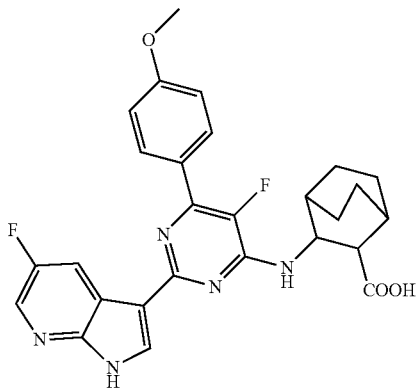 [SMILES: COc1ccc(-c2nc(-c3c[nH]c4ncc(F)cc34)nc(NC3C4CCC(CC4)C3C(=O)O)c2F)cc1]

Step 1: (+/−)-trans-methyl 3-((2-chloro-5-fluoro-6-(4-methoxyphenyl)pyrimidin-4-yl)amino) bicyclo[2.2.2]octane-2-carboxylate To acetonitrile (25 mL) were added (+/−)-trans-methyl 3-((2,6-dichloro-5-fluoropyrimidin-4-yl)amino)bicyclo[2.2.2]octane-2-carboxylate (0.50 g, 1.44 mmol), p-methoxyphenylboronic acid (0.22 g, 1.44 mmol), potassium acetate (0.42 g, 4.31 mmol) and Pd(dppf)Cl$_2$ (0.13 g, 0.14 mmol), then to the mixture was added water (1 mL). The resulting mixture was stirred at 80° C. for 12 h under nitrogen protection. The mixture was filtered to remove solid impurities. The filtrate was concentrated in vacuo, and the residue was purified by silica gel column chromatography (PE/EtOAc (v/v)=20/1) to give the title compound as a yellow solid (200 mg, 33%).

MS (ESI, pos. ion) m/z: 420.2 [M+H]$^+$.

Step 2: (+/−)-trans-methyl 3-((5-fluoro-2-(5-fluoro-1-tosyl-1H-pyrrolo[2,3-b]pyridin-3-yl)-6-(4-methoxyphenyl)pyrimidin-4-yl)amino)bicyclo[2.2.2]octane-2-carboxylate To THF (10 mL) were added 5-fluoro-3-(4,4,5,5-tetramethyl-1,3,2-dioxaborolan-2-yl)-1-tosyl-1H-pyrrolo[2,3-b]pyridine (363 mg, 0.52 mmol, 60%), potassium carbonate (263 mg, 1.90 mmol), palladium acetate (21 mg, 0.09 mmol), X-Phos (100 mg, 0.20 mmol) and (+/−)-trans-methyl 3-((2-chloro-5-fluoro-6-(4-methoxyphenyl)pyrimidin-4-yl)amino)bicyclo [2.2.2]octane-2-carboxylate (200 mg, 0.47 mmol). Then H$_2$O (0.5 mL) was added to the mixture, and the mixture was heated to 80° C. and stirred for 12 h. The mixture was filtered to remove solid impurities. The filtrate was concentrated in vacuo, and the residue was purified by silica gel column chromatography (PE/EtOAc (v/v)=8/1) to give the title compound as a light yellow solid (230 mg, 72%).

MS (ESI, pos. ion) m/z: 674.2 [M+H]$^+$.

Step 3: (+/−)-trans-3-((5-fluoro-2-(5-fluoro-1H-pyrrolo[2,3-b]pyridin-3-yl)-6-(4-methoxy phenyl)pyrimidin-4-yl)amino)bicyclo[2.2.2]octane-2-carboxylic Acid To a solution of (+/−)-trans-methyl 3-((5-fluoro-2-(5-fluoro-1-tosyl-1H-pyrrolo[2,3-b]pyridin-3-yl)-6-(4-methoxyphenyl)pyrimidin-4-yl)amino)bicyclo[2.2.2]octane-2-carboxylate (230 mg, 0.34 mmol) in THF/MeOH (v/v=8 mL/4 mL) was added a solution of sodium hydroxide (136 mg, 3.40 mmol) in water (1 mL). The mixture was stirred at rt overnight. To the reaction mixture was added water (10 mL), and the resulting mixture was acidified with hydrochloric acid (1 M) to pH about 3 to 4. The mixture was extracted with ethyl acetate (20 mL×3), and the combined organic layers were washed with saturated brine (50 mL), dried over anhydrous sodium sulfate, then filtered. The filtrate was concentrated in vacuo and the residue was purified by silica gel column chromatography (DCM/MeOH (v/v)=10/1-5/1) to give the title compound as a white solid (130 mg, 75%).

MS (ESI, pos. ion) m/z: 506.3 [M+H]$^+$;

HRMS (ESI, pos. ion) m/z: 506.2014 [M+H]±, (C$_{27}$H$_{26}$F$_2$N$_5$O$_3$) [M+H]$^+$ theoretical value: 506.2004;

$^1$H NMR (400 MHz, DMSO-d$_6$) δ (ppm): 12.27 (s, 1H), 8.55 (d, J=8.6 Hz, 1H), 8.30 (s, 2H), 8.07 (d, J=7.8 Hz, 2H), 7.54 (d, J=5.1 Hz, 1H), 7.13 (d, J=8.0 Hz, 2H), 4.73 (s, 1H), 3.85 (s, 3H), 2.90 (d, J=5.0 Hz, 1H), 2.02 (s, 2H), 1.80 (d, J=9.9 Hz, 3H), 1.70-1.42 (m, 5H);

$^{13}$C NMR (101 MHz, DMSO-d$_6$) δ (ppm): 176.06, 161.00, 157.22, 154.89, 152.91, 152.81, 151.92, 146.41, 139.61, 131.84, 131.55, 131.19, 130.56, 130.50, 128.48, 126.89, 125.35, 118.86, 115.53, 114.48, 55.74, 40.42, 40.22, 40.01, 39.80, 39.59, 30.88.

Example 53: (+/−)-trans-3-((6-(4-(tert-butyl)phenyl)-5-fluoro-2-(5-fluoro-1H-pyrrolo[2,3-b]pyridin-3-yl)pyrimidin-4-yl)amino)bicyclo[2.2.2]octane-2-carboxylic Acid

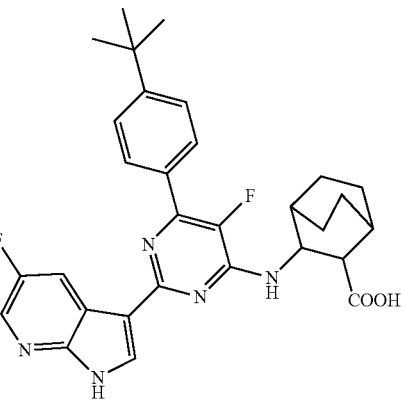

Step 1: (+/−)-trans-methyl 3-((6-(4-(tert-butyl)phenyl)-2-chloro-5-fluoropyrimidin-4-yl)amino) bicyclo [2.2.2]octane-2-carboxylate To acetonitrile (25 mL) were added (+/−)-trans-methyl 3-((2,6-dichloro-5-fluoropyrimidin-4-yl)amino)bicyclo [2.2.2]octane-2-carboxylate (0.50 g, 1.44 mmol), (4-(tert-butyl)phenyl)boronic acid (0.26 g, 1.44 mmol), potassium acetate (0.42 g, 4.31 mmol) and Pd(dppf)Cl$_2$ (0.13 g, 0.14 mmol), then to the mixture was added water (1 mL). The resulting mixture was stirred at 80° C. for 12 h under nitrogen protection. The mixture was filtered to remove solid impurities. The filtrate was concentrated in vacuo, and the residue was purified by silica gel column chromatography (PE/EtOAc (v/v)=20/1) to give the title compound as a yellow solid (180 mg, 28%).

MS (ESI, pos. ion) m/z: 446.2 [M+H]$^+$.

Step 2: (+/−)-trans-methyl 3-((6-(4-(tert-butyl)phenyl)-5-fluoro-2-(5-fluoro-1-tosyl-1H-pyrrolo[2,3-b]pyridin-3-yl)pyrimidin-4-yl)amino)bicyclo[2.2.2]octane-2-carboxylate To THF (10 mL) were added 5-fluoro-3-(4,4,5,5-tetramethyl-1,3,2-dioxaborolan-2-yl)-1-tosyl-1H-pyrrolo[2,3-b]pyridine (308 mg, 0.44 mmol, 60%), potassium carbonate (223 mg, 1.61 mmol), palladium acetate (18 mg, 0.08 mmol), X-Phos (76 mg, 0.16 mmol) and (+/−)-trans-methyl 3-((6-(4-(tert-butyl)phenyl)-2-chloro-5-fluoropyrimidin-4-yl)amino)bicyclo [2.2.2]octane-2-carboxylate (180 mg, 0.40 mmol). Then H$_2$O (0.5 mL) was added to the mixture, and the mixture was heated to 80° C. under nitrogen protection and stirred for 12 h. The mixture was filtered to remove solid impurities. The filtrate was concentrated in vacuo, and the residue was purified by silica gel column chromatography (PE/EtOAc (v/v)=8/1) to give the title compound as a light yellow solid (110 mg, 39%).

Step 3: (+/−)-trans-3-((6-(4-(tert-butyl)phenyl)-5-fluoro-2-(5-fluoro-1H-pyrrolo[2,3-b]pyridin-3-yl)pyrimidin-4-yl)amino)bicyclo[2.2.2]octane-2-carboxylic Acid To a solution of (+/−)-trans-methyl 3-((6-(4-(tert-butyl)phenyl)-5-fluoro-2-(5-fluoro-1-tosyl-1H-pyrrolo[2,3-b]

pyridin-3-yl)pyrimidin-4-yl)amino)bicyclo[2.2.2]octane-2-carboxylate (110 mg, 0.16 mmol) in THF/MeOH (v/v=8 mL/4 mL) was added a solution of sodium hydroxide (62 mg, 1.60 mmol) in water (1 mL). The mixture was stirred at rt overnight. To the reaction mixture was added water (10 mL), and the resulting mixture was acidified with hydrochloric acid (1 M) to pH about 3 to 4. The mixture was extracted with ethyl acetate (20 mL×3), and the combined organic layers were washed with saturated brine (50 mL), dried over anhydrous sodium sulfate, then filtered. The filtrate was concentrated in vacuo and the residue was purified by silica gel column chromatography (DCM/MeOH (v/v)=10/1-5/1) to give the title compound as a white solid (51 mg, 61%).

MS (ESI, pos. ion) m/z: 532.3 [M+H]$^+$;

HRMS (ESI, pos. ion) m/z: 532.2523 [M+H]$^+$, ($C_{30}H_{32}F_2N_5O_2$) [M+H]$^+$ theoretical value: 532.2524;

$^1$H NMR (600 MHz, DMSO-d$_6$) δ (ppm): 12.52 (s, 1H), 12.27 (s, 1H), 8.70 (dd, J=9.7, 2.5 Hz, 1H), 8.37 (s, 1H), 8.29 (d, J=8.2 Hz, 2H), 8.24 (s, 1H), 7.58 (d, J=8.3 Hz, 2H), 7.54 (d, J=6.6 Hz, 1H), 4.69 (t, J=6.6 Hz, 1H), 2.88 (d, J=6.9 Hz, 1H), 2.01 (s, 1H), 1.95 (s, 1H), 1.84-1.72 (m, 3H), 1.64-1.40 (m, 5H), 1.34 (s, 9H);

$^{13}$C NMR (151 MHz, DMSO-d$_6$) δ (ppm): 176.11, 158.23, 155.11, 153.03, 151.94, 145.84, 139.65, 135.85, 133.10, 132.59, 132.40, 132.14, 132.03, 128.49, 127.75, 125.81, 125.37, 118.81, 116.27, 108.31, 50.90, 48.00, 40.24, 40.10, 39.96, 39.82, 39.68, 34.84, 31.52, 30.88.

Example 54: (+/−)-trans-3-((6-(benzofuran-2-yl)-5-fluoro-2-(5-fluoro-1H-pyrrolo[2,3-b]pyridin-3-yl)pyrimidin-4-yl)amino)bicyclo[2.2.2]octane-2-carboxylic Acid

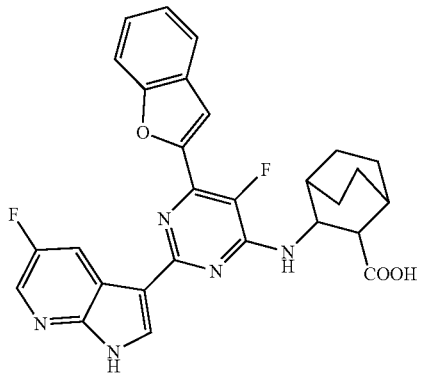 [SMILES: O=C(O)C1C2CCC(CC2)C1Nc1nc(-c2c[nH]c3ncc(F)cc23)nc(-c2cc3ccccc3s2)c1F]

Step 1: (+/−)-trans-methyl 3-((6-(benzofuran-2-yl)-2-chloro-5-fluoropyrimidin-4-yl)amino) bicyclo[2.2.2]octane-2-carboxylate To acetonitrile (25 mL) were added (+/−)-trans-methyl 3-((2,6-dichloro-5-fluoropyrimidin-4-yl)amino)bicyclo[2.2.2]octane-2-carboxylate (0.50 g, 1.44 mmol), benzofuran-2-ylboronic acid (0.23 g, 1.44 mmol), potassium acetate (0.42 g, 4.31 mmol) and Pd(dppf)Cl$_2$ (0.13 g, 0.14 mmol), then to the mixture was added water (1 mL). The resulting mixture was stirred at 80° C. for 12 h under nitrogen protection. The mixture was filtered to remove solid impurities. The filtrate was concentrated in vacuo, and the residue was purified by silica gel column chromatography (PE/EtOAc (v/v)=20/1) to give the title compound as a yellow solid (230 mg, 37%).

MS (ESI, pos. ion) m/z: 430.2 [M+H]$^+$.

Step 2: (+/−)-trans-methyl 3-((6-(benzofuran-2-yl)-5-fluoro-2-(5-fluoro-1-tosyl-1H-pyrrolo [2,3-b]pyridin-3-yl)pyrimidin-4-yl)amino)bicyclo[2.2.2]octane-2-carboxylate To THF (10 mL) were added 5-fluoro-3-(4,4,5,5-tetramethyl-1,3,2-dioxaborolan-2-yl)-1-tosyl-1H-pyrrolo[2,3-b]pyridine (445 mg, 0.64 mmol, 60%), potassium carbonate (300 mg, 2.14 mmol), palladium acetate (24 mg, 0.10 mmol), X-Phos (102 mg, 0.20 mmol) and (+/−)-trans-methyl 3-((6-(benzofuran-2-yl)-2-chloro-5-fluoropyrimidin-4-yl)amino)bicyclo[2.2.2]octane-2-carboxylate (230 mg, 0.54 mmol). Then H$_2$O (0.5 mL) was added to the mixture, and the mixture was heated to 110° C. and stirred for 12 h. The mixture was filtered to remove solid impurities. The filtrate was concentrated in vacuo to remove solvent, and the residue was purified by silica gel column chromatography (PE/EtOAc (v/v)=8/1) to give the title compound as a light yellow solid (180 mg, 49%).

Step 3: (+/−)-trans-3-((6-(benzofuran-2-yl)-5-fluoro-2-(5-fluoro-1H-pyrrolo[2,3-b]pyridin-3-yl) pyrimidin-4-yl)amino)bicyclo[2.2.2]octane-2-carboxylic Acid To a solution of (+/−)-trans-methyl 3-((6-(benzofuran-2-yl)-5-fluoro-2-(5-fluoro-1-tosyl-1H-pyrrolo[2,3-b]pyridin-3-yl)pyrimidin-4-yl)amino)bicyclo[2.2.2]octane-2-carboxylate (180 mg, 0.26 mmol) in THF/MeOH (v/v=8 mL/4 mL) was added a solution of sodium hydroxide (105 mg, 2.63 mmol) in water (1 mL). The mixture was stirred at rt overnight. To the reaction mixture was added water (10 mL), and the resulting mixture was acidified with hydrochloric acid (1 M) to pH about 3 to 4. The mixture was extracted with ethyl acetate (20 mL×3), and the combined organic layers were washed with saturated brine (50 mL), dried over anhydrous sodium sulfate, then filtered. The filtrate was concentrated in vacuo to remove the solvent and the residue was purified by silica gel column chromatography (DCM/MeOH (v/v)=10/1-5/1) to give the title compound as a white solid (91 mg, 67%).

MS (ESI, pos. ion) m/z: 516.1[M+H]$^+$;

HRMS (ESI, pos. ion) m/z: 516.1845 [M+H]$^+$, ($C_{28}H_{24}F_2N_5O_3$) [M+H]$^+$ theoretical value: 516.1847;

$^1$H NMR (400 MHz, DMSO-d$_6$) δ (ppm): 12.35 (s, 1H), 8.62 (dd, J=9.7, 2.5 Hz, 1H), 8.38-8.29 (m, 2H), 7.84 (d, J=7.7 Hz, 1H), 7.80 (d, J=6.5 Hz, 1H), 7.78-7.72 (m, 2H), 7.47 (t, J=7.6 Hz, 1H), 7.36 (t, J=7.4 Hz, 1H), 4.74 (s, 1H), 2.92 (d, J=6.4 Hz, 1H), 2.06-1.98 (m, 2H), 1.80 (m, 3H), 1.64-1.36 (m, 5H);

$^{13}$C NMR (151 MHz, DMSO-d$_6$) δ (ppm): 176.04, 155.35, 155.09, 152.73, 151.93, 150.50, 146.40, 139.64, 131.50, 128.49, 128.24, 126.63, 125.37, 124.03, 122.68, 118.85, 118.80, 115.64, 115.50, 112.08, 110.33, 110.27, 40.24, 40.10, 39.96, 39.82, 39.68, 30.87.

Example 55: (+/−)-trans-3-((6-(benzo[b]thiophen-2-yl)-5-fluoro-2-(5-fluoro-1H-pyrrolo [2,3-b]pyridin-3-yl)pyrimidin-4-yl)amino)bicyclo[2.2.2]octane-2-carboxylic Acid

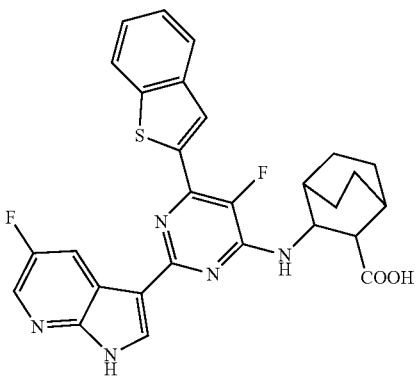

Step 1: (+/−)-trans-methyl 3-((6-(benzo [b]thiophen-2-yl)-2-chloro-5-fluoropyrimidin-4-yl)amino) bicyclo[2.2.2]octane-2-carboxylate To acetonitrile (25 mL) were added (+/−)-trans-methyl 3-((2,6-dichloro-5-fluoropyrimidin-4-yl)amino)bicyclo [2.2.2]octane-2-carboxylate (0.50 g, 1.44 mmol), benzo[b]thiophen-2-ylboronic acid (0.25 g, 1.44 mmol), potassium acetate (0.42 g, 4.31 mmol) and Pd(dppf)Cl$_2$ (0.13 g, 0.14 mmol), then to the mixture was added water (1 mL). The resulting mixture was stirred at 80° C. for 12 h under nitrogen protection. The mixture was filtered to remove solid impurities. The filtrate was concentrated in vacuo, and the residue was purified by silica gel column chromatography (PE/EtOAc (v/v)=20/1) to give the title compound as a yellow solid (300 mg, 47%).
MS (ESI, pos. ion) m/z: 446.0 [M+H]$^+$.

Step 2: (+/−)-trans-methyl 3-((6-(benzo [b]thiophen-2-yl)-5-fluoro-2-(5-fluoro-1-tosyl-1H-pyrrolo [2,3-b]pyridin-3-yl)pyrimidin-4-yl)amino)bicyclo [2.2.2]octane-2-carboxylate To THF (10 mL) were added 5-fluoro-3-(4,4,5,5-tetramethyl-1,3,2-dioxaborolan-2-yl)-1-tosyl-1H-pyrrolo[2,3-b] pyridine (513 mg, 0.74 mmol, 60%), potassium carbonate (371 mg, 2.69 mmol), palladium acetate (30 mg, 0.13 mmol), X-Phos (128 mg, 0.26 mmol) and (+/−)-trans-methyl 3-((6-(benzo [b]thiophen-2-yl)-2-chloro-5-fluoropyrimidin-4-yl)amino) bicyclo[2.2.2]octane-2-carboxylate (300 mg, 0.67 mmol). Then H$_2$O (0.5 mL) was added to the mixture, and the mixture was heated to 80° C. and stirred for 12 h. The mixture was filtered to remove solid impurities. The filtrate was concentrated in vacuo, and the residue was purified by silica gel column chromatography (PE/EtOAc (v/v)=8/1) to give the title compound as a light yellow solid (200 mg, 42%).

Step 3: (+/−)-trans-3-((6-(benzo[b]thiophen-2-yl)-5-fluoro-2-(5-fluoro-1H-pyrrolo[2,3-b]pyridin-3-yl)pyrimidin-4-yl)amino)bicyclo[2.2.2]octane-2-carboxylic Acid To a solution of (+/−)-trans-methyl 3-((6-(benzo[b]thiophen-2-yl)-5-fluoro-2-(5-fluoro-1-tosyl-1H-pyrrolo[2,3-b] pyridin-3-yl)pyrimidin-4-yl)amino)bicyclo[2.2.2]octane-2-carboxylate (200 mg, 0.28 mmol) in THF/MeOH (v/v=8 mL/4 mL) was added a solution of sodium hydroxide (114 mg, 2.80 mmol) in water (1 mL). The mixture was stirred at rt overnight. To the reaction mixture was added water (10 mL), and the resulting mixture was acidified with hydrochloric acid (1 M) to pH about 3 to 4. The mixture was extracted with ethyl acetate (20 mL×3), and the combined organic layers were washed with saturated brine (50 mL), dried over anhydrous sodium sulfate, then filtered. The filtrate was concentrated in vacuo and the residue was purified by silica gel column chromatography (DCM/MeOH (v/v)=10/1-5/1) to give the title compound as a white solid (91 mg, 60%).
MS (ESI, pos. ion) m/z: 532.1[M+H]$^+$;
HRMS (ESI, pos. ion) m/z: 532.1608[M+H]$^+$, (C$_{28}$H$_{24}$F$_2$N$_5$O$_2$S) [M+H]$^+$ theoretical value: 532.1619;
$^1$H NMR (400 MHz, DMSO-d$_6$) δ (ppm): 12.34 (s, 1H), 8.63 (dd, J=9.6, 2.4 Hz, 1H), 8.32 (s, 1H), 8.27 (d, J=2.4 Hz, 1H), 8.17 (s, 1H), 8.13-8.08 (m, 1H), 8.05-8.00 (m, 1H), 7.77 (d, J=6.4 Hz, 1H), 7.49-7.43 (m, 2H), 4.72 (s, 1H), 2.90 (d, J=6.4 Hz, 1H), 2.02 (d, J=9.4 Hz, 2H), 1.87-1.75 (m, 3H), 1.65-1.42 (m, 5H);
$^{13}$C NMR (151 MHz, DMSO-d$_6$) δ (ppm): 176.07, 155.37, 151.94, 146.43, 140.73, 139.65, 131.47, 128.50, 126.35, 125.37, 125.27, 123.00, 119.13, 118.75, 118.72, 118.70, 115.54, 115.47, 115.40, 114.32, 113.87, 113.84, 40.25, 40.11, 39.97, 39.83, 39.69, 30.88.

Example 56: (+/−)-trans-3-((6-(4-cyanophenyl)-5-fluoro-2-(5-fluoro-1H-pyrrolo[2,3-b]pyridin-3-yl) pyrimidin-4-yl)amino)bicyclo[2.2.2]octane-2-carboxylic Acid

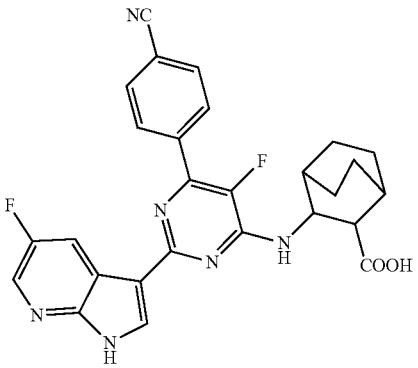 [SMILES: N#Cc1ccc(-c2nc(-c3c[nH]c4ncc(F)cc34)nc(NC3C4CCC(CC4)C3C(=O)O)c2F)cc1]

Step 1: (+/−)-trans-methyl 3-((2-chloro-6-(4-cyanophenyl)-5-fluoropyrimidin-4-yl)amino) bicyclo [2.2.2]octane-2-carboxylate To acetonitrile (25 mL) were added (+/−)-trans-methyl 3-((2,6-dichloro-5-fluoropyrimidin-4-yl)amino)bicyclo [2.2.2]octane-2-carboxylate (0.50 g, 1.44 mmol), (4-cyanophenyl)boronic acid (0.22 g, 1.44 mmol), potassium acetate (0.42 g, 4.31 mmol) and Pd(dppf)Cl$_2$ (0.13 g, 0.14 mmol), then to the mixture was added water (1 mL). The resulting mixture was stirred at 80° C. for 12 h under nitrogen protection. The mixture was filtered to remove solid impurities. The filtrate was concentrated in vacuo, and the residue was purified by silica gel column chromatography (PE/EtOAc (v/v)=20/1) to give the title compound as a yellow solid (250 mg, 42%).

MS (ESI, pos. ion) m/z: 415.1 [M+H]+.

Step 2: (+/−)-trans-methyl 3-((6-(4-cyanophenyl)-5-fluoro-2-(5-fluoro-1-tosyl-1H-pyrrolo [2,3-b]pyridin-3-yl)pyrimidin-4-yl)amino)bicyclo[2.2.2]octane-2-carboxylate To THF (10 mL) were added 5-fluoro-3-(4,4,5,5-tetramethyl-1,3,2-dioxaborolan-2-yl)-1-tosyl-1H-pyrrolo[2,3-b]pyridine (460 mg, 0.66 mmol, 60%), potassium carbonate (333 mg, 2.41 mmol), palladium acetate (27 mg, 0.12 mmol), X-Phos (114 mg, 0.24 mmol) and (+/−)-trans-methyl 3-((2-chloro-6-(4-cyanophenyl)-5-fluoropyrimidin-4-yl)amino)bicyclo[2.2.2]octane-2-carboxylate (250 mg, 0.60 mmol). Then H$_2$O (0.5 mL) was added to the mixture, and the mixture was heated to 80° C. and stirred for 12 h. The mixture was filtered to remove solid impurities. The filtrate was concentrated in vacuo, and the residue was purified by silica gel column chromatography (PE/EtOAc (v/v)=8/1) to give the title compound as a light yellow solid (250 mg, 62%).

Step 3: (+/−)-trans-3-((6-(4-cyanophenyl)-5-fluoro-2-(5-fluoro-1H-pyrrolo[2,3-b]pyridin-3-yl) pyrimidin-4-yl)amino)bicyclo[2.2.2]octane-2-carboxylic Acid To a solution of (+/−)-trans-methyl 3-((6-(4-cyanophenyl)-5-fluoro-2-(5-fluoro-1-tosyl-1H-pyrrolo[2,3-b]pyridin-3-yl)pyrimidin-4-yl)amino)bicyclo[2.2.2]octane-2-carboxylate (250 mg, 0.37 mmol) in THF/MeOH (v/v=8 mL/4 mL) was added a solution of sodium hydroxide (149 mg, 3.70 mmol) in water (2 mL). The mixture was stirred at rt overnight. To the reaction mixture was added water (10 mL), and the resulting mixture was acidified with hydrochloric acid to pH about 3 to 4. The mixture was extracted with ethyl acetate (20 mL×3), and the combined organic layers were washed with saturated brine (50 mL), dried over anhydrous sodium sulfate, then filtered. The filtrate was concentrated in vacuo and the residue was purified by silica gel column chromatography (DCM/MeOH (v/v)=10/1-5/1) to give the title compound as a white solid (120 mg, 64%).

MS (ESI, pos. ion) m/z: 501.1[M+H]+;

HRMS (ESI, pos. ion) m/z: 501.1846 [M+H]+, (C$_{27}$H$_{23}$F$_2$N$_6$O$_2$) [M+H]+ theoretical value: 501.1851;

$^1$H NMR (400 MHz, DMSO-d$_6$) δ (ppm): 12.31 (s, 1H), 8.50 (dd, J=9.5, 2.2 Hz, 1H), 8.32 (d, J=2.2 Hz, 1H), 8.28 (s, 1H), 8.23 (d, J=8.1 Hz, 2H), 8.02 (d, J=8.2 Hz, 2H), 7.76 (d, J=6.2 Hz, 1H), 4.75 (s, 1H), 2.92 (d, J=6.2 Hz, 1H), 2.02 (d, J=11.4 Hz, 2H), 1.80 (m, 3H), 1.69-1.40 (m, 5H);

$^{13}$C NMR (151 MHz, DMSO-d$_6$) δ (ppm): 176.05, 157.69, 157.64, 156.89, 155.29, 153.00, 152.92, 151.93, 146.38, 140.98, 139.64, 139.06, 139.03, 132.96, 131.72, 131.55, 129.83, 129.79, 128.49, 125.37, 119.09, 112.65, 40.24, 40.10, 39.96, 39.82, 39.68, 30.87.

Example 57: (+/−)-trans-3-((6-(3,4-difluorophenyl)-5-fluoro-2-(5-fluoro-1H-pyrrolo[2,3-b]pyridin-3-yl)pyrimidin-4-yl)amino)bicyclo[2.2.2]octane-2-carboxylic Acid

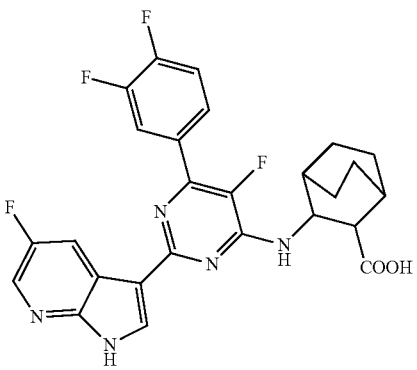 [SMILES: O=C(O)C1C2CCC(CC2)C1Nc1nc(-c2c[nH]c3ncc(F)cc23)nc(-c2ccc(F)c(F)c2)c1F]

Step 1: (+/−)-trans-methyl 3-((2-chloro-6-(3,4-difluorophenyl)-5-fluoropyrimidin-4-yl)amino) bicyclo [2.2.2]octane-2-carboxylate To acetonitrile (25 mL) were added (+/−)-trans-methyl 3-((2,6-dichloro-5-fluoropyrimidin-4-yl)amino)bicyclo [2.2.2]octane-2-carboxylate (0.50 g, 1.44 mmol), (3,4-difluorophenyl)boronic acid (0.23 g, 1.44 mmol), potassium acetate (0.42 g, 4.31 mmol) and Pd(dppf)Cl$_2$ (0.13 g, 0.14 mmol), then to the mixture was added water (1 mL). The resulting mixture was stirred at 80° C. for 12 h under nitrogen protection. The mixture was filtered to remove solid impurities. The filtrate was concentrated in vacuo, and the residue was purified by silica gel column chromatography (PE/EtOAc (v/v)=20/1) to give the title compound as a yellow solid (290 mg, 47%).

MS (ESI, pos. ion) m/z: 426.1 [M+H]+.

Step 2: (+/−)-trans-methyl 3-((6-(3,4-difluorophenyl)-5-fluoro-2-(5-fluoro-1-tosyl-1H-pyrrolo[2,3-b]pyridin-3-yl)pyrimidin-4-yl)amino)bicyclo[2.2.2]octane-2-carboxylate To THF (10 mL) were added 5-fluoro-3-(4,4,5,5-tetramethyl-1,3,2-dioxaborolan-2-yl)-1-tosyl-1H-pyrrolo[2,3-b]pyridine (520 mg, 0.74 mmol, 60%), potassium carbonate (376 mg, 2.72 mmol), palladium acetate (30 mg, 0.14 mmol), X-Phos (130 mg, 0.28 mmol) and (+/−)-trans-methyl 3-((2-chloro-6-(3,4-difluorophenyl)-5-fluoropyrimidin-4-yl)amino)bicyclo [2.2.2]octane-2-carboxylate (290 mg, 0.68 mmol). Then H$_2$O (0.5 mL) was added to the mixture, and the mixture was heated to 80° C. and stirred for 12 h. The mixture was filtered to remove solid impurities. The filtrate was concentrated in vacuo, and the residue was purified by silica gel column chromatography (PE/EtOAc (v/v)=8/1) to give the title compound as a light yellow solid (240 mg, 52%).

MS (ESI, pos. ion) m/z: 680.1 [M+H]+.

Step 3: (+/−)-trans-3-((6-(3,4-difluorophenyl)-5-fluoro-2-(5-fluoro-1H-pyrrolo[2,3-b]pyridin-3-yl)pyrimidin-4-yl)amino)bicyclo[2.2.2]octane-2-carboxylic Acid To a solution of (+/−)-trans-methyl 3-((6-(3,4-difluorophenyl)-5-fluoro-2-(5-fluoro-1-tosyl-1H-pyrrolo[2,3-b]

pyridin-3-yl)pyrimidin-4-yl)amino)bicyclo[2.2.2]octane-2-carboxylate (240 mg, 0.35 mmol) in THF/MeOH (v/v=8 mL/4 mL) was added a solution of sodium hydroxide (141 mg, 3.40 mmol) in water (1 mL). The mixture was stirred at rt overnight. To the reaction mixture was added water (10 mL), and the resulting mixture was acidified with hydrochloric acid (1 M) to pH about 3 to 4. The mixture was extracted with ethyl acetate (20 mL×3), and the combined organic layers were washed with saturated brine (50 mL), dried over anhydrous sodium sulfate, then filtered. The filtrate was concentrated in vacuo and the residue was purified by silica gel column chromatography (DCM/MeOH (v/v)=10/1-5/1) to give the title compound as a white solid (97 mg, 54%).

MS (ESI, pos. ion) m/z: 512.2[M+H]$^+$;

HRMS (ESI, pos. ion) m/z: 512.1699 [M+H]$^+$, ($C_{26}H_{22}F_4N_5O_2$) [M+H]$^+$ theoretical value: 512.1710;

$^1$H NMR (400 MHz, DMSO-$d_6$) δ (ppm): 12.30 (s, 1H), 8.51 (dd, J=9.7, 2.5 Hz, 1H), 8.36 (d, J=2.6 Hz, 1H), 8.28 (s, 1H), 8.10 (dd, J=10.1, 8.5 Hz, 1H), 7.93 (s, 1H), 7.70 (d, J=6.5 Hz, 1H), 7.62 (d, J=8.7 Hz, 1H), 4.74 (t, J=6.1 Hz, 1H), 2.92 (d, J=6.6 Hz, 1H), 2.02 (d, J=12.5 Hz, 2H), 1.87-1.73 (m, 3H), 1.69-1.40 (m, 5H);

$^{13}$C NMR (151 MHz, DMSO-$d_6$) δ (ppm): 176.04, 158.28, 157.52, 157.46, 157.03, 156.88, 155.29, 152.99, 152.90, 151.93, 146.39, 140.60, 139.64, 131.63, 128.49, 126.29, 125.36, 118.72, 118.29, 118.17, 114.11, 40.23, 40.09, 39.95, 39.81, 39.68, 30.86.

Example 58: (+/−)-trans-3-((5-fluoro-2-(5-fluoro-1H-pyrrolo[2,3-b]pyridin-3-yl)-6-(furan-3-yl)pyrimidin-4-yl)amino)bicyclo[2.2.2]octane-2-carboxylic Acid

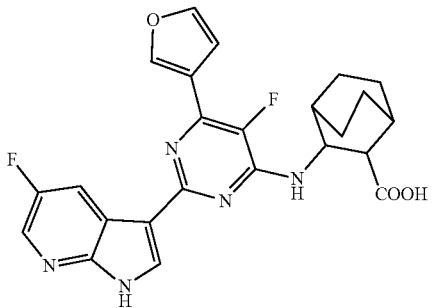 [SMILES: O=C(O)C1C2CCC(CC2)C1Nc1nc(-c2c[nH]c3ncc(F)cc23)nc(-c2ccoc2)c1F]

Step 1: (+/−)-trans-methyl 3-((2-chloro-5-fluoro-6-(furan-3-yl)pyrimidin-4-yl)amino)bicyclo [2.2.2]octane-2-carboxylate To acetonitrile were added (+/−)-trans-methyl-3-((2,6-dichloro-5-fluoropyrimidin-4-yl)amino)bicyclo[2.2.2]octane-2-carboxylate (0.50 g, 1.44 mmol), furan-3-ylboronic acid (0.16 g, 1.44 mmol), potassium acetate (0.42 g, 4.31 mmol) and Pd(dppf)Cl$_2$ (0.13 g, 0.14 mmol), then to the mixture was added water (1 mL). The resulting mixture was stirred at 80° C. for 12 h under nitrogen protection. The mixture was filtered to remove solid impurities. The filtrate was concentrated in vacuo, and the residue was purified by silica gel column chromatography (PE/EtOAc (v/v)=20/1) to give the title compound as a yellow solid (140 mg, 30%).

MS (ESI, pos. ion) m/z: 380.2 [M+H]$^+$.

Step 2: (+/−)-trans-methyl 3-((5-fluoro-2-(5-fluoro-1-tosyl-1H-pyrrolo[2,3-b]pyridin-3-yl)-6-(furan-3-yl)pyrimidin-4-yl)amino)bicyclo[2.2.2]octane-2-carboxylate To THF (10 mL) were added 5-fluoro-3-(4,4,5,5-tetramethyl-1,3,2-dioxaborolan-2-yl)-1-tosyl-1H-pyrrolo[2,3-b]pyridine (442 mg, 0.63 mmol, 60%), potassium carbonate (203 mg, 1.46 mmol), palladium acetate (16 mg, 0.07 mmol), X-Phos (70 mg, 0.14 mmol) and (+/−)-trans-methyl 3-((2-chloro-5-fluoro-6-(furan-3-yl)pyrimidin-4-yl)amino)bicyclo[2.2.2]octane-2-carboxylate (140 mg, 0.36 mmol). Then H$_2$O (0.5 mL) was added to the mixture, and the mixture was heated to 80° C. and stirred for 12 h. The mixture was filtered to remove solid impurities. The filtrate was concentrated in vacuo, and the residue was purified by silica gel column chromatography (PE/EtOAc (v/v)=8/1) to give the title compound as a light yellow solid (198 mg, 85%).

MS (ESI, pos. ion) m/z: 634.2 [M+H]$^+$.

Step 3: (+/−)-trans-3-((5-fluoro-2-(5-fluoro-1H-pyrrolo[2,3-b]pyridin-3-yl)-6-(furan-3-yl) pyrimidin-4-yl)amino)bicyclo[2.2.2]octane-2-carboxylic Acid To a solution of (+/−)-trans-methyl 3-((5-fluoro-2-(5-fluoro-1-tosyl-1H-pyrrolo [2,3-b]pyridin-3-yl)-6-(furan-3-yl)pyrimidin-4-yl)amino)bicyclo[2.2.2]octane-2-carboxylate (198 mg, 0.31 mmol) in THF/MeOH (v/v=8 mL/4 mL) was added a solution of sodium hydroxide (125 mg, 3.10 mmol) in water (2 mL). The mixture was stirred at rt overnight. To the reaction mixture was added water (10 mL), and the resulting mixture was acidified with hydrochloric acid (1 M) to pH about 3 to 4. The mixture was extracted with ethyl acetate (20 mL×3), and the combined organic layers were washed with saturated brine (50 mL), dried over anhydrous sodium sulfate, then filtered. The filtrate was concentrated in vacuo and the residue was purified by silica gel column chromatography (DCM/MeOH (v/v)=10/1-5/1) to give the title compound as a white solid (130 mg, 89%).

MS (ESI, pos. ion) m/z: 466.1[M+H]$^+$;

HRMS (ESI, pos. ion) m/z: 466.1689 [M+H]$^+$, ($C_{24}H_{22}F_2N_5O_3$) [M+H]$^+$ theoretical value: 466.1691;

$^1$H NMR (400 MHz, DMSO-$d_6$) δ (ppm): 12.28 (s, 1H), 8.54 (dd, J=9.6, 2.1 Hz, 1H), 8.40 (s, 1H), 8.33 (d, J=2.2 Hz, 1H), 8.29 (s, 1H), 7.89 (s, 1H), 7.57 (d, J=6.4 Hz, 1H), 7.16 (s, 1H), 4.72 (s, 1H), 2.89 (d, J=6.4 Hz, 1H), 2.00 (d, J=12.4 Hz, 2H), 1.79 (m, 3H), 1.51 (m, 5H);

$^{13}$C NMR (151 MHz, DMSO-$d_6$) δ (ppm): 176.07, 157.61, 156.88, 155.29, 152.23, 151.93, 146.39, 144.92, 144.61, 139.64, 131.47, 128.50, 125.37, 121.30, 118.72, 115.52, 114.24, 109.92, 55.36, 51.03, 48.15, 34.83, 30.87, 28.81.

Example 59: (+/−)-trans-3-((5-fluoro-2-(5-fluoro-1H-pyrrolo[2,3-b]pyridin-3-yl)-6-(4-(trifluoromethyl)phenyl)pyrimidin-4-yl)amino)bicyclo[2.2.2]octane-2-carboxylic Acid

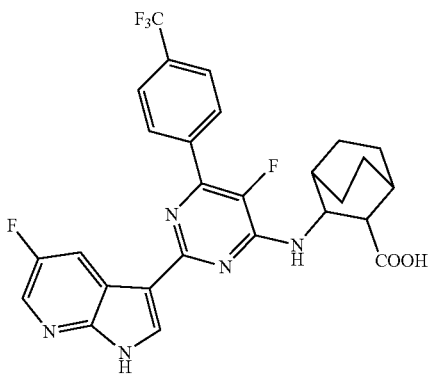 [SMILES: O=C(O)C1C2CCC(CC2)C1Nc1nc(-c2c[nH]c3ncc(F)cc23)nc(-c2ccc(C(F)(F)F)cc2)c1F]

Step 1: (+/−)-trans-methyl 3-((2-chloro-5-fluoro-6-(4-(trifluoromethyl)phenyl)pyrimidin-4-yl) amino)bicyclo[2.2.2]octane-2-carboxylate To acetonitrile (25 mL) were added (+/−)-trans-methyl 3-((2,6-dichloro-5-fluoropyrimidin-4-yl)amino)bicyclo[2.2.2]octane-2-carboxylate (0.50 g, 1.44 mmol), (4-(trifluoromethyl)phenyl)boronic acid (0.27 g, 1.44 mmol), potassium acetate (0.42 g, 4.31 mmol) and Pd(dppf)Cl$_2$ (0.13 g, 0.14 mmol), then to the mixture was added water (1 mL). The resulting mixture was stirred at 80° C. for 12 h under nitrogen protection. The mixture was filtered to remove solid impurities. The filtrate was concentrated in vacuo, and the residue was purified by silica gel column chromatography (PE/EtOAc (v/v)=20/1) to give the title compound as a yellow solid (230 mg, 45%).

MS (ESI, pos. ion) m/z: 458.2 [M+H]$^+$.

Step 2: (+/−)-trans-methyl 3-((5-fluoro-2-(5-fluoro-1-tosyl-1H-pyrrolo[2,3-b]pyridin-3-yl)-6-(4-(trifluoromethyl)phenyl)pyrimidin-4-yl)amino)bicyclo[2.2.2]octane-2-carboxylate To THF (10 mL) were added 5-fluoro-3-(4,4,5,5-tetramethyl-1,3,2-dioxaborolan-2-yl)-1-tosyl-1H-pyrrolo[2,3-b]pyridine (383 mg, 0.55 mmol, 60%), potassium carbonate (277 mg, 2.01 mmol), palladium acetate (22 mg, 0.10 mmol), X-Phos (95 mg, 0.20 mmol) and (+/−)-trans-methyl 3-((2-chloro-5-fluoro-6-(4-(trifluoromethyl)phenyl)pyrimidin-4-yl)amino) bicyclo[2.2.2]octane-2-carboxylate (230 mg, 0.50 mmol). Then H$_2$O (0.5 mL) was added to the mixture, and the mixture was heated to 80° C. and stirred for 12 h. The mixture was filtered to remove solid impurities. The filtrate was concentrated in vacuo, and the residue was purified by silica gel column chromatography (PE/EtOAc (v/v)=8/1) to give the title compound as a light yellow solid (180 mg, 50%).

Step 3: (+/−)-trans-3-((5-fluoro-2-(5-fluoro-1H-pyrrolo[2,3-b]pyridin-3-yl)-6-(4-(trifluoromethyl) phenyl)pyrimidin-4-yl)amino)bicyclo[2.2.2]octane-2-carboxylic Acid To a solution of (+/−)-trans-methyl 3-((5-fluoro-2-(5-fluoro-1-tosyl-1H-pyrrolo [2,3-b]pyridin-3-yl)-6-(4-(trifluoromethyl)phenyl)pyrimidin-4-yl)amino)bicyclo[2.2.2]octane-2-carboxylate (180 mg, 0.25 mmol) in THF/MeOH (v/v=8 mL/4 mL) was added a solution of sodium hydroxide (101 mg, 2.50 mmol) in water (2 mL). The mixture was stirred at rt overnight. To the reaction mixture was added water (10 mL), and the resulting mixture was acidified with hydrochloric acid (1 M) to pH about 3 to 4. The mixture was extracted with ethyl acetate (20 mL×3), and the combined organic layers were washed with saturated brine (50 mL), dried over anhydrous sodium sulfate, then filtered. The filtrate was concentrated in vacuo to remove the solvent and the residue was purified by silica gel column chromatography (DCM/MeOH (v/v)=10/1-5/1) to give the title compound as a white solid (90 mg, 65%).

MS (ESI, pos. ion) m/z: 544.3 [M+H]$^+$;
HRMS (ESI, pos. ion) m/z: 544.1770 [M+H]$^+$, (C$_{26}$H$_{24}$F$_2$N$_5$O$_2$) [M+H]$^+$ theoretical value: 544.1772;
$^1$H NMR (400 MHz, DMSO-d$_6$) δ (ppm): 12.54 (s, 1H), 8.60 (d, J=8.0 Hz, 1H), 8.51 (d, J=7.9 Hz, 2H), 8.35 (s, 1H), 8.24 (s, 1H), 7.91 (d, J=8.0 Hz, 2H), 7.66 (d, J=6.1 Hz, 1H), 4.68 (s, 1H), 2.87 (d, J=6.2 Hz, 1H), 2.00 (s, 1H), 1.93 (s, 1H), 1.76 (m, 3H), 1.49 (m, 5H);
$^{13}$C NMR (151 MHz, DMSO-d$_6$) δ (ppm): 176.12, 156.79, 155.12, 152.12, 145.84, 143.49, 142.22, 142.02, 140.30, 132.67, 132.47, 132.37, 132.27, 130.27, 126.04, 125.88, 124.21, 118.69, 116.05, 108.45, 51.04, 48.07, 28.81, 25.82, 24.30, 21.58.

Example 60: (+/−)-trans-3-((5-fluoro-2-(5-fluoro-1H-pyrrolo[2,3-b]pyridin-3-yl)-6-(p-tolyl) pyrimidin-4-yl)amino)bicyclo[2.2.2]octane-2-carboxylic Acid

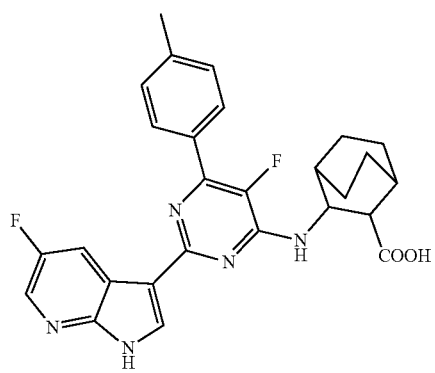 [SMILES: Cc1ccc(-c2nc(-c3c[nH]c4ncc(F)cc34)nc(NC3C4CCC(CC4)C3C(=O)O)c2F)cc1]

Step 1: (+/−)-trans-methyl 3-((2-chloro-5-fluoro-6-(p-tolyl)pyrimidin-4-yl)amino)bicyclo[2.2.2]octane-2-carboxylate To acetonitrile (25 mL) were added (+/−)-trans-methyl-3-((2,6-dichloro-5-fluoropyrimidin-4-yl)amino)bicyclo

[2.2.2]octane-2-carboxylate (0.50 g, 1.44 mmol), p-methylphenylboronic acid (0.20 g, 1.44 mmol), potassium acetate (0.42 g, 4.31 mmol) and Pd(dppf)Cl₂ (0.13 g, 0.14 mmol), then to the mixture was added water (1 mL). The resulting mixture was stirred at 80° C. for 12 h under nitrogen protection. The mixture was filtered to remove solid impurities. The filtrate was concentrated in vacuo to remove solvent, and the residue was purified by silica gel column chromatography (PE/EtOAc (v/v)=20/1) to give the title compound as a yellow solid (300 mg, 52%).

MS (ESI, pos. ion) m/z: 404.2 [M+H]⁺.

Step 2: (+/−)-trans-methyl 3-((5-fluoro-2-(5-fluoro-1-tosyl-1H-pyrrolo[2,3-b]pyridin-3-yl)-6-(p-tolyl)pyrimidin-4-yl)amino)bicyclo[2.2.2]octane-2-carboxylate To THF (10 mL) were added 5-fluoro-3-(4,4,5,5-tetramethyl-1,3,2-dioxaborolan-2-yl)-1-tosyl-1H-pyrrolo[2,3-b]pyridine (550 mg, 0.81 mmol, 60%), potassium carbonate (410 mg, 2.97 mmol), palladium acetate (33 mg, 0.14 mmol), X-Phos (141 mg, 0.28 mmol) and (+/−)-trans-methyl 3-((2-chloro-5-fluoro-6-(p-tolyl)pyrimidin-4-yl)amino)bicyclo[2.2.2]octane-2-carboxylate (300 mg, 0.74 mmol). Then H₂O (0.5 mL) was added to the mixture, and the mixture was heated to 80° C. and stirred for 12 h. The mixture was filtered to remove the solid impurity. The filtrate was concentrated in vacuo, and the residue was purified by silica gel column chromatography (PE/EtOAc (v/v)=8/1) to give the title compound as a light yellow solid (300 mg, 61%).

MS (ESI, pos. ion) m/z: 658.1 [M+H]⁺.

Step 3: (+/−)-trans-3-((5-fluoro-2-(5-fluoro-1H-pyrrolo[2,3-b]pyridin-3-yl)-6-(p-tolyl)pyrimidin-4-yl)amino)bicyclo[2.2.2]octane-2-carboxylic Acid To a solution of (+/−)-trans-methyl 3-((5-fluoro-2-(5-fluoro-1-tosyl-1H-pyrrolo[2,3-b]pyridin-3-yl)-6-(p-tolyl)pyrimidin-4-yl)amino)bicyclo[2.2.2]octane-2-carboxylate (300 mg, 0.45 mmol) in THF/MeOH (v/v=8 mL/4 mL) was added a solution of sodium hydroxide (182 mg, 4.50 mmol) in water (2 mL). The mixture was stirred at rt overnight. To the reaction mixture was added water (10 mL), and the resulting mixture was acidified with hydrochloric acid (1 M) to pH about 3 to 4. The mixture was extracted with ethyl acetate (20 mL×3), and the combined organic layers were washed with saturated brine (50 mL), dried over anhydrous sodium sulfate, then filtered. The filtrate was concentrated in vacuo and the residue was purified by silica gel column chromatography (DCM/MeOH (v/v)=10/1-5/1) to give the title compound as a white solid (140 mg, 63%).

MS (ESI, pos. ion) m/z: 490.3[M+H]⁺;
HRMS (ESI, pos. ion) m/z: 490.2053 [M+H]⁺, (C₂₇H₂₆F₂N₅O₂) [M+H]⁺ theoretical value: 490.2055;
¹H NMR (400 MHz, DMSO-d₆) δ (ppm): 12.27 (s, 1H), 8.56 (d, J=8.6 Hz, 1H), 8.29 (s, 2H), 7.97 (d, J=7.4 Hz, 2H), 7.56 (d, J=5.6 Hz, 1H), 7.36 (d, J=7.6 Hz, 2H), 4.74 (s, 1H), 2.91 (d, J=5.6 Hz, 1H), 2.00 (d, J=15.6 Hz, 2H), 1.88-1.73 (m, 3H), 1.53 (m, 5H);
¹³C NMR (101 MHz, DMSO-d₆) δ (ppm): 176.06, 157.33, 154.90, 152.94, 151.93, 146.42, 145.13, 142.66, 139.98, 139.59, 131.84, 131.19, 129.59, 128.92, 128.86, 125.34, 118.88, 118.81, 115.56, 115.34, 114.42, 51.17, 48.26, 34.80, 30.86, 28.84, 21.39, 19.50.

Example 61: (R)-3-((5-fluoro-2-(5-fluoro-1H-pyrrolo[2,3-b]pyridin-3-yl)-6-(furan-2-yl) pyrimidin-4-yl)amino)-4,4-dimethylpentanoic Acid

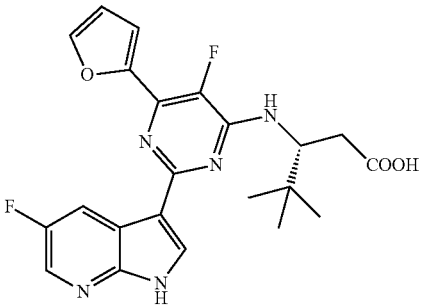 [SMILES: CC(C)(C)[C@@H](CC(=O)O)Nc1nc(-c2c[nH]c3ncc(F)cc23)nc(-c2ccco2)c1F]

Step 1: (R)-methyl 3-((2,6-dichloro-5-fluoropyrimidin-4-yl)amino)-4,4-dimethylpentanoate To a reaction flask were added 2,4,6-trichloro-5-fluoropyrimidine (0.64 g, 3.16 mmol), DIPEA (1.02 g, 7.91 mmol), (R)-methyl 3-amino-4,4-dimethylpentanoate (0.42 g, 2.63 mmol) and dichloromethane (10 mL). The mixture was stirred at rt for 24 h. After the reaction was completed, to the mixture was added water (20 mL). The resulting mixture was extracted with DCM (20 mL). The organic layer was washed with saturated brine (10 mL), dried over anhydrous Na₂SO₄ and concentrated in vacuo. The residue was purified by silica gel chromatography eluted with PE/EtOAc (v/v=20/1) to give the title compound as a light yellow solid (420 mg, 49%).

MS (ESI, pos. ion) m/z: 324.10 [M+H]⁺.

Step 2: (R)-methyl 3-((2-chloro-5-fluoro-6-(furan-2-yl)pyrimidin-4-yl)amino)4,4-dimethyl pentanoate To acetonitrile (25 mL) were added (R)-methyl 3-((2,6-dichloro-5-fluoropyrimidin-4-yl)amino)-4,4-dimethylpentanoate (420 mg, 1.29 mmol), furan-2-ylboronic acid (145 mg, 1.29 mmol), potassium acetate (381 mg, 3.88 mmol) and Pd(dppf)Cl₂ (105 mg, 0.13 mmol), then to the mixture was added water (1 mL). The resulting mixture was stirred at 80° C. for 12 h under nitrogen protection. The mixture was filtered to remove solid impurities. The filtrate was concentrated in vacuo to remove the solvent, and the residue was purified by silica gel column chromatography (PE/EtOAc (v/v)=20/1) to give the title compound as a yellow solid (180 mg, 39%).

MS (ESI, pos. ion) m/z: 356.2 [M+H]⁺.

Step 3: (R)-methyl 3-((5-fluoro-2-(5-fluoro-1-tosyl-1H-pyrrolo[2,3-b]pyridin-3-yl)-6-(furan-2-yl)pyrimidin-4-yl)amino)-4,4-dimethylpentanoate To THF (10 mL) were added 5-fluoro-3-(4,4,5,5-tetramethyl-1,3,2-dioxaborolan-2-yl)-1-tosyl-1H-pyrrolo[2,3-b]pyridine (386 mg, 0.56 mmol, 60%), potassium carbonate (280 mg, 2.02 mmol), palladium acetate (22 mg, 0.10 mmol), X-Phos (100 mg, 0.20 mmol) and (R)-methyl 3-((2-chloro-5-fluoro-6-(furan-2-yl)pyrimidin-4-yl)amino)-4,4-dimethylpentanoate (180 mg, 0.50 mmol). Then H₂O (1 mL) was added to the mixture, and the mixture was heated to 100° C. and stirred for 12 h. The mixture was filtered to remove solid impurities. The filtrate was concentrated in vacuo, and the residue was purified by silica gel column chromatography (PE/EtOAc (v/v)=8/1) to give the title compound as a light yellow solid (230 mg, 74%).

MS (ESI, pos. ion) m/z: 610.2 [M+H]$^+$.

Step 4: (R)-3-((5-fluoro-2-(5-fluoro-1H-pyrrolo[2,3-b]pyridin-3-yl)-6-(furan-2-yl)pyrimidin-4-yl)amino)-4,4-dimethylpentanoic Acid To a solution of (R)-methyl 3-((5-fluoro-2-(5-fluoro-1-tosyl-1H-pyrrolo[2,3-b]pyridin-3-yl)-6-(furan-2-yl)pyrimidin-4-yl)amino)-4,4-dimethylpentanoate (230 mg, 0.37 mmol) in THF/MeOH (v/v=8 mL/4 mL) was added a solution of sodium hydroxide (150 mg, 3.70 mmol) in water (2 mL). The mixture was stirred at rt overnight. To the reaction mixture was added water (20 mL), and the resulting mixture was acidified with hydrochloric acid (1 M) to pH about 3 to 4. The mixture was extracted with ethyl acetate (20 mL×3), and the combined organic layers were washed with saturated brine (50 mL), dried over anhydrous sodium sulfate, then filtered. The filtrate was concentrated in vacuo to remove the solvent and the residue was purified by silica gel column chromatography (DCM/MeOH (v/v)=10/1-5/1) to give the title compound as a white solid (110 mg, 66%).

MS (ESI, pos. ion) m/z: 442.3[M+H]$^+$;

HRMS (ESI, pos. ion) m/z: 442.1687 [M+H]±, (C$_{22}$H$_{22}$F$_2$N$_5$O$_3$) [M+H]$^+$ theoretical value: 442.1691;

$^1$H NMR (400 MHz, DMSO-d$_6$) δ (ppm): 12.26 (s, 1H), 12.05 (s, 1H), 8.65 (d, J=8.0 Hz, 1H), 8.29 (s, 1H), 8.25 (s, 1H), 8.02 (s, 1H), 7.45 (d, J=8.7 Hz, 1H), 7.25 (s, 1H), 6.77 (s, 1H), 4.84 (t, J=8.4 Hz, 1H), 2.73-2.56 (m, 2H), 0.99 (s, 9H).

Example 62: (+/−)-trans-3-((6-(dibenzo[b,d]furan-4-yl)-5-fluoro-2-(5-fluoro-1H-pyrrolo [2,3-b]pyridin-3-yl)pyrimidin-4-yl)amino)bicyclo[2.2.2]octane-2-carboxylic Acid

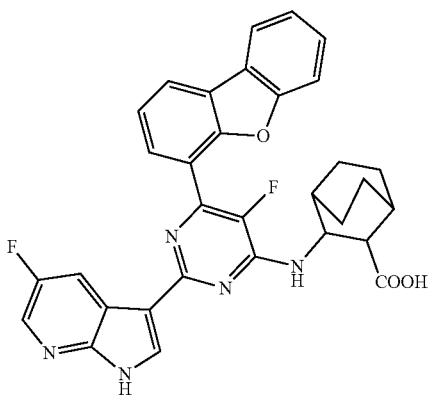 [SMILES: O=C(O)C1C2CCC(CC2)C1Nc1nc(-c2c[nH]c3ncc(F)cc23)nc(-c2cccc3c2oc2ccccc23)c1F]

Step 1: (+/−)-trans-methyl 3-((2-chloro-6-(dibenzo[b,d]furan-4-yl)-5-fluoropyrimidin-4-yl) amino)bicyclo[2.2.2]octane-2-carboxylate To acetonitrile (25 mL) were added (+/−)-trans-methyl 3-((2,6-dichloro-5-fluoropyrimidin-4-yl)amino)bicyclo [2.2.2]octane-2-carboxylate (0.40 g, 1.15 mmol), dibenzo[b,d]furan-4-ylboronic acid (0.244 g, 1.15 mmol), potassium acetate (0.33 g, 3.45 mmol) and Pd(dppf)Cl$_2$ (0.09 g, 0.11 mmol), then to the mixture was added water (1 mL). The resulting mixture was stirred at 80° C. for 12 h under nitrogen protection. The mixture was filtered to remove solid impurities. The filtrate was concentrated in vacuo, and the residue was purified by silica gel column chromatography (PE/EtOAc (v/v)=20/1) to give the title compound as a yellow solid (170 mg, 31%).

MS (ESI, pos. ion) m/z: 480.1 [M+H]$^+$.

Step 2: (+/−)-trans-methyl 3-((6-(dibenzo [b,d] furan-4-yl)-5-fluoro-2-(5-fluoro-1-tosyl-1H-pyrrolo [2,3-b]pyridin-3-yl)pyrimidin-4-yl)amino)bicyclo [2.2.2]octane-2-carboxylate To THF (10 mL) were added 5-fluoro-3-(4,4,5,5-tetramethyl-1,3,2-dioxaborolan-2-yl)-1-tosyl-1H-pyrrolo[2,3-b] pyridine (286 mg, 0.41 mmol, 60%), potassium carbonate (207 mg, 1.50 mmol), palladium acetate (16 mg, 0.07 mmol), X-Phos (71 mg, 0.14 mmol) and (+/−)-trans-methyl 3-((2-chloro-6-(dibenzo [b,d]furan-4-yl)-5-fluoropyrimidin-4-yl)amino) bicyclo[2.2.2]octane-2-carboxylate (180 mg, 0.37 mmol). Then H$_2$O (0.5 mL) was added to the mixture, and the mixture was heated to 80° C. and stirred for 12 h. The mixture was filtered to remove the solid impurities. The filtrate was concentrated in vacuo, and the residue was purified by silica gel column chromatography (PE/EtOAc (v/v)=8/1) to give the title compound as a light yellow solid (200 mg, 73%).

MS (ESI, pos. ion) m/z: 734.1[M+H]$^+$.

Step 3: (+/−)-trans-3-((6-(dibenzo[b,d]furan-4-yl)-5-fluoro-2-(5-fluoro-1H-pyrrolo[2,3-b]pyridin-3-yl) pyrimidin-4-yl)amino)bicyclo[2.2.2]octane-2-carboxylic Acid To a solution of (+/−)-trans-methyl 3-((6-(dibenzo[b,d] furan-4-yl)-5-fluoro-2-(5-fluoro-1-tosyl-1H-pyrrolo[2,3-b] pyridin-3-yl)pyrimidin-4-yl)amino)bicyclo[2.2.2]octane-2-carboxylate (200 mg, 0.27 mmol) in THF/MeOH (v/v=8 mL/4 mL) was added a solution of sodium hydroxide (109 mg, 2.72 mmol) in water (1 mL). The mixture was stirred at rt overnight. To the reaction mixture was added water (10 mL), and the resulting mixture was acidified with hydrochloric acid (1 M) to pH about 3 to 4. The mixture was extracted with ethyl acetate (20 mL×3), and the combined organic layers were washed with saturated brine (50 mL), dried over anhydrous sodium sulfate, then filtered. The filtrate was concentrated in vacuo and the residue was purified by silica gel column chromatography (DCM/MeOH (v/v)=10/1-5/1) to give the title compound as a white solid (130 mg, 84%).

MS (ESI, pos. ion) m/z: 566.1[M+H]$^+$;

HRMS (ESI, pos. ion) m/z: 566.1982 [M+H]±, (C$_{32}$H$_{26}$F$_2$N$_5$O$_3$) [M+H]$^+$ theoretical value: 566.2004;

$^1$H NMR (400 MHz, DMSO-d$_6$) δ (ppm): 12.30 (s, 1H), 8.61 (d, J=8.3 Hz, 1H), 8.29 (s, 3H), 8.22 (d, J=6.5 Hz, 1H), 7.91 (d, J=6.3 Hz, 1H), 7.80 (s, 1H), 7.75 (d, J=7.4 Hz, 1H), 7.64-7.51 (m, 2H), 7.44 (s, 1H), 4.80 (s, 1H), 2.93 (s, 1H), 2.06 (s, 2H), 1.65 (m, 8H);

$^{13}$C NMR (101 MHz, DMSO-d$_6$) δ (ppm): 176.08, 157.96, 157.88, 156.03, 154.95, 153.30, 152.53, 152.41, 151.93, 146.43, 143.29, 143.18, 140.09, 139.61, 131.96, 131.67, 131.26, 128.61, 128.48, 128.43, 125.35, 124.73, 123.76, 122.95, 121.77, 119.62, 118.95, 118.87, 115.68, 115.46, 114.33, 112.13, 51.22, 48.25, 34.80, 30.87, 28.83, 28.75, 22.30, 22.04.

Example 63: (+/−)-trans-3-((5-fluoro-2-(5-fluoro-1H-pyrrolo[2,3-b]pyridin-3-yl)-6-phenyl ethynyl)pyrimidin-4-yl)amino)bicyclo[2.2.2]octane-2-carboxylic Acid

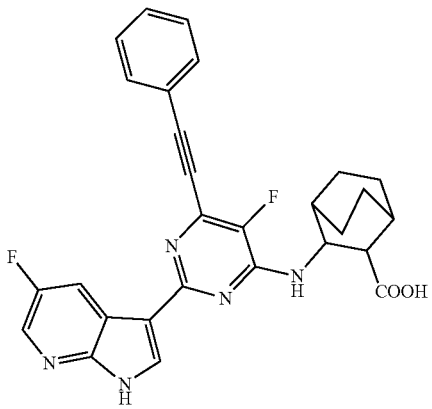 [SMILES: O=C(O)C1C2CCC(CC2)C1Nc1nc(-c2c[nH]c3ncc(F)cc23)nc(C#Cc2ccccc2)c1F]

Step 1: 2,4-dichloro-5-fluoro-6-(phenylethynyl)pyrimidine

To THF (20 mL) were added 2,4,6-trichloro-5-fluoropyrimidine (1.00 g, 4.96 mmol), cuprous iodide (0.19 g, 9.92 mmol), bis(triphenylphosphine)palladium(II) chloride (0.35 g, 0.49 mmol) and triethylamine (1.51 g, 14.9 mmol). Then to the mixture was added dropwise slowly phenylacetylene (0.48 g, 4.70 mmol) under nitrogen protection, and the mixture was stirred at rt for 4 h. The mixture was filtered to remove solid impurities. The filtrate was concentrated in vacuo, and the residue was purified by silica gel column chromatography (PE) to give the title compound as a yellow solid (550 mg, 42%).

MS (ESI, pos. ion) m/z: 266.9 [M+H]$^+$.

Step 2: (+/−)-trans-methyl 3-((2-chloro-5-fluoro-6-(phenylethynyl)pyrimidin-4-yl)amino) bicyclo[2.2.2]octane-2-carboxylate To a reaction flask were added 2,4-dichloro-5-fluoro-6-(phenylethynyl)pyrimidine (0.55 g, 2.05 mmol), DIPEA (0.53 g, 4.11 mmol), (+/−)-trans-methyl 3-aminobicyclo[2.2.2]octane-2-carboxylate (0.46 g, 2.47 mmol) and DCM (10 mL). The mixture was stirred at rt for 18 h. After the reaction was completed, to the reaction mixture was added water (20 mL), and the resulting mixture was extracted with DCM (20 mL×3). The combined organic layers were washed with saturated brine (10 mL), dried over anhydrous sodium sulfate and filtered. The filtrate was concentrated in vacuo and the residue was purified by silica gel column chromatography (PE/EtOAc (v/v)=8/1) to give the title compound as a light yellow solid (0.58 g, 68%).

MS (ESI, pos. ion) m/z: 414.3[M+H]$^+$.

Step 3: (+/−)-trans-methyl 3-((5-fluoro-2-(5-fluoro-1-tosyl-1H-pyrrolo[2,3-b]pyridin-3-yl)-6-phenylethynyl)pyrimidin-4-yl)amino)bicyclo[2.2.2]octane-2-carboxylate To THF (10 mL) were added 5-fluoro-3-(4,4,5,5-tetramethyl-1,3,2-dioxaborolan-2-yl)-1-tosyl-1H-pyrrolo[2,3-b]pyridine (400 mg, 0.58 mmol, 60%), potassium carbonate (267 mg, 1.93 mmol), palladium acetate (21 mg, 0.09 mmol), X-Phos (92 mg, 0.18 mmol) and (+/−)-trans-methyl 3-((2-chloro-5-fluoro-6-(phenylethynyl)pyrimidin-4-yl)amino)bicyclo[2.2.2]octane-2-carboxylate (200 mg, 0.48 mmol). Then H$_2$O (0.5 mL) was added to the mixture, and the mixture was heated to 80° C. and stirred for 12 h. The mixture was filtered to remove solid impurities. The filtrate was concentrated in vacuo, and the residue was purified by silica gel column chromatography (PE/EtOAc (v/v)=8/1) to give the title compound as a light yellow solid (162 mg, 50%).

Step 4: (+/−)-trans-3-((5-fluoro-2-(5-fluoro-1H-pyrrolo[2,3-b]pyridin-3-yl)-6-(phenylethynyl) pyrimidin-4-yl)amino)bicyclo[2.2.2]octane-2-carboxylic Acid To a solution of (+/−)-trans-methyl 3-((5-fluoro-2-(5-fluoro-1-tosyl-1H-pyrrolo [2,3-b]pyridin-3-yl)-6-(phenylethynyl)pyrimidin-4-yl)amino)bicyclo[2.2.2]octane-2-carboxylate (162 mg, 0.24 mmol) in THF/MeOH (v/v=8 mL/4 mL) was added a solution of sodium hydroxide (97 mg, 2.40 mmol) in water (2 mL). The mixture was stirred at rt overnight. To the reaction mixture was added water (10 mL), and the resulting mixture was acidified with hydrochloric acid (1 M) to pH about 3 to 4. The mixture was extracted with ethyl acetate (20 mL×3), and the combined organic layers were washed with saturated brine (50 mL), dried over anhydrous sodium sulfate, then filtered. The filtrate was concentrated in vacuo to remove the solvent and the residue was purified by silica gel column chromatography (DCM/MeOH (v/v)=10/1-5/1) to give the title compound as a white solid (99 mg, 82%).

MS (ESI, pos. ion) m/z: 500.1 [M+H]$^+$;

HRMS (ESI, pos. ion) m/z: 500.1892 [M+H]±, (C$_{28}$H$_{24}$F$_2$N$_5$O$_2$) [M+H]$^+$ theoretical value: 500.1898;

$^1$H NMR (400 MHz, DMSO-d$_6$) δ (ppm): 12.32 (s, 1H), 8.51 (dd, J=9.6, 2.2 Hz, 1H), 8.31-8.25 (m, 2H), 7.80 (d, J=6.6 Hz, 1H), 7.70-7.64 (m, 2H), 7.50 (d, J=6.7 Hz, 3H), 4.74 (s, 1H), 2.90 (d, J=6.4 Hz, 1H), 2.03 (s, 1H), 1.98 (s, 1H), 1.80 (m, 3H), 1.69-1.41 (m, 5H).

Example 64: (+/−)-trans-3-((5-fluoro-2-(5-fluoro-1H-pyrrolo[2,3-b]pyridin-3-yl)-6-(1-methyl-1H-pyrrol-3-yl)pyrimidin-4-yl)amino)bicyclo[2.2.2]octane-2-carboxylic Acid

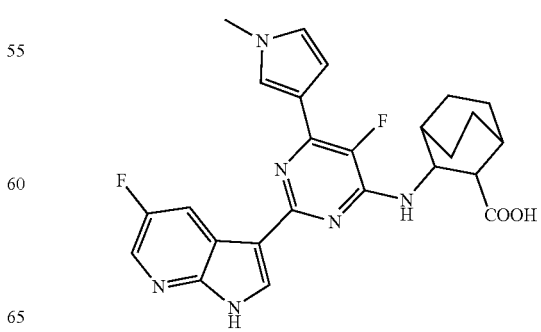

Step 1: (+/−)-trans-methyl 3-((2-chloro-5-fluoro-6-(1-methyl-1H-pyrrol-3-yl)pyrimidin-4-yl) amino) bicyclo[2.2.2]octane-2-carboxylate To acetonitrile (25 mL) were added (+/−)-trans-methyl 3-((2,6-dichloro-5-fluoropyrimidin-4-yl)amino)bicyclo [2.2.2]octane-2-carboxylate (0.40 g, 1.14 mmol), (1-methyl-1H-pyrrol-3-yl)boronic acid (0.23 g, 1.14 mmol), potassium acetate (0.34 g, 3.46 mmol) and Pd(dppf)Cl$_2$ (0.09 g, 0.11 mmol), then to the mixture was added water (1 mL). The resulting mixture was stirred at 80° C. for 12 h under nitrogen protection. The mixture was filtered to remove solid impurities. The filtrate was concentrated in vacuo, and the residue was purified by silica gel column chromatography (PE/EtOAc (v/v)=20/1) to give the title compound as a yellow solid (150 mg, 33%).
MS (ESI, pos. ion) m/z: 393.1 [M+H]$^+$.

Step 2: (+/−)-trans-methyl 3-((5-fluoro-2-(5-fluoro-1-tosyl-1H-pyrrolo[2,3-b]pyridin-3-yl)-6-1-methyl-1H-pyrrol-3-yl)pyrimidin-4-yl)amino)bicyclo[2.2.2] octane-2-carboxylate To THF (10 mL) were added 5-fluoro-3-(4,4,5,5-tetramethyl-1,3,2-dioxaborolan-2-yl)-1-tosyl-1H-pyrrolo[2,3-b]pyridine (423 mg, 0.46 mmol, 45%), potassium carbonate (211 mg, 1.52 mmol), palladium acetate (17 mg, 0.07 mmol), X-Phos (72 mg, 0.14 mmol) and (+/−)-trans-methyl 3-((2-chloro-5-fluoro-6-(1-methyl-1H-pyrrol-3-yl)pyrimidin-4-yl)amino) bicyclo[2.2.2]octane-2-carboxylate (150 mg, 0.38 mmol). Then H$_2$O (0.5 mL) was added to the mixture, and the mixture was heated to 80° C. and stirred for 12 h. The mixture was filtered to remove solid impurities. The filtrate was concentrated in vacuo to remove the solvent, and the residue was purified by silica gel column chromatography (PE/EtOAc (v/v)=8/1) to give the title compound as a light yellow solid (230 mg, 93%).
MS (ESI, pos. ion) m/z: 647.1 [M+H]$^+$.

Step 3: (+/−)-trans-3-((5-fluoro-2-(5-fluoro-1H-pyrrolo[2,3-b]pyridin-3-yl)-6-(1-methyl 1H-pyrrol-3-yl) pyrimidin-4-yl)amino)bicyclo[2.2.2]octane-2-carboxylic Acid To a solution of (+/−)-trans-methyl 3-((5-fluoro-2-(5-fluoro-1-tosyl-1H-pyrrolo [2,3-b]pyridin-3-yl)-6-(1-methyl-1H-pyrrol-3-yl)pyrimidin-4-yl)amino)bicyclo[2.2.2]octane-2-carboxylate (230 mg, 0.35 mmol) in THF/MeOH (v/v=8 mL/4 mL) was added a solution of sodium hydroxide (142 mg, 3.55 mmol) in water (2 mL). The mixture was stirred at rt overnight. To the reaction mixture was added water (10 mL), and the resulting mixture was acidified with hydrochloric acid (1 M) to pH about 3 to 4. The mixture was extracted with ethyl acetate (20 mL×3), and the combined organic layers were washed with saturated brine (50 mL), dried over anhydrous sodium sulfate, then filtered. The filtrate was concentrated in vacuo to remove the solvent and the residue was purified by silica gel column chromatography (DCM/MeOH (v/v)=10/1-5/1) to give the title compound as a white solid (120 mg, 71%).
MS (ESI, pos. ion) m/z: 479.1[M+H]$^+$;
HRMS (ESI, pos. ion) m/z: 479.2024 [M+H]±, (C$_{26}$H$_{24}$F$_2$N$_5$O$_2$) [M+H]$^+$ theoretical value: 479.2007;
$^1$H NMR (400 MHz, DMSO-d$_6$) δ (ppm): 12.21 (s, 1H), 8.58 (d, J=8.8 Hz, 1H), 8.27 (s, 2H), 7.52 (s, 1H), 7.28 (d, J=4.1 Hz, 1H), 6.87 (s, 2H), 4.69 (s, 1H), 3.74 (s, 3H), 2.87 (d, J=3.9 Hz, 1H), 2.00 (s, 2H), 1.80 (m, 3H), 1.67-1.45 (m, 5H).

Example 65: (+/−)-trans-3-((2-(5-fluoro-1H-pyrrolo[2,3-b]pyridin-3-yl)-7-methyl-7H-pyrrolo[2,3-d]pyrimidin-4-yl)amino)bicyclo[2.2.2]octane-2-carboxylic Acid

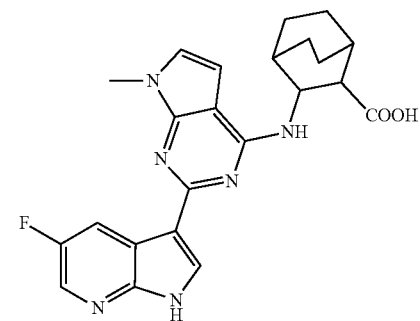 [SMILES: Cn1ccc2c(NC3C4CCC(CC4)C3C(=O)O)nc(-c3c[nH]c4ncc(F)cc34)nc21]

Step 1: (+/−)-trans-methyl 3-((2-(5-fluoro-1-tosyl-1H-pyrrolo[2,3-b]pyridin-3-yl)-7-methyl-7H-pyrrolo[2,3-d]pyrimidin-4-yl)amino)bicyclo[2.2.2]octane-2-carboxylate To a microwave tube were added 5-fluoro-3-(4,4,5,5-tetramethyl-1,3,2-dioxaborolan-2-yl)-1-tosyl-1H-pyrrolo[2,3-b]pyridine (347 mg, 0.50 mmol, 60%), (+/−)-trans-methyl 3-((2-chloro-7-methyl-7H-pyrrolo[2,3-d]pyrimidin-4-yl) amino)bicyclo[2.2.2]octane-2-carboxylate (146 mg, 0.41 mmol), potassium carbonate (114 mg, 0.82 mmol), Pd(dppf) Cl$_2$ (30 mg, 0.04 mmol), 1,4-dioxane (5 mL) and water (0.5 mL). The air in the mixture was removed by bubbling with nitrogen for 10 min, then the mixture in the microwave tube was stirred at 110° C. with microwave heating for 2 hours. The mixture was filtered through a celite pad, and the filter cake was washed with ethyl acetate (50 mL). The filtrate was washed with saturated brine (50 mL), dried over anhydrous sodium sulfate and filtered. The filtrate was concentrated in vacuo and the residue was purified by silica gel column chromatography (n-hexane/EtOAc(v/v)=5/1) to give the title compound as a yellow solid (214 mg, 56%).
$^1$H NMR (400 MHz, CDCl$_3$) δ (ppm): 8.75 (dd, J=9.0, 2.8 Hz, 1H), 8.67 (s, 1H), 8.31 (d, J=1.8 Hz, 1H), 8.13 (d, J=8.3 Hz, 2H), 7.27 (d, J=6.1 Hz, 2H), 6.92 (d, J=3.4 Hz, 1H), 6.38 (d, J=3.3 Hz, 1H), 5.13 (d, J=6.9 Hz, 1H), 4.90 (d, J=5.9 Hz, 1H), 3.86 (s, 3H), 3.75 (s, 3H), 2.48 (d, J=5.6 Hz, 1H), 2.37 (s, 3H), 2.07 (d, J=2.0 Hz, 2H), 2.01 (s, 1H), 1.94 (m, 1H), 1.79 (m, 8H).

Step 2: (+/−)-trans-3-((2-(5-fluoro-1H-pyrrolo[2,3-b]pyridin-3-yl)-7-methyl-7H-pyrrolo[2,3-d]pyrimidin-4-yl)amino)bicyclo[2.2.2]octane-2-carboxylic Acid To a solution of (+/−)-trans-methyl 3-((2-(5-fluoro-1-tosyl-1H-pyrrolo[2,3-b]pyridin-3-yl)-7-methyl-7H-pyrrolo [2,3-d]pyrimidin-4-yl)amino)bicyclo[2.2.2]octane-2-carboxylate (197 mg, 0.33 mmol) in a mixed solvent of THF and MeOH (v/v=1/1, 6 mL) was added a aqueous sodium hydroxide solution (4 M, 0.90 mL, 3.60 mmol). The mixture was stirred at 30° C. overnight. To the reaction mixture was added water (10 mL), and the resulting mixture was acidified with hydrochloric acid (1 M) to pH about 5.5. The mixture was extracted with ethyl acetate (20 mL×3), and the combined organic layers were washed with saturated brine (50 mL), dried over anhydrous sodium sulfate, then filtered. The filtrate was concentrated in vacuo to remove the solvent and the residue was purified by silica gel column chromatography (DCM/MeOH (v/v)=10/1) to give the title compound as a yellow solid (80 mg, 56%).

MS (ESI, pos.ion) m/z: 435.2[M+H]$^+$;

HRMS (ESI, pos. ion) m/z: 435.1941 [M+H]$^+$, ($C_{23}H_{24}FN_6O_2$) [M+H]$^+$ theoretical value: 435.1945;

$^1$H NMR (600 MHz, DMSO-d$_6$) δ (ppm): 12.28 (s, 1H), 12.09 (s, 1H), 8.73 (d, J=8.5 Hz, 1H), 8.27 (s, 1H), 8.24 (s, 1H), 7.22 (d, J=5.7 Hz, 1H), 7.08 (s, 1H), 6.62 (s, 1H), 4.80 (s, 1H), 3.78 (s, 3H), 2.72 (d, J=5.7 Hz, 1H), 2.03 (d, J=15.2 Hz, 2H), 1.80 (m, 3H), 1.49 (m, 5H);

$^{13}$C NMR (101 MHz, DMSO-d$_6$) δ (ppm): 176.22, 157.13, 156.03, 154.75, 150.65, 146.43, 131.51, 131.22, 130.00, 124.76, 119.07, 118.99, 116.07, 115.99, 115.95, 115.86, 101.15, 98.95, 50.63, 49.11, 31.05, 28.98, 28.87, 26.09, 24.23, 21.59, 19.52.

Example 66: (+/−)-trans-3-((5-(5-fluoro-1H-pyrrolo[2,3-b]pyridin-3-yl)thiazolo[5,4-d]pyrimidin-7-yl)amino)bicyclo[2.2.2]octane-2-carboxylic Acid

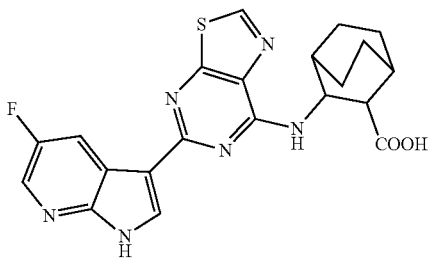 [SMILES: O=C(O)C1C2CCC(CC2)C1Nc1nc(-c2c[nH]c3ncc(F)cc23)nc2scnc12]

Step 1: (+/−)-trans-methyl 3-((5-chlorothiazolo[5,4-d]pyrimidin-7-yl)amino)bicyclo[2.2.2]octane-2-carboxylate (+/−)-trans-Methyl 3-aminobicyclo[2.2.2]octane-2-carboxylate (284 mg, 1.55 mmol) and 5,7-dichlorothiazolo[5,4-d]pyrimidine (352 mg, 1.71 mmol) were dissolved in DMF (5 mL), then potassium carbonate (428 mg, 3.10 mmol) was added. The mixture was stirred at rt overnight. The reaction was stopped, and to the reaction mixture was added water (50 mL). The resulting mixture was extracted with ethyl acetate (50 mL×2). The combined organic layers were washed with saturated brine (80 mL), dried over anhydrous sodium sulfate and filtered. The filtrate was concentrated in vacuo to remove the solvent and the residue was purified by silica gel column chromatography (PE/EtOAc (v/v)=10/1) to give the title compound as a yellow solid (317 mg, 58%).

MS (ESI, pos.ion) m/z: 353.0 [M+H]$^+$;

$^1$H NMR (600 MHz, CDCl$_3$) δ (ppm): 8.75 (s, 1H), 6.49 (d, J=4.7 Hz, 1H), 4.63 (s, 1H), 3.76 (s, 3H), 2.50 (d, J=5.6 Hz, 1H), 2.01 (d, J=1.8 Hz, 1H), 1.95 (d, J=2.5 Hz, 1H), 1.88-1.76 (m, 2H), 1.73-1.53 (m, 6H).

Step 2: (+/−)-trans-methyl 3-((5-(5-fluoro-1-tosyl-1H-pyrrolo[2,3-b]pyridin-3-yl)thiazolo[5,4-d]pyrimidin-7-yl)amino)bicyclo[2.2.2]octane-2-carboxylate To 1,4-dioxane (8 mL) were added 5-fluoro-3-(4,4,5,5-tetramethyl-1,3,2-dioxaborolan-2-yl)-1-tosyl-1H-pyrrolo[2,3-b]pyridine (180 mg, 0.21 mmol, 50%), K$_2$CO$_3$ (39 mg, 0.28 mmol), PdCl$_2$(dppf) (8 mg, 0.01 mmol) and (+/−)-trans-methyl 3-((5-chlorothiazolo[5,4-d]pyrimidin-7-yl)amino)bicyclo[2.2.2]octane-2-carboxylate (51 mg, 0.14 mmol). Then H$_2$O (1 mL) was added to the mixture, and the air in the mixture was removed by bubbling with nitrogen for 10 min. The mixture was stirred for 2 h at 110° C. with microwave heating. The mixture was filtered through a celite pad to remove solid impurities. The filtrate was concentrated in vacuo, and the residue was purified by silica gel column chromatography (PE/EtOAc (v/v)=10/1-5/1) to give the title compound as a white solid (61 mg, 70%).

Step 3: (+/−)-trans-3-((5-(5-fluoro-1H-pyrrolo[2,3-b]pyridin-3-yl)thiazolo[5,4-d]pyrimidin-7-yl)amino)bicyclo[2.2.2]octane-2-carboxylic Acid To a mixed solvent of THF and MeOH (v/v=2 mL/2 mL) was added (+/−)-trans-methyl 3-((5-(5-fluoro-1-tosyl-1H-pyrrolo[2,3-b]pyridin-3-yl)thiazolo[5,4-d]pyrimidin-7-yl)amino)bicyclo[2.2.2]octane-2-carboxylate (61 mg, 0.10 mmol), then a solution of NaOH (40 mg, 1.00 mmol) in water (1 mL) was added. The resulting mixture was stirred overnight at rt, then water (10 mL) was added. The mixture was acidified with hydrochloric acid (1 M) to pH about 6, then extracted with ethyl acetate (15 mL×3). The combined organic layers were washed with saturated brine (40 mL), dried over anhydrous sodium sulfate and filtered. The filtrate was concentrated in vacuo, and the residue was purified by silica gel column chromatography (DCM/MeOH (v/v)=10/1-5/1) to give the title compound as a white solid (16 mg, 36%).

MS (ESI, pos. ion) m/z: 439.1 [M+H]$^+$;

HRMS (ESI, pos. ion) m/z: 439.1329, ($C_{21}H_{20}FN_6O_2S$) [M+H]$^+$ theoretical value: 439.1352;

$^1$H NMR (600 MHz, DMSO-d$_6$) δ (ppm): 12.38 (s, 1H), 9.13 (s, 1H), 8.63 (d, J=9.4 Hz, 1H), 8.35 (s, 1H), 8.29 (s, 1H), 8.21 (d, J=6.5 Hz, 1H), 4.89 (s, 1H), 3.03 (d, J=5.4 Hz, 1H), 2.03 (s, 2H), 1.83 (m, 3H), 1.70-1.43 (m, 5H);

$^{13}$C NMR (151 MHz, DMSO-d$_6$) δ (ppm): 162.39, 159.26, 155.57, 155.35, 150.28, 146.39, 132.01, 131.87, 131.82, 128.61, 118.97, 118.92, 115.79, 115.65, 114.35, 114.32, 51.02, 47.92, 28.90, 28.77, 25.62, 24.34, 21.64, 19.59.

Example 67: (+/−)-trans-3-((2-(5-fluoro-1H-pyrrolo[2,3-b]pyridin-3-yl)-9-methyl-9H-purin-6-yl)amino)bicyclo[2.2.2]octane-2-carboxylic Acid

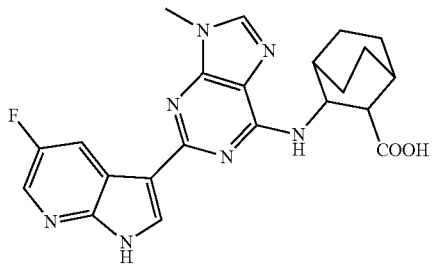 [SMILES: Cn1cnc2c(NC3C4CCC(CC4)C3C(=O)O)nc(-c3c[nH]c4ncc(F)cc34)nc21]

Step 1: (+/−)-trans-methyl 3-((2-chloro-9-methyl-9H-purin-6-yl)amino)bicyclo[2.2.2]octane-2-carboxylate (+/−)-trans-Methyl 3-aminobicyclo[2.2.2]octane-2-carboxylate (400 mg, 2.18 mmol) and 2,6-dichloro-9-methyl-9H-purine (400 mg, 1.97 mmol) were dissolved in acetonitrile (8 mL), then DIPEA (1.75 mL, 9.95 mmol) was added. The mixture was stirred at 50° C. overnight under nitrogen protection. To the reaction mixture was added water (50 mL), and the resulting mixture was partitioned. The aqueous layer was extracted with ethyl acetate (50 mL×2). The combined organic layers were washed with saturated brine (80 mL), dried over anhydrous sodium sulfate and filtered. The filtrate was concentrated in vacuo to remove the solvent and the residue was purified by silica gel column chromatography (PE/EtOAc (v/v)=3/1) to give the title compound as a yellow solid (457 mg, 66%).

MS (ESI, pos.ion) m/z: 350.1 [M+H]$^+$;
$^1$H NMR (400 MHz, CDCl$_3$) δ (ppm): 7.66 (s, 1H), 6.37 (s, 1H), 4.55 (s, 1H), 3.74 (s, 3H), 3.72 (s, 3H), 3.21 (s, 1H), 2.43 (s, 1H), 1.94 (s, 1H), 1.88 (d, J=2.5 Hz, 1H), 1.78 (d, J=10.6 Hz, 2H), 1.66-1.44 (m, 5H).

Step 2: (+/−)-trans-methyl 3-((2-(5-fluoro-1-tosyl-1H-pyrrolo[2,3-b]pyridin-3-yl)-9-methyl-9H-purin-6-yl)amino)bicyclo[2.2.2]octane-2-carboxylate To 1,4-dioxane (8 mL) were added 5-fluoro-3-(4,4,5,5-tetramethyl-1,3,2-dioxaborolan-2-yl)-1-tosyl-1H-pyrrolo[2,3-b]pyridine (540 mg, 0.52 mmol, 40%), K$_2$CO$_3$ (119 mg, 0.86 mmol), PdCl$_2$(dppf) (29 mg, 0.04 mmol) and (+/−)-trans-methyl 3-((2-chloro-9-methyl-9H-purin-6-yl)amino)bicyclo[2.2.2]octane-2-carboxylate (151 mg, 0.43 mmol). Then H$_2$O (1 mL) was added to the mixture, and the air in the mixture was removed by bubbling with nitrogen for 10 min. The mixture was stirred for 2 h at 110° C. with microwave heating. The mixture was filtered through a celite pad to remove solid impurities. The filtrate was concentrated in vacuo, and the residue was purified by silica gel column chromatography (PE/EtOAc (v/v)=10/1-2/1) to give the title compound as a white solid (166 mg, 64%).

Step 3: (+/−)-trans-3-((2-(5-fluoro-1H-pyrrolo[2,3-b]pyridin-3-yl)-9-methyl-9H-purin-6-yl) amino) bicyclo[2.2.2]octane-2-carboxylic Acid To a solution of (+/−)-trans-methyl 3-((2-(5-fluoro-1-tosyl-1H-pyrrolo[2,3-b]pyridin-3-yl)-9-methyl-9H-purin-6-yl)amino)bicyclo[2.2.2]octane-2-carboxylate (166 mg, 0.28 mmol) in THF/MeOH (v/v=3 mL/3 mL) was added a solution of NaOH (112 mg, 2.8 mmol) in water (2 mL). The mixture was stirred at rt overnight, then acidified with hydrochloric acid (1 M) to pH about 6. The resulting mixture was extracted with ethyl acetate (15 mL×3). The combined organic layers were washed with saturated brine (40 mL), dried over anhydrous sodium sulfate and filtered. The filtrate was concentrated in vacuo to remove the solvent and the residue was purified by silica gel column chromatography (DCM/MeOH (v/v)=10/1-5/1) to give the title compound as a white solid (71 mg, 59%).

MS (ESI, pos. ion) m/z: 436.1 [M+H]$^+$;
HRMS (ESI, pos. ion) m/z: 436.1874, (C$_{22}$H$_{23}$FN$_7$O$_2$) [M+H]$^+$ theoretical value: 436.1897;
$^1$H NMR (400 MHz, DMSO-d$_6$) δ (ppm): 12.26 (s, 2H), 8.70 (s, 1H), 8.25 (d, J=10.4 Hz, 2H), 8.06 (s, 1H), 7.67 (s, 1H), 4.83 (s, 1H), 3.79 (s, 3H), 2.95 (s, 1H), 2.00 (s, 2H), 1.84-1.74 (m, 3H), 1.50 (m, 5H);
$^{13}$C NMR (101 MHz, DMSO-d$_6$) δ (ppm): 176.19, 157.22, 157.08, 154.84, 146.36, 141.10, 131.67, 131.38, 130.58, 119.01, 118.93, 115.33, 110.00, 61.82, 50.56, 48.35, 29.69, 28.89, 25.80, 24.28, 21.63, 19.50.

Example 68: (+/−)-trans-3-((6-cyclopropyl-2-(5-fluoro-1H-pyrrolo[2,3-b]pyridin-3-yl) pyrimidin-4-yl)amino)bicyclo[2.2.2]octane-2-carboxylic Acid

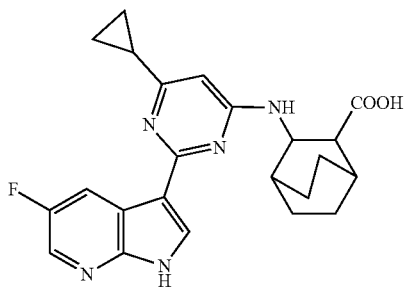 [SMILES: O=C(O)C1C2CCC(CC2)C1Nc1cc(C2CC2)nc(-c2c[nH]c3ncc(F)cc23)n1]

Step 1: (+/−)-trans-methyl 3-((2-chloro-6-cyclopropylpyrimidin-4-yl)amino)bicyclo[2.2.2]octane-2-carboxylate To a solution of (+/−)-trans-methyl 3-((2,6-dichloropyrimidin-4-yl)amino) bicyclo[2.2.2]octane-2-carboxylate (100 mg, 0.30 mmol) in tetrahydrofuran (5 mL) were added Pd(dppf)Cl$_2$ (25 mg, 0.03 mmol), potassium phosphate (160 mg, 0.75 mmol) and cyclopropylboronic acid (27 mg, 0.31 mmol). The mixture was refluxed overnight under nitrogen protection. The reaction mixture was cooled to rt and concentrated in vacuo to dry. To the residue was added ethyl acetate (20 mL), and the mixture was washed with saturated aqueous sodium bicarbonate (20 mL) and saturated brine (20 mL). The organic layer was dried over anhydrous sodium sulfate, and filtered. The filtrate was concentrated in vacuo to dry and the residue was purified by silica gel column chromatography (PE/EA (v/v)=5/1) to give the title compound as colorless oil (59 mg, 58%).

MS (ESI, pos. ion) m/z: 336.2 [M+H]$^+$;
$^1$H NMR (400 MHz, CDCl$_3$) δ (ppm): 6.18 (s, 1H), 5.37-5.13 (m, 1H), 4.17 (d, J=19.1 Hz, 1H), 3.76-3.73 (m, 3H), 2.35-2.31 (m, 1H), 2.07-2.03 (m, 1H), 1.84-1.79 (m, 2H), 1.70 (d, J=7.3 Hz, 2H), 1.65 (d, J=7.0 Hz, 2H), 1.54 (d, J=10.7 Hz, 2H), 1.46 (d, J=7.3 Hz, 1H), 1.36-1.23 (m, 1H), 1.08 (tt, J=9.1, 4.5 Hz, 2H), 1.02-0.96 (m, 2H).

Step 2: (+/−)-trans-methyl 3-((6-cyclopropyl-2-(5-fluoro-1-tosyl-1H-pyrrolo[2,3-b]pyridin-3-yl) pyrimidin-4-yl)amino)bicyclo[2.2.2]octane-2-carboxylate To a microwave tube were added were added 5-fluoro-3-(4,4,5,5-tetramethyl-1,3,2-dioxaborolan-2-yl)-1-tosyl-1H-pyrrolo[2,3-b]pyridine (1.03 g, 1.49 mmol, 60%), (+/−)-trans-methyl 3-((2-chloro-6-cyclopropylpyrimidin-4-yl)amino)bicyclo[2.2.2]octane-2-carboxylate (400 mg, 1.191 mmol), water (0.5 mL), 1,4-dioxane (15 mL), potassium carbonate (442 mg, 3.20 mmol) and Pd(dppf)Cl$_2$ (130 mg, 0.16 mmol). The air in the mixture was removed by bubbling with nitrogen for 10 min. The mixture was stirred for 1 h at 110° C. with microwave heating. The mixture was filtered through a celite pad, and the filter cake was washed with ethyl acetate (50 mL). The filtrate was concentrated in vacuo and the residue was purified by silica gel column chromatography (PE/EA (v/v)=15/1) to give the title compound as light yellow oil (251 mg, 36%).

MS (ESI, pos.ion) m/z: 590.5 [M+H]$^+$;

$^1$H NMR (400 MHz, CDCl$_3$) δ (ppm): 8.57 (s, 1H), 8.49 (dd, J=9.0, 2.7 Hz, 1H), 8.32 (s, 1H), 8.30 (s, 1H), 8.10 (d, J=6.1 Hz, 2H), 8.09 (s, 2H), 6.20 (s, 1H), 5.03 (s, 1H), 3.77 (s, 1H), 3.74 (s, 3H), 2.38 (s, 3H), 1.95-1.87 (m, 4H), 1.79 (s, 4H), 1.01 (dt, J=11.3, 5.5 Hz, 4H).

Step 3: (+/−)-trans-3-((6-cyclopropyl-2-(5-fluoro-1H-pyrrolo[2,3-b]pyridin-3-yl)pyrimidin-4-yl)amino)bicyclo[2.2.2]octane-2-carboxylic Acid To a solution of (+/−)-trans-methyl 3-((6-cyclopropyl-2-(5-fluoro-1-tosyl-1H-pyrrolo[2,3-b]pyridin-3-yl)pyrimidin-4-yl)amino)bicyclo[2.2.2]octane-2-carboxylate (250 mg, 0.42 mmol) in a mixed solvent of THF (5 mL), methanol (5 mL) and water (5 mL), then to the mixture was added NaOH (170 mg, 4.25 mmol) in portions. The mixture was stirred at rt overnight and concentrated in vacuo to remove the organic solvent. To the residue was added water (15 mL), and the resulting mixture was acidified with diluted hydrochloric acid (1 mol/L) to pH about 6. The resulting mixture was extracted with ethyl acetate (20 mL×3). The combined organic layers were washed with saturated brine (50 mL), dried over anhydrous sodium sulfate and filtered. The filtrate was concentrated in vacuo to remove the solvent and the residue was purified by silica gel column chromatography (DCM/MeOH (v/v)=30/1-10/1) to give the title compound as a white solid (90 mg, 50%).

MS (ESI, pos.ion) m/z: 422.2[M+H]$^+$;

HRMS (ESI, pos. ion) m/z: 422.1964 [M+H]$^+$, (C$_{23}$H$_{26}$FN$_5$O$_2$) [M+H]$^+$ theoretical value: 422.1992;

$^1$H NMR (600 MHz, DMSO-d$_6$) δ (ppm): 12.96 (s, 1H), 8.79 (s, 1H), 8.40 (s, 1H), 7.26 (s, 1H), 7.18 (s, 1H), 7.09 (s, 1H), 6.07 (s, 1H), 4.78 (s, 1H), 2.55 (s, 1H), 2.12 (s, 1H), 2.04 (s, 1H), 1.91 (s, 1H), 1.73-1.39 (m, 8H), 1.12 (d, J=4.3 Hz, 2H), 1.00 (s, 2H);

$^{13}$C NMR (151 MHz, DMSO-d$_6$) δ (ppm): 175.37, 162.36, 159.01, 158.81, 157.35, 155.74, 146.17, 134.80, 133.52, 133.33, 118.79, 118.74, 115.81, 115.67, 95.75, 51.41, 48.79, 29.07, 28.45, 25.60, 24.09, 21.50, 21.20, 19.33, 12.87, 10.50, 10.34.

Example 69: (R)-3-((5-fluoro-2-(5-fluoro-1H-pyrrolo[2,3-b]pyridin-3-yl)-6-phenylpyrimidin-4-yl)amino)-4,4-dimethylpentanoic Acid

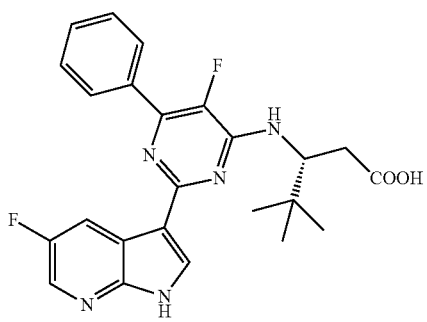 [SMILES: CC(C)(C)[C@@H](CC(=O)O)Nc1nc(-c2c[nH]c3ncc(F)cc23)nc(-c2ccccc2)c1F]

Step 1: (R)-methyl 3-((2,6-dichloro-5-fluoropyrimidin-4-yl)amino)-4,4-dimethylpentanoate To a reaction flask were added 2,4,6-trichloro-5-fluoropyrimidine (0.64 g, 3.16 mmol), DIPEA (1.02 g, 7.91 mmol), (R)-methyl 3-amino-4,4-dimethylpentanoate (0.42 g, 2.63 mmol) and dichloromethane (10 mL), and the reaction mixture was stirred at rt for 24 h. To the reaction mixture was added water (20 mL), and the resulting mixture was extracted with dichloromethane (20 mL×3). The combined organic layers were washed with saturated brine (30 mL), dried over anhydrous sodium sulfate and filtered. The filtrate was concentrated in vacuo and the residue was purified by silica gel column chromatography (PE/EtOAc (v/v)=20/1) to give the title compound as a light yellow solid (420 mg, 49%).

MS (ESI, pos. ion) m/z: 324.10[M+H]$^+$.

Step 2: (R)-methyl 3-((2-chloro-5-fluoro-6-phenylpyrimidin-4-yl)amino)-4,4-dimethylpentanoate To acetonitrile (25 mL) were added (R)-methyl 3-((2,6-dichloro-5-fluoropyrimidin-4-yl)amino)-4,4-dimethylpentanoate (420 mg, 1.29 mmol), phenylboronic acid (680 mg, 2.09 mmol), potassium acetate (617 mg, 6.29 mmol) and Pd(dppf)Cl$_2$ (171 mg, 0.21 mmol), then to the mixture was added water (1 mL). The resulting mixture was stirred at 80° C. for 12 h under nitrogen protection. The mixture was filtered to remove solid impurities. The filtrate was concentrated in vacuo, and the residue was purified by silica gel column chromatography (PE/EtOAc (v/v)=20/1) to give the title compound as a yellow solid (480 mg, 63%).

MS (ESI, pos. ion) m/z: 366.2[M+H]$^+$.

Step 3: (R)-methyl 3-((5-fluoro-2-(5-fluoro-1-tosyl-1H-pyrrolo[2,3-b]pyridin-3-yl)-6-phenyl pyrimidin-4-yl)amino)-4,4-dimethylpentanoate To THF (10 mL) were added 5-fluoro-3-(4,4,5,5-tetramethyl-1,3,2-dioxaborolan-2-yl)-1-tosyl-1H-pyrrolo[2,3-b]pyridine (695 mg, 0.75 mmol, 45%), potassium carbonate (337 mg, 2.73 mmol), palladium acetate (30 mg, 0.14 mmol), X-Phos (130 mg, 0.27 mmol) and (R)-methyl 3-((2-chloro-5-fluoro-6-phenylpyrimidin-4-yl)amino)-4,4-dimethylpentanoate (250 mg, 0.68 mmol). Then H$_2$O (1 mL) was added to the mixture, and the mixture was heated to 100° C. under nitrogen protection and stirred for 12 h. The mixture was filtered to remove solid impurities. The filtrate was concentrated in vacuo, and the residue was purified by silica gel column chromatography (PE/EtOAc (v/v)=8/1) to give the title compound as a light yellow solid (200 mg, 47%).

MS (ESI, pos. ion) m/z: 620.2 [M+H]$^+$.

Step 4: (R)-3-((5-fluoro-2-(5-fluoro-1H-pyrrolo[2,3-b]pyridin-3-yl)-6-phenylpyrimidin-4-yl) amino)-4,4-dimethylpentanoic Acid To a solution of (R)-methyl 3-((5-fluoro-2-(5-fluoro-1-tosyl-1H-pyrrolo[2,3-b]pyridin-3-yl)-6-phenylpyrimidin-4-yl)amino)-4,4-dimethylpentanoate (200 mg, 0.33 mmol) in THF/MeOH (v/v=8 mL/4 mL) was added a solution of NaOH (129 mg, 3.22 mmol) in water (2 mL). The mixture was stirred at rt overnight, then diluted with water (10 mL). The resulting mixture was acidified with hydrochloric acid (1 M) to pH about 3 to 4. The resulting mixture was extracted with ethyl acetate (20 mL×3). The combined organic layers were washed with saturated brine (50 mL), dried over anhydrous sodium sulfate and filtered. The filtrate was concentrated in vacuo to remove the solvent and the residue was purified by silica gel column chromatography (DCM/MeOH (v/v)=10/1-5/1) to give the title compound as a white solid (40 mg, 27%).

MS (ESI, pos. ion) m/z: 452.1[M+H]$^+$;
HRMS (ESI, pos. ion) m/z: 452.1896 [M+H]$^+$, ($C_{24}H_{24}F_2N_5O_2$) [M+H]$^+$ theoretical value: 452.1898;
$^1$H NMR (400 MHz, DMSO-$d_6$) δ (ppm): 12.38 (s, 1H), 8.62 (d, J=9.0 Hz, 1H), 8.37 (s, 1H), 8.31 (s, 1H), 8.04 (d, J=6.6 Hz, 2H), 7.68 (s, 1H), 7.59 (d, J=7.5 Hz, 3H), 4.89 (s, 1H), 2.76-2.58 (m, 2H), 1.22 (s, 1H), 1.00 (s, 9H).

Example 70: (R)-3-((2-(5-fluoro-1H-pyrrolo[2,3-b]pyridin-3-yl)-6-(furan-2-yl)pyrimidin-4-yl)amino)-4,4-dimethylpentanoic Acid

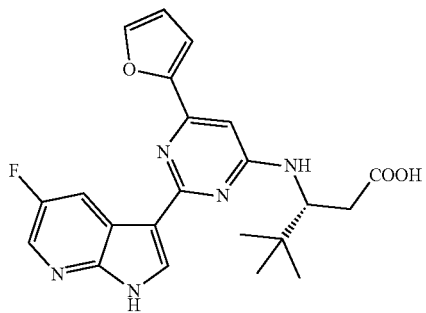 [SMILES: CC(C)(C)[C@@H](CC(=O)O)Nc1cc(-c2ccco2)nc(-c2c[nH]c3ncc(F)cc23)n1]

Step 1: (R)-methyl 3-((2-chloro-6-(furan-2-yl)pyrimidin-4-yl)amino)-4,4-dimethylpentanoate A suspension of 2,4-dichloro-6-(furan-2-yl)pyrimidine (0.30 g, 1.40 mmol), potassium carbonate (0.39 g, 2.80 mmol), (R)-methyl 3-amino-4,4-dimethylpentanoate (0.48 g, 1.80 mmol) in DMF (10 mL) was stirred at 80° C. for 24 h. To the reaction mixture was added water (40 mL), and the resulting mixture was extracted with ethyl acetate (30 mL×3). The combined organic layers were washed with saturated brine (50 mL), dried over anhydrous sodium sulfate and filtered. The filtrate was concentrated in vacuo and the residue was purified by silica gel column chromatography (PE/EtOAc (v/v)=15/1) to give the title compound as a pale solid (300 mg, 64%).

MS (ESI, pos. ion) m/z: 338.2[M+H]$^+$.

Step 2: (R)-methyl 3-((2-(5-fluoro-1-tosyl-1H-pyrrolo[2,3-b]pyridin-3-yl)-6-(furan-2-yl) pyrimidin-4-yl)amino)-4,4-dimethylpentanoate To THF (10 mL) were added 5-fluoro-3-(4,4,5,5-tetramethyl-1,3,2-dioxaborolan-2-yl)-1-tosyl-1H-pyrrolo[2,3-b]pyridine (821 mg, 0.88 mmol, 45%), potassium carbonate (491 mg, 3.55 mmol), palladium acetate (39 mg, 0.17 mmol), X-Phos (169 mg, 0.35 mmol) and (R)-methyl 3-((2-chloro-6-(furan-2-yl)pyrimidin-4-yl)amino)-4,4-dimethylpentanoate (300 mg, 0.88 mmol). Then H$_2$O (0.5 mL) was added to the mixture, and the mixture was heated to 100° C. and stirred for 12 h. The mixture was filtered to remove solid impurities. The filtrate was concentrated in vacuo, and the residue was purified by silica gel column chromatography (PE/EtOAc (v/v)=8/1) to give the title compound as a light yellow solid (300 mg, 57%).

MS (ESI, pos. ion) m/z: 592.2 [M+H]$^+$.

Step 3: (R)-3-((2-(5-fluoro-1H-pyrrolo[2,3-b]pyridin-3-yl)-6-(furan-2-yl)pyrimidin-4-yl)amino)-4,4-dimethylpentanoic Acid To a solution of (R)-methyl 3-((2-(5-fluoro-1-tosyl-1H-pyrrolo[2,3-b]pyridin-3-yl)-6-(furan-2-yl)pyrimidin-4-yl)amino)-4,4-dimethylpentanoate (300 mg, 0.50 mmol) in THF/MeOH (v/v=8 mL/4 mL) was added a solution of NaOH (202 mg, 5.07 mmol) in water (2 mL). The mixture was stirred at rt overnight, then diluted with water (10 mL). The resulting mixture was acidified with hydrochloric acid (1 M) to pH about 3 to 4. The resulting mixture was extracted with ethyl acetate (20 mL×3). The combined organic layers were washed with saturated brine, dried over anhydrous sodium sulfate and filtered. The filtrate was concentrated in vacuo to remove the solvent and the residue was purified by silica gel column chromatography (DCM/MeOH (v/v)=10/1-5/1) to give the title compound as a white solid (180 mg, 83%).

MS (ESI, pos. ion) m/z: 424.3[M+H]$^+$;
HRMS (ESI, pos. ion) m/z: 424.1793[M+H]$^+$, ($C_{22}H_{23}FN_5O_3$) [M+H]$^+$ theoretical value: 424.1785;
$^1$H NMR (400 MHz, DMSO-$d_6$) δ (ppm): 12.25 (s, 1H), 12.05 (s, 1H), 8.67 (d, J=9.0 Hz, 1H), 8.30 (d, J=10.6 Hz, 2H), 7.88 (s, 1H), 7.34 (d, J=9.4 Hz, 1H), 7.23 (s, 1H), 6.70 (s, 1H), 6.66 (s, 1H), 4.82 (s, 1H), 2.68 (d, J=12.7 Hz, 1H), 2.35-2.23 (m, 1H), 0.98 (s, 9H).

Example 71: (R)-3-((2-(5-fluoro-1H-pyrrolo[2,3-b]pyridin-3-yl)-6-phenylpyrimidin-4-yl) amino)-4,4-dimethylpentanoic Acid

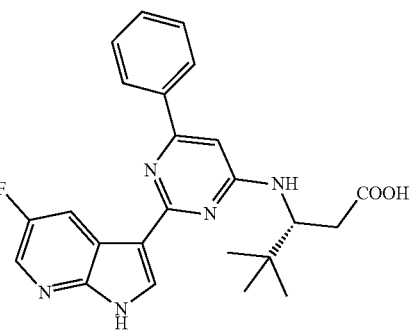

Step 1: (R)-methyl 3-((2-chloro-6-phenylpyrimidin-4-yl)amino)-4,4-dimethylpentanoate To the reaction flask were added 2,4-dichloro-6-phenylpyrimidine (0.30 g, 1.30 mmol), potassium carbonate (0.37 g, 2.70 mmol), (R)-methyl 3-amino-4,4-dimethylpentanoate (0.46 g, 1.70 mmol) and DMF (10 mL). The mixture was stirred at 80° C. for 24 h. Water (40 mL) was added, and the resulting mixture was extracted with EtOAc (30 mL×3). The combined organic phases were washed with saturated brine (60 mL), dried over anhydrous Na$_2$SO$_4$, filtered, and the filtrate was concentrated in vacuo. The residue was purified by silica gel chromatograph (PE/EtOAc (v/v)=15/1) to give the title compound as a white solid (120 mg, 26%).
MS (ESI, pos. ion) m/z: 348.1[M+H]+.

Step 2: (R)-methyl 3-((2-(5-fluoro-1-tosyl-1H-pyrrolo[2,3-b]pyridin-3-yl)-6-phenylpyrimidin-4-yl)amino)-4,4-dimethylpentanoate To THF (10 mL) were added 5-fluoro-3-(4,4,5,5-tetramethyl-1,3,2-dioxaborolan-2-yl)-1-tosyl-1H-pyrrolo[2,3-b]pyridine (383 mg, 0.41 mmol, 45%), potassium carbonate (190 mg, 1.38 mmol), palladium acetate (15 mg, 0.07 mmol), X-Phos (65 mg, 0.14 mmol) and (R)-methyl 3-((2-chloro-6-phenylpyrimidin-4-yl)amino)-4,4-dimethylpentanoate (120 mg, 0.34 mmol). Then H$_2$O (0.5 mL) was added to the mixture, and the mixture was heated to 100° C. and stirred for 12 h. The mixture was filtered to remove solid impurities. The filtrate was concentrated in vacuo, and the residue was purified by silica gel column chromatography (PE/EtOAc (v/v)=8/1) to give the title compound as a light yellow solid (180 mg, 86%).
MS (ESI, pos. ion) m/z: 602.3 [M+H]+.

Step 3: (R)-3-((2-(5-fluoro-1H-pyrrolo[2,3-b]pyridin-3-yl)-6-phenylpyrimidin-4-yl)amino)-4,4-dimethylpentanoic Acid To a solution of (R)-methyl 3-((2-(5-fluoro-1-tosyl-1H-pyrrolo[2,3-b]pyridin-3-yl)-6-phenylpyrimidin-4-yl)amino)-4,4-dimethylpentanoate (180 mg, 0.30 mmol) in THF/MeOH (v/v=8 mL/4 mL) was added a solution of NaOH (120 mg, 2.99 mmol) in water (2 mL). The mixture was stirred at rt overnight, then diluted with water (10 mL). The resulting mixture was acidified with hydrochloric acid (1 M) to pH about 3 to 4. The resulting mixture was extracted with ethyl acetate (20 mL×3). The combined organic layers were washed with saturated brine, dried over anhydrous sodium sulfate and filtered. The filtrate was concentrated in vacuo to remove the solvent and the residue was purified by silica gel column chromatography (DCM/MeOH (v/v)=10/1-5/1) to give the title compound as a white solid (94 mg, 72%).
MS (ESI, pos. ion) m/z: 434.2[M+H]+;
HRMS (ESI, pos. ion) m/z: 434.2013[M+H]+, (C$_{24}$H$_{25}$FN$_5$O$_2$) [M+H]+ theoretical value: 434.1992;
$^1$H NMR (400 MHz, DMSO-d$_6$) δ (ppm): 12.26 (s, 1H), 12.05 (s, 1H), 8.70 (d, J=9.3 Hz, 1H), 8.37 (s, 1H), 8.29 (s, 1H), 8.09 (d, J=6.6 Hz, 2H), 7.54 (dt, J=13.2, 6.8 Hz, 3H), 7.30 (d, J=9.0 Hz, 1H), 6.82 (s, 1H), 4.86 (s, 1H), 2.70 (d, J=12.8 Hz, 1H), 2.38-2.24 (m, 1H), 0.99 (s, 9H).

Example 72: (R)-3-((2-(5-fluoro-1H-pyrrolo[2,3-b]pyridin-3-yl)-7-isopropyl-7H-pyrrolo [2,3-d]pyrimidin-4-yl)amino)-4,4-dimethylpentanoic Acid

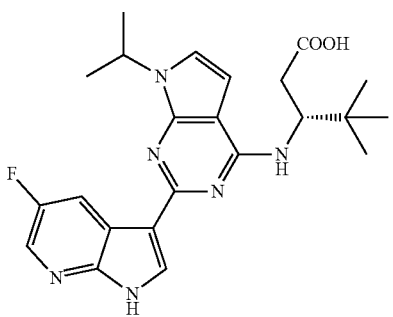 [SMILES: CC(C)n1ccc2c(N[C@H](CC(=O)O)C(C)(C)C)nc(-c3c[nH]c4ncc(F)cc34)nc21]

Step 1: (R)-methyl 3-((2-chloro-7-isopropyl-7H-pyrrolo[2,3-d]pyrimidin-4-yl)amino)-4,4-dimethylpentanoate To a reaction flask were added 2,4-dichloro-7-isopropyl-7H-pyrrolo[2,3-d]pyrimidine (0.30 g, 1.30 mmol), potassium carbonate (0.36 g, 2.61 mmol), (R)-methyl 3-amino-4,4-dimethylpentanoate (0.42 g, 1.56 mmol) and DMF (10 mL), and the mixture was stirred at 80° C. for 24 h. After the reaction was completed, to the reaction mixture was added water (20 mL), and the resulting mixture was extracted with ethyl acetate (30 mL×3). The combined organic layers were washed with saturated brine (60 mL), dried over anhydrous sodium sulfate and filtered. The filtrate was concentrated in vacuo and the residue was purified by silica gel column chromatography (PE/EtOAc (v/v)=15/1) to give the title compound as a pale solid (260 mg, 56%).
MS (ESI, pos. ion) m/z: 353.10[M+H]+.

Step 2: (R)-methyl 3-((2-(5-fluoro-1-tosyl-1H-pyrrolo[2,3-b]pyridin-3-yl)-7-isopropyl-7H-pyrrolo[2,3-d]pyrimidin-4-yl)amino)-4,4-dimethylpentanoate To THF (10 mL) were added 5-fluoro-3-(4,4,5,5-tetramethyl-1,3,2-dioxaborolan-2-yl)-1-tosyl-1H-pyrrolo[2,3-b]pyridine (749 mg, 0.81 mmol, 45%), potassium carbonate (407 mg, 2.95 mmol), palladium acetate (33 mg, 0.15 mmol), X-Phos (140 mg, 0.30 mmol) and (R)-methyl 3-((2-chloro-7-isopropyl-7H-pyrrolo[2,3-d]pyrimidin-4-yl)amino)-4,4-dimethylpentanoate (260 mg, 0.74 mmol). Then H$_2$O (0.5 mL) was added to the mixture, and the mixture was heated to 100° C. and stirred for 12 h. The mixture was filtered to remove solid impurities. The filtrate was concentrated in vacuo, and the residue was purified by silica gel column chromatography (PE/EtOAc (v/v)=8/1) to give the title compound as a light yellow solid (310 mg, 69%).
MS (ESI, pos. ion) m/z: 607.3 [M+H]+.

Step 3: (R)-3-((2-(5-fluoro-1H-pyrrolo[2,3-b]pyridin-3-yl)-7-isopropyl-7H-pyrrolo[2,3-d]pyrimidin-4-yl)amino)-4,4-dimethylpentanoic Acid To a solution of (R)-methyl 3-((2-(5-fluoro-1-tosyl-1H-pyrrolo[2,3-b]pyridin-3-yl)-7-isopropyl-7H-pyrrolo[2,3-d]pyrimidin-4-yl)amino)-4,4-dimethylpentanoate (300 mg, 0.49 mmol) in THF/MeOH (v/v=8 mL/4 mL) was added a solution of NaOH (197 mg, 4.95 mmol) in water (2 mL). The mixture was stirred at rt overnight, then diluted with water (10 mL). The resulting mixture was acidified with hydrochloric acid (1 M) to pH about 3 to 4. The resulting mixture was extracted with ethyl acetate (20 mL×3). The combined organic layers were washed with saturated brine (50 mL), dried over anhydrous sodium sulfate and filtered. The filtrate was concentrated in vacuo to remove the solvent and the residue was purified by silica gel column chromatography (DCM/MeOH (v/v)=10/1-5/1) to give the title compound as a white solid (180 mg, 83%).
MS (ESI, pos. ion) m/z: 439.3[M+H]+;
HRMS (ESI, pos. ion) m/z: 439.2271[M+H]+, (C$_{23}$H$_{28}$FN$_6$O$_2$) [M+H]+ theoretical value: 439.2258;
$^1$H NMR (400 MHz, DMSO-d$_6$) δ (ppm): 12.06 (s, 1H), 11.94 (s, 1H), 8.74 (d, J=9.4 Hz, 1H), 8.23 (d, J=18.8 Hz, 2H), 7.18 (d, J=3.0 Hz, 1H), 7.04 (d, J=8.9 Hz, 1H), 6.70 (d, J=3.0 Hz, 1H), 5.09-4.96 (m, 2H), 2.70 (d, J=12.7 Hz, 1H), 1.50 (dd, J=6.2, 3.5 Hz, 6H), 1.24 (s, 2H), 1.00 (s, 9H).

Example 73: (2S,3S)-3-((2-(6-fluoro-1H-pyrrolo[2,3-b]pyridin-3-yl)-6-(furan-2-yl) pyrimidin-4-yl)amino)bicyclo[2.2.2]octane-2-carboxylic Acid

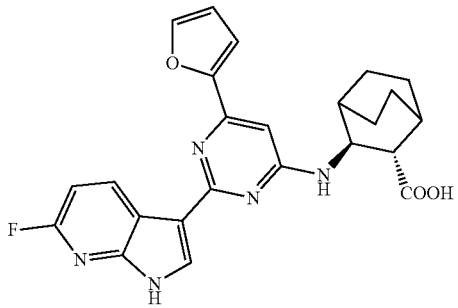 [SMILES: O=C(O)[C@H]1C2CCC(CC2)[C@@H]1Nc1cc(-c2ccco2)nc(-c2c[nH]c3nc(F)ccc23)n1]

Step 1: (2S,3S)-ethyl 3-aminobicyclo[2.2.2]octane-2-carboxylate hydrochloride The title compound can be prepared according to the synthetic method disclosed in patent application WO 2015073491.

Step 2: (2S,3S)-ethyl 3-((2-chloro-6-(furan-2-yl)pyrimidin-4-yl)amino)bicyclo[2.2.2]octane-2-carboxylate To a reaction flask were added 2,4-dichloro-6-(furan-2-yl)pyrimidine (0.50 g, 2.30 mmol), potassium carbonate (0.83 g, 6.00 mmol), (2S,3S)-ethyl 3-aminobicyclo[2.2.2]octane-2-carboxylate hydrochloride (0.70 g, 3.00 mmol) and DMF (10 mL). The mixture was stirred at 50° C. for 24 h. To the reaction mixture was added water (40 mL), and the resulting mixture was extracted with ethyl acetate (30 mL×3). The combined organic layers were washed with saturated brine (60 mL), dried over anhydrous sodium sulfate and filtered. The filtrate was concentrated in vacuo and the residue was purified by silica gel column chromatography (PE/EtOAc (v/v)=15/1) to give the title compound as a pale solid (610 mg, 70%).

MS (ESI, pos. ion) m/z: 376.0[M+H]$^+$.

Step 3: 3-bromo-6-fluoro-1H-pyrrolo[2,3-b]pyridine

To a solution of 6-fluoro-1H-pyrrolo[2,3-b]pyridine (2.50 g, 18.36 mmol) in DMF (50 mL) was added a solution of bromine (3.20 g, 20.00 mmol) in DMF (20 mL) at 0° C. After the addition, the mixture was stirred at rt for 2 h. To the mixture was added water (100 mL), then there was a lot of solid precipitated out. The mixture was filtered under reduced pressure, and the filter cake was washed with water (30 mL) for two times and then dried in vacuo at 60° C. for 24 h to give the title compound as a white solid (3.44 g, 87%).

MS (ESI, pos. ion) m/z: 217.1 [M+H]$^+$;
$^1$H NMR (400 MHz, DMSO-d$_6$) δ (ppm): 12.20 (s, 1H), 8.04-7.95 (m, 1H), 7.67 (d, J=2.5 Hz, 1H), 6.94 (t, J=9.7 Hz, 1H).

Step 4: 3-bromo-6-fluoro-1-tosyl-1H-pyrrolo[2,3-b]pyridine

To a solution of 3-bromo-6-fluoro-1H-pyrrolo[2,3-b]pyridine (3.44 g, 16.00 mmol) in THF (68 mL) was added sodium hydride (1.30 g, 32.00 mmol, 60%) at 0° C. Then the reaction mixture was stirred for 30 min at 0° C. TsCl (4.58 g, 24.00 mmol) was added and the reaction mixture was stirred at rt for 3 h. Water (200 mL) was added to quench the reaction, and the resulting mixture was extracted with EtOAc (100 mL×2). The combined organic phases were washed with saturated brine (200 mL), dried over anhydrous Na$_2$SO$_4$, filtered, and the filtrate was concentrated in vacuo. The residue was purified by silica gel chromatograph to give the title compound as a brown solid (5.70 g, 97%).

MS (ESI, pos. ion) m/z: 369.0 [M+H]$^+$;
$^1$H NMR (400 MHz, CDCl$_3$) δ (ppm): 8.11 (d, J=8.2 Hz, 2H), 7.88 (t, J=7.8 Hz, 1H), 7.75 (s, 1H), 7.34 (d, J=7.8 Hz, 2H), 6.91 (d, J=8.3 Hz, 1H), 2.41 (s, 3H).

Step 5: 6-fluoro-3-(4,4,5,5-tetramethyl-1,3,2-dioxaborolan-2-yl)-1-tosyl-1H-pyrrolo[2,3-b]pyridine To a suspension of 3-bromo-6-fluoro-1-tosyl-1H-pyrrolo[2,3-b]pyridine (5.70 g, 15.00 mmol), tetrakis(triphenylphosphine)platinum (1.80 g, 1.50 mmol) and potassium acetate (4.50 g, 46.00 mmol) in 1,4-dioxane (120 mL) was added bis(pinacolato)diboron (5.90 g, 23.00 mmol). The mixture was stirred at 100° C. for 24 h under nitrogen protection. To the reaction mixture was added ethyl acetate (50 mL), and the mixture was filtered through a celite pad. The filter cake was washed with ethyl acetate (20 mL×2). The combined filtrates was concentrated in vacuo, and the residue was purified by silica gel column chromatography (PE/EtOAc (v/v)=40/1) to give the title compound as a yellow solid (3.50 g, 54%).

MS (ESI, pos.ion) m/z: 417.30 [M+H]$^+$.

Step 6: (2S,3S)-ethyl 3-((2-(6-fluoro-1-tosyl-1H-pyrrolo[2,3-b]pyridin-3-yl)-6-(furan-2-yl) pyrimidin-4-yl)amino)bicyclo[2.2.2]octane-2-carboxylate To THF (10 mL) were added 6-fluoro-3-(4,4,5,5-tetramethyl-1,3,2-dioxaborolan-2-yl)-1-tosyl-1H-pyrrolo[2,3-b]pyridine (610 mg, 0.64 mmol, 45%), potassium carbonate (338 mg, 2.45 mmol), palladium acetate (27 mg, 0.12 mmol), X-Phos (116 mg, 0.24 mmol) and (2S,3S)-ethyl 3-((2-chloro-6-(furan-2-yl)pyrimidin-4-yl)amino)bicyclo[2.2.2]octane-2-carboxylate (230 mg, 0.61 mmol). Then H$_2$O (0.5 mL) was added to the mixture, and the mixture was heated to 80° C. and stirred for 12 h. The mixture was filtered to remove solid impurities. The filtrate was concentrated in vacuo, and the residue was purified by silica gel column chromatography (PE/EtOAc (v/v)=8/1) to give the title compound as a light yellow solid (260 mg, 67%).

MS (ESI, pos. ion) m/z: 630.1 [M+H]$^+$.

Step 7: (2S,3S)-3-((2-(6-fluoro-1H-pyrrolo[2,3-b]pyridin-3-yl)-6-(furan-2-yl)pyrimidin-4-yl) amino)bicyclo[2.2.2]octane-2-carboxylic Acid To a solution of (2S,3S)-ethyl 3-((2-(6-fluoro-1-tosyl-1H-pyrrolo[2,3-b]pyridin-3-yl)-6-(furan-2-yl)pyrimidin-4-yl)amino)bicyclo[2.2.2]octane-2-carboxylate (260 mg, 0.41 mmol) in THF/MeOH (v/v=8 mL/4 mL) was added a solution of NaOH (146 mg, 4.12 mmol) in water (2 mL). The mixture was stirred at rt overnight, then diluted with water (10 mL). The resulting mixture was acidified with hydrochloric acid (1 M) to pH about 3 to 4. The resulting mixture was extracted with ethyl acetate (20 mL×3). The combined organic layers were washed with saturated brine (50 mL), dried over anhydrous sodium sulfate and filtered. The filtrate was concentrated in vacuo to remove the solvent and the residue was purified by silica gel column chromatography (DCM/MeOH (v/v)=10/1-5/1) to give the title compound as a white solid (150 mg, 81%).

MS (ESI, pos. ion) m/z: 448.1[M+H]$^+$;

HRMS (ESI, pos. ion) m/z: 448.1793[M+H]$^+$, ($C_{24}H_{23}FN_5O_3$) [M+H]$^+$ theoretical value: 448.1785;

$^1$H NMR (600 MHz, DMSO-d$_6$) δ (ppm): 12.21 (s, 1H), 9.00 (s, 1H), 8.20 (s, 1H), 7.88 (s, 1H), 7.55 (s, 1H), 7.28 (s, 1H), 6.98 (d, J=8.4 Hz, 1H), 6.70 (s, 1H), 6.66 (s, 1H), 4.59 (s, 1H), 2.51 (s, 1H), 1.94 (s, 1H), 1.80-1.71 (m, 2H), 1.68 (s, 1H), 1.62-1.53 (m, 3H), 1.48-1.36 (m, 3H).

Example 74: (2S,3S)-3-((2-(6-fluoro-1H-pyrrolo[2,3-b]pyridin-3-yl)-7-isopropyl-7H-pyrrolo[2,3-d]pyrimidin-4-yl)amino)bicyclo[2.2.2]octane-2-carboxylic Acid

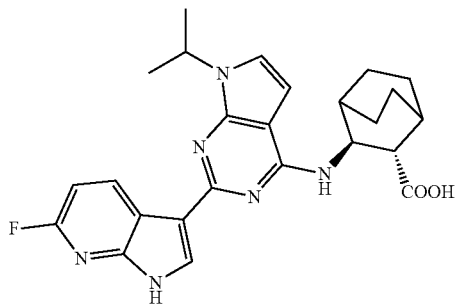 [SMILES: CC(C)n1ccc2c(N[C@H]3C4CCC(CC4)[C@@H]3C(=O)O)nc(-c3c[nH]c4nc(F)ccc34)nc21]

Step 1: (2S,3S)-ethyl 3-aminobicyclo[2.2.2]octane-2-carboxylate hydrochloride

The title compound can be prepared according to the synthetic method disclosed in patent application WO 2015073491.

Step 2: (2S,3S)-ethyl 3-((2-chloro-7-isopropyl-7H-pyrrolo[2,3-d]pyrimidin-4-yl)amino) bicyclo[2.2.2]octane-2-carboxylate To the reaction flask were added 2,4-dichloro-7-isopropyl-7H-pyrrolo[2,3-d]pyrimidine (0.60 g, 2.61 mmol), potassium carbonate (1.01 g, 7.31 mmol), (2S,3S)-ethyl 3-aminobicyclo[2.2.2]octane-2-carboxylate hydrochloride (0.85 g, 3.65 mmol) and DMF (10 mL), and the mixture was stirred at 50° C. for 24 h. Water (20 mL) was added to quench the reaction, and the resulting mixture was extracted with EtOAc (30 mL×3). The combined organic phases were washed with saturated brine (60 mL), dried over anhydrous Na$_2$SO$_4$, filtered, and the filtrate was concentrated in vacuo. The residue was purified by silica gel chromatograph (PE/EtOAc (v/v)=15/1) to give the title compound as a pale solid (732 mg, 71%).

MS (ESI, pos. ion) m/z: 391.10[M+H]$^+$.

Step 3: (2S,3S)-ethyl 3-((2-(6-fluoro-1-tosyl-1H-pyrrolo[2,3-b]pyridin-3-yl)-7-isopropyl-7H-pyrrolo[2,3-d]pyrimidin-4-yl)amino)bicyclo[2.2.2]octane-2-carboxylate To THF (10 mL) were added 6-fluoro-3-(4,4,5,5-tetramethyl-1,3,2-dioxaborolan-2-yl)-1-tosyl-1H-pyrrolo[2,3-b]pyridine (580 mg, 0.56 mmol, 40%), potassium carbonate (282 mg, 2.05 mmol), palladium acetate (22 mg, 0.10 mmol), X-Phos (97 mg, 0.20 mmol) and (2S,3S)-ethyl 3-((2-chloro-7-isopropyl-7H-pyrrolo[2,3-d]pyrimidin-4-yl)amino)bicyclo[2.2.2]octane-2-carboxylate (200 mg, 0.51 mmol). Then H$_2$O (0.5 mL) was added to the mixture, and the mixture was heated to 80° C. and stirred for 12 h. The mixture was filtered to remove solid impurities. The filtrate was concentrated in vacuo, and the residue was purified by silica gel column chromatography (PE/EtOAc (v/v)=8/1) to give the title compound as a light yellow solid (280 mg, 84%).

MS (ESI, pos. ion) m/z: 645.3 [M+H]$^+$.

Step 4: (2S,3S)-3-((2-(6-fluoro-1H-pyrrolo[2,3-b]pyridin-3-yl)-7-isopropyl-7H-pyrrolo[2,3-d]pyrimidin-4-yl)amino)bicyclo[2.2.2]octane-2-carboxylic Acid To a solution of (2S,3S)-ethyl 3-((2-(6-fluoro-1-tosyl-1H-pyrrolo[2,3-b]pyridin-3-yl)-7-isopropyl-7H-pyrrolo[2,3-d]pyrimidin-4-yl)amino)bicyclo[2.2.2]octane-2-carboxylate (280 mg, 0.43 mmol) in THF/MeOH (v/v=8 mL/4 mL) was added a solution of NaOH (173 mg, 4.34 mmol) in water (2 mL). The mixture was stirred at rt overnight, then diluted with water (10 mL). The resulting mixture was acidified with hydrochloric acid (1 M) to pH about 3 to 4. The resulting mixture was extracted with ethyl acetate (20 mL×3). The combined organic layers were washed with saturated brine (50 mL), dried over anhydrous sodium sulfate and filtered. The filtrate was concentrated in vacuo to remove the solvent and the residue was purified by silica gel column chromatography (DCM/MeOH (v/v)=10/1-5/1) to give the title compound as a white solid (180 mg, 89%).

MS (ESI, pos. ion) m/z: 463.2[M+H]$^+$;

HRMS (ESI, pos. ion) m/z: 463.2268[M+H]$^+$, ($C_{25}H_{28}FN_6O_2$) [M+H]$^+$ theoretical value: 463.2258;

$^1$H NMR (400 MHz, DMSO-d$_6$) δ (ppm): 12.04 (s, 1H), 9.04 (t, J=8.1 Hz, 1H), 8.05 (s, 1H), 7.22 (d, J=6.3 Hz, 1H), 7.19 (s, 1H), 6.94 (d, J=8.6 Hz, 1H), 6.66 (s, 1H), 5.01 (d, J=6.6 Hz, 1H), 4.75 (s, 1H), 2.68 (s, 1H), 1.98 (s, 1H), 1.75 (m, 3H), 1.51 (m, 11H).

Example 75: (2S,3S)-3-((2-(6-fluoro-1H-pyrrolo[2,3-b]pyridin-3-yl)-6-phenylpyrimidin-4-yl) amino)bicyclo[2.2.2]octane-2-carboxylic Acid

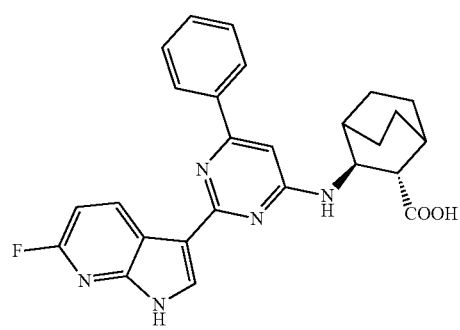 [SMILES: O=C(O)[C@H]1C2CCC(CC2)[C@@H]1Nc1cc(-c2ccccc2)nc(-c2c[nH]c3nc(F)ccc23)n1]

Step 1: (2S,3S)-ethyl 3-aminobicyclo[2.2.2]octane-2-carboxylate hydrochloride The title compound can be prepared according to the synthetic method disclosed in patent application WO 2015073491.

Step 2: (2S,3S)-ethyl 3-((2-chloro-6-phenylpyrimidin-4-yl)amino)bicyclo[2.2.2]octane-2-carboxylate To a reaction flask were added 2,4-dichloro-6-phenylpyrimidine (0.76 g, 3.40 mmol), potassium carbonate (0.93 g, 6.80 mmol), (2S,3S)-ethyl 3-aminobicyclo[2.2.2]octane-2-carboxylate hydrochloride (0.96 g, 4.10 mmol) and DMF (10 mL). The mixture was stirred at 50° C. for 24 h. Water (40 mL) was added to quench the reaction, and the resulting mixture was extracted with EtOAc (30 mL×3). The combined organic phases were washed with saturated brine (60 mL), dried over anhydrous $Na_2SO_4$, filtered, and the filtrate was concentrated in vacuo. The residue was purified by silica gel chromatograph (PE/EtOAc (v/v)=15/1) to give the title compound as a white solid (0.70 g, 50%).
MS (ESI, pos. ion) m/z: 386.1[M+H]$^+$.

Step 3: (2S,3S)-ethyl 3-((2-(6-fluoro-1-tosyl-1H-pyrrolo[2,3-b]pyridin-3-yl)-6-phenylpyrimidin-4-yl)amino)bicyclo[2.2.2]octane-2-carboxylate To THF (10 mL) were added 6-fluoro-3-(4,4,5,5-tetramethyl-1,3,2-dioxaborolan-2-yl)-1-tosyl-1H-pyrrolo[2,3-b]pyridine (503 mg, 0.54 mmol, 45%), potassium carbonate (286 mg, 2.07 mmol), palladium acetate (23 mg, 0.10 mmol), X-Phos (98 mg, 0.20 mmol) and (2S,3S)-ethyl 3-((2-chloro-6-phenylpyrimidin-4-yl)amino)bicyclo[2.2.2]octane-2-carboxylate (200 mg, 0.52 mmol). Then $H_2O$ (0.5 mL) was added to the mixture, and the mixture was heated to 80° C. and stirred for 12 h. The mixture was filtered to remove solid impurities. The filtrate was concentrated in vacuo, and the residue was purified by silica gel column chromatography (PE/EtOAc (v/v)=8/1) to give the title compound as a pale yellow solid (240 mg, 72%).
MS (ESI, pos. ion) m/z: 640.2 [M+H]$^+$.

Step 4: (2S,3S)-3-((2-(6-fluoro-1H-pyrrolo[2,3-b]pyridin-3-yl)-6-phenylpyrimidin-4-yl)amino) bicyclo[2.2.2]octane-2-carboxylic Acid To a solution of (2S,3S)-ethyl 3-((2-(6-fluoro-1-tosyl-1H-pyrrolo[2,3-b]pyridin-3-yl)-6-phenylpyrimidin-4-yl)amino)bicyclo[2.2.2]octane-2-carboxylate (240 mg, 0.37 mmol) in THF/MeOH (v/v=8 mL/4 mL) was added a solution of NaOH (150 mg, 3.75 mmol) in water (2 mL). The mixture was stirred at rt overnight, then diluted with water (10 mL). The resulting mixture was acidified with hydrochloric acid (1 M) to pH about 3 to 4. The resulting mixture was extracted with ethyl acetate (20 mL×3). The combined organic layers were washed with saturated brine (50 mL), dried over anhydrous sodium sulfate and filtered. The filtrate was concentrated in vacuo to remove the solvent and the residue was purified by silica gel column chromatography (DCM/MeOH (v/v)=10/1-5/1) to give the title compound as a white solid (150 mg, 87%).
MS (ESI, pos. ion) m/z: 458.1[M+H]$^+$;
HRMS (ESI, pos. ion) m/z: 458.2003[M+H]$^+$, ($C_{26}H_{25}FN_5O_2$) [M+H]$^+$ theoretical value: 458.1992;
$^1$H NMR (400 MHz, DMSO-d$_6$) δ (ppm): 12.36-12.25 (m, 1H), 12.21 (s, 1H), 9.03 (s, 1H), 8.23 (s, 1H), 8.12 (s, 2H), 7.61-7.48 (m, 4H), 7.00 (d, J=8.3 Hz, 1H), 6.79 (s, 1H), 4.62 (s, 1H), 1.99 (s, 3H), 1.69 (m, 8H).

Example 76: (+/−)-trans-3-((5-fluoro-2-(6-fluoro-1H-pyrrolo[2,3-b]pyridin-3-yl)-6-(furan-2-yl)pyrimidin-4-yl)amino)bicyclo[2.2.2]octane-2-carboxylic Acid

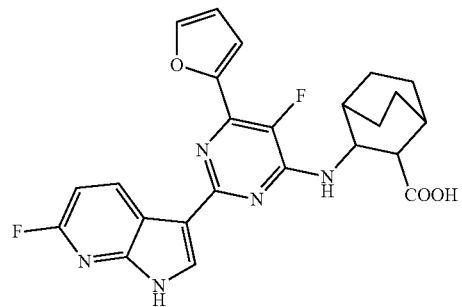 [SMILES: O=C(O)C1C2CCC(CC2)C1Nc1nc(-c2c[nH]c3nc(F)ccc23)nc(-c2ccco2)c1F]

Step 1: (+/−)-trans-methyl 3-((5-fluoro-2-(6-fluoro-1-tosyl-1H-pyrrolo[2,3-b]pyridin-3-yl)-6-(furan-2-yl)pyrimidin-4-yl)amino)bicyclo[2.2.2]octane-2-carboxylate To THF (10 mL) were added 6-fluoro-3-(4,4,5,5-tetramethyl-1,3,2-dioxaborolan-2-yl)-1-tosyl-1H-pyrrolo[2,3-b]pyridine (517 mg, 0.49 mmol, 40%), potassium carbonate (262 mg, 1.89 mmol), palladium acetate (21 mg, 0.09 mmol), X-Phos (90 mg, 0.18 mmol) and (+/−)-trans-methyl 3-((2-chloro-5-fluoro-6-(furan-2-yl)pyrimidin-4-yl)amino) bicyclo[2.2.2]octane-2-carboxylate (180 mg, 0.47 mmol). Then $H_2O$ (1 mL) was added to the mixture, and the mixture was heated to 80° C. and stirred for 12 h. The mixture was filtered to remove the solid impurity. The filtrate was concentrated in vacuo, and the residue was purified by silica gel column chromatography (PE/EtOAc (v/v)=8/1) to give the title compound as a light yellow solid (240 mg, 79%).
MS (ESI, pos. ion) m/z: 634.1 [M+H]$^+$.

Step 2: (+/−)-trans-3-((5-fluoro-2-(6-fluoro-1H-pyrrolo[2,3-b]pyridin-3-yl)-6-(furan-2-yl) pyrimidin-4-yl)amino)bicyclo[2.2.2]octane-2-carboxylic Acid To a solution of (+/−)-trans-methyl 3-((5-fluoro-2-(6-fluoro-1-tosyl-1H-pyrrolo [2,3-b]pyridin-3-yl)-6-(furan-2-yl)pyrimidin-4-yl)amino)bicyclo[2.2.2]octane-2-carboxylate (240 mg, 0.38 mmol) in THF/MeOH (v/v=8 mL/4 mL) was added a solution of NaOH (150 mg, 3.75 mmol) in water (2 mL). The mixture was stirred at rt overnight, then diluted with water (10 mL). The resulting mixture was acidified with hydrochloric acid (1 M) to pH about 3 to 4. The resulting mixture was extracted with ethyl acetate (20 mL×3). The combined organic layers were washed with saturated brine (50 mL), dried over anhydrous sodium sulfate and filtered. The filtrate was concentrated in vacuo to remove the solvent and the residue was purified by silica gel column chromatography (DCM/MeOH (v/v)=10/1-5/1) to give the title compound as a white solid (150 mg, 85%).
MS (ESI, pos. ion) m/z: 466.3[M+H]$^+$;
HRMS (ESI, pos. ion) m/z: 466.1702 [M+H]±, ($C_{24}H_{22}F_2N_5O_3$) [M+H]$^+$ theoretical value: 466.1691;

¹H NMR (400 MHz, DMSO-d₆) δ (ppm): 12.29 (s, 1H), 12.20 (s, 1H), 8.96 (t, J=8.4 Hz, 1H), 8.09 (d, J=2.1 Hz, 1H), 8.02 (s, 1H), 7.61 (d, J=6.8 Hz, 1H), 7.27 (s, 1H), 7.00 (d, J=8.4 Hz, 1H), 6.77 (s, 1H), 4.67 (s, 1H), 2.86 (d, J=6.8 Hz, 1H), 2.01 (s, 1H), 1.97 (s, 1H), 1.78 (s, 3H), 1.65-1.39 (m, 5H).

Example 77: (+/−)-trans-3-((5-fluoro-2-(5-fluoro-1H-pyrrolo[2,3-b]pyridin-3-yl)-6-(isoxazol-5-yl)pyrimidin-4-yl)amino)bicyclo[2.2.2]octane-2-carboxylic Acid

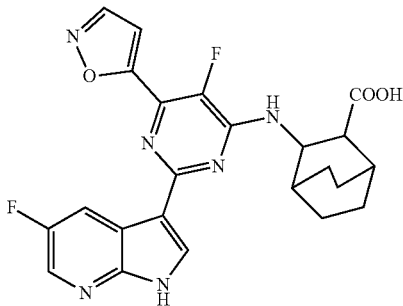 [SMILES: O=C(O)C1C2CCC(CC2)C1Nc1nc(-c2c[nH]c3ncc(F)cc23)nc(-c2ccno2)c1F]

Step 1: 1-(2,6-dichloro-5-fluoropyrimidin-4-yl)ethanone

To a mixture of glacial acetic acid (40 mL) and sulfuric acid solution (64 mL, 1.5 mol/L) was added 2,4-dichloro-5-fluoropyrimidine (2.00 g, 12.00 mmol). To the mixture was added acetaldehyde aqueous solution (16 mL, 100 mmol, 40% wt) and ammonium sulfate solution (24 mL, 24 mmol, 1 mol/L) and ferrous sulfate (24 mL, 36 mmol, 1.5 mol/L) were added dropwise successively. The resulting mixture was stirred at 10° C. for 2 h. The mixture was filtered to give the title compound as a gray white solid (436 mg, 17%).

MS (ESI, pos. ion) m/z: 210.9 [M+H]⁺;
¹H NMR (400 MHz, CDCl₃) δ (ppm): 2.72 (s, 3H).

Step 2: (+/−)-trans-methyl 3-((6-acetyl-2-chloro-5-fluoropyrimidin-4-yl)amino)bicyclo[2.2.2]octane-2-carboxylate To a solution of (+/−)-trans-methyl 3-aminobicyclo[2.2.2]octane-2-carboxylate (53 mg, 0.29 mmol) and 1-(2,6-dichloro-5-fluoropyrimidin-4-yl)ethanone (50 mg, 0.24 mmol) in THF (5 mL) was added DIPEA (0.2 mL, 0.96 mmol), and the mixture was stirred at rt overnight. The mixture was diluted with water (40 mL), and the resulting mixture was extracted with ethyl acetate (40 mL×3). The combined organic layers were washed with saturated brine (50 mL), dried over anhydrous sodium sulfate and filtered. The filtrate was concentrated in vacuo to dry. The residue was purified by silica gel column chromatography (PE/EtOAc (v/v)=5/1) to give the title compound as a white solid (33 mg, 39%).

MS (ESI, pos.ion) m/z: 356.2 [M+H]⁺;
¹H NMR (400 MHz, CDCl₃) δ (ppm): 5.56 (s, 1H), 4.51 (s, 1H), 3.78 (s, 3H), 2.62 (s, 3H), 2.40 (d, J=5.8 Hz, 1H), 2.03 (s, 1H), 1.90 (s, 1H), 1.67 (d, J=11.0 Hz, 8H).

Step 3: (+/−)-trans-methyl 3-((2-chloro-6-((E)-3-(dimethylamino)acryloyl)-5-fluoropyrimidin-4-yl)amino)bicyclo[2.2.2]octane-2-carboxylate A solution of (+/−)-trans-methyl 3-((6-acetyl-2-chloro-5-fluoropyrimidin-4-yl)amino)bicyclo[2.2.2]octane-2-carboxylate (33 mg, 0.09 mmol) in DMF-DMA (1 mL) was stirred at rt overnight. To the reaction mixture was added water (25 mL), and the resulting mixture was extracted with ethyl acetate (25 mL×3). The combined organic layers were washed with saturated brine (20 mL), dried over anhydrous sodium sulfate and filtered. The filtrate was concentrated in vacuo and the residue was purified by silica gel column chromatography (PE/EtOAc (v/v)=5/1) to give the title compound as yellow oil (33 mg, 87%).

MS (ESI, pos.ion) m/z: 411.2 [M+H]⁺;
¹H NMR (400 MHz, CDCl₃) δ (ppm): 7.84 (s, 1H), 5.87 (s, 1H), 5.46 (s, 1H), 4.49 (s, 1H), 3.77 (s, 3H), 3.19 (s, 3H), 2.97 (s, 3H), 2.40 (d, J=5.8 Hz, 1H), 2.01 (s, 1H), 1.89 (s, 1H), 1.67 (s, 8H).

Step 4: (+/−)-trans-methyl 3-((2-chloro-5-fluoro-6-(isoxazol-5-yl)pyrimidin-4-yl)amino) bicyclo[2.2.2]octane-2-carboxylate To a solution of (+/−)-trans-methyl 3-((2-chloro-6-((E)-3-(dimethylamino)acryloyl)-5-fluoropyrimidin-4-yl)amino)bicyclo[2.2.2]octane-2-carboxylate (200 mg, 0.4867 mmol) in ethanol (3 mL) was added hydroxylammonium chloride (67 mg, 0.96 mmol). The reaction mixture was stirred at 78° C. overnight. The mixture was concentrated in vacuo to remove the solvent and the residue was dissolved in ethyl acetate (20 mL). The mixture was washed with saturated brine (20 mL), dried over anhydrous sodium sulfate and filtered. The filtrate was concentrated in vacuo and the residue was purified by silica gel column chromatography (PE/EtOAc (v/v)=5/1) to give the title compound as a red solid (35 mg, 19%).

MS (ESI, pos.ion) m/z: 381.2 [M+H]⁺;
¹H NMR (400 MHz, CDCl₃) δ (ppm): 8.40 (d, J=1.6 Hz, 1H), 6.99 (s, 1H), 5.63 (d, J=3.8 Hz, 1H), 4.55 (t, J=4.9 Hz, 1H), 3.78 (s, 3H), 2.45 (d, J=5.8 Hz, 1H), 2.04 (d, J=2.2 Hz, 1H), 1.93 (d, J=2.2 Hz, 1H), 1.77-1.60 (m, 8H).

Step 5: (+/−)-trans-methyl 3-((5-fluoro-2-(5-fluoro-1-tosyl-1H-pyrrolo[2,3-b]pyridin-3-yl)-6-(isoxazol-5-yl)pyrimidin-4-yl)amino)bicyclo[2.2.2]octane-2-carboxylate To a microwave tube were added 5-fluoro-3-(4,4,5,5-tetramethyl-1,3,2-dioxaborolan-2-yl)-1-tosyl-1H-pyrrolo[2,3-b]pyridine (170 mg, 0.25 mmol), (+/−)-trans-methyl 3-((2-chloro-5-fluoro-6-(isoxazol-5-yl)pyrimidin-4-yl)amino)bicyclo[2.2.2]octane-2-carboxylate (78 mg, 0.21 mmol), water (0.2 mL), 1,4-dioxane (3 mL), potassium carbonate (84 mg, 0.61 mmol) and X-phos (19 mg, 0.04 mmol). The air in the mixture was removed by bubbling with nitrogen for 10 min. The mixture was stirred for 3 h at 110° C. with microwave heating. The filtrate was concentrated in vacuo to dry and the residue was purified by silica gel column chromatography (PE/EtOAc(v/v)=2/1) to give the title compound as yellow oil (28 mg, 22%).

MS (ESI, pos.ion) m/z: 637.2 [M+H]⁺.

Step 6: (+/−)-trans-3-((5-fluoro-2-(5-fluoro-1H-pyrrolo[2,3-b]pyridin-3-yl)-6-(isoxazol-5-yl) pyrimidin-4-yl)amino)bicyclo[2.2.2]octane-2-carboxylic Acid To a solution of (+/−)-trans-methyl 3-((5-fluoro-2-(5-fluoro-1-tosyl-1H-pyrrolo[2,3-b]pyridin-3-yl)-6-(isoxazol- 5-yl)pyrimidin-4-yl)amino)bicyclo[2.2.2]octane-2-carboxylate (27 mg, 0.04 mmol) in THF/MeOH (v/v=1/1, 2 mL) was added aqueous sodium hydroxide solution (4 M, 0.10 mL, 0.40 mmol). The mixture was stirred at 30° C. overnight, then diluted with water (10 mL). The resulting mixture was acidified with hydrochloric acid (1 M) to pH about 5.5, then extracted with ethyl acetate (20 mL×3). The combined organic layers were washed with saturated brine (50 mL), dried over anhydrous sodium sulfate, filtered, and the filtrate was concentrated in vacuo. The residue was purified by silica gel column chromatography (DCM/MeOH (v/v)=10/1) to give the title compound as a yellow solid (15 mg, 76%).

MS (ESI, pos.ion) m/z: 467.2 [M+H]$^+$;

HRMS (ESI, pos. ion) m/z: 467.1644 [M+H]$^+$, ($C_{23}H_{21}F_2N_6O_3$) [M+H]$^+$ theoretical value: 467.1643;

$^1$H NMR (400 MHz, DMSO-$d_6$) δ (ppm): 12.39 (s, 1H), 9.19 (s, 1H), 8.53 (d, J=9.5 Hz, 1H), 8.33 (s, 1H), 8.30 (s, 1H), 7.88 (d, J=6.2 Hz, 1H), 7.24 (s, 1H), 4.75 (s, 1H), 2.89 (s, 1H), 2.03 (s, 1H), 1.87-1.73 (m, 3H), 1.70-1.42 (m, 6H).

Example 78: (2S,3S)-3-((2-(5-fluoro-1H-pyrrolo[2,3-b]pyridin-3-yl)-7-isopropyl-7H-pyrrolo [2,3-d]pyrimidin-4-yl)amino)bicyclo[2.2.2]octane-2-carboxylic Acid

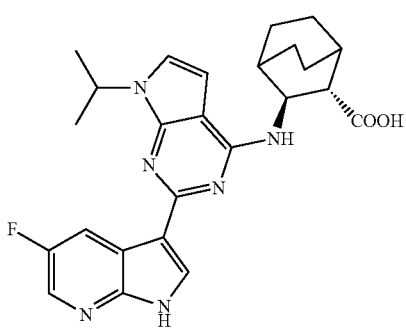 [SMILES: CC(C)n1ccc2c(N[C@H]3C4CCC(CC4)[C@@H]3C(=O)O)nc(-c3c[nH]c4ncc(F)cc34)nc21]

Step 1: (2S,3S)-ethyl 3-aminobicyclo[2.2.2]octane-2-carboxylate hydrochloride

The title compound can be prepared according to the synthetic method disclosed in patent application WO 2015073491.

Step 2: (2S,3S)-ethyl 3-((2-chloro-7-isopropyl-7H-pyrrolo[2,3-d]pyrimidin-4-yl)amino)bicyclo [2.2.2]octane-2-carboxylate To a solution of (2S,3S)-ethyl 3-aminobicyclo[2.2.2]octane-2-carboxylate hydrochloride (458 mg, 1.96 mmol), 2,4-dichloro-7-isopropyl-7H-pyrrolo[2,3-d]pyrimidine (410 mg, 1.78 mmol) in dichloromethane (15 mL) was added slowly DIPEA (0.97 mL, 5.88 mmol). The mixture was stirred at 30° C. overnight under nitrogen protection. The reaction mixture was washed with water (10 mL), 5% aqueous sodium bisulfate solution (10 mL) and saturated brine (10 mL) in turn, dried over anhydrous sodium sulfate and filtered. The filtrate was concentrated in vacuo and the residue was purified by silica gel column chromatography (PE/EtOAc (v/v)=10/1) to give the title compound as a yellow solid (333 mg, 50%).

Step 3: (2S,3S)-ethyl 3-((2-(5-fluoro-1-tosyl-1H-pyrrolo[2,3-b]pyridin-3-yl)-7-isopropyl-7H-pyrrolo [2,3-d]pyrimidin-4-yl)amino)bicyclo[2.2.2]octane-2-carboxylate To 1,4-dioxane (3 mL) were added 5-fluoro-3-(4,4,5,5-tetramethyl-1,3,2-dioxaborolan-2-yl)-1-tosyl-1H-pyrrolo[2,3-b]pyridine (284 mg, 0.31 mmol, 45% wt), potassium carbonate (106 mg, 0.77 mmol), PdCl$_2$(dppf) (41 mg, 0.05 mmol) and (2S,3S)-ethyl 3-((2-chloro-7-isopropyl-7H-pyrrolo[2,3-d]pyrimidin-4-yl)amino)bicyclo[2.2.2]octane-2-carboxylate (100 mg, 0.26 mmol). Then H$_2$O (0.2 mL) was added to the mixture, and the air in the mixture was removed by bubbling with nitrogen for 10 min. The mixture was stirred for 2 h at 110° C. with microwave heating. The mixture was filtered to remove solid impurities. The filtrate was concentrated in vacuo, and the residue was purified by silica gel column chromatography (PE/EtOAc (v/v)=10/1-5/1) to give the title compound as a white solid (146 mg, 89%).

$^1$H NMR (400 MHz, CDCl$_3$) δ (ppm): 8.73 (dd, J=9.1, 2.7 Hz, 1H), 8.66 (s, 1H), 8.32 (s, 1H), 8.13 (d, J=8.2 Hz, 2H), 7.30 (s, 2H), 7.06 (d, J=3.5 Hz, 1H), 6.41 (d, J=2.9 Hz, 1H), 4.90 (s, 1H), 2.45 (d, J=5.2 Hz, 1H), 2.38 (s, 3H), 2.08 (s, 2H), 2.00-1.66 (m, 8H), 1.57 (d, J=6.7 Hz, 6H), 1.28 (s, 5H).

Step 4: (2S,3S)-3-((2-(5-fluoro-1H-pyrrolo[2,3-b]pyridin-3-yl)-7-isopropyl-7H-pyrrolo[2,3-d]pyrimidin-4-yl)amino)bicyclo[2.2.2]octane-2-carboxylic Acid To a solution of (2S,3S)-ethyl 3-((2-(5-fluoro-1-tosyl-1H-pyrrolo[2,3-b]pyridin-3-yl)-7-isopropyl-7H-pyrrolo[2,3-d]pyrimidin-4-yl)amino)bicyclo[2.2.2]octane-2-carboxylat e (146 mg, 0.23 mmol) in THF/MeOH (v/v=5 mL/5 mL) was added a solution of NaOH (90 mg, 2.26 mmol) in water (1 mL). The mixture was stirred at rt overnight, then diluted with water (10 mL). The resulting mixture was acidified with hydrochloric acid (1 M) to pH about 6. The resulting mixture was extracted with ethyl acetate (15 mL×3). The combined organic layers were washed with saturated brine (40 mL), dried over anhydrous sodium sulfate and filtered. The filtrate was concentrated in vacuo to remove the solvent and the residue was purified by silica gel column chromatography (DCM/MeOH (v/v)=10/1-5/1) to give the title compound as a yellow solid (65 mg, 62%).

MS (ESI, pos. ion) m/z: 463.4 [M+H]$^+$;

HRMS (ESI, pos. ion) m/z: 463.2264 [M+H]$^+$, ($C_{25}H_{28}FN_6O_2$) [M+H]$^+$ theoretical value: 463.2258;

$^1$H NMR (600 MHz, DMSO-$d_6$) δ (ppm): 12.28 (s, 1H), 12.08 (s, 1H), 8.68 (d, J=8.8 Hz, 1H), 8.26 (s, 1H), 8.22 (d, J=2.1 Hz, 1H), 7.21 (d, J=2.5 Hz, 2H), 6.64 (s, 1H), 5.02 (m, 1H), 4.79 (s, 1H), 2.72 (d, J=6.3 Hz, 1H), 2.03 (d, J=12.3 Hz, 2H), 1.79 (m, 3H), 1.54 (m, 11H).

Example 79: (+/−)-trans-3-((2-(5-fluoro-1H-pyrrolo[2,3-b]pyridin-3-yl)-6-(4-morpholino phenyl)pyrimidin-4-yl)amino)bicyclo[2.2.2]octane-2-carboxylic Acid

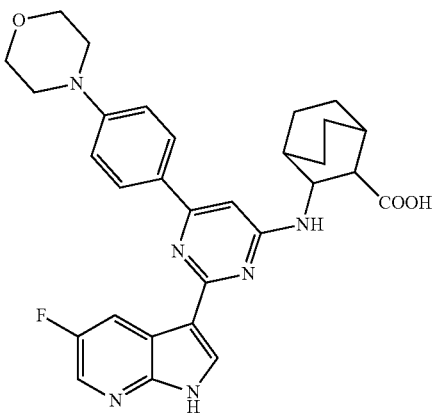 [SMILES: O=C(O)C1C2CCC(CC2)C1Nc1cc(-c2ccc(N3CCOCC3)cc2)nc(-c2c[nH]c3ncc(F)cc23)n1]

Step 1: 4-(4-(2,6-dichloropyrimidin-4-yl)phenyl)morpholine

To a solution of 2,4,6-trichloropyrimidine (500 mg, 2.73 mmol) in tetrahydrofuran (8.18 mL) were added palladium acetate (63 mg, 0.28 mmol), triphenylphosphine (150 mg, 0.548 mmol), (4-morpholinophenyl)boronic acid (570 mg, 2.75 mmol) and aqueous sodium carbonate solution (1 M, 8.18 mL, 8.18 mmol). The mixture was stirred at 70° C. for 6 h under nitrogen protection, then water (50 mL) was added. The mixture was extracted with EtOAc (50 mL×3). The combined organic layers were washed with saturated brine (50 mL), dried over anhydrous sodium sulfate and filtered. The filtrate was concentrated in vacuo and the residue was purified by silica gel column chromatography (PE) to give the title compound as a white solid (374 mg, 44%).

MS (ESI, pos.ion) m/z: 310.0 [M+H]$^+$;

$^1$H NMR (400 MHz, CDCl$_3$) δ (ppm): 8.04 (d, J=9.1 Hz, 2H), 7.56 (s, 1H), 6.96 (d, J=9.1 Hz, 2H), 3.92-3.88 (m, 4H), 3.37-3.33 (m, 4H).

Step 2: (+/−)-trans-methyl 3-((2-chloro-6-(4-morpholinophenyl)pyrimidin-4-yl)amino)bicycle [2.2.2] octane-2-carboxylate To a solution of (+/−)-trans-methyl 3-aminobicyclo[2.2.2]octane-2-carboxylate (230 mg, 1.25 mmol) and 4-(4-(2,6-dichloropyrimidin-4-yl)phenyl)morpholine (353 mg, 1.14 mmol) in DMF (5 mL) was added potassium carbonate (173 mg, 1.25 mmol), and the mixture was stirred at rt overnight. To the reaction mixture was added water (40 mL), and the resulting mixture was extracted with ethyl acetate (40 mL×3). The combined organic layers were washed with saturated brine (50 mL), dried over anhydrous sodium sulfate and filtered. The filtrate was concentrated in vacuo to dry and the residue was purified by silica gel column chromatography (PE/EA (v/v)=20/1) to give the title compound as a white solid (192 mg, 37%).

MS (ESI, pos.ion) m/z: 457.3 [M+H]$^+$;

$^1$H NMR (400 MHz, CDCl$_3$) δ (ppm): 7.96 (d, J=8.8 Hz, 2H), 6.96 (d, J=8.9 Hz, 2H), 6.71 (s, 1H), 5.41-5.34 (m, 1H), 4.32 (s, 1H), 3.92-3.86 (m, 4H), 3.75 (s, 3H), 3.32-3.25 (m, 4H), 2.39 (d, J=4.8 Hz, 1H), 2.07 (d, J=3.3 Hz, 1H), 1.88 (d, J=2.7 Hz, 1H), 1.81-1.62 (m, 6H), 1.53-1.41 (m, 2H).

Step 3: (+/−)-trans-methyl 3-((2-(5-fluoro-1-tosyl-1H-pyrrolo[2,3-b]pyridin-3-yl)-6-(4-morpholinophenyl)pyrimidin-4-yl)amino)bicyclo[2.2.2]octane-2-carboxylate To a sealed tub were added 5-fluoro-3-(4,4,5,5-tetramethyl-1,3,2-dioxaborolan-2-yl)-1-tosyl-1H-pyrrolo[2,3-b]pyridine (396 mg, 0.38 mmol), (+/−)-trans-methyl 3-((2-chloro-6-(4-morpholinophenyl)pyrimidin-4-yl)amino)bicyclo[2.2.2]octane-2-carboxylate (145 mg, 0.32 mmol), potassium carbonate (131 mg, 0.95 mmol), Pd(dppf)Cl$_2$ (51 mg, 0.06 mmol), 1,4-dioxane (3 mL) and water (0.2 mL). The air in the mixture was removed by bubbling with nitrogen for 10 min and the mixture in sealed tub was stirred at 110° C. for 2 h. The reaction mixture was filtered through a celite pad, and the filter cake was washed with ethyl acetate (50 mL). The filtrate was washed with saturated brine (50 mL), dried over anhydrous sodium sulfate and filtered. The filtrate was concentrated in vacuo and the residue was purified by silica gel column chromatography (n-hexane/EtOAc(v/v)=5/1) to give the title compound as a yellow solid (148 mg, 66%).

MS (ESI, pos.ion) m/z: 712.2[M+H]$^+$;

$^1$H NMR (400 MHz, CDCl$_3$) δ (ppm): 8.71 (dd, J=8.1, 3.6 Hz, 2H), 8.33 (d, J=1.8 Hz, 1H), 8.13 (d, J=8.3 Hz, 2H), 8.07 (d, J=8.8 Hz, 2H), 7.30 (s, 2H), 7.04 (d, J=8.9 Hz, 2H), 6.67 (s, 1H), 5.12 (s, 1H), 4.52 (s, 1H), 3.96-3.87 (m, 4H), 3.35-3.26 (m, 4H), 2.45 (d, J=4.9 Hz, 1H), 2.39 (s, 3H), 2.10 (s, 1H), 1.98 (s, 1H), 1.84 (d, J=10.1 Hz, 2H), 1.69 (m, 6H).

Step 4: (+/−)-trans-3-((2-(5-fluoro-1H-pyrrolo[2,3-b]pyridin-3-yl)-6-(4-morpholinophenyl) pyrimidin-4-yl)amino)bicyclo[2.2.2]octane-2-carboxylic Acid To a solution of (+/−)-trans-methyl 3-((2-(5-fluoro-1-tosyl-1H-pyrrolo[2,3-b]pyridin-3-yl)-6-(4-morpholinophenyl)pyrimidin-4-yl)amino)bicyclo[2.2.2]octane-2-carboxylate (144 mg, 0.20 mmol) in THF/MeOH (v/v=1/1, 3 mL) was added aqueous sodium hydroxide solution (4 M, 0.5 mL, 2 mmol). The mixture was stirred at 30° C. overnight, then diluted with water (10 mL). The resulting mixture was acidified with hydrochloric acid (1 M) to pH 5.5, then extracted with ethyl acetate (20 mL×3). The combined organic layers were washed with saturated brine (50 mL), dried over anhydrous sodium sulfate, filtered, and the filtrate was concentrated in vacuo to remove the solvent. The residue was purified by silica gel column chromatography (DCM/MeOH (v/v)=10/1) to give the title compound as a yellow solid (36 mg, 33%).

MS (ESI, pos.ion) m/z: 543.2 [M+H]$^+$;

HRMS (ESI, pos. ion) m/z: 543.2513 [M+H]$^+$, (C$_{30}$H$_{32}$FN$_6$O$_3$) [M+H]$^+$ theoretical value: 543.2520;

$^1$H NMR (600 MHz, DMSO-d$_6$) δ (ppm): 12.24 (s, 1H), 8.65 (s, 1H), 8.36 (s, 1H), 8.29 (s, 1H), 8.01 (s, 2H), 7.33 (s, 1H), 7.09 (d, J=7.9 Hz, 2H), 6.67 (s, 1H), 4.63 (s, 1H), 4.03 (d, J=7.0 Hz, 1H), 3.77 (s, 4H), 3.60 (s, 1H), 3.24 (s, 4H), 1.93-1.29 (m, 10H).

Example 80: (+/−)-trans-3-((2-(5-fluoro-6-methyl-1H-pyrrolo[2,3-b]pyridin-3-yl)-6-phenyl pyrimidin-4-yl)amino)bicyclo[2.2.2]octane-2-carboxylic Acid

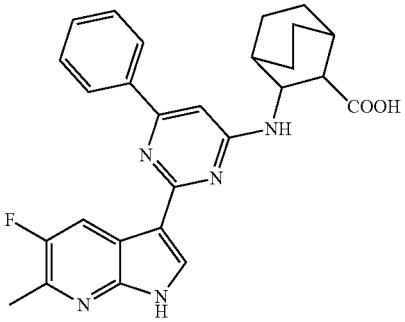 [SMILES: Cc1nc2[nH]cc(-c3nc(NC4C5CCC(CC5)C4C(=O)O)cc(-c4ccccc4)n3)c2cc1F]

Step 1: 3-bromo-5-fluoro-6-methylpyridin-2-amine

To a solution of 5-fluoro-6-methylpyridin-2-amine (1.55 g, 12.3 mmol) in acetonitrile (16 mL) was added NBS (2.83 g, 15.9 mmol) in portions at −5° C. After the addition, the mixture was stirred at −5° C. for 1.5 h. To the mixture was added ethyl acetate (80 mL), and the resulting mixture was washed with water (80 mL) and saturated brine (80 mL), dried over anhydrous sodium sulfate and filtered. The filtrate was concentrated in vacuo and the residue was purified by silica gel column chromatography (n-hexane/EtOAc (v/v) =10/1-3/1) to give the title compound as a light yellow solid (1.72 g, 68%).

$^1$H NMR (400 MHz, CDCl$_3$) δ (ppm): 7.41 (d, J=7.9 Hz, 1H), 4.78 (s, 2H), 2.34 (d, J=2.9 Hz, 3H).

Step 2: 5-fluoro-6-methyl-3-((trimethylsilyl)ethynyl)pyridin-2-amine

To a two-neck flask were added 3-bromo-5-fluoro-6-methylpyridin-2-amine (1.50 g, 7.32 mmol), bis(triphenylphosphine)palladium(II) chloride (513 mg, 0.73 mmol), cuprous iodide (263 mg, 1.38 mmol), triethylamine (6.0 mL, 43.2 mmol) and tetrahydrofuran (1.0 mL). To the mixture was added dropwise slowly trimethylsilylacetylene (1.95 mL, 13.8 mmol) at rt under nitrogen protection, and the resulting mixture was heated to 50° C. and stirred for 4 h. The reaction mixture was cooled to rt, and saturated aqueous ammonium chloride (30 mL) was added. The resulting mixture was extracted with ethyl acetate (30 mL×3). The combined organic layers were washed with saturated aqueous sodium chloride (80 mL), dried over anhydrous sodium sulfate and filtered. The filtrate was concentrated in vacuo and the residue was purified by silica gel column chromatography (PE/EtOAc (v/v)=15/1-4/1) to give the title compound as a gray solid (1.30 g, 80%).

$^1$H NMR (400 MHz, CDCl$_3$) δ (ppm): 7.23 (d, J=9.1 Hz, 1H), 4.84 (s, 2H), 2.37 (d, J=2.9 Hz, 3H), 0.28 (s, 9H).

Step 3: 5-fluoro-6-methyl-1H-pyrrolo[2,3-b]pyridine

To a suspension of potassium tert-butoxide (855 mg, 7.62 mmol) in NMP (15 mL) was added 5-fluoro-6-methyl-3-((trimethylsilyl)ethynyl)pyridin-2-amine (1.30 g, 5.85 mmol) in portions at 50° C. After the addition, the mixture was heated to 80° C. under nitrogen protection and stirred for 3 h. The reaction mixture was cooled to rt and TsCl (1.35 g, 7.08 mmol) was added in portions into the reaction mixture. After the addition, the mixture was stirred at 30° C. for 2 h. To the mixture was added water (40 mL), and the resulting mixture was filtered. The filter cake was purified by silica gel column chromatography (PE/EtOAc (v/v)=20/1-6/1) to give the title compound as a white solid (820 mg, 46%).

$^1$H NMR (400 MHz, CDCl$_3$) δ (ppm): 8.11 (d, J=8.3 Hz, 2H), 7.70 (d, J=3.9 Hz, 1H), 7.44 (d, J=9.3 Hz, 1H), 7.31 (s, 2H), 6.51 (d, J=4.0 Hz, 1H), 2.61 (d, J=3.2 Hz, 3H), 2.40 (s, 3H).

Step 4: 3-bromo-5-fluoro-6-methyl-1-tosyl-1H-pyrrolo[2,3-b]pyridine

The solution of 5-fluoro-6-methyl-1-tosyl-1H-pyrrolo[2,3-b]pyridine (590 mg, 1.94 mmol) in DMF (8 mL) was cooled to 0° C., and bromine (0.3 mL, 6 mmol) was added dropwise slowly to the solution. After the addition, the mixture was stirred at rt for 2 h. The mixture was added dropwise into a saturated aqueous sodium thiosulfate solution (30 mL), and the resulting mixture was extracted with EtOAc (30 mL×3). The combined organic phases were dried over anhydrous Na$_2$SO$_4$, filtered, and the filtrate was concentrated in vacuo. The residue was purified by silica gel chromatograph (PE/EtOAc (v/v)=5/1) to give the title compound as a yellow solid (468 mg, 63%).

$^1$H NMR (400 MHz, CDCl$_3$) δ (ppm): 8.10 (d, J=8.3 Hz, 2H), 7.76 (s, 1H), 7.41 (d, J=8.7 Hz, 1H), 7.31 (d, J=8.1 Hz, 2H), 2.63 (d, J=3.2 Hz, 3H), 2.41 (s, 3H).

Step 5: 5-fluoro-6-methyl-3-(4,4,5,5-tetramethyl-1,3,2-dioxaborolan-2-yl)-1-tosyl-1H-pyrrolo[2,3-b]pyridine To a microwave tub were added 3-bromo-5-fluoro-6-methyl-1-tosyl-1H-pyrrolo[2,3-h]pyridine (468 mg, 1.23 mmol), bis(pinacolato)diboron (483 mg, 1.90 mmol), potassium acetate (248 mg, 2.53 mmol), Pd(dppf)Cl$_2$ (95 mg, 0.13 mmol) and DME (5 mL). The air in the mixture was removed by bubbling with nitrogen for 10 min and then the mixture was stirred at 130° C. for 2 h with microwave heating. The reaction mixture was filtered through a celit pad, and the filter cake was washed with ethyl acetate (30 mL). The filtrate was concentrated in vacuo, and the residue was used for the next step with out further purification.

MS (ESI, pos.ion) m/z: 431.1 [M+H]$^+$.

Step 6: (+/−)-trans-methyl 3-((2-(5-fluoro-6-methyl-1-tosyl-1H-pyrrolo[2,3-b]pyridin-3-yl)-6-phenylpyrimidin-4-yl)amino)bicyclo[2.2.2]octane-2-carboxylate To a microwave tub were added 5-fluoro-6-methyl-3-(4,4,5,5-tetramethyl-1,3,2-dioxaborolan-2-yl)-1-tosyl-1H-pyrrolo[2,3-b]pyridine (187 mg, 0.26 mmol, 60%), (+/−)-trans-methyl 3-((2-chloro-6-phenylpyrimidin-4-yl)amino)bicyclo[2.2.2]octane-2-carboxylate (80 mg, 0.22 mmol), potassium carbonate (89 mg, 0.65 mmol), Pd(dppf)Cl$_2$ (35 mg, 0.04 mmol), 1,4-dioxane (3 mL) and water (0.2 mL). The air in the mixture was removed by bubbling with nitrogen for 10 min and the mixture in sealed tub was stirred at 110° C. for 3 h. The mixture was filtered through a celite pad, and the filter cake was washed with ethyl acetate (50 mL). The filtrate was washed with saturated brine (50 mL), dried over anhydrous sodium sulfate and filtered. The filtrate was concentrated in vacuo and the residue was purified by silica gel column chromatography (n-hexane/EtOAc (v/v)=2/1) to give the title compound as a yellow solid (77 mg, 56%).

$^1$H NMR (400 MHz, CDCl$_3$) δ (ppm): 8.64 (s, 1H), 8.57 (d, J=9.9 Hz, 1H), 8.17 (d, J=8.2 Hz, 2H), 8.11 (d, J=6.8 Hz, 2H), 7.54 (dd, J=14.6, 7.0 Hz, 3H), 7.39 (d, J=4.3 Hz, 1H), 7.31 (s, 1H), 6.73 (s, 1H), 5.18 (s, 1H), 4.54 (s, 1H), 3.74 (s, 3H), 2.64 (d, J=3.0 Hz, 3H), 2.45 (d, J=4.8 Hz, 1H), 2.40 (s, 3H), 2.10 (s, 1H), 1.99 (s, 1H), 1.92-1.62 (m, 8H).

Step 7: (+/−)-trans-3-((2-(5-fluoro-6-methyl-1H-pyrrolo[2,3-b]pyridin-3-yl)-6-phenylpyrimidin-4-yl)amino)bicyclo[2.2.2]octane-2-carboxylic Acid To a solution of (+/−)-trans-methyl 3-((2-(5-fluoro-6-methyl-1-tosyl-1H-pyrrolo [2,3-b]pyridin-3-yl)-6-phenylpyrimidin-4-yl)amino)bicyclo[2.2.2]octane-2-carboxylate (77 mg, 0.12 mmol) in THF/MeOH (v/v=1/1, 3 mL) was added aqueous sodium hydroxide solution (4 M, 0.30 mL, 1.20 mmol). The mixture was stirred at 30° C. overnight, then diluted with water (20 mL). The resulting mixture was acidified with hydrochloric acid (1 M) to pH about 5.5, then extracted with ethyl acetate (20 mL×3). The combined organic layers were washed with saturated brine (50 mL), dried over anhydrous sodium sulfate, filtered, and the filtrate was concentrated in vacuo to remove the solvent. The residue was purified by silica gel column chromatography (DCM/MeOH (v/v)=10/1) to give the title compound as a yellow solid (25 mg, 44%).

MS (ESI, pos.ion) m/z: 472.5 [M+H]$^+$;
HRMS (ESI, pos. ion) m/z: 472.2156[M+H]$^+$, (C$_{27}$H$_{27}$FN$_5$O$_2$) [M+H]$^+$ theoretical value: 472.2149;
$^1$H NMR (400 MHz, DMSO-d$_6$) δ (ppm): 12.31 (s, 1H), 12.07 (s, 1H), 8.55 (s, 1H), 8.27 (d, J=2.0 Hz, 1H), 8.10 (s, 2H), 7.60-7.38 (m, 4H), 6.76 (s, 1H), 4.64 (s, 1H), 2.53 (d, J=2.5 Hz, 4H), 1.99 (s, 2H), 1.86-1.39 (m, 8H).

EXAMPLES OF BIOLOGICAL ASSAY

Using parts of the compounds of the invention as examples, the inventors have detected antiviral and cytotoxicity activities and pharmacokinetic properties of the compounds of the invention in the following examples.

Example A: Cytopathic Effect Assay (CPE Assay)

Detection of the inhibitory effect of the compound of the invention against cytopathic effect (CPE) of virus H1N1 A/Weiss/43 on cellular level in vitro.

Scheme 1: MDCK cells (Madin-Daby canine kidney cells) were seeded in a 384-well plate with 2000 cells per well and cultured at 37° C. and 5% CO$_2$ overnight. Next day, cell culture medium was replenished with fresh medium containing appropriate concentrations of test compounds and virus H1N1 A/Weiss/43 at an multiplicity of infection to yield 80-95% CPE (or the titer was 1 TCID90/well). The top final concentration of the test compounds were 100 μM and then diluted by 3-fold serially for a total of 8 concentrations at 100 μM, 33.33 μM, 11.11 μM, 3.70 μM, 1.23 μM, 0.41 μM, 0.14 μM, 0.05 μM. The test condition of cytotoxicity test group was the same as described above, except that the cell culture medium of cytotoxicity test group didn't contain influenza virus. A virus control group without drug and a no virus infected cell control group without drug were set at the same time. Each group was set in duplicate, and incubated at 37° C. under 5% CO$_2$ condition for 5 days. The cell activity was detected by using CCK-8 kits, and the data were used for calculating the antiviral effect and cytotoxicity against virus-infected cell of the compound. Data were analyzed by using GraphPad Prism software, and the CPE inhibition ratio and cell survival ratio were calculated. EC$_{50}$ and CC$_{50}$ values were obtained according to the curve fitting.

CPE inhibition ratio=[(absorbance of dosing well−absorbance of virus control well)/(absorbance of cell control well−absorbance of virus control well)]×100% cell survival ratio=[(absorbance of dosing well−absorbance of medium control well)/(absorbance of cell control well−absorbance of medium control well)]×100%

Table 1 shows inhibitory activities of compounds of the invention against influenza virus (A/Weiss/43(H1N1))

TABLE 1

| Example No. | EC$_{50}$ (μM) |
|---|---|
| Example 1 | <0.05 |
| Example 2 | <0.05 |
| Example 3 | <0.05 |
| Example 4 | <0.05 |
| Example 6 | <0.05 |

The assay shows that the compounds of the invention have good anti-influenza virus activities.

Scheme 2: MDCK cells (Madin-Daby canine kidney cells) were seeded in a 384-well plate with 2000 cells per well and cultured at 37° C. and 5% CO$_2$ overnight. Next day, cell culture medium was replenished with fresh medium containing appropriate concentrations of test compounds and virus H1N1 A/Weiss/43 at an multiplicity of infection to yield 80-95% CPE (or the titer was 1 TCID90/well). The top final concentration of the test compounds were 50 nM and then diluted by 3-fold serially for a total of 8 concentrations at 50 nM, 16.67 nM, 5.56 nM, 1.85 nM, 0.62 nM, 0.21 nM, 0.068 nM, 0.023 nM. The test condition of cytotoxicity test group was the same as described above, except that the cell culture medium of cytotoxicity test group didn't contain influenza virus. A Virus control group without drug and a no virus infected cell control group without drug were set at the same time. Each group was set in duplicate, and incubated at 37° C. under 5% CO$_2$ condition for 5 days. The cell activity was detected by using CCK-8 kits, and the data were used for calculating the antiviral effect and cytotoxicity against virus-infected cell of the compound. Data were analyzed by using GraphPad Prism software, and the CPE inhibition ratio and cell survival ratio was calculated. EC$_{50}$ and CC$_{50}$ values were obtained according to the curve fitting.

CPE inhibition ratio=[(absorbance of dosing well−absorbance of virus control well)/(absorbance of cell control well−absorbance of virus control well)]×100% cell survival ratio=[(absorbance of dosing well−absorbance of medium control well)/(absorbance of cell control well−absorbance of medium control well)]×100%

Table 2 shows inhibitory activities of compounds of the invention against influenza virus (A/Weiss/43(H1N1))

TABLE 2

| Example Number | $EC_{50}$ (nM) |
| --- | --- |
| Example 4 | 0.20 |
| Example 4a | 0.17 |
| Example 9 | 0.066 |
| Example 9a | 0.039 |
| Example 16 | 0.54 |
| Example 17 | 0.54 |
| Example 23 | 0.104 |
| Example 24a | 0.744 |
| Example 25 | 0.26 |
| Example 49 | 0.068 |
| Example 54 | 0.261 |
| Example 55 | 0.874 |
| Example 65 | 0.66 |
| Example 78 | 0.236 |

The assay shows that the compounds of the invention have good anti-influenza virus activities.

Example B: Pharmacokinetic Evaluation after Administering a Certain Amount of the Compound of the Invention by Intravenous or Oral to Rats, Dogs or Monkeys Pharmacokinetic characteristics of the compound of the invention and the control compound VX-787 (also named JNJ-872, the structure as shown below) in SD rat, dog or monkey were evaluated. The compounds disclosed herein were administered in form of a saline solution containing 5% DMSO, 5% Kolliphor HS 15 and 90% Saline. For intravenous administration (iv), the animals were administered with a dose of 1 mg/kg, and blood samples (0.3 mL) were collected at the time points of 0.083, 0.25, 0.5, 1.0, 2.0, 5.0, 7.0 and 24 h after drug administration, then each blood sample was processed to separate plasma by centrifugation at 3000 rpm or 4000 rpm for 10 minutes. For oral administration (po), the animals were administered with a dose of 5 mg/kg, and blood samples (0.3 mL) were collected at the time points of 0.25, 0.5, 1.0, 2.0, 5.0, 7.0 and 24 h after drug administration, then each blood sample was processed to separate plasma by centrifugation at 3000 rpm or 4000 rpm for 10 minutes. Plasma samples were collected and stored at −20° C. or −70° C. until LC/MS/MS analysis.

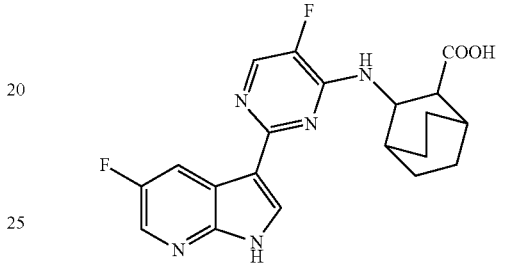

VX-787

The assay shows that the compounds of the invention have high exposure level and good absorption in animals in vivo, and the pharmacokinetic properties of the compounds of the invention have significant advantages.

Table 3 shows pharmacokinetic data of the compounds of the invention in vivo of SD rat

TABLE 3

| Test Compound | Administration route | Dosage mg/kg | $T_{max}$ h | $C_{max}$ ng/mL | $t_{1/2}$ h | $AUC_{last}$ hr*ng/mL | $AUC_{INF}$ hr*ng/mL | F % | CL L/h/Kg | Vss L/Kg |
| --- | --- | --- | --- | --- | --- | --- | --- | --- | --- | --- |
| Control VX-787 (racemization) | iv | 1 | 0.083 | 2840 | 5.72 | 1180 | 1210 | N/A | 13.8 | 1.81 |
|  | po | 5 | 0.333 | 1970 | 4.14 | 3510 | 3530 | 58.4 | N/A | N/A |
| Example 1 | iv | 1 | 0.083 | 5900 | 1.13 | 4960 | 5020 | N/A | 17.1 | 1.03 |
|  | po | 5 | 0.833 | 3130 | 1.48 | 10100 | 10600 | 42.1 | N/A | N/A |
| Example 2 | iv | 1 | 0.083 | 4910 | 1.06 | 3440 | 3470 | N/A | 24.5 | 1.26 |
|  | po | 5 | 0.417 | 4020 | 1.33 | 8080 | 8180 | 47.1 | N/A | N/A |
| Example 4 | iv | 1 | 0.083 | 5980 | 2.71 | 4540 | 4610 | N/A | 3.66 | 0.412 |
|  | po | 5 | 0.667 | 3480 | 2.97 | 12800 | 12800 | 56.4 | N/A | N/A |
| Example 9 | iv | 1 | 0.083 | 10900 | 1.52 | 7260 | 7350 | N/A | 5.86 | 0.551 |
|  | po | 5 | 0.5 | 5270 | 3.15 | 17400 | 17500 | 47.5 | N/A | N/A |
| Example 17 | iv | 1 | 0.083 | 4420 | 1.12 | 2510 | 2520 | N/A | 33.1 | 1.49 |
|  | po | 5 | 0.5 | 2660 | 0.911 | 8270 | 8360 | 66.4 | N/A | N/A |
| Example 18 | iv | 1 | 0.083 | 4470 | 4.37 | 3130 | 3190 | N/A | 5.3 | 0.598 |
|  | po | 5 | 2 | 1690 | 3.71 | 6840 | 6880 | 43.1 | N/A | N/A |
| Example 61 | iv | 1 | 0.083 | 8540 | 0.542 | 4030 | 4050 | N/A | 4.17 | 0.585 |
|  | po | 5 | 1.5 | 2710 | 5.95 | 10400 | 10700 | 53.1 | N/A | N/A |
| Example 63 | iv | 1 | 0.083 | 4990 | 3.85 | 4710 | 4750 | N/A | 3.55 | 0.416 |
|  | po | 5 | 2 | 3280 | 3.59 | 15300 | 15400 | 65 | N/A | N/A |
| Example 65 | iv | 1 | 0.083 | 6830 | 0.965 | 5340 | 5360 | N/A | 3.13 | 0.168 |
|  | po | 5 | 0.417 | 7940 | 1.14 | 12000 | 12100 | 44.9 | N/A | N/A |
| Example 68 | iv | 1 | 0.083 | 3750 | 2.01 | 2760 | 2880 | N/A | 5.86 | 0.551 |
|  | po | 5 | 0.417 | 2960 | 3.24 | 8310 | 8330 | 60.1 | N/A | N/A |
| Example 73 | iv | 1 | 0.083 | 14800 | 1.41 | 24200 | 24800 | N/A | 0.681 | 0.212 |
|  | po | 5 | 1.5 | 9300 | 5.58 | 50600 | 52800 | 42.6 | N/A | N/A |
| Example 80 | iv | 1 | 0.083 | 5630 | 1.53 | 3320 | 3380 | N/A | 24.7 | 1.5 |
|  | po | 5 | 0.833 | 3130 | 1.48 | 10100 | 10600 | 62.5 | N/A | N/A |

Notes:
Control compound—(+/−)-trans-3-((5-fluoro-2-(5-fluoro-1H-pyrrolo[2,3-b]pyridin-3-yl)pyrimidin-4-yl)amino)bicyclo[2.2.2]octane-2-carboxylic acid (The specific synthetic procedure can be seen in patent WO 2010148197);
$AUC_{last}$—AUC of 0 to 24 h;
$AUC_{INF}$—AUC of 0 to infinite time.

Table 3 shows that $C_{max}$, $AUC_{last}$ and $AUC_{INF}$ of the compounds of the invention in SD rat were higher than these of the compound VX-787 for both intravenous administration and oral administration. It indicates that the compounds of the invention have high exposure level and good absorption in SD rat, and the pharmacokinetic properties of the compounds of the invention is significantly better than the control compound VX-787.

Reference throughout this specification to "an embodiment," "some embodiments," "one embodiment", "another example," "an example," "a specific examples," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example, "in an example," "in a specific examples," or "in some examples," in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A compound having Formula (IIIA) or (IIIB) or a stereoisomer, a tautomer, an N-oxide, a solvate, or a pharmaceutically acceptable salt thereof,

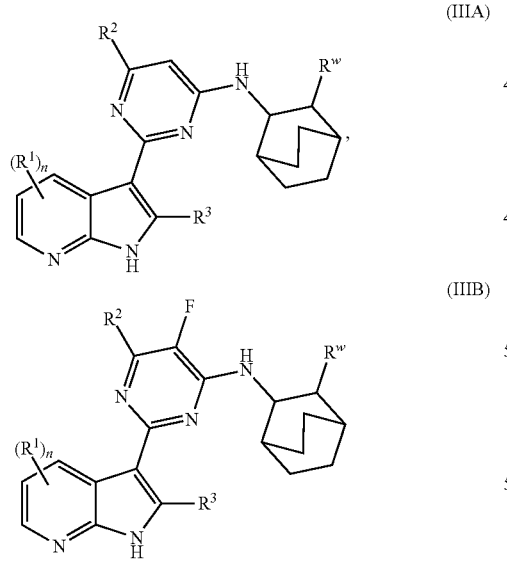

wherein
each $R^2$ is independently $C_{2-6}$ alkynyl, $C_{6-10}$ aryl, or 5- to 14-membered heteroaryl; and wherein each of the $C_{2-6}$ alkynyl, $C_{6-10}$ aryl, and 5- to 14-membered heteroaryl is independently unsubstituted or substituted with one, two, three, four or five R';
$R^w$ is —C(=O)$R^a$, —C(=O)O$R^b$, or —C(=O) N$R^cR^d$;

each $R^1$ and $R^3$ is independently H, F, Cl, Br, CN, NO$_2$, —C(=O)$R^a$, —C(=O)O$R^b$, —C(=O)N$R^cR^d$, O$R^b$, —N$R^cR^d$, $R^b$O—$C_{1-4}$ alkylene, $R^dR^cN$—$C_{1-4}$ alkylene, $C_{1-6}$ alkyl, $C_{2-6}$ alkenyl, $C_{2-6}$ alkynyl, $C_{3-8}$ cycloalkyl, $C_{3-8}$ cycloalkyl-$C_{1-4}$ alkylene, 3- to 12-membered heterocyclyl, (3- to 12-membered heterocyclyl)-$C_{1-4}$ alkylene, $C_{6-10}$ aryl, $C_{6-10}$ aryl-$C_{1-4}$ alkylene, 5- to 10-membered heteroaryl or (5- to 10-membered heteroaryl)-$C_{1-4}$ alkylene, and wherein each of the $C_{1-6}$ alkyl, $C_{2-6}$ alkenyl, $C_{2-6}$ alkynyl, $C_{3-8}$ cycloalkyl, $C_{3-8}$ cycloalkyl-$C_{1-4}$ alkylene, 3- to 12-membered heterocyclyl, (3- to 12-membered heterocyclyl)-$C_{1-4}$ alkylene, $C_{6-10}$ aryl, $C_{6-10}$ aryl-$C_{1-4}$ alkylene, 5- to 10-membered heteroaryl and (5- to 10-membered heteroaryl)-$C_{1-4}$ alkylene is independently unsubstituted or substituted with one, two, three or four substituents independently selected from F, Cl, Br, CN, O$R^b$, —N$R^cR^d$, $C_{1-6}$ alkyl, $C_{1-6}$ haloalkyl, $R^b$O—$C_{1-4}$ alkylene or $R^dR^cN$—$C_{1-4}$alkylene;

n is 0, 1, 2 or 3;

each R' is independently F, Cl, Br, CN, NO$_2$, =O, O$R^b$, —N$R^cR^d$, $R^b$O—$C_{1-4}$ alkylene, $R^dR^cN$—$C_{1-4}$ alkylene, —C(=O)$R^a$, —C(=O)O$R^b$, —C(=O) N$R^cR^d$, $C_{1-10}$ alkyl, $C_{1-6}$ haloalkyl, $C_{3-6}$ cycloalkyl, $C_{3-6}$ cycloalkyl-$C_{1-4}$ alkylene, 3- to 6-membered heterocyclyl, (3- to 6-membered heterocyclyl)-$C_{1-4}$ alkylene, $C_{6-10}$ aryl, $C_{6-10}$ aryl-$C_{1-4}$ alkylene, 5- to 6-membered heteroaryl or (5- to 6-membered heteroaryl)-$C_{1-4}$ alkylene, and wherein each of the $C_{1-10}$ alkyl, $C_{1-6}$ haloalkyl, $C_{3-6}$ cycloalkyl, $C_{3-6}$ cycloalkyl-$C_{1-4}$ alkylene, 3- to 6-membered heterocyclyl, (3- to 6-membered heterocyclyl)-$C_{1-4}$ alkylene, $C_{6-10}$ aryl, $C_{6-10}$ aryl-$C_{1-4}$ alkylene, 5- to 6-membered heteroaryl and (5- to 6-membered heteroaryl)-$C_{1-4}$ alkylene is independently unsubstituted or substituted with one, two, three, or four substituents independently selected from F, Cl, Br, CN, NO$_2$, O$R^b$, —N$R^cR^d$, $C_{1-6}$ alkyl, $C_{1-6}$ haloalkyl, $R^b$O—$C_{1-4}$ alkylene or $R^dR^cN$—$C_{1-4}$ alkylene; and each $R^a$, $R^b$, $R^c$, and $R^d$ is independently H, $C_{1-6}$ alkyl, $C_{1-6}$ haloalkyl, $C_{2-6}$ alkenyl, $C_{2-6}$ alkynyl, $C_{3-6}$ cycloalkyl, $C_{3-6}$ cycloalkyl-$C_{1-4}$ alkylene, 3- to 6-membered heterocyclyl, (3- to 6-membered heterocyclyl)-$C_{1-4}$ alkylene, $C_{6-10}$ aryl, $C_{6-10}$ aryl-$C_{1-4}$ alkylene, 5- to 10-membered heteroaryl, (5- to 10-membered heteroaryl)-$C_{1-4}$ alkylene; or $R^c$ and $R^d$, together with the nitrogen atom to which they are attached, form a 3- to 6-membered heterocyclic ring, and wherein each of the $C_{1-6}$ alkyl, $C_{2-6}$ alkenyl, $C_{2-6}$ alkynyl, $C_{3-6}$ cycloalkyl, $C_{3-6}$ cycloalkyl-$C_{1-4}$ alkylene, 3- to 6-membered heterocyclyl, (3- to 6-membered heterocyclyl)-$C_{1-4}$ alkylene, $C_{6-10}$ aryl, $C_{6-10}$ aryl-$C_{1-4}$ alkylene, 5- to 10-membered heteroaryl, (5- to 10-membered heteroaryl)-$C_{1-4}$ alkylene and 3- to 6-membered heterocyclic ring is independently unsubstituted or substituted with one, two, three, or four substituents independently selected from F, Cl, CN, OH, NH$_2$, $C_{1-6}$ alkyl, $C_{1-6}$ haloalkyl, $C_{1-6}$ alkoxy or $C_{1-6}$ alkylamino.

2. The compound of claim 1, wherein each $R^1$ and $R^3$ is independently H, F, Cl, —C(=O)$R^a$, —C(=O)O$R^b$, —C(=O)N$R^cR^d$, O$R^b$, —N$R^cR^d$, $C_{1-3}$ alkyl, $C_{3-6}$ cycloalkyl, 5- to 6-membered heterocyclyl, phenyl or 5- to 6-membered heteroaryl, and wherein each of the $C_{1-3}$ alkyl, $C_{3-6}$ cycloalkyl, 5- to 6-membered heterocyclyl, phenyl or 5- to 6-membered heteroaryl is independently unsubstituted or substituted with one, two, three or four substituents independently selected from F, Cl, $OR^b$, $-NR^cR^d$, $C_{1-3}$ alkyl, $C_{1-3}$ haloalkyl or $R^bO-C_{1-2}$ alkylene.

3. The compound of claim 1, wherein each $R^2$ is independently $C_{2-6}$ alkynyl, phenyl, naphthyl, or 5- to 6-membered heteroaryl; and wherein each of the $C_{2-6}$ alkynyl, phenyl, naphthyl, and 5- to 6-membered heteroaryl is independently unsubstituted or substituted with one, two, three, four or five R'.

4. The compound of claim 1, wherein each R' is independently F, Cl, Br, CN, $NO_2$, $OR^b$, $-NR^cR^d$, $-C(=O)R^a$, $-C(=O)NR^cR^d$, $C_{1-9}$ alkyl, $C_{1-3}$ haloalkyl, $C_{3-6}$ cycloalkyl, 5- to 6-membered heterocyclyl, phenyl, phenyl-$C_{1-2}$ alkylene or 5- to 6-membered heteroaryl, and wherein each of the $C_{1-9}$ alkyl, $C_{1-3}$ haloalkyl, $C_{3-6}$ cycloalkyl, 5- to 6-membered heterocyclyl, phenyl, phenyl-$C_{1-2}$ alkylene and 5- to 6-membered heteroaryl is independently unsubstituted or substituted with one, two, three, or four substituents independently selected from F, Cl, Br, CN, $NO_2$, $OR^b$, $-NR^cR^d$, methyl, ethyl, n-propyl or i-propyl.

5. The compound of claim 1, wherein each $R^a$, $R^b$, $R^c$, and $R^d$ is independently H, methyl, ethyl, i-propyl, n-propyl, n-butyl, t-butyl, $C_{1-3}$ haloalkyl, $C_{3-6}$ cycloalkyl, $C_{3-6}$ cycloalkyl-$C_{1-2}$ alkylene, 3- to 6-membered heterocyclyl, phenyl, phenyl-$C_{1-2}$ alkylene; or $R^c$ and $R^d$, together with the nitrogen atom to which they are attached, form a 5- to 6-membered heterocyclic ring, and wherein each of methyl, ethyl, i-propyl, n-propyl, n-butyl, t-butyl, $C_{3-6}$ cycloalkyl, $C_{3-6}$ cycloalkyl-$C_{1-2}$ alkylene, phenyl, phenyl-$C_{1-2}$ alkylene and 5- to 6-membered heterocyclic ring is independently unsubstituted or substituted with one, two, three, or four substituents independently selected from F, Cl, CN, OH, $NH_2$, $C_{1-3}$ alkyl, $C_{1-3}$ haloalkyl or methoxy.

6. The compound of claim 1, wherein each $R^2$ is independently ethynyl, propynyl, phenyl, naphthyl, furyl, benzofuryl, pyrrolyl, pyridyl, pyrazolyl, imidazolyl, benzimidazolyl, triazolyl, tetrazolyl, oxazolyl, oxadiazolyl, 1,3,5-triazinyl, thiazolyl, thienyl, benzothienyl, pyrazinyl, pyridazinyl, pyrimidyl, indolyl, purinyl, quinolyl, isoquinolyl, phenoxthinyl,

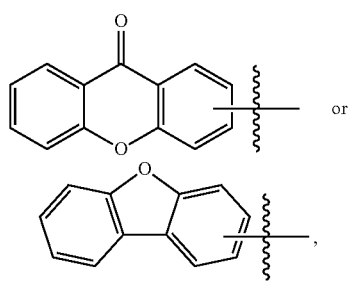 or

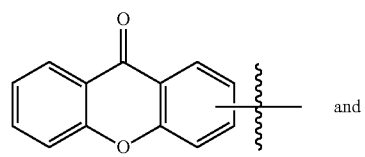 and

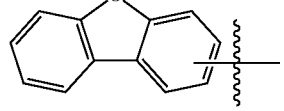

is independently unsubstituted or substituted with one, two, three, four or five R'.

7. The compound of claim 1, wherein $R^w$ is $-C(=O)OR^b$.

8. The compound of claim 7, wherein each $R^2$ is independently $C_{2-6}$ alkynyl, phenyl, naphthyl, or 5- to 6-membered heteroaryl; and wherein each of the $C_{2-6}$ alkynyl, phenyl, naphthyl, and 5- to 6-membered heteroaryl is independently unsubstituted or substituted with one, two, three, four or five R'.

9. The compound of claim 7, wherein each $R^2$ is independently F, ethynyl, propynyl, phenyl, naphthyl, furyl, benzofuryl, pyrrolyl, pyridyl, pyrazolyl, imidazolyl, benzimidazolyl, triazolyl, tetrazolyl, oxazolyl, oxadiazolyl, 1,3,5-triazinyl, thiazolyl, thienyl, benzothienyl, pyrazinyl, pyridazinyl, pyrimidyl, indolyl, purinyl, quinolyl, isoquinolyl, phenoxthinyl,

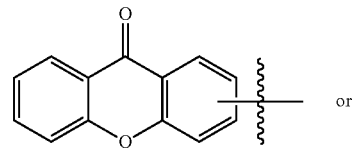 or

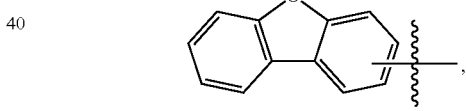

and wherein each ethynyl, propynyl, phenyl, naphthyl, furyl, benzofuryl, pyrrolyl, pyridyl, pyrazolyl, imidazolyl, benzimidazolyl, triazolyl, tetrazolyl, oxazolyl, oxadiazolyl, 1,3,5-triazinyl, thiazolyl, thienyl, benzothienyl, pyrazinyl, pyridazinyl, pyrimidyl, indolyl, purinyl, quinolyl, isoquinolyl, phenoxthinyl,

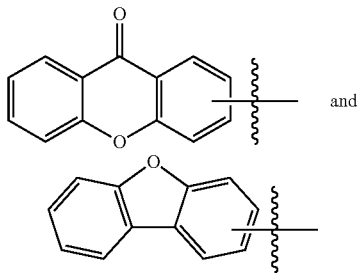

is independently unsubstituted or substituted with one, two, three, four or five R'.

10. The compound of claim 1, wherein the compound having one of the following structures:
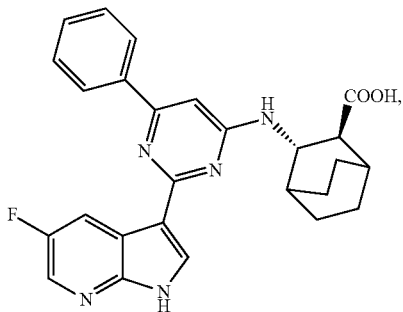
(87)
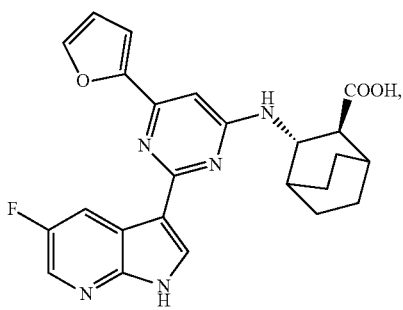
(88)
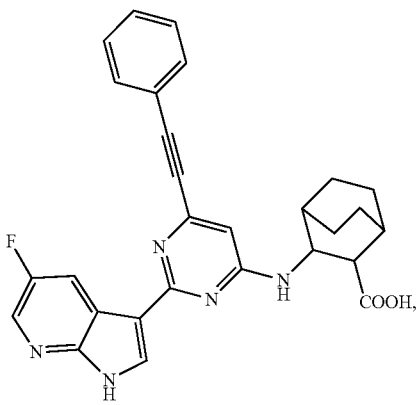
(89)
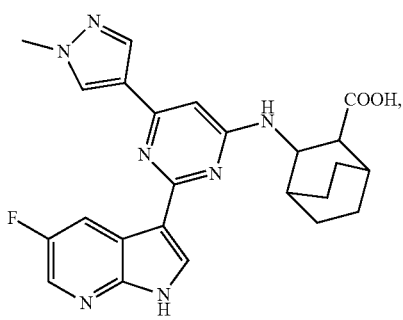
(91)
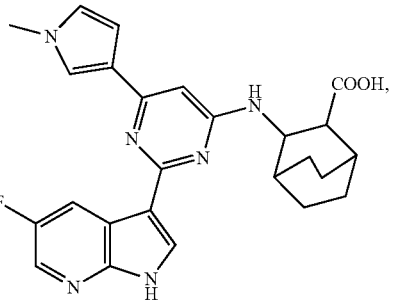
(92)
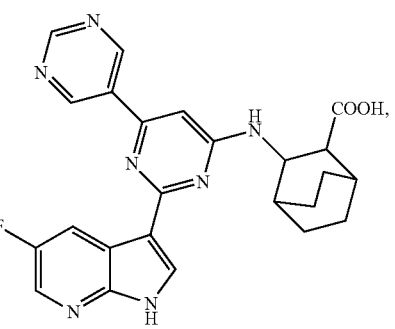
(93)
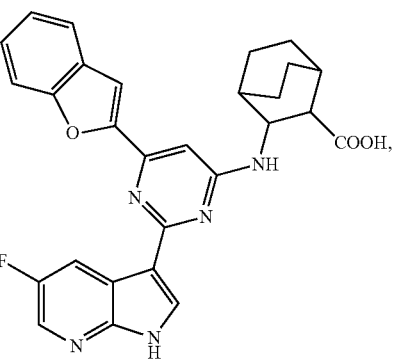
(95)
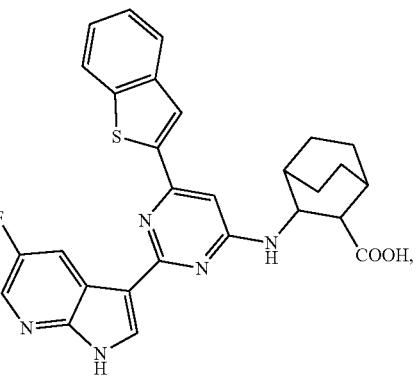
(96)

(97)
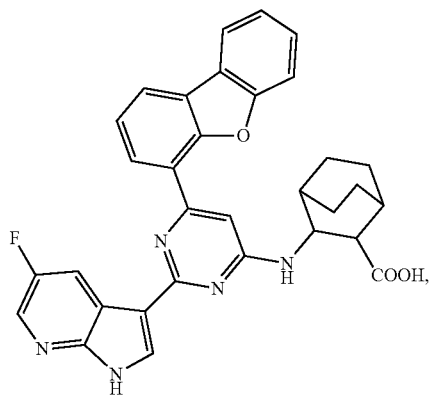
(99)
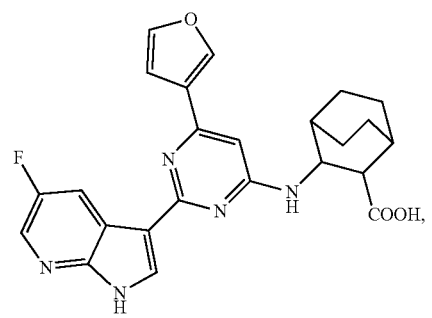
(102)
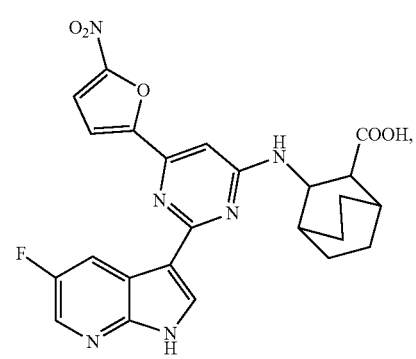
(117)
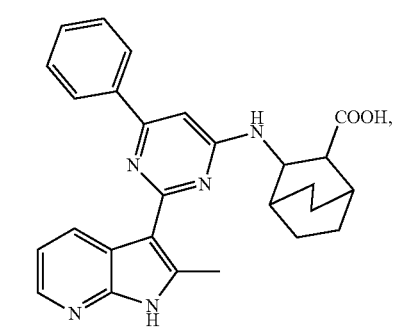
(121)
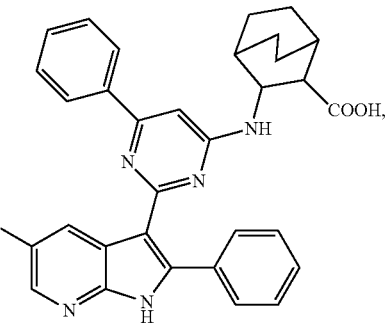
(124)
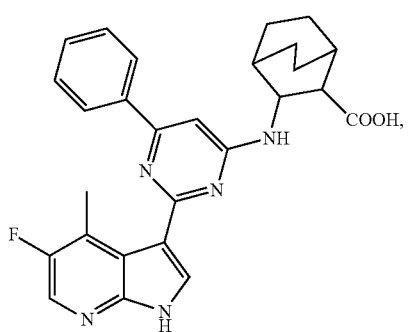
(126)
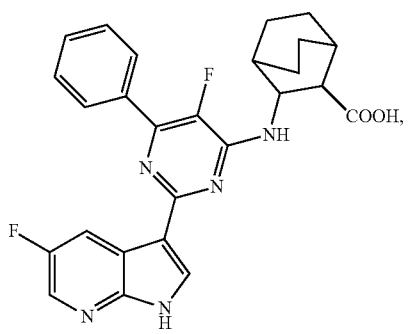
(127)
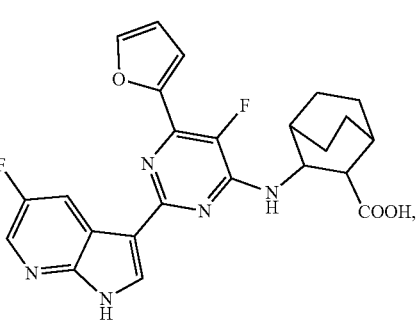

(128)
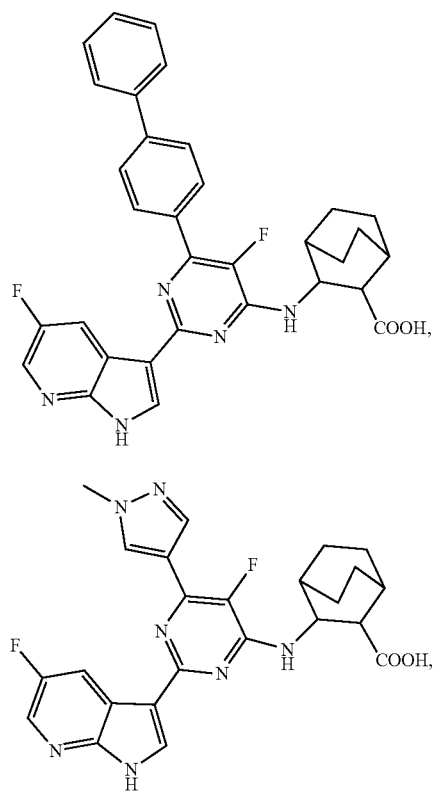
(129)
(130)
(131)
(132)
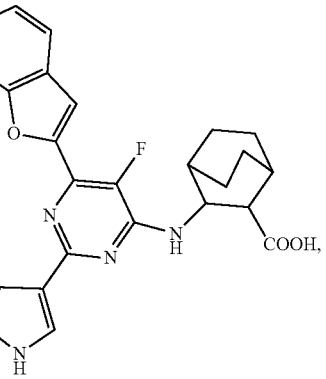
(133)
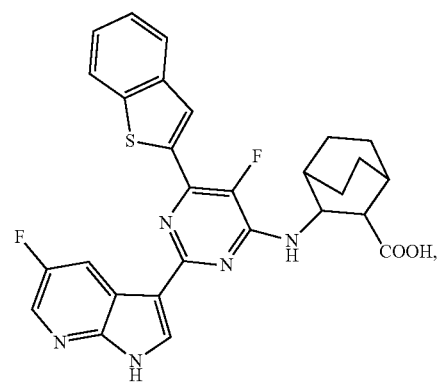
(134)
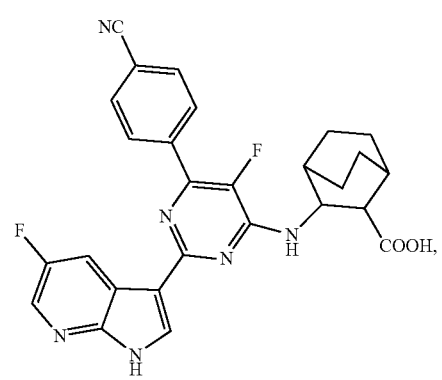
(135)
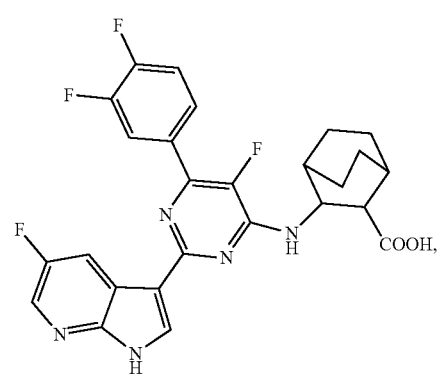

(136)
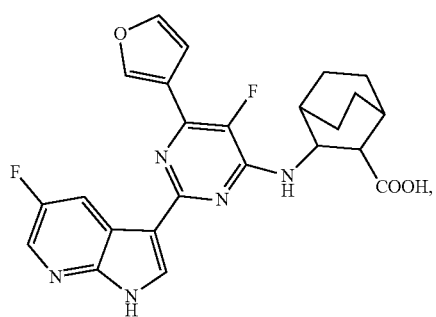
(137)
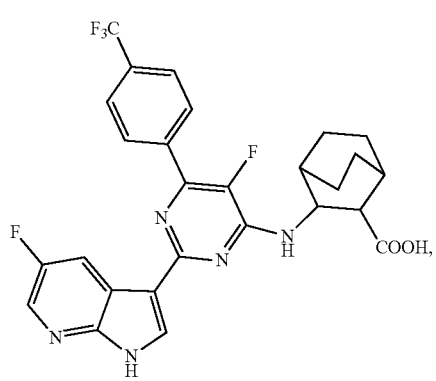
(138)
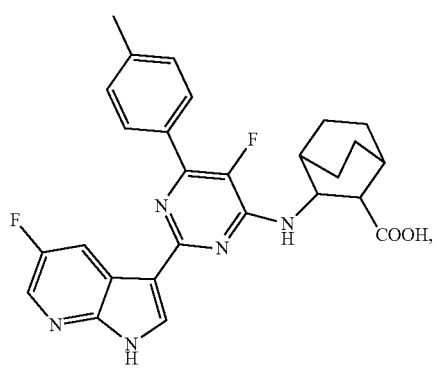
(140)
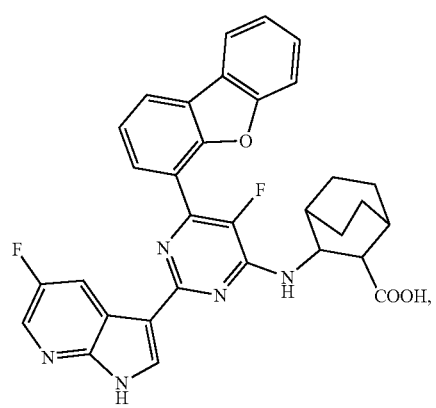
(141)
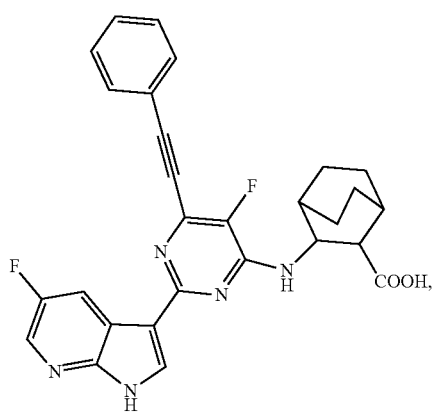
(142)
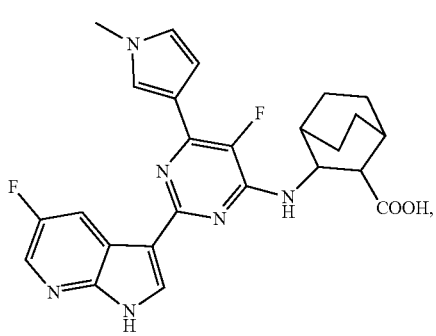
(145)
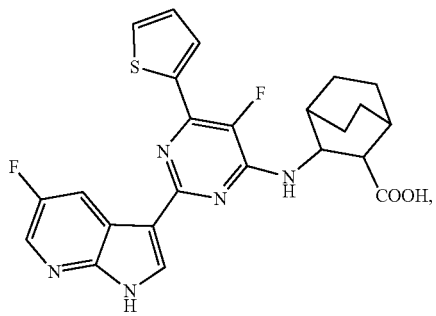
(148)
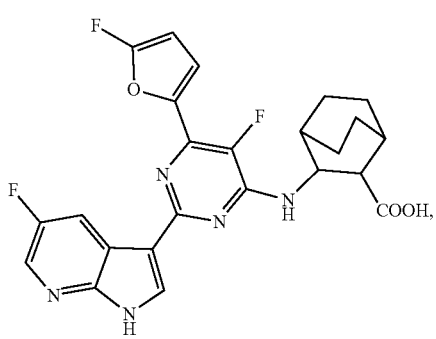

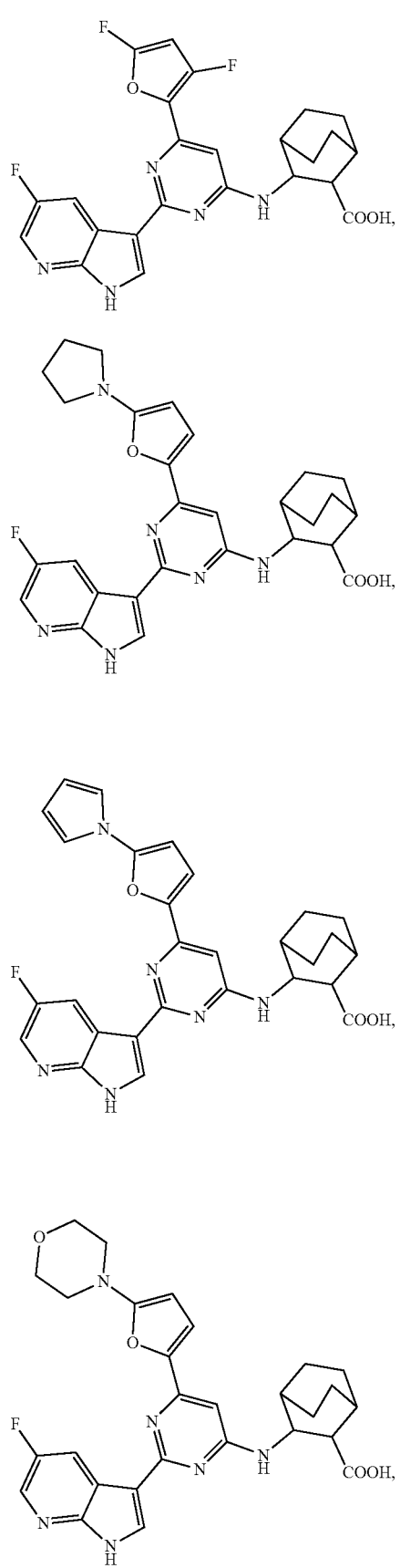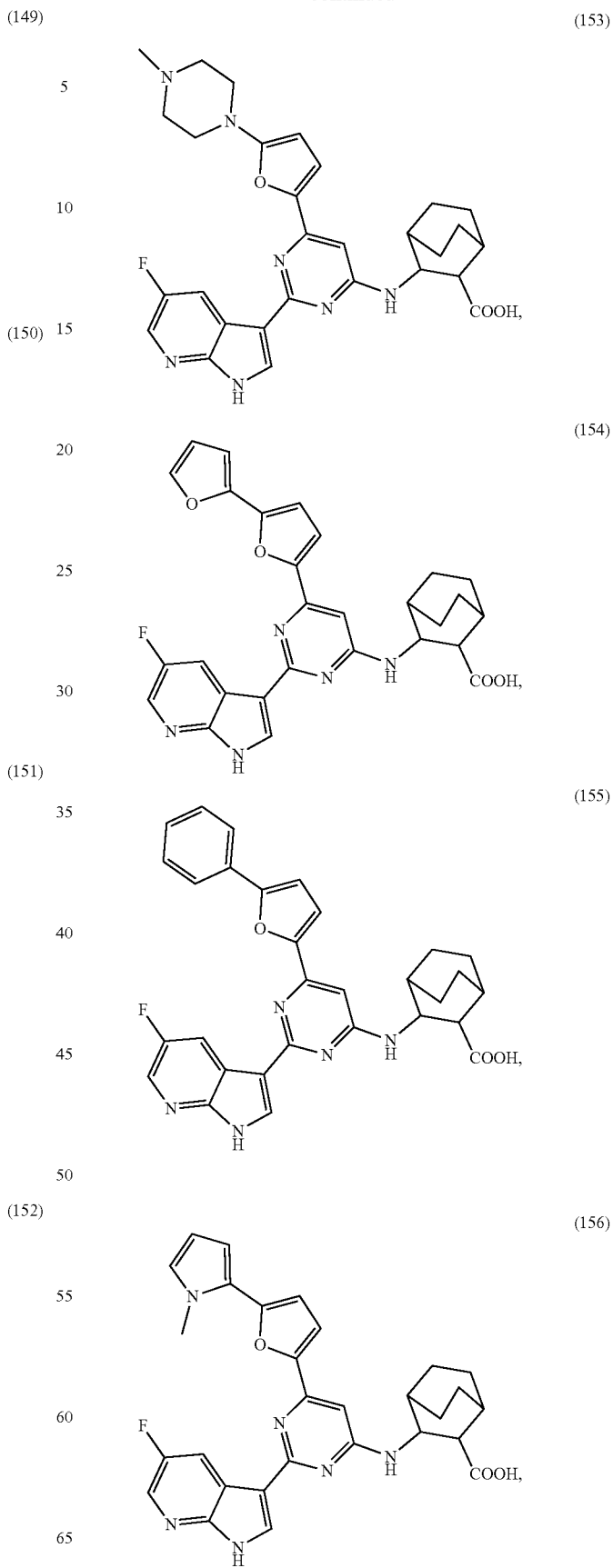

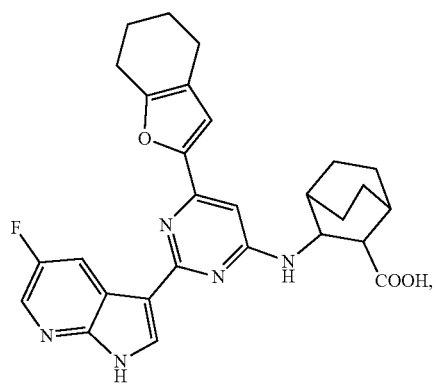
(157)
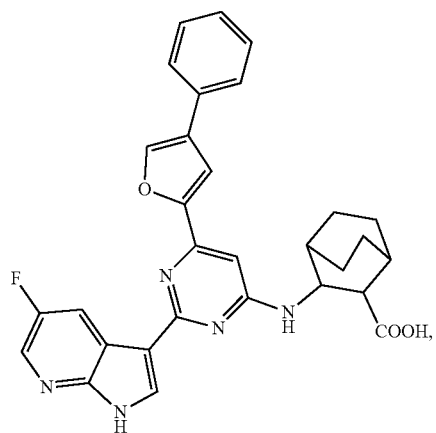
(158)
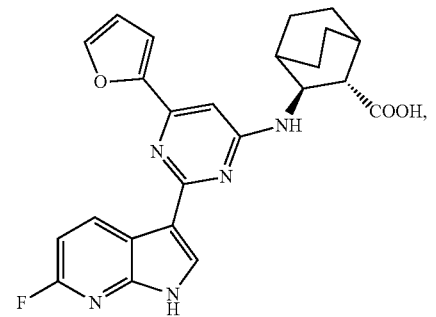
(163)
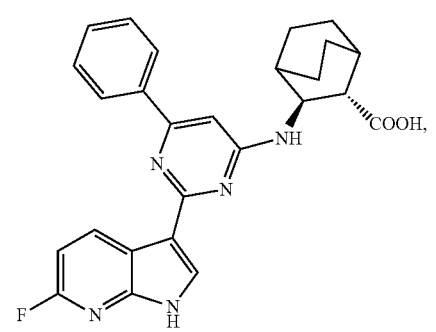
(165)
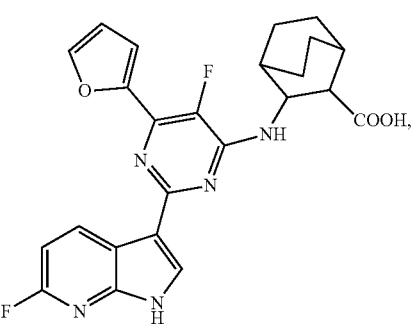
(166)
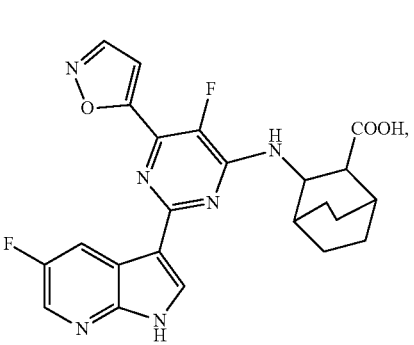
(167)
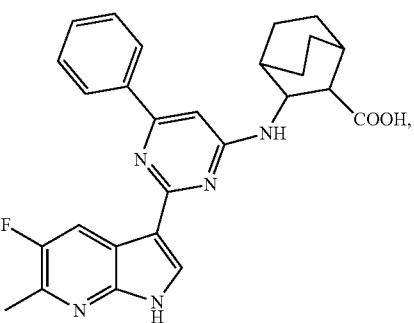
(169)
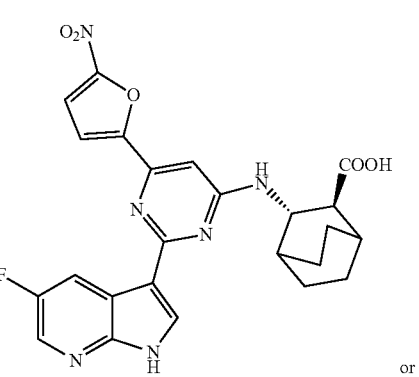
(170)
or

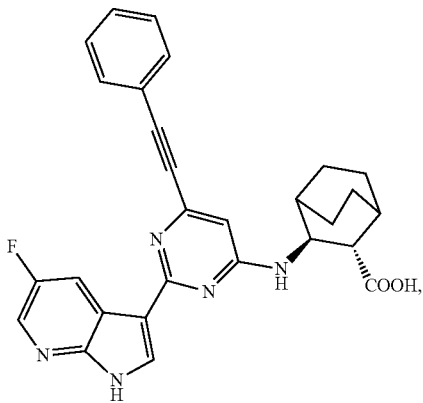

(171)

or a stereoisomer, or a stereoisomer, a tautomer, an N-oxide, a solvate, or a pharmaceutically acceptable salt thereof.

11. A pharmaceutical composition comprising an effective amount of the compound of claim 1, optionally, further comprising a pharmaceutically acceptable carrier, adjuvant, vehicle or a combination thereof.

12. The pharmaceutical composition of claim 11 further comprising one or more therapeutic agents, and wherein the therapeutic agent is an anti-influenza virus agent or anti-influenza virus vaccine.

13. The pharmaceutical composition of claim 12, wherein the therapeutic agent is amantadine, rimantadine, oseltamivir, zanamivir, peramivir, laninamivir, laninamivir octanoate hydrate, favipiravir, umifenovir, ribavirin, stachyflin, 5-[2-(1H-imidazol-5-yl)ethylamino]-5-oxopentanoic acid, (R)-3-((5-fluoro-2-(5-fluoro-1H-pyrrolo[2,3-b]pyridin-3-yl)-pyrimidin-4-yl)amino)-4,4-dimethyl pentanoic acid, pimodivir, an influenza vaccine or a combination thereof.

14. A method of managing, treating or lessening a disorder or disease caused by a virus infection in a patient, comprising administering to the patient a therapeutically effective amount of the compound of claim 1, wherein the virus infection is influenza virus infection.

15. A method of inhibiting RNA polymerase of influenza virus in a patient, comprising administering to the patient a therapeutically effective amount of the compound of claim 1.

16. A method of managing, treating or lessening a disorder or disease caused by a virus infection in a patient, comprising administering to the patient a therapeutically effective amount of the pharmaceutical composition of claim 11, wherein the virus infection is influenza virus infection.

17. A method of inhibiting RNA polymerase of influenza virus in a patient, comprising administering to the patient a therapeutically effective amount of the compound of the pharmaceutical composition of claim 11.

* * * * *